US011807658B2

(12) United States Patent
Du et al.

(10) Patent No.: US 11,807,658 B2
(45) Date of Patent: *Nov. 7, 2023

(54) CD73 INHIBITORS

(71) Applicant: ORIC Pharmaceuticals, Inc., South San Francisco, CA (US)

(72) Inventors: Xiaohui Du, Belmont, CA (US); John Eksterowicz, Burlingame, CA (US); Valeria R. Fantin, San Mateo, CA (US); Daqing Sun, Foster City, CA (US); Qiuping Ye, Foster City, CA (US); Jared Moore, San Rafael, CA (US); Tatiana Zavorotinskaya, Moraga, CA (US); Brian R. Blank, Daly City, CA (US); Yosup Rew, Foster City, CA (US); Kejia Wu, South San Francisco, CA (US); Liusheng Zhu, Foster City, CA (US); Johnny Pham, San Bruno, CA (US); Hiroyuki Kawai, Pacifica, CA (US)

(73) Assignee: ORIC PHARMACEUTICALS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/697,318

(22) Filed: Mar. 17, 2022

(65) Prior Publication Data

US 2022/0220147 A1 Jul. 14, 2022

Related U.S. Application Data

(63) Continuation of application No. 17/078,567, filed on Oct. 23, 2020, now Pat. No. 11,325,938, which is a continuation of application No. PCT/US2019/030068, filed on Apr. 30, 2019.

(60) Provisional application No. 62/810,790, filed on Feb. 26, 2019, provisional application No. 62/777,697, filed on Dec. 10, 2018, provisional application No. 62/757,714, filed on Nov. 8, 2018, provisional application No. 62/737,647, filed on Sep. 27, 2018, provisional application No. 62/664,841, filed on Apr. 30, 2018.

(51) Int. Cl.
*C07H 19/23* (2006.01)
*A61K 45/06* (2006.01)

(52) U.S. Cl.
CPC .............. *C07H 19/23* (2013.01); *A61K 45/06* (2013.01)

(58) Field of Classification Search
None
See application file for complete search history.

(56) References Cited

U.S. PATENT DOCUMENTS

| 10,239,912 | B2 | 3/2019 | Debien et al. |
| 11,028,120 | B2 | 6/2021 | Du et al. |
| 11,129,841 | B2 | 9/2021 | Du et al. |
| 11,130,778 | B2 | 9/2021 | Du et al. |
| 11,377,469 | B2 | 7/2022 | Du et al. |
| 11,530,236 | B2 | 12/2022 | Du et al. |
| 2004/0229839 | A1 | 11/2004 | Babu et al. |
| 2004/0266723 | A1 | 12/2004 | Otto et al. |
| 2009/0029949 | A1 | 1/2009 | Parrill-Baker et al. |
| 2009/0274686 | A1 | 11/2009 | Or et al. |
| 2017/0044203 | A1 | 2/2017 | Cacatian et al. |
| 2018/0072742 | A1 | 3/2018 | Chen et al. |
| 2019/0309010 | A1 | 10/2019 | Debien et al. |
| 2020/0093844 | A1 | 3/2020 | Du et al. |
| 2020/0347090 | A1 | 11/2020 | Du et al. |
| 2021/0047359 | A1 | 2/2021 | Du et al. |
| 2021/0130389 | A1 | 5/2021 | Du et al. |
| 2021/0130390 | A1 | 5/2021 | Du et al. |
| 2021/0214387 | A1 | 7/2021 | Du et al. |
| 2022/0054512 | A1 | 2/2022 | Du et al. |
| 2022/0259253 | A1 | 8/2022 | Du et al. |
| 2022/0331343 | A1 | 10/2022 | Du et al. |
| 2023/0131747 | A1 | 4/2023 | Du et al. |

FOREIGN PATENT DOCUMENTS

| CN | 104530166 B | 8/2016 |
| EP | 0477454 A1 | 4/1992 |
| WO | WO-2005020885 A2 | 3/2005 |
| WO | WO-2008083949 A2 | 7/2008 |
| WO | WO-2009127230 A1 | 10/2009 |
| WO | WO-2015164573 A1 | 10/2015 |
| WO | WO-2017120508 A1 | 7/2017 |
| WO | WO-2018049145 A1 | 3/2018 |
| WO | WO-2018067424 A1 | 4/2018 |
| WO | WO-2018094148 A1 | 5/2018 |
| WO | WO-2018119284 A1 | 6/2018 |
| WO | WO-2018183635 A1 | 10/2018 |
| WO | WO-2018208727 A1 | 11/2018 |
| WO | WO-2018208980 A1 | 11/2018 |
| WO | WO-2019090111 A1 | 5/2019 |
| WO | WO-2019213174 A1 | 11/2019 |
| WO | WO-2019232319 A1 | 12/2019 |
| WO | WO-2019246403 A1 | 12/2019 |
| WO | WO-2020046813 A1 | 3/2020 |
| WO | WO-2020257429 A1 | 12/2020 |
| WO | WO-2021011689 A1 | 1/2021 |
| WO | WO-2021087136 A1 | 5/2021 |

OTHER PUBLICATIONS

Berge et al. Pharmaceutical Salts. Journal of Pharmaceutical Sciences 66(1):1-19 (Jan. 1977).
Boothroyd et al. Why Do Some Molecules Form Hydrates or Solvates? Cryst Growth Des 18:1903-1908 (2018).

(Continued)

*Primary Examiner* — Layla D Berry
(74) *Attorney, Agent, or Firm* — WILSON SONSINI GOODRICH & ROSATI

(57) ABSTRACT

Described herein are CD73 inhibitors and pharmaceutical compositions comprising said compounds. The subject compounds and compositions are useful for the treatment of cancer, infections, and neurodegenerative diseases.

19 Claims, No Drawings

(56) References Cited

OTHER PUBLICATIONS

Caiazzo et al. The Ecto-5'-Nucleotidase/CD73 Inhibitor, α,β-Methylene Adenosine 5'-Diphosphate, Exacerbates Carrageenan-Induced Pleurisy in Rat. Frontiers in Pharmacology 10:775 (2019).
Chan et al. Poster #LB-115. An Orally Bioavailable Inhibitor of CD73 Reverts Intratumoral Immunosuppression and Promotes Anti-Tumor Response. AACR Virtual Annual Meeting II, Jun. 22-24, 2020.
Co-pending U.S. Appl. No. 17/626,731, inventors Du; Xiaohui et al., filed Jan. 12, 2022.
Du. Abstract #1242. Orally Bioavailable Small Molecule CD73 Inhibitor Reverses Immunosuppression by Reduction of Adenosine Production. PowerPoint Presentation AACR Annual Meeting Apr. 20, 2020.
Du et al. Orally Bioavailable Small-Molecule CD73 Inhibitor (OP-5244) Reverses Immunosuppression through Blockade of Adenosine Production. J Med Chem 63(18):10433-10459 (2020).
Freireich et al. Quantitative comparison of toxicity of anticancer agents in mouse, rat, hamster, dog, monkey, and man. Cancer Chemother. Rep. 50:219-244 (1966).
Ghalamfarsa et al., CD73 as a potential opportunity for cancer immunotherapy. Expert Opinion on Therapeutic Targets 23(2):127-142 (2019).
Gillerman et al., 2-Hexylthio-β,γ-CH2-ATP is an effective and selective NTPDase2 inhibitor. J Med Chem. 57(14):5919-34 (2014).
Jeffrey et al. Targeting Metabolism of Extracellular Nucleotides via Inhibition of Ectonucleotidases CD73 and CD39. J Med Chem 63(22):13444-13465 (2020).
Metzger et al. Intratumoral Immunosuppression is Reversed by Blocking Adenosine Production with an Oral Inhibitor of CD73. AACR-NCI-EORTC Oct. 27, 2019 Boston, MA.
Morisette et al. High-throughput crystallization: polymorphs, slats, co-crystals, and solvates of pharmaceutical solids. Advanced Drug Delivery Reviews 56:275-300 (2004).
Nguyen et al. Chiral drugs an overview. Int J Biomed Sci 2(2):85-100 (2006).
PCT/US2018/031891 International Search Report and Written Opinion dated Aug. 24, 2018.
PCT/US2018/059004 International Search Report and Written Opinion dated Feb. 26, 2019.
PCT/US2019/030068 International Search Report and Written Opinion dated Aug. 16, 2019.
PCT/US2020/042183 International Search Report and Written Opinion dated Oct. 27, 2020.
PCT/US2020/057996 International Search Report and Written Opinion dated Feb. 23, 2021.
U.S. Appl. No. 16/760,380 Office Action dated Jul. 12, 2021.
U.S. Appl. No. 17/078,567 Office Action dated Sep. 14, 2021.
U.S. Appl. No. 17/114,993 Office Action dated Jan. 27, 2021.
Xin et al. Solvate Prediction for Pharmaceutical Organic Molecules with Machine Learning. Cryst Growth Des 19:1903-1911 (2019).
Zavorotinskaya et al. Poster #1023. CD73 Inhibition with a Novel Orally Bioavailable Small Molecule Blocks Adenosine Production and Rescues T-cell Activation. AACR Virtual Annual Meeting II, Jun. 22-24, 2020.
Zhang. CD73: A Novel Target for Cancer Immunotherapy. Cancer Research 70(16):6407-6411 (2010).
Co-pending U.S. Appl. No. 18/051,125, inventors Du; Xiaohui et al., filed Oct. 31, 2022.
U.S. Appl. No. 17/083,871 Office Action dated May 24, 2022.

CD73 INHIBITORS

CROSS REFERENCE

This application is a continuation of U.S. application Ser. No. 17/078,567, filed Oct. 23, 2020, which is a continuation of international Application No. PCT/US2019/030068 filed Apr. 30, 2019, which claims the benefit of U.S. Application Ser. No. 62/664,841 filed Apr. 30, 2018. U.S. Application Ser. No. 62/737,647 filed Sep. 27, 2018, U.S. Application Ser. No. 62/757,714 filed Nov. 8, 2018, U.S. Application Ser. No. 62/777,597 filed Dec. 10, 2018, U.S. Application Ser. No. 62/810,790 filed Feb. 26, 2019, which are hereby incorporated by reference in their entirety.

BACKGROUND

A need exists in the art for an effective treatment of cancer, infections, and neurodegenerative diseases.

BRIEF SUMMARY OF THE INVENTION

Provided herein are compounds of Formulas (II) and (IV) or pharmaceutically acceptable salts, solvates, stereoisomers, or isotopic variants thereof, and pharmaceutical compositions comprising said compounds. The subject compounds and compositions are useful as CD73 inhibitors. Furthermore, the subject compounds and compositions are useful for the treatment of cancers, infections, and neurodegenerative diseases.

Provided herein are compounds having the structure of Formula (II), or a pharmaceutically acceptable salt, solvate, stereoisomer, or isotopic variant thereof:

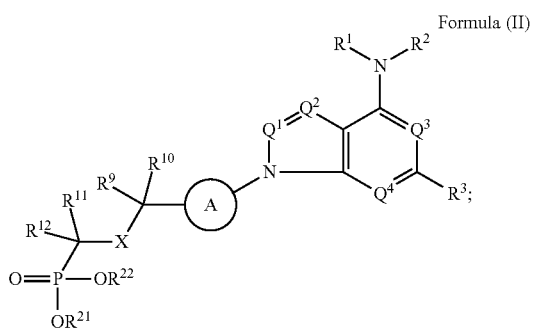

Formula (II)

wherein:
Ring A is

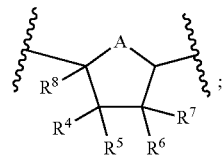

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is independently hydrogen, halogen, —CN, —$OR^b$, —$NR^cR^d$, $C_1$-$C_6$ alkyl, or $C_1$-$C_6$ haloalkyl;
A is —O—;
X is —S— or —O—;

$R^1$ and $R^2$ are independently hydrogen, $C_1$-$C_6$ alkyl, $C_1$-$C_6$ haloalkyl $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl (heterocycloalkyl); wherein each alkyl, alkenyl, alkynyl, cycloalkyl, heterocycloalkyl, and heteroaryl is independently optionally substituted with one, two, or three $R^{1a}$;
or $R^1$ and $R^2$ are taken together with the nitrogen atom to which they are attached to forma heterocycloalkyl optionally substituted with one, two, or three $R^{1b}$;
each $R^{1a}$ and $R^{1b}$ is independently oxo (when feasible) halogen, —CN, —$OR^b$, —$SR^b$, —S(=O)$R^a$, —$NO_2$, —$NR^cR^d$, —S(=O)$_2R^a$, —$NR^bS(=O)_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl (cycloalkyl), or $C_1$-$C_6$ alkyl(heterocycloalkyl);
$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;
each $R^{3a}$ is independently oxo (when feasible) halogen, —CN, $OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;
$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl,
$R^8$ is hydrogen, halogen, —$OR^b$, —$NR^cR^d$, $C_2$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;

or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —OR$^{13}$, —SR$^{13}$, —S(=O) $R^{14}$, —NO$_2$, —NR$^{15}$R$^{16}$, —S(=O)$_2$R$^{14}$, —NR$^{13}$S(=O)$_2$ $R^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$ alkyl, $C_1$-$C_6$ haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14b}$, $R^{15a}$, and $R^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl (cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —OR$^b$, —S(=O)R$^a$, —NO$_2$, —NR$^c$R$^d$, —S(=O)$_2$ R$^a$, —S(=O)$_2$NR$^c$R$^d$, —C(=O)R$^a$, —C(=O)OR$^b$, —C(=O)NR$^c$R$^d$, $C_1$-$C_6$alkyl $C_1$-$C_6$ haloalkyl, $C_2$-$C_6$ alkenyl, or $C_2$-$C_6$ alkynyl;

$R^{21}$ and $R^{22}$ are independently hydrogen, $C_1$-$C_{20}$ alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl (cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$ NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O) OR$^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

Also provided herein are compounds having the structure of Formula (IV), or a pharmaceutically acceptable salt, solvate, stereoisomer, or isotopic variant thereof:

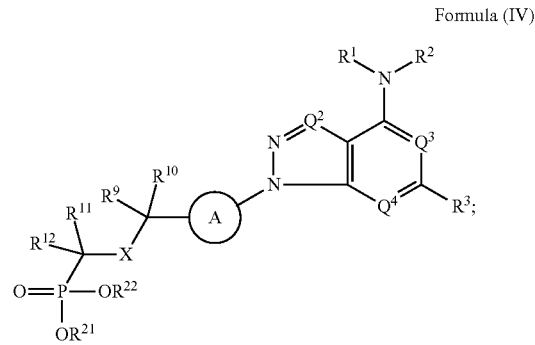

Formula (IV)

wherein:
Ring A is

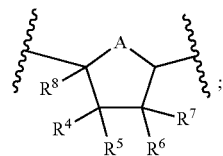

$Q^2$ is N or CW;
$Q^3$ is N and $Q^4$ is CW;
or $Q^3$ is CW and $Q^4$ is N;
each W is independently hydrogen, halogen, —CN, $OR^b$, $NR^cR^d$, $C_1$-$C_6$ alkyl, or $C_1$-$C_6$ haloalkyl;
A is —O— or —CH$_2$—;
X is —O—, —S—, —S(=O)$_2$—, —NR$^{17}$—, or —C(R$^{18}$)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —$OR^b$, —$SR^b$, —S(=O)$R^a$, —NO$_2$, —$NR^cR^d$, —S(=O)$_2R^a$, —$NR^bS(=O)_2R^a$, —S(=O)$_2$$NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;
each $R^{3a}$ is independently oxo (when feasible) halogen; —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;
$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^8$ is hydrogen, halogen, —$OR^b$, —$NR^cR^d$, $C_1$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is hydrogen; halogen; —CN, —$OR^{13}$, —$SR^{13}$, —S(=O)$R^{14}$, —NO$_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl heterocycloalkyl, aryl, and heteroaryl is independently optionally substituted with one, two, or three $R^{11a}$;
$R^{12}$ is hydrogen, halogen, —CN, —$OR^{13}$, —$SR^{13}$, —S(=O)$R^{14}$, —NO$_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$alkyl $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —$OR^{13}$, —$SR^{13}$, —S(=O)$R^{14}$, —NO$_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —$OR^b$, —$SR^b$, —S(=O)$R^a$, —NO$_2$, —$NR^cR^d$, —S(=O)$_2R^a$, —$NR^bS(=O)_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl cycloalkyl, heterocycloalkyl, aryl, heteroaryl, $C_1$-$C_6$ alkyl(aryl), alkyl(heteroaryl), $C_1$-$C_6$ alkyl(cycloalkyl), or $C_1$-$C_6$ alkyl(heterocycloalkyl);
each $R^{13}$ is independently hydrogen, $C_1$-$C_6$ alkyl, $C_1$-$C_6$ haloalkyl $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, or three $R^{13a}$;
each $R^{14}$ is independently $C_1$-$C_6$ alkyl, $C_1$-$C_6$ haloalkyl, $C_2$-$C_6$ alkenyl, $C_2$-$C_6$ alkynyl, heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;
each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —$OR^b$, —$S(=O)R^a$, —$NO_2$, —$NR^cR^d$, —$S(=O)_2 R^a$, —$S(=O)_2NR^cR^d$, —$C(=O)R^a$, —$C(=O)OR^b$, —$C(=O)NR^cR^d$, $C_1$-$C_6$ alkyl, $C_1$-$C_6$ haloalkyl, $C_2$-$C_6$ alkenyl, or $C_2$-$C_6$ alkynyl;

$R^{17}$ is hydrogen, —CN, —$OR^b$, —$S(=O)_2R^a$, —$C(=O)R^a$, —$C(=O)OR^b$, —$C(=O)NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl), each $R^{18}$ is independently hydrogen, halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_6$ cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

Also disclosed herein are pharmaceutical compositions comprising a compound disclosed herein, or a pharmaceutically acceptable salt, solvate, stereoisomer, or isotopic variant thereof, and a pharmaceutically acceptable excipient.

Also disclosed herein are methods of inhibiting CD73 comprising contacting CD73 with a compound disclosed herein, or a pharmaceutically acceptable salt, solvate, stereoisomer, or isotopic variant thereof.

Also disclosed herein are methods of treating cancer in a subject, comprising administering to the subject a compound disclosed herein, or a pharmaceutically acceptable salt, solvate, stereoisomer, or isotopic variant thereof or administering to the subject a pharmaceutical composition comprising a compound disclosed herein, or a pharmaceutically acceptable salt, solvate, stereoisomer, or isotopic variant thereof, and a pharmaceutically acceptable excipient.

Also disclosed herein are methods of treating an infection in a subject, comprising administering to the subject a compound disclosed herein, or a pharmaceutically acceptable salt, solvate, stereoisomer, or isotopic variant thereof or administering to the subject a pharmaceutical composition comprising a compound disclosed herein, or a pharmaceutically acceptable salt, solvate, stereoisomer, or isotopic variant thereof, and a pharmaceutically acceptable excipient.

Also disclosed herein are methods of treating a neurodegenerative disease in a subject, comprising administering to the subject a compound disclosed herein, or a pharmaceutically acceptable salt, solvate, stereoisomer, or isotopic variant thereof or administering to the subject a pharmaceutical composition comprising a compound disclosed herein, or a pharmaceutically acceptable salt, solvate, stereoisomer, or isotopic variant thereof, and a pharmaceutically acceptable excipient.

INCORPORATION BY REFERENCE

All publications, patents, and patent applications mentioned in this specification are herein incorporated by reference for the specific purposes identified herein.

DETAILED DESCRIPTION OF THE INVENTION

CD73 is a glycotylphosphatidylinositol (GPI) anchored cell surface protein that catalyzes the hydrolysis of AMP to adenosine, and works in concert with CD39, which converts ATP into AMP. The resulting adenosine functions as a signaling molecule that activates the P1 receptors expressed on the cell surface in many different tissues. Four G protein-coupled P1 or adenosine receptors have been cloned and designated as A1, A2A, A2B, and A3. Adenosine impacts a wide range of physiological processes including neural function, vascular perfusion, and immune responses. In doing so, this metabolite regulates CNS, cardiovascular, and immune system functions, to name a few.

Increasing evidence suggests that interactions between tumor cells and their microenvironment are essential for tumorigenesis. The purinergic signaling pathway in which CD73 plays a critical role, has emerged as an important player in cancer progression. It has become clear in recent years that adenosine is one of the most important immunosuppressive regulatory molecules in the tumor microenvironment, and contributes to immune escape and tumor progression.

CD73 is a key protein molecule in cancer development. CD73 has been found to be overexpressed many cancer cell lines and tumor types including, for example, breast cancer, colorectal cancer, ovarian cancer, gastric cancer, gallbladder cancer, and cancers associated with poor prognosis.

The expression of CD73 in tumors is regulated by a variety of mechanisms. CD73 expression is negatively regulated by estrogen receptor (ER) in breast cancer. Thus, CD73 is highly expressed in ER negative breast cancer patients. The hypoxia-inducible factor-1α (HIF-1α) has also been shown to regulate CD73 transcription. Additionally, inflammatory factors such as IFN-γ affect CD73 levels. CD73 expression is also epigenetically regulated by CpG island methylation in cell lines and clinical tumor samples.

In addition to being a prognostic biomarker in cancer patients, overexpression of CD73 has also been found to be functionally linked to therapy resistance. Elevated levels of CD73 were initially linked to resistance to a variety of chemotherapeutic agents including vincristine and doxorubicin.

CD73 has also been shown to be involved in immunotherapy resistance. This ectonucleotidase participates in the process of tumor immune escape by inhibiting the activation, clonal expansion, and homing of tumor-specific T cells (in particular, T helper and cytotoxic T cells); impairing tumor cell killing by cytolytic effector T lymphocytes; driving, via pericellular generation of adenosine, the suppressive capabilities of Treg and Th17 cells; enhancing the conversion of type 1 macrophages into tumor-promoting type 2 macrophages; and promoting the accumulation of MDSCs.

Small molecular inhibitors and monoclonal antibodies targeting CD have shown anti-tumor activity in a variety of immune-competent but not in immune-deficient mouse tumor models. Overall, these studies suggest that anti-CD73 therapy activity is dependent on its ability to elicit immune responses in vivo.

Antibodies which block PD-1, PD-L1, and CTLA-4 have shown impressive objective response in cancer patients. Recent data demonstrates that anti-CD73 mAb significantly enhances the activity of both anti-CTLA-4 and anti-PD-1 mAbs in several mouse tumor models. In addition to checkpoint blockade, CD73-mediated production of adenosine could contribute to resistance to additional immunotherapy modalities including CAR-T cells and cancer vaccines.

Interfering with CD73 activity represents a strategy to re-sensitize tumors to therapy. Based on the link between CD73 and therapy resistance, combining anti-CD73 treatment with chemotherapy or immunotherapy is an effective approach to enhance their activity in cancer patients with high CD73 levels. In some instances, CD73 expression serves as a biomarker to identify patients that could benefit from anti-CD73 combination therapy.

In some instances, the CD39/CD73 couple turns ATP-driven pro-inflammatory cell activity toward an adenosine-mediated anti-inflammatory state. A number of studies have shown changes in the activity of the CD39/CD73 axis during infections induced by a variety of microorganisms. An increase in CD73 expression has also been observed in the brain of mice infected with *Toxoplasma gondii*, which promotes the parasite life cycle through the production of adenosine. Thus, the pharmacological blockade of CD73 is a promising therapeutic approach to treat human toxoplasmosis.

Enhanced expression and activity of CD39 and CD73 have been observed in endothelial cells infected with cytomegalovirus (CMV). The increase in local adenosine production, associated with the upregulation of ecto-nucleotidases, generates an immunosuppressive and antithrombotic microenvironment, which facilitates viral entry into target cells.

In some instances, inhibitors of CD73, by driving a decrease on adenosine production, have applications as antiviral agents. The elevated expression/activity of CD39 and CD73 on lymphocytes of individuals infected with human immunodeficiency virus (HIV) indicates a role for ecto-nucleotidases in the immune dysfunction associated with this disease. In fact, an increased proportion of Tregs expressing CD39, as well as a positive correlation between CD39 expression on Tregs and disease progression has been observed in different cohorts of HIV-infected patients. It has also been shown that HIV-positive patients had a higher number of CD39+ Treg, and that their Tat exhibited an increased sensitivity in vitro to the suppressive effect of adenosine, which was related to the elevated expression of immunosuppressive A2A receptors.

In the central nervous system, adenosine plays a critical role in controlling a multitude of neural functions. Through the activation of P1 receptors, adenosine is involved in diverse physiological and pathological processes such as regulation of sleep, general arousal state and activity, local neuronal excitability, and coupling of the cerebral blood flow to the energy demand. In some instances, manipulation of adenosine production via CD73 inhibitors is useful for treating neurodegenerative diseases such as Alzheimer's disease, Parkinson's disease and Huntington's disease, and psychiatric disorders such as schizophrenia and autism.

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to an optionally substituted straight-chain, or optionally substituted branched-chain saturated hydrocarbon monoradical having from one to about ten carbon atoms, or from one to six carbon atoms. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t butyl, n-pentyl, isopentyl, neopentyl, tert-amyl and hexyl, and longer alkyl groups, such as heptyl, octyl, and the like.

Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted for example, with oxo, halogen, amino, nitrite, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted for example, with oxo, halogen, amino, nitrile, nitro, hydroxyl, haloalkyl alkoxy, aryl, cycloalkyl, heterocycloalkyl, heteroaryl and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted for example, with oxo, halogen, amino, nitrile, nitro, hydroxyl, haloalkyl alkoxy, acyl, cycloalkyl, heterocycloalkyl, heteroaryl and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocycle, bicycle, tricyclic or tetracyclic ring system, which may include fused (when fused with a cycloalkyl or heterocycloalkyl ring, the amyl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indene, indene, naphthalene, phenalene, phenanthrene, pleiadene, pyrene, and triphenylene. In some embodiments, the an is phenyl. Unless stated otherwise specifically in the specification, an aryl may be optionally substituted for example, with halogen, amino, nitrite, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OMe, —$NH_2$, or —$NO_2$. In some embodiments, an aryl is optionally substituted with halogen, methyl, ethyl, —CN, —CF$_3$, —OH, or —OMe. In some embodiments, the amyl is optionally substituted with halogen.

"Cycloalkyl" refers to a stable, partially or fully saturated, monocycle or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocycle cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooetenyl. Unless stated otherwise specifically in the specification, a cycloalkyl is optionally substituted for example, with oxo, halogen, amino, nitrile, nitro, hydroxyl, alkyl, alkenyl, alkynyl, haloalkyl, alkoxy, acyl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substitute (by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b]

[1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl carbazolyl, cinnolinyl, dibenzofuranyl, dibenzothiophenyl, furanyl, furanonyl, isothiazolyl, imidazolyl indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrazolyl, pyridinyl, pyrazinyl, pyrimidinyl, pyridazinyl, quinazolinyl, quinoxalinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted for example, with halogen, amino, nitrile, nitro, hydroxyl, alkyl, alkenyl, alkenyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

"Hydroxyalkyl" refers to an alkyl radical, as defined above, that is substituted by one or more —OH e.g., hydroxymethyl, hydroxyethyl, hydroxypropyl, hydroxybutyl, hydroxypentyl, dihydroxymethyl, dihydroxyethyl, dihydroxypropyl, dihydroxybutyl, dihydroxypentyl, and the like.

"Oxo" refers to =O.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The terms "inhibit," "block," "suppress," and grammatical variants thereof are used interchangeably herein and refer to any statistically significant decrease in biological activity, including full blocking of the activity. In some embodiments, "inhibition" refers to a decrease of about 10%, about 20%, about 30%, about 40%, about 50%, about 60%, about 70%, about 80%, about 90% or about 100% in biological activity. Accordingly, when the terms "inhibition" or "suppression" are applied to describe, e.g., an effect on the enzymatic activity of CD73, the term refers to the ability of a compound disclosed herein to statistically significantly decrease the 5'-nucleotidase activity of CD73 (catabolizing the hydrolysis of adenosine monophosphate, AMP, to adenosine), relative to the CD73-mediated 5'-nucleotidase activity in an untreated (control) cell. In some instances, the cell which expresses CD73 is a naturally occurring cell or cell line (e.g., a cancer cell) or is recombinantly produced by introducing a nucleic acid encoding CD73 into a host cell. In some aspects, compounds disclosed herein statistically significantly decrease the 5'-nucleotidase activity of a soluble form of CD73 in a biological fluid. In one aspect, the compound disclosed herein inhibit CD73-mediated 5'-nucleotidase activity by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or about 100%, as determined, for example, by the methods described in the Examples and/or methods known in the art.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

Compounds

Described herein are compounds that are CD73 inhibitors. These compounds, and compositions comprising these compounds, are useful for the treatment of cancer, infections, and neurodegenerative diseases.

In some embodiments provided herein is a compound having the structure of Formula (I), or a pharmaceutically acceptable salt, solvate, stereoisomer, or isotopic variant thereof:

Formula (I)

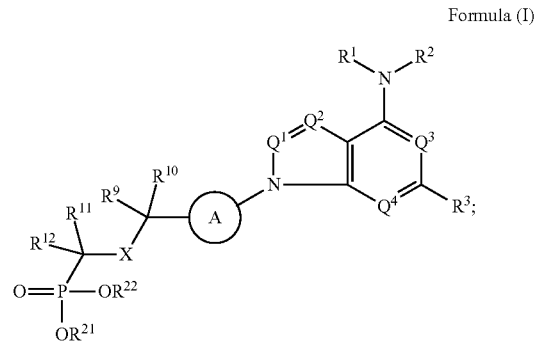

wherein:

Ring A is

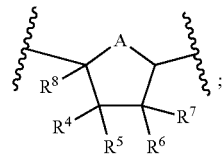

$Q^1$ and $Q^2$ are independently N or CW;

$Q^3$ and $Q^4$ are independently N or CW; provided that at least one of $Q^3$ or $Q^4$ is N;

each W is independently hydrogen, halogen, —CN, —OR$^b$, NR$^c$R$^d$, C$_1$-C$_6$ alkyl, or C$_1$-C$_6$ haloalkyl;

A is —O— or —CH$_2$—;

X is —S(=O)$_2$—;

$R^1$ and $R^2$ are independently hydrogen, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ fluoroalkyl, C$_2$-C$_6$ alkenyl, C$_2$-C$_6$ alkynyl cycloalkyl, heterocycloalkyl aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

$R^3$ is hydrogen, halogen, —CN, —OR$^b$, —SR$^b$, —NR$^c$R$^d$, C$_1$-C$_6$ alkyl, C$_2$-C$_6$ alkenyl, C$_2$-C$_6$ alkynyl, C$_1$-C$_6$ haloalkyl, C$_1$-C$_6$ hydroxyalkyl, C$_1$-C$_6$ heteroalkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl (cycloalkyl), or C$_1$-C$_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —OR$^b$, —NR$^c$R$^d$, —C(O)R$^a$, —C(=O)OR$^b$, —C(=O)NR$^c$R$^d$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, or heteroaryl;

$R^4$ and $R^7$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

$R^5$ and $R^6$ are independently hydrogen, halogen, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

$R^8$ is hydrogen, halogen, —OR$^b$, —NR$^c$R$^d$, C$_1$-C$_6$ alkyl, or C$_1$-C$_6$ haloalkyl;

$R^9$ and $R^{10}$ are independently hydrogen, halogen, C$_1$-C$_6$ alkyl, or C$_1$-C$_6$ haloalkyl;

$R^{11}$ is halogen, —CN, —OR$^{13}$, —SR$^{13}$, —S(=O)R$^{14}$, —NO$_2$, —NR$^{15}$R$^{16}$, —S(=O)$_2$R$^{13}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;

$R^{12}$ is hydrogen, halogen, —CN, —OR$^{13}$, —SR$^{33}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_1$-C$_6$ alkynyl, C$_1$-C$_6$ heteroalkyl, cycloalkyl, heterocycloalkyl, aryl, or heteroaryl, wherein each alkyl, alkenyl, alkynyl, cycloalkyl, heterocycloalkyl, aryl, and heteroaryl is independently optionally substituted with one, two, or three $R^{12a}$;

or $R^{11}$ and $R^{12}$ are taken together to form a cycloalkyl or heterocycloalkyl each optionally-substituted with one, two, or three $R^{11b}$;

each $R^{11a}$, $R^{11b}$, and $R^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{18}$, —NR$^{13}$C(=O)R$^{14}$, —NR$^{13}$C(=O)OR$^{13}$, C$_1$-C$_6$ alkyl, C$_1$-C$_6$ haloalkyl, C$_2$-C$_6$ alkenyl, C$_2$-C$_6$ alkynyl, C$_1$-C$_6$ hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_3$NR$^c$R$^d$, —C(=O)R$^a$, —OC(=O)R$^a$, —C(=O)OR$^b$, —OC(=O)OR$^b$, —C(=O)NR$^c$R$^d$ OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkynyl, C$_2$-C$_6$ alkenyl, cycloalkyl, heterocycloalkyl, aryl, heteroaryl, C$_1$-C$_6$ alkyl (aryl), C$_1$-C$_6$ alkyl(heteroaryl), C$_1$-C$_6$ alkyl(cycloalkyl), or C$_1$-C$_6$ alkyl(heterocycloalkyl);

each $R^{13}$ is independently hydrogen, C$_1$-C$_6$ alkyl, C$_1$-C$_6$ haloalkyl, C$_2$-C$_6$ alkenyl, C$_2$-C$_6$alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl and heteroaryl is independently optionally substituted with one, two, or three $R^{13a}$;

each $R^{14}$ is independently C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

19 each $R^{13a}$, $R^{14a}$, $R^{15a}$, and $R^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$alkynyl, cycloalkyl, heterocycloalkyl, aryl, heteroaryl, alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —OR$^b$, —S(=O)R$^a$, —NO$_2$, —S(=O)$_2$R$^a$, —S(=O)$_2$NR$^c$R$^d$, —C(=O)R$^a$, —C(=O)OR$^b$, —C(=O)NR$^c$R$^d$, $C_1$-$C_6$ alkyl, $C_1$-$C_6$ haloalkyl, $C_2$-$C_6$ alkenyl, or $C_2$-$C_6$ alkynyl;

$R^{21}$ and $R^{22}$ are independently hydrogen, $C_1$-$C_{20}$ alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (I), or a pharmaceutically acceptable salt, solvate, stereoisomer, or isotopic variant thereof:

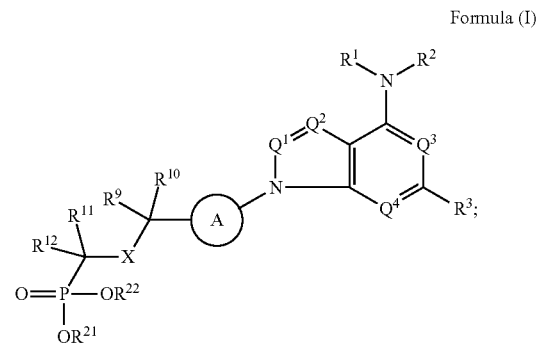

Formula (I)

wherein:

Ring A is

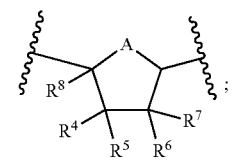

$Q^1$ and $Q^2$ are independently N or CW;

$Q^3$ and $Q^4$ are independently N or CW; provided that at least one of $Q^3$ or $Q^4$ is N;

each W is independently hydrogen, halogen, —CN, —OR$^b$, NR$^c$R$^d$, $C_1$-$C_6$ alkyl, or $C_1$-$C_6$ haloalkyl;

A is —O— or —CH$_2$—;

X is —S(=O)$_2$—;

$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$alkyl(cycloalkyl), or $C_1$-$C_6$ alkyl (heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —OR$^b$, —SR$^b$, —NR$^c$R$^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl), wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$ fluoroalkyl C$_2$-C$_6$ alkenyl, C$_2$-C$_6$ alkynyl, cycloalkyl, heterocycloalkyl, aryl, or heteroaryl;

R$^4$ and R$^7$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

R$^5$ and R$^6$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

R$^8$ is hydrogen, halogen, —OR$^b$, —NR$^c$R$^d$, C$_1$-C$_6$ alkyl, or C$_1$-C$_6$ haloalkyl;

R$^9$ and R$^{10}$ are independently hydrogen, halogen, C$_1$-C$_6$ alkyl, or C$_1$-C$_6$ haloalkyl;

R$^{11}$ is halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11a}$;

R$^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$(=O)R$^{14}$, —NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{12a}$;

or R$^{11}$ and R$^{12}$ are taken together to form a cycloalkyl or heterocycloalkyl each optionally substituted with one, two, or three R$^{11b}$;

each R$^{11a}$, R$^{11b}$, and R$^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$ haloalkyl, C$_2$-C$_6$ alkenyl, C$_2$-C$_6$ alkynyl, C$_1$-C$_6$ hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11c}$;

each R$^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^{13}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl, wherein each alkyl, alkenyl, alkynyl, cycloalkyl, aryl, and heteroaryl is independently optionally substituted with one, two, or three R$^{13a}$;

each R$^{14}$ is independently C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{14a}$;

each R$^{15}$ and R$^{16}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{15a}$;

or R$^{15}$ and R$^{16}$ are taken together with the nitrogen atom to which they are attached to form a heterocycloalkyl optionally substituted with one, two, or three R$^{15b}$;

each R$^{13a}$, R$^{14a}$, R$^{15a}$, and R$^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^{21}$ and R$^{22}$ are independently hydrogen, C$_1$-C$_{20}$ alkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), C$_1$-C$_6$ alkyl(heterocycloalkyl); wherein each alkyl, cycloalkyl, heterocycloalkyl, aryl, and heteroaryl is independently optionally substituted with one, two, or three R$^{21a}$;

or R$^{21}$ and R$^{22}$ are taken together with the atoms to which they are attached to form a heterocycloalkyl optionally substituted with one, two, or three R$^{21b}$;

each R$^{21a}$ and R$^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(Cycloalkyl), or C$_1$-C$_6$ alkyl(heterocycloalkyl);

each R$^a$ is independently C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

each R$^b$ is independently hydrogen, C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl; and each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (I), or a pharmaceutically acceptable salt, solvate, stereoisomer, or isotopic variant thereof:

Formula (I)

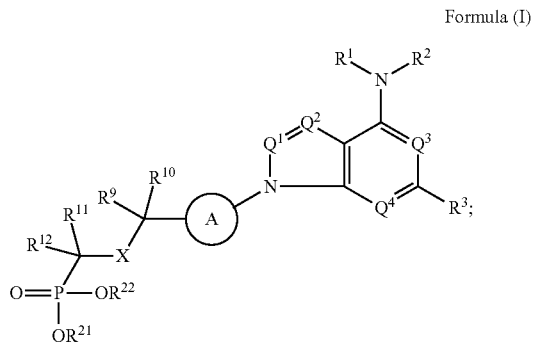

wherein:
Ring A is

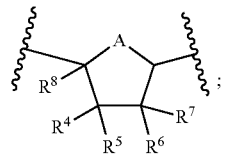

$Q^1$ and $Q^2$ are independently N or CW;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O— or —$CH_2$—;
X is —S(=O)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloakyl), or $C_1$-$C_6$ alkyl (heterocycloalkyl), wherein each alkyl, alkenyl, alkynyl, cycloalkyl, heterocycloalkyl, aryl, and heteroaryl is independently optionally substituted with one, two, or three $R^{1a}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2$ $NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O) $OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), alkyl (cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl (cycloalkyl), or $C_1$-$C_6$ alkyl(heterocycloalkyl);
$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —$OR^b$, $C_1$-$C_6$ alkyl, $C_1$-$C_6$ haloalkyl $C_2$-$C_6$ alkenyl, $C_2$-$C_6$ alkynyl, cycloalkyl, heterocycloalkyl, aryl, or heteroaryl;
$R^8$ is hydrogen, halogen, —$OR^b$, —$NR^cR^d$, $C_1$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O) $NR^{15}R^{16}$, —OC(=O)$NR^{15}R^{15}$, —$NR^{13}C$(=O)$NR^{15}R^{16}$, —$NR^{13}C$(=O)$R^{14}$, —$NR^{13}C$(=O)$OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$ (=O)$NR^{15}R^{16}$, —$NR^{13}C$(=O)$R^{14}$, —$NR^{13}C$(=O) $OR^{13}$, $C_1$-$C_6$alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —$OR^{13}$, —$SR^{13}$, —S(=O) $R^{14}$, —$NO_2$, —$NR^{15}R^{16}$, —S(=O)$_2R^{14}$, —$NR^{13}S$(=O)$_2$ $R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$ (=O)$R^{14}$, —$NR^{13}C$(=O)$OR^{13}$, $C_1$-$C_6$ alkyl, $C_1$-$C_6$ haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O) $OR^b$, —C(=O)$NR^cR^d$, —OC(=O)$NR^cR^d$, —$NR^bC$ (=O)$NR^cR^d$, —$NR^bC$(=O)$R^a$, —$NR^bC$(=O)$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R_{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —S(=O)$R^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$.

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O) OR$^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl;

provided that the compound is not:

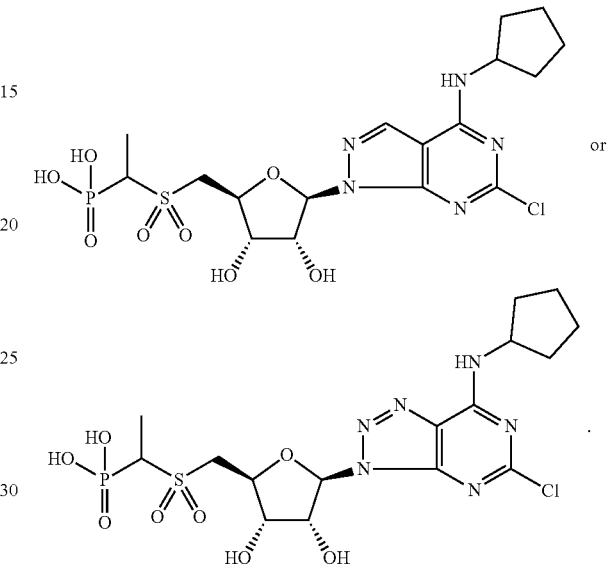

In some embodiments of a compound of Formula (I), $Q^1$ is N and $Q^2$ is CW. In some embodiments of a compound of Formula (I), $Q^1$ is CW and $Q^2$ is N. In some embodiments of a compound of Formula (I), $Q^1$ is N and $Q^2$ is N. In some embodiments of a compound of Formula (I), $Q^1$ is CW and $Q^2$ is CW. In some embodiments of a compound of Formula (I), $Q^1$ is N and $Q^2$ is N or $Q^1$ is N and $Q^2$ is CW.

In some embodiments of a compound of Formula (I), $Q^3$ is N and $Q^4$ is CW. In some embodiments of a compound of Formula (I), $Q^4$ is N and $Q^3$ is CW. In some embodiments of a compound of Formula (I), $Q^3$ is N and $Q^4$ is N.

In some embodiments of a compound of Formula (I), each W is independently hydrogen, halogen, $C_1$-$C_6$ alkyl, or $C_1$-$C_6$ haloalkyl. In some embodiments of a compound of Formula (I), each W is independently hydrogen, halogen, or $C_1$-$C_6$ alkyl. In some embodiments of a compound of Formula (I), each W is hydrogen.

In some embodiments of a compound of Formula (I), $R^3$ is halogen, —CN, —$OR^b$, —NR$^c$R$^d$, $C_1$-$C_6$ alkyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, or heterocycloalkyl; wherein each alkyl, alkynyl, cycloalkyl, and heterocycloalkyl is independently optionally substituted with one, two, or three $R^{3a}$. In some embodiments of a compound of Formula (I), $R^3$ is halogen, $C_1$-$C_6$ alkyl, $C_2$-$C_6$ alkynyl, $C_1$-$C_6$ hydroxyalkyl, or $C_1$-$C_6$ heteroalkyl; wherein each alkyl and alkynyl is independently optionally substituted with one, two, or three $R^{3a}$.

In some embodiments of a compound of Formula (I), $R^3$ is halogen, —CN, —$OR^b$, —NR$^c$R$^d$, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (I), $R^3$ is halogen, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (I), $R^3$ is halogen, or $C_1$-$C_6$ hydroxyalkyl, $C_1$-$C_6$ heteroalkyl. In some embodiments of a compound of Formula (I), $R^3$ is halogen.

In some embodiments of a compound of Formula (I), each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{3a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{3a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (I), each $R^{3a}$ is independently oxo (when feasible) halogen, $C_1$-$C_6$alkyl, or $C_1$-$C_6$ fluoroalkyl. In some embodiments of a compound of Formula (I), each $R^{3a}$ is independently halogen or $C_1$-$C_6$ alkyl. In some embodiments of a compound of Formula (I), each $R^{3a}$ is independently halogen, —OR$^b$, $C_1$-$C_6$ alkyl, or cycloalkyl.

In some embodiments of a compound of Formula (I), $R^1$ is $C_1$-$C_6$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (I), $R^1$ is $C_1$-$C_6$ alkyl, cycloalkyl, heterocycloalkyl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (I), $R^1$ is cycloalkyl or $C_1$-$C_6$ alkyl(cycloalkyl); wherein each alkyl and cycloalkyl is independently optionally substituted with one, two, or three $R^{1a}$. In some embodiments of a compound of Formula (I), $R^1$ is cycloalkyl optionally substituted with one, two, or three $R^{1a}$.

In some embodiments of a compound of Formula (I), each $R^{1a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{1a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{1a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (I), each $R^{1a}$ is independently oxo (when feasible) halogen, $C_1$-$C_6$alkyl, or $C_1$-$C_6$ fluoroalkyl. In some embodiments of a compound of Formula (I), each $R^{1a}$ is independently halogen or $C_1$-$C_6$ alkyl.

In some embodiments of a compound of Formula (I), $R^2$ is hydrogen or $C_1$-$C_6$ alkyl. In some embodiments of a compound of Formula (I), $R^2$ is hydrogen. In some embodiments of a compound of Formula (I), $R^1$ and $R^2$ are taken together with the nitrogen atom to which they are attached to form a heterocycloalkyl optionally substituted with one, two, or three $R^{1b}$.

In some embodiments of a compound of Formula (I), each $R^{1b}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{1b}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (I), each $R^{1b}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (I), each $R^{1b}$ is independently oxo (when feasible) halogen, $C_1$-$C_6$ alkyl, or $C_1$-$C_6$ fluoroalkyl. In some embodiments of a compound of Formula (I), each $R^{1b}$ is independently halogen or $C_1$-$C_6$ alkyl.

In some embodiments of a compound of Formula (I), $R^8$ is hydrogen or $C_1$-$C_6$ alkyl. In some embodiments of a compound of Formula (I), $R^8$ is hydrogen.

In some embodiments of a compound of Formula (I), $R^9$ and $R^{10}$ are independently hydrogen or $C_1$-$C_6$ alkyl. In some embodiments of a compound of Formula (I), $R^9$ and $R^{10}$ are hydrogen.

In some embodiments of a compound of Formula (I), A is —O—. In some embodiments of a compound of Formula (I), A is —CH$_2$—.

In some embodiments of a compound of Formula (I), $R^5$ and $R^6$ are independently hydrogen, halogen, —OR$^b$, $C_1$-$C_6$ alkyl, or $C_1$-$C_6$ haloalkyl. In some embodiments of a compound of Formula (I), $R^5$ and $R^6$ are independently hydrogen, halogen, —OR$^b$, or $C_1$-$C_6$ alkyl. In some embodiments of a compound of Formula (I), $R^5$ and $R^6$ are hydrogen.

In some embodiments of a compound of Formula (I), $R^4$ and $R^7$ are independently hydrogen, halogen, —OR$^b$, $C_1$-$C_6$ alkyl, or $C_1$-$C_6$ haloalkyl. In some embodiments of a compound of Formula (I), $R^4$ and $R^7$ are independently hydrogen, halogen, —OR$^b$, or $C_1$-$C_6$ alkyl. In some embodiments of a compound of Formula (I), $R^4$ and $R^7$ are independently hydrogen, halogen, or —OR$^b$. In some embodiments of a compound of Formula (I), $R^4$ and $R^7$ are independently hydrogen, halogen, or —OH. In some embodiments of a compound of Formula (I), $R^4$ and $R^7$ are independently halogen or —OH. In some embodiments of a compound of Formula (I), $R^4$ and $R^7$ are independently hydrogen or —OH. In some embodiments of a compound of Formula (I), $R^4$ and $R^7$ are —OH.

In some embodiments of a compound of Formula (I), $R^5$ and $R^6$ are hydrogen and $R^4$ and $R^7$ are —OH. In some embodiments of a compound of Formula (I), $R^5$ and $R^6$ are hydrogen and $R^4$ and $R^7$ are independently halogen or —OH. In some embodiments of a compound of Formula (I), $R^5$ and $R^6$ are hydrogen and $R^4$ and $R^7$ are independently hydrogen or —OH.

In some embodiments of a compound of Formula (I), $R^{21}$ and $R^{22}$ are independently hydrogen, $C_1$-$C_{20}$ alkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{21a}$. In some embodiments of a compound of Formula (I), $R^{21}$ and $R^{22}$ are independently hydrogen, $C_1$-$C_{20}$alkyl or aryl; wherein each alkyl and aryl is independently optionally substituted with one, two, or three $R^{21a}$. In some embodiments of a compound of Formula (I), $R^{21}$ and $R^{22}$ are independently hydrogen, $C_1$-$C_{20}$alkyl optionally substituted with one, two, or three $R^{21a}$. In some embodiments of a compound of Formula (I), $R^{21}$ and $R^{22}$ are hydrogen.

In some embodiments of a compound of Formula (I), each $R^{21a}$ is independently oxo (when feasible), halogen, —CN, —OR$^b$, —NR$^c$R$^d$, —C(=O)R$^a$, —OC(=O)R$^a$, —C(=O)OR$^b$, —OC(=O)OR$^b$, —OC(=O)NR$^c$R$^d$, —NR$^b$C(=O)NR$^c$R$^d$, —NR$^b$C(=O)R$^a$, —NR$^b$C(=O)OR$^b$, or $C_1$-$C_6$ alkyl. In some embodiments of a compound of Formula (I), each $R^{21a}$ is independently —C(=O)$R^a$, —OC(=O)$R^a$, —C(=O)O$R^b$, —OC(=O)O$R^b$, or —OC(=O)N$R^c R^d$. In some embodiments of a compound of Formula (I), each $R^{21a}$ is independently —C(=O)O$R^b$ or —OC(=O)O$R^b$.

In some embodiments of a compound of Formula (I), $R^1$ and $R^{22}$ are taken together with the atoms to which they are attached to form a heterocycloalkyl optionally substituted with one, two, or three $R^{21b}$.

In some embodiments of a compound of Formula (I), each $R^{21b}$ is independently oxo (when feasible), halogen, —CN, —O$R^b$, —N$R^c R^d$, —C(=O)$R^a$, —OC(=O)$R^a$, —C(=O)O$R^b$, —OC(=O)O$R^b$, —OC(=O)N$R^c R^d$, —N$R^b$C(=O)N$R^c R^d$, —N$R^b$C(=O)$R^a$, —N$R^b$C(=O)O$R^b$, $C_1$-$C_6$ alkyl, cycloalkyl, or heterocycloalkyl. In some embodiments of a compound of Formula (I), each $R^{21b}$ is independently halogen, —CN, —O$R^b$, —N$R^c R^d$, $C_1$-$C_6$ alkyl, cycloalkyl, or heterocycloalkyl. In some embodiments of a compound of Formula (I), each $R^{21b}$ is independently halogen or $C_1$-$C_6$ alkyl.

In some embodiments of a compound of Formula (I), $R^{12}$ hydrogen, halogen, —CN, —O$R^{13}$, —N$R^{15}R^{16}$, —C(=O)$R^{14}$, —C(=O)O$R^{13}$, —C(=O)N$R^{15}R^{16}$, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (I), $R^{12}$ is halogen, —CN, —O$R^{13}$, —N$R^{15}R^{16}$, —C(=O)$R^{14}$, —C(=O)O$R^{13}$, —C(=O)N$R^{15}R^{16}$, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (I), $R^{12}$ is hydrogen, halogen, $C_1$-$C_6$ alkyl, $C_1$-$C_6$ haloalkyl, or $C_1$-$C_6$ hydroxyalkyl. In some embodiments of a compound of Formula (I), $R^{12}$ is $C_1$-$C_6$ alkyl. In some embodiments of a compound of Formula (I), $R^{12}$ is $C_1$-$C_6$ hydroxyalkyl. In some embodiments of a compound of Formula (I), $R^{12}$ is hydrogen. In some embodiments of a compound of Formula (I), $R^{12}$ is not hydrogen.

In some embodiments of a compound of Formula (I), each $R^{12a}$ is independently halogen, —CN, —O$R^{13}$, —N$R^{15}R^{16}$, —S(=O)$_2R^{14}$, —N$R^{14}$S(=O)$_2$R, —S(=O)$_2$N$R^{15}R^{16}$, —C(=O)$R^{14}$, —OC(=O)$R^{14}$, —C(=O)O$R^{13}$, —C(=O)N$R^{15}R^{16}$, —N$R^{13}$C(=O)$R^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$.

In some embodiments of a compound of Formula (I), each $R^{12a}$ is independently halogen, —CN, —O$R^{13}$, —N$R^{15}R^{16}$, —S(=O)$_2R^{14}$, —N$R^{14}$S(=O)$_2R^{14}$, —S(=O)$_2$N$R^{15}R^{16}$, —C(=O)$R^{14}$, —OC(=O)$R^{14}$, —C(=O)O$R^{13}$, —C(=O)N$R^{15}R^{16}$, —N$R^{13}$C(=O)$R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11c}$.

In some embodiments of a compound of Formula (I), each $R^{12a}$ is independently —O$R^{13}$, —S(=O)$_2R^{14}$, —N$R^{13}$C(=O)$R^{14}$, cycloalkyl, aryl, or heteroaryl; wherein each cycloalkyl, aryl, and heteroaryl is independently optionally substituted with one, two, or three $R^{11c}$.

In some embodiments of a compound of Formula (I), $R^{11}$ is halogen, —CN, —O$R^{13}$, —N$R^{15}R^{16}$, —S(=O)$_2R^{14}$, —C(=O)$R^{14}$, —C(=O)O$R^{13}$, —C(=O)N$R^{15}R^{16}$, $C_1$-$C_6$alkyl, $C_1$-$C_6$ haloalkyl, $C_1$-$C_6$ hydroxyalkyl, $C_1$-$C_6$ heteroalkyl, cycloalkyl, heterocycloalklyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (I), $R^{11}$ is halogen, —CN, —S(=O)$_2R^{14}$, —C(=O)$R^{14}$, —C(=O)O$R^{13}$, $C_1$-$C_6$ alkyl, $C_1$-$C_6$ haloalkyl, $C_1$-$C_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (I), $R^{11}$ is —CN, —S(=O)$_2R^{14}$, —C(=O)O$R^{13}$, $C_1$-$C_6$ alkyl, $C_1$-$C_6$ haloalkyl, $C_1$-$C_6$ hydroxyalkyl, or heteroaryl; wherein each alkyl and heteroaryl is independently optionally substituted with one, two, or three $R^{11a}$. In some embodiments of a compound of Formula (I) $R^{11}$ is $C_1$-$C_6$ alkyl optionally substituted with one, two, or three $R^{11a}$. In some embodiments of a compound of Formula (I), $R^{11}$ is $C_1$-$C_6$alkyl substituted with one $R^{11a}$. In some embodiments of a compound of Formula (I), $R^{11}$ is $C_1$-$C_6$ hydroxyalkyl.

In some embodiments of a compound of Formula (I), each $R^{11a}$ is independently halogen, —CN, —O$R^{13}$, —N$R^{15}R^{16}$, —S(=O)$_2R^{14}$, —N$R^{14}$S(=O)$_2R^{14}$, —S(=O)$_2$N$R^{15}R^{16}$, —C(=O)$R^{14}$, —OC(=O)$R^{14}$, —C(=O)O$R^{13}$, —C(=O)N$R^{15}R^{16}$, —N$R^{13}$C(=O)$R^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (I), each $R^{11a}$ is independently halogen, —CN, —O$R^{13}$, —N$R^{15}R^{16}$, —S(=O)$_2R^{14}$, —N$R^{14}$S(=O)$_2R^{14}$, —S(=O)$_2$N$R^{15}R^{16}$, —C(=O)$R^{14}$, —OC(=O)$R^{14}$, —C(=O)O$R^{13}$, —C(=O)N$R^{15}R^{16}$, —N$R^{13}$C(=O)$R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11c}$. In some embodiments of a compound of Formula (I), each $R^{11a}$ is independently —O$R^{13}$, —S(=O)$_2R^{14}$, —N$R^{13}$C(=O)$R^{14}$, cycloalkyl, aryl, or heteroaryl; wherein each cycloalkyl, aryl, and heteroaryl is independently optionally substituted with one, two, or three $R^{11c}$. In some embodiments of a compound of Formula (I), each $R^{11a}$ is independently aryl optionally substituted with one, two, or three $R^{11c}$.

In some embodiments of a compound of Formula (I), each $R^{11a}$ is independently —O$R^{13}$. In some embodiments of a compound of Formula (I), each $R^{11a}$ is independently —S(=O)$_2R^{14}$. In some embodiments of a compound of Formula (I), each $R^{11a}$ is independently cycloalkyl optionally substituted with one, two, or three $R^{11c}$. In some embodiments of a compound of Formula (I), each $R^{11a}$ is independently —N$R^{13}$C(=O)$R^{14}$.

In some embodiments of a compound of Formula (I), each $R^{11a}$ is independently oxo (when feasible), halogen, —CN, —O$R^b$, —N$R^c R^d$, —C(=O)$R^a$, —C(=O)O$R^b$, —C(=O)N$R^c R^d$, $C_1$-$C_6$ alkyl, or $C_1$-$C_6$haloalkyl. In some embodiments of a compound of Formula (I), each $R^{11c}$ is independently halogen, —CN, —O$R^b$, —N$R^c R^d$, $C_1$-$C_6$ alkyl, or $C_1$-$C_6$ haloalkyl. In some embodiments of a compound of Formula (I), each $R^{11c}$ is independently halogen, $C_1$-$C_6$ alkyl, or $C_1$-$C_6$haloalkyl.

In some embodiments of a compound of Formula (I), $R^{11}$ and $R^{12}$ are taken together to form a cycloalkyl or heterocycloalkyl each optionally substituted with one, two, or three $R_{11b}$. In some embodiments of a compound of Formula (I), $R^{11}$ and $R^{12}$ are taken together to form a cycloalkyl optionally substituted with one, two, or three $R^{11b}$. In some embodiments of a compound of Formula (I), $R^{11}$ and $R^{12}$ are taken together to form a heterocycloalkyl optionally substituted with one, two, or three $R^{11b}$.

In some embodiments of a compound of Formula (I), each $R^{11b}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, or $C_1$-$C_6$haloalkyl. In some embodiments of a compound of Formula (I), each $R^{11b}$ is independently oxo (when feasible), halogen, —CN, —$OR^b$, —$NR^cR^d$, $C_1$-$C_6$ alkyl, or $C_1$-$C_6$haloalkyl. In some embodiments of a compound of Formula (I), each $R^{11b}$ is independently oxo (when feasible), halogen, $C_1$-$C_6$alkyl, or $C_1$-$C_6$haloalkyl.

In some embodiments of a compound of Formula (I), each $R^{13}$ is independently hydrogen, $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{13a}$. In some embodiments of a compound of Formula (I), each $R^{13}$ is independently hydrogen, $C_1$-$C_6$ alkyl, or $C_1$-$C_6$haloalkyl; wherein each alkyl is independently optionally substituted with one, two, or three $R^{13a}$. In some embodiments of a compound of Formula (I), each $R^{13}$ is independently hydrogen or $C_1$-$C_6$ alkyl.

In some embodiments of a compound of Formula (I), each $R^{13a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, $C_1$-$C_6$haloalkyl, cycloalkyl, or heterocycloalkyl. In some embodiments of a compound of Formula (I), each $R^{13a}$ is independently halogen, —CN, —$OR^b$, —$NR^cR^d$, $C_1$-$C_6$alkyl, $C_1$-$C_6$haloalkyl, cycloalkyl, or heterocycloalkyl. In some embodiments of a compound of Formula (I), each $R^{13a}$ is independently halogen, $C_1$-$C_6$ alkyl, or $C_1$-$C_6$ haloalkyl.

In some embodiments of a compound of Formula (I), each $R^{14}$ is independently $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{14a}$. In some embodiments of a compound of Formula (I), each $R^{14}$ is independently $C_1$-$C_6$ alkyl, or $C_1$-$C_6$ haloalkyl; wherein each alkyl is independently optionally substituted with one, two, or three $R^{14}$. In some embodiments of a compound of Formula (I), each $R^{14}$ is independently $C_1$-$C_6$ alkyl.

In some embodiments of a compound of Formula (I), each $R^{14a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, $C_1$-$C_6$haloalkyl, cycloalkyl, or heterocycloalkyl. In some embodiments of a compound of Formula (I), each $R^{14a}$ is independently halogen, —CN, —$OR^b$, —$NR^cR^d$, $C_1$-$C_6$alkyl, $C_1$-$C_6$haloalkyl, cycloalkyl, or heterocycloalkyl. In some embodiments of a compound of Formula (I), each $R^{14a}$ is independently halogen, $C_1$-$C_6$ alkyl, or $C_1$-$C_6$ haloalkyl.

In some embodiments of a compound of Formula (I), each $R^{15}$ and $R^{16}$ is independently hydrogen, $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{15a}$. In some embodiments of a compound of Formula (I), each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$. In some embodiments of a compound of Formula (I), each $R^{15}$ and $R^{16}$ is independently hydrogen, $C_1$-$C_6$ alkyl, or $C_1$-$C_6$ haloalkyl. In some embodiments of a compound of Formula (I), each $R^{15}$ and $R^{16}$ is independently hydrogen or $C_1$-$C_6$ alkyl.

In some embodiments of a compound of Formula (I), each $R^{15a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, $C_1$-$C_6$haloalkyl, cycloalkyl, or heterocycloalkyl. In some embodiments of a compound of Formula (I), each $R^{15a}$ is independently halogen, —CN, —$OR^b$, —$NR^cR^d$, $C_1$-$C_6$alkyl, $C_1$-$C_6$haloalkyl, cycloalkyl, or heterocycloalkyl. In some embodiments of a compound of Formula (I), each $R^{15a}$ is independently halogen, $C_1$-$C_6$ alkyl, or $C_1$-$C_6$ haloalkyl.

In some embodiments of a compound of Formula (I), $R^1$ and $R^{16}$ are taken together with the nitrogen atom to which they are attached to form a heterocycloalkyl optionally substituted with one, two, or three $R^{15b}$. In some embodiments of a compound of Formula (I), $R^{15}$ and $R^{16}$ are taken together with the nitrogen atom to which they are attached to form a heterocycloalkyl.

In some embodiments of a compound of Formula (I), each $R^{15b}$ is independently oxo (when feasible), halogen, —CN, —$OR^b$, —$NR^cR^d$, —$C(=O)R^a$, —$C(=O)OR$, —$C(=O)NR^cR^d$, $C_1$-$C_6$ alkyl, $C_1$-$C_6$haloalkyl, cycloalkyl, or heterocycloalkyl. In some embodiments of a compound of Formula (I), each $R^{15b}$ is independently halogen, —CN, —$OR^b$, —$NR^cR^d$, $C_1$-$C_6$alkyl, $C_1$-$C_6$haloalkyl, cycloalkyl, or heterocycloalkyl. In some embodiments of a compound of Formula (I), each $R^{15b}$ is independently halogen, $C_1$-$C_6$ alkyl, or $C_1$-$C_6$ haloalkyl.

In some embodiments provided herein is a compound having the structure of Formula (II), or a pharmaceutically acceptable salt, solvate, stereoisomer, or isotopic variant thereof:

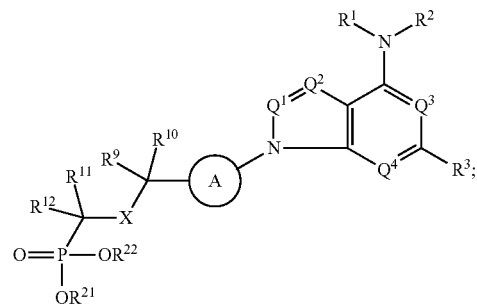

Formula (II)

wherein:
Ring A is

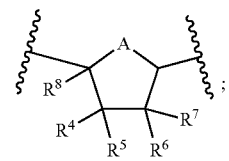

;

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O—;
X is —S— or —O—;

$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl (heterocycloalkyl); wherein each alkyl, alkenyl, alkynyl, cycloalkyl, hetercycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;

$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^8$ is hydrogen, halogen, —$OR^b$, —$NR^cR^d$, $C_1$-$C_6$ alkyl, or $C_1$-$C_6$ haloalkyl;

$R^9$ and $R^{10}$ are independently hydrogen, halogen, $C_1$-$C_6$ alkyl, or $C_1$-$C_6$ haloalkyl;

$R^{11}$ is halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$alkyl, $C_1$-$C_6$haloalkyl, $C_1$-$C_6$hydroxyalkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;

$R^{12}$ is hydrogen, halogen, —CN, —$OR^{13}$, —$SR^{14}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;

or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$alkyl, $C_1$-$C_6$haloalkyl, $C_2$-$C_6$ alkenyl, $C_2$-$C_6$ alkynyl, $C_1$-$C_6$hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ haloalkyl, $C_2$-$C_6$alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two or three oxo (when feasible), halogen, —CN, —$OR^b$, —S(=O)$R^a$, —$NO_2$, —$NR^cR^d$, —S(=O)$_2R^a$, —S(=O)$_2NR^cR^d$, —C(=O)$R^a$, —C(=O)$OR^b$, —C(=O)$NR^cR^d$, $C_1$-$C_6$alkyl, $C_1$-$C_6$ haloalkyl, $C_2$-$C_6$ alkenyl, or $C_2$-$C_6$ alkynyl;

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —S(=O)$R^a$, —NO$_2$, —$NR^cR^d$, —S(=O)$_2R^a$, —$NR^bS(=O)_2R^a$, —S(=O)$_2$ $NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)$ $OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (II), or a pharmaceutically acceptable salt, solvate, stereoisomer, or isotopic variant thereof:

Formula (II)

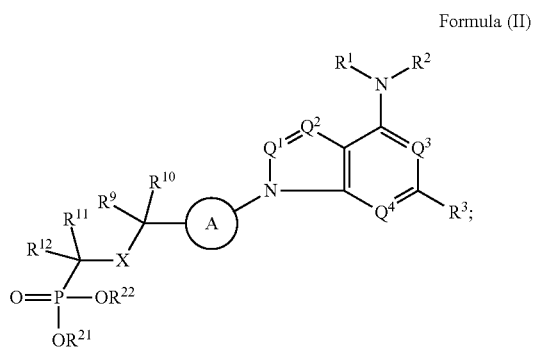

wherein:
Ring A is

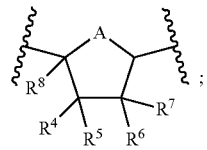

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O—;
X is —S— or —O—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$.

each $R^{1a}$ and $R^{1b}$ is independently oxo (when feasible) halogen, —CN, —$OR^b$, —$SR^b$, —S(=O)$R^a$, —NO$_2$, —$NR^cR^d$, —S(=O)$_2R^a$, —$NR^bS(=O)_2R^a$, —S(=O)$_2$ $NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)$ $OR^b$, $C_1$-$C_6$ alkyl, $C_1$-$C_6$ fluoroalkyl, $C_2$-$C_6$ alkenyl, $C_1$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;

$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^8$ is hydrogen, halogen, —$OR^b$, —$NR^cR^d$, $C_1$-$C_6$ alkyl, or $C_1$-$C_6$ haloalkyl;

$R^9$ and $R^{10}$ are independently hydrogen, halogen, $C_1$-$C_6$ alkyl, or $C_1$-$C_6$ haloalkyl;

$R^{11}$ is halogen, —CN, —$OR^{13}$, —$SR^{13}$, —S(=O)$R^a$, —NO$_2$, —$NR^{15}R^{16}$, —S(=O)$_2R^{14}$, —$NR^{13}S(=O)_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C(=O)NR^{15}R^{16}$, —$NR^{13}C$ (=O)R$^{14}$, —NR$^{13}$C(=O)OR$^{13}$, C$_1$-C$_6$alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11a}$;

R$^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11a}$;

or R$^{11}$ and R$^{12}$ are taken together to form a cycloalkyl or heterocycloalkyl each optionally substituted with one, two, or three R$^{11b}$;

each R$^{11a}$, R$^{11b}$, and R$^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_2$-C$_6$ alkenyl, C$_2$-C$_6$ alkynyl, C$_1$-C$_6$hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11c}$;

each R$^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^{13}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{13a}$;

each R$^{14}$ is independently C$_1$-C$_6$ alkyl, C$_1$-C$_6$haloalkyl, C$_2$-C$_6$ alkenyl, C$_2$-C$_5$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{14a}$;

each R$^{15}$ and R$^{16}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{15a}$;

or R$^{15}$ and R$^{16}$ are taken together with the nitrogen atom to which they are attached to form a heterocycloalkyl optionally substituted with one, two, or three R$^{15b}$;

each R$^{13a}$, R$^{14a}$, R$^{15a}$, and R$^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^{21}$ and R$^{22}$ are independently hydrogen, C$_1$-C$_{20}$alkyl, cycloalkyl, heterocycloalkyl, aryl, heteroaryl, C$_1$-C$_6$ alkyl (aryl), C$_1$-C$_6$ alkyl(heteroaryl), C$_1$-C$_6$ alkyl(cycloalkyl), C$_1$-C$_6$ alkyl(heterocycloalkyl); wherein each alkyl, cycloalkyl, heterocycloalkyl, aryl, and heteroaryl is independently optionally substituted with one, two, or three R$^{21a}$;

or R$^{21}$ and R$^{22}$ are taken together, with the atoms to which they are attached to form a heterocycloalkyl optionally substituted with one, two, or three R$^{21b}$;

each R$^{21a}$ and R$^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^a$ is independently C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

each R$^b$ is independently hydrogen, C$_1$-C$_6$ alkyl, C$_2$-C$_6$ alkenyl, C$_2$-C$_6$ alkynyl, C$_1$-C$_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl; and each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

or R$^c$ and R$^d$ are taken together with the nitrogen atom to which they are attached to form a heterocycloalkyl optionally substituted with one, two, or three oxo, halogen, C$_1$-C$_6$ alkyl, or C$_1$-C$_6$ haloalkyl.

In some embodiments provided herein is a compound having the structure of Formula (II), or a pharmaceutically acceptable salt, solvate, stereoisomer, or isotopic variant thereof:

Formula (II)

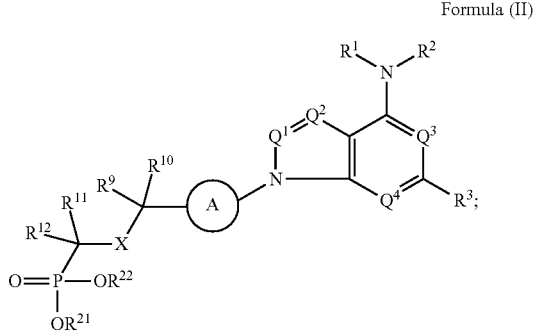

wherein:
Ring A is

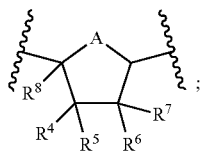

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is independently hydrogen, halogen, —CN, —OR$^b$, NR$^c$R$^d$, C$_1$-C$_6$ alkyl, or C$_1$-C$_6$ haloalkyl;
A is —O—;
X is —S— or —O—;
$R^1$ and $R^2$ are independently hydrogen, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ fluoroalkyl, C$_2$-C$_6$ alkenyl, C$_1$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);
$R^3$ is hydrogen, halogen, —CN, —OR$^b$, —SR$^b$, —NR$^c$R$^d$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);
$R^4$ and $R^7$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;
$R^5$ and $R^6$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;
$R^8$ is hydrogen, halogen, —OR$^b$, —NR$^c$R$^d$, C$_1$-C$_6$ alkyl, or C$_1$-C$_6$ haloalkyl;
$R^9$ and $R^{10}$ are independently hydrogen, halogen, C$_1$-C$_6$ alkyl, or C$_1$-C$_6$ haloalkyl;
$R^{11}$ is halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_2$-C$_6$ alkenyl, C$_2$-C$_6$ alkynyl, C$_1$-C$_6$hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);
each $R^{13}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;
each $R^{14}$ is independently C$_1$-C$_6$ alkyl, C$_1$-C$_6$haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$haloalkyl, $C_2$-$C_6$alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^2$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_2$-$C_6$ alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl;

provided that the compound is not:

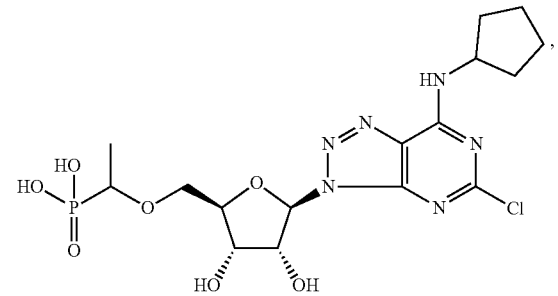

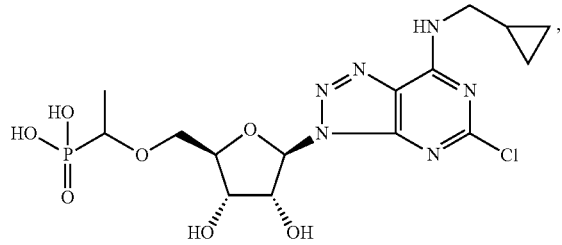

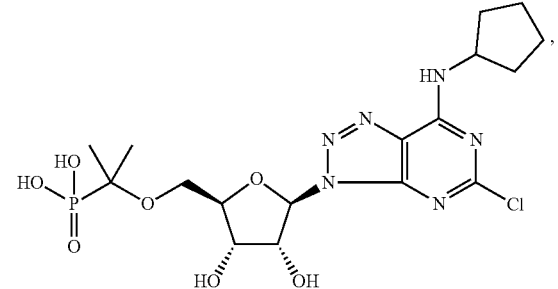

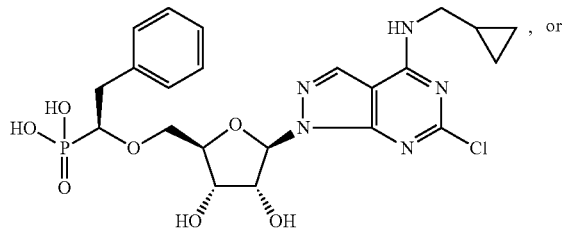, or

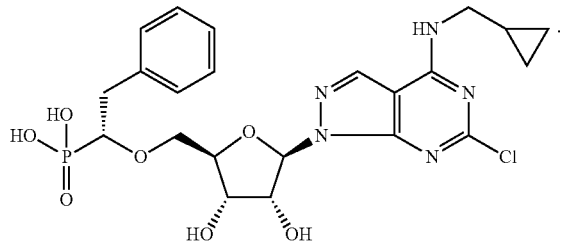.

In some embodiments provided herein is a compound having the structure of Formula (II), or a pharmaceutically acceptable salt, solvate, stereoisomer, or isotopic variant thereof:

Formula (II)

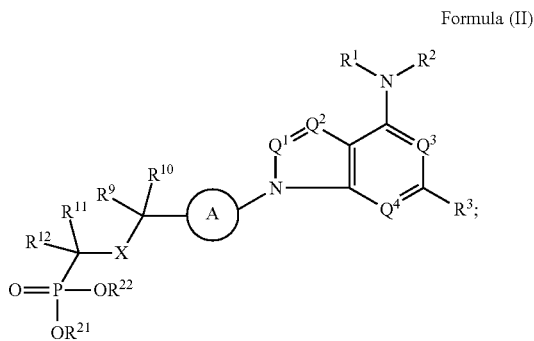

wherein:
Ring A is

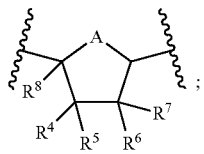

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is independently hydrogen, halogen, or $C_1$-$C_6$ alkyl;
A is —O—;
X is —O—;
$R^1$ and $R^2$ are independently hydrogen, $C_1$-$C_6$ alkyl, $C_1$-$C_6$ haloalkyl, cycloalkyl, heterocycloalkyl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$;
each $R^{1a}$ is independently oxo (when feasible) halogen, —CN, —OR$^b$, $C_1$-$C_6$ alkyl, or $C_1$-$C_6$ fluoroalkyl;
$R^3$ is halogen, —OR$^b$, $C_1$-$C_6$ alkyl, $C_2$-$C_6$ alkynyl, $C_1$-$C_6$ haloalkyl, $C_1$-$C_6$ hydroxyalkyl, or $C_1$-$C_6$ heteroalkyl; wherein each alkyl and alkynyl is independently optionally substituted with one, two, or three $R^{3a}$;
each $R^{3a}$ is independently oxo (when feasible) halogen, or —OR$^b$;
$R^4$ and $R^7$ are independently hydrogen, halogen, or —OR$^b$;
$R^5$ and $R^6$ are independently hydrogen, halogen, or $C_1$-$C_6$ alkyl;
$R^8$ is hydrogen;
$R^9$ and $R^{10}$ are hydrogen;
$R^{11}$ is halogen, —CN, —OR$^{13}$, —NR$^{15}$R$^{16}$, —S(=O)$_2$R$^{14}$, —C(=O)OR$^{13}$, $C_1$-$C_6$ alkyl, $C_1$-$C_6$ haloalkyl, $C_1$-$C_6$ hydroxyalkyl, $C_2$-$C_6$ alkynyl, $C_1$-$C_6$ heteroalkyl, cycloalkyl, heterocycloalkyl, aryl, or heteroaryl; wherein each alkyl, alkynyl, cycloalkyl, heterocycloalkyl, aryl, and heteroaryl is independently optionally substituted with one, two, or three $R^{11a}$;
$R^{12}$ is hydrogen, halogen, —OR$^{13}$, $C_1$-$C_6$ alkyl, $C_1$-$C_6$ haloalkyl, $C_1$-$C_6$ hydroxyalkyl, $C_2$-$C_6$ alkynyl, or $C_1$-$C_6$ heteroalkyl; wherein each alkyl and alkynyl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —OR$^{13}$, —SR$^{13}$, —S(=O)R$^{14}$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —C(=O)OR$^{13}$, —C(=O)NR$^{15}$R$^{16}$, —OC(=O)NR$^c$R$^d$, —NR$^{13}$C(=O)R$^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$;
each $R^{11c}$ is independently oxo (when feasible), halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$haloalkyl, $C_1$-$C_6$hydroxyalkyl, cycloalkyl, heterocycloalkyl, aryl, or heteroaryl;
each $R^{13}$ is independently hydrogen, $C_1$-$C_6$ alkyl, $C_1$-$C_6$ haloalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{13a}$;
each $R^{14}$ is independently $C_1$-$C_6$ alkyl, or $C_1$-$C_6$ haloalkyl; wherein each alkyl is independently optionally substituted with one, two, or three $R^{14a}$;
each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$;
or $R^{15}$ and $R^{16}$ are taken together with the nitrogen atom to which they are attached to form a heterocycloalkyl optionally substituted with one, two, or three $R^{15b}$;
each $R^{13a}$, $R^{14a}$, $R^{15a}$, and $R^{15b}$ is independently oxo (when feasible), halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one, two, or three oxo (when feasible), halogen, —CN, —OR$^b$, —NR$^c$R$^d$, $C_1$-$C_6$ alkyl, or $C_1$-$C_6$ haloalkyl;
$R^{21}$ and $R^{22}$ are independently hydrogen, or $C_1$-$C_{20}$alkyl;
each $R^a$ is independently $C_1$-$C_6$ alkyl, $C_1$-$C_6$heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;
each $R^b$ is independently hydrogen, $C_1$-$C_6$ alkyl, $C_1$-$C_6$ heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and
each $R^c$ and $R^d$ is independently hydrogen, $C_1$-$C_6$ alkyl, $C_1$-$C_6$heteroalkyl, cycloalkyl, heterocycloalkyl, aryl, or heteroaryl; wherein the alkyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;
or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (II) or a pharmaceutically acceptable salt, solvate, stereoisomer, or isotopic variant thereof:

Formula (II)

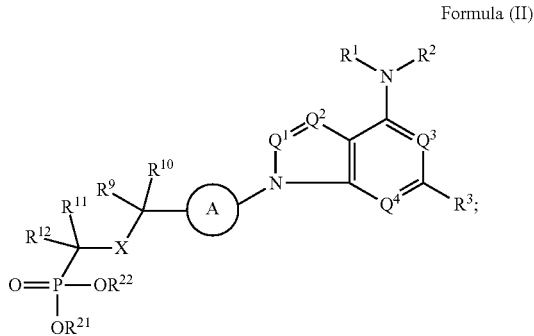

wherein:
Ring A is

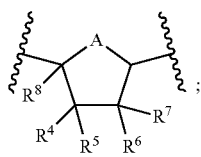

$Q^1$ is N and $Q^2$ is CW or $Q^1$ is N and $Q^2$ is N;
$Q^3$ and $Q^4$ are independently N or CW; provided that at least one of $Q^3$ or $Q^4$ is N;
each W is hydrogen;
A is —O—;
X is —O—;
$R^1$ and $R^2$ are independently hydrogen, $C_1$-$C_6$ alkyl, cycloalkyl, $C_1$-$C_6$ alkyl(aryl), or $C_1$-$C_6$ alkyl(cycloalkyl); wherein each alkyl, cycloalkyl, and aryl is independently optionally substituted with one, two, or three $R^{1a}$;
each $R^{1a}$ is independently halogen or $C_1$-$C_6$ alkyl;
$R^3$ is halogen, —$OR^b$, $C_2$-$C_6$ alkynyl, or $C_1$-$C_6$ hydroxyalkyl; wherein each alkyl and alkynyl is independently optionally substituted with one, two, or three $R^{3a}$;
each $R^{3a}$ is independently oxo (when feasible) halogen, or —$OR^b$;
$R^4$ and $R^7$ are independently hydrogen, halogen, or —$OR^b$;
$R^5$ and $R^6$ are independently hydrogen, halogen, or $C_1$-$C_6$ alkyl;
$R^8$ is hydrogen;
$R^9$ and $R^{10}$ are hydrogen;
$R^{11}$ is —CN, —S(=O)$_2R^{14}$, —C(=O)$OR^{13}$, $C_1$-$C_6$ alkyl, $C_1$-$C_6$ haloalkyl, $C_1$-$C_6$ hydroxyalkyl $C_2$-$C_6$ alkynyl, or heteroaryl; wherein each alkyl, alkynyl, and heteroaryl is independently optionally substituted with one, two, or three $R^{11a}$;
$R^{12}$ is hydrogen, $C_1$-$C_6$ alkyl, $C_1$-$C_6$ hydroxyalkyl, or $C_2$-$C_6$ alkynyl; wherein each alkyl and alkynyl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —$OR^{13}$, —$SR^{13}$, —$NR^{15}R^{16}$, —S(=O)$_2R^{14}$, —$NR^{13}$S(=O)$_2R^{14}$, —S(=O)$_2NR^{15}R^{16}$, —C(=O)$OR^{13}$, —OC(=O)$NR^{15}R^{16}$, —$NR^{13}$C(=O) $R^{14}$, heterocycloalkyl, aryl, or heteroaryl; wherein each heterocycloalkyl, aryl, and heteroaryl is independently optionally substituted with one, two, or three $R^{11c}$;

each $R^{11c}$ is independently —$OR^b$, —C(=O)$OR^b$, or $C_1$-$C_6$ hydroxyalkyl;
each $R^{13}$ is independently $C_1$-$C_6$ alkyl, $C_1$-$C_6$ haloalkyl, or cycloalkyl; wherein each alkyl and cycloalkyl is independently optionally substituted with one, two, or three $R^{13a}$;
each $R^{14}$ is independently $C_1$-$C_6$ alkyl;
each $R^{15}$ and $R^{16}$ is independently hydrogen or $C_1$-$C_6$ alkyl;
each $R^{13a}$ is independently —$OR^b$, —C(=O)$OR^b$, cycloalkyl, aryl, or heteroaryl;
$R^{21}$ and $R^{22}$ are hydrogen;
each $R^a$ is independently $C_1$-$C_6$ alkyl optionally substituted with one, two, or three oxo (when feasible), halogen, —OH, $C_1$-$C_6$ alkyl, or $C_1$-$C_6$ haloalkyl;
each $R^b$ is independently hydrogen or $C_1$-$C_6$ alkyl optionally substituted with one, two, or three oxo (when feasible), halogen, —OH, $C_1$-$C_6$ alkyl, or $C_1$-$C_6$ haloalkyl; and
each $R^c$ and $R^d$ is independently hydrogen or $C_1$-$C_6$ alkyl optionally substituted with one, two, or three oxo (when feasible), halogen, —OH, $C_1$-$C_6$ alkyl, or $C_1$-$C_6$ haloalkyl;
or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (I), or a pharmaceutically acceptable salt, solvate, stereoisomer, or isotopic variant thereof:

Formula (II)

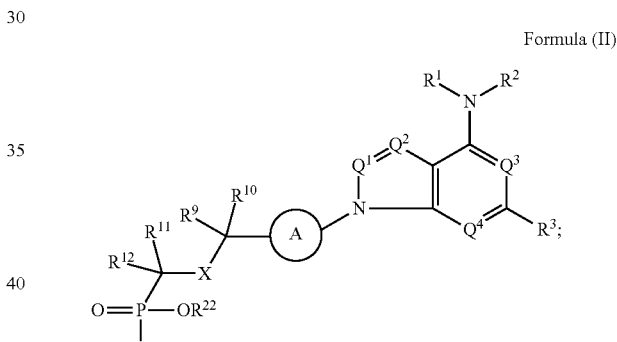

wherein:
Ring A is

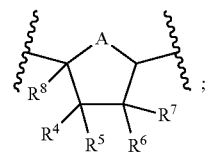

$Q^1$ is N and $Q^2$ is CW or $Q^1$ is N and $Q^2$ is N;
$Q^3$ and $Q^4$ are N;
W is hydrogen;
A is —O—;
X is —O—;
$R^1$ is cycloalkyl or $C_1$-$C_6$ alkyl(cycloalkyl);
$R^2$ hydrogen;
$R^3$ is halogen or $C_1$-$C_6$ hydroxyalkyl;
$R^4$ and $R^7$ are independently —$OR^b$;
$R^5$ and $R^6$ hydrogen;
$R^8$ is hydrogen;
$R^9$ and $R^{10}$ are hydrogen;

$R^{11}$ is $C_1$-$C_6$ alkyl or $C_1$-$C_6$ hydroxyalkyl; wherein each alkyl is independently optionally substituted with one $R^{11a}$;

$R^{12}$ is $C_1$-$C_6$ alkyl or $C_1$-$C_6$ hydroxyalkyl;

each $R^{11a}$ is —$OR^{13}$ or heteroaryl;

$R^{13}$ is $C_1$-$C_6$ alkyl;

$R^{21}$ and $R^{22}$ are hydrogen;

each $R^a$ is independently $C_1$-$C_6$ alkyl optionally substituted with one, two, or three halogen, —OH, $C_1$-$C_6$ alkyl, or $C_1$-$C_6$ haloalkyl;

each $R^b$ is independently hydrogen or $C_1$-$C_6$ alkyl optionally substituted with one, two, or three halogen, —OH, $C_1$-$C_6$ alkyl, or $C_1$-$C_6$ haloalkyl; and each $R^c$ and $R^d$ is independently hydrogen or $C_1$-$C_6$ alkyl optionally substituted with one, two, or three halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments of a compound of Formula (II), $Q^1$ is N and $Q^2$ is CW. In some embodiments of a compound of Formula (I), $Q^1$ is N and $Q^2$ is N.

In some embodiments of a compound of Formula (II), $Q^3$ is N and $Q^4$ is CW. In some embodiments of a compound of Formula (II) $Q^4$ is N and $Q^3$ is CW. In some embodiments of a compound of Formula (II), $Q^3$ is N and $Q^4$ is N.

In some embodiments of a compound of Formula (II), $Q^1$ is N, $Q^2$ is CW, $Q^1$ is N, and $Q^4$ is CW. In some embodiments of a compound of Formula (II), $Q^1$ is N, $Q^2$ is CW, $Q^3$ is CW, and $Q^4$ is N. In some embodiments of a compound of Formula (II), $Q^1$ is N, $Q^2$ is CW, $Q^3$ is N, and $Q^4$ is N. In some embodiments of a compound of Formula (II), $Q^1$ is N, $Q^1$ is N, $Q^2$ is N, and $Q^4$ is CW. In some embodiments of a compound of Formula (II), $Q^1$ is N, $Q^2$ is N, $Q^3$ is CW, and $Q^4$ is N. In some embodiments of a compound of Formula (II), $Q^1$ is N, $Q^2$ is N, $Q^3$ is N, and $Q^1$ is N.

In some embodiments of a compound of Formula (II), each W is independently hydrogen, halogen, $C_1$-$C_6$ alkyl, or $C_1$-$C_6$ haloalkyl. In some embodiments of a compound of Formula (II), each W is independently hydrogen, halogen, or $C_1$-$C_6$alkyl. In some embodiments of a compound of Formula (II), each W is hydrogen.

In some embodiments of a compound of Formula (II), $R^3$ is halogen, —CN, —$OR^b$, —$NR^cR^d$, $C_1$-$C_6$ alkyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, or heterocycloalkyl; wherein each alkyl, alkynyl, cycloalkyl, and heterocycloalkyl is independently optionally substituted with one, two, or three $R^{3a}$. In some embodiments of a compound of Formula (II). $R^3$ is halogen, $C_1$-$C_6$ alkyl, $C_2$-$C_6$ alkynyl, $C_1$-$C_6$ hydroxyalkyl, or $C_1$-$C_6$ heteroalkyl; wherein each alkyl and alkynyl is independently optionally substituted with one, two, or three $R^{3a}$. In some embodiments of a compound of Formula (II), $R^3$ is halogen, —CN, —$OR^b$, —$NR^cR^d$, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (II), $R^3$ is halogen, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (II), $R^3$ is halogen, or $C_1$-$C_6$ hydroxyalkyl, $C_1$-$C_6$ heteroalkyl. In some embodiments of a compound of Formula (I), $R^3$ is halogen. In some embodiments of a compound of Formula (II), $R^3$ is halogen, —$OR^b$, $C_1$-$C_6$ alkyl, $C_2$-$C_6$ alkynyl, $C_1$-$C_6$ haloalkyl, $C_1$-$C_6$ hydroxyalkyl, or $C_1$-$C_6$ heteroalkyl; wherein each alkyl and alkynyl is independently optionally substituted with one, two, or three $R^{3a}$. In some embodiments of a compound of Formula (II), $R^3$ is halogen, —$OR^b$, $C_2$-$C_6$ alkynyl, or $C_1$-$C_6$ hydroxyalkyl; wherein each alkyl and alkenyl is independently optionally substituted with one, two, or three $R^3$. In some embodiments of a compound of Formula (II), $R^3$ is halogen or $C_1$-$C_6$ hydroxyalkyl.

In some embodiments of a compound of Formula (II), each $R^{3a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (II), each $R^{3a}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (II), each $R^{3a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (II), each $R^3$ is independently oxo (when feasible) halogen, $C_1$-$C_6$ alkyl, or $C_1$-$C_6$ fluoroalkyl. In some embodiments of a compound of Formula (II), each $R^{3a}$ is independently halogen or $C_1$-$C_6$ alkyl. In some embodiments of a compound of Formula (II), each $R^{3a}$ is independently halogen, —$OR^b$, $C_1$-$C_6$ alkyl, or cycloalkyl. In some embodiments of a compound of Formula (II), each $R^{3a}$ is independently oxo (when feasible) halogen, or —$OR^b$.

In some embodiments of a compound of Formula (II), $R^1$ is $C_1$-$C_6$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (II), $R^1$ is $C_1$-$C_6$ alkyl, cycloalkyl, heterocycloalkyl, $C_1$-$C_6$ alkyl (aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (II), $R^1$ is cycloalkyl or $C_1$-$C_6$ alkyl(cycloalkyl); wherein each alkyl and cycloalkyl is independently optionally substituted with one, two, or three $R^{1a}$. In some embodiments of a compound of Formula (II), $R^1$ is cycloalkyl optionally substituted with one, two, or three $R^{1a}$. In some embodiments of a compound of Formula (II), $R^1$ is $C_1$-$C_6$ alkyl, $C_1$-$C_6$ haloalkyl, cycloalkyl, heterocycloalkyl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (II), $R^1$ is $C_1$-$C_6$ alkyl, cycloalkyl, $C_1$-$C_6$ alkyl(aryl), or $C_1$-$C_6$ alkyl(cycloalkyl); wherein each alkyl, cycloalkyl, and aryl is independently optionally substituted with one, two, or three $R^{1a}$. In some embodiments of a compound of Formula (II), $R^1$ is cycloalkyl or $C_1$-$C_6$ alkyl(cycloalkyl).

In some embodiments of a compound of Formula (II), each $R^{1a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (II), each $R^{1a}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (II), each $R^{1a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (II), each $R^{1a}$ is independently oxo (when feasible) halogen, $C_1$-$C_6$ alkyl, or $C_1$-$C_6$ fluoroalkyl. In some embodiments of a compound of Formula (II), each $R^{1a}$ is independently halogen or $C_1$-$C_6$ alkyl. In some embodiments of a compound of Formula (II), each $R^{1a}$ is independently oxo (when feasible) halogen, —CN, —$OR^b$, $C_1$-$C_6$ alkyl, or $C_1$-$C_6$ fluoroalkyl. In some embodiments of a compound of Formula (II), each $R^{1a}$ is independently halogen or $C_1$-$C_6$ alkyl.

In some embodiments of a compound of Formula (II), $R^2$ is hydrogen or $C_1$-$C_6$ alkyl. In some embodiments of a compound of Formula (II), $R^2$ is hydrogen. In some embodiments of a compound of Formula (II), $R^1$ and $R^2$ are taken together with the nitrogen atom to which they are attached to form a heterocycloalkyl optionally substituted with one, two, or three $R^{1b}$.

In some embodiments of a compound of Formula (II), each $R^{1b}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (II), each $R^{1b}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (II), each $R^{1b}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (II), each $R^{1b}$ is independently oxo (when feasible) halogen, $C_1$-$C_6$ alkyl, or $C_1$-$C_6$ fluoroalkyl. In some embodiments of a compound of Formula (II), each $R^{1b}$ is independently halogen or $C_1$-$C_6$ alkyl.

In some embodiments of a compound of Formula (II), $R^8$ is hydrogen or $C_1$-$C_6$ alkyl. In some embodiments of a compound of Formula (II), $R^8$ is hydrogen.

In some embodiments of a compound of Formula (II), $R^9$ and $R^{10}$ are independently hydrogen or $C_1$-$C_6$ alkyl. In some embodiments of a compound of Formula (II), $R^9$ and $R^{10}$ are hydrogen.

In some embodiments of a compound of Formula (II), X is —O—. In some embodiments of a compound of Formula (II), X is —S—.

In some embodiments of a compound of Formula (II), $R^5$ and $R^6$ are independently hydrogen, halogen, —$OR^b$, $C_1$-$C_6$ alkyl, or $C_1$-$C_6$ haloalkyl. In some embodiments of a compound of Formula (II), $R^5$ and $R^6$ are independently hydrogen, halogen, —$OR^b$, or $C_1$-$C_6$ alkyl. In some embodiments of a compound of Formula (II), $R^5$ and $R^6$ are hydrogen.

In some embodiments of a compound of Formula (II), $R^4$ and $R^7$ are independently hydrogen, halogen, —$OR^b$, $C_1$-$C_6$ alkyl, or $C_1$-$C_6$ haloalkyl. In some embodiments of a compound of Formula (II), $R^4$ and $R^7$ are independently hydrogen, halogen, —$OR^b$, or $C_1$-$C_6$ alkyl. In some embodiments of a compound of Formula (II), $R^4$ and $R^7$ are independently hydrogen, halogen, or —$OR^b$. In some embodiments of a compound of Formula (II), $R^4$ and $R^7$ are independently hydrogen, halogen, or —OH. In some embodiments of a compound of Formula (II), $R^4$ and $R^7$ are independently halogen or —OH. In some embodiments of a compound of Formula (II), $R^4$ and $R^7$ are independently hydrogen or —OH. In some embodiments of a compound of Formula (II), $R^4$ and $R^7$ are —OH.

In some embodiments of a compound of Formula (II), $R^5$ and $R^6$ are hydrogen and $R^4$ and $R^7$ are —OH. In some embodiments of a compound of Formula (II), $R^5$ and $R^6$ are hydrogen and $R^4$ and $R^7$ are independently halogen or —OH. In some embodiments of a compound of Formula (II), $R^5$ and $R^6$ are hydrogen and $R^4$ and $R^7$ are independently hydrogen or —OH.

In some embodiments of a compound of Formula (II), $R^{21}$ and $R^{22}$ are independently hydrogen, $C_1$-$C_{20}$ alkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{21a}$. In some embodiments of a compound of Formula (II), $R^{21}$ and $R^{22}$ are independently hydrogen, $C_1$-$C_{20}$ alkyl or aryl; wherein each alkyl and aryl is independently optionally substituted with one, two, or three $R^{21a}$. In some embodiments of a compound of Formula (II), $R^{21}$ and $R^{22}$ are independently hydrogen, $C_1$-$C_{20}$ alkyl optionally substituted with one, two, or three $R^{21a}$. In some embodiments of a compound of Formula (II), $R^{21}$ and $R^{22}$ are hydrogen.

In some embodiments of a compound of Formula (II), each $R^{21a}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC(=O)NR^cR^d$, —$NR^bC(=O)R^a$, —$NR^bC(=O)OR^b$, or $C_1$-$C_6$ alkyl. In some embodiments of a compound of Formula (II), each $R^{21a}$ is independently —C(=O)$R^a$, —OC(=O)$R^a$, —C(=O)$OR^b$, —OC(=O)$OR^b$, or —OC(=O)$NR^cR^d$. In some embodiments of a compound of Formula (II), each $R^{21a}$ is independently —C(=O)$OR^b$ or —OC(=O)$OR^b$.

In some embodiments of a compound of Formula (II), $R^{21}$ and $R^{22}$ are taken together with the atoms to which they are attached to form a heterocycloalkyl optionally substituted with one, two, or three $R^{21b}$.

In some embodiments of a compound of Formula (II), each $R^{21b}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC(=O)NR^cR^d$, —$NR^bC(=O)R^a$, —$NR^bC(=O)OR^b$, $C_1$-$C_6$ alkyl, cycloalkyl, or heterocycloalkyl. In some embodiments of a compound of Formula (II), each $R^{21b}$ is independently halogen, —CN, —$OR^b$, —$NR^cR^d$, $C_1$-$C_6$ alkyl, cycloalkyl, or heterocycloalkyl. In some embodiments of a compound of Formula (II), each $R^{21b}$ is independently halogen or $C_1$-$C_6$ alkyl.

In some embodiments of a compound of Formula (II), $R^{12}$ is hydrogen, halogen, —CN, —$OR^{13}$, —$NR^{15}R^{16}$, —C(=O)$R^{14}$, —C(=O)$OR^{13}$, —C(=O)$NR^{15}R^{16}$, $C_1$-$C_6$alkyl, $C_1$-$C_6$haloalkyl, $C_1$-$C_6$hydroxyalkyl, $C_1$-$C_6$ heteroalkyl, cycloalkyl, or heterocycloalkyl. In some embodiments of a compound of Formula (II), $R^{12}$ is halogen, —CN, —$OR^{13}$, —$NR^{15}R^{16}$, —C(=O)$R^{14}$, —C(=O)$OR^{13}$, —C(=O)$NR^{15}R^{16}$, $C_1$-$C_6$alkyl, $C_1$-$C_6$haloalkyl, $C_1$-$C_6$ hydroxyalkyl, $C_1$-$C_6$ heteroalkyl, cycloalkyl, or heterocycloalkyl. In some embodiments of a compound of Formula (II), $R^{12}$ is hydrogen, halogen, $C_1$-$C_6$alkyl, $C_1$-$C_6$haloalkyl, or $C_1$-$C_6$hydroxyalkyl. In some embodiments of a compound of Formula (II), $R^{12}$ is $C_1$-$C_6$ alkyl. In some embodiments of a compound of Formula (II), $R^{12}$ is $C_1$-$C_6$ hydroxyalkyl. In some embodiments of a compound of Formula (II), $R^{12}$ is hydrogen. In some embodiments of a compound of Formula (II), $R^{12}$ is not hydrogen. In some embodiments of a compound of Formula (II), $R^{12}$ is hydrogen, halogen, —$OR^{13}$, $C_1$-$C_6$alkyl, $C_1$-$C_6$haloalkyl, $C_1$-$C_6$ hydroxyalkyl, $C_2$-$C_6$ alkynyl, or $C_1$-$C_6$ heteroalkyl; wherein each alkyl and alkynyl is independently optionally substituted with one, two, or three $R^{12a}$. In some embodiments of a compound of Formula (II), $R^{12}$ is hydrogen, $C_1$-$C_6$ alkyl, $C_1$-$C_6$ hydroxyalkyl, or $C_2$-$C_6$ alkynyl; wherein each alkyl and alkynyl is independently optionally substituted with one, two, or three $R^{12a}$.

In some embodiments of a compound of Formula (II), each $R^{12a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{11}$, —$OC(=O)R^{14}$, —$C(=O)OR^{13}$, —$C(=O)NR^{15}R^{16}$, —$NR^{13}C(=O)R^{14}$, $C_1$-$C_6$alkyl, $C_1$-$C_6$ haloalkyl, $C_1$-$C_6$hydroxyalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (II), each $R^{12a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R^{16}$, —$NR^{13}C(=O)R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11c}$. In some embodiments of a compound of Formula (II), each $R^{12a}$ is independently —$OR^{13}$, —$S(=O)_2R^{14}$, —$NR^{13}C(=O)R^{14}$, cycloalkyl, aryl, or heteroaryl; wherein each cycloalkyl, aryl, and heteroaryl is independently optionally substituted with one, two, or three $R^{11c}$. In some embodiments of a compound of Formula (II), each $R^{12a}$ is independently oxo (when feasible), halogen, —CN, —$OR^{13}$, —$SR^{13}$, —$S(=O)R^{14}$, —$NR^{15}R^{16}$, —$S(=O)_2R^{14}$, —$NR^{13}S(=O)_2R^{14}$, —$S(=O)_2NR^{15}R^{16}$, —$C(=O)R^{14}$, —$C(=O)OR^{13}$, —$C(=O)NR^{15}R^{16}$, —$OC(=O)NR^{15}R^{16}$, —$NR^{13}C(=O)R^{14}$, $C_1$-$C_6$ alkyl, $C_1$-$C_6$ haloalkyl, $C_1$-$C_6$ hydroxyalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (II), each $R^{12a}$ is independently oxo (when feasible), halogen, —$OR^{13}$, —$SR^{13}$, —$NR^{15}R^{16}$, —$S(=O)_2R^{14}$, —$NR^{13}S(=O)_2R^{14}$, —$S(=O)_2NR^{15}R^{16}$, —$C(=O)OR^{13}$, —$OC(=O)NR^{15}R^{16}$, —$NR^{13}C(=O)R^{14}$, heterocycloalkyl, aryl, or heteroaryl; wherein each heterocycloalkyl, aryl, and heteroaryl is independently optionally substituted with one, two, or three $R^{11c}$.

In some embodiments of a compound of Formula (II), $R^{11}$ is halogen, —CN, —$OR^{13}$, —$NR^{15}R^{16}$, —$S(=O)_2R^{14}$, —$C(=O)R^{14}$, —$C(=O)OR^{13}$, —$C(=O)NR^{15}R^{16}$, $C_1$-$C_6$alkyl, $C_1$-$C_6$ haloalkyl, $C_1$-$C_6$hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (II), $R^{11}$ is halogen, —CN, —$S(=O)_2R^{14}$, —$C(=O)R^{14}$, —$C(=O)OR^{13}$, $C_1$-$C_6$ alkyl, $C_1$-$C_6$ haloalkyl, $C_1$-$C_6$ hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (II), $R^{11}$ is —CN, —$S(=O)_2R^{14}$, —$C(=O)OR^{13}$, $C_1$-$C_6$ alkyl, $C_1$-$C_6$ haloalkyl, $C_1$-$C_6$ hydroxyalkyl, or heteroaryl; wherein each alkyl and heteroaryl is independently optionally substituted with one, two, or three $R^{11a}$. In some embodiments of a compound of Formula (II), $R^1$ is $C_1$-$C_6$ alkyl optionally substituted with one, two, or three $R^{11a}$. In some embodiments of a compound of Formula (II), $R^{11}$ is $C_1$-$C_6$ alkyl substituted with one $R^{11a}$. In some embodiments of a compound of Formula (II), $R^{11}$ is $C_1$-$C_6$ hydroxyalkyl. In some embodiments of a compound of Formula (II), $R^{11}$ is halogen, —CN, —$OR^{13}$, —$NR^{15}R^{16}$, —$S(=O)_2R^{14}$, —$C(=O)OR^{13}$, $C_1$-$C_6$alkyl, $C_1$-$C_6$haloalkyl, $C_1$-$C_6$hydroxyalkyl, $C_2$-$C_6$ alkynyl, $C_1$-$C_6$ heteroalkyl, cycloalkyl, heterocycloalkyl, aryl, or heteroaryl; wherein each alkyl, alkynyl, cycloalkyl, heterocycloalkyl, aryl, and heteroaryl is independently optionally substituted with one, two, or three $R^{11a}$. In some embodiments of a compound of Formula (II), $R^{11}$ is —CN, —$S(=O)_2R^{14}$, —$C(=O)OR^{13}$, $C_1$-$C_6$ alkyl, $C_1$-$C_6$ haloalkyl, $C_1$-$C_6$ hydroxyalkyl, $C_2$-$C_6$ alkynyl, or heteroaryl; wherein each alkyl, alkynyl, and heteroaryl is independently optionally substituted with one, two, or three $R^{11a}$. In some embodiments of a compound of Formula (II), $R^{11}$ is $C_1$-$C_6$ alkyl or $C_1$-$C_6$ hydroxyalkyl; wherein each alkyl is independently optionally substituted with one $R^{11a}$.

In some embodiments of a compound of Formula (II), each $R^{11a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R^{16}$, —$NR^{13}C(=O)R^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (II), each $R^{11a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R^{16}$, —$NR^{13}C(=O)R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11}$. In some embodiments of a compound of Formula (II), each $R^{11a}$ is independently —$OR^{13}$, —$S(=O)_2R^{14}$, —$NR^{13}C(=O)R^{14}$, cycloalkyl, aryl, or heteroaryl; wherein each cycloalkyl, aryl, and heteroaryl is independently optionally substituted with one, two, or three $R^{11c}$. In some embodiments of a compound of Formula (II), each $R^{11a}$ is independently aryl optionally substituted with one, two, or three $R^{11c}$. In some embodiments of a compound of Formula (II), each $R^{11a}$ is independently —$OR^{13}$. In some embodiments of a compound of Formula (II), each $R^{11a}$ is independently —$S(=O)_2R^{14}$. In some embodiments of a compound of Formula (II), each $R^{11a}$ is independently cycloalkyl optionally substituted with one, two, or three $R^{11c}$. In some embodiments of a compound of Formula (II), each $R^{11a}$ is independently —$NR^{13}C(=O)R^{14}$. In some embodiments of a compound of Formula (II), each $R^{11a}$ is independently oxo (when feasible), halogen, —CN, —$OR^{13}$, —$SR^{13}$, —$S(=O)R^{14}$, —$NR^{15}R^{16}$, —$S(=O)_2R^{14}$, —$NR^{13}S(=O)_2R^{14}$, —$S(=O)_2NR^{15}R^{16}$, —$C(=O)R^{14}$, —$C(=O)OR^{13}$, —$C(=O)NR^{15}R^{16}$, —$OC(=O)NR^{15}R^{16}$, —$NR^{13}C(=O)R^{14}$, $C_1$-$C_6$alkyl, $C_1$-$C_6$ haloalkyl, $C_1$-$C_6$hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (II), each $R^{11a}$ is independently oxo (when feasible), halogen, —$OR^{13}$, —$SR^{13}$, —$NR^{15}R^{16}$, —$S(=O)_2R^{14}$, —$NR^{13}S(=O)_2R^{14}$, —$S(=O)_2NR^{15}R^{16}$, —$C(=O)OR^{13}$, —$OC(=O)NR^{15}R^{16}$, —$NR^{13}C(=O)R^{14}$, heterocycloalkyl, aryl, or heteroaryl; wherein each heterocycloalkyl, aryl, and heteroaryl is independently optionally substituted with one, two, or three $R^{11c}$. In some embodiments of a compound of Formula (II), each $R^{11a}$ is independently —$OR^{13}$ or heteroaryl.

In some embodiments of a compound of Formula (II), each $R^{11c}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (II), each R$^{11c}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$haloalkyl, or C$_1$-C$_6$ hydroxyalkyl. In some embodiments of a compound of Formula (II), each R$^{11c}$ is independently halogen, —CN, —OR$^b$, —NR$^c$R$^d$, C$_1$-C$_6$ alkyl, or C$_1$-C$_6$ haloalkyl. In some embodiments of a compound of Formula (II), each R$^{11c}$ is independently halogen, C$_1$-C$_6$ alkyl, or C$_1$-C$_6$haloalkyl. In some embodiments of a compound of Formula (II), each R$^{11c}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$haloalkyl, C$_1$-C$_6$hydroxyalkyl, cycloalkyl, heterocycloalkyl, aryl, or heteroaryl. In some embodiments of a compound of Formula (II), each R$^{11c}$ is independently —OR$^b$, —C(=O)OR$^b$, or C$_1$-C$_6$ hydroxyalkyl.

In some embodiments of a compound of Formula (II), R$^{11}$ and R$^{12}$ are taken together to form a cycloalkyl or heterocycloalkyl each optionally substituted with one, two, or three R$^{11b}$. In some embodiments of a compound of Formula (II), R$^{11}$ and R$^{12}$ are taken together to form a cycloalkyl optionally substituted with one, two, or three R$^{11b}$. In some embodiments of a compound of Formula (II), R$^{11}$ and R$^{12}$ are taken together to form a heterocycloalkyl optionally substituted with one, two, or three R$^{11b}$.

In some embodiments of a compound of Formula (II), each R$^{11b}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (II), each R$^{11b}$ is independently oxo (when feasible), halogen, —CN, —OR$^b$, —NR$^c$R$^d$, C$_1$-C$_6$ alkyl, or C$_1$-C$_6$ haloalkyl. In some embodiments of a compound of Formula (II), each R$^{11b}$ is independently oxo (when feasible), halogen, C$_1$-C$_6$ alkyl, or C$_1$-C$_6$ haloalkyl.

In some embodiments of a compound of Formula (II), each R$^{13}$ is independently hydrogen, C$_1$-C$_6$ alkyl, C$_1$-C$_6$ haloalkyl, C$_1$-C$_6$ heteroalkyl, cycloalkyl, or heterocycloalkyl; wherein each alkyl, cycloalkyl, and heterocycloalkyl is independently optionally substituted with one, two, or three R$^{13a}$. In some embodiments of a compound of Formula (II), each R$^{13}$ is independently hydrogen, C$_1$-C$_6$ alkyl, or C$_1$-C$_6$ haloalkyl; wherein each alkyl is independently optionally substituted with one, two, or three R$^{11a}$. In some embodiments of a compound of Formula (II), each R$^{13}$ is independently hydrogen or C$_1$-C$_6$ alkyl. In some embodiments of a compound of Formula (II), each R$^{13}$ is independently C$_1$-C$_6$ alkyl. In some embodiments of a compound of Formula (II), each R$^{13}$ is independently hydrogen, C$_1$-C$_6$ alkyl, C$_1$-C$_6$ haloalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{13a}$. In some embodiments of a compound of Formula (II), each R$^{13}$ is independently C$_1$-C$_6$ alkyl, C$_1$-C$_6$haloalkyl, or cycloalkyl; wherein each alkyl and cycloalkyl is independently optionally substituted with one, two, or three R$^{13a}$.

In some embodiments of a compound of Formula (II), each R$^{13}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (II), each R$^{13a}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (II), each R$^{13a}$ is independently halogen, C$_1$-C$_6$ alkyl, or C$_1$-C$_6$ haloalkyl. In some embodiments of a compound of Formula (II), each R$_{13a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, heterocycloalkyl, aryl, or heteroaryl; wherein each alkyl, cycloalkyl, heterocycloalkyl, aryl, and heteroaryl is independently optionally substituted with one, two, or three oxo (when feasible), halogen, —CN, —OR$^b$, —NR$^c$R$^d$, C$_1$-C$_6$ alkyl, or C$_1$-C$_6$haloalkyl. In some embodiments of a compound of Formula (II), each R$^{13a}$ is independently —OR$^b$, —C(=O)OR$^b$, cycloalkyl, aryl, or heteroaryl; wherein each cycloalkyl, aryl, and heteroaryl is independently optionally substituted with one, two, or three oxo (when feasible), halogen, —CN, —OR$^b$, —NR$^c$R$^d$, C$_1$-C$_6$ alkyl, or C$_1$-C$_6$haloalkyl. In some embodiments of a compound of Formula (I), each R$^{13a}$ is independently —OR$^b$, —C(=O)OR$^b$, cycloalkyl, aryl, or heteroaryl.

In some embodiments of a compound of Formula (II), each R$^{14}$ is independently C$_1$-C$_6$ alkyl, C$_1$-C$_6$ haloalkyl, C$_1$-C$_6$ heteroalkyl, cycloalkyl, or heterocycloalkyl; wherein each alkyl, cycloalkyl, and heterocycloalkyl is independently optionally substituted with one, two, or three R$^{14a}$. In some embodiments of a compound of Formula (II), each R$^{14}$ is independently C$_1$-C$_6$ alkyl, or C$_1$-C$_6$haloalkyl; wherein each alkyl is independently optionally substituted with one, two, or three R$^{14a}$. In some embodiments of a compound of Formula (II), each R$^{14}$ is independently C$_1$-C$_6$ alkyl.

In some embodiments of a compound of Formula (II), each R$^{14a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (II), each R$^{14a}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (II), each R$^{14a}$ is independently halogen, C$_1$-C$_6$ alkyl, or C$_1$-C$_6$ haloalkyl.

In some embodiments of a compound of Formula (II), each R$^{15}$ and R$^{16}$ is independently hydrogen, C$_1$-C$_6$ alkyl, C$_1$-C$_6$ haloalkyl, C$_1$-C$_6$ heteroalkyl, cycloalkyl, or heterocycloalkyl; wherein each alkyl, cycloalkyl, and heterocycloalkyl is independently optionally substituted with one, two, or three R$^{15a}$. In some embodiments of a compound of Formula (II), each R$^{15}$ and R$^{16}$ is independently hydrogen, C$_1$-C$_6$ alkyl, or C$_1$-C$_6$ haloalkyl; wherein each alkyl is independently optionally substituted with one, two, or three R$^{15}$. In some embodiments of a compound of Formula (II), each R$^{15}$ and R$^{16}$ is independently hydrogen, C$_1$-C$_6$ alkyl, or C$_1$-C$_6$ haloalkyl; wherein each alkyl is independently optionally substituted with one, two, or three R$^1$. In some embodiments of a compound of Formula (II), each R$^{15}$ and R$^{16}$ is independently hydrogen or C$_1$-C$_6$ alkyl.

In some embodiments of a compound of Formula (II), each R$^{15a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (II), each R$^{15a}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (II), each R$^{15}$ is independently halogen, C$_1$-C$_6$ alkyl, or C$_1$-C$_6$ haloalkyl.

In some embodiments of a compound of Formula (II), R$^{15}$ and R$^{16}$ are taken together with the nitrogen atom to which they are attached to form a heterocycloalkyl optionally substituted with one, two, or three R$^{15b}$. In some embodiments of a compound of Formula (II), $R^{15}$ and $R^{16}$ are taken together with the nitrogen atom to which they are attached to form a heterocycloalkyl.

In some embodiments of a compound of Formula (II), each $R^{15b}$ is independently oxo (when feasible), halogen, —CN, —OR$^b$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, cycloalkyl, or heterocycloalkyl. In some embodiments of a compound of Formula (II), each $R^{15b}$ is independently halogen, —CN, —OR$^b$, —NR$^c$R$^d$, $C_1$-$C_6$ alkyl, $C_1$-$C_6$haloalkyl, cycloalkyl, or heterocycloalkyl. In some embodiments of a compound of Formula (II), each $R^{15b}$ is independently halogen, $C_1$-$C_6$alkyl, or $C_1$-$C_6$ haloalkyl.

In some embodiments provided herein is a compound having the structure of Formula (III), or a pharmaceutically acceptable salt, solvate, stereoisomer, or isotopic variant thereof:

Formula (III)

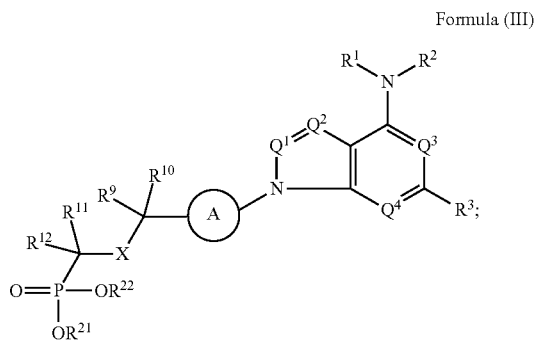

wherein:
Ring A is

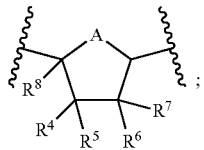

$Q^1$ is CW and $Q^2$ is N;
$Q^3$ and $Q^4$ are independently N or CW; provided that at least one of $Q^3$ or $Q^4$ is N;
each W is independently hydrogen, halogen, —CN, —OR$^b$, NR$^c$R$^d$, $C_1$-$C_6$ alkyl, or $C_1$-$C_6$ haloalkyl;
A is —O— or —CH$_2$—;
X is —O—, —S—, or —S(=O)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl (heterocycloalkyl); wherein each alkyl, alkenyl, alkynyl, cycloalkyl, heterocycloalkyl, aryl, and heteroaryl is independently optionally substituted with one, two, or three $R^{1a}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^b$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
$R^3$ is hydrogen, halogen, —CN, —OR$^b$, —SR$^b$, —NR$^c$R$^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;
each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, $C_2$-$C_6$alkenyl, $C_2$-$C_6$ alkynyl, cycloalkyl, heterocycloalkyl, aryl, or heteroaryl:
$R^4$ and $R^7$ are independently hydrogen, halogen, —OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^8$ is hydrogen, halogen, —OR$^b$, —NR$^c$R$^d$, $C_1$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —OR$^{13}$, —SR$^{13}$, —S(=O) R$^{14}$, —NO$_2$, —NR$^{15}$R$^{16}$, —S(=O)$_2$R$^{14}$, —NR$^{13}$S(=O)$_2$ R$^{14}$, —S(=O)$_2$NR$^{15}$R$^{16}$, —C(=O)R, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_2$-$C_6$ alkenyl, $C_2$-$C_6$ alkynyl, $C_1$-$C_6$hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS(=O)_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS(=O)_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three oxo (when feasible), halogen, —CN, —$OR^b$, —S(=O)$R^a$, —$NO_2$, —$NR^cR^d$, —S(=O)$_2R^a$, —S(=O)$_2NR^cR^d$, —C(=O)$R^a$, —C(=O)$OR^b$, —C(=O)$NR^cR^d$, $C_1$-$C_6$alkyl, $C_1$-$C_6$ haloalkyl, $C_2$-$C_6$ alkenyl, or $C_2$-$C_6$ alkynyl;

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS(=O)_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC(=O)NR^cR^d$, —$NR^bC(=O)R^a$, —$NR^bC(=O)$ $OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl, wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (III), or a pharmaceutically acceptable salt, solvate, stereoisomer, or isotopic variant thereof:

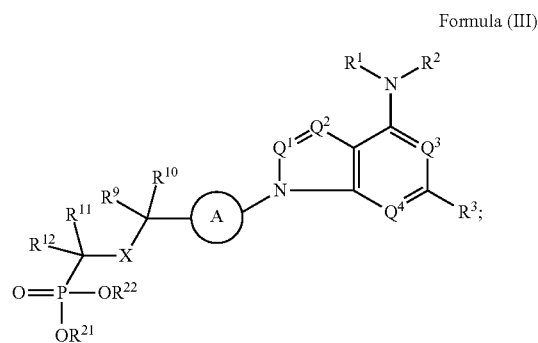

Formula (III)

wherein:
Ring A is

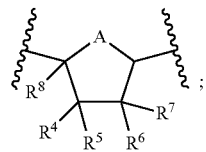

;

$Q^1$ is CW and $Q^2$ is N;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;

A is —O— or —CH$_2$—;

X is —O—, —S—, or —S(=O)$_2$—;

R$^1$ and R$^2$ are independently hydrogen, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl (heterocycloalkyl); wherein each alkyl, alkenyl, alkynyl, cycloalkyl, heterocycloalkyl, aryl, and heteroaryl is independently optionally substituted with one, two, or three R$^{1a}$;

or R$^1$ and R$^2$ are taken together with the nitrogen atom to which they are attached to form a heterocycloalkyl optionally substituted with one, two, or three R$^{1b}$:

each R$^{1a}$ and R$^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^3$ is hydrogen, halogen, —CN, —OR$^b$, —SR$^b$, —NR$^c$R$^d$, C$_1$-C$_6$ alkyl, C$_2$-C$_6$ alkenyl, C$_2$-C$_6$ alkynyl, C$_1$-C$_6$ haloalkyl, C$_1$-C$_6$ hydroxyalkyl, C$_1$-C$_6$ heteroalkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, alkenyl, alkynyl, cycloalkyl, heterocycloalkyl, aryl, and heteroaryl is independently optionally substituted with one, two, or three R$^{3a}$;

each R$^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, or heteroaryl;

R$^4$ and R$^7$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

R$^5$ and R$^6$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

R$^8$ is hydrogen, halogen, —OR$^b$, —NR$^c$R$^d$, C$_1$-C$_6$ alkyl, or C$_1$-C$_6$ haloalkyl;

R$^9$ and R$^{10}$ are independently hydrogen, halogen, C$_1$-C$_6$ alkyl, or C$_1$-C$_6$ haloalkyl;

R$^{11}$ is halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_1$-C$_6$ hydroxyalkyl, C$_2$-C$_6$ alkenyl, C$_2$-C$_6$ alkynyl, C$_1$-C$_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11a}$;

R$^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{12a}$;

or R$^{11}$ and R$^{12}$ are taken together to form a cycloalkyl or heterocycloalkyl each optionally substituted with one, two, or three R$^{11b}$;

each R$^{11a}$, R$^{11b}$, and R$^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$alkyl, C$_1$-C$_6$haloalkyl, C$_2$-C$_6$ alkenyl, C$_2$-C$_6$ alkynyl, C$_1$-C$_6$hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11c}$;

each R$^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^{13}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{13a}$;

each R$^{14}$ is independently C$_1$-C$_6$ alkyl, C$_1$-C$_6$haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{14a}$;

each R$^{15}$ and R$^{16}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{15a}$;

or R$^{15}$ and R$^{16}$ are taken together with the nitrogen atom to which they are attached to form a heterocycloalkyl optionally substituted with one, two, or three R$^{15b}$;

each R$^{13a}$, R$^{14a}$, R$^{15a}$, and R$^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^{21}$ and R$^{22}$ are independently hydrogen, C$_1$-C$_{20}$alkyl, cycloalkyl, heterocycloalkyl, aryl, heteroaryl, C$_1$-C$_6$ alkyl (aryl), C$_1$-C$_6$ alkyl(heteroaryl), C$_1$-C$_6$ alkyl(cycloalkyl), C$_1$-C$_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —$S(=O)R^a$, —$NO_2$, —$NR^cR^d$, —$S(=O)_2R^a$, —$NR^bS(=O)_2R^a$, —$S(=O)_2NR^cR^d$, —$C(=O)R^a$, —$OC(=O)R^a$, —$C(=O)OR^b$, —$C(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (III), or a pharmaceutically acceptable salt, solvate, stereoisomer, or isotopic variant thereof:

Formula (III)

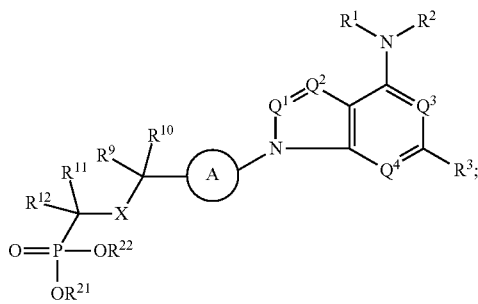

wherein:
Ring A is

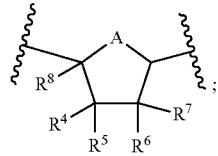

$Q^1$ is CW and $Q^2$ is N;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O— or —$CH_2$—;
X is —O—, —S—, or —$S(=O)_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —$OR^b$, —$SR^b$, —$S(=O)R^a$, —$NO_2$, —$NR^cR^d$, —$S(=O)_2R^a$, —$NR^bS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^4$ and $R^7$ are independently hydrogen, halogen, —$OR^b$, $C_1$-$C_6$ alkyl, $C_1$-$C_6$ haloalkyl, $C_1$-$C_6$ alkenyl, $C_2$-$C_6$ alkynyl, cycloalkyl, heterocycloalkyl, aryl, or heteroaryl;

$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^8$ is hydrogen, halogen, —$OR^b$, —$NR^cR^d$, $C_1$-$C_6$ alkyl, or $C_1$-$C_6$ haloalkyl;

$R^9$ and $R^{10}$ are independently hydrogen, halogen, $C_1$-$C_6$ alkyl, or $C_1$-$C_6$ haloalkyl;

$R^{12}$ is halogen, —CN, —$OR^{13}$, —$SR^{13}$, —$S(=O)R^{14}$, —$NO_2$, —$NR^{15}R^{16}$, —$S(=O)_2R^{14}$, —$NR^{13}S(O)_2R^{14}$, —$S(=O)_2NR^{15}R^{16}$, —$C(=O)R^{14}$, —$OC(=O)R^{14}$, —$C(=O)OR^{13}$, —$OC(=O)OR^{13}$, —$C(=O)NR^{15}R^{16}$, —$OC(=O)NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;

$R^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12b}$;

or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_2$-$C_6$ alkenyl, $C_2$-$C_6$ alkynyl, $C_1$-$C_6$hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$—R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

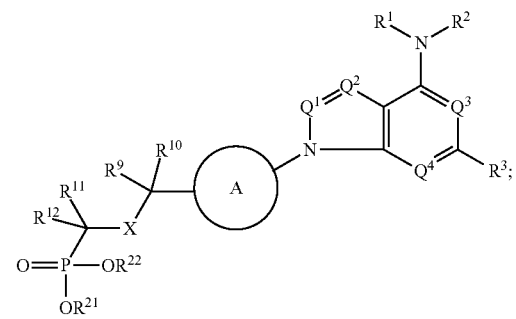

Formula (III)

wherein:
Ring A is

[structure depicting ring A with substituents $R^4$, $R^5$, $R^6$, $R^7$, $R^8$ and label A]

$Q^1$ is CW and $Q^2$ is N;
$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O— or —$CH_2$—;
X is —O—, —S—, or —S($=$O)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$; provided that one of $R^1$ or $R^2$ is not hydrogen;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —$OR^b$, —$SR^b$, —S($=$O)$R^a$, —$NO_2$, —$NR^cR^d$, —S($=$O)$_2R^a$, —$NR^bS(=O)_2R^a$, —S($=$O)$_2NR^cR^d$, —C($=$O)$R^a$, —OC($=$O)$R^a$, —C($=$O)$OR^b$, —OC($=$O)$OR^b$, —C($=$O)$NR^cR^d$, —OC($=$O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
$R^3$ is halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;
each $R^{3a}$ is independently oxo (when feasible) halogen, —CN, —$OR^b$, —$NR^cR^d$, —C($=$O)$R^a$, —C($=$O)$OR^b$, —C($=$O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;
$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^8$ is hydrogen, halogen, —$OR^b$, —$NR^cR^d$, $C_1$-$C_6$ alkyl, or $C_1$-$C_6$ haloalkyl;
$R^9$ and $R^{10}$ are independently hydrogen, $C_1$-$C_6$ alkyl, or $C_1$-$C_6$ haloalkyl;
$R^{11}$ is halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —OC($=$O)$OR^{13}$, —OC($=$O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$; provided that $R^{11}$ is not $CF_3$;
$R^{12}$ is hydrogen, halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —OC($=$O)$OR^{13}$, —C($=$O)$NR^{15}R^{16}$, —OC($=$O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —C($=$O)$OR^{13}$, —OC($=$O)$OR^{13}$, —C($=$O)$NR^{15}R^{16}$, —OC($=$O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$ haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —$OR^b$, —$SR^b$, —S($=$O)$R^a$, —$NO_2$, —$NR^cR^d$, —S($=$O)$_2R^a$, —$NR^bS(=O)_2R^a$, —S($=$O)$_2NR^cR^d$, —C($=$O)$R^a$, —OC($=$O)$R^a$, —C($=$O)$OR^b$, —OC($=$O)$OR^b$, —C($=$O)$NR^cR^d$, —OC($=$O)$NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;
each $R^{14}$ is independently $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;
each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;
or $R^{15}$ and $R^{16}$ are taken together with the nitrogen atom to which they are attached to form a heterocycloalkyl optionally substituted with one, two, or three $R^{15b}$;
each $R^{13a}$, $R^{14a}$, $R^{15a}$, and $R^{15b}$ is independently oxo (when feasible), halogen, —CN, —$OR^b$, —$SR^b$, —S($=$O)$R^a$, —$NO_2$, —$NR^cR^d$, —S($=$O)$_2R^a$, —$NR^bS(=O)_2R^a$, —S(=O)NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —OR$^b$, —S(=O)R$^a$, —NO$_2$, —NR$^c$R$^d$, —S(=O)$_2$ R$^a$, —S(=O)$_2$NR$^c$R$^d$, —C(=O)R$^a$, —C(=O)OR$^b$, —C(=O)NR$^c$R$^d$, C$_1$-C$_6$ alkyl, C$_1$-C$_6$ haloalkyl, C$_2$-C$_6$ alkenyl, or C$_2$-C$_6$ alkynyl;

R$^{21}$ and R$^{22}$ are independently hydrogen, C$_1$-C$_{20}$alkyl, cycloalkyl, heterocycloalkyl, aryl, heteroaryl, C$_1$-C$_6$ alkyl (aryl), C$_1$-C$_6$ alkyl(heteroaryl), C$_1$-C$_6$ alkyl(cycloalkyl), C$_1$-C$_6$ alkyl(heterocycloalkyl); wherein each alkyl, cycloalkyl, heterocycloalkyl, aryl, and heteroaryl is independently optionally substituted with one, two, or three R$^{21a}$;

or R$^{21}$ and R$^{22}$ are taken together with the atoms to which they are attached to form a heterocycloalkyl optionally substituted with one, two, or three R$^{21b}$;

each R$^{21a}$ and R$^{21b}$ is independently oxo (when feasible), halogen, —CN, —OR$^b$, —SR$^b$, —S(=O)R$^a$, —NO$_2$, —NR$^c$R$^d$, —S(=O)$_2$R$^2$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O))R$^a$, —NR$^b$C(=O) OR$^b$, C$_1$-C$_6$ alkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^a$ is independently C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

each R$^b$ is independently hydrogen, C$_1$-C$_6$ alkyl, C$_2$-C$_6$ alkenyl, C$_2$-C$_6$ alkynyl, C$_1$-C$_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl; and each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

or R$^c$ and R$^d$ are taken together with the nitrogen atom to which they are attached to form a heterocycloalkyl optionally substituted with one, two, or three oxo, halogen, C$_1$-C$_6$ alkyl, or C$_1$-C$_6$ haloalkyl.

In some embodiments of a compound of Formula (III), Q$^3$ is N and Q$^4$ is CW. In some embodiments of a compound of Formula (III), Q$^4$ is N and Q$^3$ is CW. In some embodiments of a compound of Formula (III), Q$^3$ is N and Q$^4$ is N.

In some embodiments of a compound of Formula (III), each W is independently hydrogen, halogen, C$_1$-C$_6$ alkyl, or C$_1$-C$_6$ haloalkyl. In some embodiments of a compound of Formula (III), each W is independently hydrogen, halogen, or C$_1$-C$_6$alkyl. In some embodiments of a compound of Formula (III), each W is hydrogen.

In some embodiments of a compound of Formula (III), R$^3$ is halogen, —CN, —OR$^b$, —NR$^c$R$^d$, C$_1$-C$_6$ alkyl, C$_2$-C$_6$ alkynyl, C$_1$-C$_6$haloalkyl, C$_1$-C$_6$hydroxyalkyl, C$_1$-C$_6$ heteroalkyl, cycloalkyl, or heterocycloalkyl; wherein each alkyl, alkynyl, cycloalkyl, and heterocycloalkyl is independently optionally substituted with one, two, or three R$^{3a}$. In some embodiments of a compound of Formula (III), R$^3$ is halogen, C$_1$-C$_6$ alkyl, C$_2$-C$_6$ alkynyl, C$_1$-C$_6$ hydroxyalkyl, or C$_1$-C$_6$ heteroalkyl; wherein each alkyl and alkynyl is independently optionally substituted with one, two, or three R$^{3a}$.

In some embodiments of a compound of Formula (III), R$^3$ is halogen, —CN, —OR$^b$, —NR$^c$R$^d$, C$_1$-C$_6$ alkyl, C$_1$-C$_6$ haloalkyl, C$_1$-C$_6$ hydroxyalkyl, C$_1$-C$_6$ heteroalkyl, cycloalkyl, or heterocycloalkyl. In some embodiments of a compound of Formula (III), R$^3$ is halogen, C$_1$-C$_6$ alkyl, C$_1$-C$_6$ haloalkyl, C$_1$-C$_6$ hydroxyalkyl, C$_1$-C$_6$ heteroalkyl, cycloalkyl, or heterocycloalkyl. In some embodiments of a compound of Formula (III), R$^3$ is halogen, or C$_1$-C$_6$ hydroxyalkyl, C$_1$-C$_6$ heteroalkyl. In some embodiments of a compound of Formula (III), R$^3$ is halogen. In some embodiments of a compound of Formula (III), R$^3$ is not hydrogen.

In some embodiments of a compound of Formula (III), each R$^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$ fluoroalkyl, cycloalkyl, or heterocycloalkyl. In some embodiments of a compound of Formula (III), each R$^{3a}$ is independently oxo (when feasible) halogen, —CN, —OR$^b$, —NR$^c$R$^d$, C$_1$-C$_6$ alkyl, C$_1$-C$_6$ fluoroalkyl, cycloalkyl, or heterocycloalkyl. In some embodiments of a compound of Formula (III), each R$^{3a}$ is independently oxo (when feasible) halogen, C$_1$-C$_6$ alkyl, C$_1$-C$_6$ fluoroalkyl, cycloalkyl, or heterocycloalkyl. In some embodiments of a compound of Formula (III), each R$^{3a}$ is independently oxo (when feasible) halogen, C$_1$-C$_6$alkyl, or C$_1$-C$_6$ fluoroalkyl. In some embodiments of a compound of Formula (in), each R$^{3a}$ is independently halogen or C$_1$-C$_6$ alkyl. In some embodiments of a compound of Formula (III), each R$^{3a}$ is independently halogen, —OR$^b$, C$_1$-C$_6$ alkyl, or cycloalkyl.

In some embodiments of a compound of Formula (III), R$^1$ is C$_1$-C$_6$ alkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, cycloalkyl, heterocycloalkyl, aryl, and heteroaryl is independently optionally substituted with one, two, or three R$^{1a}$. In some embodiments of a compound of Formula (III), R$^1$ is cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, cycloalkyl, heterocycloalkyl, aryl, and heteroaryl is independently optionally substituted with one, two, or three R$^{1a}$. In some embodiments of a compound of Formula (III), R$^1$ is C$_1$-C$_6$ alkyl, cycloalkyl, aryl, heteroaryl, C$_1$-C$_6$ alkyl (aryl), C$_1$-C$_6$ alkyl(heteroaryl), or C$_1$-C$_6$ alkyl(cycloalkyl); wherein each alkyl, cycloalkyl, aryl, and heteroaryl is independently optionally substituted with one, two, or three R$^{1a}$. In some embodiments of a compound of Formula (III), R$^1$ is C$_1$-C$_6$ alkyl, cycloalkyl, C$_1$-C$_6$ alkyl(aryl), C$_1$-C$_6$ alkyl (heteroaryl), or C$_1$-C$_6$ alkyl(cycloalkyl); wherein each alkyl, cycloalkyl, aryl, and heteroaryl is independently optionally substituted with one, two, or three R$^{1a}$. In some embodiments of a compound of Formula (III), R$^1$ is C$_1$-C$_6$ alkyl, cycloalkyl, heterocycloalkyl, C$_1$-C$_6$ alkyl(aryl), C$_1$-C$_6$ alkyl (heteroaryl), C$_1$-C$_6$ alkyl(cycloalkyl), or C$_1$-C$_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (III), $R^1$ is cycloalkyl or $C_1$-$C_6$ alkyl(cycloalkyl); wherein each alkyl and cycloalkyl is independently optionally substituted with one, two, or three $R^{1a}$. In some embodiments of a compound of Formula (III), $R^1$ is cycloalkyl optionally substituted with one, two, or three $R^{1a}$.

In some embodiments of a compound of Formula (III), each $R^{1a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (III), each $R^{1a}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (III), each $R^{1a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (III), each $R^{1a}$ is independently oxo (when feasible) halogen, $C_1$-$C_6$ alkyl, or $C_1$-$C_6$ fluoroalkyl. In some embodiments of a compound of Formula (III), each $R^{1a}$ is independently halogen or $C_1$-$C_6$ alkyl.

In some embodiments of a compound of Formula (III), $R^2$ is hydrogen or $C_1$-$C_6$ alkyl. In some embodiments of a compound of Formula (III), $R^2$ is hydrogen. In some embodiments of a compound of Formula (III), $R^1$ and $R^2$ are taken together with the nitrogen atom to which they are attached to form a heterocycloalkyl optionally substituted with one, two, or three $R^{1b}$.

In some embodiments of a compound of Formula (III), each $R^{1b}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (III), each $R^{1b}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (III), each $R^{1b}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (III), each $R^{1b}$ is independently oxo (when feasible)halogen, $C_1$-$C_6$ alkyl, or $C_1$-$C_6$ fluoroalkyl. In some embodiments of a compound of Formula (III), each $R^{1b}$ is independently halogen or $C_1$-$C_6$ alkyl.

In some embodiments of a compound of Formula (III), $R^8$ is hydrogen or $C_1$-$C_6$ alkyl. In some embodiments of a compound of Formula (III), $R^8$ is hydrogen.

In some embodiments of a compound of Formula (III), $R^9$ and $R^{10}$ are independently hydrogen or $C_1$-$C_6$ alkyl. In some embodiments of a compound of Formula (III), $R^9$ and $R^{10}$ are hydrogen.

In some embodiments of a compound of Formula (III), X is —O— or —S—. In some embodiments of a compound of Formula (II), X is —O—. In some embodiments of a compound of Formula (III), X is —S—.

In some embodiments of a compound of Formula (III), A is —O—. In some embodiments of a compound of Formula (III), A is —$CH_2$—.

In some embodiments of a compound of Formula (III), $R^5$ and $R^6$ are independently hydrogen, halogen, —$OR^b$, $C_1$-$C_6$ alkyl, or $C_1$-$C_6$ haloalkyl. In some embodiments of a compound of Formula (III), $R^5$ and $R^6$ are independently hydrogen, halogen, —$OR^b$, or $C_1$-$C_6$ alkyl. In some embodiments of a compound of Formula (III), $R^5$ and $R^6$ are hydrogen.

In some embodiments of a compound of Formula (III), $R^4$ and $R^7$ are independently hydrogen, halogen, —$OR^b$, $C_1$-$C_6$ alkyl, or $C_1$-$C_6$ haloalkyl. In some embodiments of a compound of Formula (III), $R^4$ and $R^7$ are independently hydrogen, halogen, —$OR^b$, or $C_1$-$C_6$ alkyl. In some embodiments of a compound of Formula (III), $R^4$ and $R^7$ are independently hydrogen, halogen, or —$OR^b$. In some embodiments of a compound of Formula (III), $R^4$ and $R^7$ are independently hydrogen, halogen, or —OH. In some embodiments of a compound of Formula (III), $R^4$ and $R^7$ are independently halogen or —OH. In some embodiments of a compound of Formula (III), $R^4$ and $R^7$ are independently hydrogen or —OH. In some embodiments of a compound of Formula (III), $R^4$ and $R^7$ are —OH.

In some embodiments of a compound of Formula (III), $R^5$ and $R^6$ are hydrogen and $R^4$ and $R^7$ are —OH. In some embodiments of a compound of Formula (III), $R^5$ and $R^6$ are hydrogen and $R^4$ and $R^7$ are independently halogen or —OH. In some embodiments of a compound of Formula (III), $R^5$ and $R^6$ are hydrogen and $R^4$ and $R^7$ are independently hydrogen or —OH.

In some embodiments of a compound of Formula (III), $R^{21}$ and $R^{22}$ are independently hydrogen, $C_1$-$C_{20}$ alkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{21a}$. In some embodiments of a compound of Formula (III), $R^{21}$ and $R^{22}$ are independently hydrogen, $C_1$-$C_{20}$alkyl or aryl; wherein each alkyl and aryl is independently optionally substituted with one, two, or three $R^{21a}$. In some embodiments of a compound of Formula (III), $R^{21}$ and $R^{22}$ are independently hydrogen, $C_1$-$C_{20}$ alkyl optionally substituted with one, two, or three $R^{21a}$. In some embodiments of a compound of Formula (III), $R^{21}$ and $R^{22}$ are hydrogen.

In some embodiments of a compound of Formula (III), each $R^{21a}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC$(=O)$NR^cR^d$, —$NR^bC$(=O)$R^a$, —$NR^bC$(=O)$OR^b$, or $C_1$-$C_6$ alkyl. In some embodiments of a compound of Formula (III), each $R^{21a}$ is independently —C(=O)$R^a$, —OC(=O)$R^a$, —C(=O)$OR^b$, —OC(=O)$OR^b$, or —OC(=O)$NR^cR^d$. In some embodiments of a compound of Formula (III), each $R^{21a}$ is independently —C(=O)$OR^b$ or —OC(=O)$OR^b$.

In some embodiments of a compound of Formula (III), $R^{21}$ and $R^{22}$ are taken together with the atoms to which they are attached to form a heterocycloalkyl optionally substituted with one, two, or three $R^{21b}$.

In some embodiments of a compound of Formula (III), each $R^{21b}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, cycloalkyl, or heterocycloalkyl. In some embodiments of a compound of Formula (III), each $R^{21b}$ is independently halogen, —CN, —$OR^b$, —$NR^cR^d$, $C_1$-$C_6$ alkyl, cycloalkyl, or heterocycloalkyl. In some embodiments of a compound of Formula (III), each $R^{21b}$ is independently halogen or $C_1$-$C_6$ alkyl.

In some embodiments of a compound of Formula (III), $R^{12}$ is hydrogen, halogen, —CN, —$OR^{13}$, —$NR^{15}R^{16}$, —C(=O)$R^{14}$, —C(=O)$OR^{13}$, —C(=O)$NR^{15}R^{16}$, $C_1$-$C_6$alkyl, $C_1$-$C_6$haloalkyl, $C_1$-$C_6$hydroxyalkyl, $C_1$-$C_6$ heteroalkyl, cycloalkyl, or heterocycloalkyl. In some embodiments of a compound of Formula (III), $R^{12}$ is halogen, —CN, —$OR^{13}$, —$NR^{15}R^{16}$, —C(=O)$R^{14}$, —C(=O)$OR^{13}$, —C(=O)NR$^{15}$R$^{16}$, C$_1$-C$_6$alkyl, C$_1$-C$_6$haloalkyl, C$_1$-C$_6$ hydroxyalkyl, C$_1$-C$_6$ heteroalkyl, cycloalkyl, or heterocycloalkyl. In some embodiments of a compound of Formula (III), R$^{12}$ is hydrogen, halogen, C$_1$-C$_6$ alkyl, C$_1$-C$_6$ haloalkyl, or C$_1$-C$_6$ hydroxyalkyl. In some embodiments of a compound of Formula (III), R$^{12}$ is halogen, C$_1$-C$_6$alkyl, C$_1$-C$_6$haloalkyl, or C$_1$-C$_6$ hydroxyalkyl. In some embodiments of a compound of Formula (III), R$^2$ is C$_1$-C$_6$alkyl. In some embodiments of a compound of Formula (III), R$^1$ is C$_1$-C$_6$ hydroxyalkyl. In some embodiments of a compound of Formula (III), R$^{12}$ is hydrogen. In some embodiments of a compound of Formula (III), R$^{12}$ is not hydrogen.

In some embodiments of a compound of Formula (III), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11c}$. In some embodiments of a compound of Formula (III), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, cycloalkyl, heterocycloalkyl, aryl, or heteroaryl; wherein each cycloalkyl, heterocycloalkyl, aryl, and heteroaryl is independently optionally substituted with one, two, or three R$^{11c}$. In some embodiments of a compound of Formula (III), each R$^{12a}$ is independently —OR$^{13}$, —S(=O)$_2$R$^{14}$, —NR$^{13}$C(=O)R$^{14}$, cycloalkyl, aryl, or heteroaryl; wherein each cycloalkyl, aryl, and heteroaryl is independently optionally substituted with one, two, or three R$^{11c}$.

In some embodiments of a compound of Formula (III), R$^{11}$ is halogen, —CN, —OR$^{13}$, —NR$^{15}$R$^{16}$, —S(=O)$_2$R$^{14}$, —C(=O)R$^{14}$, —C(=O)OR$^{13}$, —C(=O)NR$^{15}$R$^{16}$, C$_1$-C$_6$ alkyl, C$_1$-C$_6$haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$.

In some embodiments of a compound of Formula (III), R$^{11}$ is R$^{11}$ is halogen, —CN, —OR$^{13}$, —NR$^{15}$R$^{16}$, —S(=O)$_2$ R$^{14}$, —C(=O)R$^{14}$, C$_1$-C$_6$ alkyl, C$_1$-C$_6$haloalkyl, C$_1$-C$_6$hydroxyalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$; provided that R$^{11}$ is not CF$_3$.

In some embodiments of a compound of Formula (III), R$^{11}$ is halogen, —CN, —OR$^{13}$, ..NR$^{13}$R$^{16}$, —S(=O)$_2$R$^{14}$, —C(=O)R$^{14}$, C$_1$-C$_6$ alkyl, C$_1$-C$_6$ haloalkyl, C$_1$-C$_6$ hydroxyalkyl, C$_1$-C$_6$heteroalkyl, cycloalkyl, heterocycloalkyl, or aryl; wherein each alkyl, cycloalkyl, heterocycloalkyl, and aryl is independently optionally substituted with one, two, or three R$^{11a}$.

In some embodiments of a compound of Formula (III), R$^{11}$ is halogen, —CN, —OR$^{13}$, —NR$^{15}$R$^{16}$, —S(=O)$_2$R$^{14}$, —C(=O)R$^{14}$, —C(=O)NR$^{15}$R$^{16}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$.

In some embodiments of a compound of Formula (III), R$^{11}$ is halogen, —CN, —OR$^{13}$, —NR$^{15}$R$^{16}$, —S(=O)$_2$R$^{14}$, —C(=O)R$^{14}$, —C(=O)OR$^{13}$, —C(=O)NR$^{15}$R$^{16}$, C$_1$-C$_6$ alkyl, C$_1$-C$_6$haloalkyl, C$_1$-C$_6$hydroxyalkyl, C$_1$-C$_6$ heteroalkyl, cycloalkyl, heterocycloalkyl, or aryl; wherein each alkyl, cycloalkyl, heterocycloalkyl, and aryl is independently optionally substituted with one, two, or three R$^{11a}$.

In some embodiments of a compound of Formula (III), R$^{11}$ is halogen, —CN, —OR$^{13}$, —NR$^{15}$R$^{16}$, —S(=O)$_2$R$^{14}$, —C(=O)R$^{14}$, —C(=O)OR$^{13}$, C$_1$-C$_6$alkyl, C$_1$-C$_6$haloalkyl, C$_1$-C$_6$hydroxyalkyl, C$_1$-C$_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$.

In some embodiments of a compound of Formula (III), R$^{11}$ is halogen, —CN, —S(=O)$_2$R$^{14}$, —C(=O)R$^{14}$, —C(=O)OR$^{13}$, C$_1$-C$_6$ alkyl, C$_1$-C$_6$ haloalkyl, C$_1$-C$_6$ hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$.

In some embodiments of a compound of Formula (III), R$^{11}$ is halogen, —CN, —S(=O)$_2$R$^{14}$, —C(=O)R$^{14}$, C$_1$-C$_6$alkyl, C$_1$-C$_6$haloalkyl, C$_1$-C$_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$; provided that R$^{11}$ is not CF$_3$.

In some embodiments of a compound of Formula (III), R$^{11}$ is halogen, —CN, —S(=O)$_2$R$^{14}$, —C(=O)R$^{14}$, C$_1$-C$_6$ alkyl, C$_1$-C$_6$ haloalkyl, C$_1$-C$_6$ hydroxyalkyl, cycloalkyl, heterocycloalkyl, or aryl; wherein each alkyl, cycloalkyl, heterocycloalkyl, and aryl is independently optionally substituted with one, two, or three R$^{11a}$.

In some embodiments of a compound of Formula (III), R$^{11}$ is halogen, —CN, —S(=O)$_2$R$^{14}$, —C(=O)R$^{14}$, C$_1$-C$_6$alkyl, C$_1$-C$_6$haloalkyl, C$_1$-C$_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$.

In some embodiments of a compound of Formula (III), R$^{11}$ is halogen, —CN, —S(=O)$_2$R$^{14}$, —C(=O)R$^{14}$, —C(=O)OR$^{13}$, C$_1$-C$_6$ alkyl, C$_1$-C$_6$ haloalkyl, C$_1$-C$_6$ hydroxyalkyl, cycloalkyl, heterocycloalkyl, or aryl; wherein each alkyl, cycloalkyl, heterocycloalkyl, and aryl is independently optionally substituted with one, two, or three R$^{11a}$.

In some embodiments of a compound of Formula (III), R$^{11}$ is —CN, —S(=O)$_2$R$^{14}$, —C(=O)OR$^{13}$, C$_1$-C$_6$ alkyl, C$_1$-C$_6$ haloalkyl, C$_1$-C$_6$ hydroxyalkyl, or heteroaryl; wherein each alkyl and heteroaryl is independently optionally substituted with one, two, or three R$^{11a}$.

In some embodiments of a compound of Formula (III), R$^{11}$ is —CN, —S(=O)$_2$R$^{14}$, C$_1$-C$_6$ alkyl, C$_1$-C$_6$ haloalkyl, C$_1$-C$_6$ hydroxyalkyl, or heteroaryl; wherein each alkyl and heteroaryl is independently optionally substituted with one, two, or three R$^{11a}$; provided that R$^{11}$ is not CF$_3$.

In some embodiments of a compound of Formula (III), R$^{11}$ is —CN, —S(=O)$_2$R$^{14}$, C$_1$-C$_6$ alkyl, C$_1$-C$_6$ haloalkyl, or C$_1$-C$_6$ hydroxyalkyl; wherein each alkyl is independently optionally substituted with one, two, or three R$^{11a}$.

In some embodiments of a compound of Formula (III), R$^{11}$ is —CN, —S(=O)$_2$R$^{14}$, C$_1$-C$_6$ alkyl, C$_1$-C$_6$ haloalkyl, C$_1$-C$_6$ hydroxyalkyl, or heteroaryl; wherein each alkyl and heteroaryl is independently optionally substituted with one, two, or three R$^{11a}$.

In some embodiments of a compound of Formula (III), R$^{11}$ is —CN, —S(=O)$_2$R$^{14}$, —C(=O)OR$^{13}$, C$_1$-C$_6$ alkyl, $C_1$-$C_6$ haloalkyl, or $C_1$-$C_6$ hydroxyalkyl; wherein each alkyl is independently optionally substituted with one, two, or three $R^{11a}$.

In some embodiments of a compound of Formula (III), $R^{11}$ is $C_1$-$C_6$ alkyl optionally substituted with one, two, or three $R^{11a}$. In some embodiments of a compound of Formula (III), $R^{11}$ is $C_1$-$C_6$ alkyl optionally substituted with one, two, or three $R^{11a}$; provided that $R^{11}$ is not $CF_3$. In some embodiments of a compound of Formula (III), $R^{11}$ is $C_1$-$C_6$ alkyl substituted with one $R^{11a}$. In some embodiments of a compound of Formula (III), $R^{11}$ is $C_1$-$C_6$ hydroxyalkyl.

In some embodiments of a compound of Formula (III), $R^{11}$ is not $CF_3$.

In some embodiments of a compound of Formula (III), each $R^{11}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R_{16}$, —$NR^{13}C(=O)R^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (III), each $R^{11a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R^{16}$, —$NR^{13}C(=O)R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11c}$. In some embodiments of a compound of Formula (III), each $R^{11a}$ is independently —$OR^{13}$, —$S(=O)_2R^{14}$, —$NR^{13}C(=O)R^{14}$, cycloalkyl, aryl, or heteroaryl; wherein each cycloalkyl, aryl, and heteroaryl is independently optionally substituted with one, two, or three $R^{11c}$. In some embodiments of a compound of Formula (III), each $R^{11a}$ is independently aryl optionally substituted with one, two, or three $R^{11c}$.

In some embodiments of a compound of Formula (III), each $R^{11a}$ is independently —$OR^{13}$. In some embodiments of a compound of Formula (III), each $R^{11a}$ is independently —$S(=O)_2R^{14}$. In some embodiments of a compound of Formula (III), each $R^{11a}$ is independently cycloalkyl optionally substituted with one, two, or three $R^{11c}$. In some embodiments of a compound of Formula (III), each $R^{11a}$ is independently —$NR^{13}C(=O)R^{14}$.

In some embodiments of a compound of Formula (III), each $R^{11c}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, or $C_1$-$C_6$haloalkyl. In some embodiments of a compound of Formula (III), each $R^{11c}$ is independently halogen, —CN, —$OR^b$, —$NR^cR^d$, $C_1$-$C_6$ alkyl, or $C_1$-$C_6$haloalkyl. In some embodiments of a compound of Formula (III), each $R^{11c}$ is independently halogen, $C_1$-$C_6$ alkyl, or $C_1$-$C_6$ haloalkyl.

In some embodiments of a compound of Formula (III), $R^{11}$ and $R^{12}$ are taken together to form a cycloalkyl or heterocycloalkyl each optionally substituted with one, two, or three $R^{11b}$. In some embodiments of a compound of Formula (III), $R^{11}$ and $R^{12}$ are taken together to form a cycloalkyl optionally substituted with one, two, or three $R^{11b}$. In some embodiments of a compound of Formula (III), $R^{11}$ and $R^{12}$ are taken together to form a heterocycloalkyl optionally substituted with one, two, or three $R^{11b}$.

In some embodiments of a compound of Formula (III), each $R^{11b}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, or $C_1$-$C_6$haloalkyl. In some embodiments of a compound of Formula (III), each $R^{11b}$ is independently oxo (when feasible), halogen, —CN, —$OR^b$, —$NR^cR^d$, $C_1$-$C_6$ alkyl, or $C_1$-$C_6$ haloalkyl. In some embodiments of a compound of Formula (III), each $R^{11b}$ is independently oxo (when feasible), halogen, $C_1$-$C_6$alkyl, or $C_1$-$C_6$haloalkyl.

In some embodiments of a compound of Formula (III), each $R^{13}$ is independently hydrogen, $C_1$-$C_6$ alkyl, $C_1$-$C_6$ haloalkyl, $C_1$-$C_6$heteroalkyl, cycloalkyl, or heterocycloalkyl; wherein each alkyl, cycloalkyl, and heterocycloalkyl is independently optionally substituted with one, two, or three $R^{13}$. In some embodiments of a compound of Formula (III), each $R^{13}$ is independently hydrogen, $C_1$-$C_6$ alkyl, or $C_1$-$C_4$ haloalkyl; wherein each alkyl is independently optionally substituted with one, two, or three $R^{13a}$. In some embodiments of a compound of Formula (III), each $R^{13}$ is independently hydrogen or $C_1$-$C_6$ alkyl.

In some embodiments of a compound of Formula (III), each $R^{13a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, $C_1$-$C_6$haloalkyl, cycloalkyl, or heterocycloalkyl. In some embodiments of a compound of Formula (III), each $R^{13a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (III), each $R^{13a}$ is independently halogen, $C_1$-$C_6$ alkyl, or $C_1$-$C_6$ haloalkyl.

In some embodiments of a compound of Formula (III), each $R^{14}$ is independently $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{14a}$. In some embodiments of a compound of Formula (III), each $R^{14}$ is independently $C_1$-$C_6$ alkyl, or $C_1$-$C_6$ haloalkyl; wherein each alkyl is independently optionally substituted with one, two, or three $R^{14a}$. In some embodiments of a compound of Formula (III), each $R^{14}$ is independently $C_1$-$C_6$ alkyl.

In some embodiments of a compound of Formula (III), each $R^{14a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, $C_1$-$C_6$haloalkyl, cycloalkyl, or heterocycloalkyl. In some embodiments of a compound of Formula (III), each $R^{14a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (III), each $R^{14a}$ is independently halogen, $C_1$-$C_6$alkyl, or $C_1$-$C_6$ haloalkyl.

In some embodiments of a compound of Formula (III), each $R^{15}$ and $R^{16}$ is independently hydrogen, $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{15a}$. In some embodiments of a compound of Formula (III), each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$. In some embodiments of a compound of Formula (III), each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$. In some embodiments of a compound of Formula (III), each $R^{15}$ and $R^{16}$ is independently hydrogen or $C_1$-$C_6$ alkyl.

In some embodiments of a compound of Formula (III), each $R^{14a}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, $C_1$-$C_6$haloalkyl, cycloalkyl, or heterocycloalkyl. In some embodiments of a compound of Formula (III), each $R^{14a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (III), each $R^{15a}$ is independently halogen, $C_1$-$C_6$alkyl, or $C_1$-$C_6$ haloalkyl.

In some embodiments of a compound of Formula (III), $R^{15}$ and $R^{16}$ are taken together with the nitrogen atom to which they are attached to form a heterocycloalkyl optionally substituted with one, two, or three $R^{15b}$. In some embodiments of a compound of Formula (III), $R^{15}$ and $R^{16}$ are taken together with the nitrogen atom to which they are attached to form a heterocycloalkyl.

In some embodiments of a compound of Formula (III), each $R^{15b}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, or heterocycloalkyl. In some embodiments of a compound of Formula (III), each $R^{15a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (III), each $R^{15b}$ is independently halogen, $C_1$-$C_6$ alkyl, or $C_1$-$C_6$ haloalkyl.

In some embodiments provided herein is a compound having the structure of Formula (IV), or a pharmaceutically acceptable salt, solvate, stereoisomer, or isotopic variant thereof:

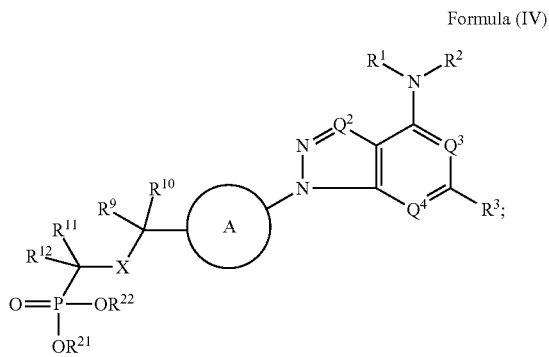

Formula (IV)

wherein:
Ring A is

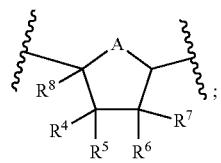

$Q^2$ is N or CW;
$Q^3$ is N and $Q^4$ is CW;
or $Q^3$ is CW and $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O— or —$CH_2$—;
X is —O—, —S—, —S(=O)$_2$—, —$NR^{17}$—, or —C($R^{18}$)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl (heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;

$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^8$ is hydrogen, halogen, —$OR^b$, —$NR^cR^d$, $C_1$-$C_6$ alkyl, or $C_1$-$C_6$ haloalkyl;

$R^9$ and $R^{10}$ are independently hydrogen, halogen, $C_1$-$C_6$ alkyl, or $C_1$-$C_6$ haloalkyl;

$R^{11}$ is hydrogen, halogen, —CN, —$OR^{13}$, —$SR^{13}$, —S(=O)$R^{14}$, —$NO_2$, —$NR^{15}R^{16}$, —S(=O)$_2R^{14}$, —NR S(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O) $NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;

$R^{12}$ is hydrogen, halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$ (=O)$NR^{15}R^{16}$, —$NR^{13}C$(=O)$R^{14}$, —$NR^{13}C$(=O) $OR^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;

or R$^{11}$ and R$^{12}$ are taken together to form a cycloalkyl or heterocycloalkyl each optionally substituted with one, two, or three R$^{11b}$;

each R$^{11a}$, R$^{11b}$, and R$^{12a}$ is independently oxo (when feasible), halogen, —CN, —OR$^{13}$, —SR$^{13}$, —S(=O) R$^{14}$, —NO$_2$, —NR$^{15}$R$^{16}$, —S(=O)$_2$R$^{14}$, —NR$^{13}$S(=O)$_2$ R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$ alkyl, C$_1$-C$_6$haloalkyl, C$_2$-C$_6$ alkenyl, C$_2$-C$_6$ alkynyl, C$_1$-C$_6$hydroxyalkyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{11c}$;

each R$^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^{13}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{13a}$;

each R$^{14}$ is independently C$_1$-C$_6$ alkyl, C$_1$-C$_6$haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{14a}$;

each R$^{15}$ and R$^{16}$ is independently hydrogen, C$_1$-C$_6$ alkyl, C$_1$-C$_6$ haloalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^{15a}$;

or R$^{15}$ and R$^{16}$ are taken together with the nitrogen atom to which they are attached to form a heterocycloalkyl optionally substituted with one, two, or three R$^{15b}$;

each R$^{13a}$, R$^{14a}$, R$^{15a}$, and R$^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —OR$^b$, —S(=O)R$^a$, —NO$_2$, —NR$^c$R$^d$, —S(=O)$_2$ R$^a$, —S(=O)$_2$NR$^c$R$^d$, —C(=O)R$^a$, —C(=O)OR$^b$, —C(=O)NR$^c$R$^d$, C$_1$-C$_6$alkyl, C$_1$-C$_6$ haloalkyl, C$_2$-C$_6$ alkenyl, or C$_2$-C$_6$ alkynyl;

R$^{17}$ is hydrogen, —CN, —OR$^b$, —S(=O)R$^a$, —C(=O)R$^a$, —C(=O)OR$^b$, —C(=O)NR$^c$R$^d$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^{18}$ is independently hydrogen, halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O) OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, C$_1$-C$_6$haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^{21}$ and R$^{22}$ are independently hydrogen, C$_1$-C$_{20}$alkyl, cycloalkyl, heterocycloalkyl, aryl, heteroaryl, C$_1$-C$_6$ alkyl (aryl), C$_1$-C$_6$ alkyl(heteroaryl), C$_1$-C$_6$ alkyl(cycloalkyl), C$_1$-C$_6$ alkyl(heterocycloalkyl); wherein each alkyl, cycloalkyl, heterocycloalkyl, aryl, and heteroaryl is independently optionally substituted with one, two, or three R$^{21a}$;

or R$^{21}$ and R$^{22}$ are taken together with the atoms to which they are attached to form a heterocycloalkyl optionally substituted with one, two, or three R$^{21b}$;

each R$^{21a}$ and R$^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$ NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O) OR$^b$, C$_1$-C$_6$ alkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

each R$^a$ is independently C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

each R$^b$ is independently hydrogen, C$_1$-C$_6$ alkyl, C$_2$-C$_6$ alkenyl, C$_2$-C$_6$ alkynyl, C$_1$-C$_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl; and each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, C$_1$-C$_6$ alkyl, or C$_1$-C$_6$ haloalkyl;

or R$^c$ and R$^d$ are taken together with the nitrogen atom to which they are attached to form a heterocycloalkyl optionally substituted with one, two, or three oxo, halogen, C$_1$-C$_6$ alkyl, or C$_1$-C$_6$ haloalkyl.

In some embodiments provided herein is a compound having the structure of Formula (IV), or a pharmaceutically acceptable salt, solvate, stereoisomer, or isotopic variant thereof:

Formula (IV)

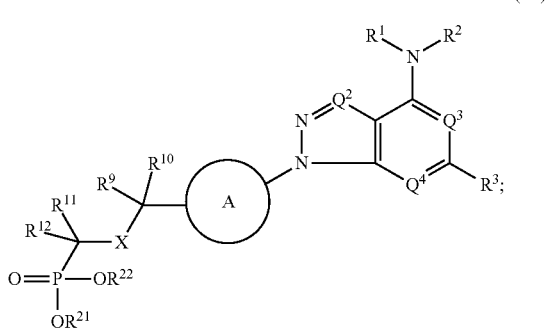

wherein:
Ring A is

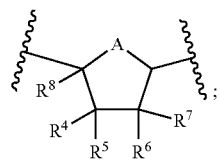

$Q^2$ is N or CW;
$Q^3$ is N and $Q^4$ is CW;
or $Q^3$ is CW and $Q^4$ is N;
each W is independently hydrogen, halogen, —CN, —OR$^b$, NR$^c$R$^d$, $C_1$-$C_6$ alkyl, or $C_1$-$C_6$ haloalkyl;
A is —O— or —CH$_2$—;
X is —O—, —S—, —S(=O)$_2$—, —NR$^{17}$—, or —C(R$^{18}$)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{1a}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ fluoroalkyl, $C_2$-$C_6$ alkenyl, $C_1$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
$R^3$ is hydrogen, halogen, —CN, —OR$^b$, —SR$^b$, —NR$^c$R$^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;
each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;
$R^4$ and $R^7$ are independently hydrogen, halogen, —OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^8$ is hydrogen, halogen, —OR$^b$, —NR$^c$R$^d$, $C_1$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$alkyl, $C_1$-$C_6$haloalkyl, $C_2$-$C_6$ alkenyl, $C_2$-$C_6$ alkynyl, $C_1$-$C_6$hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$ haloalkyl, $C_2$-$C_6$ alkenyl, $C_2$-$C_4$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{17}$ is hydrogen, —CN, —$OR^b$, —$S(=O)_2R^a$, —$C(=O)R^a$, —$C(=O)OR^b$, —$C(=O)NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{18}$ is independently hydrogen, halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_1$-$C_6$haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —$S(=O)R^a$, —$NO_2$, —$NR^cR^d$, —$S(=O)_2R^a$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl, wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments of a compound of Formula (IV), $Q^2$ is CW. In some embodiments of a compound of Formula (IV), $Q^2$ is N.

In some embodiments of a compound of Formula (IV), $Q^3$ is N and $Q^4$ is CW. In some embodiments of a compound of Formula (IV), $Q^4$ is N and $Q^3$ is CW.

In some embodiments of a compound of Formula (IV), $Q^2$ is CW, $Q^1$ is N, and $Q^4$ is CW. In some embodiments of a compound of Formula (IV), $Q^2$ is CW, $Q^1$ is CW, and $Q^4$ is N. In some embodiments of a compound of Formula (IV), $Q^2$ is N, $Q^3$ is N, and $Q^4$ is CW. In some embodiments of a compound of Formula (IV), $Q^2$ is N, $Q^3$ is CW, and $Q^4$ is N.

In some embodiments of a compound of Formula (IV), each W is independently hydrogen, halogen, $C_1$-$C_6$ alkyl, or $C_1$-$C_6$ haloalkyl. In some embodiments of a compound of Formula (IV), each W is independently hydrogen, halogen, or $C_1$-$C_6$alkyl. In some embodiments of a compound of Formula (IV), each W is hydrogen.

In some embodiments of a compound of Formula (IV), $R^3$ is halogen, —CN, —$OR^b$, —$NR^cR^d$, $C_1$-$C_6$ alkyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, or heterocycloalkyl; wherein each alkyl, alkynyl, cycloalkyl, and heterocycloalkyl is independently optionally substituted with one, two, or three $R^{3a}$. In some embodiments of a compound of Formula (IV), $R^3$ is halogen, $C_1$-$C_6$ alkyl, $C_2$-$C_6$ alkynyl, $C_1$-$C_6$ hydroxyalkyl, or $C_1$-$C_6$ heteroalkyl; wherein each alkyl and alkynyl is independently optionally substituted with one, two, or three $R^{3a}$. In some embodiments of a compound of Formula (IV), $R^3$ is halogen, —CN, —$OR^b$, —$NR^cR^d$, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (IV), $R^3$ is halogen, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (IV), $R^3$ is halogen, or $C_1$-$C_6$ hydroxyalkyl, $C_1$-$C_6$ heteroalkyl. In some embodiments of a compound of Formula (IV), $R^3$ is halogen. In some embodiments of a compound of Formula (IV), $R^3$ is halogen, —$OR^b$, $C_1$-$C_6$ alkyl, $C_2$-$C_6$ alkynyl, $C_1$-$C_6$ haloalkyl, $C_1$-$C_6$ hydroxyalkyl, or $C_1$-$C_6$ heteroalkyl; wherein each alkyl and alkynyl is independently optionally substituted with one, two, or three $R^{3a}$. In some embodiments of a compound of Formula (IV), $R^3$ is halogen, —$OR^b$, $C_2$-$C_6$ alkynyl, or $C_1$-$C_6$ hydroxyalkyl; wherein each alkyl and alkynyl is independently optionally substituted with one, two, or three $R^{3a}$. In some embodiments of a compound of Formula (IV), $R^3$ is halogen or $C_1$-$C_6$ hydroxyalkyl.

In some embodiments of a compound of Formula (IV), each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{3a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{3a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (IV), each $R^{3a}$ is independently oxo (when feasible) halogen, $C_1$-$C_6$ alkyl, or $C_1$-$C_6$ fluoroalkyl. In some embodiments of a compound of Formula (IV), each $R^{3a}$ is independently halogen or $C_1$-$C_6$ alkyl. In some embodiments of a compound of Formula (IV), each $R^{3a}$ is independently halogen, —OR$^b$ $C_1$-$C_6$ alkyl, or cycloalkyl. In some embodiments of a compound of Formula (IV), each $R^{3a}$ is independently oxo (when feasible) halogen, or —OR$^b$.

In some embodiments of a compound of Formula (IV), $R^1$ is $C_1$-$C_6$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (IV), $R^1$ is $C_1$-$C_6$ alkyl, cycloalkyl, heterocycloalkyl, $C_1$-$C_6$ alkyl (aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (IV), $R^1$ is cycloalkyl or $C_1$-$C_6$ alkyl(cycloalkyl); wherein each alkyl and cycloalkyl is independently optionally substituted with one, two, or three $R^{1a}$. In some embodiments of a compound of Formula (IV), $R^1$ is cycloalkyl optionally substituted with one, two, or three $R^{1a}$. In some embodiments of a compound of Formula (IV), $R^1$ is $C_1$-$C_6$ alkyl, $C_1$-$C_6$ haloalkyl, cycloalkyl, heterocycloalkyl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (IV), $R^1$ is $C_1$-$C_6$ alkyl, cycloalkyl, $C_1$-$C_6$ alkyl(aryl), or $C_1$-$C_6$ alkyl(cycloalkyl); wherein each alkyl, cycloalkyl, and aryl is independently optionally substituted with one, two, or three $R^{1a}$. In some embodiments of a compound of Formula (IV), $R^1$ is cycloalkyl or $C_1$-$C_6$ alkyl(cycloalkyl).

In some embodiments of a compound of Formula (IV), each $R^{1a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{1a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{1a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (IV), each $R^{1a}$ is independently oxo (when feasible) halogen, $C_1$-$C_6$alkyl, or $C_1$-$C_6$ fluoroalkyl. In some embodiments of a compound of Formula (IV) each $R^{1a}$ is independently halogen or $C_1$-$C_6$ alkyl. In some embodiments of a compound of Formula (IV), each $R^{1a}$ is independently oxo (when feasible) halogen, —OR$^b$, $C_1$-$C_6$alkyl, or $C_1$-$C_6$ fluoroalkyl. In some embodiments of a compound of Formula (IV), each $R^{1a}$ is independently halogen or $C_1$-$C_6$ alkyl.

In some embodiments of a compound of Formula (IV), $R^2$ is hydrogen or $C_1$-$C_6$ alkyl. In some embodiments of a compound of Formula (IV), $R^2$ is hydrogen. In some embodiments of a compound of Formula (IV), $R^1$ and $R^2$ are taken together with the nitrogen atom to which they are attached to form a heterocycloalkyl optionally substituted with one, two, or three $R^{1b}$.

In some embodiments of a compound of Formula (IV), each $R^{1b}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{1b}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (IV), each $R^{1b}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (IV), each $R^{1b}$ is independently oxo (when feasible) halogen, $C_1$-$C_6$ alkyl, or $C_1$-$C_6$ fluoroalkyl. In some embodiments of a compound of Formula (IV), each $R^{1b}$ is independently halogen or $C_1$-$C_6$ alkyl.

In some embodiments of a compound of Formula (IV), $R^8$ is hydrogen or $C_1$-$C_6$ alkyl. In some embodiments of a compound of Formula (IV), $R^8$ is hydrogen.

In some embodiments of a compound of Formula (IV), $R^9$ and $R^{10}$ are independently hydrogen or $C_1$-$C_6$ alkyl. In some embodiments of a compound of Formula (IV), $R^9$ and $R^{10}$ are hydrogen.

In some embodiments of a compound of Formula (IV), A is —O—. In some embodiments of a compound of Formula (IV), A is —CH$_2$—.

In some embodiments of a compound of Formula (IV), $R^5$ and $R^6$ are independently hydrogen, halogen, —OR$^b$, $C_1$-$C_6$ alkyl, or $C_1$-$C_6$ haloalkyl. In some embodiments of a compound of Formula (IV), $R^5$ and $R^6$ are independently hydrogen, halogen, —OR$^b$, or $C_1$-$C_6$ alkyl. In some embodiments of a compound of Formula (IV), $R^5$ and $R^6$ are hydrogen.

In some embodiments of a compound of Formula (IV), $R^4$ and $R^7$ are independently hydrogen, halogen, —OR$^b$, $C_1$-$C_6$ alkyl, or $C_1$-$C_6$ haloalkyl. In some embodiments of a compound of Formula (IV), $R^4$ and $R^7$ are independently hydrogen, halogen, —OR$^b$, or $C_1$-$C_6$ alkyl. In some embodiments of a compound of Formula (IV), $R^4$ and $R^7$ are independently hydrogen, halogen, or —OR$^b$. In some embodiments of a compound of Formula (IV), $R^4$ and $R^7$ are independently hydrogen, halogen, or —OH. In some embodiments of a compound of Formula (IV), $R^4$ and $R^7$ are independently halogen or —OH. In some embodiments of a compound of Formula (IV), $R^4$ and $R^7$ are independently hydrogen or —OH. In some embodiments of a compound of Formula (IV), $R^4$ and $R^7$ are —OH.

In some embodiments of a compound of Formula (IV), $R^5$ and $R^6$ are hydrogen and $R^4$ and $R^7$ are —OH. In some embodiments of a compound of Formula (IV), $R^5$ and $R^6$ are hydrogen and $R^4$ and $R^7$ are independently halogen or —OH. In some embodiments of a compound of Formula (IV), $R^5$ and $R^6$ are hydrogen and $R^4$ and $R^7$ are independently hydrogen or —OH.

In some embodiments of a compound of Formula (IV), X is —O— or —S(=O)$_2$—. In some embodiments of a compound of Formula (IV), X is —O—. In some embodiments of a compound of Formula (IV), X is —S(=O)$_2$—. In some embodiments of a compound of Formula (IV), X is —NR$^{17}$—. In some embodiments of a compound of Formula (IV), X is —C(R$^{18}$)$_2$—.

In some embodiments of a compound of Formula (IV), R$^{17}$ is hydrogen, —C(=O)R$^a$, —C(=O)OR$^b$, —C(=O)NR$^c$R$^d$, C$_1$-C$_6$ alkyl, C$_1$-C$_6$ fluoroalkyl, cycloalkyl, or heterocycloalkyl. In some embodiments of a compound of Formula (IV), R$^{17}$ is hydrogen, C$_1$-C$_6$alkyl, C$_1$-C$_6$ fluoroalkyl, cycloalkyl, or heterocycloalkyl. In some embodiments of a compound of Formula (IV), R$^{17}$ is hydrogen or C$_1$-C$_6$ alkyl. In some embodiments of a compound of Formula (IV), R$^{17}$ is hydrogen.

In some embodiments of a compound of Formula (IV), each R$^{18}$ is independently hydrogen, halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$haloalkyl, cycloalkyl, or heterocycloalkyl. In some embodiments of a compound of Formula (IV), each R$^{18}$ is independently hydrogen, halogen, —CN, —OR$^{13}$, —NR$^c$R$^d$, C$_1$-C$_6$alkyl, C$_1$-C$_6$ haloalkyl, cycloalkyl, or heterocycloalkyl. In some embodiments of a compound of Formula (IV), each R$^{18}$ is independently hydrogen, halogen, C$_1$-C$_6$ alkyl, or C$_1$-C$_6$ haloalkyl. In some embodiments of a compound of Formula (IV), each R$^{18}$ is independently hydrogen or halogen. In some embodiments of a compound of Formula (IV), each R$^{18}$ is hydrogen.

In some embodiments of a compound of Formula (IV), R$^{21}$ and R$^{22}$ are independently hydrogen, C$_1$-C$_{20}$ alkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{21a}$. In some embodiments of a compound of Formula (IV), R$^{21}$ and R$^{22}$ are independently hydrogen, C$_1$-C$_{20}$ alkyl or aryl; wherein each alkyl and aryl is independently optionally substituted with one, two, or three R$^{21a}$. In some embodiments of a compound of Formula (IV), R$^{21}$ and R$^{22}$ are independently hydrogen, C$_1$-C$_{20}$alkyl optionally substituted with one, two, or three R$^{21a}$. In some embodiments of a compound of Formula (IV), R$^{21}$ and R$^{22}$ are hydrogen.

In some embodiments of a compound of Formula (IV), each R$^{21a}$ is independently oxo (when feasible), halogen, —CN, —OR$^b$, —NR$^c$R$^d$, —C(=O)R$^a$, —OC(=O)R$^a$, —C(=O)OR$^b$, —OC(=O)OR$^b$, —OC(=O)NR$^c$R$^d$, —NR$^b$C(=O)NR$^c$R$^d$, —NR$^b$C(=O)R$^a$, —NR$^b$C(=O)OR$^b$, or C$_1$-C$_6$ alkyl. In some embodiments of a compound of Formula (IV), each R$^{21a}$ is independently —C(=O)R$^a$, —OC(=O)R$^a$, —C(=O)OR$^b$, —OC(=O)OR$^b$, or —OC(=O)NR$^c$R$^d$. In some embodiments of a compound of Formula (IV), each R$^{21a}$ is independently —C(=O)OR$^b$ or —OC(=O)OR$^b$.

In some embodiments of a compound of Formula (IV), R$^{21}$ and R$^{22}$ are taken together with the atoms to which they are attached to form a heterocycloalkyl optionally substituted with one, two, or three R$^{21b}$.

In some embodiments of a compound of Formula (IV), each R$^{21b}$ is independently oxo (when feasible), halogen, —CN, —OR$^b$, —NR$^c$R$^d$, —C(=O)R$^a$, —OC(=O)R$^a$, —C(=O)OR$^b$, —OC(=O)OR$^b$, —OC(=O)NR$^c$R$^d$, —NR$^b$C(=O)NR$^c$R$^d$, —NR$^b$C(=O)R$^a$, —NR$^b$C(=O)OR$^b$, C$_1$-C$_6$ alkyl, cycloalkyl, or heterocycloalkyl. In some embodiments of a compound of Formula (IV), each R$^{21b}$ is independently halogen, —CN, —OR$^b$, —NR$^c$R$^d$, C$_1$-C$_6$ alkyl, cycloalkyl, or heterocycloalkyl. In some embodiments of a compound of Formula (IV), each R$^{21b}$ is independently halogen or C$_1$-C$_6$ alkyl.

In some embodiments of a compound of Formula (IV), R$^{12}$ is hydrogen, halogen, —CN, —OR$^{13}$, —NR$^{15}$R$^{16}$, —C(=O)R$^{14}$, —C(=O)OR$^{13}$, —C(=O)NR$^{15}$R$^{16}$, C$_1$-C$_{26}$alkyl, C$_1$-C$_6$haloalkyl, C$_1$-C$_6$hydroxyalkyl, C$_1$-C$_6$ heteroalkyl, cycloalkyl, or heterocycloalkyl. In some embodiments of a compound of Formula (IV), R$^{12}$ is halogen, —CN, —OR$^{13}$, —NR$^{15}$R$^{16}$, —C(=O)R$^{14}$, —C(=O)OR$^{13}$, —C(=O)NR$^{15}$R$^{16}$, C$_1$-C$_6$alkyl, C$_1$-C$_6$haloalkyl, C$_1$-C$_6$ hydroxyalkyl, C$_1$-C$_6$ heteroalkyl, cycloalkyl, or heterocycloalkyl. In some embodiments of a compound of Formula (IV), R$^{12}$ is hydrogen, halogen, C$_1$-C$_6$ alkyl, C$_1$-C$_6$ haloalkyl, or C$_1$-C$_6$hydroxyalkyl. In some embodiments of a compound of Formula (IV), R$^{12}$ is C$_1$-C$_6$ alkyl. In some embodiments of a compound of Formula (IV), R$^{12}$ is C$_1$-C$_6$ hydroxyalkyl. In some embodiments of a compound of Formula (IV), R$^2$ is hydrogen. In some embodiments of a compound of Formula (IV), R$^2$ is not hydrogen. In some embodiments of a compound of Formula (IIV, R$^{12}$ is hydrogen, halogen, —OR$^{13}$, C$_1$-C$_6$ alkyl, C$_1$-C$_6$ haloalkyl, C$_1$-C$_6$ hydroxyalkyl, C$_2$-C$_6$ alkynyl, or C$_1$-C$_6$ heteroalkyl; wherein each alkyl and alkynyl is independently optionally substituted with one, two, or three R$^{12a}$. In some embodiments of a compound of Formula (IV), R$^{12}$ is hydrogen, C$_1$-C$_6$ alkyl, C$_1$-C$_6$ hydroxyalkyl, or C$_2$-C$_6$ alkynyl; wherein each alkyl and alkynyl is independently optionally substituted with one, two, or three R$^{12a}$. In some embodiments of a compound of Formula (IV), R$^{12}$ is hydrogen, halogen, —CN, —OR$^{13}$, —NR$^{15}$R$^{16}$, —C(=O)R$^{14}$, —C(=O)OR$^{13}$, —C(=O)NR$^{15}$R$^{16}$, C$_1$-C$_6$ alkyl, C$_1$-C$_6$ haloalkyl, C$_1$-C$_6$ hydroxyalkyl, C$_1$-C$_6$ heteroalkyl, cycloalkyl, or heterocycloalkyl. In some embodiments of a compound of Formula (IV), R$^{12}$ is hydrogen, halogen, C$_1$-C$_6$ alkyl, C$_1$-C$_6$ haloalkyl, or C$_1$-C$_6$ hydroxyalkyl.

In some embodiments of a compound of Formula (IV), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11c}$.

In some embodiments of a compound of Formula (IV), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, cycloalkyl, heterocycloalkyl, aryl, or heteroaryl; wherein each cycloalkyl, heterocycloalkyl, aryl, and heteroaryl is independently optionally substituted with one, two, or three R$^{11c}$.

In some embodiments of a compound of Formula (IV), each R$^{12a}$ is independently —OR$^{13}$, —S(=O)$_2$R$^{14}$, —NR$^{13}$C(=O)R$^{14}$, cycloalkyl, aryl, or heteroaryl; wherein each cycloalkyl, aryl, and heteroaryl is independently optionally substituted with one, two, or three R$^{11c}$. In some embodiments of a compound of Formula (IV), each R$^{12a}$ is independently oxo (when feasible), halogen, —CN, —OR$^{13}$, —SR$^{13}$, —S(=O)R$^{14}$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —C(=O)OR$^{13}$, —C(=O)NR$^{15}$R$^{16}$, —OC(=O)NR$^{15}$R$^{16}$, —NR$^{13}$C(=O)R$^{14}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (IV), each $R^{12a}$ is independently oxo (when feasible), halogen, —$OR^{13}$, —$SR^{13}$, —$NR^{15}R^{16}$, —$S(=O)_2R^{14}$, —$NR^{13}S(=O)_2R^{14}$, —$S(=O)_2NR^{15}R^{16}$, —$C(=O)OR^{13}$, —$OC(=O)NR^{15}R^{16}$, —$NR^{13}C(=O)R^{14}$, heterocycloalkyl, aryl, or heteroaryl wherein each heterocycloalkyl, aryl, and heteroaryl is independently optionally substituted with one, two, or three $R^{11c}$.

In some embodiments of a compound of Formula (IV), $R^{11}$ is hydrogen, halogen, —CN, —$OR^{13}$, —$NR^{15}R^{16}$, —$S(=O)_2R^{14}$, —$C(=O)R^{14}$, —$C(=O)OR^{13}$, —$C(=O)NR^{15}R^{16}$, $C_1$-$C_6$alkyl, $C_1$-$C_6$haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (IV), $R^{11}$ is hydrogen, halogen, —CN, —$S(=O)_2R^{14}$, —$C(=O)R^{14}$, —$C(=O)OR^{13}$, $C_1$-$C_6$alkyl, $C_1$-$C_6$ haloalkyl, $C_1$-$C_6$ hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11a}$. In some embodiments of a compound of Formula (IV), $R^{11}$ is hydrogen, —CN, —$S(=O)_2R^{14}$, —$C(=O)OR^{13}$, $C_1$-$C_6$alkyl, $C_1$-$C_6$haloalkyl, $C_1$-$C_6$ hydroxyalkyl, or heteroaryl; wherein each alkyl and heteroaryl is independently optionally substituted with one, two, or three $R^{11a}$. In some embodiments of a compound of Formula (IV), $R^{11}$ is hydrogen or $C_1$-$C_6$ alkyl optionally substituted with one, two, or three $R^{11a}$. In some embodiments of a compound of Formula (IV), $R^{11}$ is hydrogen or $C_1$-$C_6$alkyl substituted with one $R^{11a}$. In some embodiments of a compound of Formula (IV), $R^{11}$ is $C_1$-$C_6$ hydroxyalkyl.

In some embodiments of a compound of Formula (IV), $R^{11}$ is hydrogen, halogen, —CN, —$OR^{13}$, —$NR^{15}R^{16}$, —$C(=O)R^{14}$, —$C(=O)OR^{13}$, —$C(=O)NR^{15}R^{16}$. $C_1$-$C_6$ alkyl, $C_1$-$C_6$haloalkyl, $C_1$-$C_6$ hydroxyalkyl, $C_1$-$C_6$ heteroalkyl, cycloalkyl, or heterocycloalkyl. In some embodiments of a compound of Formula (IV), $R^{11}$ is hydrogen, halogen, $C_1$-$C_6$ alkyl, $C_1$-$C_6$haloalkyl, or $C_1$-$C_6$ hydroxyalkyl. In some embodiments of a compound of Formula (IV), $R^{11}$ is hydrogen. In some embodiments of a compound of Formula (IV), $R^{11}$ is not hydrogen. In some embodiments of a compound of Formula (IV), $R^{11}$ is halogen, —CN, —$OR^{13}$, —$NR^{15}R^{16}$, —$S(=O)_2R^{14}$, —$C(=O)OR^{13}$, $C_1$-$C_6$alkyl, $C_1$-$C_6$haloalkyl, $C_1$-$C_6$hydroxyalkyl, $C_2$-$C_6$ alkynyl, $C_1$-$C_6$heteroalkyl, cycloalkyl, heterocycloalkyl, aryl, or heteroaryl, wherein each alkyl, alkynyl, cycloalkyl, heterocycloalkyl, aryl, and heteroaryl is independently optionally substituted with one, two, or three $R^{11a}$. In some embodiments of a compound of Formula (IV), $R^{11}$ is —CN, —$S(=O)_2R^{14}$, —$C(=O)OR^{13}$, $C_1$-$C_6$ alkyl, $C_1$-$C_6$ haloalkyl, $C_1$-$C_6$ hydroxyalkyl, $C_2$-$C_6$ alkynyl, or heteroaryl; wherein each alkyl, alkynyl, and heteroaryl is independently optionally substituted with one, two, or three $R^{11a}$. In some embodiments of a compound of Formula (IV), $R^{11}$ is $C_1$-$C_6$ alkyl or $C_1$-$C_6$ hydroxyalkyl; wherein each alkyl is independently optionally substituted with one $R^{11a}$.

In some embodiments of a compound of Formula (IV), each $R^{11a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$C(=O)OR^{13}$, —$C(=O)OR^{13}$, —$C(=O)NR^{15}R^{16}$, —$NR^{13}C(=O)R^{14}$, $C_1$-$C_6$ alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (IV), each $R^{11a}$ is independently halogen, —CN, —$OR^{13}$, —$NR^{15}R^{16}$, —$S(=O)_2R^{14}$, —$NR^{14}S(=O)_2R^{14}$, —$S(=O)_2NR^{15}R^{16}$, —$C(=O)R^{14}$, —$OC(=O)R^{14}$, —$C(=O)OR^{13}$, —$C(=O)NR^{15}R^{16}$, —$NR^{13}C(=O)R^{14}$, cycloalkyl, heterocycloalkyl, aryl, or heteroaryl; wherein each cycloalkyl, heterocycloalkyl, aryl, and heteroaryl is independently optionally substituted with one, two, or three $R^{11c}$. In some embodiments of a compound of Formula (IV), each $R^{11a}$ is independently —$OR^{13}$, —$S(=O)_2R^{14}$, —$NR^{13}C(=O)R^{14}$, cycloalkyl, aryl, or heteroaryl; wherein each cycloalkyl, aryl, and heteroaryl is independently optionally substituted with one, two, or three $R^{11c}$. In some embodiments of a compound of Formula (IV), each $R^{11a}$ is independently aryl optionally substituted with one, two, or three $R^{11c}$. In some embodiments of a compound of Formula (IV), each $R^{11a}$ is independently —$OR^{13}$. In some embodiments of a compound of Formula (IV), each $R^{11a}$ is independently —$S(=O)_2R^{14}$. In some embodiments of a compound of Formula (IV), each $R^{11a}$ is independently cycloalkyl optionally substituted with one, two, or three $R_{11c}$. In some embodiments of a compound of Formula (IV), each $R^{11a}$ is independently —$NR^{13}C(=O)R^{14}$. In some embodiments of a compound of Formula (IV), each $R^{11a}$ is independently oxo (when feasible), halogen, —CN, —$OR^{13}$, —$SR^{13}$, —$S(=O)R^{14}$, —$NR^{15}R^{16}$, —$S(=O)_2R^{14}$, —$NR^{13}S(=O)_2R^{14}$, —$S(=O)_2NR^{15}R^{16}$, —$C(=O)R^{14}$, —$C(=O)OR^{13}$, —$C(=O)NR^{15}R^{16}$, —$OC(=O)NR^{15}R^{16}$, —$NR^{13}C(=O)R^{14}$, $C_1$-$C_6$alkyl, $C_1$-$C_6$ haloalkyl, $C_1$-$C_6$ hydroxyalkyl, $C_1$-$C_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{11c}$. In some embodiments of a compound of Formula (IV), each $R^{11a}$ is independently oxo (when feasible), halogen, —$OR^{13}$, —$SR^{13}$, —$NR^{15}R^{16}$, —$S(=O)_2R^{14}$, —$NR^{13}S(=O)_2R^{14}$, —$S(=O)_2NR^{15}R^{16}$, —$C(=O)OR^{13}$, —$OC(=O)NR^{15}R^{16}$, —$NR^{13}C(=O)R^{14}$, heterocycloalkyl, aryl, or heteroaryl; wherein each heterocycloalkyl, aryl, and heteroaryl is independently optionally substituted with one, two, or three $R^{11c}$. In some embodiments of a compound of Formula (II), each $R^{11a}$ is independently —$OR^{13}$ or heteroaryl.

In some embodiments of a compound of Formula (IV), each $R^{11c}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$alkyl, or $C_1$-$C_6$haloalkyl. In some embodiments of a compound of Formula (IV), each $R^{11c}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, $C_1$-$C_6$haloalkyl, or $C_1$-$C_6$ hydroxyalkyl. In some embodiments of a compound of Formula (IV), each $R^{11c}$ is independently halogen, —CN, —$OR^b$, —$NR^cR^d$, $C_1$-$C_6$ alkyl, or $C_1$-$C_6$ haloalkyl. In some embodiments of a compound of Formula (IV), each $R^{11c}$ is independently halogen, $C_1$-$C_6$ alkyl, or $C_1$-$C_6$ haloalkyl. In some embodiments of a compound of Formula (IV), each $R^{11c}$ is independently oxo (when feasible), halogen, —CN, —$OR^b$, —$NR^cR^d$, —$C(=O)R^a$, —$C(=O)OR^b$, —$C(=O)NR^cR^d$, $C_1$-$C_6$ alkyl, $C_1$-$C_6$haloalkyl, $C_1$-$C_6$ hydroxyalkyl, cycloalkyl, heterocycloalkyl, aryl, or heteroaryl. In some embodiments of a compound of Formula (IV), each $R^{11c}$ is independently —$OR^b$, —$C(=O)OR^b$, or $C_1$-$C_6$ hydroxyalkyl.

In some embodiments of a compound of Formula (IV), $R^{11}$ and $R^{12}$ are taken together to form a cycloalkyl or heterocycloalkyl each optionally substituted with one, two, or three $R^{11b}$. In some embodiments of a compound of Formula (IV), $R^{11}$ and $R^{12}$ are taken together to form a cycloalkyl optionally substituted with one, two, or three $R^{11b}$. In some embodiments of a compound of Formula (IV), $R^{11}$ and $R^{12}$ are taken together to form a heterocycloalkyl optionally substituted with one, two, or three $R^{11b}$.

In some embodiments of a compound of Formula (IV), each $R^{11b}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, or $C_1$-$C_6$haloalkyl. In some embodiments of a compound of Formula (IV), each $R^{11b}$ is independently oxo (when feasible), halogen, —CN, —$OR^b$, —$NR^cR^d$, $C_1$-$C_6$ alkyl, or $C_1$-$C_6$ haloalkyl. In some embodiments of a compound of Formula (IV), each $R^{11b}$ is independently oxo (when feasible), halogen, $C_1$-$C_6$ alkyl, or $C_1$-$C_6$haloalkyl.

In some embodiments of a compound of Formula (IV), each $R^{13}$ is independently hydrogen, $C_1$-$C_6$ alkyl, $C_1$-$C_6$ haloalkyl, $C_1$-$C_6$heteroalkyl, cycloalkyl, or heterocycloalkyl; wherein each alkyl, cycloalkyl, and heterocycloalkyl is independently optionally substituted with one, two, or three $R^{13a}$. In some embodiments of a compound of Formula (IV), each $R^{13}$ is independently hydrogen, $C_1$-$C_6$ alkyl, or $C_1$-$C_6$ haloalkyl; wherein each alkyl is independently optionally substituted with one, two, or three $R^{13a}$. In some embodiments of a compound of Formula (IV), each $R^{13}$ is independently hydrogen or $C_1$-$C_6$ alkyl. In some embodiments of a compound of Formula (IV), each $R^{13}$ is independently hydrogen, $C_1$-$C_6$ alkyl, $C_1$-$C_6$ haloalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{13a}$. In some embodiments of a compound of Formula (IV), each $R^{13}$ is independently $C_1$-$C_6$ alkyl, $C_1$-$C_6$haloalkyl, or cycloalkyl; wherein each alkyl and cycloalkyl is independently optionally substituted with one, two, or three $R^{13a}$.

In some embodiments of a compound of Formula (IV), each $R^{13a}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, or heterocycloalkyl. In some embodiments of a compound of Formula (IV), each $R^{13a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (IV), each $R^{13a}$ is independently halogen, $C_1$-$C_6$alkyl, or $C_1$-$C_6$ haloalkyl.

In some embodiments of a compound of Formula (IV), each $R^{13a}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, heterocycloalkyl, aryl, or heteroaryl; wherein each alkyl, cycloalkyl, heterocycloalkyl, aryl, and heteroaryl is independently optionally substituted with one, two, or three oxo (when feasible), halogen, —CN, —$OR^b$, —$NR^cR^d$, $C_1$-$C_6$ alkyl, or $C_1$-$C_6$haloalkyl. In some embodiments of a compound of Formula (IV), each $R^{13a}$ is independently —$OR^b$, —C(=O)$OR^b$, cycloalkyl, aryl, or heteroaryl; wherein each cycloalkyl, aryl, and heteroaryl is independently optionally substituted with one, two, or three oxo (when feasible), halogen, —CN, —$OR^b$, —$NR^cR^d$, $C_1$-$C_6$ alkyl, or $C_1$-$C_6$haloalkyl. In some embodiments of a compound of Formula (IV), each $R^{13a}$ is independently —$OR^b$, —C(=O)$OR^b$, cycloalkyl, aryl, or heteroaryl.

In some embodiments of a compound of Formula (IV), each $R^{14}$ is independently $C_1$-$C_6$ alkyl, $C_1$-$C_6$ haloalkyl, $C_1$-$C_6$ heteroalkyl, cycloalkyl, or heterocycloalkyl; wherein each alkyl, cycloalkyl, and heterocycloalkyl is independently optionally substituted with one, two, or three $R^{14a}$. In some embodiments of a compound of Formula (IV), each $R^{14}$ is independently $C_1$-$C_6$ alkyl, or $C_1$-$C_6$haloalkyl; wherein each alkyl is independently optionally substituted with one, two, or three $R^{14a}$. In some embodiments of a compound of Formula (IV), each $R^{14}$ is independently $C_1$-$C_6$ alkyl.

In some embodiments of a compound of Formula (IV), each $R^{14}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, or heterocycloalkyl. In some embodiments of a compound of Formula (IV), each $R^{14a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (IV), each $R^{14a}$ is independently halogen, $C_1$-$C_6$alkyl, or $C_1$-$C_6$ haloalkyl.

In some embodiments of a compound of Formula (IV), each $R^{15}$ and $R^{16}$ is independently hydrogen, $C_1$-$C_6$ alkyl, $C_1$-$C_6$haloalkyl, $C_1$-$C_6$heteroalkyl, cycloalkyl, or heterocycloalkyl; wherein each alkyl, cycloalkyl, and heterocycloalkyl is independently optionally substituted with one, two, or three $R^{15a}$. In some embodiments of a compound of Formula (IV), each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$. In some embodiments of a compound of Formula (IV), each $R^{15}$ and $R^{16}$ is independently hydrogen, $C_1$-$C_6$ alkyl, or $C_1$-$C_6$ haloalkyl; wherein each alkyl is independently optionally substituted with one, two, or three $R^{15a}$. In some embodiments of a compound of Formula (IV), each $R^{15}$ and $R^{16}$ is independently hydrogen or $C_1$-$C_6$ alkyl.

In some embodiments of a compound of Formula (IV), each $R^{15a}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, or heterocycloalkyl. In some embodiments of a compound of Formula (IV), each $R^{15a}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (IV), each $R^{15a}$ is independently halogen, $C_1$-$C_6$alkyl, or $C_1$-$C_6$ haloalkyl.

In some embodiments of a compound of Formula (IV), $R^{15}$ and $R^{16}$ are taken together with the nitrogen atom to which they are attached to form a heterocycloalkyl optionally substituted with one, two, or three $R^{15b}$. In some embodiments of a compound of Formula (IV), $R^{15}$ and $R^{16}$ are taken together with the nitrogen atom to which they are attached to form a heterocycloalkyl.

In some embodiments of a compound of Formula (IV), each $R^{15b}$ is independently oxo (when feasible), halogen, —CN, —$OR^b$, —$NR^cR^d$, —C(=O)$R^a$, —C(=O)$OR^b$, —C(=O)$NR^cR^d$, $C_1$-$C_6$alkyl, $C_1$-$C_6$haloalkyl, cycloalkyl, or heterocycloalkyl. In some embodiments of a compound of Formula (IV), each $R^{15b}$ is independently halogen, —CN, —$OR^b$, —$NR^cR^d$, $C_1$-$C_6$ alkyl, $C_1$-$C_6$haloalkyl, cycloalkyl, or heterocycloalkyl. In some embodiments of a compound of Formula (IV), each $R^{15b}$ is independently halogen, $C_1$-$C_6$ alkyl, or $C_1$-$C_6$ haloalkyl.

In some embodiments provided herein is a compound having the structure of Formula (V), or a pharmaceutically acceptable salt, solvate, stereoisomer, or isotopic variant thereof:

Formula (V)

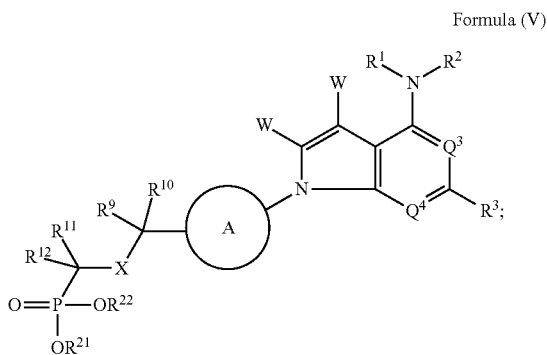

wherein:
Ring A is

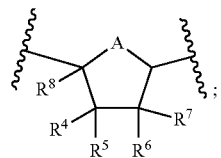

$Q^3$ and $Q^4$ are independently N or CW; provided that at least one of $Q^3$ or $Q^4$ is N;
each W is independently hydrogen, halogen, —CN, —$OR^b$, $NR^cR^d$, $C_1$-$C_6$ alkyl, or $C_1$-$C_6$ haloalkyl;
A is —O—;
X is —O—, —S—, —S($=$O)$_2$—, —$NR^{17}$—, or —C($R^{18}$)$_2$—;
$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{10}$;
or $R^1$ and $R^2$ are taken together with the nitrogen atom to which they are attached to form a heterocycloalkyl optionally substituted with one, two, or three $R^{1b}$;
each $R^{1a}$ and $R^{1b}$ is independently oxo (when feasible) halogen, —CN, —$OR^b$, —$SR^b$, —S($=$O)$R^a$, —$NO_2$, —$NR^cR^d$, —S($=$O)$_2R^a$, —$NR^bS(=O)_2R^a$, —S($=$O)$_2NR^cR^d$, —C($=$O)$R^a$, —OC($=$O)$R^a$, —C($=$O)$OR^b$, —OC($=$O)$OR^b$, —C($=$O)$NR^cR^d$, —OC($=$O)$NR^cR^d$, —$NR^bC(=O)NR^cR^d$, —$NR^bC(=O)R^a$, —$NR^bC(=O)$ $OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$; each $R^{3a}$ is independently oxo (when feasible) halogen, —CN, —$OR^b$, —$NR^cR^d$, —C($=$O)$R^a$, —C($=$O)$OR^b$, —C($=$O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;

$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;
$R^8$ is hydrogen, halogen, —$OR^b$, —$NR^cR^d$, $C_1$-$C_6$ alkyl, or $C_1$-$C_6$ haloalkyl;
$R^9$ and $R^{10}$ are independently hydrogen, halogen, $C_1$-$C_6$ alkyl, or $C_1$-$C_6$ haloalkyl;
$R^{11}$ is halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —C($=$O)$OR^{13}$, —OC($=$O)$OR^{13}$, —C($=$O)$NR^{15}R^{16}$, —OC($=$O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$haloalkyl, $C_1$-$C_6$hydroxyalkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;
$R^{12}$ is hydrogen, halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —C($=$O)$OR^{13}$, —OC($=$O)$OR^{13}$, —C($=$O)$NR^{15}R^{16}$, —OC($=$O)$NR^{15}R^{16}$, —$NR^{13}C(=O)NR^{15}R^{16}$, —$NR^{13}C(=O)R^{14}$, —$NR^{13}C(=O)$ $OR^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12b}$;
or $R^{11}$ and $R^{12}$ are taken together to form a cycloalkyl or heterocycloalkyl each optionally substituted with one, two, or three $R^{11b}$;
each $R^{11a}$, $R^{11b}$, and $R^{12a}$ is independently oxo (when feasible), halogen, —CN, —$OR^{13}$, —$SR^{13}$, —S($=$O)$R^{14}$, —$NO_2$, —$NR^{15}R^{16}$, —S($=$O)$_2R^{14}$, —$NR^{13}S(=O)_2R^{14}$, —S($=$O)$_2NR^{15}R^{16}$, —C($=$O)$R^{14}$, —OC($=$O)$R^{14}$, —C($=$O)$OR^{13}$, —OC($=$O)$OR^{13}$, —C($=$O)$NR^{15}R^{16}$, —OC($=$O)$NR^{15}R^{16}$, —$NR^{13}C(=O)NR^{15}R^{16}$, —$NR^{13}C(=O)R^{14}$, —$NR^{13}C(=O)OR^{13}$, $C_1$-$C_6$ alkyl, $C_1$-$C_6$haloalkyl, $C_2$-$C_6$ alkenyl, $C_2$-$C_6$ alkynyl, $C_1$-$C_6$hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;
each $R^{11c}$ is independently oxo (when feasible), halogen, —CN, —$OR^b$, —$SR^b$, —S($=$O)$R^a$, —$NO_2$, —$NR^cR^d$, —S($=$O)$_2R^a$, —$NR^bS(=O)_2R^a$, —S($=$O)$_2NR^cR^d$, —C($=$O)$R^a$, —OC($=$O)$R^a$, —C($=$O)$OR^b$, —OC($=$O)$OR^b$, —C($=$O)$NR^cR^d$, —OC($=$O)$NR^cR^d$, —$NR^bC(=O)NR^cR^d$, —$NR^bC(=O)R^a$, —$NR^bC(=O))OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);
each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —S(=O)$R^a$, —$NO_2$, —$NR^cR^d$, —S(=O)$R^a$, —$NR^b$S(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —$OR^b$, —S(=O)$R^a$, —$NO_2$, —$NR^cR^d$, —S(=O)$_2$ $R^a$, —S(=O)$_2NR^cR^d$, —C(=O)$R^a$, —C(=O)$OR^b$, —C(=O)$NR^cR^d$, $C_1$-$C_6$alkyl, $C_1$-$C_6$ haloalkyl, $C_2$-$C_6$ alkenyl, or $C_2$-$C_6$ alkynyl;

$R^{17}$ is hydrogen, —CN, —$OR^b$, —S(=O)$_2R^a$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{18}$ is independently hydrogen, halogen, —CN, —$OR^b$, —$SR^b$, —S(=O)$R^a$, —$NO_2$, —$NR^cR^d$, —S(=O)$_2R^a$, —NHS(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —$OR^b$, —$SR^b$, —S(=O)$R^a$, —$NO_2$, —$NR^cR^d$, —S(=O)$_2R^a$, —$NR^b$S(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments provided herein is a compound having the structure of Formula (V), or a pharmaceutically acceptable salt, solvate, stereoisomer, or isotopic variant thereof:

Formula (V)

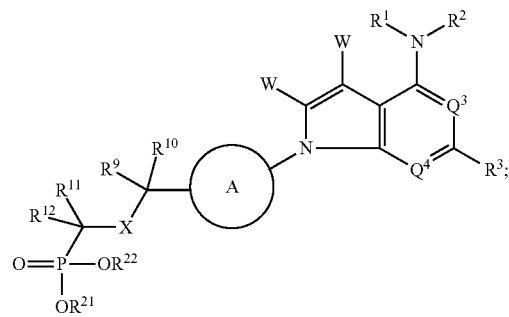

wherein:

Ring A is

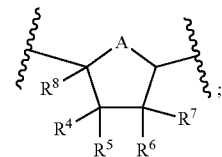

$Q^3$ and $Q^1$ are independently N or CW; provided that at least one of $Q^3$ or $Q^4$ is N;

each W is independently hydrogen, halogen, —CN, —$OR^b$, $NR^cR^d$, $C_1$-$C_6$ alkyl, or $C_1$-$C_6$ haloalkyl;

A is —O—;

X is —O—, —S—, —S(=O)$_2$—, —$NR^{17}$—, or —C($R^{18}$)$_2$—;

$R^1$ and $R^2$ are independently hydrogen, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl (heterocycloalkyl); wherein each alkyl, alkenyl, alkynyl, cycloalkyl, heterocycloalkyl, aryl, and heteroaryl is independently optionally substituted with one, two, or three $R^{1a}$;

or $R^1$ and $R^2$ are taken together with the nitrogen atom to which they are attached to form a heterocycloalkyl optionally substituted with one, two, or three $R^{1b}$;

each $R^{1a}$ and $R^{1b}$ is independently oxo (when feasible) halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^3$ is hydrogen, halogen, —CN, —$OR^b$, —$SR^b$, —$NR^cR^d$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, alkenyl, alkynyl, cycloalkyl, heterocycloalkyl, aryl, and heteroaryl is independently optionally substituted with one, two, or three $R^{3a}$;

each $R^{3a}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, or heteroaryl;

$R^4$ and $R^7$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^5$ and $R^6$ are independently hydrogen, halogen, —$OR^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, or heteroaryl;

$R^8$ is hydrogen, halogen, —$OR^b$, —$NR^cR^d$, $C_1$-$C_6$ alkyl, or $C_1$-$C_6$ haloalkyl;

$R^9$ and $R^{10}$ are independently hydrogen, halogen, $C_1$-$C_6$ alkyl, or $C_1$-$C_6$ haloalkyl;

$R^{11}$ is halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11a}$;

$R^{12}$ is hydrogen, halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{17}C$(=O)$R^{14}$, —$NR^{13}C$(=O)$OR^{13}$, $C_1$-$C_6$alkyl, $C_1$-$C_6$haloalkyl, $C_1$-$C_6$ hydroxyalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;

or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —$OR^{13}$, —$SR^{13}$, —S(=O)$R^{14}$, —$NO_2$, —$NR^{15}R^{16}$, —S(=O)$_2R^{14}$, —$NR^{13}S$(=O)$_2R^{14}$, —S(=O)$_2NR^{15}R^{16}$, —C(=O)$R^{14}$, —OC(=O)$R^{14}$, —C(=O)$OR^{13}$, —OC(=O)$OR^{13}$, —C(=O)$NR^{15}R^{16}$, —OC(=O)$NR^{15}R^{16}$, —$NR^{13}C$(=O)$NR^{15}R^{16}$, —$NR^{13}C$(=O)$R^{14}$, —$NR^{13}C$(=O)$OR^{13}$, $C_1$-$C_6$alkyl, $C_1$-$C_6$haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$_2NR^cR^d$, —C(=O)$R^a$, —OC(=O)$R^b$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —$OR^b$, —$SR^b$, —S(=O)$R^a$, —$NO_2$, —$NR^cR^d$, —S(=O)$_2R^a$, —$NR^bS$(=O)$_2R^a$, —S(=O)$NR^cR^d$, —C(=O)$R^a$, —OC(=O)$R^a$, —C(=O)$OR^b$, —OC(=O)$OR^b$, —C(=O)$NR^cR^d$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, $C_1$-$C_6$ haloalkyl, $C_2$-$C_6$ alkenyl, $C_2$-$C_6$alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{17}$ is hydrogen, —CN, —$OR^b$, —S(=O)$_2R^a$, —C(=O)$R^1$, —C(=O)$OR^b$, —C(=O)$NR^cR^d$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{18}$ is independently hydrogen, halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O) OR$^b$, —C(=O)NR$^c$R$^d$, —OC(=O)NR$^c$R$^d$, —NR$^b$C (=O)NR$^c$R$^d$, —NR$^b$C(=O)R$^a$, —NR$^b$C(=O)OR$^b$, $C_1$-$C_6$ alkyl, $C_1$-$C_6$haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$alkyl, cycloalkyl, heterocycloalkyl, aryl, heteroaryl, $C_1$-$C_6$ alkyl (aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$ NR$^c$R$^d$, —C(=O)R$^a$, —OC(=O)R$^a$, —C(=O)OR$^b$, —C(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O) OR$^b$, $C_1$-$C_6$ alkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, $C_2$-$C_6$ alkynyl, $C_1$-$C_6$heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ alkyl, or $C_1$-$C_6$ haloalkyl.

In some embodiments of a compound of Formula (V), $Q^3$ is N and $Q^4$ is CW. In some embodiments of Formula (V), $Q^4$ is N and $Q^3$ is CW. In some embodiments of a compound of Formula (V), $Q^3$ is N and $Q^4$ is N.

In some embodiments of a compound of Formula (V), each W is independently hydrogen, halogen, $C_1$-$C_6$ alkyl, or $C_1$-$C_6$ haloalkyl. In some embodiments of a compound of Formula (V), each W is independently hydrogen, halogen, or $C_1$-$C_6$alkyl. In some embodiments of a compound of Formula (V), each W is hydrogen.

In some embodiments of a compound of Formula (V), $R^3$ is halogen, —CN, —OR$^b$, —NR$^c$R$^d$, $C_1$-$C_6$ alkyl, $C_2$-$C_6$ alkynyl, $C_1$-$C_6$ haloalkyl, $C_1$-$C_6$ hydroxyalkyl, $C_1$-$C_6$ heteroalkyl, cycloalkyl, or heterocycloalkyl; wherein each alkyl, alkynyl, cycloalkyl, and heterocycloalkyl is independently optionally substituted with one, two, or three $R^{3a}$. In some embodiments of a compound of Formula (V), $R^3$ is halogen, $C_1$-$C_6$ alkyl, $C_2$-$C_6$ alkynyl, $C_1$-$C_6$ hydroxyalkyl, or $C_1$-$C_6$ heteroalkyl; wherein each alkyl and alkynyl is independently optionally substituted with one, two, or three $R^{3a}$.

In some embodiments of a compound of Formula (V), $R^3$ is halogen, —CN, —OR$^b$, —NR$^c$R$^d$, $C_1$-$C_6$ alkyl, $C_1$-$C_6$ haloalkyl, $C_1$-$C_6$hydroxyalkyl, $C_1$-$C_6$ heteroalkyl, cycloalkyl, or heterocycloalkyl. In some embodiments of a compound of Formula (V), $R^3$ is halogen, $C_1$-$C_6$ alkyl, $C_1$-$C_6$ haloalkyl, $C_1$-$C_6$ hydroxyalkyl, $C_1$-$C_6$ heteroalkyl, cycloalkyl, or heterocycloalkyl. In some embodiments of a compound of Formula (V), $R^3$ is halogen, or $C_1$-$C_6$ hydroxyalkyl, $C_1$-$C_6$ heteroalkyl. In some embodiments of a compound of Formula (V), $R^3$ is halogen.

In some embodiments of a compound of Formula (V), each $R^{3a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (V), each $R^{1a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (V), each $R^{3a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (V), each $R^{3a}$ is independently oxo (when feasible) halogen, $C_1$-$C_6$ alkyl, or $C_1$-$C_6$ fluoroalkyl. In some embodiments of a compound of Formula (V), each $R^{3a}$ is independently halogen or $C_1$-$C_6$ alkyl. In some embodiments of a compound of Formula (V), each $R^{3a}$ is independently halogen, —OR$^b$, $C_1$-$C_6$alkyl, or cycloalkyl.

In some embodiments of a compound of Formula (V), $R^1$ is $C_1$-$C_6$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$. In some embodiments of a compound of Formula (V), $R^1$ is $C_1$-$C_6$ alkyl, cycloalkyl, heterocycloalkyl, $C_1$-$C_6$ alkyl (aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, an heteroaryl is independently optionally substituted with one, two, or three $R^{1a}$. In some embodiments of a compound of Formula (V), $R^1$ is cycloalkyl or $C_1$-$C_6$ alkyl(cycloalkyl); wherein each alkyl and cycloalkyl is independently optionally substituted with one, two, or three $R^{1a}$. In some embodiments of a compound of Formula (V), $R^1$ is cycloalkyl optionally substituted with one, two, or three $R^{1a}$.

In some embodiments of a compound of Formula (V), each $R^{1a}$ is independently oxo (when feasible) halogen, —CN, —OR$^b$, —NR$^c$R$^d$, —C(=O)R$^a$, —C(=O)OR$^b$, —C(=O)NR$^c$R$^d$, $C_1$-$C_6$ alkyl, $C_1$-$C_6$ fluoroalkyl, cycloalkyl, or heterocycloalkyl. In some embodiments of a compound of Formula (V), each $R^{1a}$ is independently oxo (when feasible) halogen, —CN, —OR$^b$, —NR$^c$R$^d$, $C_1$-$C_6$ alkyl, $C_1$-$C_6$ fluoroalkyl, cycloalkyl, or heterocycloalkyl. In some embodiments of a compound of Formula (V), each $R^{1a}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (V), each $R^{1a}$ is independently oxo (when feasible) halogen, $C_1$-$C_6$ alkyl, or $C_1$-$C_6$ fluoroalkyl. In some embodiments of a compound of Formula (V), each $R^{1a}$ is independently halogen or $C_1$-$C_6$ alkyl.

In some embodiments of a compound of Formula (V), $R^2$ is hydrogen or $C_1$-$C_6$ alkyl. In some embodiments of a compound of Formula (V), $R^2$ is hydrogen. In some embodiments of a compound of Formula (V), $R^1$ and $R^2$ are taken together with the nitrogen atom to which they are attached to form a heterocycloalkyl optionally substituted with one, two, or three $R^{1b}$.

In some embodiments of a compound of Formula (V), each $R^{1b}$ is independently oxo (when feasible) halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (V), each $R^{1b}$ is independently oxo (when feasible) halogen, —CN, —$OR^b$, —$NR^cR^d$, $C_1$-$C_6$ alkyl, $C_1$-$C_6$ fluoroalkyl, cycloalkyl, or heterocycloalkyl. In some embodiments of a compound of Formula (V), each $R^{1b}$ is independently oxo (when feasible) halogen, $C_1$-$C_6$ alkyl, $C_1$-$C_6$ fluoroalkyl, cycloalkyl, or heterocycloalkyl. In some embodiments of a compound of Formula (V), each $R^{1b}$ is independently oxo (when feasible)halogen, $C_1$-$C_6$ alkyl, or $C_1$-$C_6$ fluoroalkyl. In some embodiments of a compound of Formula (V), each $R^{1b}$ is independently halogen or $C_1$-$C_6$ alkyl.

In some embodiments of a compound of Formula (V), $R^8$ is hydrogen or $C_1$-$C_6$ alkyl. In some embodiments of a compound of Formula (V), $R^8$ is hydrogen.

In some embodiments of a compound of Formula (V), $R^9$ and $R^{10}$ are independently hydrogen or $C_1$-$C_6$ alkyl. In some embodiments of a compound of Formula (V), $R^9$ and $R^{10}$ are hydrogen.

In some embodiments of a compound of Formula (V), $R^5$ and $R^6$ are independently hydrogen, halogen, —$OR^b$, $C_1$-$C_6$ alkyl, or $C_1$-$C_6$ haloalkyl. In some embodiments of a compound of Formula (V), $R^5$ and $R^6$ are independently hydrogen, halogen, —$OR^b$, or $C_1$-$C_6$ alkyl. In some embodiments of a compound of Formula (V), $R^5$ and $R^6$ are hydrogen.

In some embodiments of a compound of Formula (V), $R^4$ and $R^7$ are independently hydrogen, halogen, —$OR^b$, $C_1$-$C_6$ alkyl, or $C_1$-$C_6$ haloalkyl. In some embodiments of a compound of Formula (V), $R^4$ and $R^7$ are independently hydrogen, halogen, —$OR^b$, or $C_1$-$C_6$ alkyl. In some embodiments of a compound of Formula (V), $R^4$ and $R^7$ are independently hydrogen, halogen, or —$OR^b$. In some embodiments of a compound of Formula (V), $R^4$ and $R^7$ are independently hydrogen, halogen, or —OH. In some embodiments of a compound of Formula (V), $R^4$ and $R^7$ are independently halogen or —OR In some embodiments of a compound of Formula (V), $R^4$ and $R^7$ are independently hydrogen or —OH. In some embodiments of a compound of Formula (V), $R^4$ and $R^7$ are —OH.

In some embodiments of a compound of Formula (V), $R^5$ and $R^6$ are hydrogen and $R^4$ and $R^7$ are —OH. In some embodiments of a compound of Formula (V), $R^5$ and $R^6$ are hydrogen and $R^4$ and $R^7$ are independently halogen or —OH. In some embodiments of a compound of Formula (V), $R^5$ and $R^6$ are hydrogen and $R^4$ and $R^7$ are independently hydrogen or —OH.

In some embodiments of a compound of Formula (V), X is —O— or —S(=O)$_2$—. In some embodiments of a compound of Formula (V), X is —O—. In some embodiments of a compound of Formula (V), X is —S(=O)$_2$—. In some embodiments of a compound of Formula (V), X is —$NR^{17}$—. In some embodiments of a compound of Formula (V), X is —C($R^{18}$)$_2$—.

In some embodiments of a compound of Formula (V), $R^{17}$ is hydrogen, —C(=O)$R^a$, —C(=O)$OR^b$, —C(=O)$NR^cR^d$, $C_1$-$C_6$ alkyl, $C_1$-$C_6$ fluoroalkyl, cycloalkyl, or heterocycloalkyl. In some embodiments of a compound of Formula (V), $R^{17}$ is hydrogen, $C_1$-$C_6$ alkyl, $C_1$-$C_6$ fluoroalkyl, cycloalkyl, or heterocycloalkyl. In some embodiments of a compound of Formula (V), $R^{17}$ is hydrogen or $C_1$-$C_6$ alkyl. In some embodiments of a compound of Formula (V), $R^{17}$ is hydrogen.

In some embodiments of a compound of Formula (V), each $R^{18}$ is independently hydrogen, halogen, —CN, —$OR^b$, —$NR^cR^d$, —C(=O)$R^a$, —C(=O)$OR^b$, —C(=O)$NR^cR^d$, $C_1$-$C_6$ alkyl, $C_1$-$C_6$haloalkyl, cycloalkyl, or heterocycloalkyl. In some embodiments of a compound of Formula (V), each $R^{18}$ is independently hydrogen, halogen, —CN, —$OR^b$, —$NR^cR^d$, $C_1$-$C_6$ alkyl, $C_1$-$C_6$ haloalkyl, cycloalkyl, or heterocycloalkyl. In some embodiments of a compound of Formula (V), each $R^{13}$ is independently hydrogen, halogen, $C_1$-$C_6$alkyl, or $C_1$-$C_6$ haloalkyl. In some embodiments of a compound of Formula (V), each $R^{18}$ is independently hydrogen or halogen. In some embodiments of a compound of Formula (V), each $R^{18}$ is hydrogen.

In some embodiments of a compound of Formula (V), $R^{21}$ and $R^{22}$ are independently hydrogen, $C_1$-$C_{20}$ alkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{21a}$. In some embodiments of a compound of Formula (V), $R^{21}$ and $R^{22}$ are independently hydrogen, $C_1$-$C_{20}$alkyl or aryl; wherein each alkyl and aryl is independently optionally substituted with one, two, or three $R^{21a}$. In some embodiments of a compound of Formula (V), $R^{21}$ and $R^{22}$ are independently hydrogen, $C_1$-$C_{20}$ alkyl optionally substituted with one, two, or three $R^{21a}$. In some embodiments of a compound of Formula (V), $R^{21}$ and $R^{22}$ are hydrogen.

In some embodiments of a compound of Formula (V), each $R^{21a}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC$(=O)$NR^cR^d$, —$NR^bC$(=O)$R^a$, —$NR^bC$(=O)$OR^b$, or $C_1$-$C_6$ alkyl. In some embodiments of a compound of Formula (V), each $R^{21a}$ is independently —C(=O)$R^a$, —OC(=O)$R^a$, —C(=O)$OR^b$, —OC(=O)$OR^b$, or —OC(=O)$NR^cR^d$. In some embodiments of a compound of Formula (V), each $R^{21a}$ is independently —C(=O)$OR^b$ or —OC(=O)$OR^b$.

In some embodiments of a compound of Formula (V), $R^{21}$ and $R^{22}$ are taken together with the atoms to which they are attached to form a heterocycloalkyl optionally substituted with one, two, or throe $R^{21b}$.

In some embodiments of a compound of Formula (V), each $R^{21b}$ is independently oxo (when feasible), halogen, —CN, —$OR^b$, —$NR^cR^d$, —C(=O)$R^a$, —OC(=O)$R^a$, —C(=O)$OR^b$, —OC(=O)$OR^b$, —OC(=O)$NR^cR^d$, —$NR^bC$(=O)$NR^cR^d$, —$NR^bC$(=O)$R^a$, —$NR^bC$(=O)$OR^b$, $C_1$-$C_6$ alkyl, cycloalkyl, or heterocycloalkyl. In some embodiments of a compound of Formula (V), each $R^{21b}$ is independently halogen, —CN, —$OR^b$, —$NR^cR^d$, $C_1$-$C_6$ alkyl, cycloalkyl, or heterocycloalkyl. In some embodiments of a compound of Formula (V), each $R^{21b}$ is independently halogen or $C_1$-$C_6$ alkyl.

In some embodiments of a compound of Formula (V), $R^{12}$ is hydrogen, halogen, —CN, —$OR^{13}$, —$NR^{15}R^{16}$, —C(=O)$R^{14}$, —C(=O)$OR^{13}$, —C(=O)$NR^{15}R^{16}$, $C_1$-$C_6$ alkyl, $C_1$-$C_6$haloalkyl, $C_1$-$C_6$ hydroxyalkyl, $C_1$-$C_6$ heteroalkyl, cycloalkyl, or heterocycloalkyl. In some embodiments of a compound of Formula (V), $R^{12}$ is halogen, —CN, —OR$^{13}$, —NR$^{15}$R$^{16}$, —C(=O)R$^{14}$, —C(=O)OR$^{13}$, —C(=O)NR$^{15}$R$^{16}$, C$_1$-C$_6$alkyl, C$_1$-C$_6$haloalkyl, C$_1$-C$_6$ hydroxyalkyl, C$_1$-C$_6$ heteroalkyl, cycloalkyl, or heterocycloalkyl. In some embodiments of a compound of Formula (V), R$^{12}$ is hydrogen, halogen, C$_1$-C$_6$ alkyl, C$_1$-C$_6$haloalkyl, or C$_1$-C$_6$ hydroxyalkyl. In some embodiments of a compound of Formula (V), R$^{12}$ is C$_1$-C$_6$ alkyl. In some embodiments of a compound of Formula (V), R$^{12}$ is C$_1$-C$_6$ hydroxyalkyl. In some embodiments of a compound of Formula (V), R$^{12}$ is hydrogen. In some embodiments of a compound of Formula (V), R$^{12}$ is not hydrogen.

In some embodiments of a compound of Formula (V), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11c}$.

In some embodiments of a compound of Formula (V), each R$^{12a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, cycloalkyl, heterocycloalkyl, aryl, or heteroaryl; wherein each cycloalkyl, heterocycloalkyl, aryl, and heteroaryl is independently optionally substituted with one, two, or three R$^{11c}$.

In some embodiments of a compound of Formula (V), each R$^{12a}$ is independently —OR$^{13}$, —S(=O)$_2$R$^{14}$, —NR$^{13}$C(=O)R$^{14}$, cycloalkyl, aryl, or heteroaryl; wherein each cycloalkyl, aryl, and heteroaryl is independently optionally substituted with one, two, or three R$^{1lc}$.

In some embodiments of a compound of Formula (V), R$^{11}$ is halogen, —CN, —OR$^{13}$, —NR$^{15}$R$^{16}$, —S(=O)$_2$R$^{14}$, —C(=O)R$^{14}$, —C(=O)OR$^{13}$, —C(=O)NR$^{15}$R$^{16}$, C$_1$-C$_6$alkyl, C$_1$-C$_6$ haloalkyl, C$_1$-C$_6$hydroxyalkyl, C$_1$-C$_6$ heteroalkyl, cycloalkyl, heterocycloalkyl aryl, or heteroaryl; wherein each alkyl, cycloalkyl, heterocycloalkyl, aryl, and heteroaryl is independently optionally substituted with one, two, or three R$^{11a}$. In some embodiments of a compound of Formula (V), R$^{11}$ is halogen, —CN, —S(=O)$_2$R$^{14}$, —C(=O)R$^{14}$, —C(=O)OR$^{13}$, C$_1$-C$_6$alkyl, C$_1$-C$_6$ haloalkyl, C$_1$-C$_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11a}$. In some embodiments of a compound of Formula (V), R$^{11}$ is —CN, —S(=O)$_2$R$^{14}$, —C(=O)OR$^{13}$, C$_1$-C$_6$ alkyl, C$_1$-C$_6$ haloalkyl, C$_1$-C$_6$ hydroxyalkyl, or heteroaryl; wherein each alkyl and heteroaryl is independently optionally substituted with one, two, or three R$^{11a}$. In some embodiments of a compound of Formula (V), R$^{11}$ is C$_1$-C$_6$ alkyl optionally substituted with one, two, or three R$^{11a}$. In some embodiments of a compound of Formula (V), R$^{11}$ is C$_1$-C$_6$ alkyl substituted with one R$^{11a}$. In some embodiments of a compound of Formula (V), R$^{11}$ is C$_1$-C$_6$hydroxyalkyl.

In some embodiments of a compound of Formula (V), each R$^{11a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$ NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl; wherein each alkyl, cycloalkyl, heterocycloalkyl, aryl, and heteroaryl is independently optionally substituted with one, two, or three R$^{11c}$. In some embodiments of a compound of Formula (V), each R$^{11a}$ is independently halogen, —CN, —OR$^{13}$, —NR$^{15}$R$^{16}$, —S(=O)$_2$R$^{14}$, —NR$^{14}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —C(=O)NR$^{15}$R$^{16}$, —NR$^{13}$C(=O)R$^{14}$, cycloalkyl, heterocycloalkyl, aryl, or heteroaryl; wherein each cycloalkyl, heterocycloalkyl, aryl, and heteroaryl is independently optionally substituted with one, two, or three R$^{11c}$. In some embodiments of a compound of Formula (V), each R$^{11a}$ is independently —OR$^{13}$, —S(=O)$_2$R$^{14}$, —NR$^{13}$C(=O)R$^{14}$, cycloalkyl, aryl, or heteroaryl; wherein each cycloalkyl, aryl, and heteroaryl is independently optionally substituted with one, qtwo, or three R$^{11c}$. In some embodiments of a compound of Formula (V), each R$^{11a}$ is independently aryl optionally substituted with one, two, or three R$^{11c}$.

In some embodiments of a compound of Formula (V), each R$^{11a}$ is independently —OR$^{13}$. In some embodiments of a compound of Formula (V), each R$^{11a}$ is independently —S(=O)$_2$R$^{14}$. In some embodiments of a compound of Formula (V), each R$^{11a}$ is independently cycloalkyl optionally substituted with one, two, or three R$^{11c}$. In some embodiments of a compound of Formula (V), each R$^{11a}$ is independently —NR$^{13}$C(=O)R$^{14}$.

In some embodiments of a compound of Formula (V), each R$^{11c}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (V), each R$^{11c}$ is independently halogen, —CN, —OR$^b$, —NR$^c$R$^d$, C$_1$-C$_6$ alkyl, or C$_1$-C$_6$haloalkyl. In some embodiments of a compound of Formula (V), each R$^{11c}$ is independently halogen, C$_1$-C$_6$ alkyl, or C$_1$-C$_6$ haloalkyl.

In some embodiments of a compound of Formula (V), R$^{11}$ and R$^{12}$ are taken together to form a cycloalkyl or heterocycloalkyl each optionally substituted with one, two, or three R$^{11b}$. In some embodiments of a compound of Formula (V), R$^{11}$ and R$^{12}$ are taken together to form a cycloalkyl optionally substituted with one, two, or three R$^{11b}$. In some embodiments of a compound of Formula (V), R$^{11}$ and R$^{12}$ are taken together to form a heterocycloalkyl optionally substituted with one, two, or three R$^{11b}$.

In some embodiments of a compound of Formula (V), each R$^{11b}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, or C$_1$-C$_6$haloalkyl. In some embodiments of a compound of Formula (V), each R$^{11b}$ is independently oxo (when feasible), halogen, —CN, —OR$^b$, —NR$^c$R$^d$, C$_1$-C$_6$ alkyl, or C$_1$-C$_6$ haloalkyl. In some embodiments of a compound of Formula (V), each R$^{11b}$ is independently oxo (when feasible), halogen, C$_1$-C$_6$alkyl, or C$_1$-C$_6$ haloalkyl.

In some embodiments of a compound of Formula (V), each R$^{13}$ is independently hydrogen, C$_1$-C$_6$ alkyl, C$_1$-C$_6$haloalkyl, C$_1$-C$_6$heteroalkyl, cycloalkyl, or heterocycloalkyl; wherein each alkyl, cycloalkyl, and heterocycloalkyl is independently optionally substituted with one, two, or three R$^{13a}$. In some embodiments of a compound of Formula (V), each R$^{13}$ is independently hydrogen, C$_1$-C$_6$ alkyl, or C$_1$-C$_6$ haloalkyl; wherein each alkyl is independently optionally substituted with one, two, or three R$^{13a}$. In some embodiments of a compound of Formula (V), each R$^{13}$ is independently hydrogen or C$_1$-C$_6$ alkyl.

In some embodiments of a compound of Formula (V), each R$^{13a}$ is independently oxo (when feasible), halogen, —CN, —OR$^b$, —NR$^c$R$^d$, —C(=O)R$^b$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (V), each $R^{13a}$ is independently halogen, —CN, —OR$^b$, —NR$^c$R$^d$, C$_1$-C$_6$ alkyl, C$_1$-C$_6$ haloalkyl, cycloalkyl, or heterocycloalkyl. In some embodiments of a compound of Formula (V), each $R^{13a}$ is independently halogen, C$_1$-C$_6$ alkyl, or C$_1$-C$_6$ haloalkyl.

In some embodiments of a compound of Formula (V), each $R^{14}$ is independently C$_1$-C$_6$ alkyl, C$_1$-C$_6$ haloalkyl, C$_1$-C$_6$ heteroalkyl, cycloalkyl, or heterocycloalkyl; wherein each alkyl, cycloalkyl, and heterocycloalkyl is independently optionally substituted with one, two, or three $R^{14a}$. In some embodiments of a compound of Formula (V), each $R^{14}$ is independently C$_1$-C$_6$ alkyl, or C$_1$-C$_6$ haloalkyl; wherein each alkyl is independently optionally substituted with one, two, or three $R^{14a}$. In some embodiments of a compound of Formula (V), each $R^{14}$ is independently C$_1$-C$_6$ alkyl.

In some embodiments of a compound of Formula (V), each $R^{14a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (V), each $R^{14a}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (V), each $R^{14a}$ is independently halogen, C$_1$-C$_6$ alkyl, or C$_1$-C$_6$ haloalkyl.

In some embodiments of a compound of Formula (V), each $R^{15}$ and $R^{16}$ is independently hydrogen, C$_1$-C$_6$ alkyl, C$_1$-C$_6$ haloalkyl, C$_1$-C$_6$ heteroalkyl, cycloalkyl, or heterocycloalkyl; wherein each alkyl, cycloalkyl, and heterocycloalkyl is independently optionally substituted with one, two, or three $R^{15a}$. In some embodiments of a compound of Formula (V), each $R^{15}$ and $R^{16}$ is independently hydrogen, C$_1$-C$_6$ alkyl, or C$_1$-C$_6$ haloalkyl; wherein each alkyl is independently optionally substituted with one, two, or three $R^{15a}$. In some embodiments of a compound of Formula (V), each $R^{15}$ and $R^{16}$ is independently hydrogen, C$_1$-C$_6$ alkyl, or C$_1$-C$_6$ haloalkyl; wherein each alkyl is independently optionally substituted with one, two, or three $R^{15a}$. In some embodiments of a compound of Formula (V), each $R^{15}$ and $R^{16}$ is independently hydrogen or C$_1$-C$_6$ alkyl.

In some embodiments of a compound of Formula (V), each $R^{15a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (V), each $R^{15a}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (V), each $R^{15a}$ is independently halogen, C$_1$-C$_6$ alkyl, or C$_1$-C$_6$ haloalkyl.

In some embodiments of a compound of Formula (V), $R^{15}$ and $R^{16}$ are taken together with the nitrogen atom to which they are attached to form a heterocycloalkyl optionally substituted with one, two, or three $R^{15b}$. In some embodiments of a compound of Formula (V), $R^{15}$ and $R^{16}$ are taken together with the nitrogen atom to which they are attached to form a heterocycloalkyl.

In some embodiments of a compound of Formula (V), each $R^{15b}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, cycloalkyl, or heterocycloalkyl. In some embodiments of a compound of Formula (V), each $R^{15b}$ is independently halogen, —CN, —OR$^b$, —NR$^c$R$^d$, C$_1$-C$_6$ alkyl, C$_1$-C$_6$haloalkyl, cycloalkyl, or heterocycloalkyl. In some embodiments of a compound of Formula (V), each $R^{15b}$ is independently halogen, C$_1$-C$_6$alkyl, or C$_1$-C$_6$ haloalkyl.

In some embodiments of a compound of Formula (I), (II), (III), (IV), or (V), each $R^a$ is independently C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl. In some embodiments of a compound of Formula (I), (II), (III), (IV), or (V), each $R^a$ is independently C$_1$-C$_6$ alkyl, C$_1$-C$_6$ haloalkyl, or cycloalkyl. In some embodiments of a compound of Formula (I), (II), (III), (IV), or (V), each $R^a$ is independently C$_1$-C$_6$ alkyl or C$_1$-C$_6$ haloalkyl. In some embodiments of a compound of Formula (I), (II), (III), (IV), or (V), each $R^a$ is independently C$_1$-C$_6$ alkyl.

In some embodiments of a compound of Formula (I), (II), (III), (IV), or (V), each $R^b$ is independently hydrogen, C$_1$-C$_6$ alkyl, C$_1$-C$_6$ haloalkyl, C$_1$-C$_6$ hydroxyalkyl, C$_1$-C$_6$ heteroalkyl, cycloalkyl, heterocycloalkyl, aryl, or heteroaryl. In some embodiments of a compound of Formula (I), (II), (III), (IV), or (V), each $R^b$ is independently hydrogen, C$_1$-C$_6$ alkyl, C$_1$-C$_6$ haloalkyl, or cycloalkyl. In some embodiments of a compound of Formula (I), (II), (II), (IV), or (V), each $R^b$ is independently hydrogen, C$_1$-C$_6$ alkyl, or C$_1$-C$_6$ haloalkyl. In some embodiments of a compound of Formula (I), (II), (III), (IV), or (V), each $R^b$ is independently hydrogen or C$_1$-C$_6$ alkyl. In some embodiments of a compound of Formula (I), (II), (III), (IV), or (V), each $R^b$ is hydrogen. In some embodiments of a compound of Formula (I), (II), (III), (IV), or (V), each $R^b$ is independently C$_1$-C$_6$ alkyl.

In some embodiments of a compound of Formula (I), (II), (III), (IV), or (V), $R^c$ and $R^d$ are each independently hydrogen, C$_1$-C$_6$ alkyl, C$_1$-C$_6$ haloalkyl, C$_1$-C$_6$ hydroxyalkyl, C$_1$-C$_6$heteroalkyl, cycloalkyl, heterocycloalkyl, aryl, or heteroaryl. In some embodiments of a compound of Formula (I), (II), (III), (IV), or (V), $R^c$ and $R^d$ are each independently hydrogen, C$_1$-C$_6$ alkyl, C$_1$-C$_6$ haloalkyl, or cycloalkyl. In some embodiments of a compound of Formula (I), (II), (III), (IV), or (V), $R^c$ and $R^d$ are each independently hydrogen, C$_1$-C$_6$ alkyl, or C$_1$-C$_6$ haloalkyl. In some embodiments of a compound of Formula (I), (II), (III), (IV), or (V), $R^c$ and $R^d$ are each independently hydrogen or C$_1$-C$_6$ alkyl. In some embodiments of a compound of Formula (I), (II), (III), (IV), or (V), $R^c$ and $R^d$ are each hydrogen. In some embodiments of a compound of Formula (I), (II), (III), (IV), or (V), $R^c$ and $R^d$ are each independently C$_1$-C$_6$ alkyl.

In some embodiments of a compound of Formula (I), (II), (III), (IV), or (V), $R^c$ and $R^d$ are taken together with the nitrogen atom to which they are attached to form a heterocycloalkyl optionally substituted with one, two, or three halogen, C$_1$-C$_6$ alkyl, or C$_1$-C$_6$ haloalkyl. In some embodiments of a compound of Formula (I), (II), (III), (IV), or (V), $R^c$ and $R^d$ are taken together with the nitrogen atom to which they are attached to form a pyrrolidine optionally substituted with one, two, or three halogen or C$_1$-C$_6$ alkyl. In some embodiments of a compound of Formula (I), (II), (III), (IV), or (V), $R^c$ and $R^d$ are taken together with the nitrogen atom to which they are attached to form a piperidine optionally substituted with one, two, or three halogen or C$_1$-C$_6$ alkyl. In some embodiments of a compound of Formula (I), (II), (III), (IV), or (V), $R^c$ and $R^d$ are taken together with the nitrogen atom to which they are attached to form a piperazine optionally substituted with one, two, or three halogen or C$_1$-C$_6$ alkyl.

Any combination of the groups described above for the various variables is contemplated herein. Throughout the specification, groups and substituents thereof are chosen by one skilled in the field to provide stable moieties and compounds.

In some embodiments is a compound, or a pharmaceutically acceptable salt, solvate, stereoisomer, or isotopic variant thereof, having a structure selected from Table 1.

TABLE 1

| Ex | Structure | Name |
|---|---|---|
| 1 | 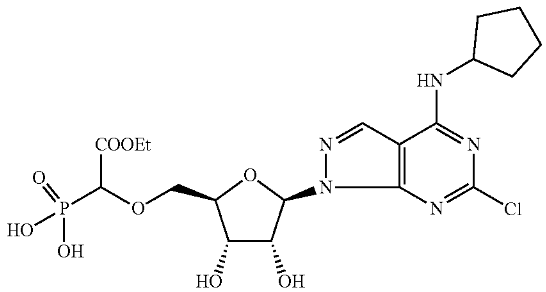 [SMILES: CCOC(=O)C(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-ethoxy-2-oxoethyl)phosphonic acid |
| 2 | 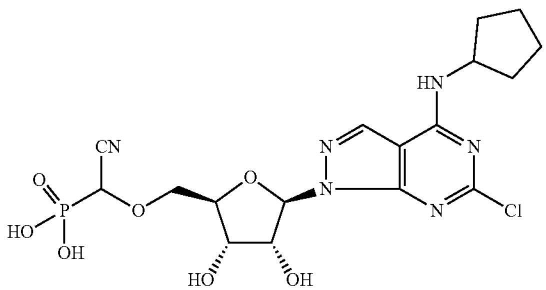 [SMILES: N#CC(OC[C@H]1O[C@@H](n2ncc3c(NC4CCCC4)nc(Cl)nc32)[C@H](O)[C@@H]1O)P(=O)(O)O] | ((((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)(cyano)methyl)phosphonic acid |
| 3 | 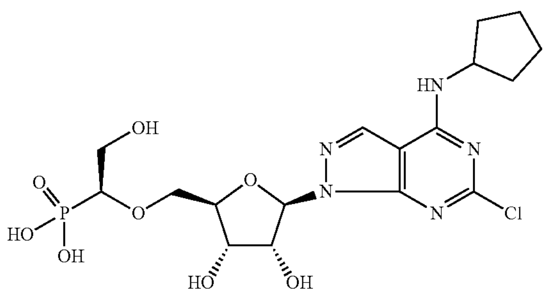 [SMILES: O=P(O)(O)[C@@H](CO)OC[C@H]1O[C@@H](n2ncc3c(NC4CCCC4)nc(Cl)nc32)[C@H](O)[C@@H]1O] | ((S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxyethyl)phosphonic acid |
| 4 | 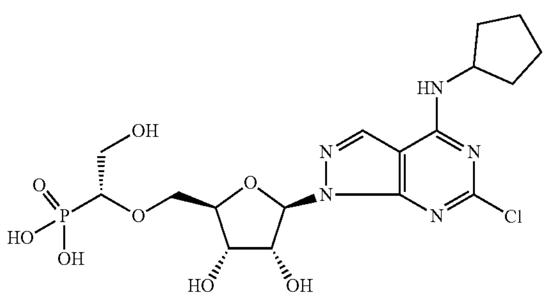 [SMILES: O=P(O)(O)[C@H](CO)OC[C@H]1O[C@@H](n2ncc3c(NC4CCCC4)nc(Cl)nc32)[C@H](O)[C@@H]1O] | ((R)-1-(((2R.,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxyethyl)phosphonic acid |
| 5 | 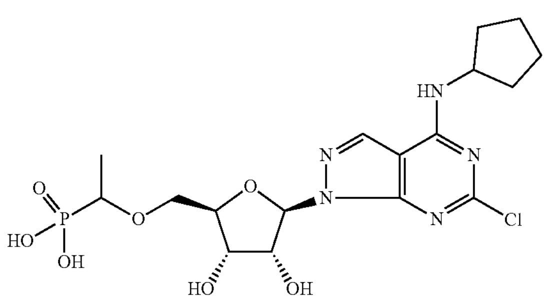 [SMILES: CC(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)ethyl)phosphonic acid |

TABLE 1-continued

| Ex | Structure | Name |
|---|---|---|
| 6 | 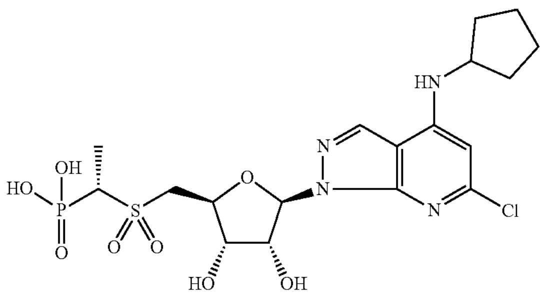 [SMILES: C[C@@H](P(=O)(O)O)S(=O)(=O)C[C@H]1O[C@@H](n2ncc3c(NC4CCCC4)cc(Cl)nc32)[C@H](O)[C@@H]1O] | ((S)-1-(((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)ethyl) phosphonic acid |
| 7 | 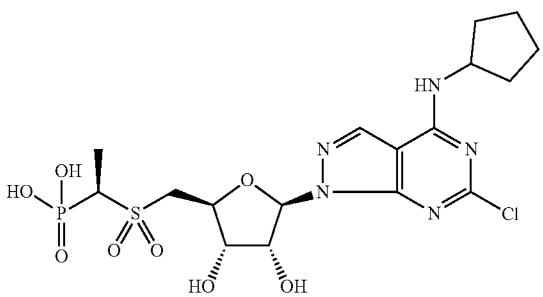 [SMILES: C[C@H](P(=O)(O)O)S(=O)(=O)C[C@H]1O[C@@H](n2ncc3c(NC4CCCC4)nc(Cl)nc32)[C@H](O)[C@@H]1O] | ((R)-1-(((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)ethyl) phosphonic acid |
| 8 | 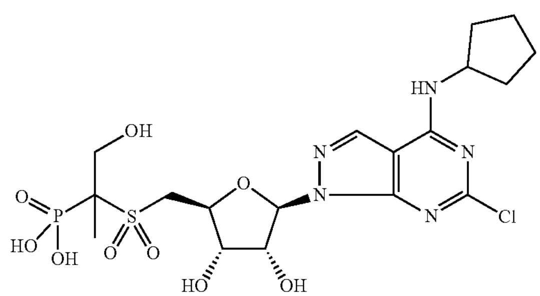 [SMILES: CC(CO)(P(=O)(O)O)S(=O)(=O)C[C@H]1O[C@@H](n2ncc3c(NC4CCCC4)nc(Cl)nc32)[C@H](O)[C@@H]1O] | (2-(((((2S,3S,4R,5R)-5-(6-chloro-(cyclopentylamino)-1H-pyrazolo[3,4-d]pyrimidin-1-yl)-3,4-dihydroxytetrahydrofuran-2-yl)methyl)sulfonyl)-1-hydroxypropan-2-yl) phosphonic acid |
| 9 | 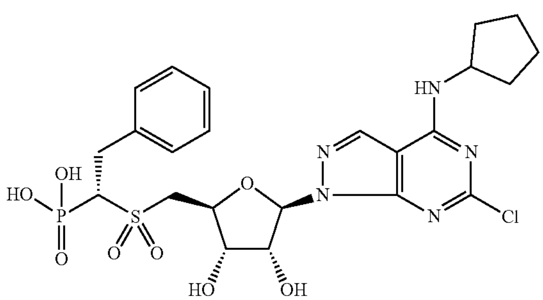 [SMILES: O=P(O)(O)[C@H](Cc1ccccc1)S(=O)(=O)C[C@H]1O[C@@H](n2ncc3c(NC4CCCC4)nc(Cl)nc32)[C@H](O)[C@@H]1O] | ((S)-1-(((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)-2-phenylethyl) phosphonic acid |
| 10 | 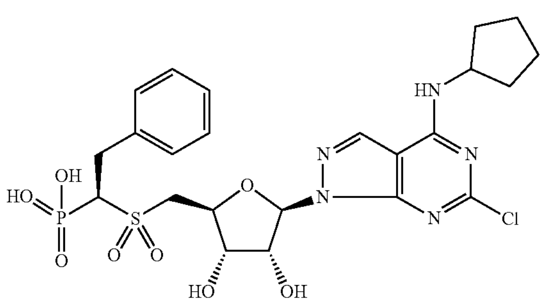 | ((R)-1-(((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)-2-phenylethyl) phosphonic acid |

TABLE 1-continued

| Ex | Structure | Name |
|---|---|---|
| 11 | 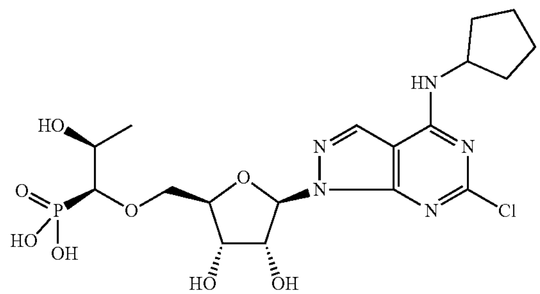 [SMILES: C[C@H](O)[C@@H](OC[C@H]1O[C@@H](n2ncc3c(NC4CCCC4)nc(Cl)nc32)[C@H](O)[C@@H]1O)P(=O)(O)O] | ((1S,2S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxypropyl)phosphonic acid |
| 12 | 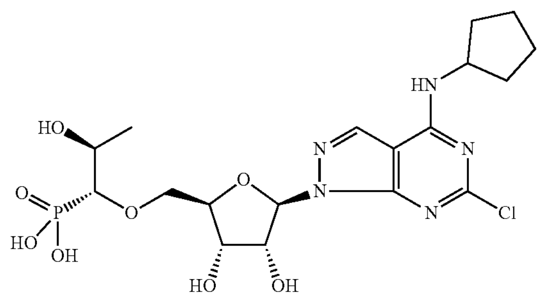 [SMILES: C[C@H](O)[C@H](OC[C@H]1O[C@@H](n2ncc3c(NC4CCCC4)nc(Cl)nc32)[C@H](O)[C@@H]1O)P(=O)(O)O] | ((1R,2S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxypropyl)phosphonic acid |
| 13 | 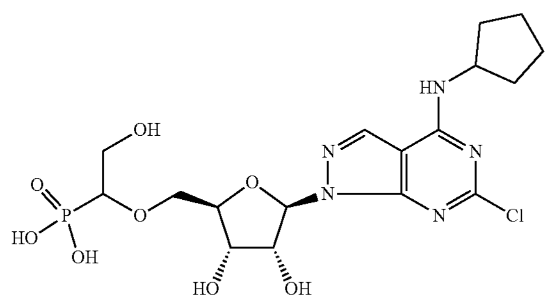 [SMILES: O=P(O)(O)C(CO)OC[C@H]1O[C@@H](n2ncc3c(NC4CCCC4)nc(Cl)nc32)[C@H](O)[C@@H]1O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxypropyl)phosphonic acid |
| 14 | 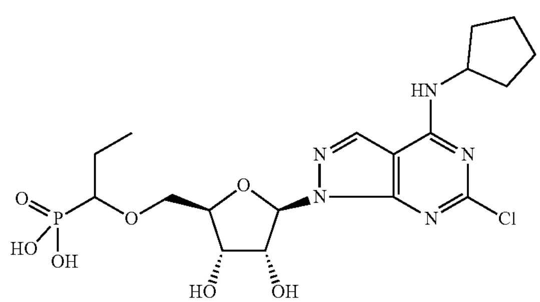 [SMILES: CCC(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)propyl)phosphonic acid |
| 15 | 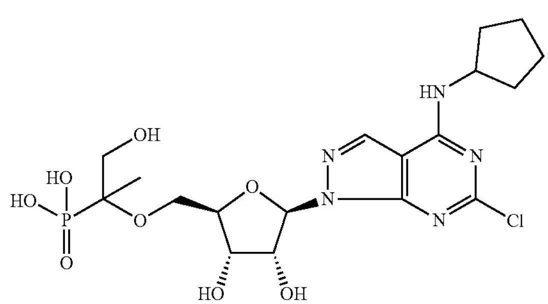 [SMILES: CC(CO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 16 | 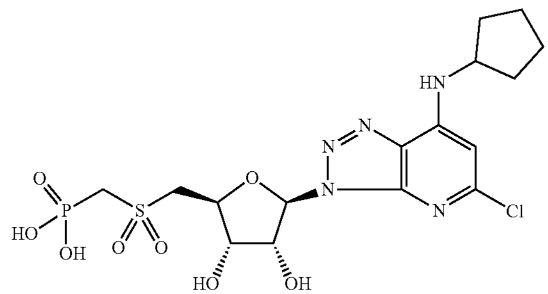 [SMILES: O=P(O)(O)CS(=O)(=O)C[C@H]1O[C@@H](n2nnc3c(NC4CCCC4)cc(Cl)nc32)[C@H](O)[C@@H]1O] | (((((2S,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)sulfonyl)methyl)phosphonic acid |
| 17 | 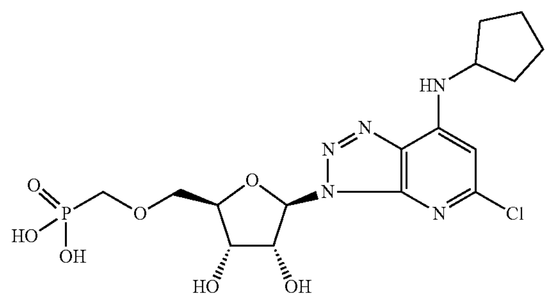 [SMILES: O=P(O)(O)COC[C@H]1O[C@@H](n2nnc3c(NC4CCCC4)cc(Cl)nc32)[C@H](O)[C@@H]1O] | ((((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)methyl)phosphonic acid |
| 18 | 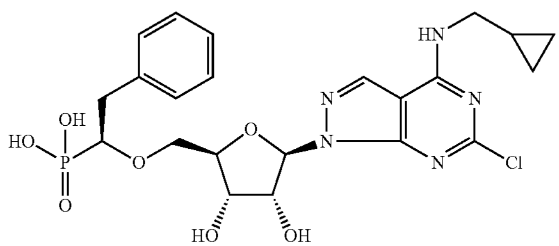 [SMILES: O=P(O)(O)[C@@H](Cc1ccccc1)OC[C@H]1O[C@@H](n2ncc3c(NCC4CC4)nc(Cl)nc32)[C@H](O)[C@@H]1O] | ((S)-1-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-2-phenylethyl)phosphonic acid |
| 19 | 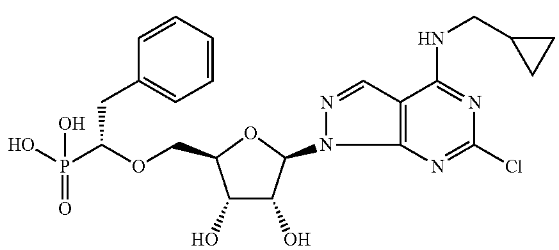 [SMILES: O=P(O)(O)[C@H](Cc1ccccc1)OC[C@H]1O[C@@H](n2ncc3c(NCC4CC4)nc(Cl)nc32)[C@H](O)[C@@H]1O] | ((R)-1-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-2-phenylethyl)phosphonic acid |
| 20 | 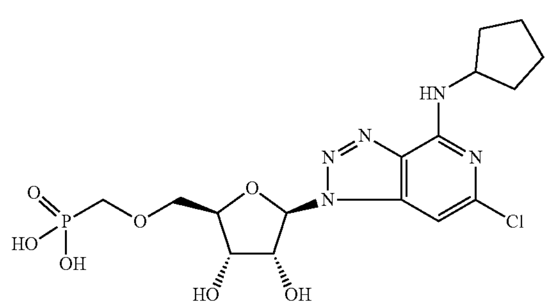 [SMILES: O=P(O)(O)COC[C@H]1O[C@@H](n2nnc3c(NC4CCCC4)nc(Cl)cc32)[C@H](O)[C@@H]1O] | (((((2R,3S,4R,5R)-5-(6-chloro-4-(cyclopentylamino)-1H-[1,2,3]triazolo[4,5-c]pyridin-1-yl)-3,4-dihydroxytetrahydrofuran-2-yl)methoxy)methyl)phosphonic acid |

TABLE 1-continued

| Ex | Structure | Name |
|---|---|---|
| 21 | 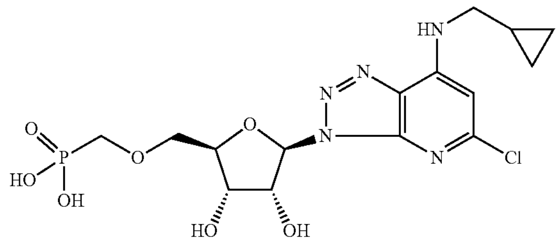 [SMILES: O=P(O)(O)COC[C@H]1O[C@@H](n2nnc3c(NCC4CC4)cc(Cl)nc32)[C@H](O)[C@@H]1O] | ((((2R,3S,4R,5R)-5-(5-chloro-7-((cyclopropylmethyl)amino)-3H-[1,2,3]triazolo[4,5-b]pyridin-3-yl)-3,4-dihydroxytetrahydrofuran-2-yl)methoxy)methyl)phosphonic acid |
| 22 | 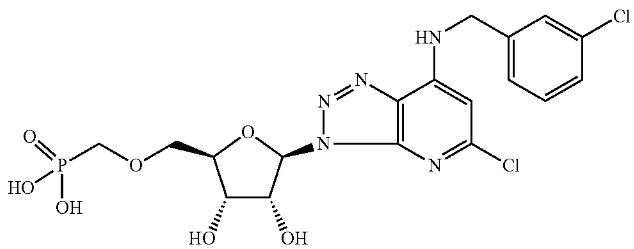 [SMILES: O=P(O)(O)COC[C@H]1O[C@@H](n2nnc3c(NCc4cccc(Cl)c4)cc(Cl)nc32)[C@H](O)[C@@H]1O] | (((((2R,3S,4R,5R)-5-(5-chloro-7-((3-chlorobenzyl)amino)-3H-[1,2,3]triazolo[4,5-b]pyridin-3-yl)-3,4-dihydroxytetrahydrofuran-2-yl)methoxy)methyl)phosphoinic acid. |
| 23 | 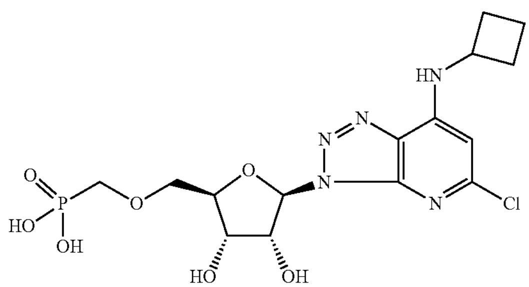 [SMILES: O=P(O)(O)COC[C@H]1O[C@@H](n2nnc3c(NC4CCC4)cc(Cl)nc32)[C@H](O)[C@@H]1O] | ((((2R,3S,4R,5R)-5-(5-chloro-7-(cyclobutylamino)-3H-[1,2,3]triazolo[4,5-b]pyridin-3-yl)-3,4-dihydroxytetrahydrofuran-2-yl)methoxy)methyl)phosphonic acid |
| 24 | 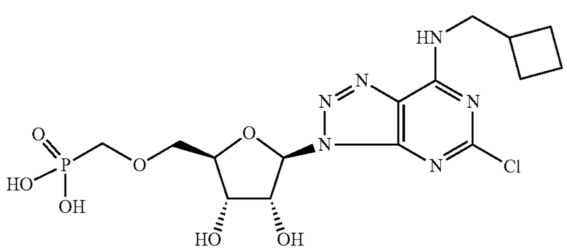 [SMILES: O=P(O)(O)COC[C@H]1O[C@@H](n2nnc3c(NCC4CCC4)nc(Cl)nc32)[C@H](O)[C@@H]1O] | ((((2R,3S,4R,5R)-5-(5-chloro-7-((cyclobutylmethyl)amino)-3H-[1,2,3]triazolo[4,5-b]pyridin-3-yl)-3,4-dihydroxytetrahydrofuran-2-yl)methoxy)methyl)phosphonic acid |
| 25 | 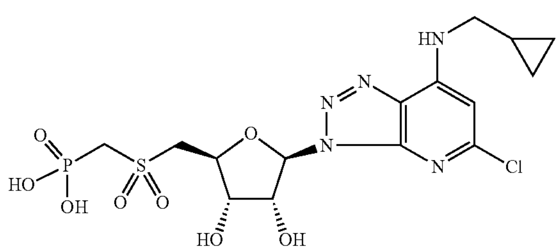 [SMILES: O=P(O)(O)CS(=O)(=O)C[C@H]1O[C@@H](n2nnc3c(NCC4CC4)cc(Cl)nc32)[C@H](O)[C@@H]1O] | ((((2R,3S,4R,5R)-5-(5-chloro-7-((cyclopropylmethyl)amino)-3H-[1,2,3]triazolo[4,5-b]pyridin-3-yl)-3,4-dihydroxytetrahydrofuran-2-yl)methoxy)sulfonyl)methyl)phosphonic acid |
| 26 | 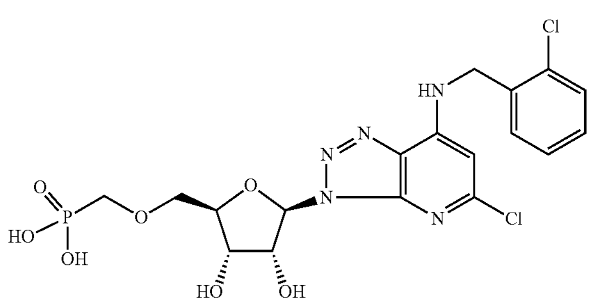 [SMILES: O=P(O)(O)COC[C@H]1O[C@@H](n2nnc3c(NCc4ccccc4Cl)cc(Cl)nc32)[C@H](O)[C@@H]1O] | ((((2R,3S,4R,5R)-5-(5-chloro-7-((2-chlorobenzyl)amino)-3H-[1,2,3]triazolo[4,5-b]pyridin-3-yl)-3,4-dihydroxytetrahydrofuran-2-yl)methoxy)methyl)phosphonic acid |

TABLE 1-continued

| Ex | Structure | Name |
|---|---|---|
| 27 | 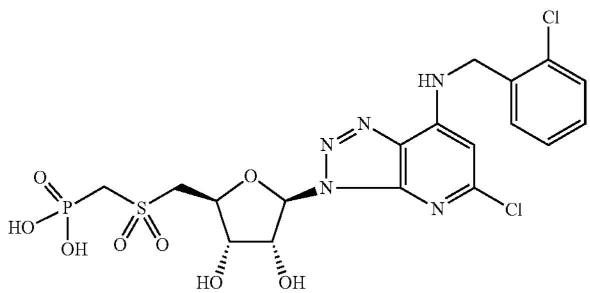 [SMILES: O=P(O)(O)CS(=O)(=O)C[C@H]1O[C@@H](n2nnc3c(NCc4ccccc4Cl)cc(Cl)nc32)[C@H](O)[C@@H]1O] | (((((2S,3S,4R,5R)-5-(5-chloro-7-((2-chlorobenzyl)amino)-3H-[1,2,3]triazolo[4,5-b]pyridin-3-yl)-3,4-dihydroxytetrahydrofuran-2-yl)methoxy)sulfonyl)methyl)phosphonic acid |
| 28 | 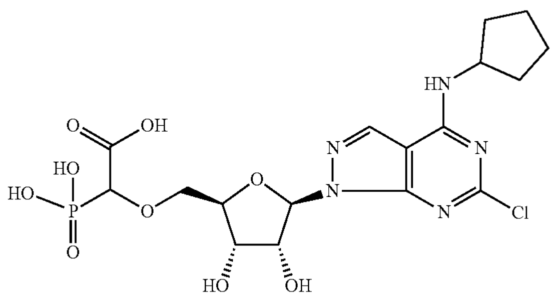 [SMILES: O=C(O)C(OC[C@H]1O[C@@H](n2ncc3c(NC4CCCC4)nc(Cl)nc32)[C@H](O)[C@@H]1O)P(=O)(O)O] | 2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-phosphonoacetic acid |
| 29 | 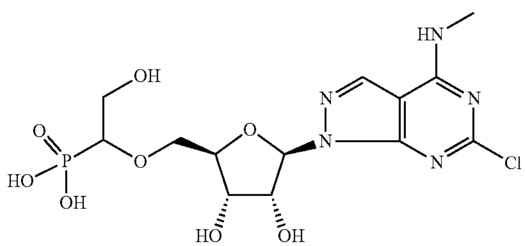 [SMILES: CNc1nc(Cl)nc2c1cnn2[C@@H]1O[C@H](COC(CO)P(=O)(O)O)[C@@H](O)[C@H]1O] | 1-(((2R,3S,4R,5R)-5-(6-chloro-4-(methylamino)-1H-pyrazolo[3,4-d]pyrimidin-1-yl)-3,4-dihydroxytetrahydrofuran-2-yl)methoxy)-2-hydroxyethyl)phosphonic acid |
| 30 | 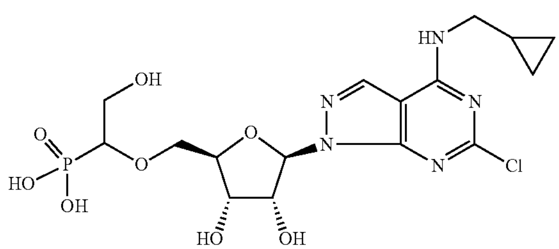 [SMILES: O=P(O)(O)C(CO)OC[C@H]1O[C@@H](n2ncc3c(NCC4CC4)nc(Cl)nc32)[C@H](O)[C@@H]1O] | 1-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-2-hydroxyethyl)phosphonic acid |
| 31 | 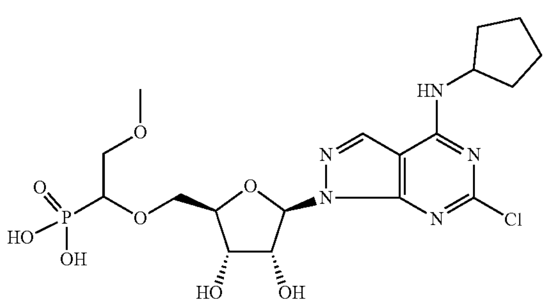 [SMILES: COCC(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-methoxyethyl)phosphonic acid |

TABLE 1-continued

| Ex | Structure | Name |
|---|---|---|
| 32 | 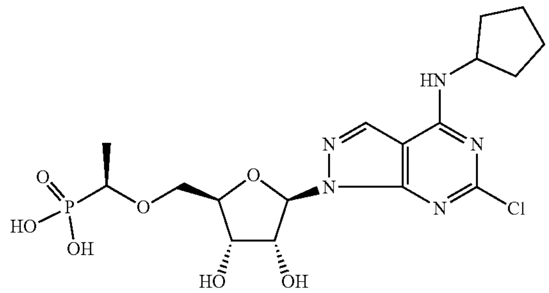 [SMILES: C[C@@H](OC[C@H]1O[C@@H](n2ncc3c(NC4CCCC4)nc(Cl)nc32)[C@H](O)[C@@H]1O)P(=O)(O)O] | ((S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)ethyl)phosphonic acid |
| 33 | 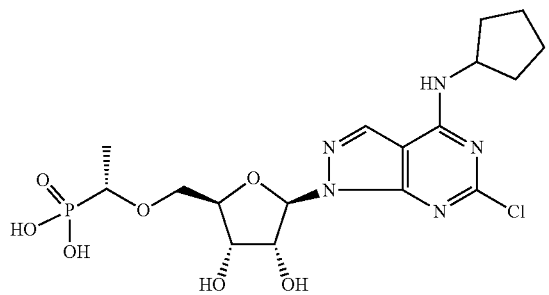 [SMILES: C[C@H](OC[C@H]1O[C@@H](n2ncc3c(NC4CCCC4)nc(Cl)nc32)[C@H](O)[C@@H]1O)P(=O)(O)O] | ((R)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)ethyl)phosphonic acid |
| 34 | 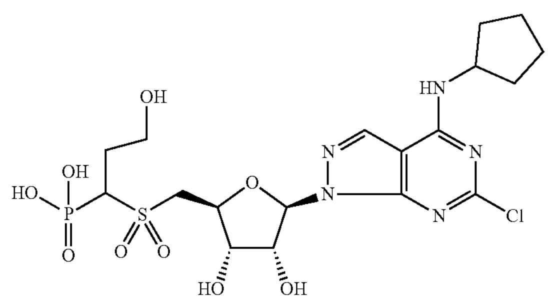 [SMILES: O=P(O)(O)C(CCO)S(=O)(=O)C[C@H]1O[C@@H](n2ncc3c(NC4CCCC4)nc(Cl)nc32)[C@H](O)[C@@H]1O] | 1-((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)-3-hydroxypropyl)phosphonic acid |
| 35 | 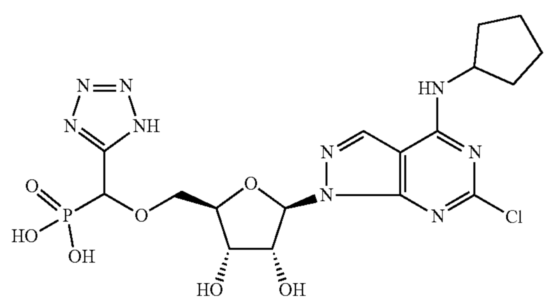 [SMILES: O=P(O)(O)C(OC[C@H]1O[C@@H](n2ncc3c(NC4CCCC4)nc(Cl)nc32)[C@H](O)[C@@H]1O)c1nnn[nH]1] | ((((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)(1H-tetrazol-5-yl)methyl)phosphonic acid |
| 36 | 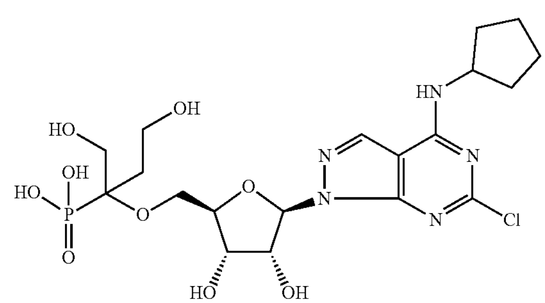 [SMILES: O=P(O)(O)C(CO)(CCO)OC[C@H]1O[C@@H](n2ncc3c(NC4CCCC4)nc(Cl)nc32)[C@H](O)[C@@H]1O] | (2-(((2R,3S,4R,5R)-5-(6-chloro-4-((cyclopentylamino)-1H-pyrazolo[3,4-d]pyrimidin-1-yl)-3,4-dihydroxytetrahydrofuran-2-yl)methoxy)-1,4-dihydroxybutan-2-yl)phosphonic acid |

TABLE 1-continued

| Ex | Structure | Name |
|---|---|---|
| 37 | 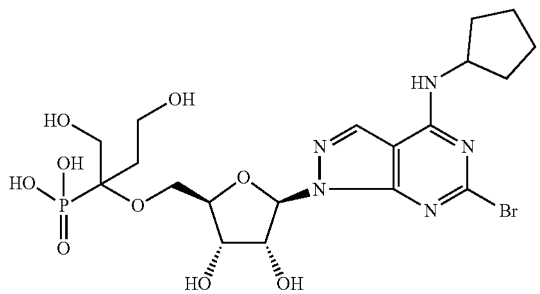 [SMILES: O=P(O)(O)C(CO)(CCO)OC[C@H]1O[C@@H](n2ncc3c(NC4CCCC4)nc(Br)nc32)[C@H](O)[C@@H]1O] | (2-((((2R,3S,4R,5R)-5-(6-bromo-4-(cyclopentylamino)-1H-pyrazolo[3,4-d]pyrimidin-1-yl)-3,4-dihydroxytetrahydrofuran-2-yl)methoxy)-1,4-dihydroxybutan-2-yl)phosphonic acid |
| 38 | 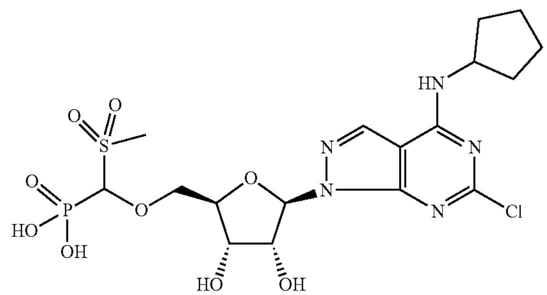 [SMILES: CS(=O)(=O)C(OC[C@H]1O[C@@H](n2ncc3c(NC4CCCC4)nc(Cl)nc32)[C@H](O)[C@@H]1O)P(=O)(O)O] | ((((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)methylsulfonyl)methyl)phosphonic acid |
| 39 | 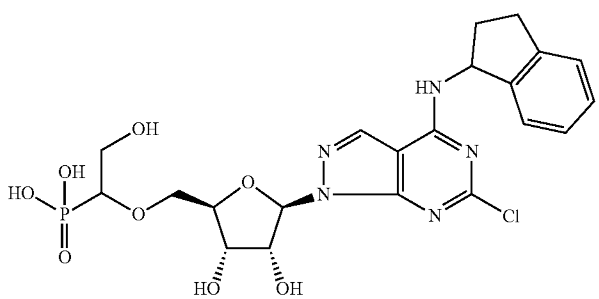 [SMILES: O=P(O)(O)C(CO)OC[C@H]1O[C@@H](n2ncc3c(NC4CCc5ccccc54)nc(Cl)nc32)[C@H](O)[C@@H]1O] | (1-(((2R,3S,4R,5R)-5-(6-chloro-4-(((S)-2,3-dihydro-1H-inden-1-yl)amino)-1H-pyrazolo[3,4-d]pyrimidin-1-yl)-3,4-dihydroxytetrahydrofuran-2-yl)methoxy)-2-hydroxyethyl)phosphonic acid |
| 40 | 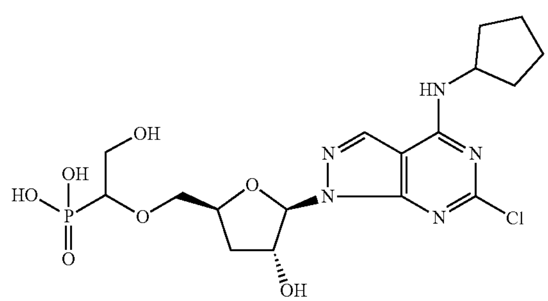 [SMILES: O=P(O)(O)C(CO)OC[C@@H]1C[C@@H](O)[C@H](n2ncc3c(NC4CCCC4)nc(Cl)nc32)O1] | (1-(((2R,4R,5R)-5-(6-chloro-4-((cyclopentylamino)-1H-pyrazolo[3,4-d]pyrimidin-1-yl)-3,4-dihydroxytetrahydrofuran-2-yl)methoxy)-2-hydroxyethyl)phosphonic acid |
| 41 | 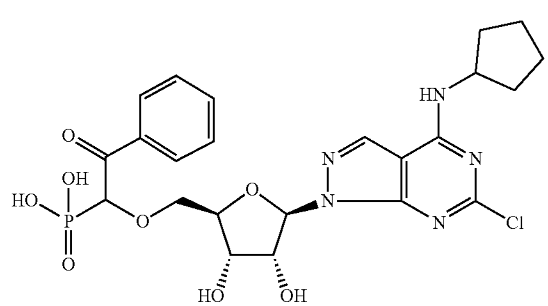 [SMILES: O=C(c1ccccc1)C(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-oxo-2-phenylethyl)phosphonic acid |

TABLE 1-continued

| Ex | Structure | Name |
|---|---|---|
| 42 | 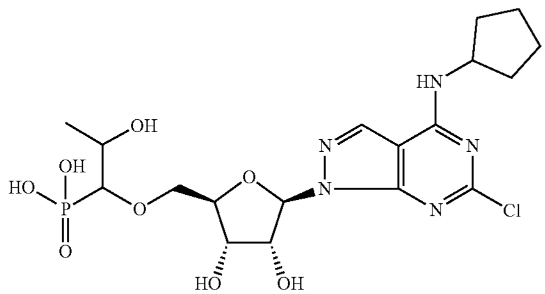 [SMILES: CC(O)C(OC[C@H]1O[C@@H](n2ncc3c(NC4CCCC4)nc(Cl)nc32)[C@H](O)[C@@H]1O)P(=O)(O)O] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxypropyl)phosphonic acid |
| 43 | 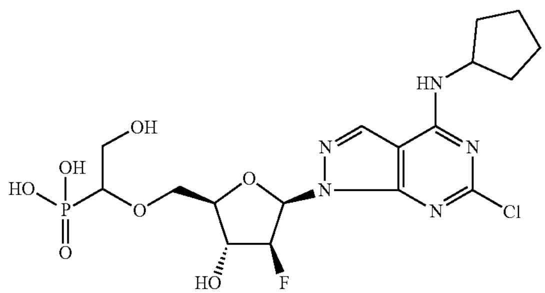 [SMILES: O=P(O)(O)C(CO)OC[C@H]1O[C@@H](n2ncc3c(NC4CCCC4)nc(Cl)nc32)[C@@H](F)[C@@H]1O] | (1-(((2R,3R,4S,5R)-5-(6-chloro-4-(cyclopentylamino)-1H-pyrazolo[3,4-d]pyrimidin-1-yl)-4-fluoro-3-hydroxytetrahydrofuran-2-yl)methoxy)-2-hydroxyethyl)phosphonic acid |
| 44 | 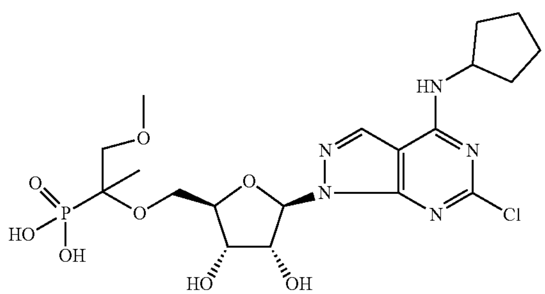 [SMILES: COCC(C)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-methoxypropan-2-yl)phosphonic acid |
| 45 | 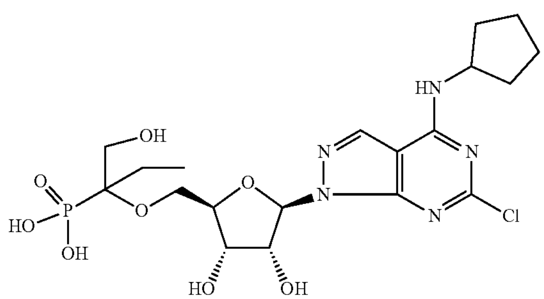 [SMILES: CCC(CO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxybutan-2-yl)phosphonic acid |
| 46 | 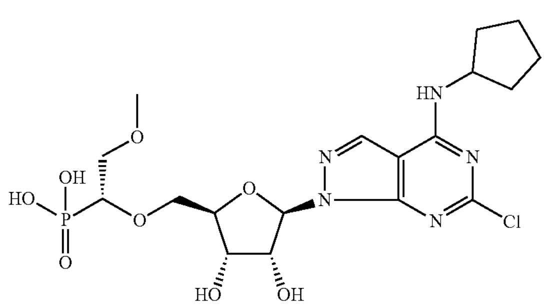 [SMILES: COC[C@H](OC[C@H]1O[C@@H](n2ncc3c(NC4CCCC4)nc(Cl)nc32)[C@H](O)[C@@H]1O)P(=O)(O)O] | ((R)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-methoxyethyl)phosphonic acid |

TABLE 1-continued

| Ex | Structure | Name |
|---|---|---|
| 47 | 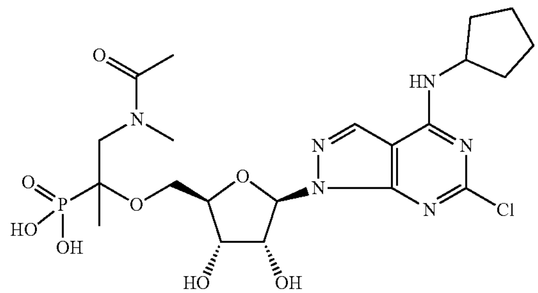 [SMILES: CC(=O)N(C)CC(C)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-((cyclopentylamino)-1H-pyrazolo[3,4-d]pyrimidin-1-yl)-3,4-dihydroxytetrahydrofuran-2-yl)methoxy)-1-(N-methylacetamido)propan-2-yl)phosphonic acid |
| 48 | 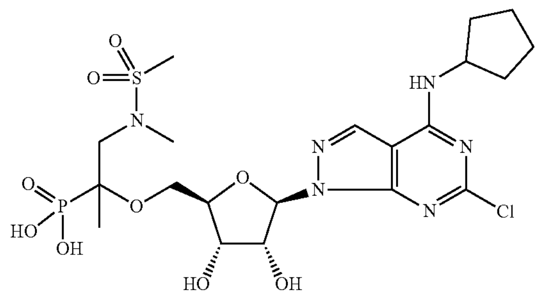 [SMILES: CN(CC(C)(OC[C@H]1O[C@@H](n2ncc3c(NC4CCCC4)nc(Cl)nc32)[C@H](O)[C@@H]1O)P(=O)(O)O)S(C)(=O)=O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(N-methylmethylsulfonamido)propan-2-yl)phosphonic acid |
| 49 | 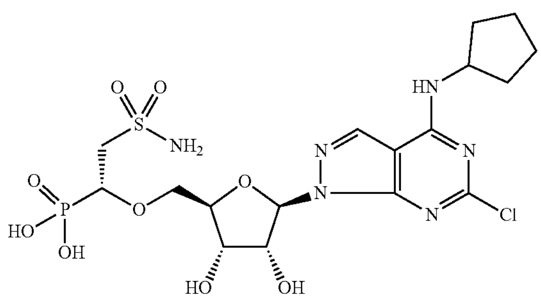 [SMILES: NS(=O)(=O)C[C@H](OC[C@H]1O[C@@H](n2ncc3c(NC4CCCC4)nc(Cl)nc32)[C@H](O)[C@@H]1O)P(=O)(O)O] | ((R)-1-(((2R,3S,4R,5R)-5-(6-chloro-4-((cyclopentylamino)-1H-pyrazolo[3,4-d]pyrimidin-1-yl)-3,4-dihydroxytetrahydrofuran-2-yl)methoxy)-2-sulfamoylethyl)phosphonic acid |
| 50 | 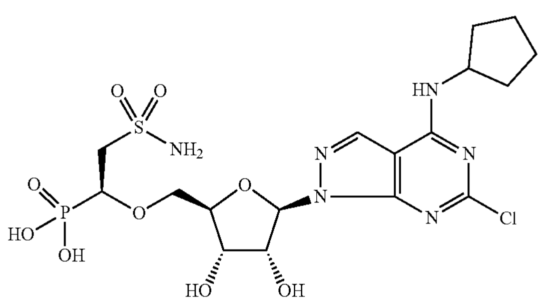 [SMILES: NS(=O)(=O)C[C@@H](OC[C@H]1O[C@@H](n2ncc3c(NC4CCCC4)nc(Cl)nc32)[C@H](O)[C@@H]1O)P(=O)(O)O] | ((S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-sulfamoylethyl)phosphonic acid |
| 51 | 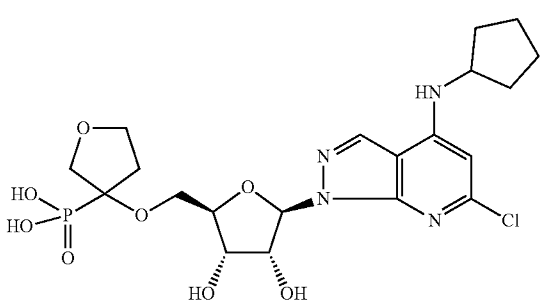 [SMILES: O=P(O)(O)C1(OC[C@H]2O[C@@H](n3ncc4c(NC5CCCC5)cc(Cl)nc43)[C@H](O)[C@@H]2O)CCOC1] | (3-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-tetrahydrofuran-3-yl)phosphonic acid |

TABLE 1-continued

| Ex | Structure | Name |
|---|---|---|
| 52 | 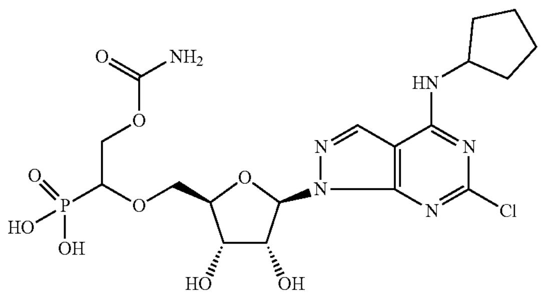 [SMILES: NC(=O)OCC(OC[C@H]1O[C@@H](n2ncc3c(NC4CCCC4)nc(Cl)nc32)[C@H](O)[C@@H]1O)P(=O)(O)O] | (2-(carbamoyloxy)-1-(((2R,3S,4R,5R)-5-(6-chloro-4-(cyclopentylamino)-1H-pyrazolo[3,4-dihydroxytetrahydrofuran-2-yl)methoxy)ethyl)phosphonic acid |
| 53 | 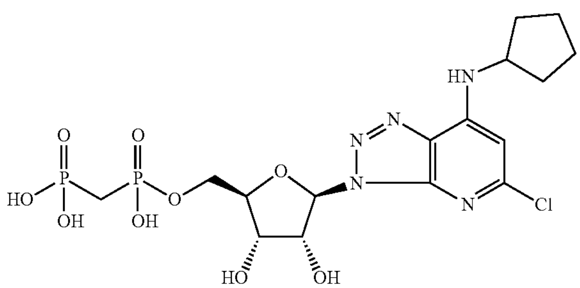 [SMILES: O=P(O)(O)CP(=O)(O)OC[C@H]1O[C@@H](n2nnc3c(NC4CCCC4)cc(Cl)nc32)[C@H](O)[C@@H]1O] | (((((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)(hydroxy)phosphoryl)methyl)phosphonic acid |
| 54 | 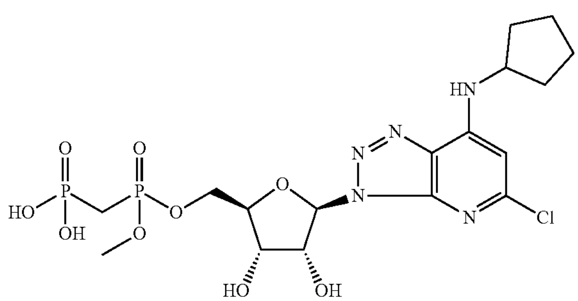 [SMILES: COP(=O)(CP(=O)(O)O)OC[C@H]1O[C@@H](n2nnc3c(NC4CCCC4)cc(Cl)nc32)[C@H](O)[C@@H]1O] | (((((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)(hydroxy)phosphoryl)methyl)phosphonic acid |
| 55 | 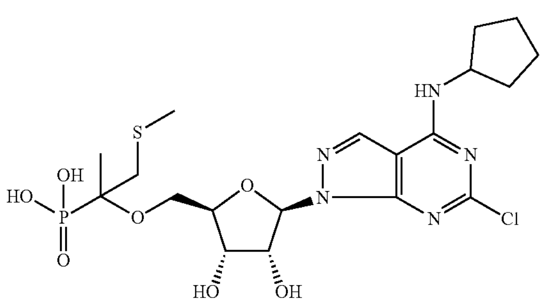 [SMILES: CSCC(C)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-methylthio)propan-2-yl)phosphonic acid |
| 56 | 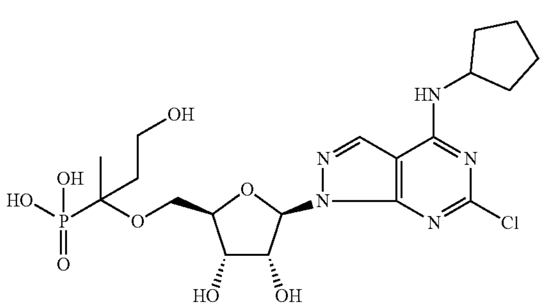 [SMILES: CC(CCO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-4-hydroxybutan-2-yl)phosphonic acid |

TABLE 1-continued

| Ex | Structure | Name |
| --- | --- | --- |
| 57 | 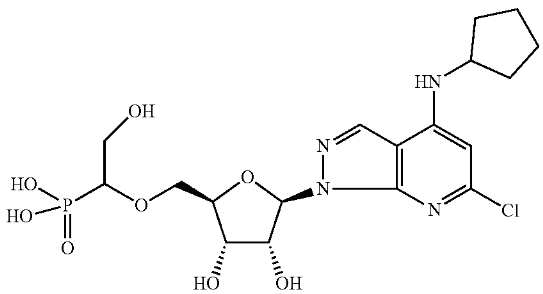 [SMILES: O=P(O)(O)C(CO)OC[C@H]1O[C@@H](n2ncc3c(NC4CCCC4)cc(Cl)nc32)[C@H](O)[C@@H]1O] | (1-(((2R,3S,4R,5R)-5-(6-chloro-4-(cyclopentylamino)-1H-pyrazolo[3,4-b]pyridin-1-yl)-3,4-dihydroxytetrahydrofuran-2-yl)methoxy)-2-hydroxyethyl)phosphonic acid |
| 58 | 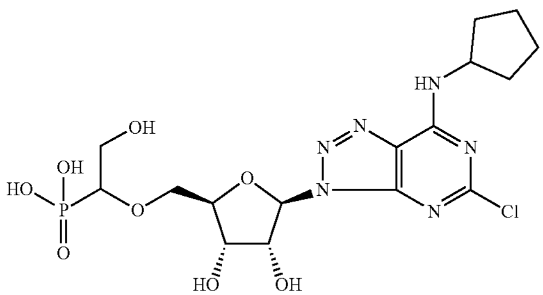 [SMILES: O=P(O)(O)C(CO)OC[C@H]1O[C@@H](n2nnc3c(NC4CCCC4)nc(Cl)nc32)[C@H](O)[C@@H]1O] | (1-(((2R,3S,4R,5R)-5-(5-chloro-7-(cyclopentylamino)-3H-[1,2,3]trizaolo[4,5-d]pyrimidin-3-yl)-3,4-dihydroxytetrahydrofuran-2-yl)methoxy)-2-hydroxyethyl)phosphonic acid |
| 59 | 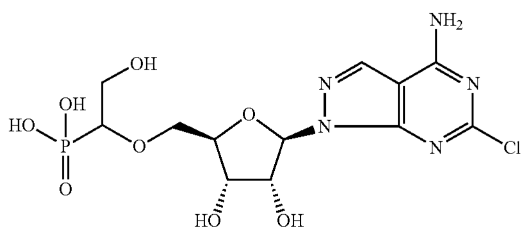 [SMILES: Nc1nc(Cl)nc2c1cnn2[C@@H]1O[C@H](COC(CO)P(=O)(O)O)[C@@H](O)[C@H]1O] | (1-(((2R,3S,4R,5R)-5-(4-amino-6-chloro-1H-pyrazolo[3,4-d]pyrimidin-1-yl)-3,4-dihydroxytetrahydrofuran-2-yl)methoxy)-2-hydroxyethyl)phosphonic acid |
| 60 | 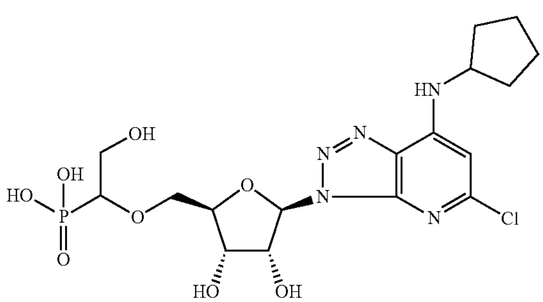 [SMILES: O=P(O)(O)C(CO)OC[C@H]1O[C@@H](n2nnc3c(NC4CCCC4)cc(Cl)nc32)[C@H](O)[C@@H]1O] | (1-(((2R,3S,4R,5R)-5-(5-chloro-7-(cyclopentylamino)-3H-[1,2,3]trizaolo[4,5-b]pyridin-3-yl)-3,4-dihydroxytetrahydrofuran-2-yl)methoxy)-2-hydroxyethyl)phosphonic acid |
| 61 | 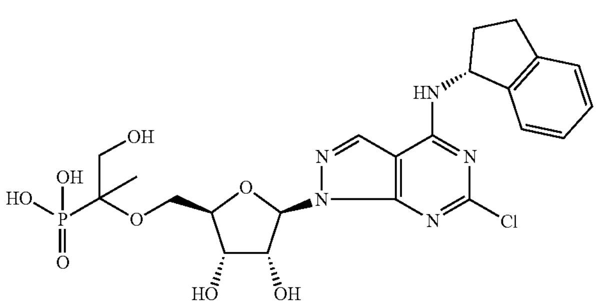 [SMILES: CC(CO)(OC[C@H]1O[C@@H](n2ncc3c(N[C@@H]4CCc5ccccc54)nc(Cl)nc32)[C@H](O)[C@@H]1O)P(=O)(O)O] | (2-(((2R,3S,4R,5R)-5-(6-chloro-4-(((R)-2,3-dihydro-1H-inden-1-yl)amino)-1H-pyrazolo[3,4-d]pyrimidin-1-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 62 | 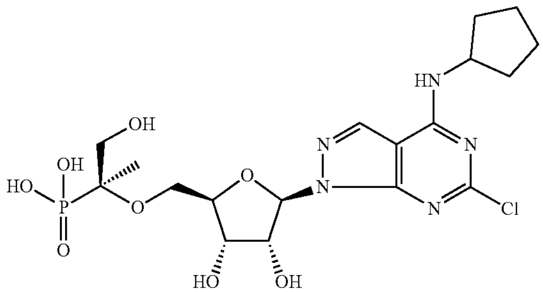 [SMILES: C[C@](CO)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxypropan-2-yl) phosphonic acid |
| 63 | 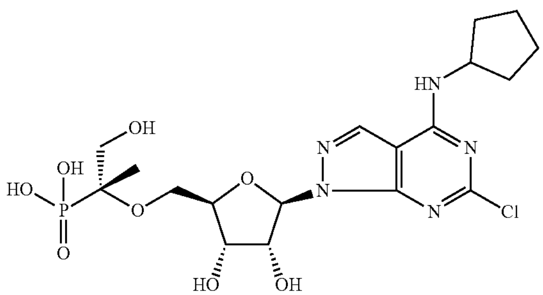 [SMILES: C[C@@](CO)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxypropan-2-yl) phosphonic acid |
| 64 | 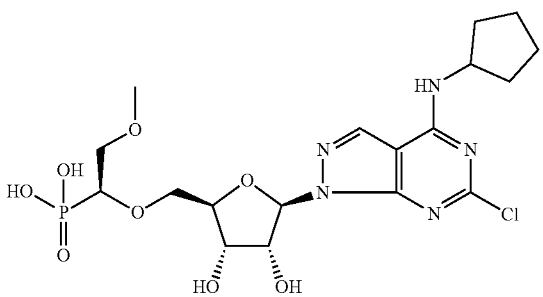 [SMILES: COC[C@@H](OC[C@H]1O[C@@H](n2ncc3c(NC4CCCC4)nc(Cl)nc32)[C@H](O)[C@@H]1O)P(=O)(O)O] | ((S)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-methoxyethyl) phosphonic acid |
| 65 | 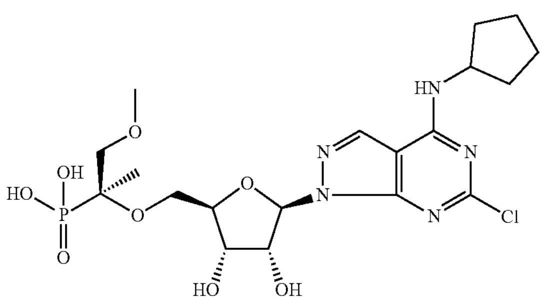 [SMILES: COC[C@@](C)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-methoxypropan-2-yl) phosphonic acid |
| 66 | 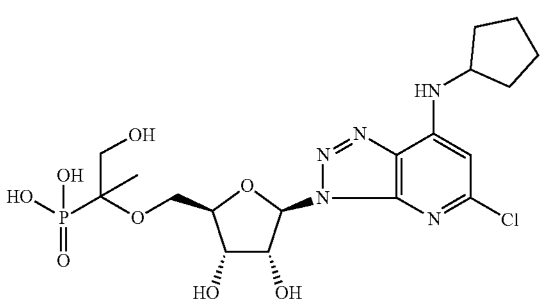 [SMILES: CC(CO)(OC[C@H]1O[C@@H](n2nnc3c(NC4CCCC4)cc(Cl)nc32)[C@H](O)[C@@H]1O)P(=O)(O)O] | (2-(((2R,3S,4R,5R)-5-(5-chloro-7-(cyclopentylamino)-3H-[1,2,3]trizaolo[4,5-b]pyridin-3-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 67 | 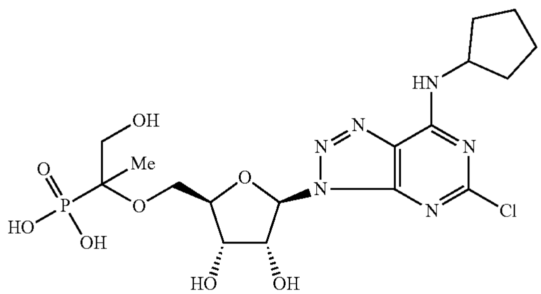 [SMILES: CC(CO)(OC[C@H]1O[C@@H](n2nnc3c(NC4CCCC4)nc(Cl)nc32)[C@H](O)[C@@H]1O)P(=O)(O)O] | (2-(((2R,3S,4R,5R)-5-(5-chloro-7-(cyclopentylamino)-3H-[1,2,3]trizaolo[4,5-d]pyridin-3-yl)-3,4-dihydroxytetrahydrofuran-2-yl)methoxy)-1-hydroxypropan-2-yl)phosphonic acid |
| 68 | 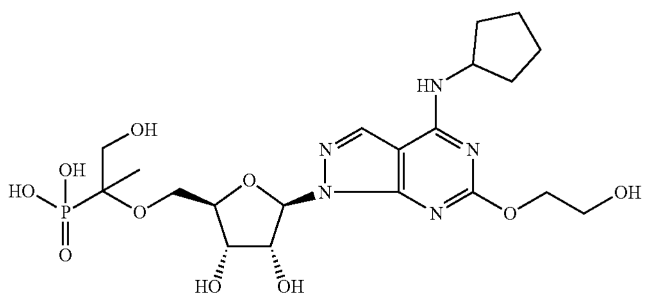 [SMILES: CC(CO)(OC[C@H]1O[C@@H](n2ncc3c(NC4CCCC4)nc(OCCO)nc32)[C@H](O)[C@@H]1O)P(=O)(O)O] | (2-(((2R,3S,4R,5R)-5-(4-(cyclopentylamino)-6-(2-hydroxyethoxy)-1H-pyrazolo[3,4-d]pyridin-3-yl)-3,4-dihydroxytetrahydrofuran-2-yl)methoxy)-1-hydroxypropan-2-yl)phosphonic acid |
| 69 | 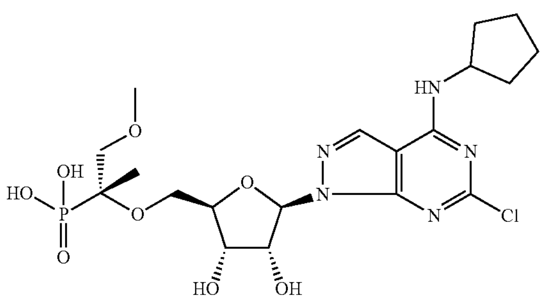 [SMILES: COC[C@](C)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-chloro-4-((cyclopentylamino)-1H-pyrazolo[3,4-d]pyrimidin-1-yl)-3,4-dihydroxytetrahydrofuran-2-yl)methoxy)-1-methoxypropan-2-yl)phosphonic acid |
| 70 | 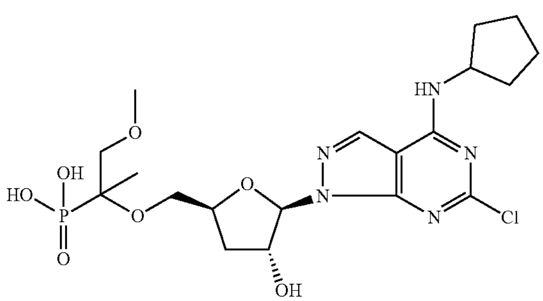 [SMILES: COCC(C)(OC[C@@H]1C[C@@H](O)[C@H](n2ncc3c(NC4CCCC4)nc(Cl)nc32)O1)P(=O)(O)O] | (2-(((2S,4R,5R)-5-(6-chloro-4-(cyclopentylamino)-1H-pyrazolo[3,4-d]pyrimidin-1-yl)-4-hydroxytetrahydrofuran-2-yl)methoxy)-1-methoxypropan-2-yl)phosphonic acid |
| 71 | 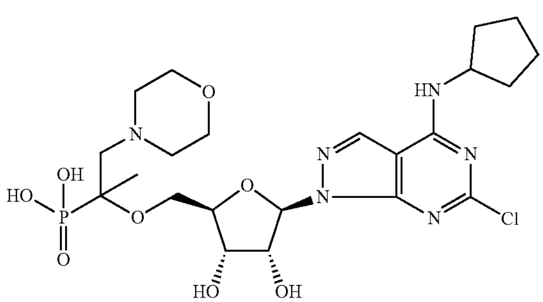 [SMILES: CC(CN1CCOCC1)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-morpholinopropan-2-yl)phosphonic acid |

TABLE 1-continued

| Ex | Structure | Name |
|---|---|---|
| 72 | 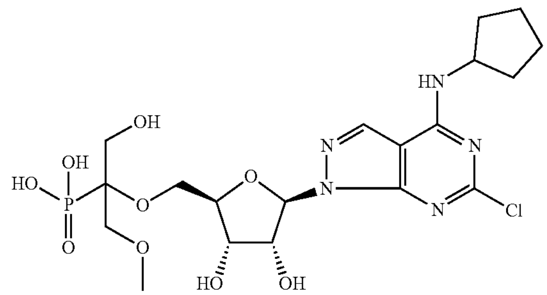 [SMILES: COCC(CO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-methoxypropan-2-yl)phosphonic acid |
| 73 | 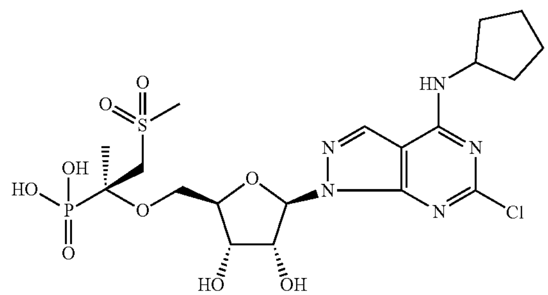 [SMILES: C[C@](CS(C)(=O)=O)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(methylsulfonyl)propan-2-yl)phosphonic acid |
| 74 | 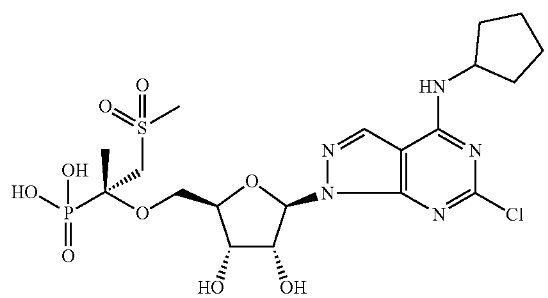 [SMILES: C[C@@](CS(C)(=O)=O)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(methylsulfonyl)propan-2-yl)phosphonic acid |
| 75 | 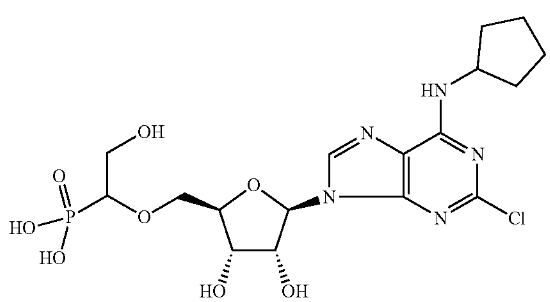 [SMILES: O=P(O)(O)C(CO)OC[C@H]1O[C@@H](n2cnc3c(NC4CCCC4)nc(Cl)nc32)[C@H](O)[C@@H]1O] | (1-(((2R,3S,4R,5R)-5-(2-chloro-6-(cyclopentylamino)-9H-purin-9-yl)-3,4-dihydroxytetrahydrofuran-2-yl)methoxy)-2-hydroxyethyl)phosphonic acid |
| 76 | 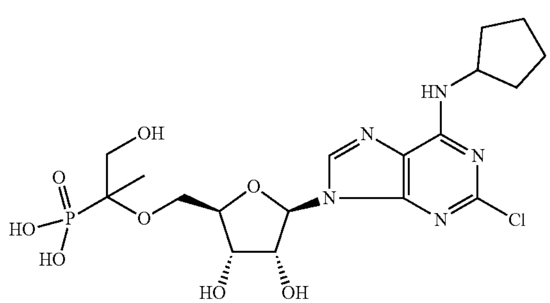 [SMILES: CC(CO)(OC[C@H]1O[C@@H](n2cnc3c(NC4CCCC4)nc(Cl)nc32)[C@H](O)[C@@H]1O)P(=O)(O)O] | (2-(((2R,3S,4R,5R)-5-(2-chloro-6-(cyclopentylamino)-9H-purin-9-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 77 | 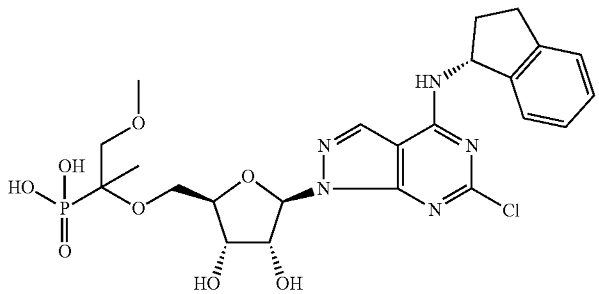 [SMILES: COCC(C)(OC[C@H]1O[C@@H](n2ncc3c(N[C@@H]4CCc5ccccc54)nc(Cl)nc32)[C@H](O)[C@@H]1O)P(=O)(O)O] | (2-(((2R,3S,4R,5R)-5-(6-chloro-4-(((R)-2,3-dihydro-1H-inden-1-yl)amino)-1H-pyrazolo[3,4-d]pyrimidin-1-yl)-3,4-dihydroxytetrahydrofuran-2-yl)methoxy)-1-methoxypropan-2-yl)phosphonic acid |
| 78 | 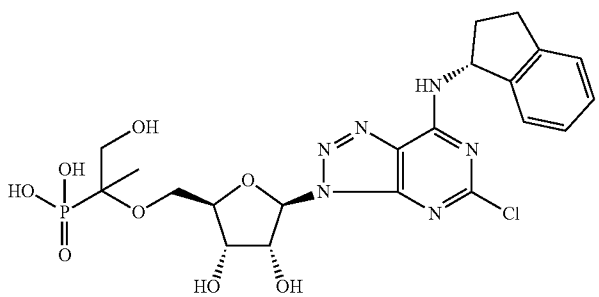 [SMILES: CC(CO)(OC[C@H]1O[C@@H](n2nnc3c(N[C@@H]4CCc5ccccc54)nc(Cl)nc32)[C@H](O)[C@@H]1O)P(=O)(O)O] | (2-(((2R,3S,4R,5R)-5-(5-chloro-7-(((R)-2,3-dihydro-1H-inden-1-yl)amino)-3H-[1,2,3]triazo[4,5-d]pyrimidin-3-yl)-3,4-dihydroxytetrahydrofuran-2-yl)methoxy)-1-hydroxypropan-2-yl)phosphonic acid |
| 79 | 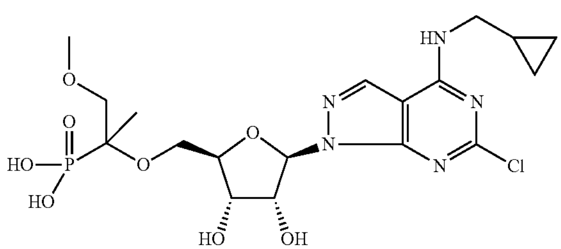 [SMILES: COCC(C)(OC[C@H]1O[C@@H](n2ncc3c(NCC4CC4)nc(Cl)nc32)[C@H](O)[C@@H]1O)P(=O)(O)O] | (2-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-methoxypropan-2-yl)phosphonic acid |
| 80 | 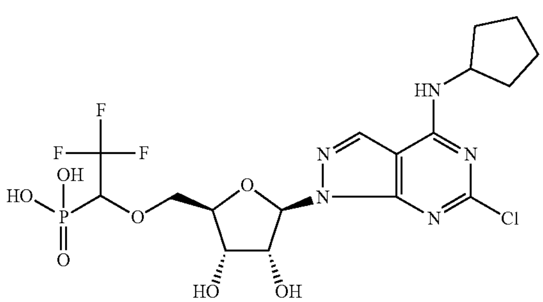 [SMILES: O=P(O)(O)C(OC[C@H]1O[C@@H](n2ncc3c(NC4CCCC4)nc(Cl)nc32)[C@H](O)[C@@H]1O)C(F)(F)F] | (1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2,2,2-trifluoroethyl)phosphonic acid |
| 81 | 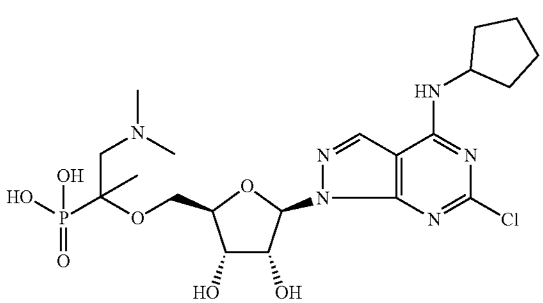 [SMILES: CN(C)CC(C)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-trifluoroethyl)phosphonic acid |

TABLE 1-continued

| Ex | Structure | Name |
|---|---|---|
| 82 | 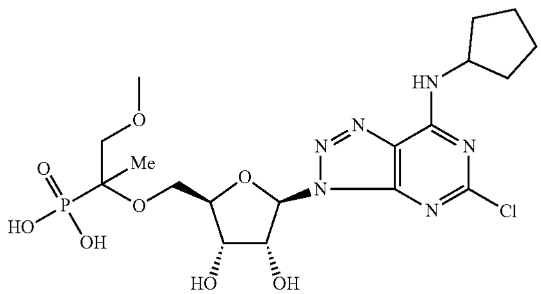 [SMILES: COCC(C)(OC[C@H]1O[C@@H](n2nnc3c(NC4CCCC4)nc(Cl)nc32)[C@H](O)[C@@H]1O)P(=O)(O)O] | (2-(((2R,3S,4R,5R)-5-(5-chloro-7-(cyclopentylamino)-3H-[1,2,3]trizaolo[4,5-d]pyrimidin-1-yl)-3,4-dihydroxytetrahydrofuran-2-yl)methoxy)-1-methoxypropan-2-yl)phosphonic acid |
| 83 | 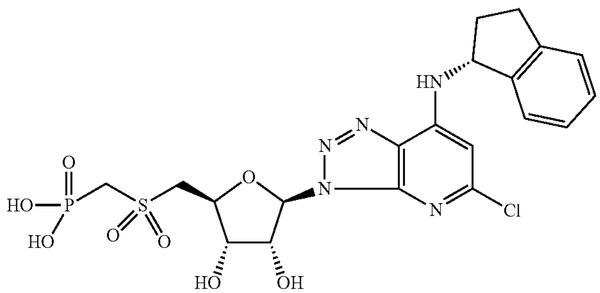 [SMILES: O=P(O)(O)CS(=O)(=O)C[C@H]1O[C@@H](n2nnc3c(N[C@@H]4CCc5ccccc54)cc(Cl)nc32)[C@H](O)[C@@H]1O] | (((((2S,3S,4R,5R)-5-(5-chloro-7-(((R)-2,3-dihydro-1H-inden-1-yl)amino)-3H-[1,2,3]triazolo[4,5-b]pyridin-3-yl)-3,4-dihydroxytetrahydrofuran-2-yl)methoxy)sulfonyl)methyl) phosphonic acid |
| 84 | 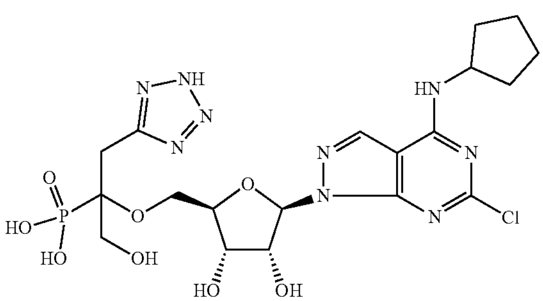 [SMILES: O=P(O)(O)C(CO)(Cc1nn[nH]n1)OC[C@H]1O[C@@H](n2ncc3c(NC4CCCC4)nc(Cl)nc32)[C@H](O)[C@@H]1O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 85 | 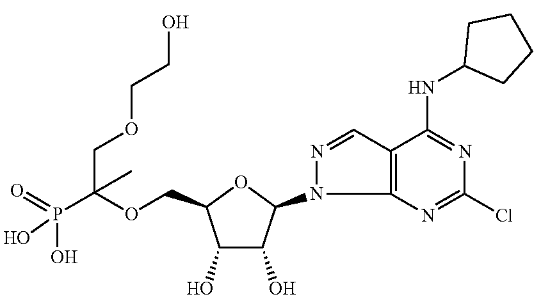 [SMILES: CC(COCCO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(2-hydroxyethoxy)propan-2-yl) phosphonic acid |
| 86 | 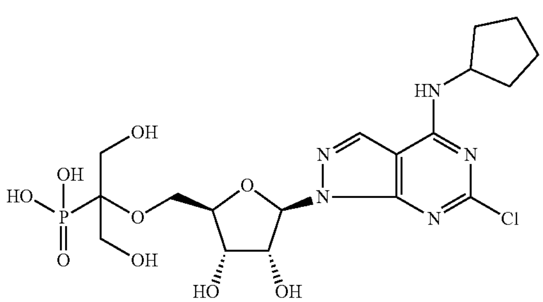 [SMILES: O=P(O)(O)C(CO)(CO)OC[C@H]1O[C@@H](n2ncc3c(NC4CCCC4)nc(Cl)nc32)[C@H](O)[C@@H]1O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
|----|-----------|------|
| 87 | 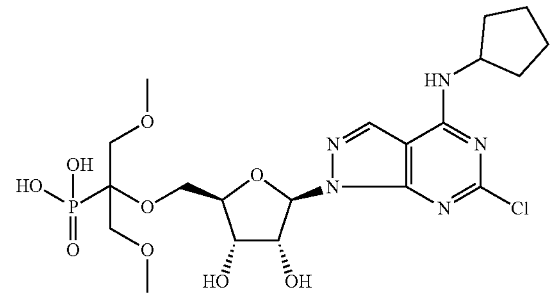 [SMILES: COCC(COC)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 88 | 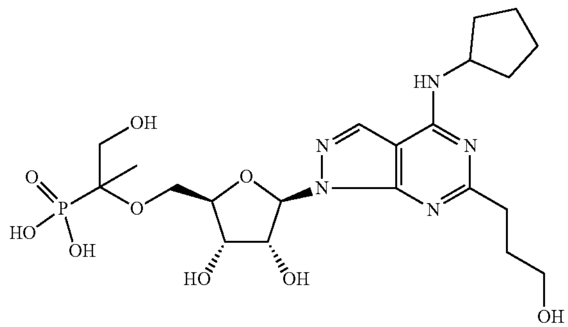 [SMILES: CC(CO)(OC[C@H]1O[C@@H](n2ncc3c(NC4CCCC4)nc(CCCO)nc32)[C@H](O)[C@@H]1O)P(=O)(O)O] | (2-(((2R,3S,4R,5R)-5-(4-(cyclopentylamino)-6-(3-hydroxypropyl)-1H-pyrazolo[3,4-d]pyrimidin-1-yl)-3,4-dihydroxytetrahydrofuran-2-yl)methoxy)-1-hydroxypropan-2-yl)phosphonic acid |
| 89 | 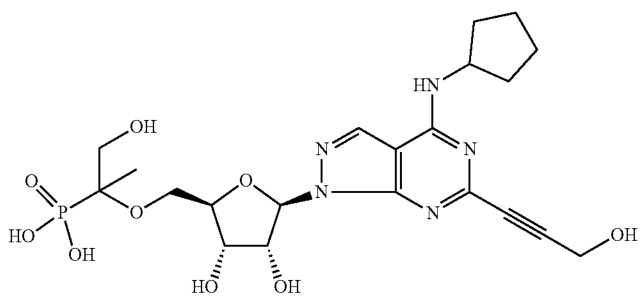 [SMILES: CC(CO)(OC[C@H]1O[C@@H](n2ncc3c(NC4CCCC4)nc(C#CCO)nc32)[C@H](O)[C@@H]1O)P(=O)(O)O] | (2-(((2R,3S,4R,5R)-5-(4-(cyclopentylamino)-6-(3-hydroxyprop-1-yn-1-yl)-1H-pyrazolo[3,4-d]pyrimidin-3-yl)-3,4-dihydroxytetrahydrofuran-2-yl)methoxy)-1-hydroxypropan-2-yl)phosphonic acid |
| 90 | 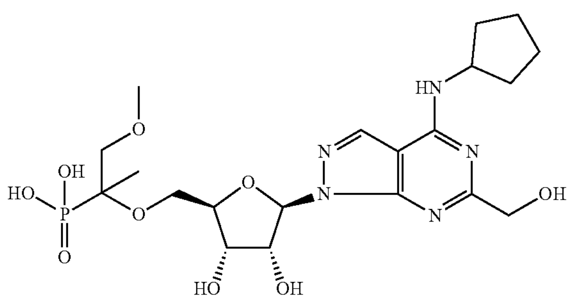 [SMILES: COCC(C)(OC[C@H]1O[C@@H](n2ncc3c(NC4CCCC4)nc(CO)nc32)[C@H](O)[C@@H]1O)P(=O)(O)O] | (2-(((2R,3S,4R,5R)-5-(4-(cyclopentylamino)-6-(hydroxymethyl)-1H-pyrazolo[3,4-d]pyrimidin-1-yl)-3,4-dihydroxytetrahydrofuran-2-yl)methoxy)-1-methoxypropan-2-yl)phosphonic acid |
| 91 | 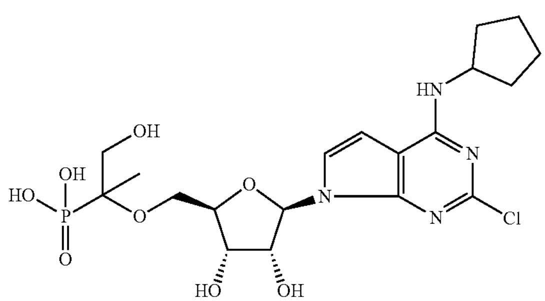 [SMILES: CC(CO)(OC[C@H]1O[C@@H](n2ccc3c(NC4CCCC4)nc(Cl)nc32)[C@H](O)[C@@H]1O)P(=O)(O)O] | (2-(((2R,3S,4R,5R)-5-(2-(chloro-4-(cyclopentylamino)-7H-pyrazolo[2,3-d]pyrimidin-7-yl)-3,4-dihydroxytetrahydrofuran-2-yl)methoxy)-1-hydoxypropan-2-yl)phosphonic acid |

TABLE 1-continued

| Ex | Structure | Name |
|---|---|---|
| 92 | 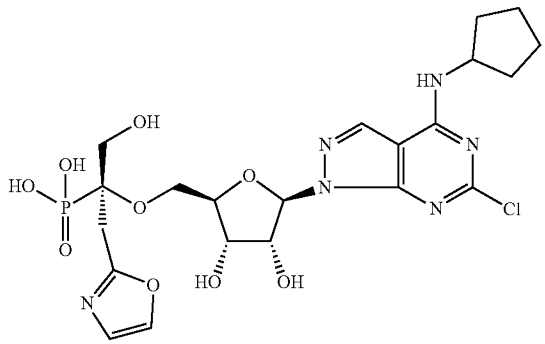 | ((S)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-(oxazol-2-yl)propan-2-yl)phosphonic acid |
| 93 | 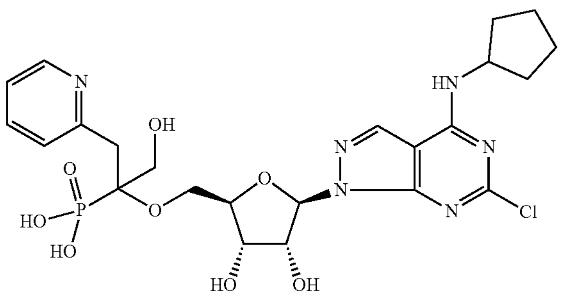 [SMILES: O=P(O)(O)C(CO)(Cc1ccccn1)OC[C@H]1O[C@@H](n2ncc3c(NC4CCCC4)nc(Cl)nc32)[C@H](O)[C@@H]1O] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-(pyridin-2-yl)propan-2-yl)phosphonic acid |
| 94 | 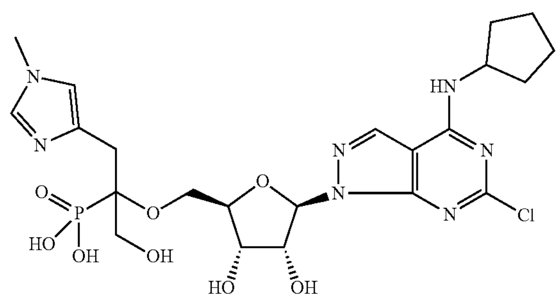 [SMILES: Cn1cnc(CC(CO)(OC[C@H]2O[C@@H](n3ncc4c(NC5CCCC5)nc(Cl)nc43)[C@H](O)[C@@H]2O)P(=O)(O)O)c1] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-(1-methyl-1H-imidazol-4-yl)propan-2-yl)phosphonic acid |
| 95 | 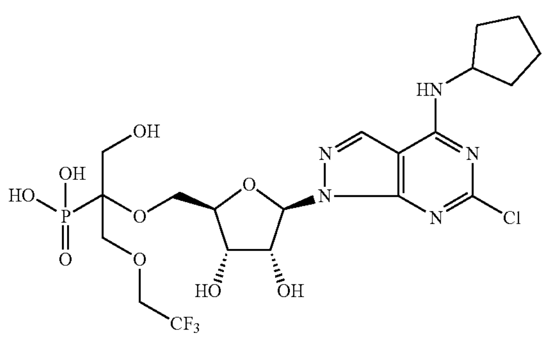 [SMILES: O=P(O)(O)C(CO)(COCC(F)(F)F)OC[C@H]1O[C@@H](n2ncc3c(NC4CCCC4)nc(Cl)nc32)[C@H](O)[C@@H]1O] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-(2,2,2-trifluoroethoxy)propan-2-yl)phosphonic acid |
| 96 | 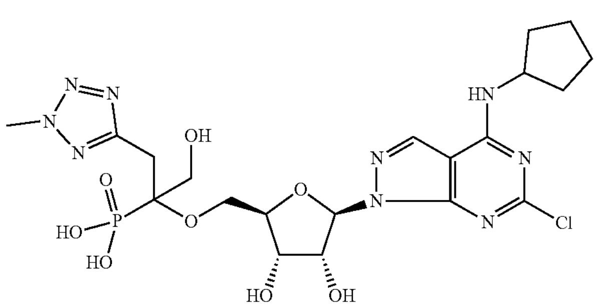 [SMILES: Cn1nnc(CC(CO)(OC[C@H]2O[C@@H](n3ncc4c(NC5CCCC5)nc(Cl)nc43)[C@H](O)[C@@H]2O)P(=O)(O)O)n1] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-(2-methyl-2H-tetrazol-5-yl)propan-2-yl)phosphonic acid |

TABLE 1-continued

| Ex | Structure | Name |
|---|---|---|
| 97 | 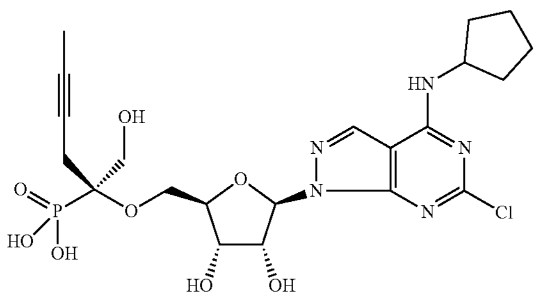 [SMILES: CC#CC[C@@](CO)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydoxyhex-4-yn-2-yl)phosphonic acid |
| 98 | 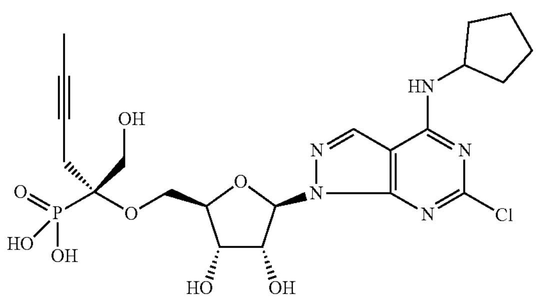 [SMILES: CC#CC[C@](CO)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydoxyhex-4-yn-2-yl)phosphonic acid |
| 99 | 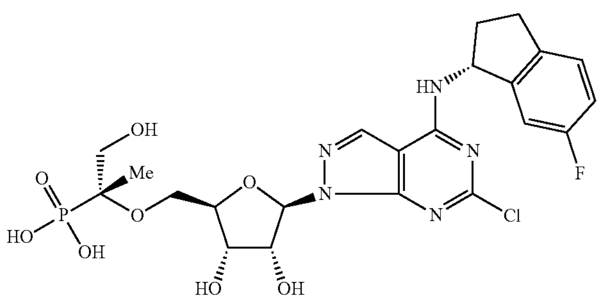 [SMILES: C[C@@](CO)(OC[C@H]1O[C@@H](n2ncc3c(N[C@@H]4CCc5ccc(F)cc54)nc(Cl)nc32)[C@H](O)[C@@H]1O)P(=O)(O)O] | ((R)-2-(((2R,3S,4R,5R)-5-(6-(chloro-4-(((R)-6-fluoro-2,3-dihydro-1H-inden-1-yl)amino)-1H-pyrazolo[3,4-d]pyrimidin-1-yl)-3,4-dihydroxytetrahydrofuran-2-yl)methoxy)-1-hydoxypropan-2-yl)phosphonic acid |
| 100 | 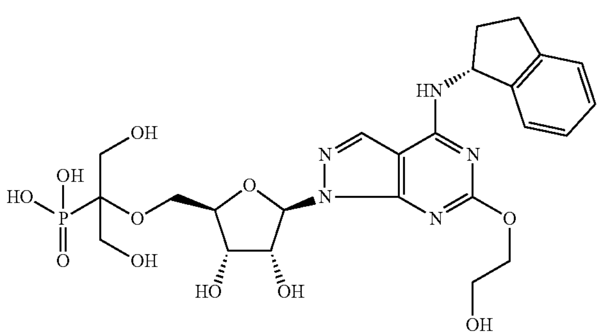 [SMILES: O=P(O)(O)C(CO)(CO)OC[C@H]1O[C@@H](n2ncc3c(N[C@@H]4CCc5ccccc54)nc(OCCO)nc32)[C@H](O)[C@@H]1O] | (2-(((2R,3S,4R,5R)-5-(4-(((R)-2,3-dihydro-1H-inden-1-yl)amino)-6-(2-hydroxyethoxy)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 101 | 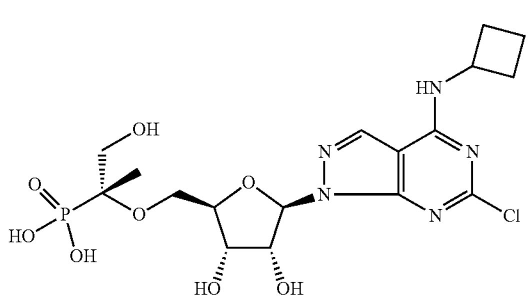 [SMILES: C[C@@](CO)(OC[C@H]1O[C@@H](n2ncc3c(NC4CCC4)nc(Cl)nc32)[C@H](O)[C@@H]1O)P(=O)(O)O] | ((R)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydoxypropan-2-yl)phosphonic acid |

TABLE 1-continued

| Ex | Structure | Name |
|---|---|---|
| 102 | 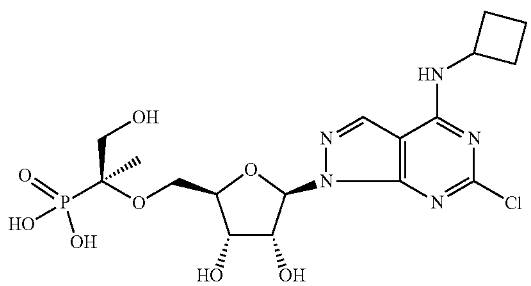 [SMILES: C[C@](CO)(OC[C@H]1O[C@@H](n2ncc3c(NC4CCC4)nc(Cl)nc32)[C@H](O)[C@@H]1O)P(=O)(O)O] | ((S)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydoxypropan-2-yl)phosphonic acid |
| 103 | 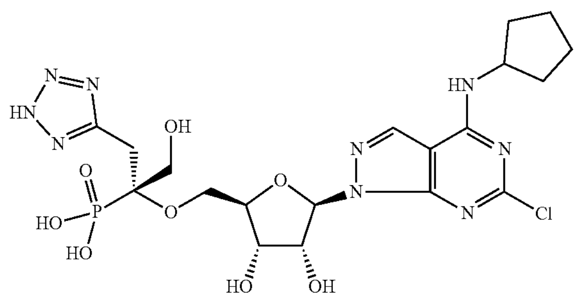 [SMILES: O=P(O)(O)[C@](CO)(Cc1nn[nH]n1)OC[C@H]1O[C@@H](n2ncc3c(NC4CCCC4)nc(Cl)nc32)[C@H](O)[C@@H]1O] | ((S)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 104 | 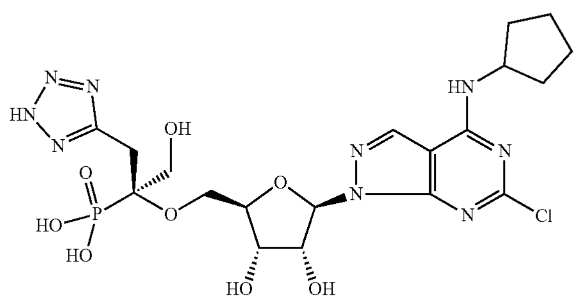 [SMILES: O=P(O)(O)[C@@](CO)(Cc1nn[nH]n1)OC[C@H]1O[C@@H](n2ncc3c(NC4CCCC4)nc(Cl)nc32)[C@H](O)[C@@H]1O] | ((R)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 105 | 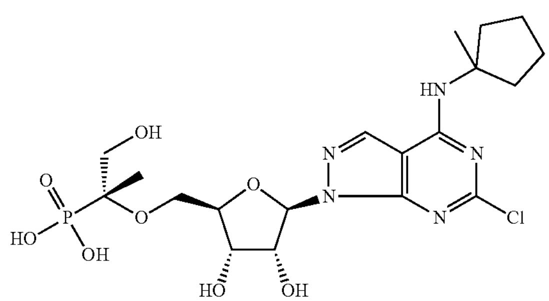 [SMILES: CC1(Nc2nc(Cl)nc3c2cnn3[C@@H]2O[C@H](CO[C@@](C)(CO)P(=O)(O)O)[C@@H](O)[C@H]2O)CCCC1] | ((R)-2-(((2R,3S,4R,5R)-5-(6-(chloro-4-((1-methylcyclopentyl)amino)-1H-pyrazolo[3,4-d]pyrimidin-1-yl)-3,4-dihydroxytetrahydrofuran-2-yl)methoxy)-1-hydroxypropan-2-yl)phosphonic acid |
| 106 | 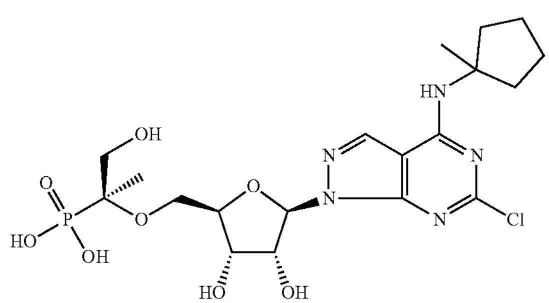 [SMILES: CC1(Nc2nc(Cl)nc3c2cnn3[C@@H]2O[C@H](CO[C@](C)(CO)P(=O)(O)O)[C@@H](O)[C@H]2O)CCCC1] | ((S)-2-(((2R,3S,4R,5R)-5-(6-(chloro-4-((1-methylcyclopentyl)amino)-1H-pyrazolo[3,4-d]pyrimidin-1-yl)-3,4-dihydroxytetrahydrofuran-2-yl)methoxy)-1-hydoxypropan-2-yl)phosphonic acid |

TABLE 1-continued

| Ex | Structure | Name |
|---|---|---|
| 107 | 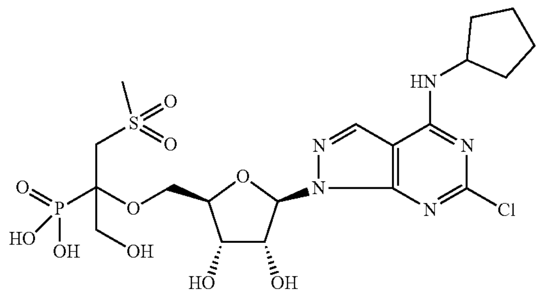 [SMILES: CS(=O)(=O)CC(CO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-(chloro-4-((1-(cyclopentylamino)-1H-pyrazolo[3,4-d]pyrimidin-1-yl)-3,4-dihydroxytetrahydrofuran-2-yl)methoxy)-1-hydroxy-3-(methylsulfonyl)propan-2-yl) phosphonic acid |
| 108 | 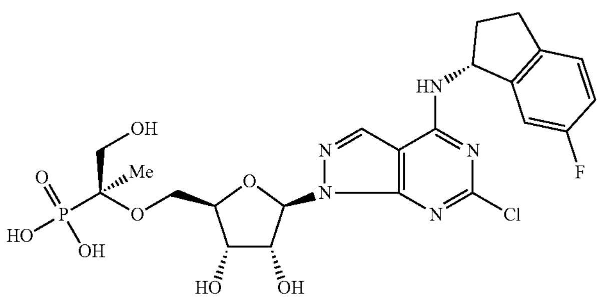 [SMILES: C[C@](CO)(OC[C@H]1O[C@@H](n2ncc3c(N[C@@H]4CCc5ccc(F)cc54)nc(Cl)nc32)[C@H](O)[C@@H]1O)P(=O)(O)O] | ((S)-2-(((2R,3S,4R,5R)-5-(6-(chloro-4-(((R)-6-fluoro-2,3-dihydro-1H-inden-1-yl)amino)-1H-pyrazolo[3,4-d]pyrimidin-1-yl)-3,4-dihydroxytetrahydrofuran-2-yl)methoxy)-1-hydoxypropan-2-yl)phosphonic acid |
| 109 | 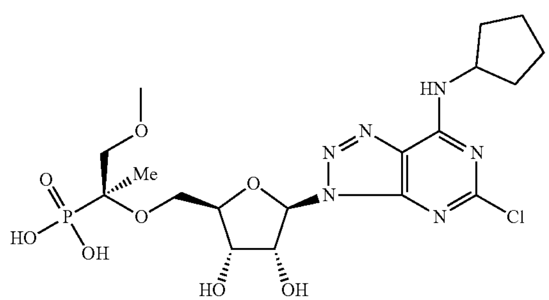 [SMILES: COC[C@@](C)(OC[C@H]1O[C@@H](n2nnc3c(NC4CCCC4)nc(Cl)nc32)[C@H](O)[C@@H]1O)P(=O)(O)O] | ((S)-2-(((2R,3S,4R,5R)-5-(5-(chloro-7-(cyclopentylamino)-3H-[1,2,3]triazolo[4,5-d]pyrimidin-3-yl)-3,4-dihydroxytetrahydrofuran-2-yl)methoxy)-1-methoxypropan-2-yl) phosphonic acid |
| 110 | 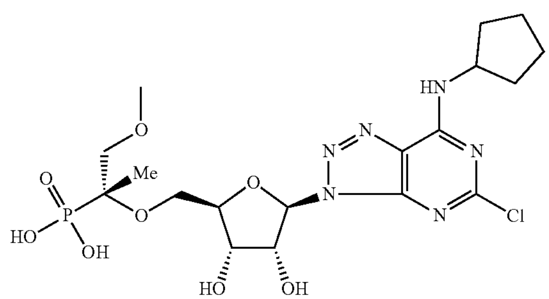 [SMILES: COC[C@](C)(OC[C@H]1O[C@@H](n2nnc3c(NC4CCCC4)nc(Cl)nc32)[C@H](O)[C@@H]1O)P(=O)(O)O] | ((R)-2-(((2R,3S,4R,5R)-5-(5-(chloro-7-(cyclopentylamino)-3H-[1,2,3]triazolo[4,5-d]pyrimidin-3-yl)-3,4-dihydroxytetrahydrofuran-2-yl)methoxy)-1-methoxypropan-2-yl) phosphonic acid |
| 111 | 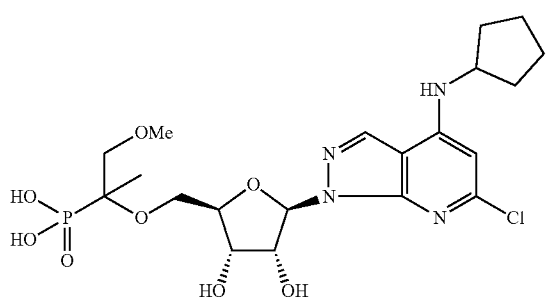 [SMILES: COCC(C)(OC[C@H]1O[C@@H](n2ncc3c(NC4CCCC4)cc(Cl)nc32)[C@H](O)[C@@H]1O)P(=O)(O)O] | (2-(((2R,3S,4R,5R)-5-(6-(chloro-4-(cyclopentylamino)-1H-pyrazolo[3,4-b]pyridin-1-yl)-3,4-dihydroxytetrahydrofuran-2-yl)methoxy)-1-methoxypropan-2-yl) phosphonic acid |

TABLE 1-continued

| Ex | Structure | Name |
|---|---|---|
| 112 | 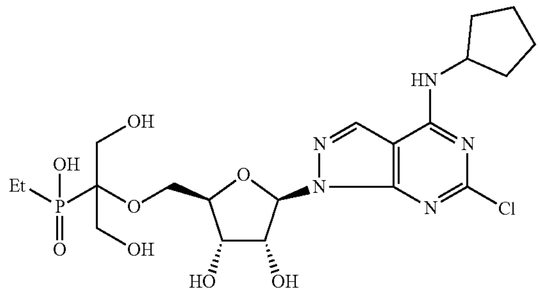 [SMILES: CCP(=O)(O)C(CO)(CO)OC[C@H]1O[C@@H](n2ncc3c(NC4CCCC4)nc(Cl)nc32)[C@H](O)[C@@H]1O] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1,3-dihydroxypropan-2-yl)(ethyl)phosphonic acid |
| 113 | 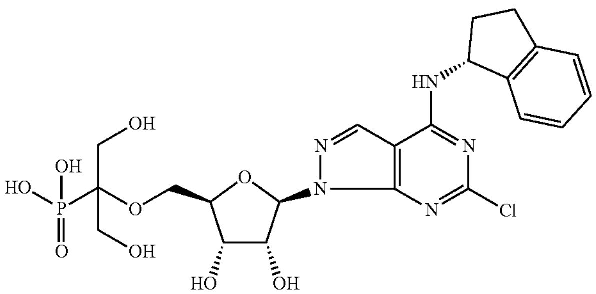 [SMILES: O=P(O)(O)C(CO)(CO)OC[C@H]1O[C@@H](n2ncc3c(N[C@@H]4CCc5ccccc54)nc(Cl)nc32)[C@H](O)[C@@H]1O] | (2-(((2R,3S,4R,5R)-5-(6-(chloro-4-(((R)-2,3-dihydro-1H-inden-1-yl)amino)-1H-pyrazolo[3,4-d]pyrimidin-1-yl)-3,4-dihydroxytetrahydrofuran-2-yl)methoxy)-1,3-dihydoxypropan-2-yl)(ethyl)phosphonic acid |
| 114 | 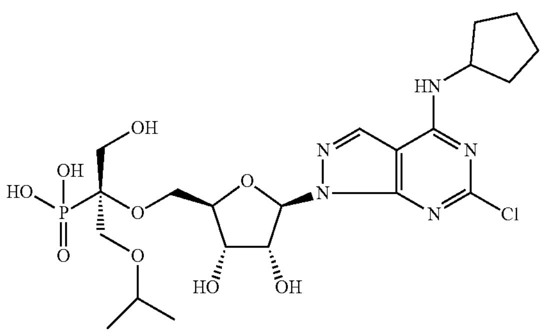 | ((R)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydroxy-3-isopropoxypropan-2-yl)phosphonic acid |
| 115 | 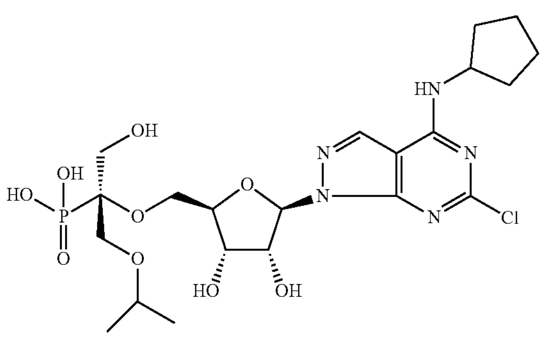 | ((S)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydroxy-3-isopropoxypropan-2-yl)phosphonic acid |
| 116 | 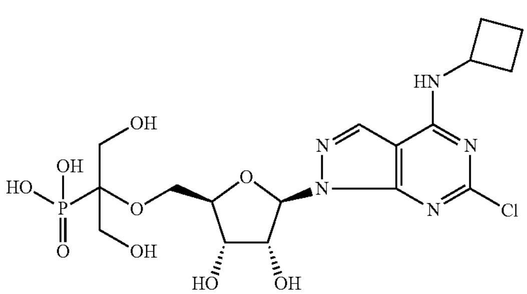 [SMILES: O=P(O)(O)C(CO)(CO)OC[C@H]1O[C@@H](n2ncc3c(NC4CCC4)nc(Cl)nc32)[C@H](O)[C@@H]1O] | (2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1,3-dihydroxypropan-2-yl)(ethyl)phosphonic acid |

| Ex | Structure | Name |
|---|---|---|
| 117 | 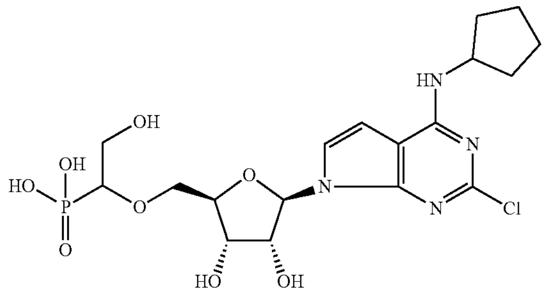 [SMILES: O=P(O)(O)C(CO)OC[C@H]1O[C@@H](n2ccc3c(NC4CCCC4)nc(Cl)nc32)[C@H](O)[C@@H]1O] | (1-(((2R,3S,4R,5R)-5-(2-(chloro-4-(cyclobutylamino)-7H-pyrrolo[2,3-d]pyrimidin-7-yl)-3,4-dihydroxytetrahydrofuran-2-yl)methoxy)-2-hydroxyethyl)phosphonic acid |
| 118 | 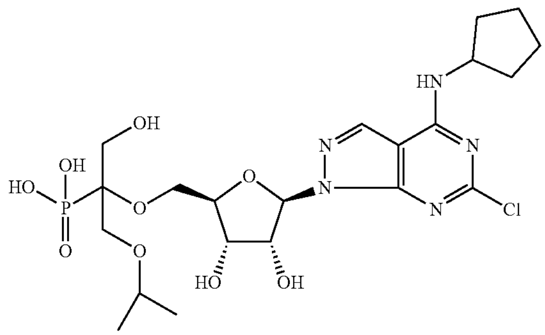 [SMILES: CC(C)OCC(CO)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-hydoxy-3-isopropoxypropan-2-yl)phosphonic acid |
| 119 | 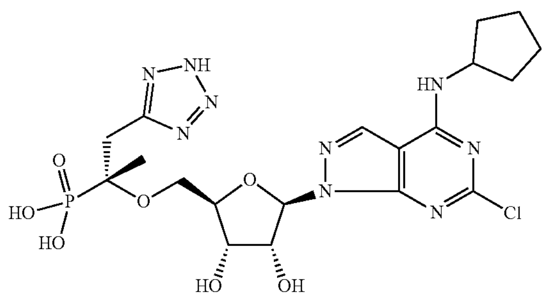 [SMILES: C[C@@](Cc1nn[nH]n1)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-(2H-tetrazol-5-yl)propan-2-yl)phosphonic acid |
| 120 | 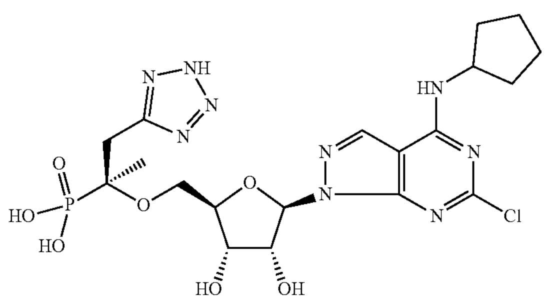 [SMILES: C[C@](Cc1nn[nH]n1)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-(2H-tetrazol-5-yl)propan-2-yl)phosphonic acid |
| 121 | 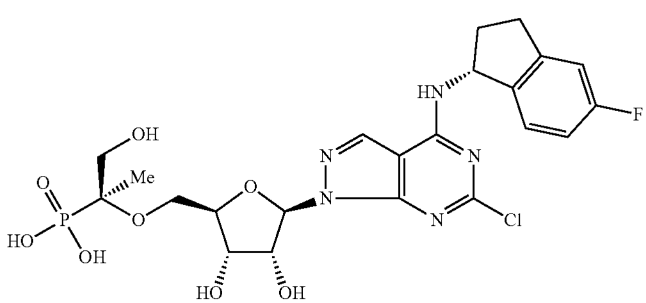 [SMILES: C[C@](CO)(OC[C@H]1O[C@@H](n2ncc3c(N[C@@H]4CCc5cc(F)ccc54)nc(Cl)nc32)[C@H](O)[C@@H]1O)P(=O)(O)O] | ((S)-2-(((2R,3S,4R,5R)-5-(6-(chloro-4-(((R)-5-fluoro-2,3-dihydro-1H-inden-1-yl)amino)-1H-pyrazolo[3,4-d]pyrimidin-1-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 122 | 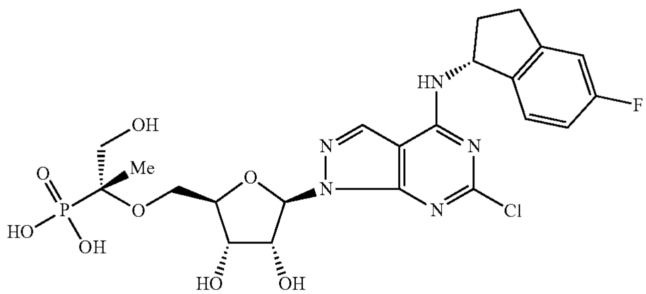 [SMILES: C[C@@](CO)(OC[C@H]1O[C@@H](n2ncc3c(N[C@@H]4CCc5cc(F)ccc54)nc(Cl)nc32)[C@H](O)[C@@H]1O)P(=O)(O)O] | ((R)-2-(((2R,3S,4R,5R)-5-(6-(chloro-4-(((R)-5-fluoro-2,3-dihydro-1H-inden-1-yl)amino)-1H-pyrazolo[3,4-d]pyrimidin-1-yl)-3,4-dihydroxytetrahydrofuran-2-yl)methoxy)-1-hydroxypropan-2-yl)phosphonic acid |
| 123 | 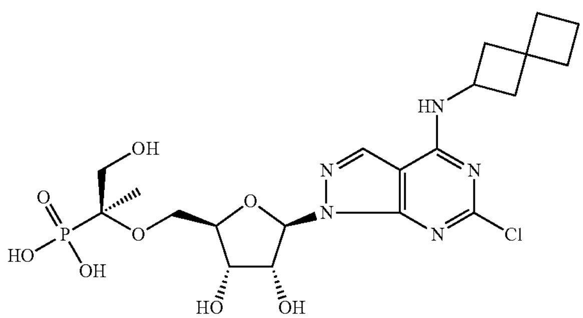 [SMILES: C[C@](CO)(OC[C@H]1O[C@@H](n2ncc3c(NC4CC5(CCC5)C4)nc(Cl)nc32)[C@H](O)[C@@H]1O)P(=O)(O)O] | ((S)-2-(((2R,3S,4R,5R)-5-(6-(chloro-4-(spiro[3.3]heptan-2-ylamino)-1H-pyrazolo[3,4-d]pyrimidin-1-yl)-3,4-dihydroxytetrahydrofuran-2-yl)methoxy)-1-hydroxypropan-2-yl)phosphonic acid |
| 124 | 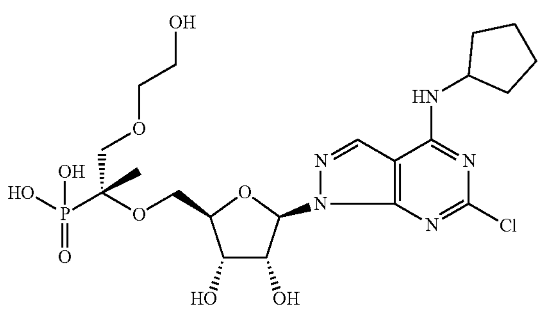 [SMILES: C[C@@](COCCO)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-(2-hydroxyethoxy)propan-2-yl)phosphonic acid |
| 125 | 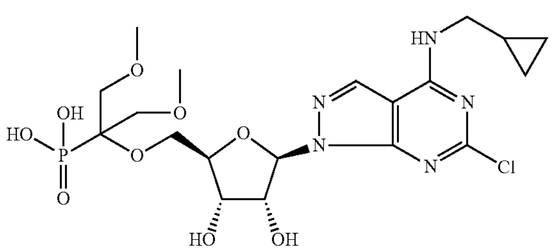 [SMILES: COCC(COC)(OC[C@H]1O[C@@H](n2ncc3c(NCC4CC4)nc(Cl)nc32)[C@H](O)[C@@H]1O)P(=O)(O)O] | (2-(((2R,3S,4R,5R)-5-(6-(chloro-4-(cyclopropylmethyl)amino)-1H-pyrazolo[3,4-d]pyrimidin-1-yl)-3,4-dihydroxytetrahydrofuran-2-yl)methoxy)-1-(3-dimethoxypropan-2-yl)phosphonic acid |
| 126 | 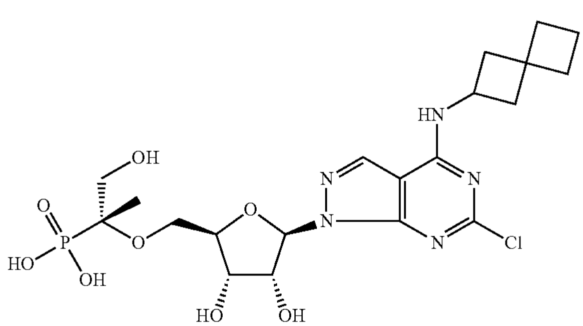 [SMILES: C[C@@](CO)(OC[C@H]1O[C@@H](n2ncc3c(NC4CC5(CCC5)C4)nc(Cl)nc32)[C@H](O)[C@@H]1O)P(=O)(O)O] | ((R)-2-(((2R,3S,4R,5R)-5-(6-(chloro-4-(spiro[3.3]heptan-2-ylamino)-1H-pyrazolo[3,4-d]pyrimidin-1-yl)-3,4-dihydroxytetrahydrofuran-2-yl)methoxy)-1-hydoxyethoxy)propan-2-yl)phosphonic acid |

TABLE 1-continued

| Ex | Structure | Name |
|---|---|---|
| 127 | 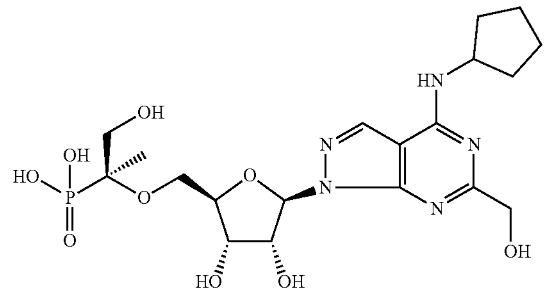 [SMILES: C[C@](CO)(OC[C@H]1O[C@@H](n2ncc3c(NC4CCCC4)nc(CO)nc32)[C@H](O)[C@@H]1O)P(=O)(O)O] | ((S)-2-(((2R,3S,4R,5R)-5-(4-cyclopentylamino)-6-(hydroxymethyl)-1H-pyrazolo[3,4-d]pyrimidin-1-yl)-3,4-dihydroxytetrahydrofuran-2-yl)methoxy)-1-hydroxypropan-2-yl)phosphonic acid |
| 128 | 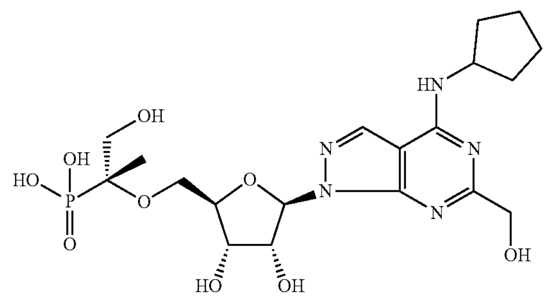 [SMILES: C[C@@](CO)(OC[C@H]1O[C@@H](n2ncc3c(NC4CCCC4)nc(CO)nc32)[C@H](O)[C@@H]1O)P(=O)(O)O] | ((R)-2-(((2R,3S,4R,5R)-5-(4-(cyclopentylamino)-6-(hydroxymethyl)-1H-pyrazolo[3,4-d]pyrimidin-1-yl)-3,4-dihydroxytetrahydrofuran-2-yl)methoxy)-1-hydoxypropan-2-yl)phosphonic acid |
| 129 | 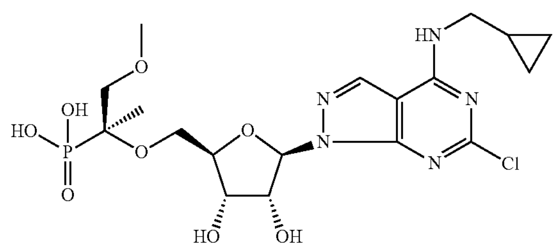 [SMILES: COC[C@@](C)(OC[C@H]1O[C@@H](n2ncc3c(NCC4CC4)nc(Cl)nc32)[C@H](O)[C@@H]1O)P(=O)(O)O] | ((S)-2-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-methoxypropan-2-yl)phosphonic acid |
| 130 | 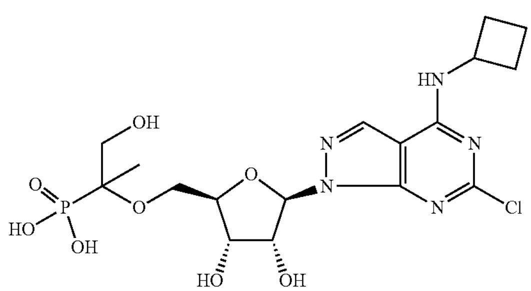 [SMILES: CC(CO)(OC[C@H]1O[C@@H](n2ncc3c(NC4CCC4)nc(Cl)nc32)[C@H](O)[C@@H]1O)P(=O)(O)O] | (2-(((2R,3S,4R,5R)-5-(6-(chloro-4-(cyclobutylamino)-1H-pyrazolo[3,4-d]pyrimidin-1-yl)-3,4-dihydroxytetrahydrofuran-2-yl)methoxy)-1-hydroxypropan-2-yl)phosphonic acid |
| 131 | 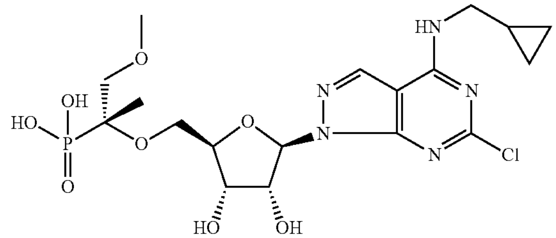 [SMILES: COC[C@](C)(OC[C@H]1O[C@@H](n2ncc3c(NCC4CC4)nc(Cl)nc32)[C@H](O)[C@@H]1O)P(=O)(O)O] | ((R)-2-(((2R,3S,4R,5R)-5-(6-(chloro-4-((cyclopropylmethylamino)-1H-pyrazolo[3,4-d]pyrimidin-1-yl)-3,4-dihydroxytetrahydrofuran-2-yl)methoxy)-1-methoxypropan-2-yl)phosphonic acid |

TABLE 1-continued

| Ex | Structure | Name |
|---|---|---|
| 132 | 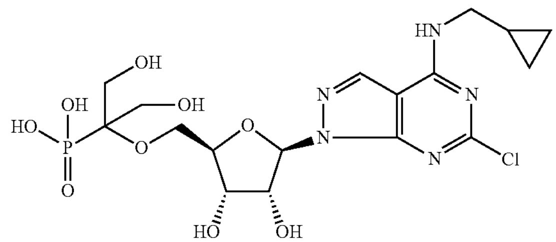 [SMILES: O=P(O)(O)C(CO)(CO)OC[C@H]1O[C@@H](n2ncc3c(NCC4CC4)nc(Cl)nc32)[C@H](O)[C@@H]1O] | (2-(((2R,3S,4R,5R)-5-(6-(chloro-4-((cyclopropylmethyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 133 | 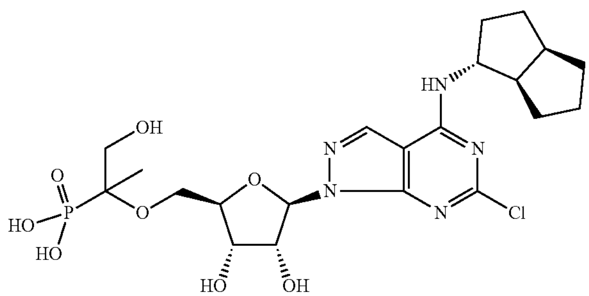 [SMILES: CC(CO)(OC[C@H]1O[C@@H](n2ncc3c(N[C@@H]4CC[C@H]5CCC[C@H]54)nc(Cl)nc32)[C@H](O)[C@@H]1O)P(=O)(O)O] | (2-(((2R,3S,4R,5R)-5-(6-(chloro-4-(((1R,3aR,6aR)-octahydropentalen-1-yl)amino)-1H-pyrazolo[3,4-d]pyrimidin-1-yl)-3,4-dihydroxytetrahydrofuran-2-yl)methoxy)-1-hydroxypropan-2-yl)phosphonic aci |
| 134 | 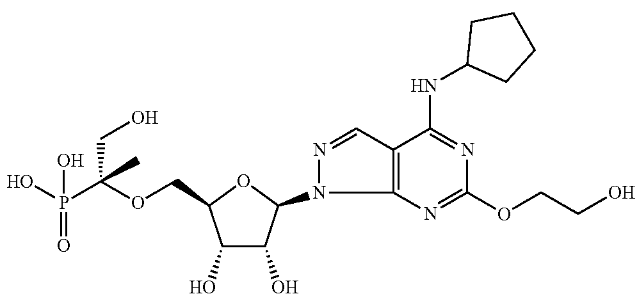 [SMILES: C[C@@](CO)(OC[C@H]1O[C@@H](n2ncc3c(NC4CCCC4)nc(OCCO)nc32)[C@H](O)[C@@H]1O)P(=O)(O)O] | ((R)-2-(((2R,3S,4R,5R)-5-(4-((cyclopentylmethylamino)-6-(2-hydroxyethoxy)-1H-pyrazolo[3,4-d]pyrimidin-1-yl)-3,4-dihydroxytetrahydrofuran-2-yl)methoxy)-1-methoxypropan-2-yl)phosphonic acid |
| 135 | 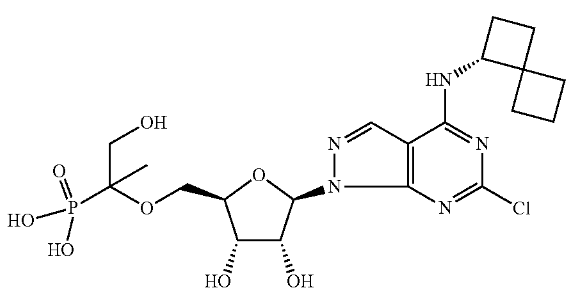 [SMILES: CC(CO)(OC[C@H]1O[C@@H](n2ncc3c(N[C@@H]4CCC45CCC5)nc(Cl)nc32)[C@H](O)[C@@H]1O)P(=O)(O)O] | (2-(((2R,3S,4R,5R)-5-(6-chloro-4-(((R)-spiro[3.3]heptan-1-yl)amino)-1H-pyrazolo[3,4-d]pyrimidin-1-yl)-3,4-dihydroxytetrahydrofuran-2-yl)methoxy)-1-hydoxypropan-2-yl)phosphonic acid |
| 136 | 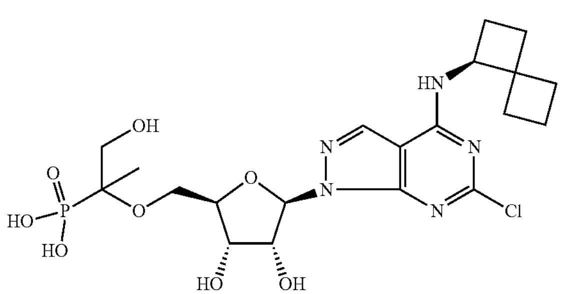 [SMILES: CC(CO)(OC[C@H]1O[C@@H](n2ncc3c(N[C@H]4CCC45CCC5)nc(Cl)nc32)[C@H](O)[C@@H]1O)P(=O)(O)O] | (2-(((2R,3S,4R,5R)-5-(6-chloro-4-(((S)-spiro[3.3]heptan-1-yl)amino)-1H-pyrazolo[3,4-d]pyrimidin-1-yl)-3,4-dihydroxytetrahydrofuran-2-yl)methoxy)-1-hydoxypropan-2-yl)phosphonic acid |

TABLE 1-continued

| Ex | Structure | Name |
|---|---|---|
| 137 | 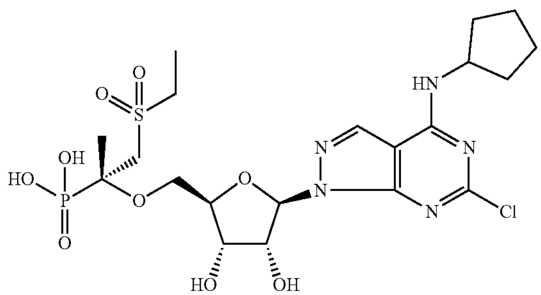 [SMILES: CCS(=O)(=O)C[C@](C)(OC[C@H]1O[C@@H](n2ncc3c(NC4CCCC4)nc(Cl)nc32)[C@H](O)[C@@H]1O)P(=O)(O)O] | ((R)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-(ethylsulfonyl)propan-2-yl)phosphonic acid |
| 138 | 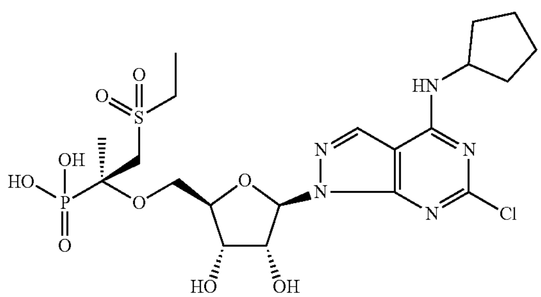 [SMILES: CCS(=O)(=O)C[C@@](C)(OC[C@H]1O[C@@H](n2ncc3c(NC4CCCC4)nc(Cl)nc32)[C@H](O)[C@@H]1O)P(=O)(O)O] | ((S)-2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-(ethylsulfonyl)propan-2-yl)phosphonic acid |
| 139 | 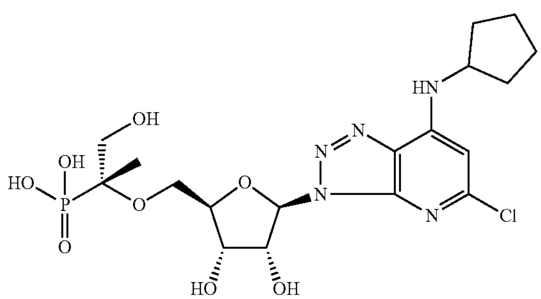 [SMILES: C[C@@](CO)(OC[C@H]1O[C@@H](n2nnc3c(NC4CCCC4)cc(Cl)nc32)[C@H](O)[C@@H]1O)P(=O)(O)O] | ((R)-2-(((2R,3S,4R,5R)-5-(5-(chloro-7-(cyclopentylamino)-3H-[1,2,3]triazolo[4,5-b]pyridin-3-yl)-3,4-dihydroxytetrahydrofuran-2-yl)methoxy)-1-hydroxypropan-2-yl)phosphonic acid |
| 140 | 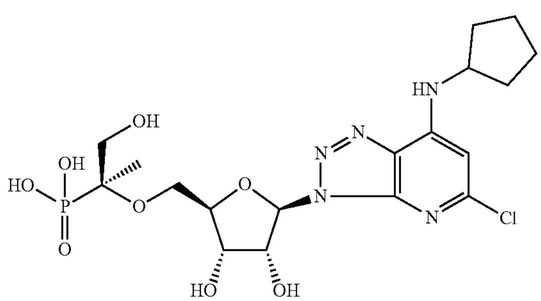 [SMILES: C[C@](CO)(OC[C@H]1O[C@@H](n2nnc3c(NC4CCCC4)cc(Cl)nc32)[C@H](O)[C@@H]1O)P(=O)(O)O] | ((S)-2-(((2R,3S,4R,5R)-5-(5-(chloro-7-(cyclopentylamino)-3H-[1,2,3]triazolo[4,5-b]pyridin-3-yl)-3,4-dihydroxytetrahydrofuran-2-yl)methoxy)-1-hydroxypropan-2-yl)phosphonic acid |
| 141 | 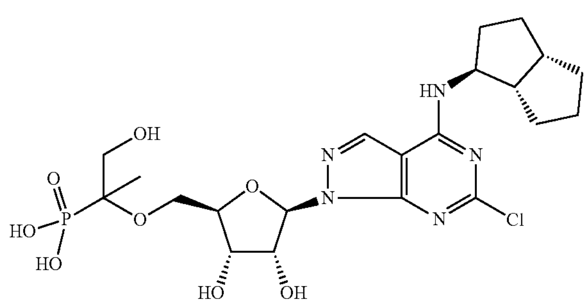 [SMILES: CC(CO)(OC[C@H]1O[C@@H](n2ncc3c(N[C@H]4CC[C@@H]5CCC[C@@H]54)nc(Cl)nc32)[C@H](O)[C@@H]1O)P(=O)(O)O] | (2-(((2R,3S,4R,5R)-5-(6-chloro-4-((((1S,3aS,6aS)-octahydropentalen-1-yl)amino)-1H-pyrazolo[3,4-d]pyrimidin-1-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 142 | 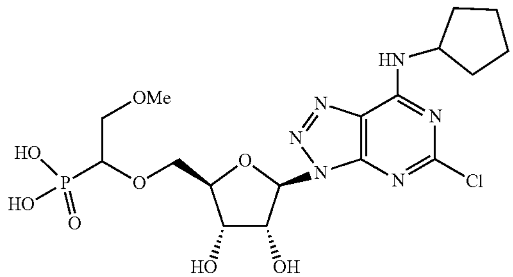 [SMILES: COCC(OC[C@H]1O[C@@H](n2nnc3c(NC4CCCC4)nc(Cl)nc32)[C@H](O)[C@@H]1O)P(=O)(O)O] | (1-(((2R,3S,4R,5R)-5-(5-(chloro-7-(cyclopentylamino)-3H-[1,2,3]triazolo[4,5-d]pyrimidin-3-yl)-3,4-dihydroxytetrahydrofuran-2-yl)methoxy)-2-methoxyethyl)phosphonic acid |
| 143 | 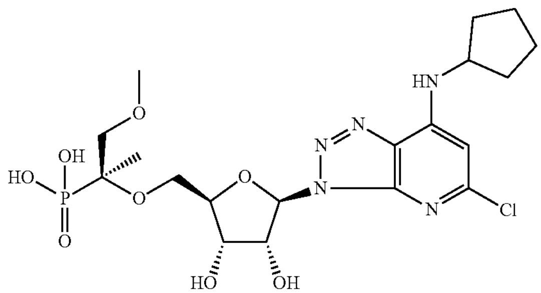 [SMILES: COC[C@@](C)(OC[C@H]1O[C@@H](n2nnc3c(NC4CCCC4)cc(Cl)nc32)[C@H](O)[C@@H]1O)P(=O)(O)O] | ((S)-2-(((2R,3S,4R,5R)-5-(5-(chloro-7-(cyclopentylamino)-3H-[1,2,3]triazolo[4,5-b]pyridin-3-yl)-3,4-dihydroxytetrahydrofuran-2-yl)methoxy)-1-methoxypropan-2-yl)phosphonic acid |
| 144 | 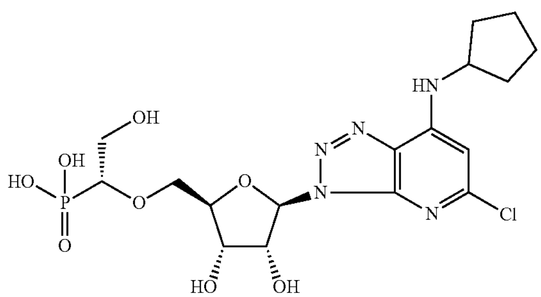 [SMILES: O=P(O)(O)[C@H](CO)OC[C@H]1O[C@@H](n2nnc3c(NC4CCCC4)cc(Cl)nc32)[C@H](O)[C@@H]1O] | ((R)-1-(((2R,3S,4R,5R)-5-(5-(chloro-7-(cyclopentylamino)-3H-[1,2,3]triazolo[4,5-b]pyridin-3-yl)-3,4-dihydroxytetrahydrofuran-2-yl)methoxy)-2-hydroxyethyl)phosphonic acid |
| 145 | 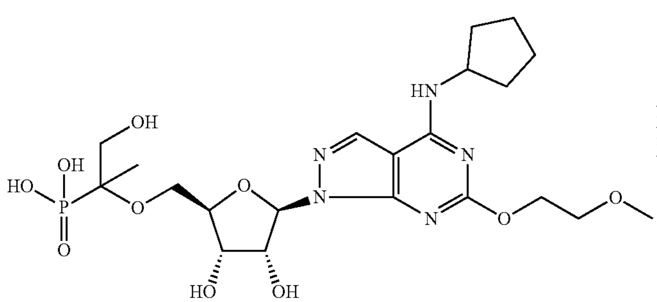 [SMILES: COCCOc1nc(NC2CCCC2)c2cnn([C@@H]3O[C@H](COC(C)(CO)P(=O)(O)O)[C@@H](O)[C@H]3O)c2n1] | (2-(((2R,3S,4R,5R)-5-(4-(cyclopentylamino)-6-(2-methoxyethoxy)-1H-pyrazolo[3,4-d]pyrimidin-1-yl)-3,4-dihydroxytetrahydrofuran-2-yl)methoxy)-1-hydroxypropan-2-yl)phosphonic acid |
| 146 | 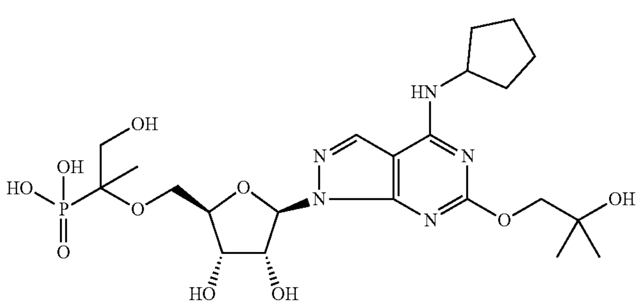 [SMILES: CC(C)(O)COc1nc(NC2CCCC2)c2cnn([C@@H]3O[C@H](COC(C)(CO)P(=O)(O)O)[C@@H](O)[C@H]3O)c2n1] | (2-(((2R,3S,4R,5R)-5-(4-(cyclopentylamino)-6-(2-hydroxy-2-methylpropoxy)-1H-pyrazolo[3,4-d]pyrimidin-1-yl)-3,4-dihydroxytetrahydrofuran-2-yl)methoxy)-1-hydroxypropan-2-yl)phosphonic acid |

TABLE 1-continued

| Ex | Structure | Name |
|---|---|---|
| 147 | 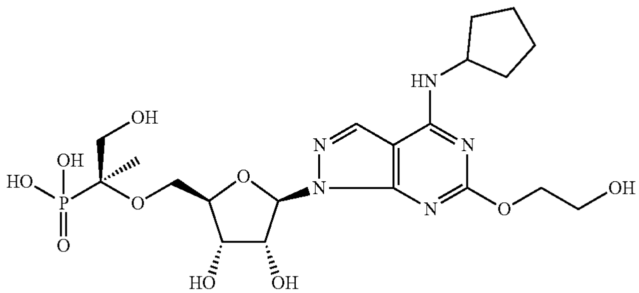 [SMILES: C[C@](CO)(OC[C@H]1O[C@@H](n2ncc3c(NC4CCCC4)nc(OCCO)nc32)[C@H](O)[C@@H]1O)P(=O)(O)O] | ((S)-2-(((2R,3S,4R,5R)-5-(4-(cyclopentylamino)-6-(2-hydroxyethoxy)-1H-pyrazolo[3,4-d]pyrimidin-1-yl)-3,4-dihydroxytetrahydrofuran-2-yl)methoxy)-1-hydroxypropan-2-yl)phosphonic acid |
| 148 | 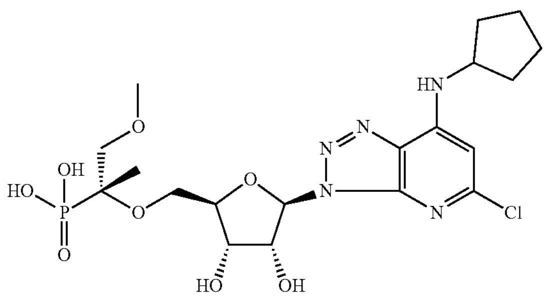 [SMILES: COC[C@](C)(OC[C@H]1O[C@@H](n2nnc3c(NC4CCCC4)cc(Cl)nc32)[C@H](O)[C@@H]1O)P(=O)(O)O] | ((R)-2-(((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)-1-methoxypropan-2-yl)phosphonic acid |
| 149 | 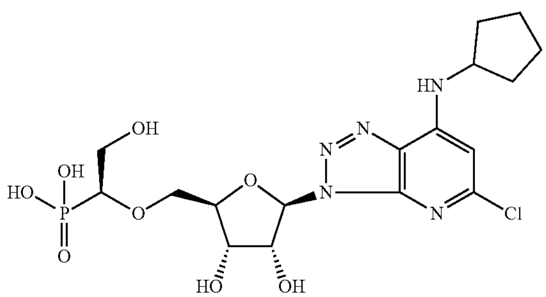 [SMILES: O=P(O)(O)[C@@H](CO)OC[C@H]1O[C@@H](n2nnc3c(NC4CCCC4)cc(Cl)nc32)[C@H](O)[C@@H]1O] | ((S)-1-(((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)-2-hydroxyethyl)phosphonic acid |
| 150 | 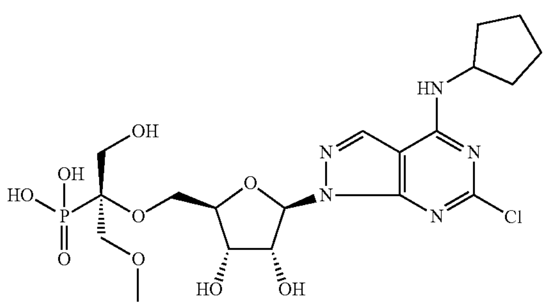 | ((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-nydroxy-3-methoxypropan-2-yl)phosphonic acid |
| 151 | 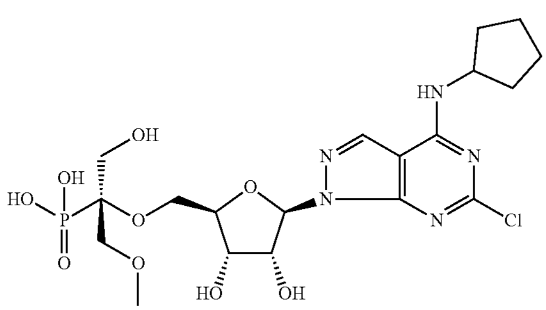 | ((S)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-methoxypropan-2-yl)phosphonic acid |

TABLE 1-continued

| Ex | Structure | Name |
|---|---|---|
| 152 | 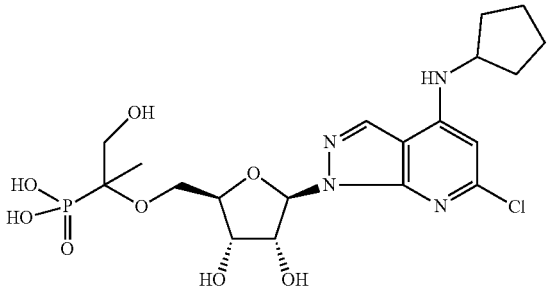 [SMILES: CC(CO)(OC[C@H]1O[C@@H](n2ncc3c(NC4CCCC4)cc(Cl)nc32)[C@H](O)[C@@H]1O)P(=O)(O)O] | (2-(((2R,3S,4R,5R)-5-(6-chloro)-4-(cyclopentylamino)-1H-pyrazolo[3,4-b]pyridin-1-yl)-3,4-dihydroxytetrahydrofuran-2-yl)methoxy)-1-hydroxypropan-2-yl)phosphonic acid |
| 153 | 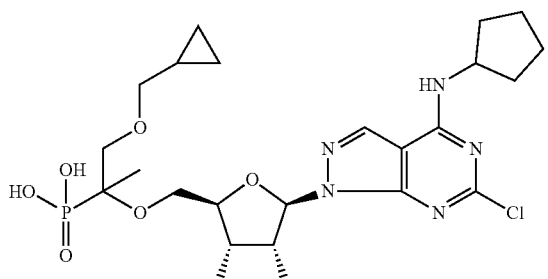 | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-(cyclopropylmethoxy)propan-2-yl)phosphonic acid |
| 154 | 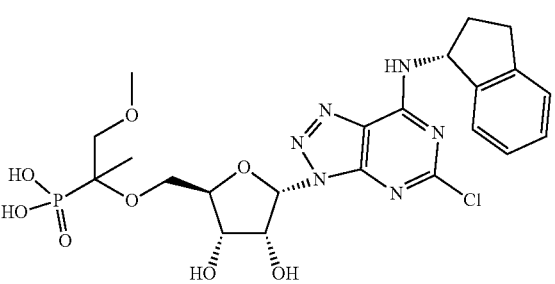 [SMILES: COCC(C)(OC[C@H]1O[C@H](n2nnc3c(N[C@@H]4CCc5ccccc54)nc(Cl)nc32)[C@H](O)[C@@H]1O)P(=O)(O)O] | (2-(((2R,3S,4R,5S)-5-(5-chloro-7-(((R)-2,3-dihydro-1H-inden-1-yl)amino)-3H-[1,2,3]triazolo[4,5-d]pyrimidin-3-yl)-3,4-dihydroxytetrahydrofuran-2-yl)methoxy)-1-methoxypropan-2-yl)phosphonic acid |
| 155 | 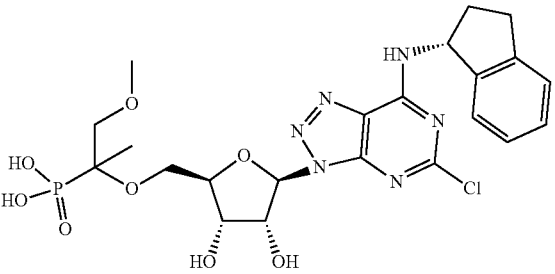 [SMILES: COCC(C)(OC[C@H]1O[C@@H](n2nnc3c(N[C@@H]4CCc5ccccc54)nc(Cl)nc32)[C@H](O)[C@@H]1O)P(=O)(O)O] | (2-(((2R,3S,4R,5R)-5-(5-(chloro-7-(((R)-2,3-dihydro-1H-inden-1-yl)amino)-3H-[1,2,3]triazolo[4,5-d]pyrimidin-3-yl)-3,4-dihydroxytetrahydrofuran-2-yl)methoxy)-1-methoxypropan-2-yl)phosphonic acid |
| 156 | 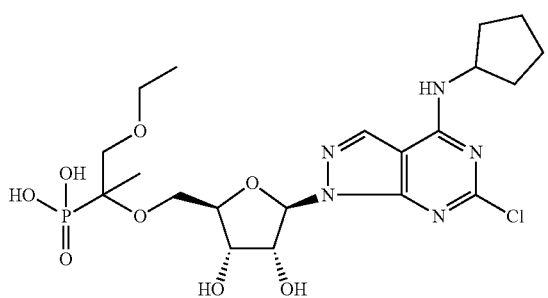 [SMILES: CCOCC(C)(OC[C@H]1O[C@@H](n2ncc3c(NC4CCCC4)nc(Cl)nc32)[C@H](O)[C@@H]1O)P(=O)(O)O] | (2-(((2R,3S,4R,5R)-5-(6-(chloro-4-(cyclopentylamino)-1H-pyrazolo[3,4-d]pyrimidin-1-yl)-3,4-dihydroxytetrahydrofuran-2-yl)methoxy)-1-ethoxypropan-2-yl)phosphonic acid |

TABLE 1-continued

| Ex | Structure | Name |
|---|---|---|
| 157 | 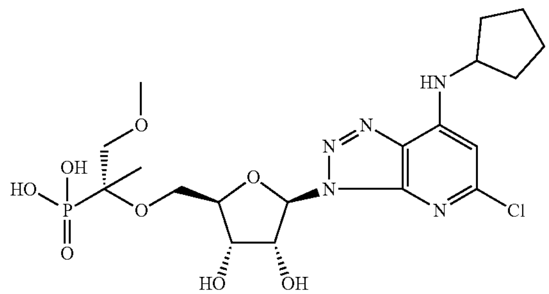 [SMILES: COC[C@](C)(OC[C@H]1O[C@@H](n2nnc3c(NC4CCCC4)cc(Cl)nc32)[C@H](O)[C@@H]1O)P(=O)(O)O] | ((R)-1-(((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxyethyl)phosphonic acid |
| 158 | 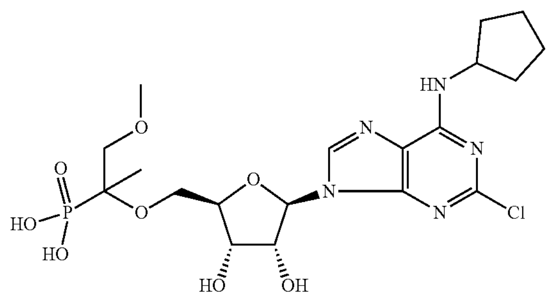 [SMILES: COCC(C)(OC[C@H]1O[C@@H](n2cnc3c(NC4CCCC4)nc(Cl)nc32)[C@H](O)[C@@H]1O)P(=O)(O)O] | (2-(((2R,3S,4R,5R)-5-(2-chloro-6-(cyclopentylamino)-9H-purin-9-yl)-3,4-dihydroxytetrahydrofuran-2-yl)methoxy)-1-methoxypropan-2-yl)phosphonic acid |
| 159 | 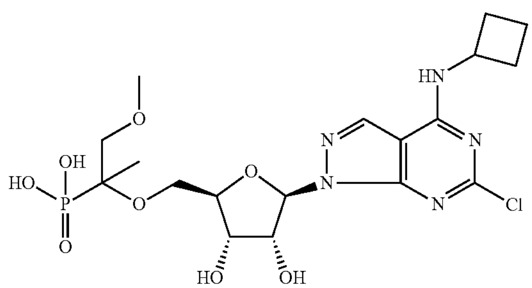 [SMILES: COCC(C)(OC[C@H]1O[C@@H](n2ncc3c(NC4CCC4)nc(Cl)nc32)[C@H](O)[C@@H]1O)P(=O)(O)O] | (2-(((2R,3S,4R,5R)-5-(6-chloro-4-(cyclobutylamino)-1H-pyrazolo[3,4-d]pyrimidin-1-yl)-3,4-dihydroxytetrahydrofuran-2-yl)methoxy)-1-methoxypropan-2-yl)phosphonic acid |
| 160 | 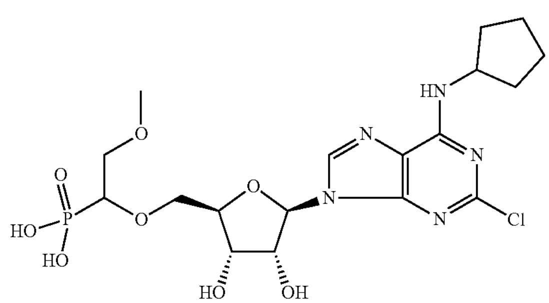 [SMILES: COCC(OC[C@H]1O[C@@H](n2cnc3c(NC4CCCC4)nc(Cl)nc32)[C@H](O)[C@@H]1O)P(=O)(O)O] | (1-(((2R,3S,4R,5R)-5-(2-chloro-6-(cyclopentylamino)-9H-purin-9-yl)-3,4-dihydroxytetrahydrofuran-2-yl)methoxy)-2-methoxyethyl)phosphonic acid |
| 161 | 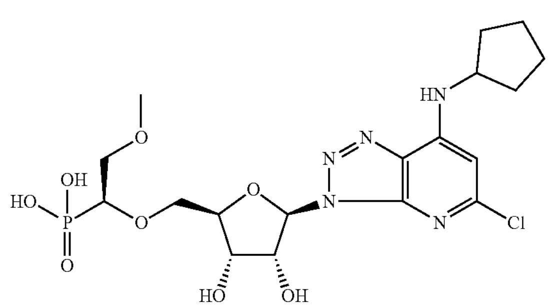 [SMILES: COC[C@@H](OC[C@H]1O[C@@H](n2nnc3c(NC4CCCC4)cc(Cl)nc32)[C@H](O)[C@@H]1O)P(=O)(O)O] | ((S)-1-(((2R,3S,4R,5R)-5-(5-chloro-7-(cyclopentylamino)-3H-[1,2,3]triazolo[4,5-b]pyridin-3-yl)-3,4-dihydroxytetrahydrofuran-2-yl)methoxy)-2-methoxyethyl)phosphonic acid |

TABLE 1-continued

| Ex | Structure | Name |
|---|---|---|
| 162 | 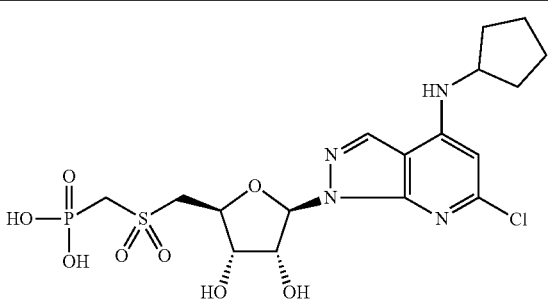 | (((((2S,3S,4R,5R)-5-(6-chloro-4-(cyclopentylamino)-1H-pyrazolo[3,4-b]pyridin-1-yl)-3,4-dihydroxytetrahydrofuran-2-yl)methyl)sulfonyl)methyl)phosphonic acid |
| 163 | 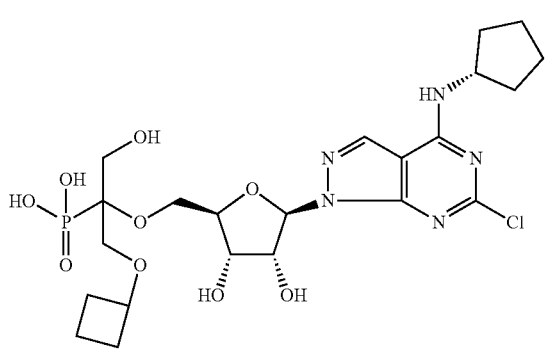 | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-cyclobutoxy-3-hydroxypropan-2-yl)phosphonic acid |
| 164 | 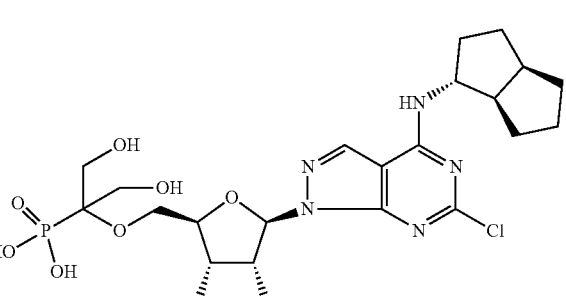 | rac-(2-(((2R,3S,4R,5R)-5-(6-chloro-4-(((1R,3aR,6aR)-octahydropentalen-1-yl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 165 | 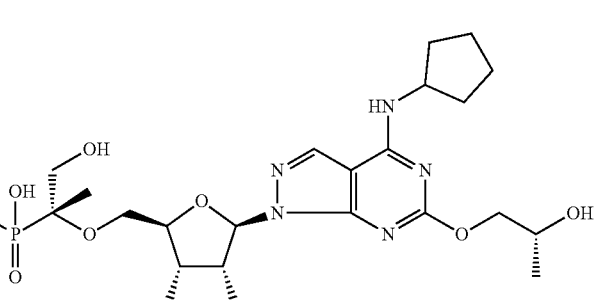 | rac-((R)-2-(((2R,3S,4R,5R)-5-(4-cyclopentylamino)-6-((R)-2-hydroxypropoxy)-1H-pyrazolo[3,4-d]pyrimidin-1-yl)-3,4-dihydroxytetrahydrofuran-2-yl)methoxy)-1-hydroxypropan-2-yl)phosphonic acid |
| 166 | 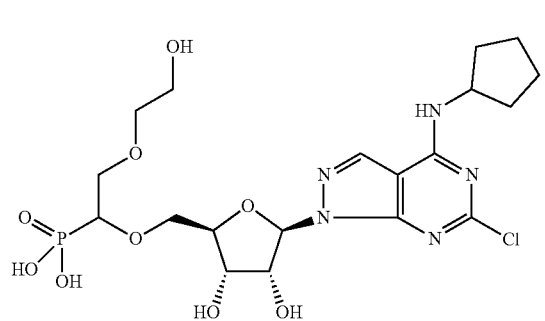 [SMILES: O=P(O)(O)C(COCCO)OC[C@H]1O[C@@H](n2ncc3c(NC4CCCC4)nc(Cl)nc32)[C@H](O)[C@@H]1O] | rac-(1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-(2-hydroxyethoxy)ethyl)phosphonic acid |

TABLE 1-continued

| Ex | Structure | Name |
|---|---|---|
| 167 | 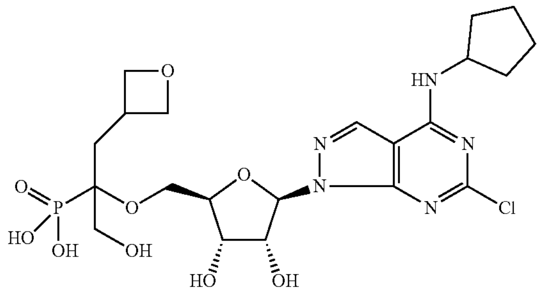 [SMILES: O=P(O)(O)C(CO)(CC1COC1)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(oxetan-3-yl)propan-2-yl)phosphonic acid |
| 168 | 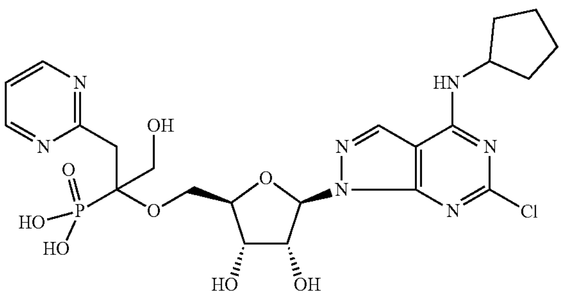 [SMILES: O=P(O)(O)C(CO)(Cc1ncccn1)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(pyrimidin-2-yl)propan-2-yl)phosphonic acid |
| 169 | 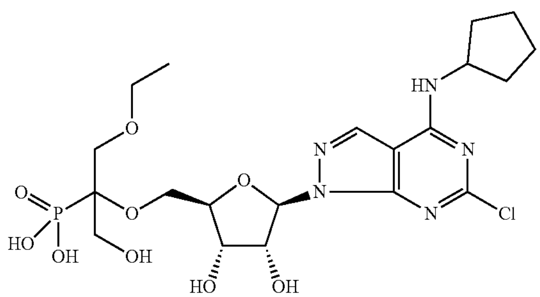 [SMILES: CCOCC(CO)(OC[C@H]1O[C@@H](n2ncc3c(NC4CCCC4)nc(Cl)nc32)[C@H](O)[C@@H]1O)P(=O)(O)O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-ethoxy-3-hydroxypropan-2-yl)phosphonic acid |
| 170 | 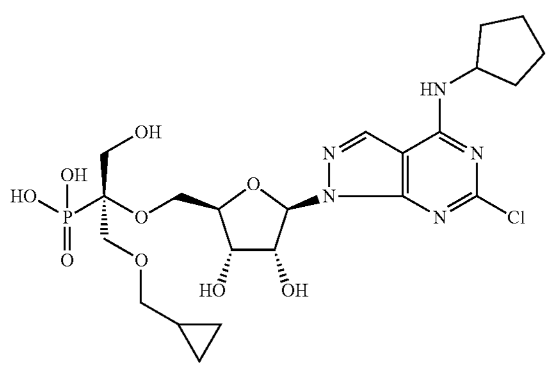 | rac-((R)-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(cyclopropylmethoxy)-3-hydroxypropan-2-yl)phosphonic acid |
| 171 | 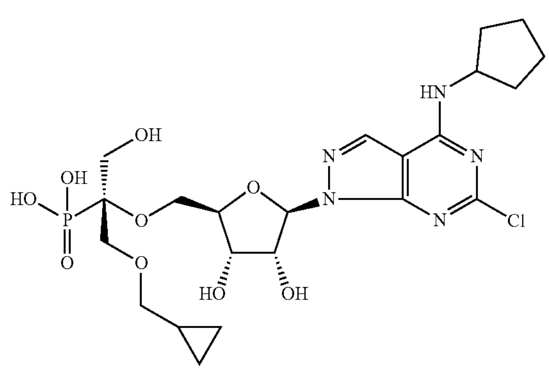 | rac-((R)-(((2R,3S,4R,5S)-5-(6-chloro-4-(cyclopentylamino)-1H-pyrazolo[3,4-d]pyrimidin-1-yl)-3,4-dihydroxytetrahydrofuran-2-yl)methoxy)-1-(cyclopropylmethoxy)-3-hydroxypropan-2-yl)phosphonic acid |

TABLE 1-continued

| Ex | Structure | Name |
|---|---|---|
| 172 | 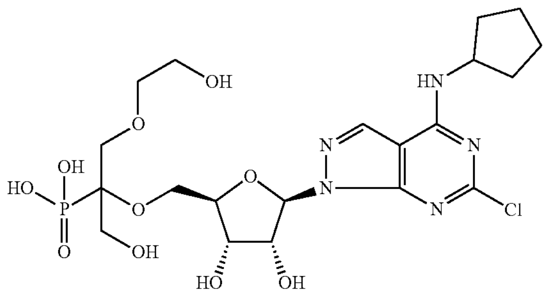 [SMILES: O=P(O)(O)C(CO)(COCCO)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(2-hydroxyethoxy)propan-2-yl)phosphonic acid |
| 173 | 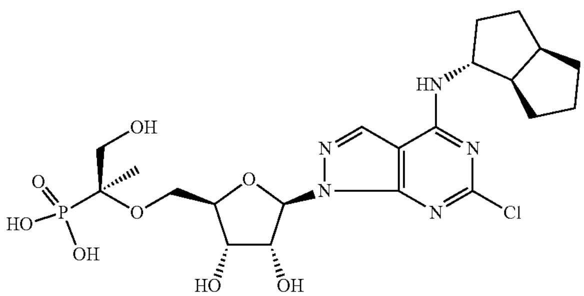 [SMILES: C[C@](CO)(OC[C@H]1O[C@@H](n2ncc3c(N[C@@H]4CC[C@H]5CCC[C@H]54)nc(Cl)nc32)[C@H](O)[C@@H]1O)P(=O)(O)O] | rac-((R)-(((2S,3R,4S,5S)-5-(6-chloro-4-(((1S,3aS,6aS)-octahydropentalen-1-yl)amino-1H-pyrazolo[3,4-d]pyrimidin-1-yl)-3,4-dihydroxytetrahydrofuran-2-yl)methoxy)-1-hydroxypropan-2-yl)phosphonic acid |
| 174 | 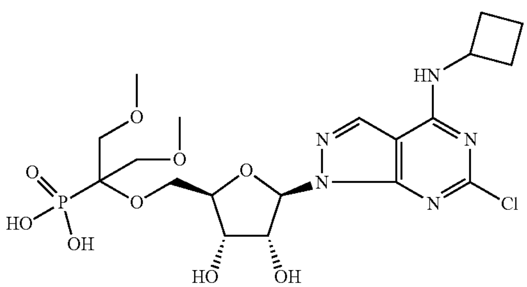 [SMILES: COCC(COC)(OC[C@H]1O[C@@H](n2ncc3c(NC4CCC4)nc(Cl)nc32)[C@H](O)[C@@H]1O)P(=O)(O)O] | rac-(2-(((2R,3S,4R,5R)-5-(6-chloro-4-(cyclobutylamino)-1H-pyrazolo[3,4-d]pyrimidin-1-yl)-3,4-dihydroxytetrahydrofuran-2-yl)methoxy)-1,3-dimethoxypropan-2-yl)phosphonic acid |
| 175 | 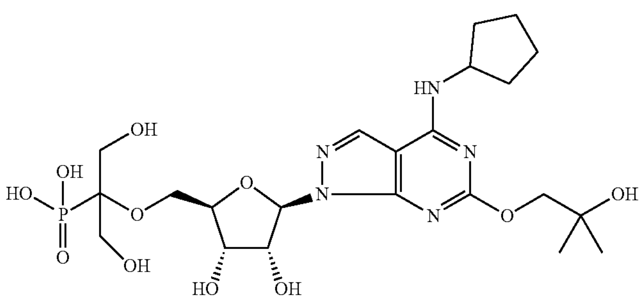 [SMILES: CC(C)(O)COc1nc(NC2CCCC2)c2cnn([C@@H]3O[C@H](COC(CO)(CO)P(=O)(O)O)[C@@H](O)[C@H]3O)c2n1] | rac-(2-(((2R,3S,4R,5R)-5-(4-(cyclopentylamino)-6-(2-hydroxy-2-methylpropoxy)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 176 | 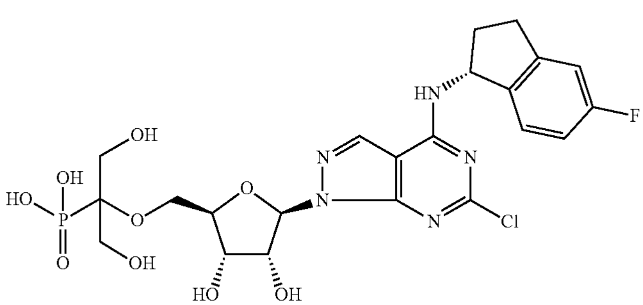 [SMILES: O=P(O)(O)C(CO)(CO)OC[C@H]1O[C@@H](n2ncc3c(N[C@@H]4CCc5cc(F)ccc54)nc(Cl)nc32)[C@H](O)[C@@H]1O] | rac-(2-(((2R,3S,4R,5R)-5-(6-chloro-4-(((R)-5-fluoro-2,3-dihydro-1H-inden-1-yl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
| --- | --- | --- |
| 177 | 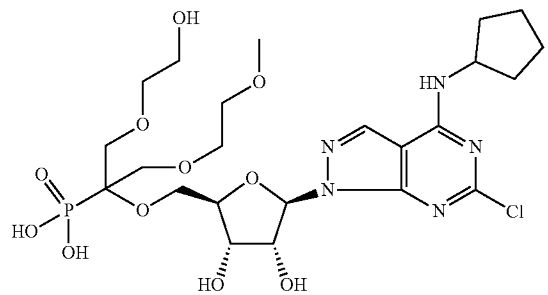 [SMILES: COCCOCC(COCCO)(OC[C@H]1O[C@@H](n2ncc3c(NC4CCCC4)nc(Cl)nc32)[C@H](O)[C@@H]1O)P(=O)(O)O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(2-hydroxyethoxy)-3-(2-methoxyethoxy)propan-2-yl)phosphonic acid |
| 178 | 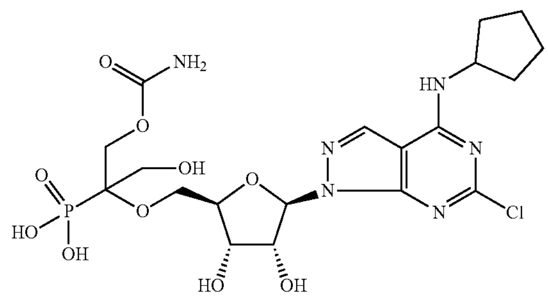 [SMILES: NC(=O)OCC(CO)(OC[C@H]1O[C@@H](n2ncc3c(NC4CCCC4)nc(Cl)nc32)[C@H](O)[C@@H]1O)P(=O)(O)O] | rac-(1-(carbamoyloxy)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxypropan-2-yl)phosphonic acid |
| 179 | 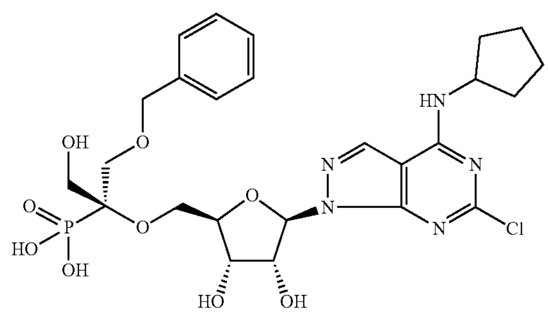 [SMILES: O=P(O)(O)[C@](CO)(COCc1ccccc1)OC[C@H]1O[C@@H](n2ncc3c(NC4CCCC4)nc(Cl)nc32)[C@H](O)[C@@H]1O] | rac-((R)-1-(benzyloxy)-2-(((2R,3S,4R,5R)-5-(6-chloro-4-((cyclopentylamino)-1H-pyrazolo[3,4-d]pyrimidin-1-dihydroxytetrahydrofuran-2-yl)methoxy)-3-hydroxypropan-2-yl)phosphonic acid |
| 180 | 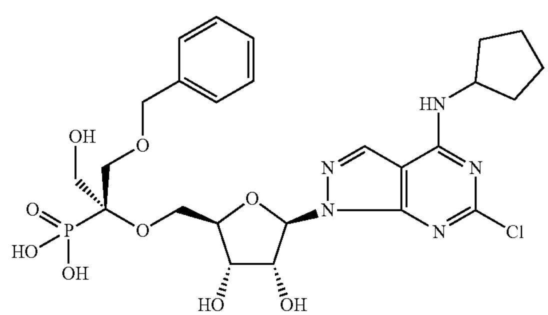 [SMILES: O=P(O)(O)[C@@](CO)(COCc1ccccc1)OC[C@H]1O[C@@H](n2ncc3c(NC4CCCC4)nc(Cl)nc32)[C@H](O)[C@@H]1O] | rac-((R)-1-(benzyloxy)-2-(((2R,3S,4S,5S)-5-(6-chloro-4-((cyclopentylamino)-1H-pyrazolo[3,4-d]pyrimidin-1-yl)-3,4-dihydroxytetrahydrofuran-2-yl)methoxy)-3-hydroxypropan-2-yl)phosphonic acid |
| 181 | 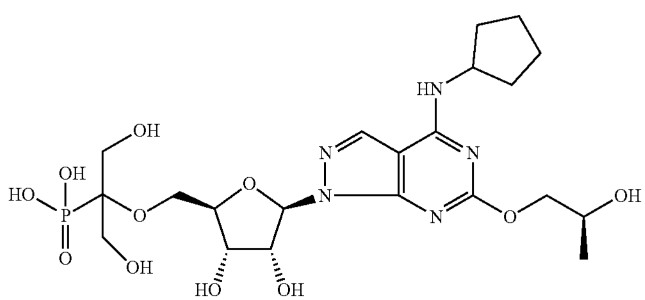 [SMILES: C[C@H](O)COc1nc(NC2CCCC2)c2cnn([C@@H]3O[C@H](COC(CO)(CO)P(=O)(O)O)[C@@H](O)[C@H]3O)c2n1] | rac-(2-(((2R,3S,4S,5R)-5-(4-(cyclopentylamino)-6-((S)-2-hydroxypropoxy)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
|---|---|---|
| 182 | 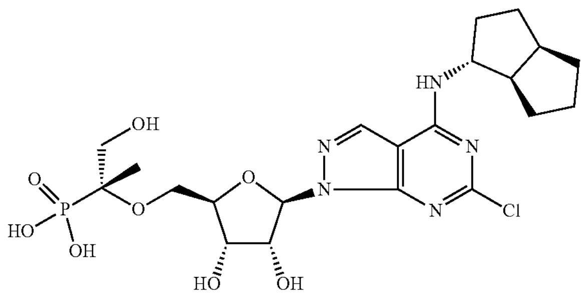 [SMILES: C[C@@](CO)(OC[C@H]1O[C@@H](n2ncc3c(N[C@@H]4CC[C@H]5CCC[C@H]54)nc(Cl)nc32)[C@H](O)[C@@H]1O)P(=O)(O)O] | rac-((R)-2-(((2R,3S,4S,5S)-5-(6-chloro-4-(((1R,3aR,6aR)-octahydropentalen-1-yl)amino-1H-pyrazolo[3,4-d]pyrimidin-1-yl)-3,4-dihydroxytetrahydrofuran-2-yl)methoxy)-1-hydroxypropan-2-yl)phosphonic acid |
| 183 | 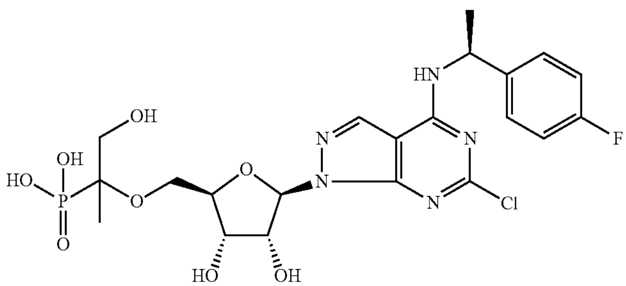 [SMILES: C[C@H](Nc1nc(Cl)nc2c1cnn2[C@@H]1O[C@H](COC(C)(CO)P(=O)(O)O)[C@@H](O)[C@H]1O)c1ccc(F)cc1] | rac-(2-(((2R,3S,4R,5R)-5-(6-chloro-4-(((S)-1-(4-fluorophenyl)ethyl)amino-1H-pyrazolo[3,4-d]pyrimidin-1-yl)-3,4-dihydroxytetrahydrofuran-2-yl)methoxy)-1-hydroxypropan-2-yl)phosphonic acid |
| 184 | 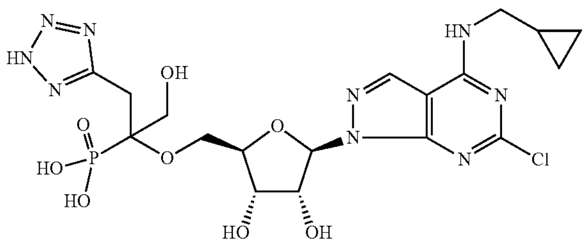 [SMILES: O=P(O)(O)C(CO)(Cc1nn[nH]n1)OC[C@H]1O[C@@H](n2ncc3c(NCC4CC4)nc(Cl)nc32)[C@H](O)[C@@H]1O] | rac-(2-(((2R,3S,4R,5R)-5-(6-chloro-4-(cyclopropylmethyl)amino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 185 | 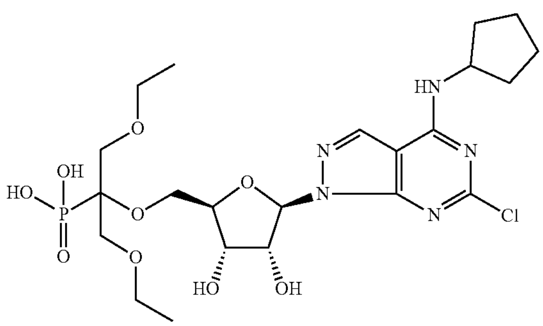 [SMILES: CCOCC(COCC)(OC[C@H]1O[C@@H](n2ncc3c(NC4CCCC4)nc(Cl)nc32)[C@H](O)[C@@H]1O)P(=O)(O)O] | rac-(2-(((2R,3S,4R,5R)-5-(6-(cyclopentylamino)-1H-pyrazolo[3,4-d]pyrimidin-1-yl)-3,4-dihydroxytetrahydrofuran-2-yl)methoxy)-1,3-diethoxypropan-2-yl)phosphonic acid |
| 186 | 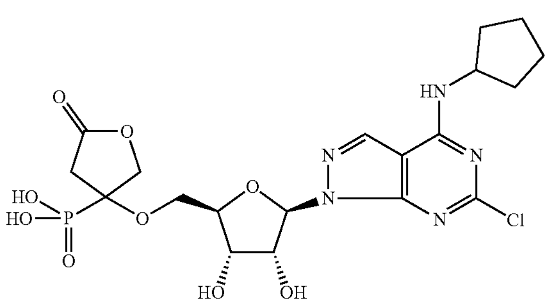 [SMILES: O=C1CC(OC[C@H]2O[C@@H](n3ncc4c(NC5CCCC5)nc(Cl)nc43)[C@H](O)[C@@H]2O)(P(=O)(O)O)CO1] | rac-(3-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-5-oxotetrahydrofuran-3-yl)phosphonic acid |

TABLE 1-continued

| Ex | Structure | Name |
|---|---|---|
| 187 | 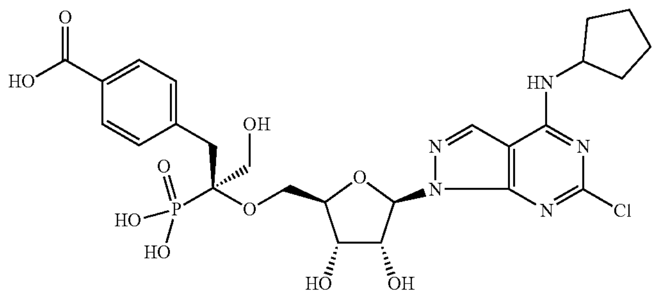 [SMILES: O=C(O)c1ccc(C[C@@](CO)(OC[C@H]2O[C@@H](n3ncc4c(NC5CCCC5)nc(Cl)nc43)[C@H](O)[C@@H]2O)P(=O)(O)O)cc1] | rac-4-((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2--yl)phosphonopropyl)benzoic acid |
| 188 | 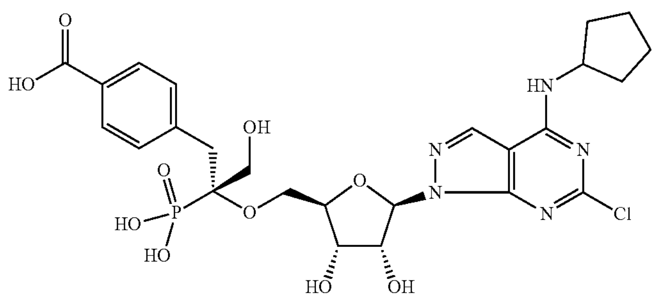 [SMILES: O=C(O)c1ccc(C[C@](CO)(OC[C@H]2O[C@@H](n3ncc4c(NC5CCCC5)nc(Cl)nc43)[C@H](O)[C@@H]2O)P(=O)(O)O)cc1] | rac-4-((R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2--phosphonopropyl)benzoic acid |
| 189 | 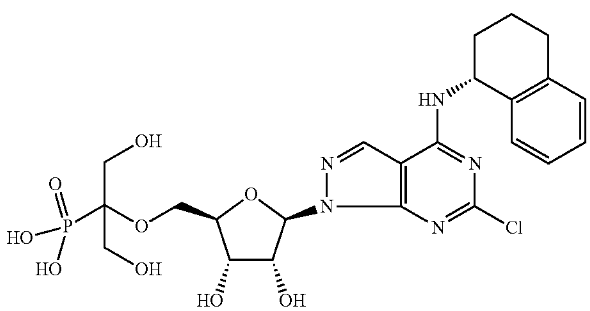 [SMILES: O=P(O)(O)C(CO)(CO)OC[C@H]1O[C@@H](n2ncc3c(N[C@@H]4CCCc5ccccc54)nc(Cl)nc32)[C@H](O)[C@@H]1O] | rac-(2-(((2R,3S,4R,5R)-5-(6-chloro-4-(((R)-1,2,3,4-tetrahydronaphthalen-1-yl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 190 | 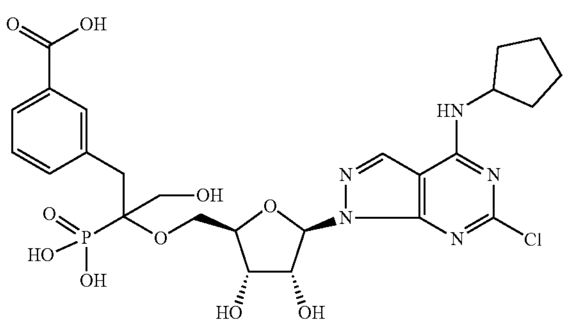 [SMILES: O=C(O)c1cccc(CC(CO)(OC[C@H]2O[C@@H](n3ncc4c(NC5CCCC5)nc(Cl)nc43)[C@H](O)[C@@H]2O)P(=O)(O)O)c1] | rac-(3-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropyl)benzoic acid |
| 191 | 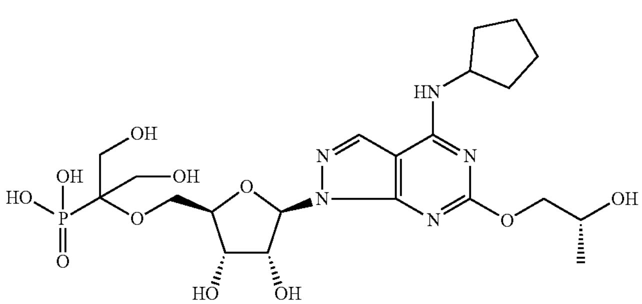 [SMILES: C[C@@H](O)COc1nc(NC2CCCC2)c2cnn([C@@H]3O[C@H](COC(CO)(CO)P(=O)(O)O)[C@@H](O)[C@H]3O)c2n1] | rac-(2-(((2R,3S,4R,5R)-5-(4-(cyclopentylamino)-6-((R)-2-hydroxypropoxy)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
|---|---|---|
| 192 | 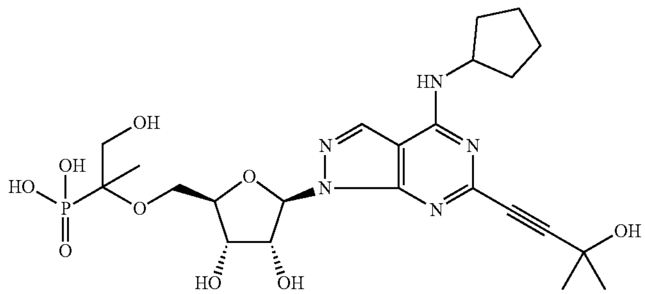 [SMILES: CC(C)(O)C#Cc1nc(NC2CCCC2)c2cnn([C@@H]3O[C@H](COC(C)(CO)P(=O)(O)O)[C@@H](O)[C@H]3O)c2n1] | rac-(2-(((2R,3S,4R,5R)-5-(4-(cyclopentylamino)-6-(3-hydroxy-3-methylbut-1-yn-1-yl)-1H-pyrazolo[3,4-d]pyrimidin-1-yl)-3,4-dihydroxytetrahydrofuran-2-yl)methoxy)-1-hydroxypropan-2-yl)phosphonic acid |
| 193 | 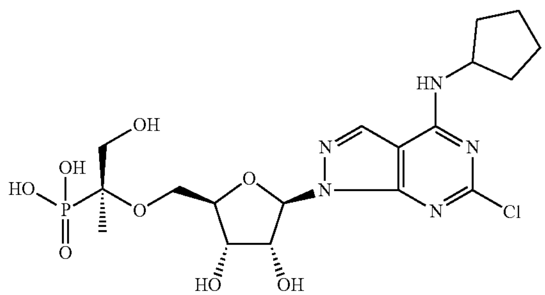 | rac-((R)-2-(((2S,3R,4S,5S)-5-(6-chloro-4-(cyclopentylamino)-1H-pyrazolo[3,4-b]pyridin-1-yl)-3,4-dihydroxytetrahydrofuran-2-yl)methoxy)-1-hydroxypropan-2-yl)phosphonic acid |
| 194 | 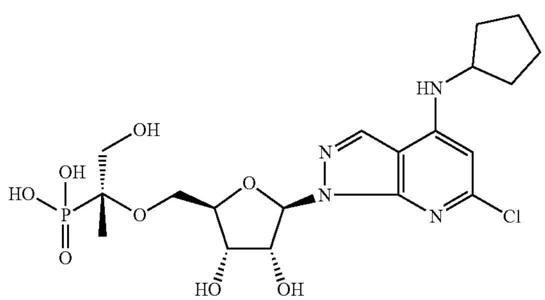 | rac-((R)-2-(((2R,3S,4R,5R)-5-(6-chloro-4-(cyclopentylamino)-1H-pyrazolo[3,4-b]pyridin-1-yl)-3,4-dihydroxytetrahydrofuran-2-yl)methoxy)-1-hydroxypropan-2-yl)phosphonic acid |
| 195 | 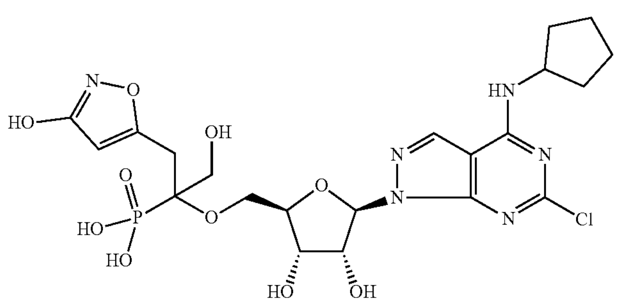 [SMILES: O=P(O)(O)C(CO)(Cc1cc(O)no1)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(3-hydroxyisoxazol-5-yl)propan-2-yl)phosphonic acid |
| 196 | 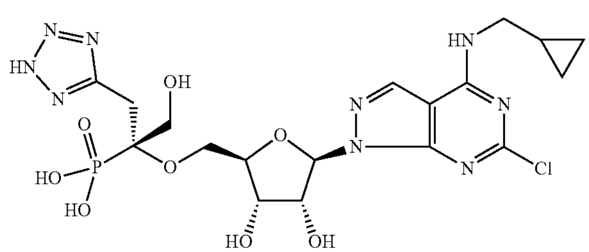 [SMILES: O=P(O)(O)[C@](CO)(Cc1nn[nH]n1)OC[C@H]1O[C@@H](n2ncc3c(NCC4CC4)nc(Cl)nc32)[C@H](O)[C@@H]1O] | rac-((R)-2-(((2S,3R,4S,5S)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |

TABLE 1-continued

| Ex | Structure | Name |
|---|---|---|
| 197 | 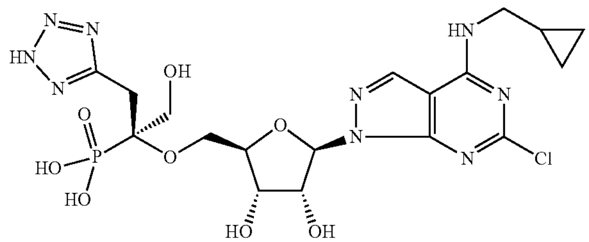 [SMILES: O=P(O)(O)[C@@](CO)(Cc1nn[nH]n1)OC[C@H]1O[C@@H](n2ncc3c(NCC4CC4)nc(Cl)nc32)[C@H](O)[C@@H]1O] | rac-((R)-2-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-hydroxy-3-2H-tetrazol-5-yl)propan-2-yl)phosphonic acid |
| 198 | 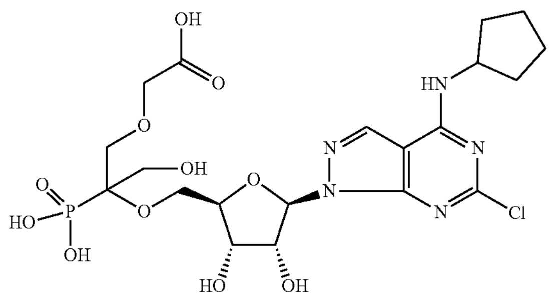 [SMILES: O=C(O)COCC(CO)(OC[C@H]1O[C@@H](n2ncc3c(NC4CCCC4)nc(Cl)nc32)[C@H](O)[C@@H]1O)P(=O)(O)O] | rac-2-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropoxy)acetic acid |
| 199 | 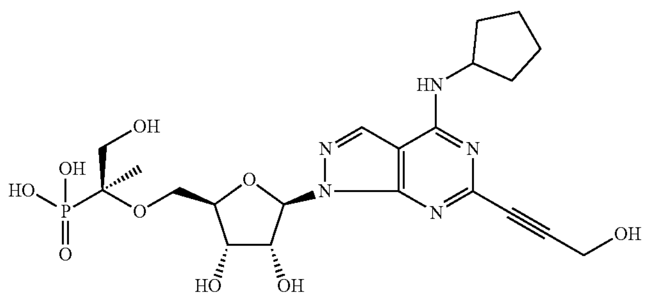 [SMILES: C[C@](CO)(OC[C@H]1O[C@@H](n2ncc3c(NC4CCCC4)nc(C#CCO)nc32)[C@H](O)[C@@H]1O)P(=O)(O)O] | rac-((R)-2-(((2S,3R,4S,5S)-5-(4-(cyclopentylamino)-6-(3-hydroxyprop-1-yn-1-yl)-1H-pyrazolo[3,4-d]pyrimidin-1-yl)-3,4-dihydroxytetrahydrofuran-2-yl)methoxy)-1-hydroxypropan-2-yl) phosphonic acid |
| 200 | 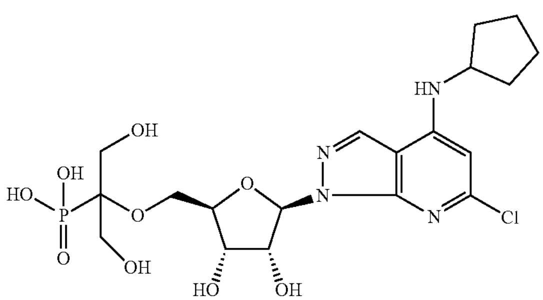 [SMILES: O=P(O)(O)C(CO)(CO)OC[C@H]1O[C@@H](n2ncc3c(NC4CCCC4)cc(Cl)nc32)[C@H](O)[C@@H]1O] | rac-(2-(((2R,3S,4R,5R)-5-(6-chloro-4-(cyclopentylamino)-1H-pyrazolo[3,4-b]pyridin-1-yl)-3,4-dihydroxytetrahydrofuran-2-yl)methoxy)-1,3-dihydroxypropan-2-yl)phosphonic acid |
| 201 | 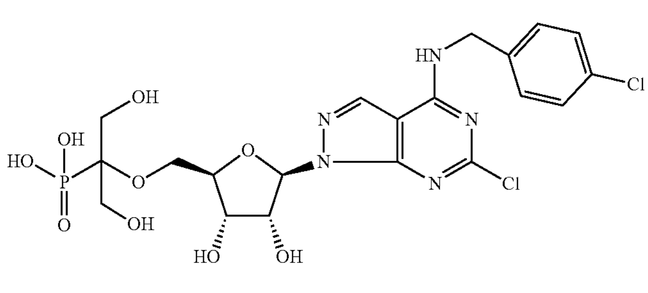 [SMILES: O=P(O)(O)C(CO)(CO)OC[C@H]1O[C@@H](n2ncc3c(NCc4ccc(Cl)cc4)nc(Cl)nc32)[C@H](O)[C@@H]1O] | rac-(2-(((2R,3S,4R,5R)-5-(6-chloro-4-((4-chlorobenzyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
|---|---|---|
| 202 | 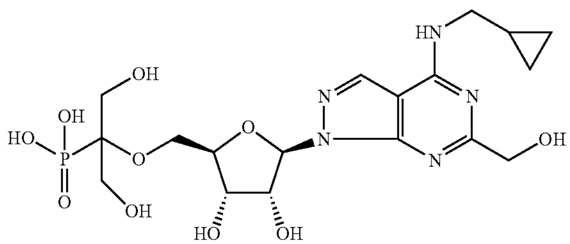 [SMILES: O=P(O)(O)C(CO)(CO)OC[C@H]1O[C@@H](n2ncc3c(NCC4CC4)nc(CO)nc32)[C@H](O)[C@@H]1O] | rac-(2-(((2R,3S,4R,5R)-5-(4-((cyclproptylmethyl)amino)-6-(hydroxymethyl)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 203 | 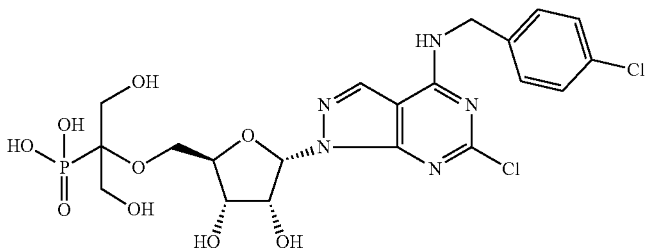 [SMILES: O=P(O)(O)C(CO)(CO)OC[C@H]1O[C@H](n2ncc3c(NCc4ccc(Cl)cc4)nc(Cl)nc32)[C@H](O)[C@@H]1O] | rac-(2-(((2R,3S,4R,5S)-5-(6-chloro-4-((4-chlorobenzyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 204 | 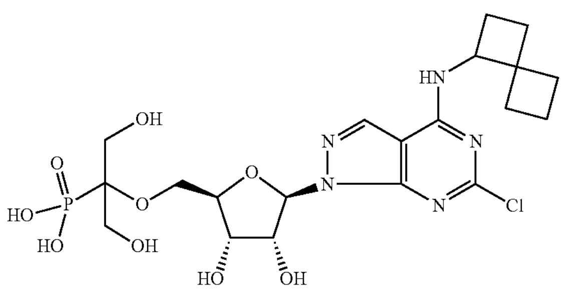 [SMILES: O=P(O)(O)C(CO)(CO)OC[C@H]1O[C@@H](n2ncc3c(NC4CCC45CCC5)nc(Cl)nc32)[C@H](O)[C@@H]1O] | rac-(2-(((2R,3S,4R,5R)-5-(6-chloro-4-(spiro[3.3]heptan-1-ylamino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 205 | 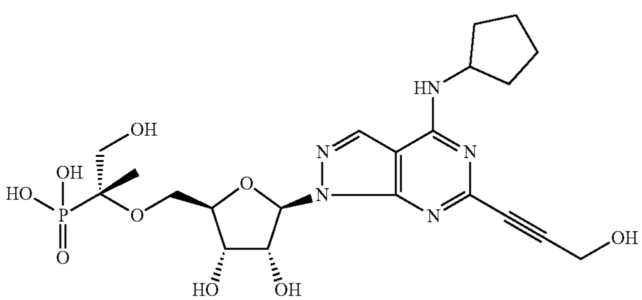 [SMILES: C[C@@](CO)(OC[C@H]1O[C@@H](n2ncc3c(NC4CCCC4)nc(C#CCO)nc32)[C@H](O)[C@@H]1O)P(=O)(O)O] | rac-((R)-2-(((2R,3S,4R,5R)-5-(4-(cyclopentylamino)-6-(3-hydroxyprop-1-yn-1-yl)-1H-pyrazolo[3,4-d]pyrimidin-1-yl)-3,4-dihydroxytetrahydrofuran-2-yl)methoxy)-1-hydroxypropan-2-yl)phosphonic acid |
| 206 | 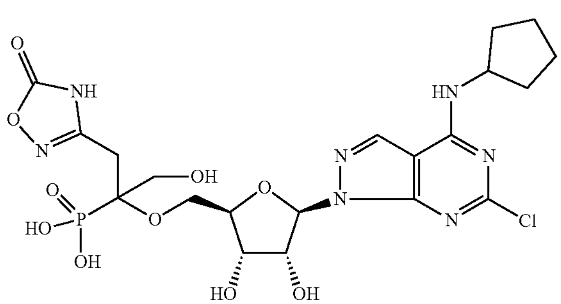 [SMILES: O=c1[nH]c(CC(CO)(OC[C@H]2O[C@@H](n3ncc4c(NC5CCCC5)nc(Cl)nc43)[C@H](O)[C@@H]2O)P(=O)(O)O)no1] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(5-oxo-4,5-dihydro-1,2,4-oxadiazol-3-yl)propan-2-yl)phosphonic acid |

TABLE 1-continued

| Ex | Structure | Name |
|---|---|---|
| 207 | 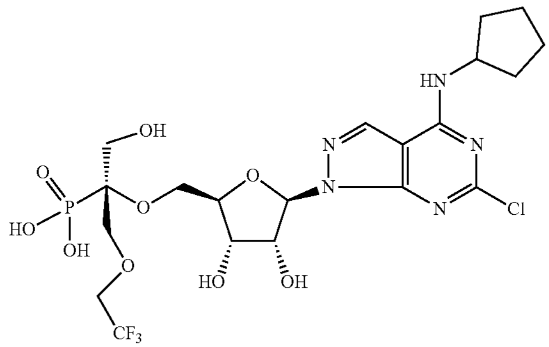 | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(2,2,2-trifluoroethoxy)propan-2-yl)phosphonic acid |
| 208 | 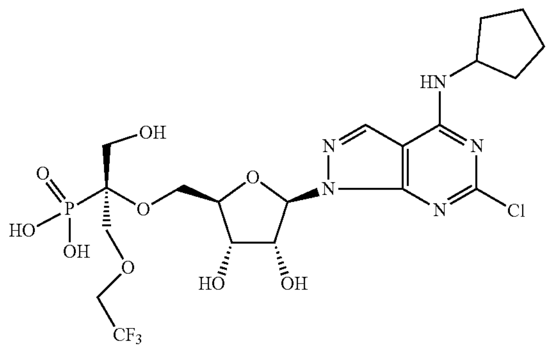 | rac-(2-(((2R,3S,4R,5R)-5-(6-chloro-4-(cyclopentylamino)-1H-pyrazolo[3,4-d]pyridin-1-yl)-3,4-dihydroxytetrahydrofuran-2-yl)methoxy)-1-hydroxy-3-(2,2,2-trifluoroethoxy)propan-2-yl) phosphonic acid |
| 209 | 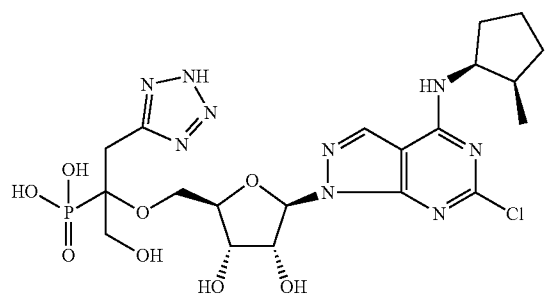 [SMILES: C[C@@H]1CCC[C@@H]1Nc1nc(Cl)nc2c1cnn2[C@@H]1O[C@H](COC(CO)(Cc2nn[nH]n2)P(=O)(O)O)[C@@H](O)[C@H]1O] | rac-(2-(((2R,3S,4R,5R)-5-(6-chloro-4-((((1S,2R)-2-methylcyclopentyl)amino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 210 | 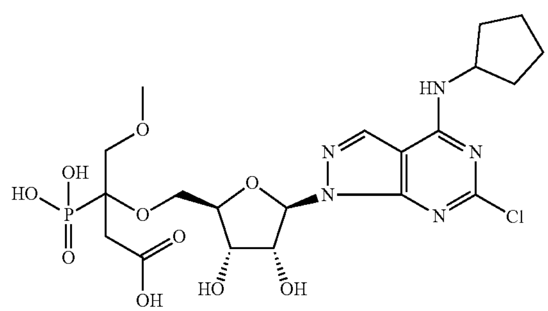 [SMILES: COCC(CC(=O)O)(OC[C@H]1O[C@@H](n2ncc3c(NC4CCCC4)nc(Cl)nc32)[C@H](O)[C@@H]1O)P(=O)(O)O] | rac-3-(((2R,3S,4R,5R)-5-(6-chloro-4-(cyclopentlyamino)-1H-pyrazolo[3,4-d]pyrimidin-1-yl)-3,4-dihydroxytetrahydrofuran-2-yl)methoxy)-4-methoxy-3-phosphobutanoic acid |
| 211 | 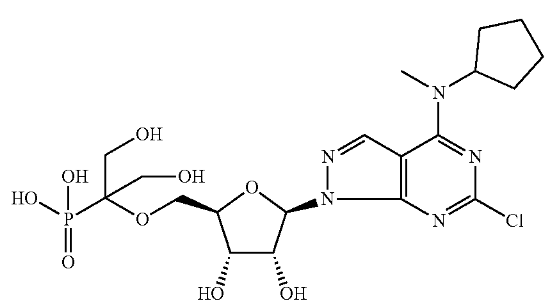 [SMILES: CN(c1nc(Cl)nc2c1cnn2[C@@H]1O[C@H](COC(CO)(CO)P(=O)(O)O)[C@@H](O)[C@H]1O)C1CCCC1] | rac-(2-(((2R,3S,4R,5R)-5-(6-chloro-4-(cyclopentyl(methyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |

TABLE 1-continued

| Ex | Structure | Name |
|---|---|---|
| 212 | 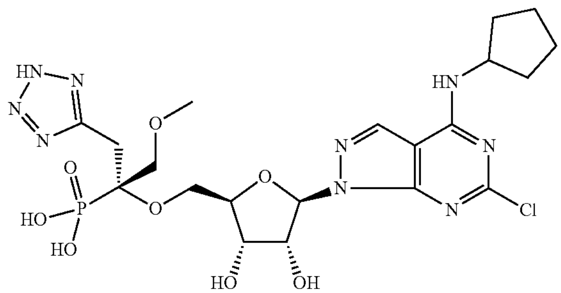 [SMILES: COC[C@@](Cc1nn[nH]n1)(OC[C@H]1O[C@@H](n2ncc3c(NC4CCCC4)nc(Cl)nc32)[C@H](O)[C@@H]1O)P(=O)(O)O] | rac-((R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-1-methoxy-3-(2H-tetrazol-5-yl)propan-2-yl)phosphonic acid |
| 213 | 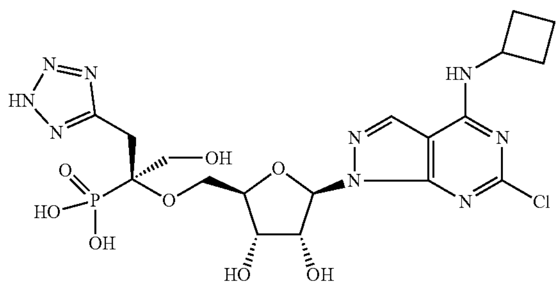 [SMILES: O=P(O)(O)[C@@](CO)(Cc1nn[nH]n1)OC[C@H]1O[C@@H](n2ncc3c(NC4CCC4)nc(Cl)nc32)[C@H](O)[C@@H]1O] | rac-((R)-2-(((2S,3S,4R,5R)-5-(6-chloro-4-(cyclobutylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 214 | 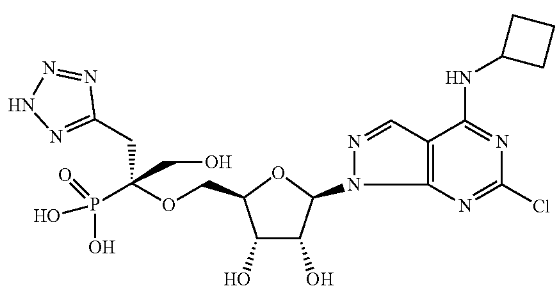 [SMILES: O=P(O)(O)[C@](CO)(Cc1nn[nH]n1)OC[C@H]1O[C@@H](n2ncc3c(NC4CCC4)nc(Cl)nc32)[C@H](O)[C@@H]1O] | rac-((R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 215 | 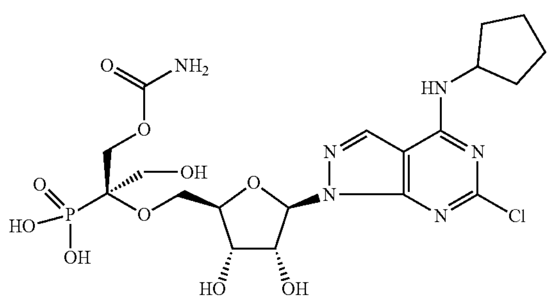 [SMILES: NC(=O)OC[C@@](CO)(OC[C@H]1O[C@@H](n2ncc3c(NC4CCCC4)nc(Cl)nc32)[C@H](O)[C@@H]1O)P(=O)(O)O] | rac-((R)-1-(carbamoyloxy)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-3-hydroxypropan-2-yl)phosphonic acid |
| 216 | 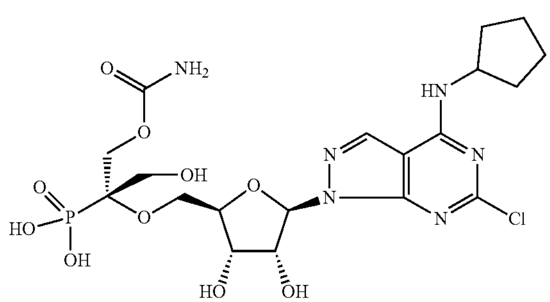 [SMILES: NC(=O)OC[C@](CO)(OC[C@H]1O[C@@H](n2ncc3c(NC4CCCC4)nc(Cl)nc32)[C@H](O)[C@@H]1O)P(=O)(O)O] | rac-((R)-1-(carbamoyloxy)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxypropan-2-yl)phosphonic acid |

TABLE 1-continued

| Ex | Structure | Name |
|---|---|---|
| 217 | 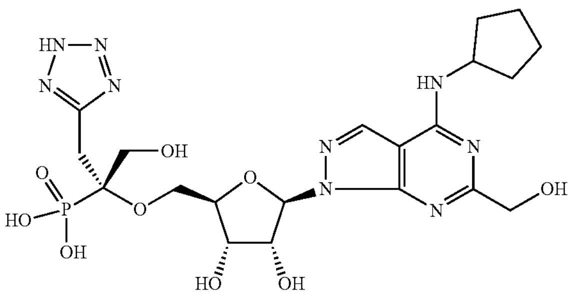 [SMILES: O=P(O)(O)[C@](CO)(Cc1nn[nH]n1)OC[C@H]1O[C@@H](n2ncc3c(NC4CCCC4)nc(CO)nc32)[C@H](O)[C@@H]1O] | rac-((R)-2-(((2S,3R,4S,5S)-5-4-(cyclopentylamino)-6-(hydroxymethyl)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 218 | 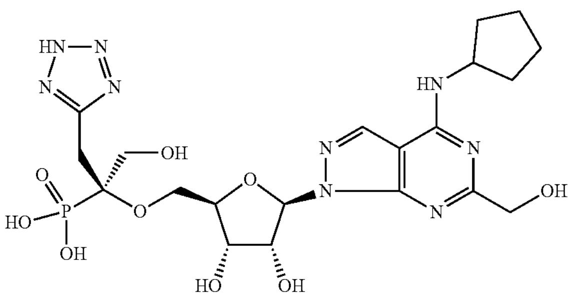 [SMILES: O=P(O)(O)[C@@](CO)(Cc1nn[nH]n1)OC[C@H]1O[C@@H](n2ncc3c(NC4CCCC4)nc(CO)nc32)[C@H](O)[C@@H]1O] | rac-((R)-2-(((2R,3S,4R,5R)-5-4-(cyclopentylamino)-6-(hydroxymethyl)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 219 | 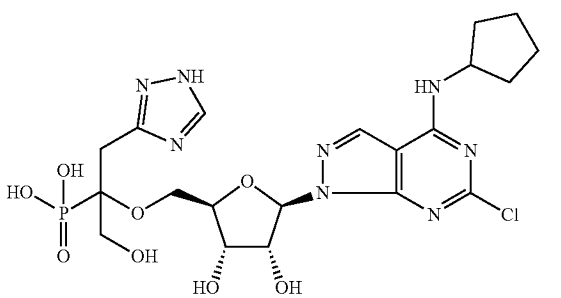 [SMILES: O=P(O)(O)C(CO)(Cc1nc[nH]n1)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(1H-1,2,4-triazol-3-yl)propan-2-yl)phosphonic acid |
| 220 | 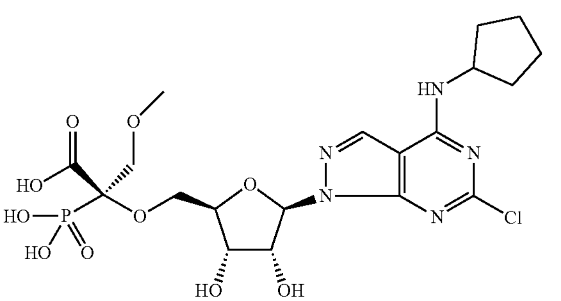 [SMILES: COC[C@@](OC[C@H]1O[C@@H](n2ncc3c(NC4CCCC4)nc(Cl)nc32)[C@H](O)[C@@H]1O)(C(=O)O)P(=O)(O)O] | rac-(R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-3-methoxy-2-phosphonic acid |
| 221 | 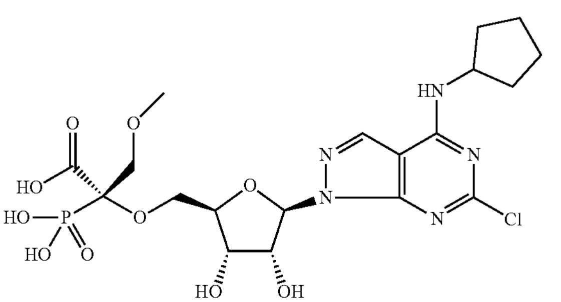 [SMILES: COC[C@](OC[C@H]1O[C@@H](n2ncc3c(NC4CCCC4)nc(Cl)nc32)[C@H](O)[C@@H]1O)(C(=O)O)P(=O)(O)O] | rac-(R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-methoxy-2-phosphonopropanoic acid |

TABLE 1-continued

| Ex | Structure | Name |
|---|---|---|
| 222 | 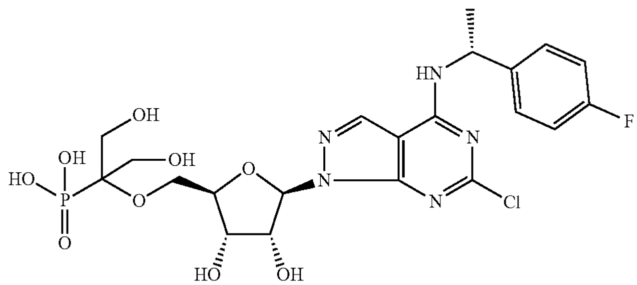 [SMILES: C[C@@H](Nc1nc(Cl)nc2c1cnn2[C@@H]1O[C@H](COC(CO)(CO)P(=O)(O)O)[C@@H](O)[C@H]1O)c1ccc(F)cc1] | rac-(2-(((2R,3S,4R,5R)-5-(6-chloro-4-(((R)-1-(4-fluorophenyl)ethyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 223 | 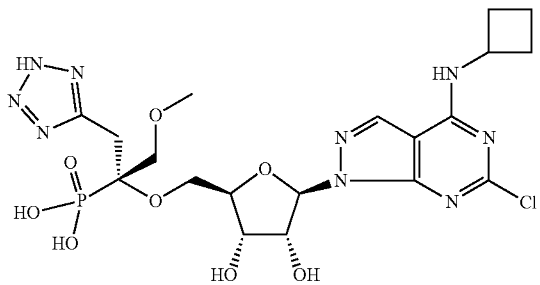 [SMILES: COC[C@@](Cc1nn[nH]n1)(OC[C@H]1O[C@@H](n2ncc3c(NC4CCC4)nc(Cl)nc32)[C@H](O)[C@@H]1O)P(=O)(O)O] | rac-((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-methoxy-3-(2H-tetrazol-5-yl)propan-2-yl)phosphonic acid |
| 224 | 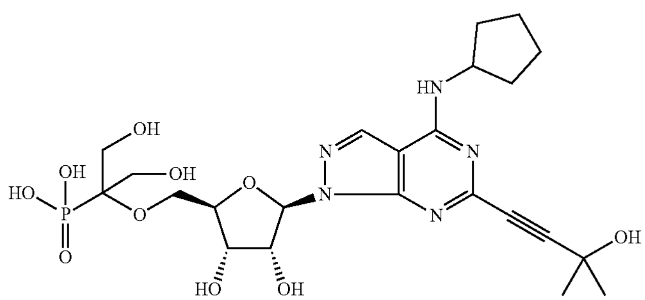 [SMILES: CC(C)(O)C#Cc1nc(NC2CCCC2)c2cnn([C@@H]3O[C@H](COC(CO)(CO)P(=O)(O)O)[C@@H](O)[C@H]3O)c2n1] | rac-(2-(((2R,3S,4R,5R)-5-(4-(cyclopentylamino)-6-(3-hydroxy-3-methylbut-1-yn-1-yl)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 225 | 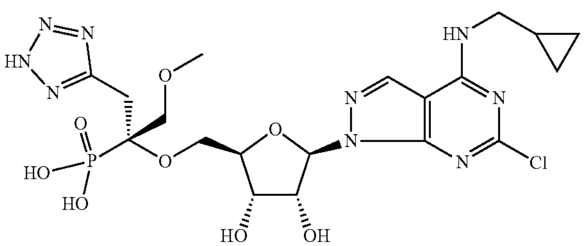 [SMILES: COC[C@@](Cc1nn[nH]n1)(OC[C@H]1O[C@@H](n2ncc3c(NCC4CC4)nc(Cl)nc32)[C@H](O)[C@@H]1O)P(=O)(O)O] | rac-((R)-2-(((2S,3R,4S,5S)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-methoxy-3-(2H-tetrazol-5-yl)propan-2-yl)phosphonic acid |
| 226 | 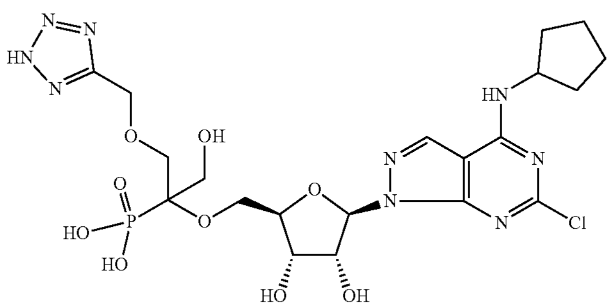 [SMILES: O=P(O)(O)C(CO)(COCc1nn[nH]n1)OC[C@H]1O[C@@H](n2ncc3c(NC4CCCC4)nc(Cl)nc32)[C@H](O)[C@@H]1O] | rac-(1-((2H-tetrazol-5-yl)methoxy)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxypropan-2-yl)phosphonic acid |

TABLE 1-continued

| Ex | Structure | Name |
|---|---|---|
| 227 | 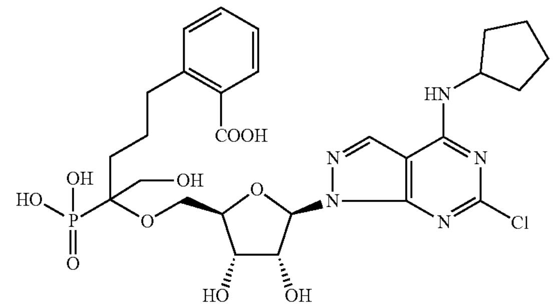 [SMILES: O=C(O)c1ccccc1CCCC(CO)(OC[C@H]1O[C@@H](n2ncc3c(NC4CCCC4)nc(Cl)nc32)[C@H](O)[C@@H]1O)P(=O)(O)O] | rac-2-((2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropoxy)methyl)benzoic acid |
| 228 | 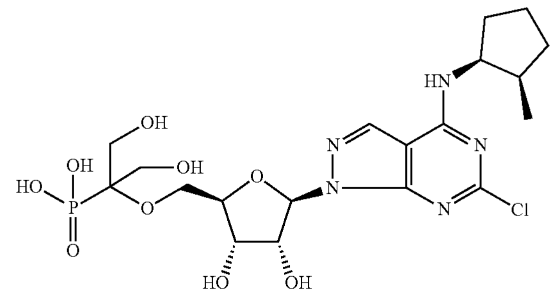 [SMILES: C[C@@H]1CCC[C@@H]1Nc1nc(Cl)nc2c1cnn2[C@@H]1O[C@H](COC(CO)(CO)P(=O)(O)O)[C@@H](O)[C@H]1O] | rac-(2-(((2R,3S,4R,5R)-5-(6-chloro-4-(((1S,2R)-2-methylcyclopentyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 229 | 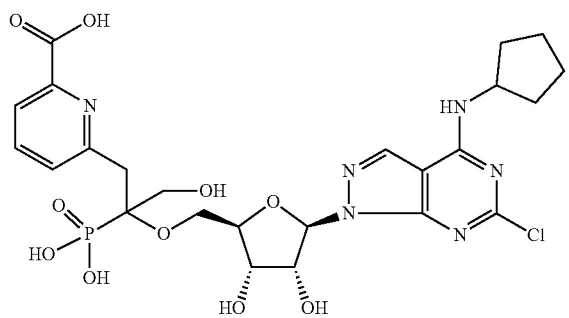 [SMILES: O=C(O)c1cccc(CC(CO)(OC[C@H]2O[C@@H](n3ncc4c(NC5CCCC5)nc(Cl)nc43)[C@H](O)[C@@H]2O)P(=O)(O)O)n1] | rac-6-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropyl)picolinic acid |
| 230 | 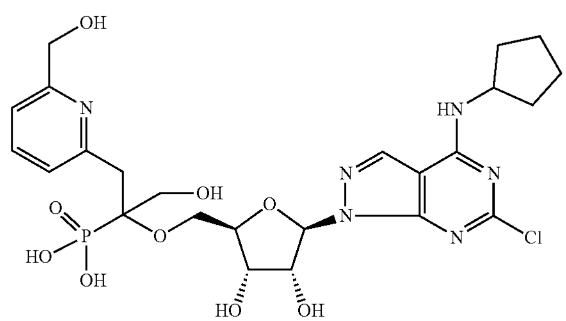 [SMILES: O=P(O)(O)C(CO)(Cc1cccc(CO)n1)OC[C@H]1O[C@@H](n2ncc3c(NC4CCCC4)nc(Cl)nc32)[C@H](O)[C@@H]1O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-hydroxy-3-(6-(hydroxymethyl)pyridin-2-yl)propan-2-yl)phosphonic acid |
| 231 | 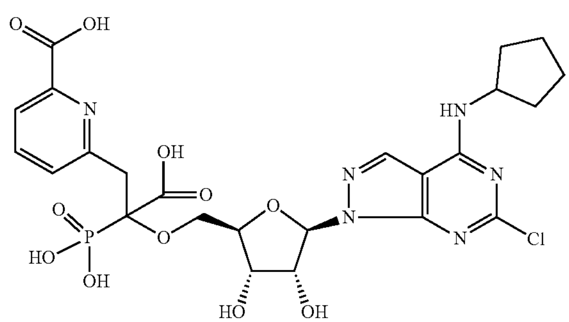 [SMILES: O=C(O)c1cccc(CC(OC[C@H]2O[C@@H](n3ncc4c(NC5CCCC5)nc(Cl)nc43)[C@H](O)[C@@H]2O)(C(=O)O)P(=O)(O)O)n1] | rac-6-(2-carboxy-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-phosphonoethyl)picolinic acid |

TABLE 1-continued

| Ex | Structure | Name |
|---|---|---|
| 232 | 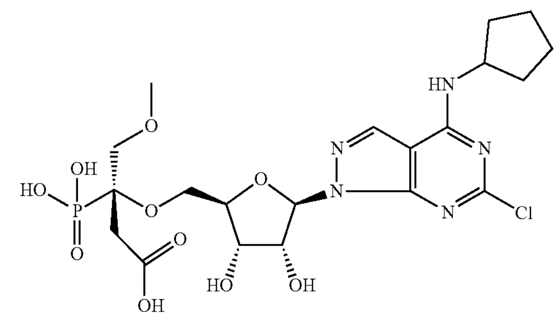 | rac-(R)-3-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-4-methoxy-3-phosphonobutanoic acid |
| 233 | 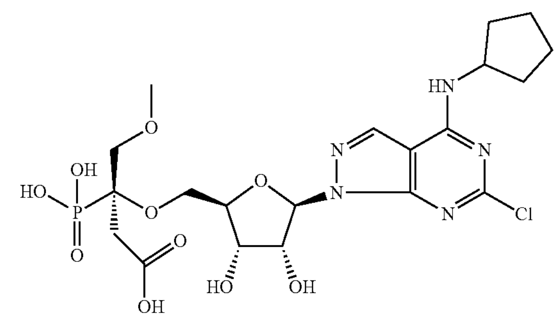 | rac-(R)-3-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-4-methoxy-3-phosphonobutanoic acid |
| 234 | 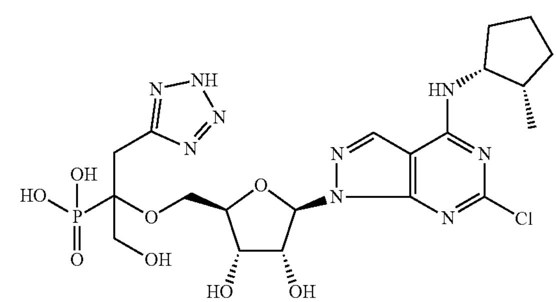 [SMILES: C[C@H]1CCC[C@H]1Nc1nc(Cl)nc2c1cnn2[C@@H]1O[C@H](COC(CO)(Cc2nn[nH]n2)P(=O)(O)O)[C@@H](O)[C@H]1O] | rac-(2-(((2R,3S,4R,5R)-5-(6-chloro-4-((((1R,2S)-2-methylcyclopentyl)amino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid |
| 235 | 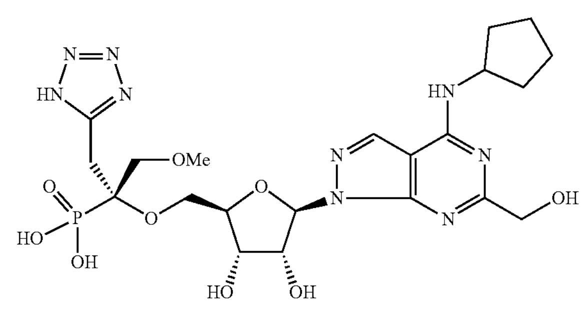 [SMILES: COC[C@@](Cc1nnn[nH]1)(OC[C@H]1O[C@@H](n2ncc3c(NC4CCCC4)nc(CO)nc32)[C@H](O)[C@@H]1O)P(=O)(O)O] | rac-((R)-2-(((2S,3R,4S,5S)-5-(4-(cyclopentylamino)-6-(hydroxymethyl)-1H-pyrazolo[3,4-d]pyrimidin-1-yl)-3,4-dihydroxytetrahydrofuran-2-yl)methoxy)-1-methoxy-3-(1H-tetrazol-5-yl)propan-2-yl)phosphonic acid |
| 236 | 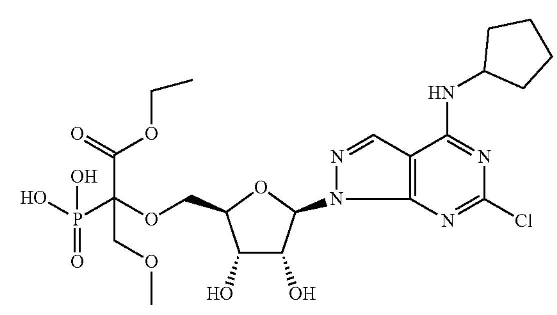 [SMILES: CCOC(=O)C(COC)(OC[C@H]1O[C@@H](n2ncc3c(NC4CCCC4)nc(Cl)nc32)[C@H](O)[C@@H]1O)P(=O)(O)O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-ethoxy-3-methoxy-1-oxopropan-2-yl)phosphonic acid |

TABLE 1-continued

| Ex | Structure | Name |
|---|---|---|
| 237 | 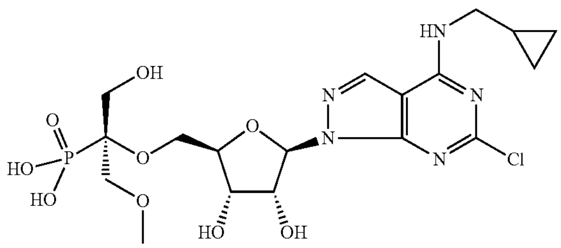 | rac-((R)-2-(((2R,3S,4R,5R)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-hydroxy-3-methoxypropan-2-yl)phosphonic acid |
| 238 | 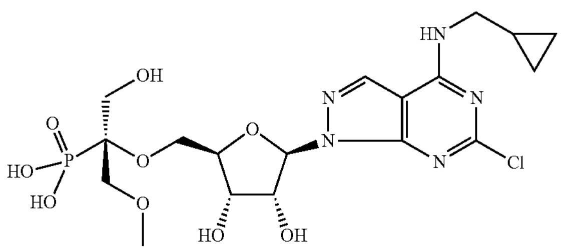 | rac-((R)-2-(((2S,3R,4S,5S)-5-(6-chloro-4-((cyclopropylmethyl)amino)-1H-pyrazolo[3,4-d]pyrimidin-1-yl)-3,4-dihydroxytetrahydrofuran-2-yl)methoxy)-1-hydroxy-3-methoxypropan-2-yl)phosphonic acid |
| 239 | 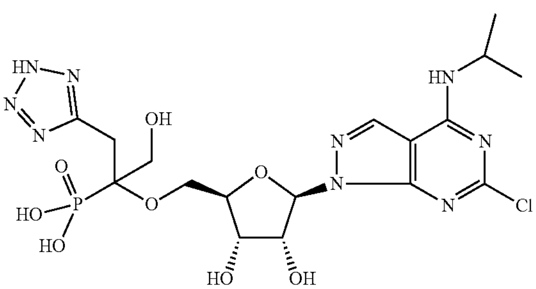 [SMILES: CC(C)Nc1nc(Cl)nc2c1cnn2[C@@H]1O[C@H](COC(CO)(Cc2nn[nH]n2)P(=O)(O)O)[C@@H](O)[C@H]1O] | rac-(2-(((2R,3S,4R,5R)-5-(6-chloro-4-(isopropylamino)-1H-pyrazolo[3,4-d]pyrimidin-1-yl)-3,4-dihydroxytetrahydrofuran-2-yl)methoxy)-1-hydroxy-(2H-tetrazol-5-yl)propan-2-yl)phosphonic acid |
| 240 | 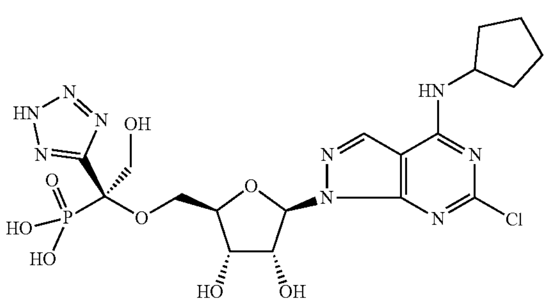 [SMILES: O=P(O)(O)[C@](CO)(OC[C@H]1O[C@@H](n2ncc3c(NC4CCCC4)nc(Cl)nc32)[C@H](O)[C@@H]1O)c1nn[nH]n1] | rac-((R)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxy-1-(2H-tetrazol-5-yl)ethyl)phosphonic acid |
| 241 | 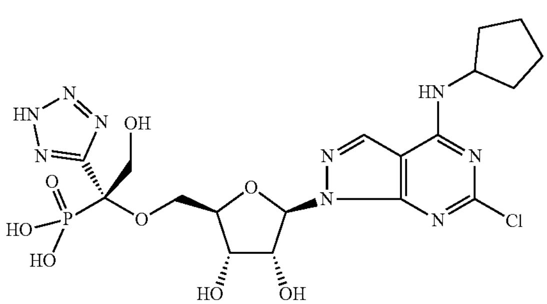 [SMILES: O=P(O)(O)[C@@](CO)(OC[C@H]1O[C@@H](n2ncc3c(NC4CCCC4)nc(Cl)nc32)[C@H](O)[C@@H]1O)c1nn[nH]n1] | rac-((R)-1-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-2-hydroxy-1-(2H-tetrazol-5-yl)ethyl)phosphonic acid |

TABLE 1-continued

| Ex | Structure | Name |
|---|---|---|
| 242 | 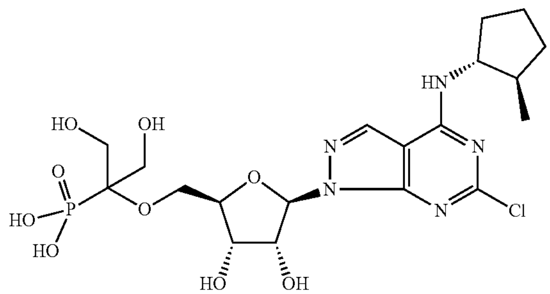 [SMILES: C[C@@H]1CCC[C@H]1Nc1nc(Cl)nc2c1cnn2[C@@H]1O[C@H](COC(CO)(CO)P(=O)(O)O)[C@@H](O)[C@H]1O] | rac-(2-((((2R,3S,4R,5R)-5-(6-chloro-4-((((1S,2R)-2-methylcyclopentyl)amino)-1H-pyrazolo[3,4-d]pyrimidin-1-yl)-3,4-dihydroxytetrahydrofuran-2-yl)methoxy)-1,3-dihydroxypropan-2-yl)phosphonic acid |
| 243 | 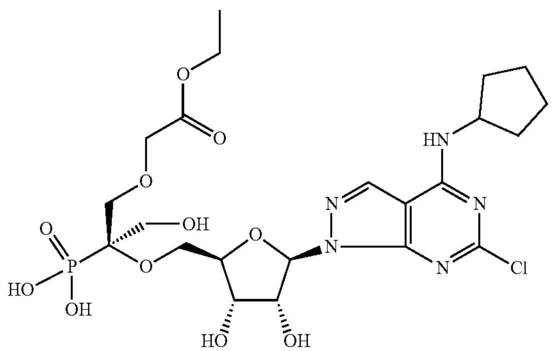 [SMILES: CCOC(=O)COC[C@@](CO)(OC[C@H]1O[C@@H](n2ncc3c(NC4CCCC4)nc(Cl)nc32)[C@H](O)[C@@H]1O)P(=O)(O)O] | rac-((R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-1-(2-ethoxy-2-oxoethoxy)-3-hydroxypropan-2-yl)phosphonic acid |
| 244 | 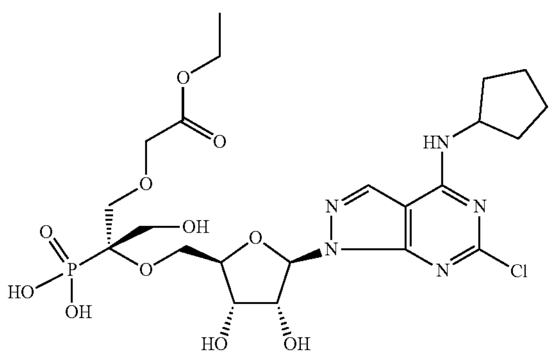 [SMILES: CCOC(=O)COC[C@](CO)(OC[C@H]1O[C@@H](n2ncc3c(NC4CCCC4)nc(Cl)nc32)[C@H](O)[C@@H]1O)P(=O)(O)O] | rac-((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-(2-ethoxy-2-oxoethoxy)-3-hydroxypropan-2-yl)phosphonic acid |
| 245 | 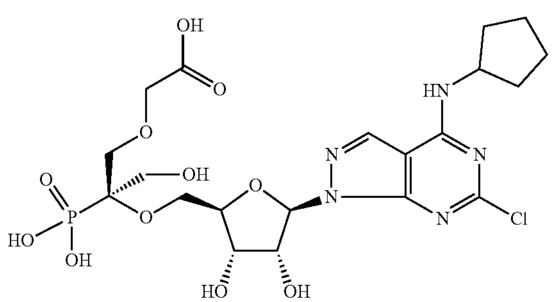 [SMILES: O=C(O)COC[C@@](CO)(OC[C@H]1O[C@@H](n2ncc3c(NC4CCCC4)nc(Cl)nc32)[C@H](O)[C@@H]1O)P(=O)(O)O] | rac-((R)-2-(((2S,3R,4S,5S)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropoxy)acetic acid |
| 246 | 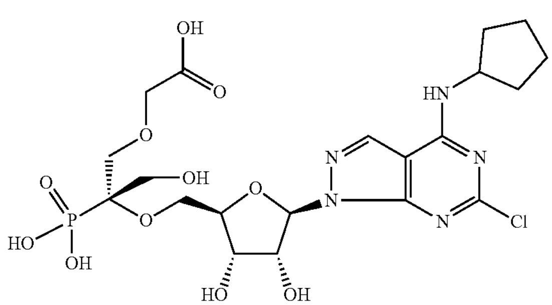 [SMILES: O=C(O)COC[C@](CO)(OC[C@H]1O[C@@H](n2ncc3c(NC4CCCC4)nc(Cl)nc32)[C@H](O)[C@@H]1O)P(=O)(O)O] | rac-2-((R)-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropoxy)acetic acid |

TABLE 1-continued

| Ex | Structure | Name |
|---|---|---|
| 247 | 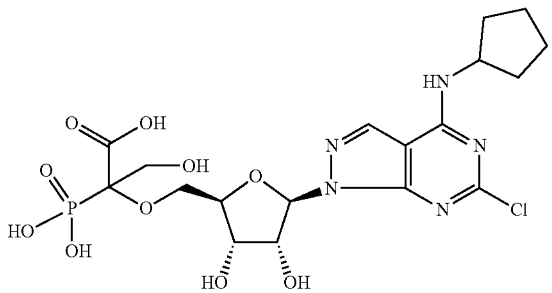 [SMILES: O=C(O)C(CO)(OC[C@H]1O[C@@H](n2ncc3c(NC4CCCC4)nc(Cl)nc32)[C@H](O)[C@@H]1O)P(=O)(O)O] | rac-2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-3-hydroxy-2-phosphonopropanoic acid |
| 248 | 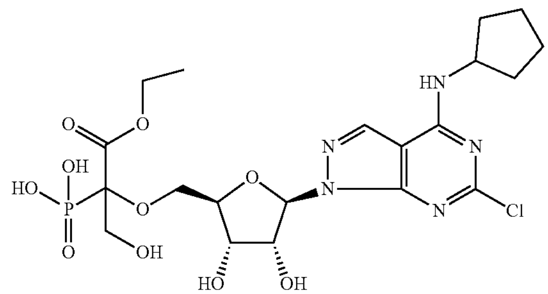 [SMILES: CCOC(=O)C(CO)(OC[C@H]1O[C@@H](n2ncc3c(NC4CCCC4)nc(Cl)nc32)[C@H](O)[C@@H]1O)P(=O)(O)O] | rac-(2-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-1-ethoxy-3-hydroxy-1-oxopropan-2-yl)phosphonic acid |

In some embodiments is a compound, or a pharmaceutically acceptable salt, solvate, stereoisomer, or isotopic variant thereof, having a structure selected from:

205
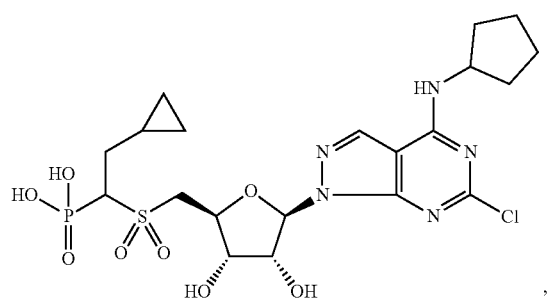
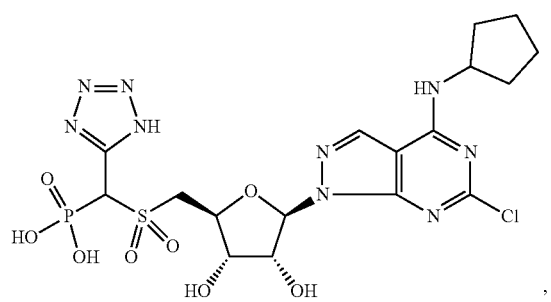
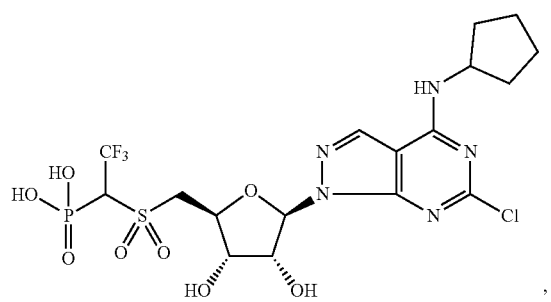
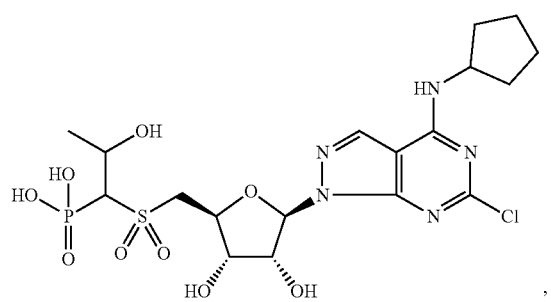
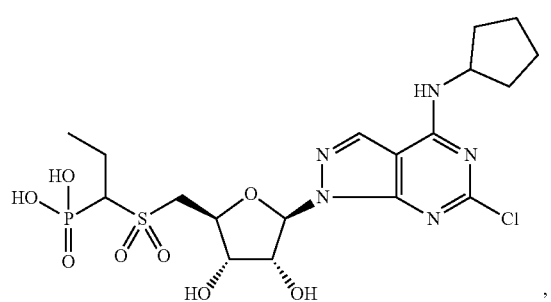
206
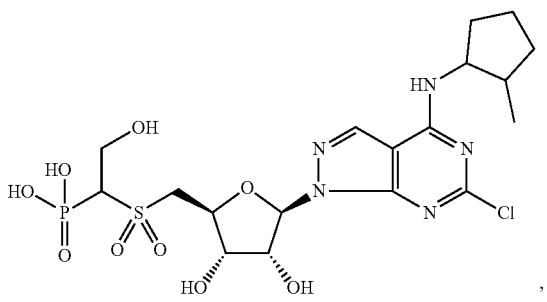
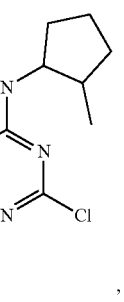
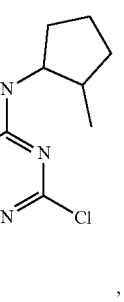
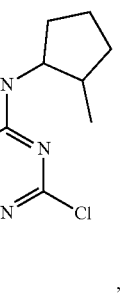
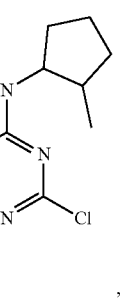

207
-continued
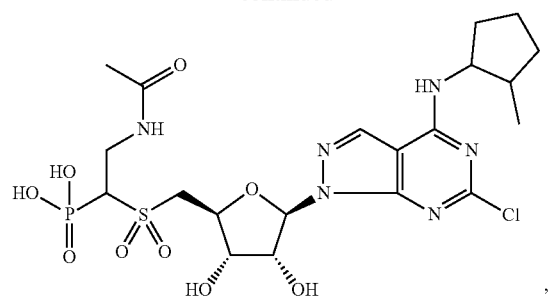
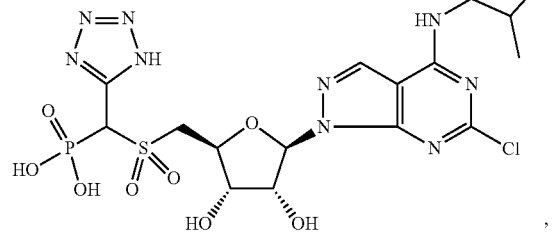
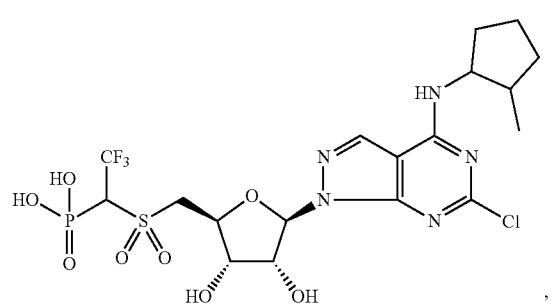
208
-continued
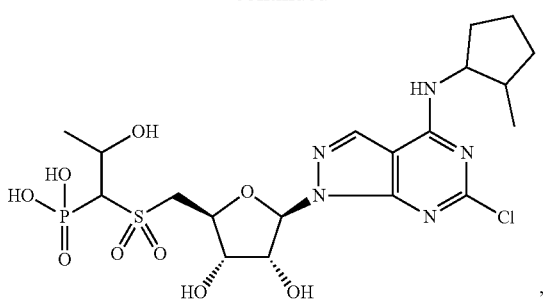
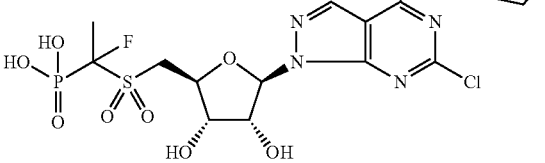

209
-continued
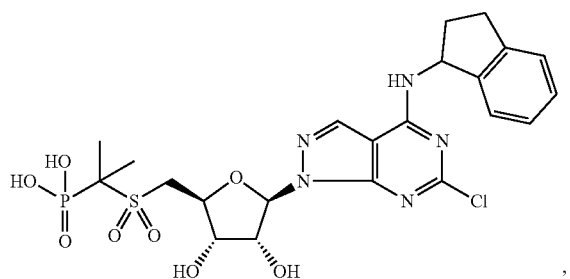
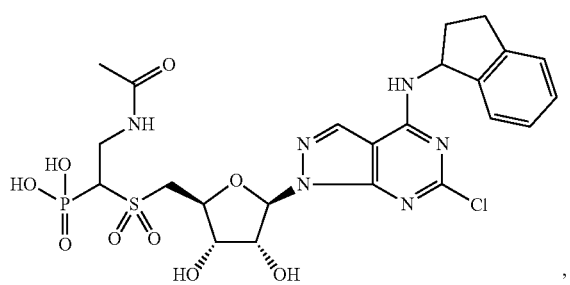
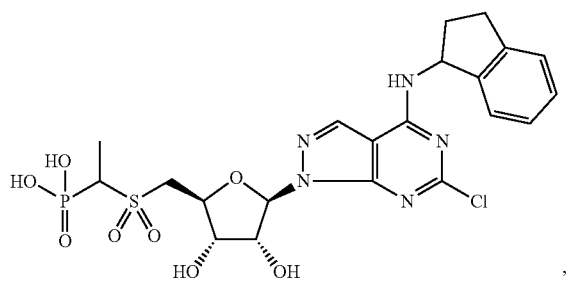
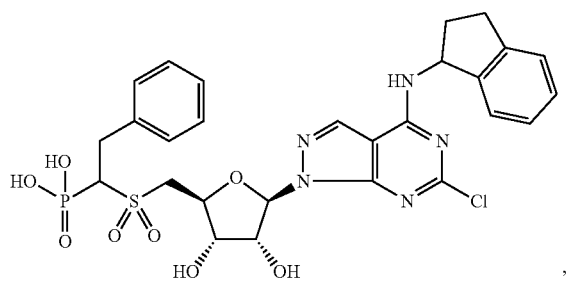
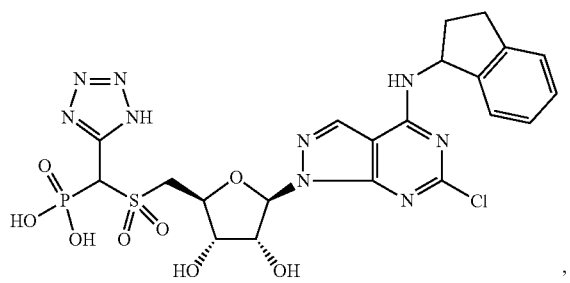
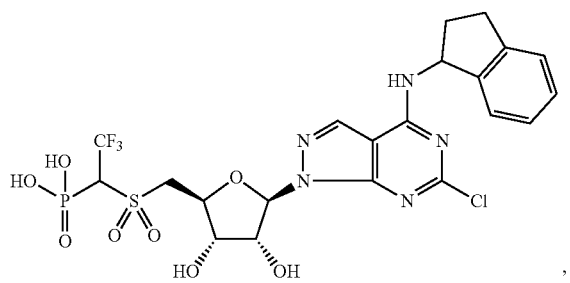
210
-continued
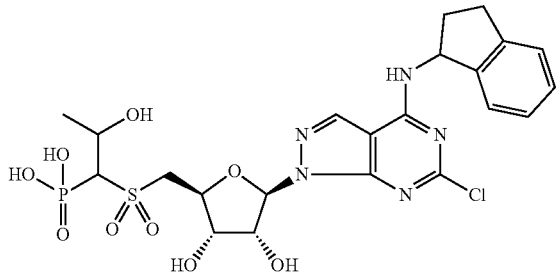
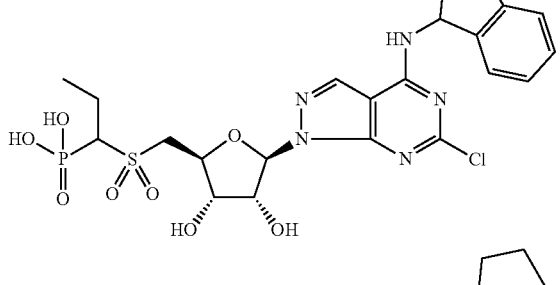
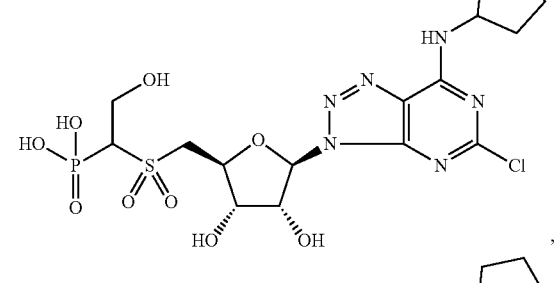
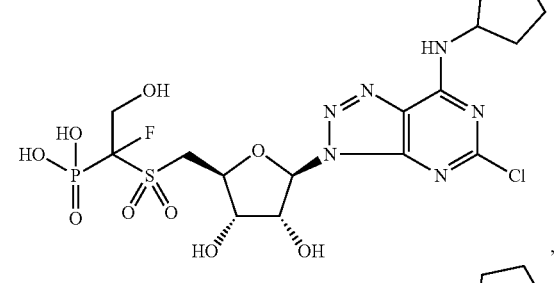
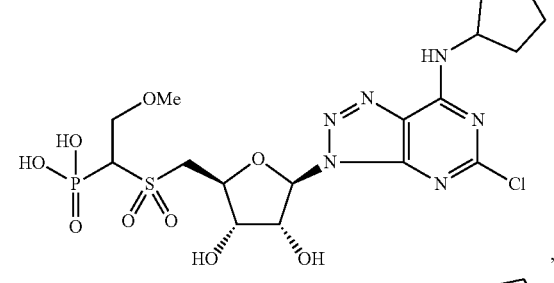
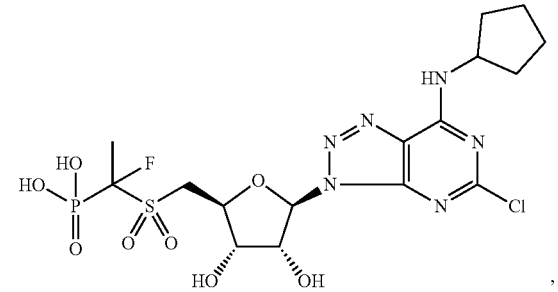

211
-continued
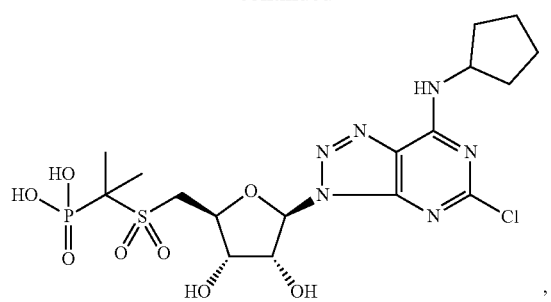
,
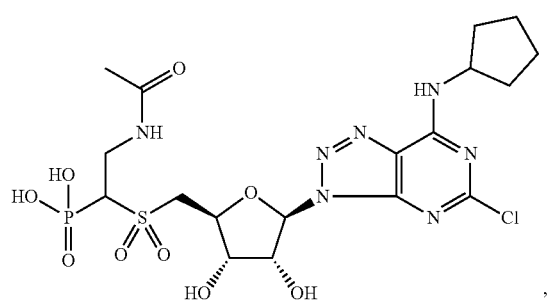
,
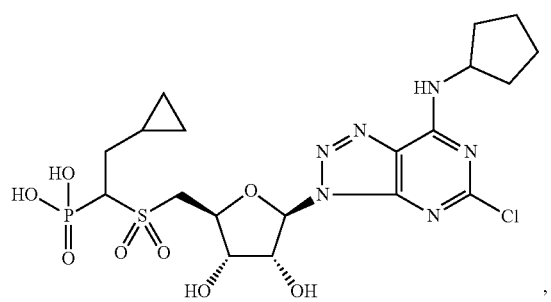
,
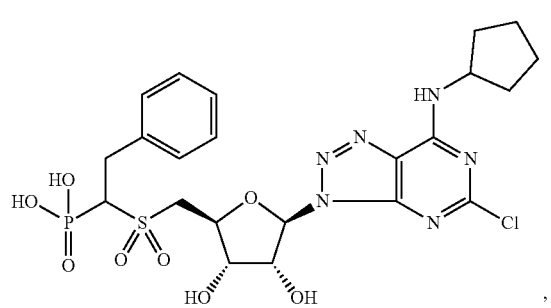
,
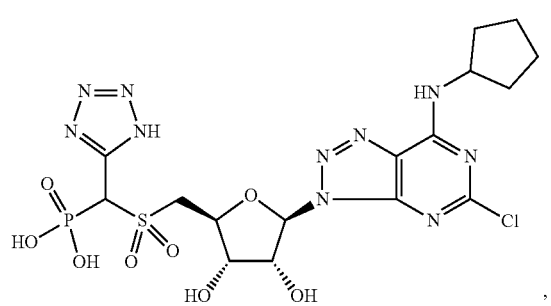
,
212
-continued
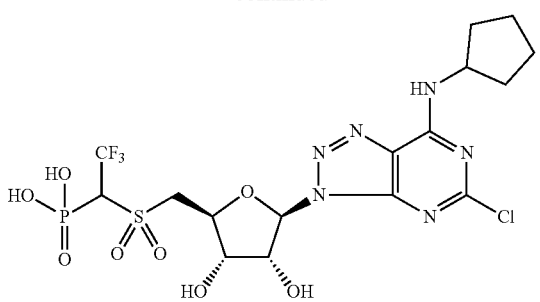
,
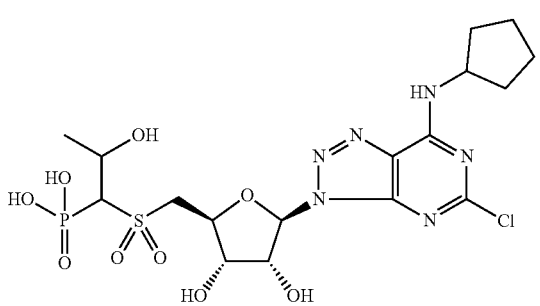
,
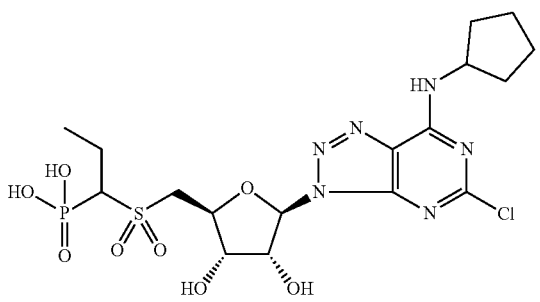
,
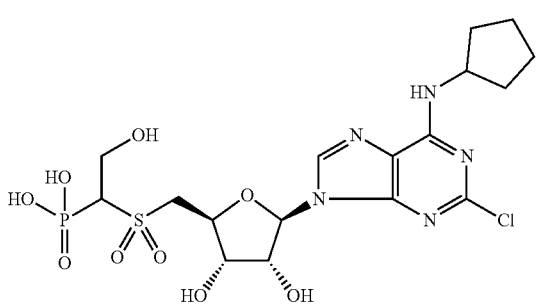
,
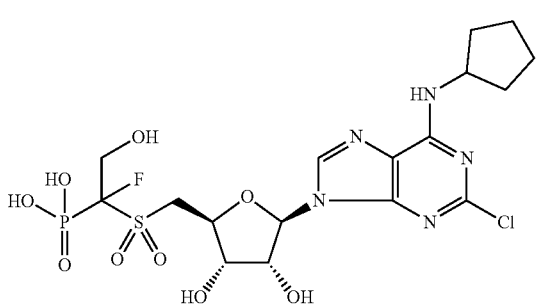
, 213
-continued
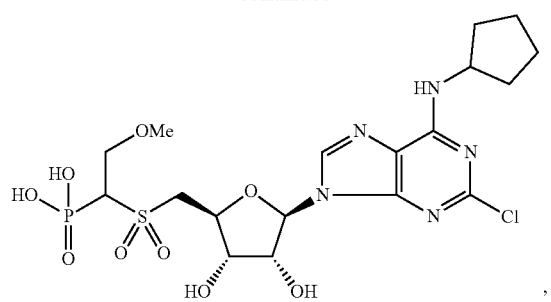
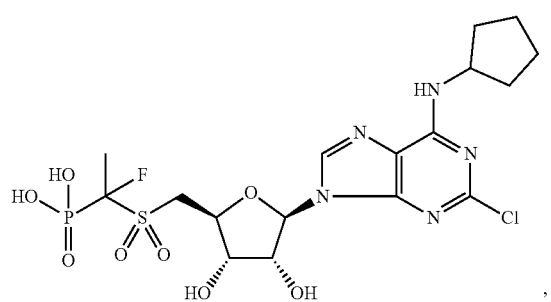
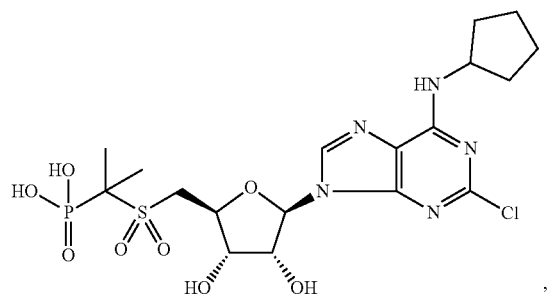
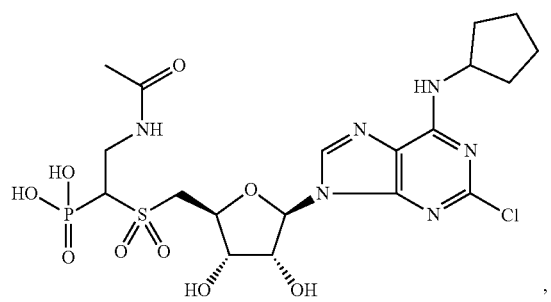
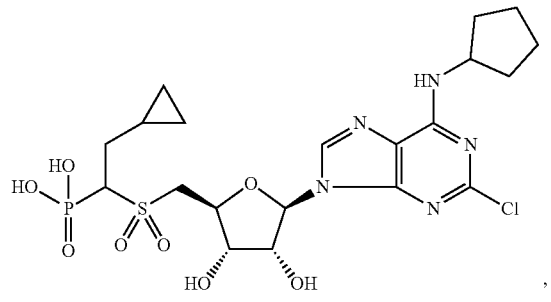
214
-continued
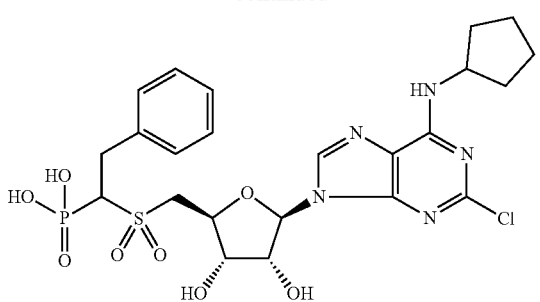
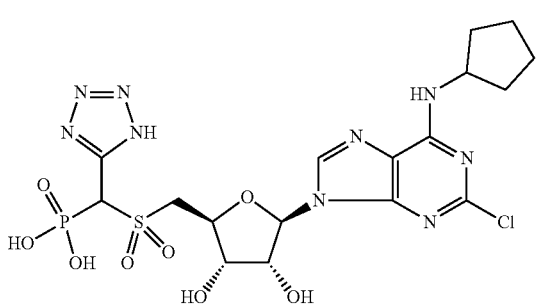
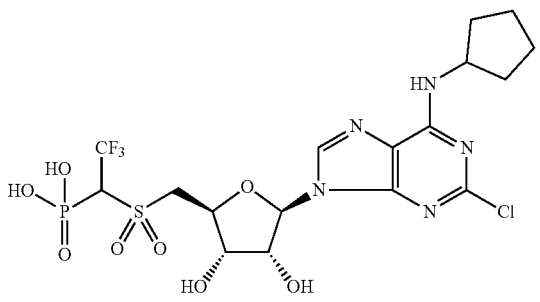
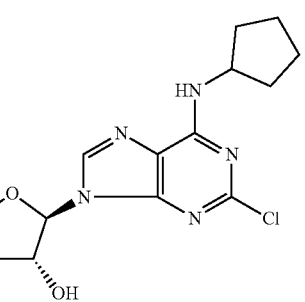
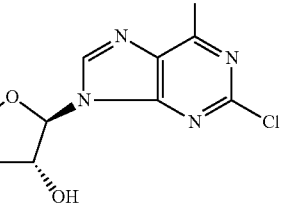

215
-continued
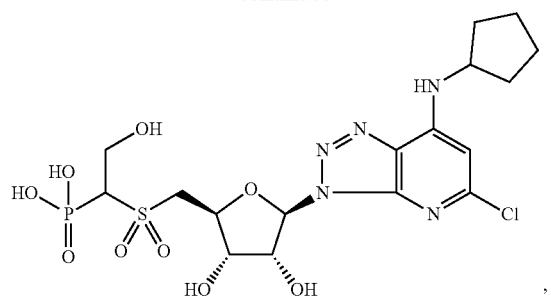
,
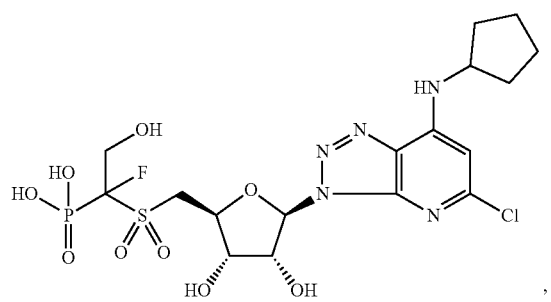
,
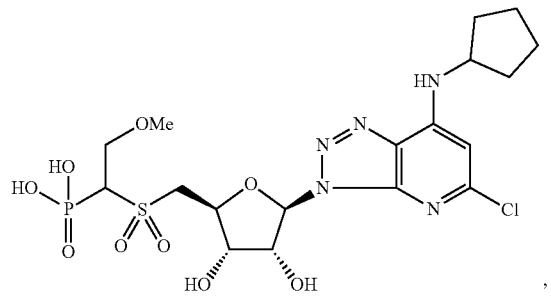
,
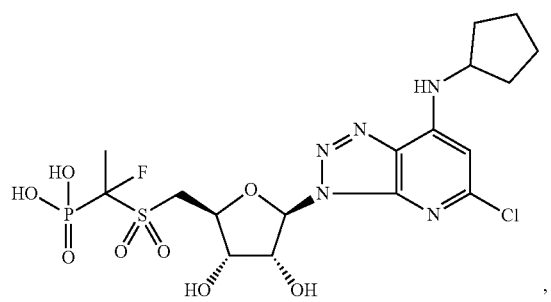
,
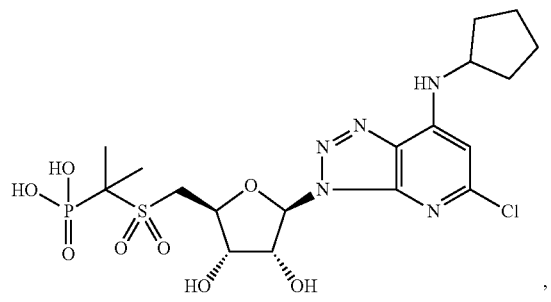
,
216
-continued
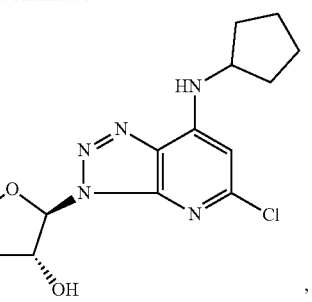
,
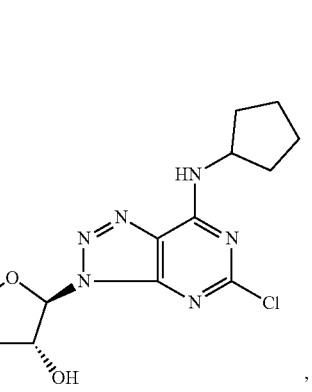
,
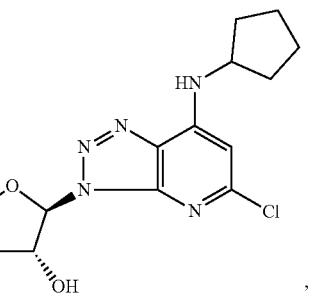
,
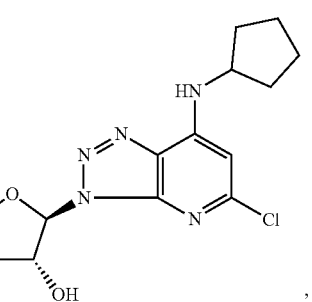
,
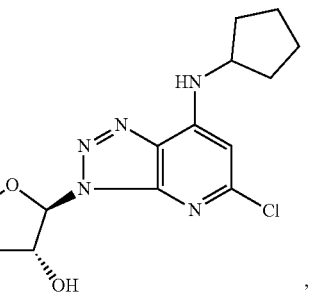
,

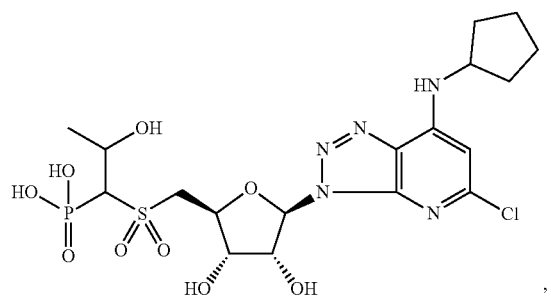
and
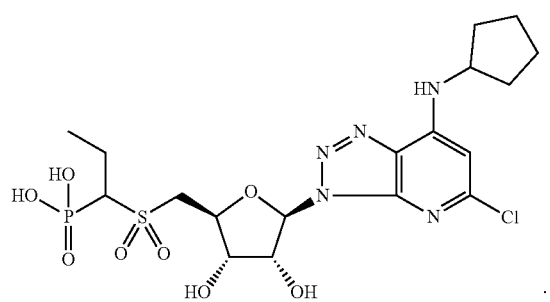
In some embodiments is a compound, or a pharmaceutically acceptable salt, solvate, stereoisomer, or isotopic variant thereof, having a structure selected from:
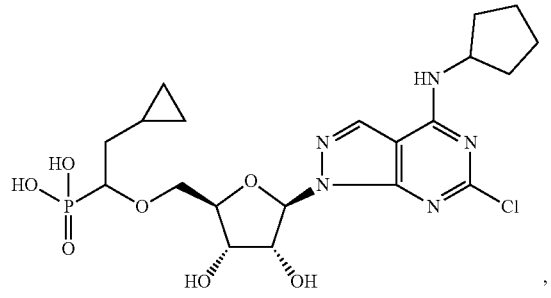
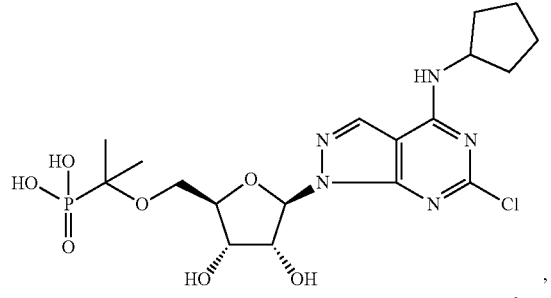
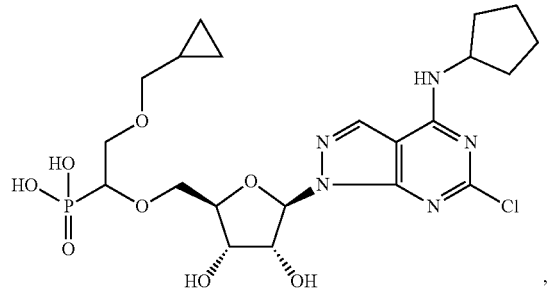
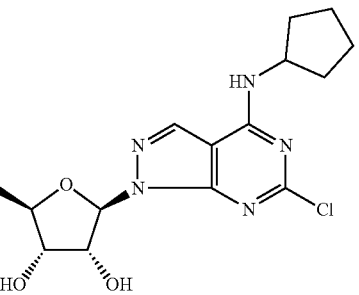
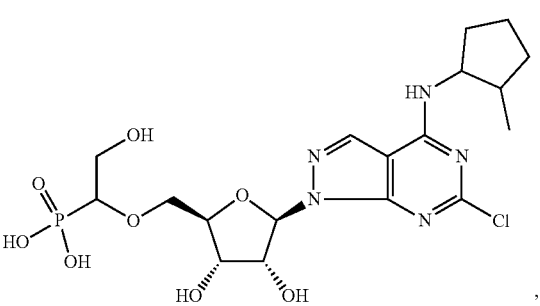
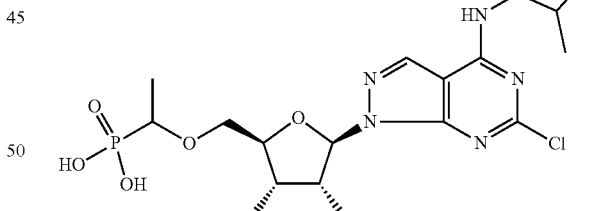
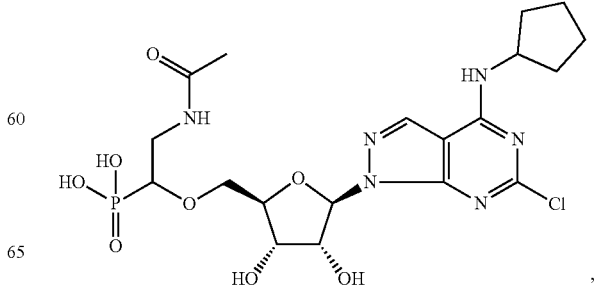

219
-continued
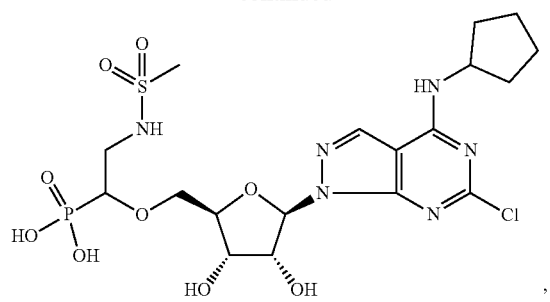
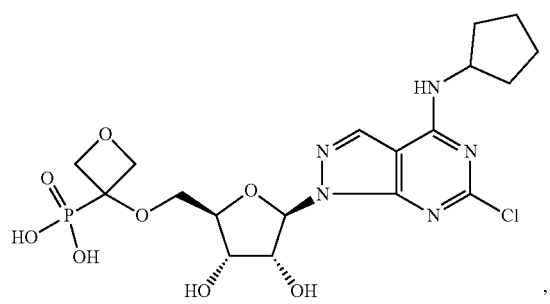
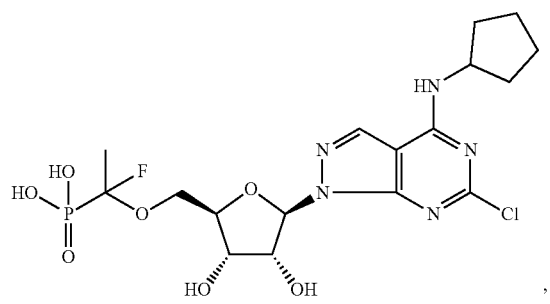
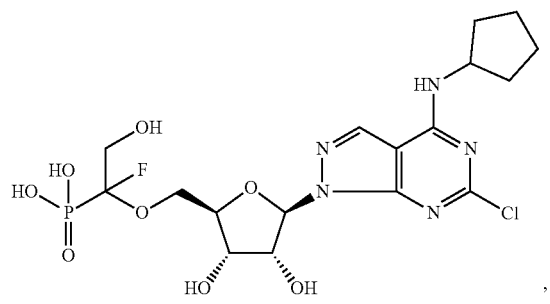
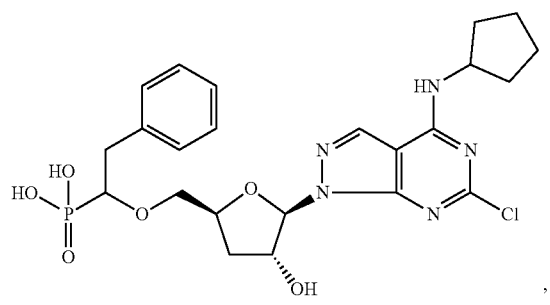
220
-continued
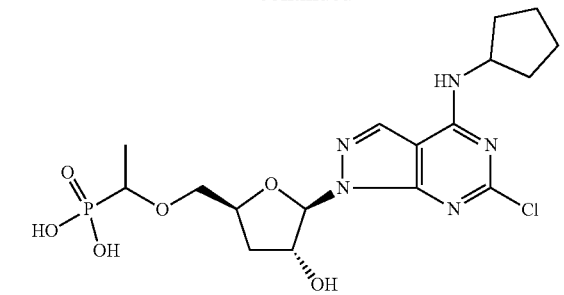
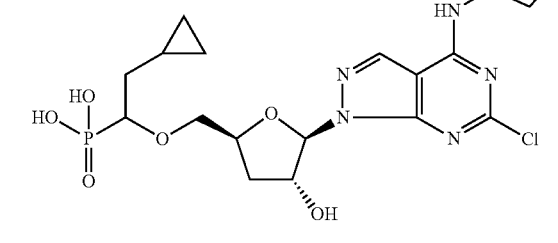
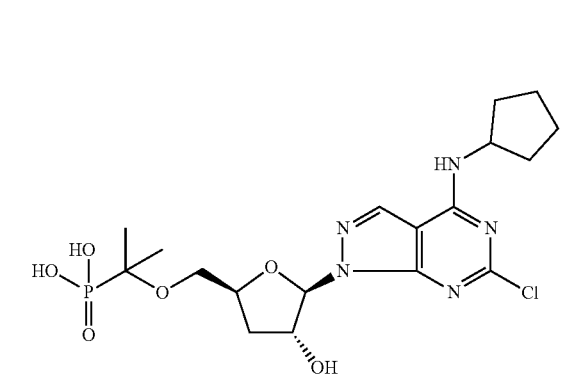
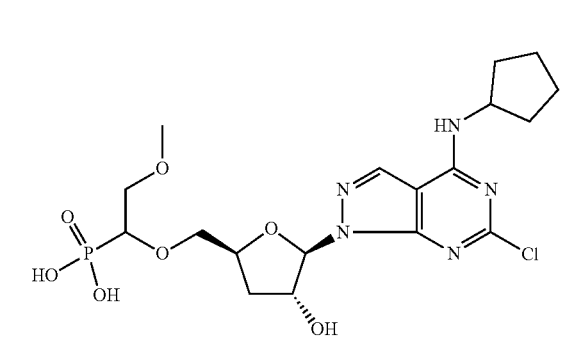
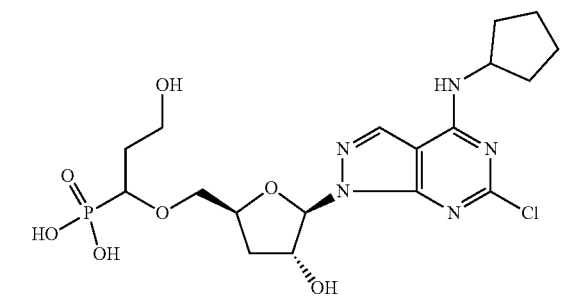

221
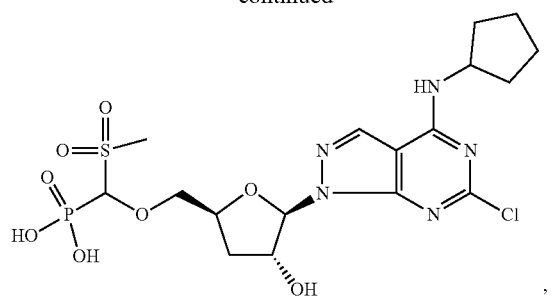
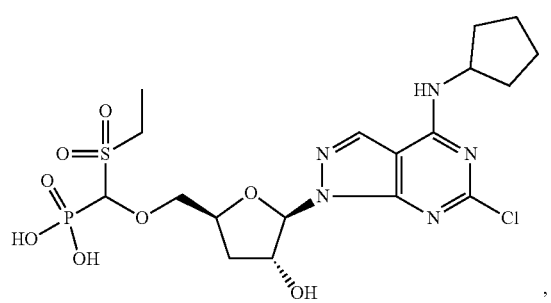
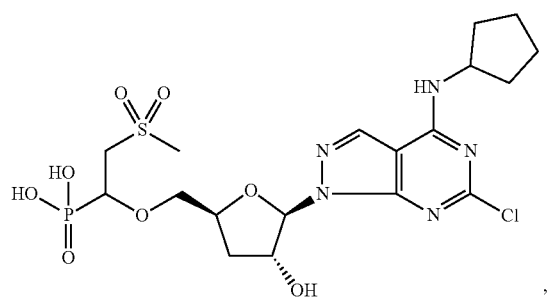
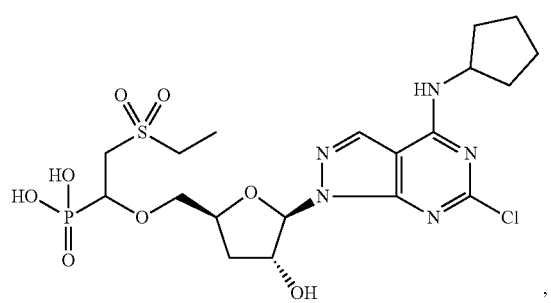
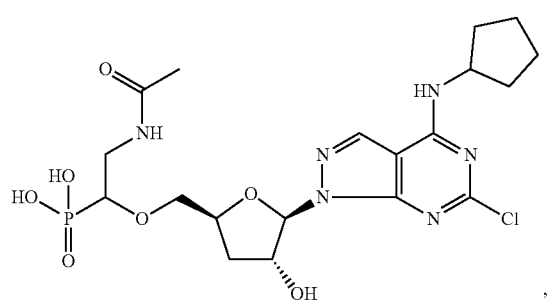
222
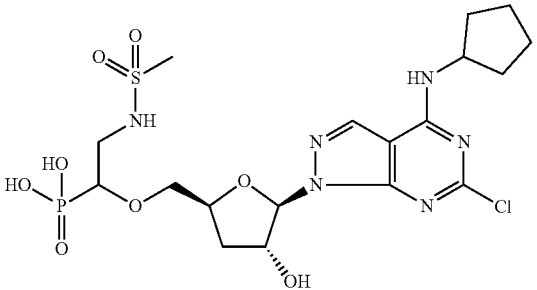
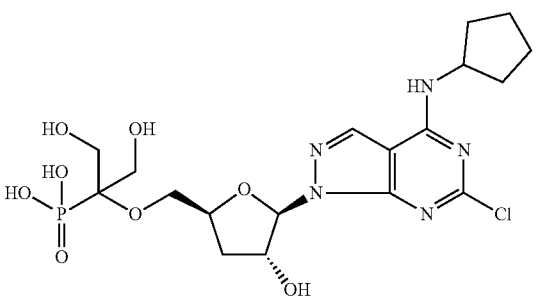
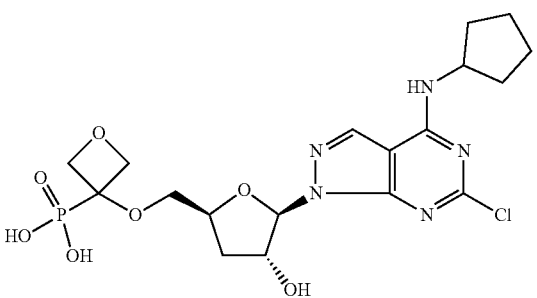

223
-continued
224
-continued
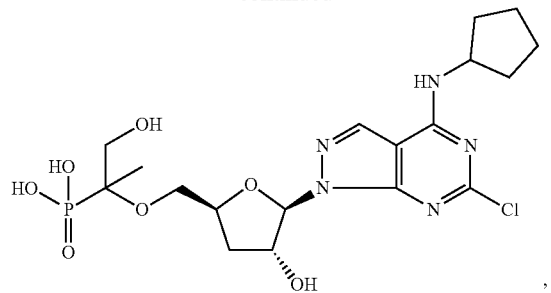
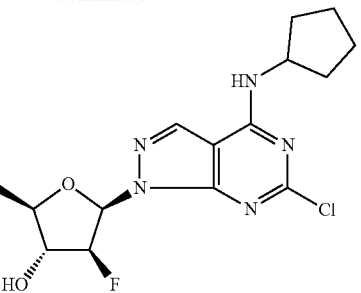
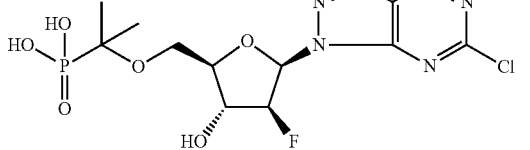
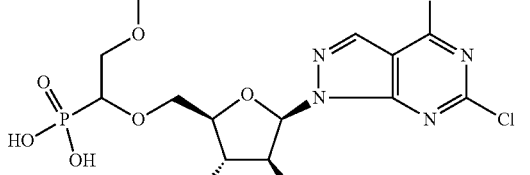
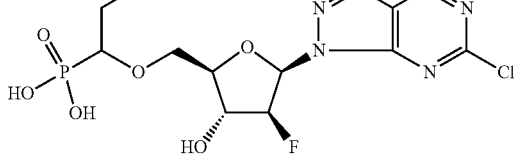
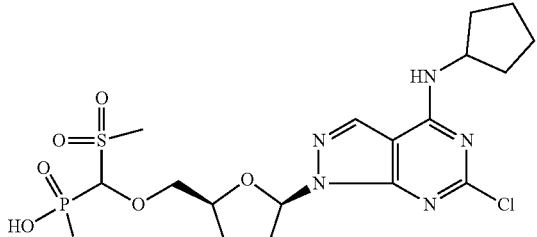
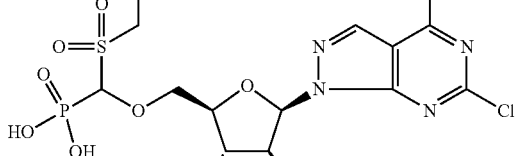

225
-continued
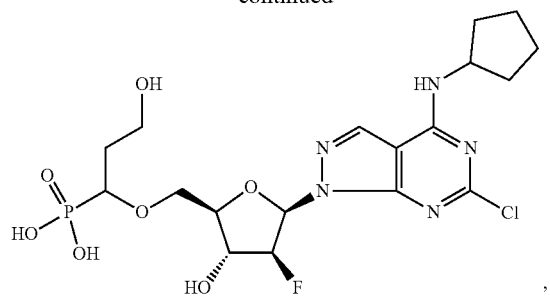
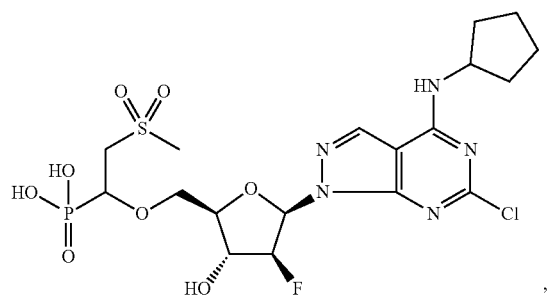
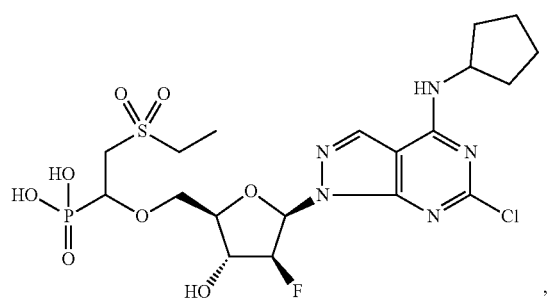
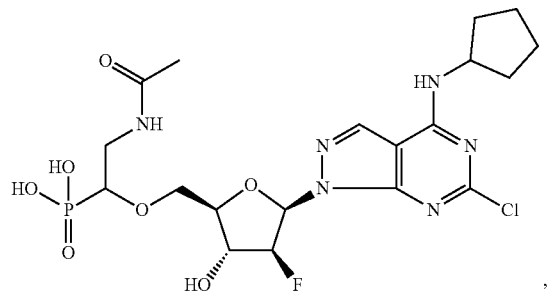
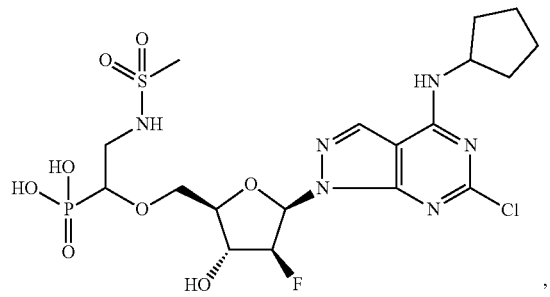
226
-continued
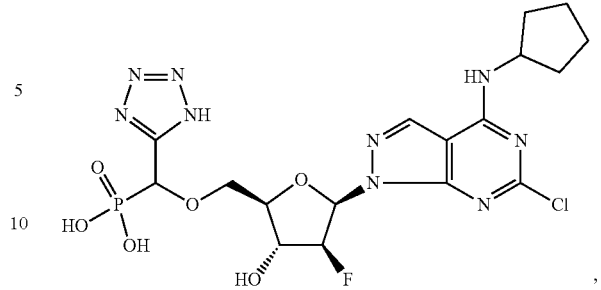
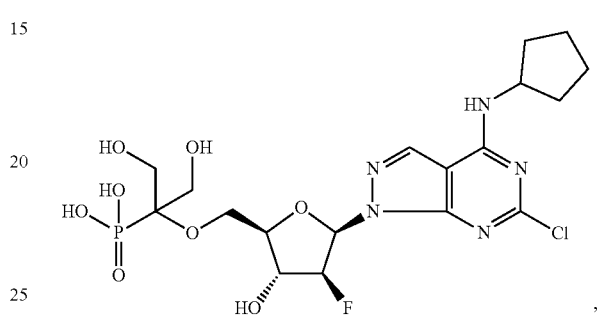
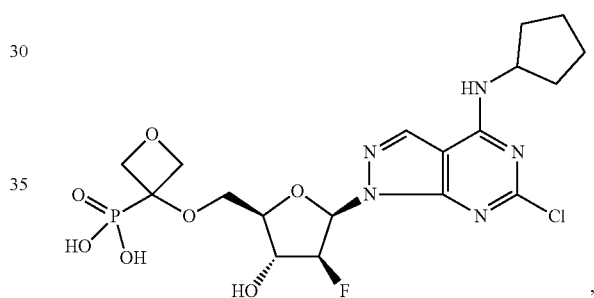
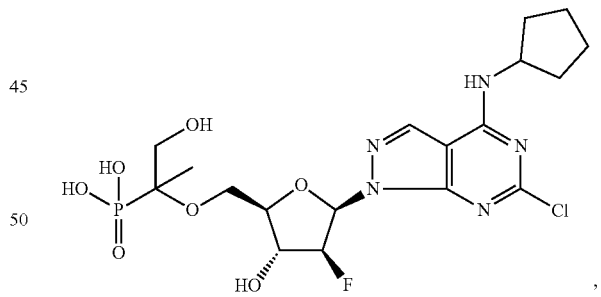
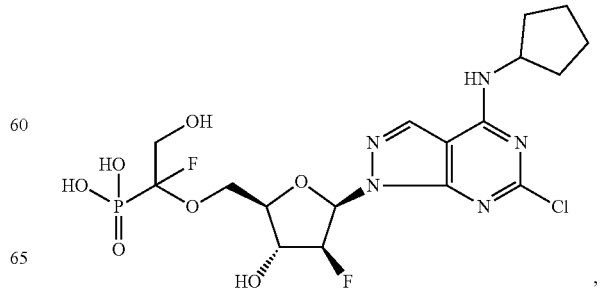

227
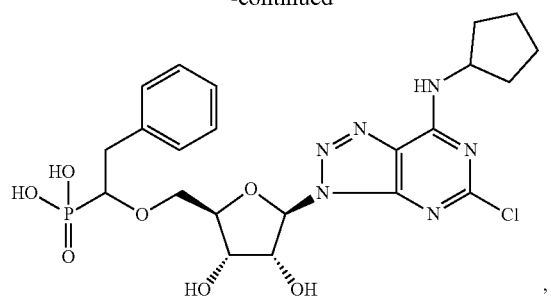
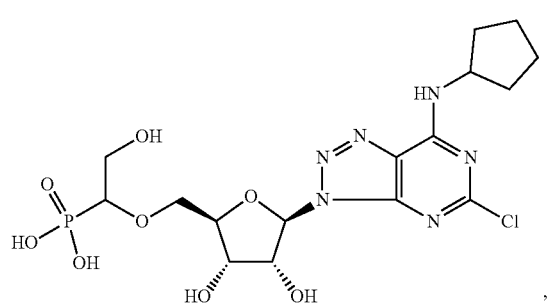
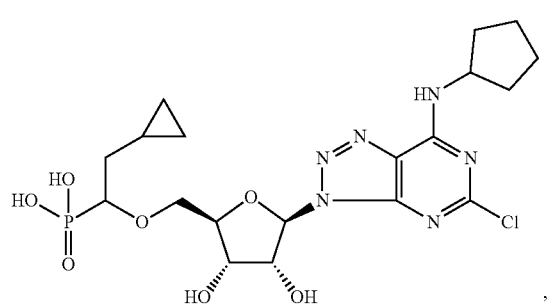
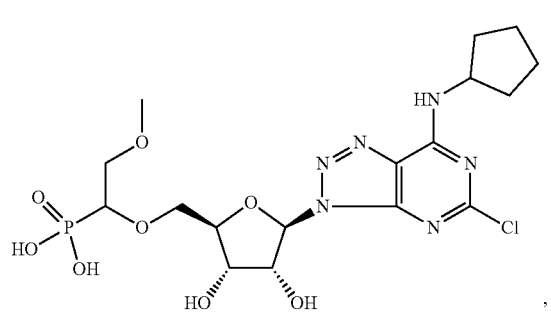
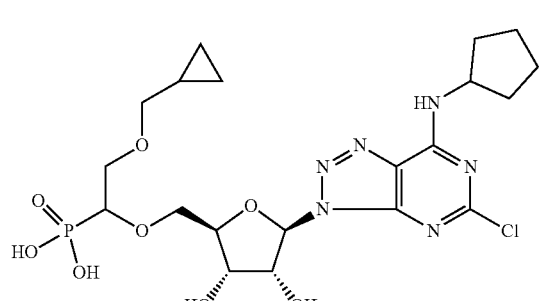
228
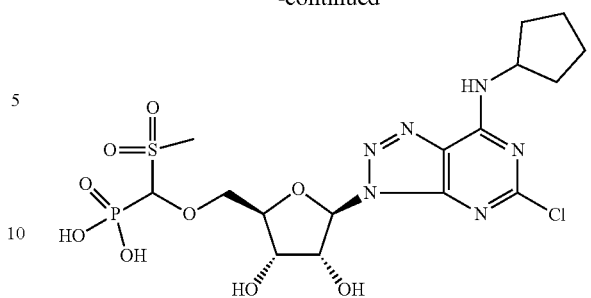
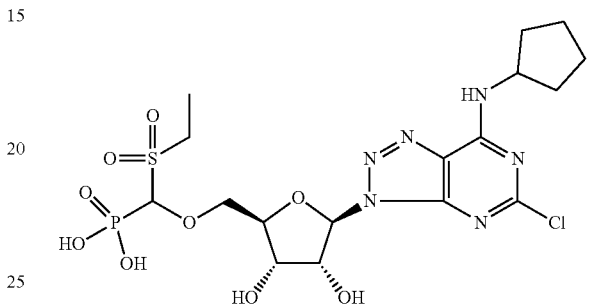
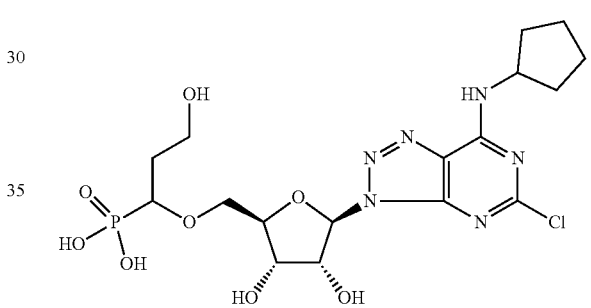
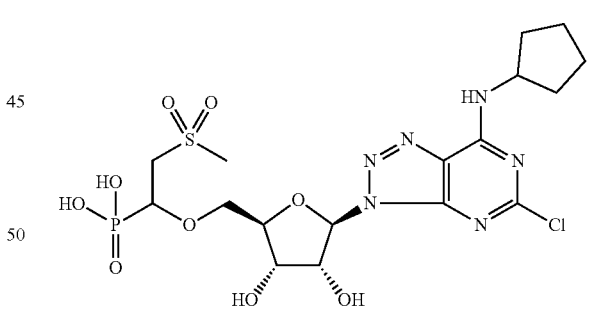
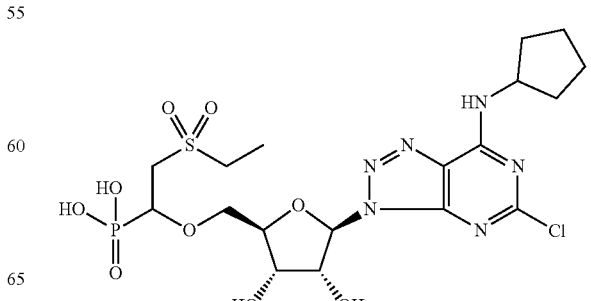

229
-continued
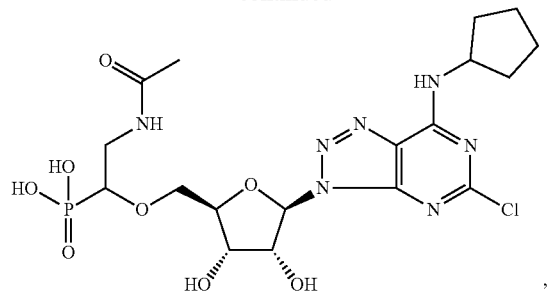
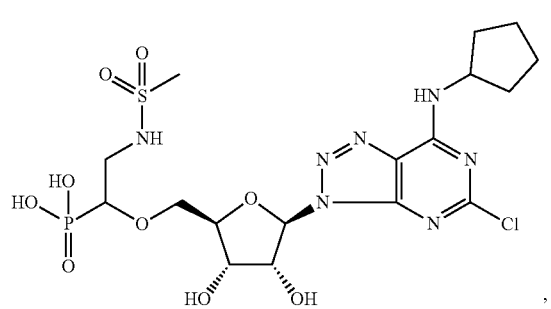
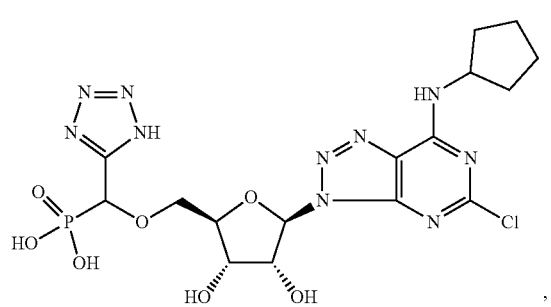
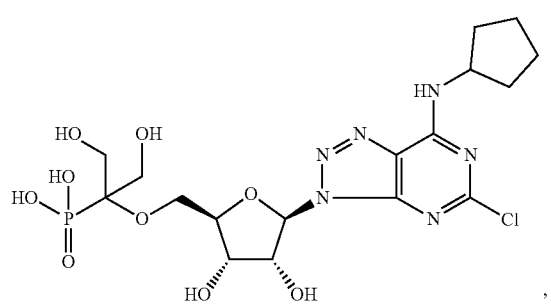
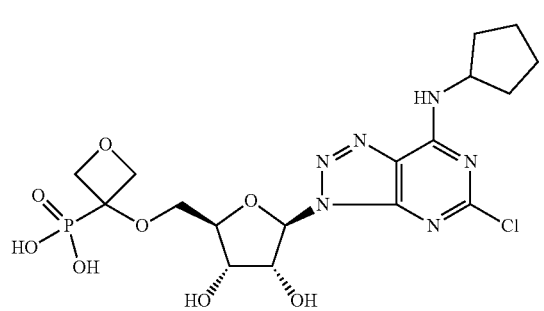
230
-continued
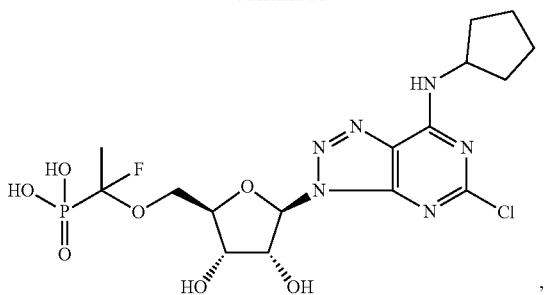
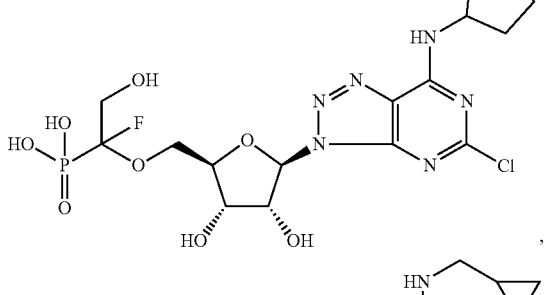
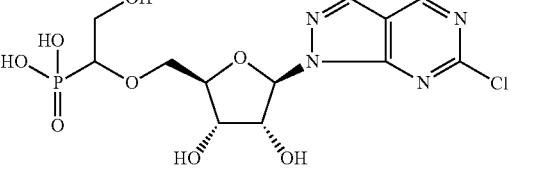
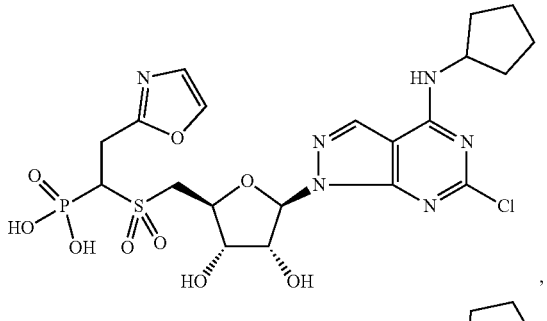
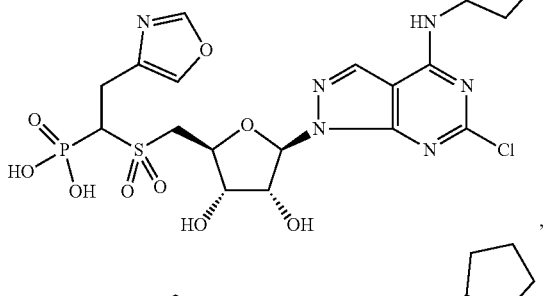
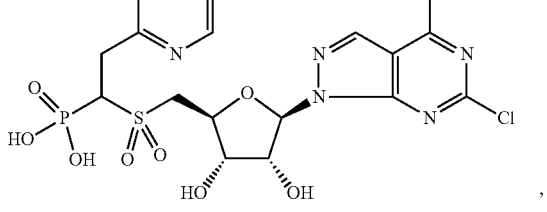

231
-continued
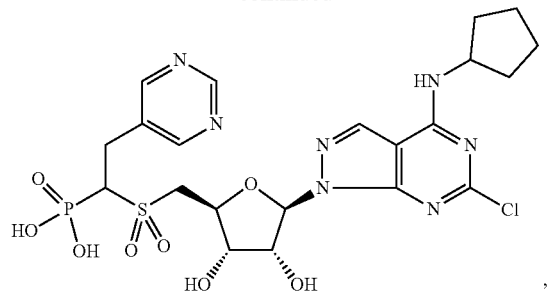
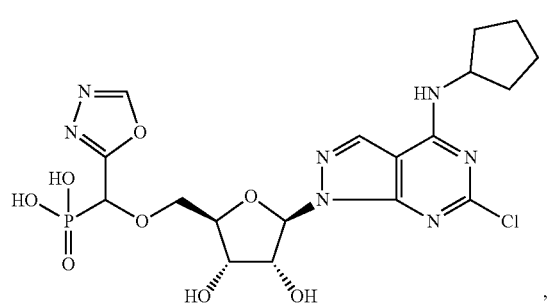
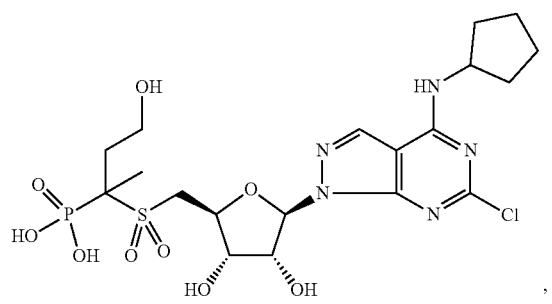
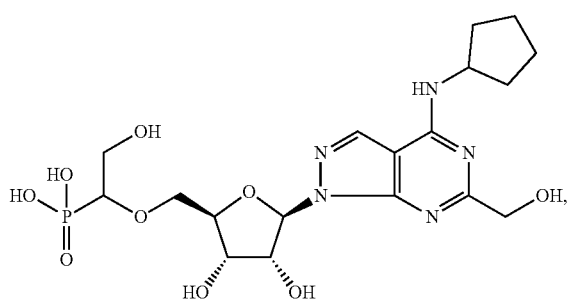
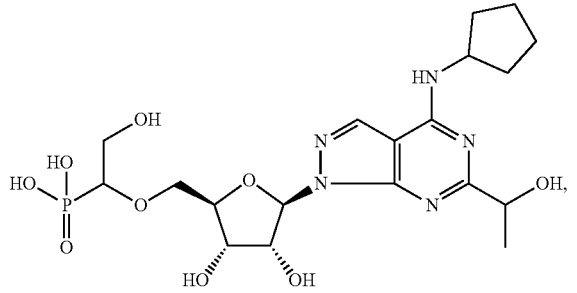
232
-continued
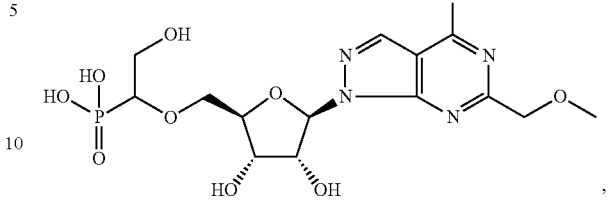
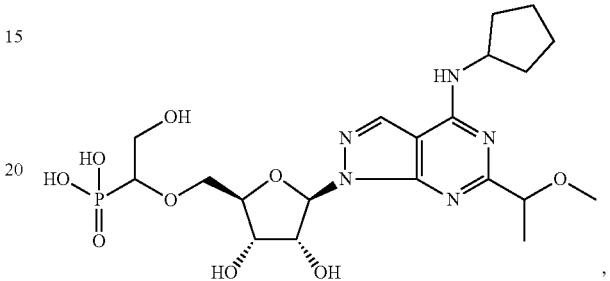
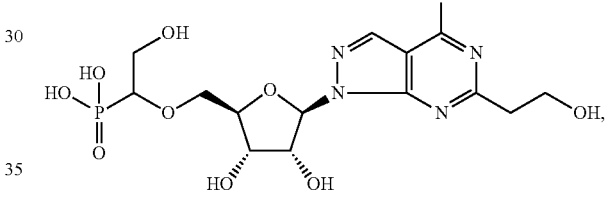
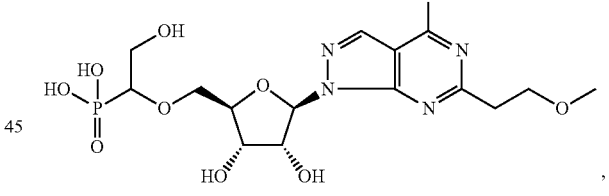
and
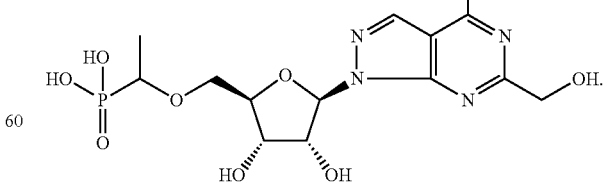
In some embodiments is a compound, or a pharmaceutically acceptable salt, solvate, stereoisomer, or isotopic variant thereof, having a structure selected from:

233
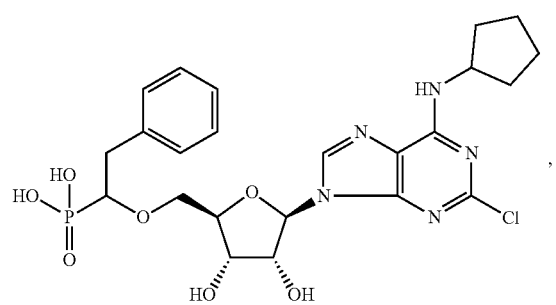
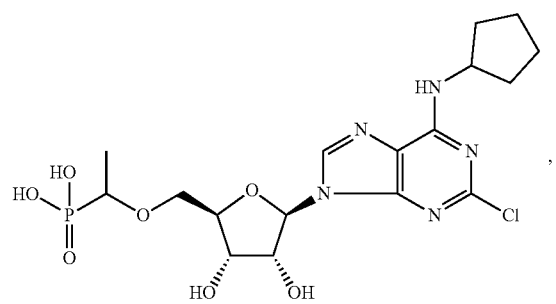
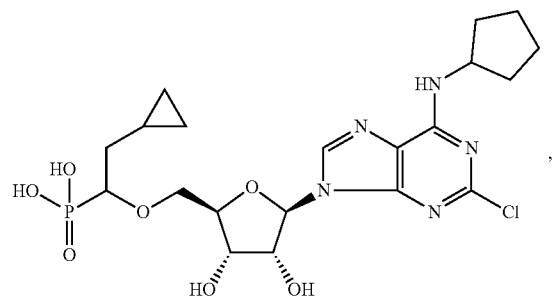
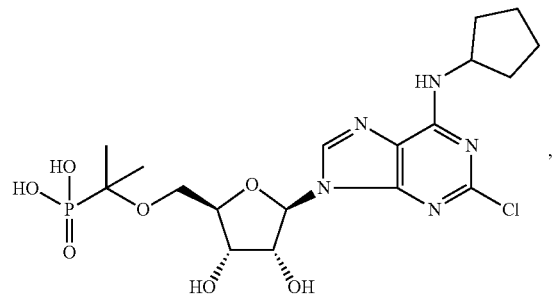
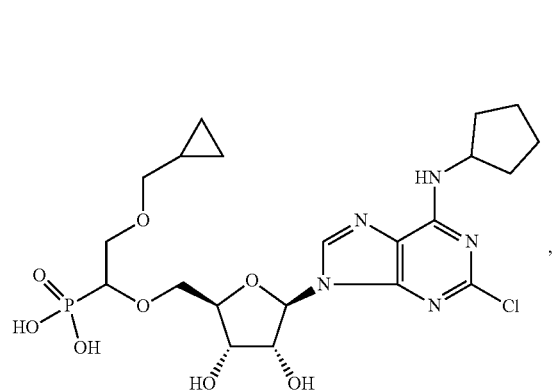
234
-continued
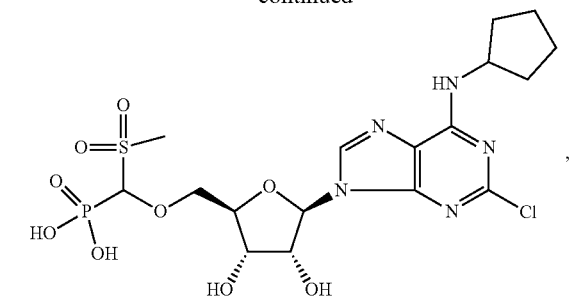
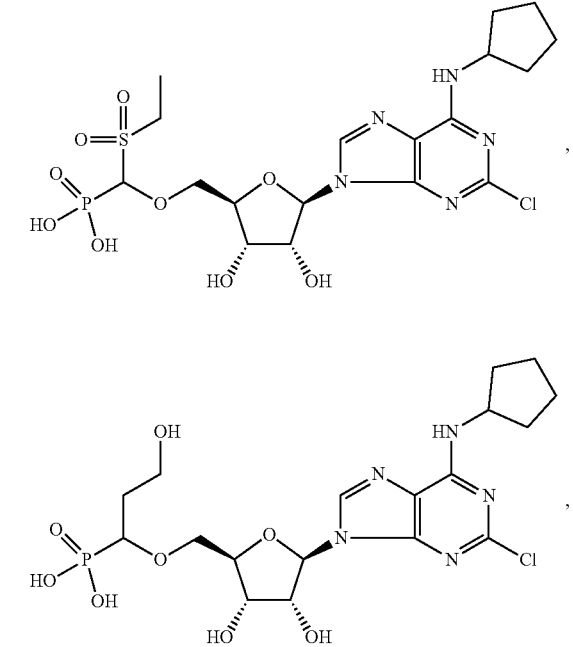
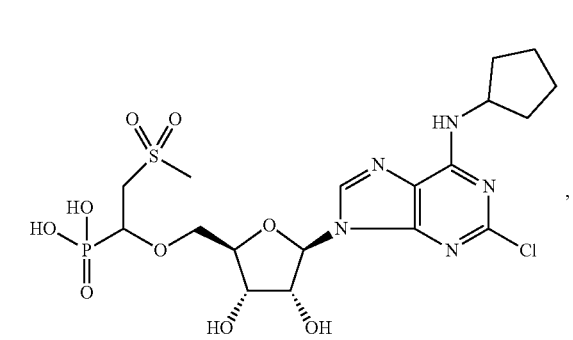
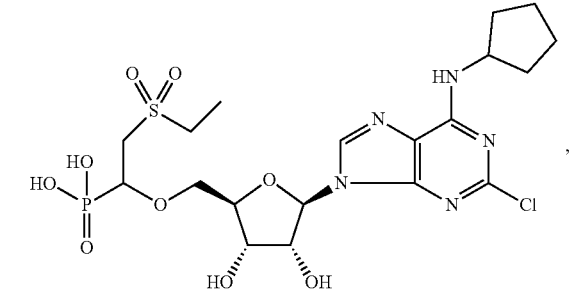

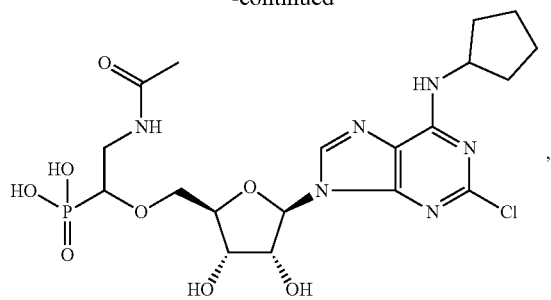
,
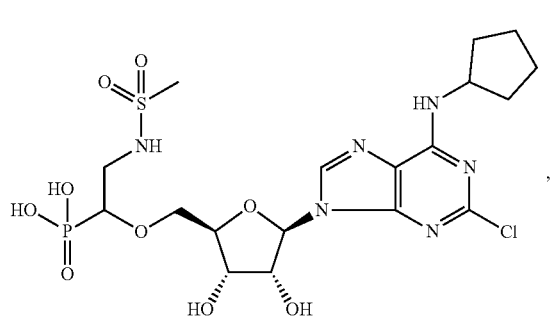
,
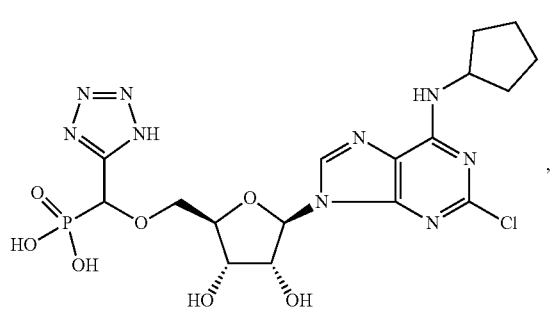
,
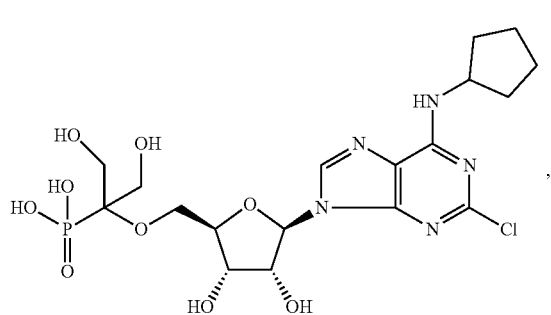
,
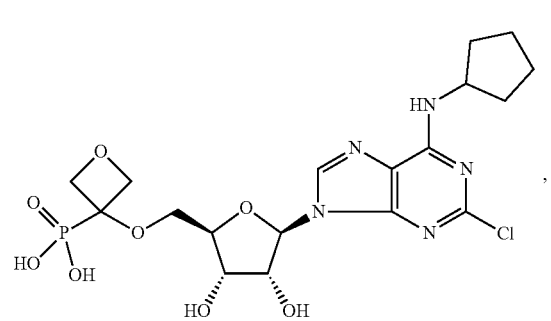
,
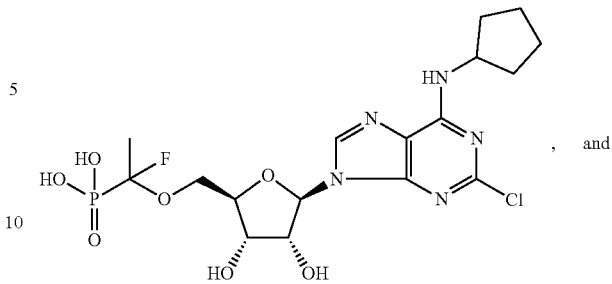
, and
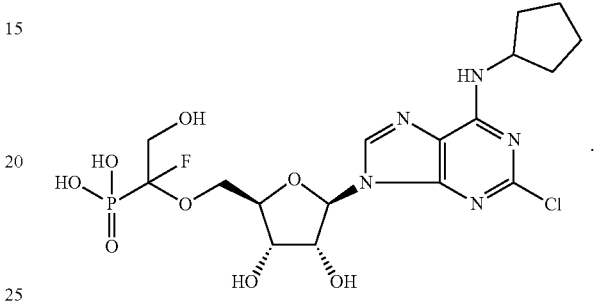
.
In some embodiments is a compound, or a pharmaceutically acceptable salt, solvate, stereoisomer, or isotopic variant thereof, having a structure selected from:
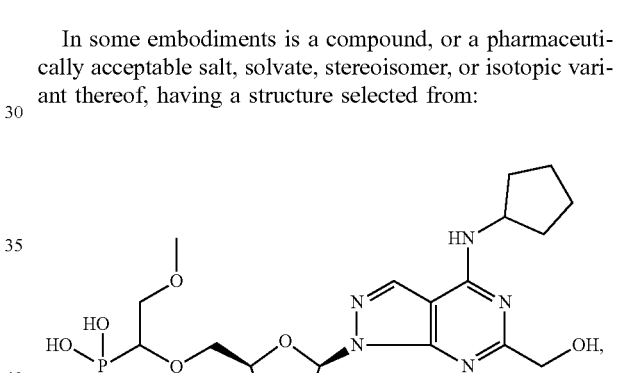
,
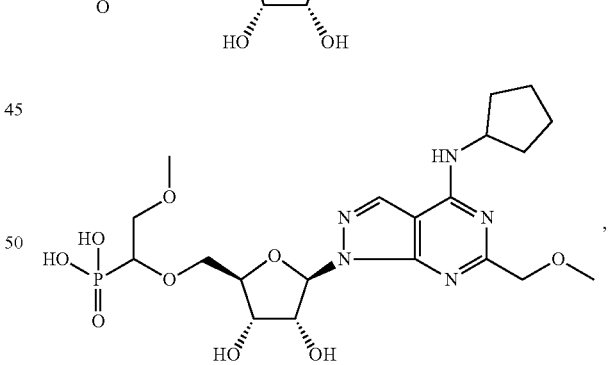
,
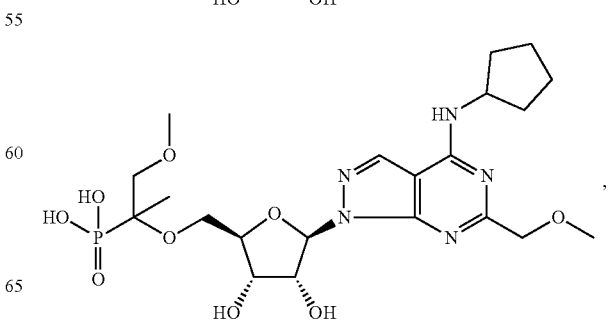
, 237
-continued
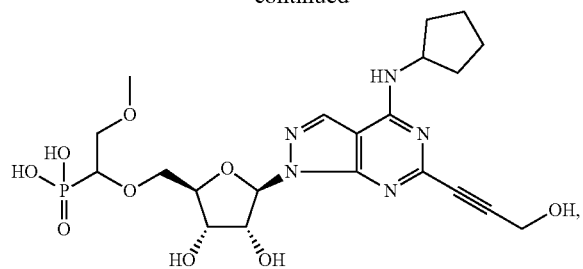
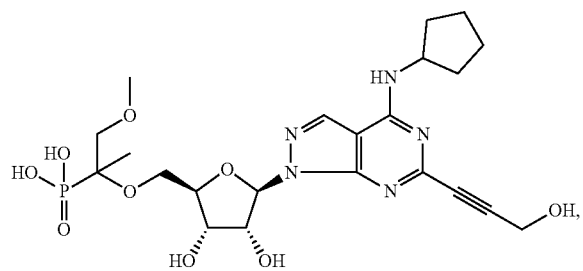
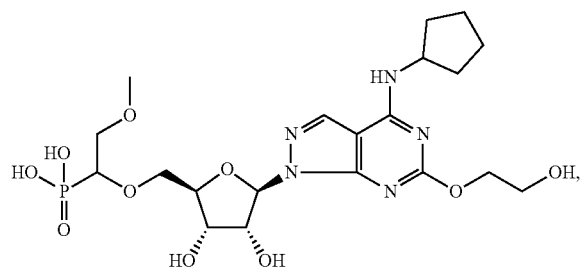
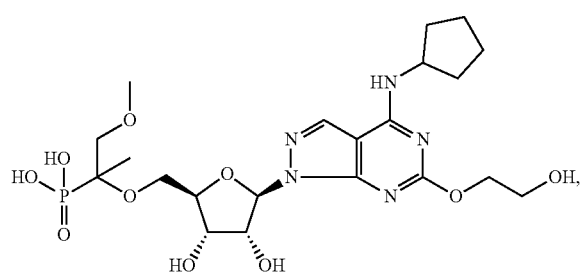
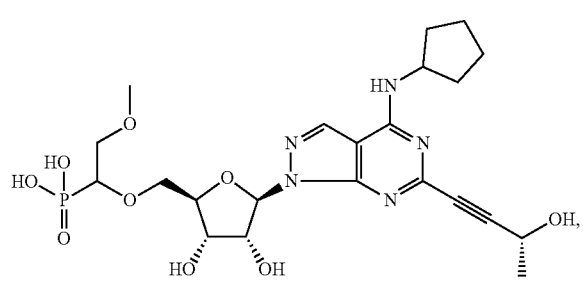
238
-continued
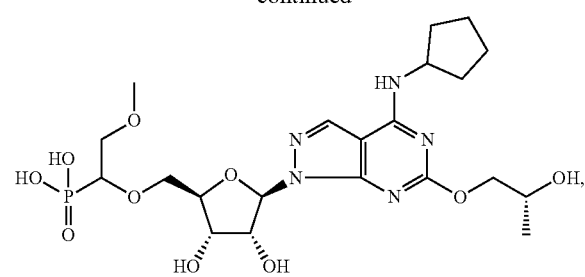
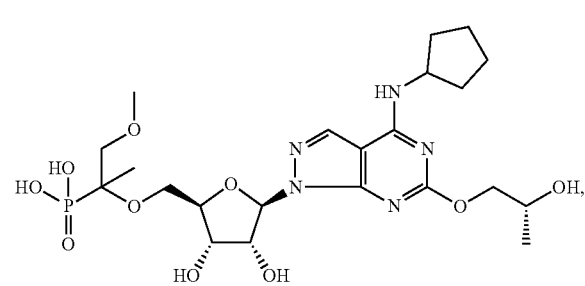
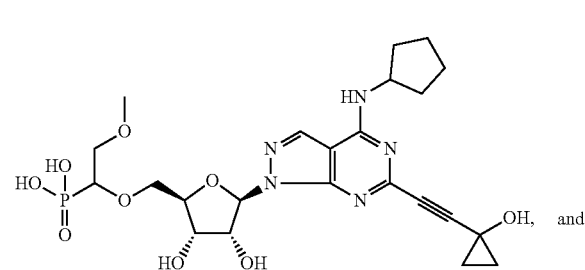
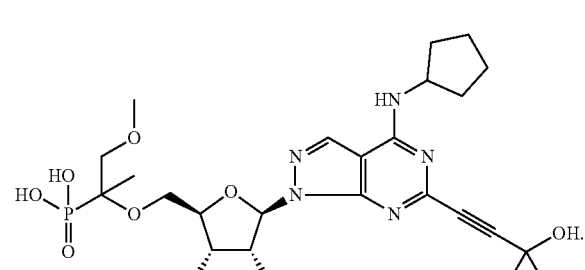
In some embodiments is a compound, or a pharmaceutically acceptable salt, solvate, stereoisomer, or isotopic variant thereof, having a structure selected from:
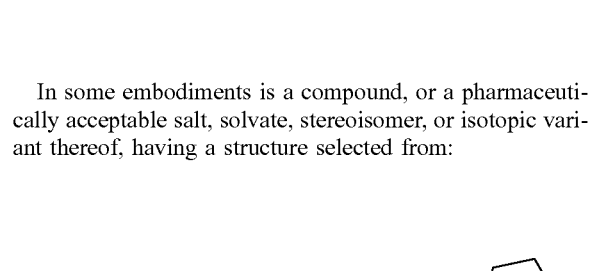

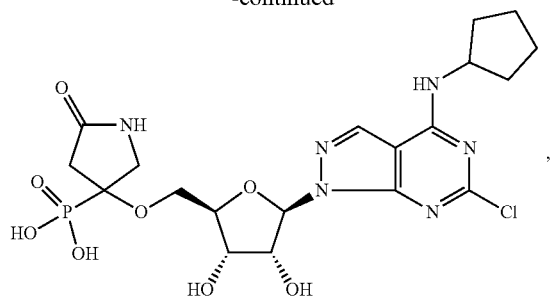
,
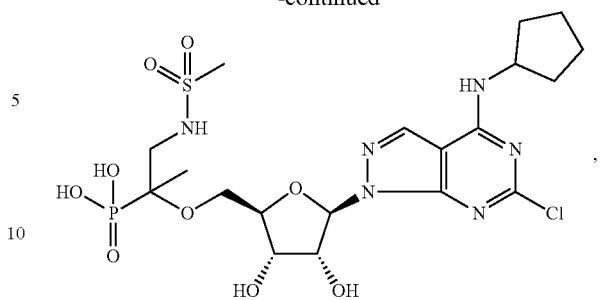
,
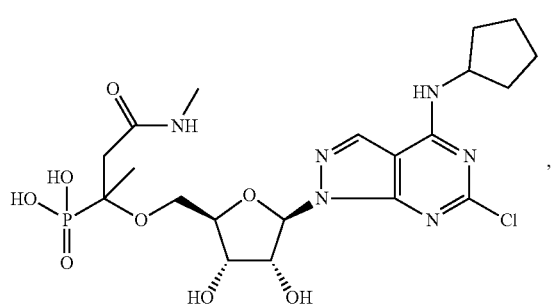
,
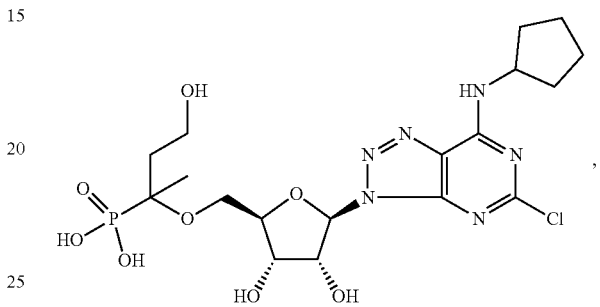
,
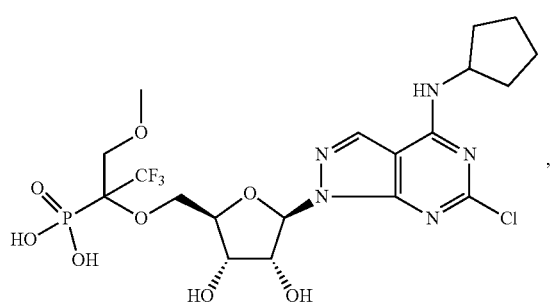
,
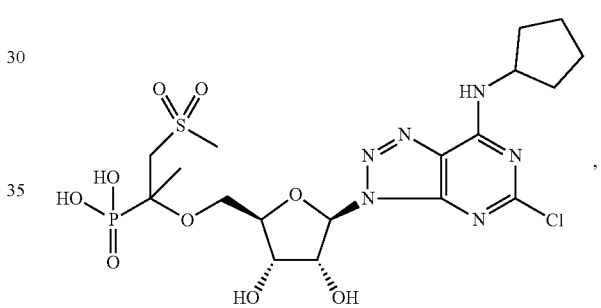
,
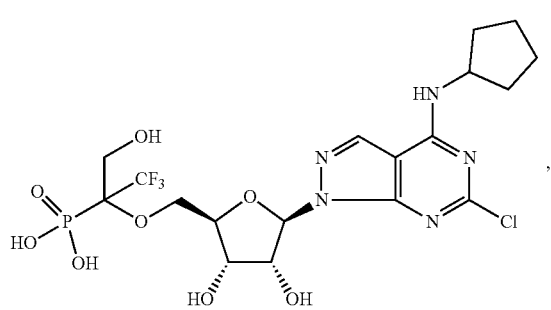
,
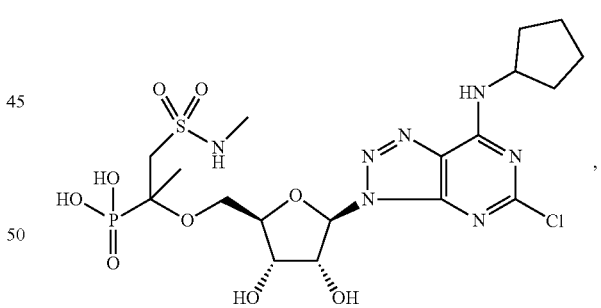
,
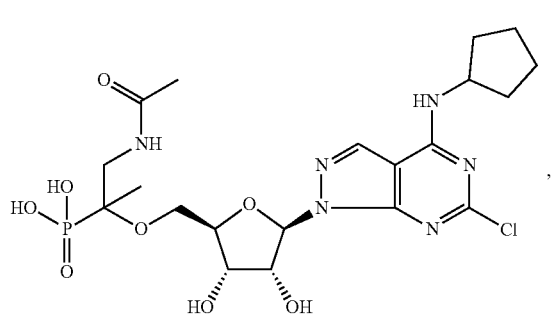
,
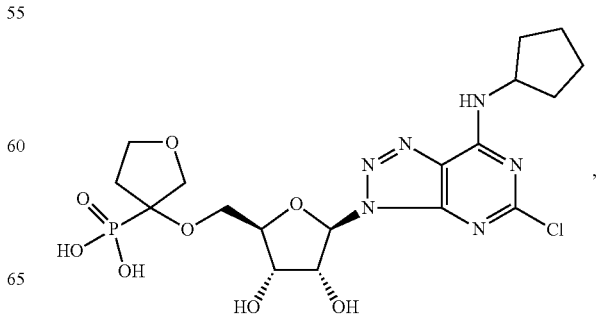
, 241
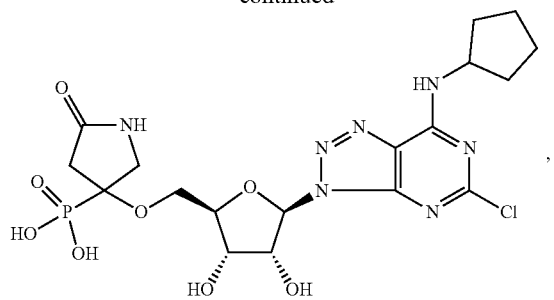
,
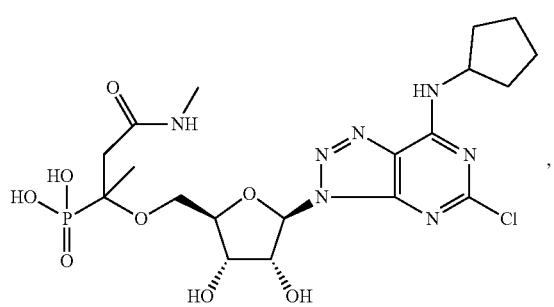
,
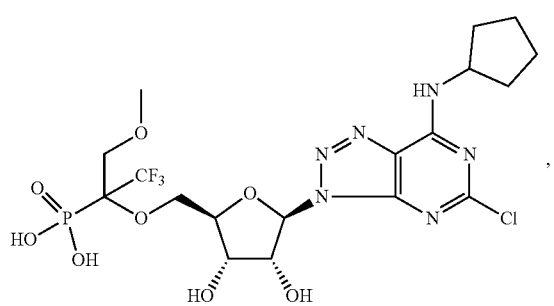
,
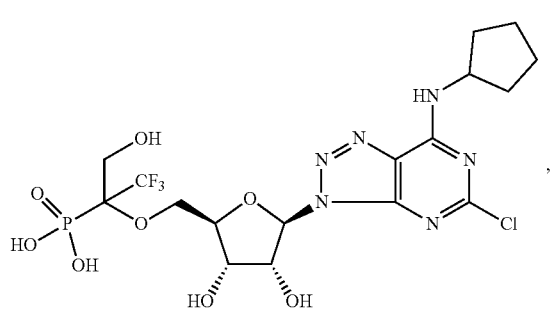
,
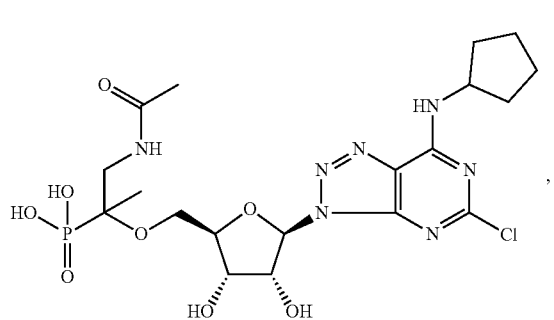
,
242
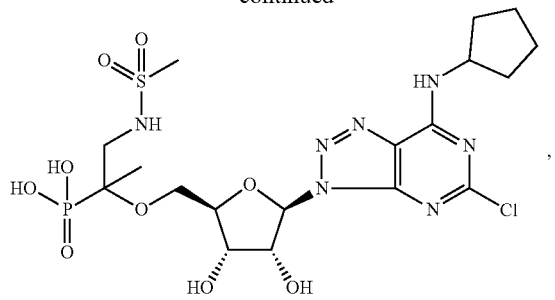
,
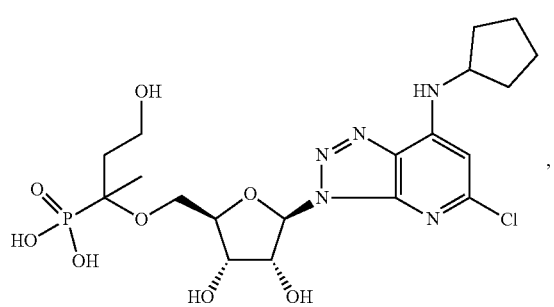
,
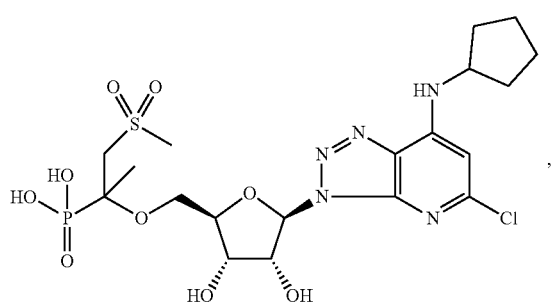
,
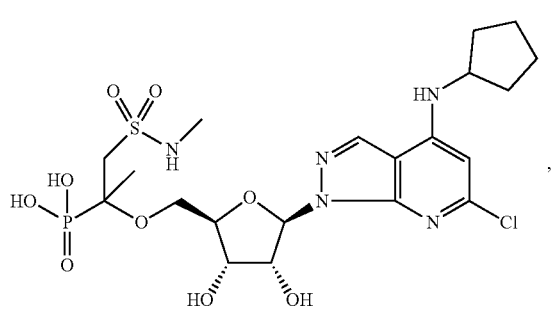
,
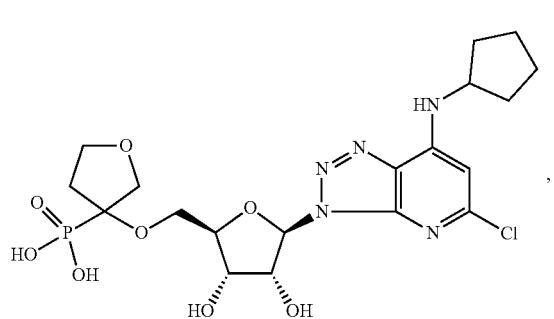
, 243
-continued
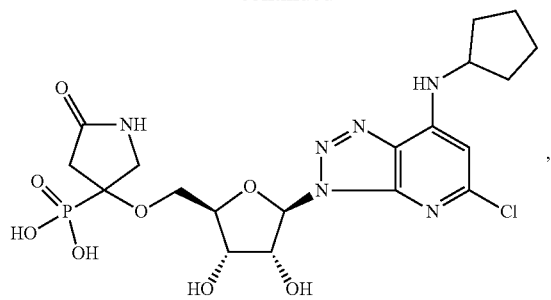
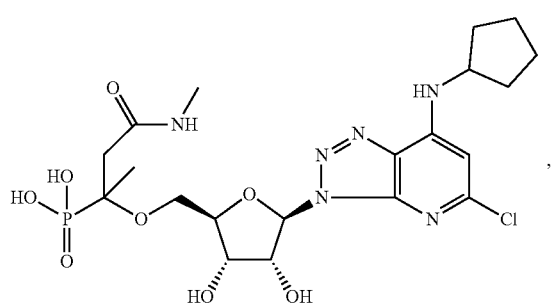
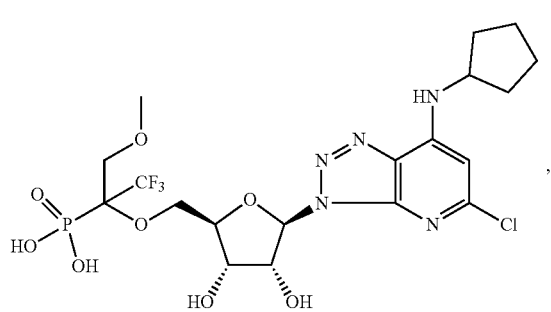
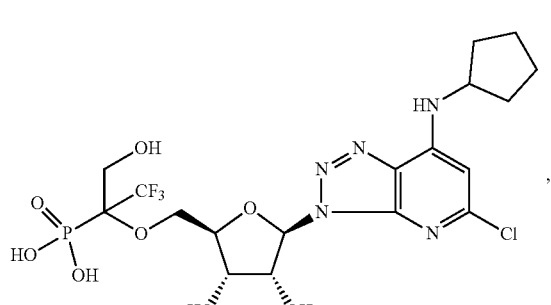
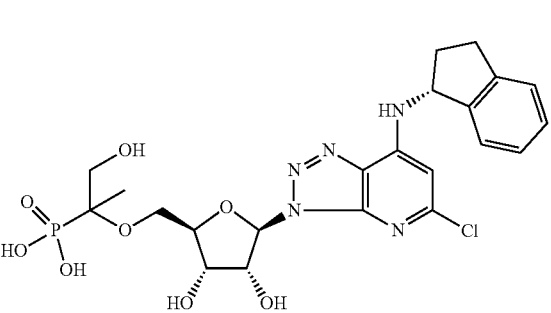
244
-continued
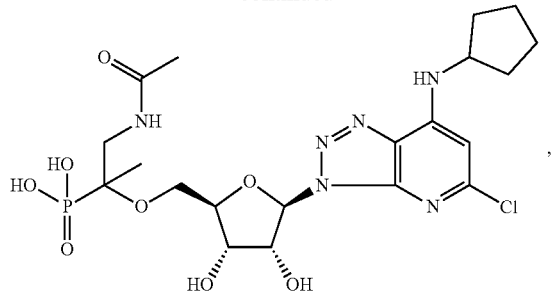
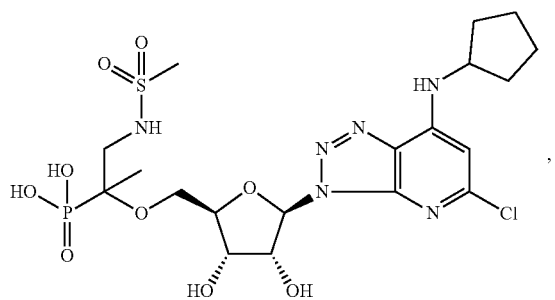
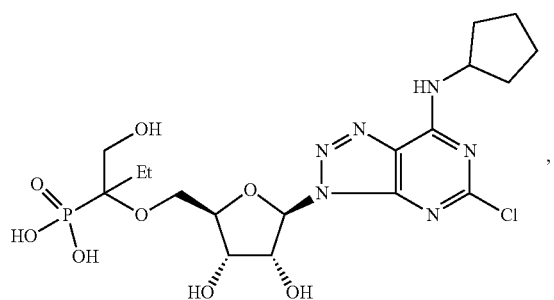
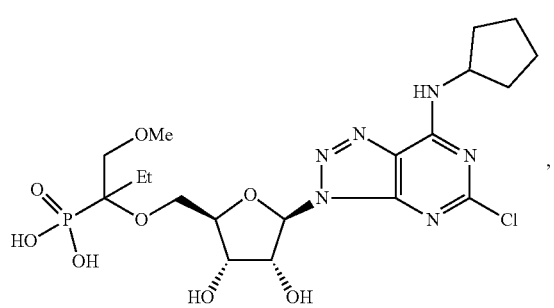
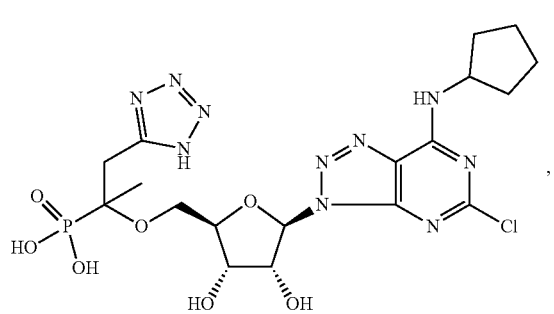

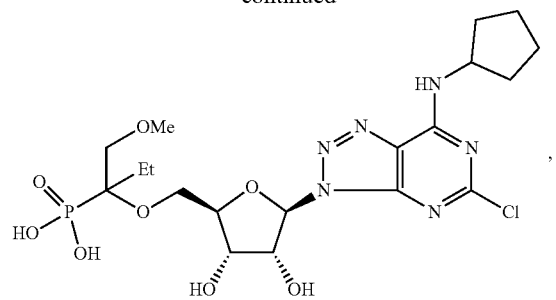
,
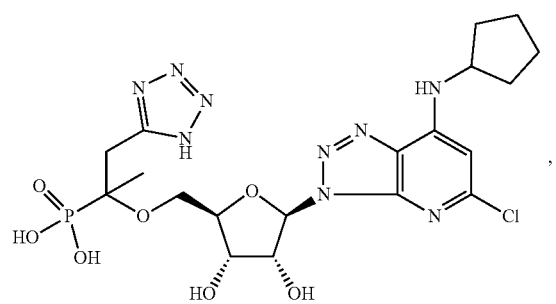
,
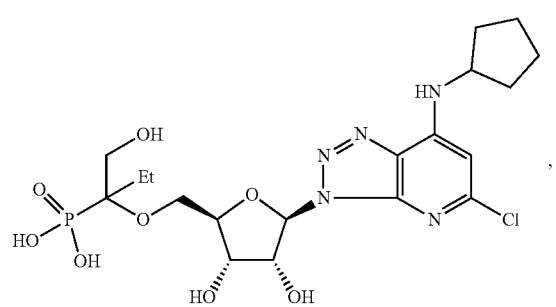
,
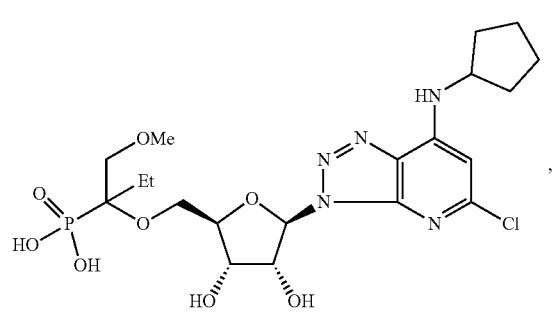
,
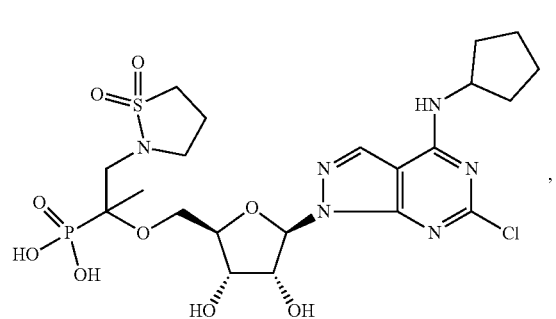
,
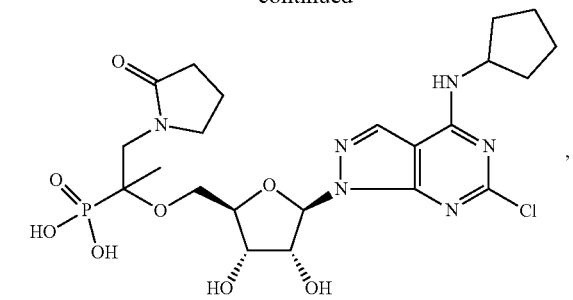
,
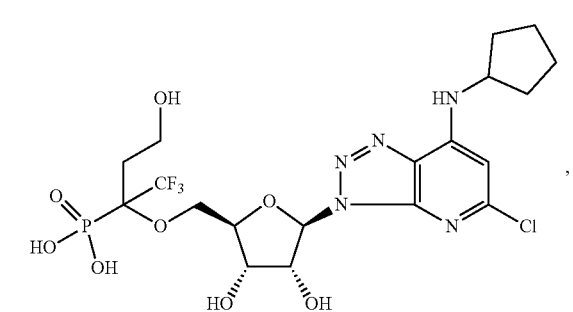
,
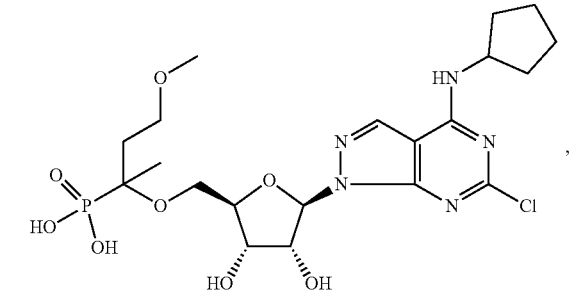
,
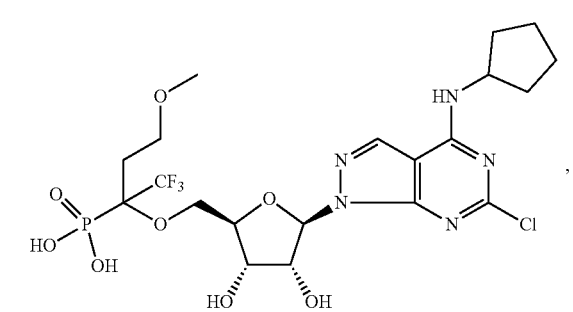
,
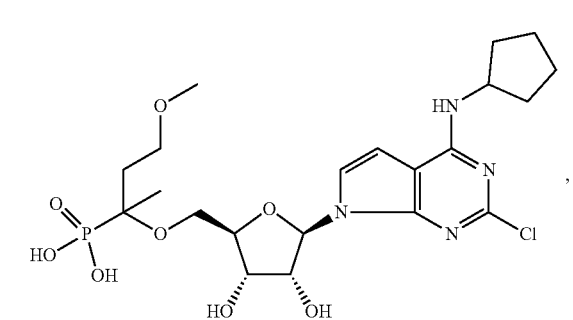
, 247
-continued
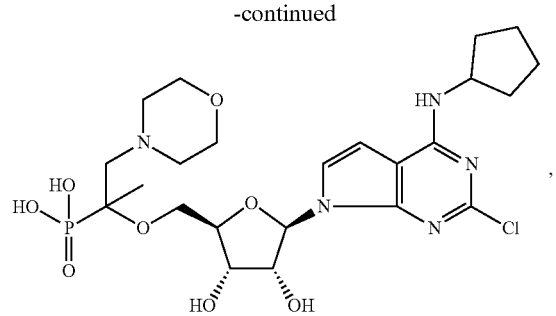
,
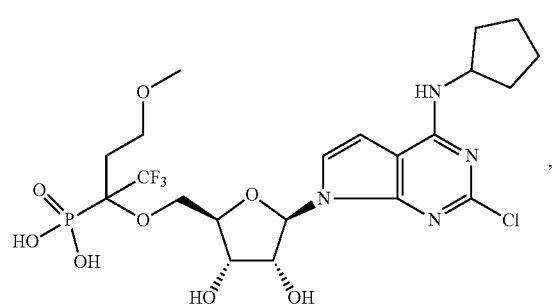
,
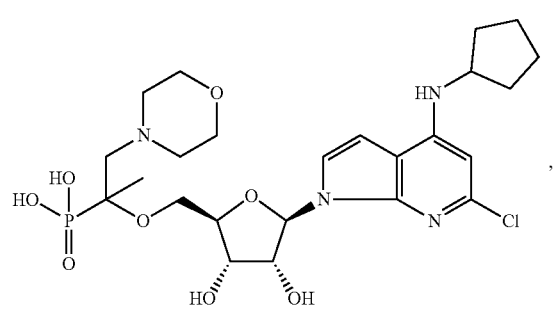
,
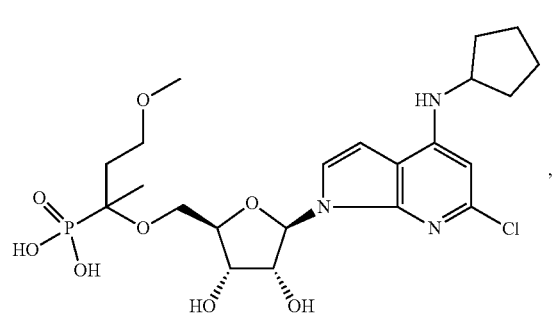
,
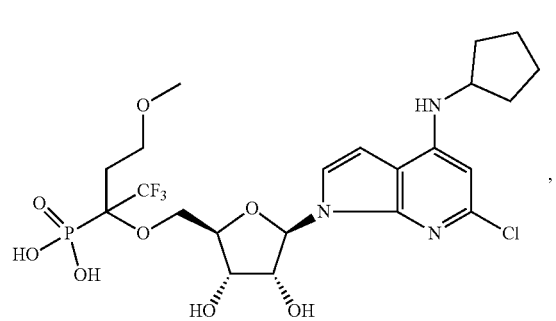
,
248
-continued
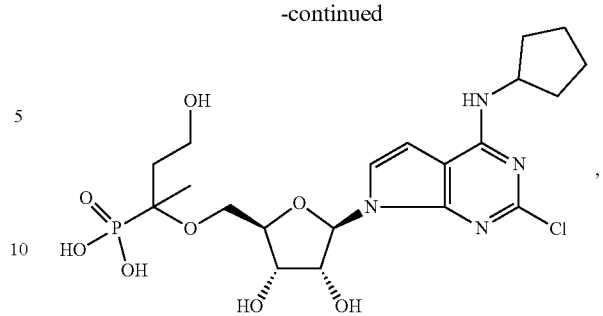
,
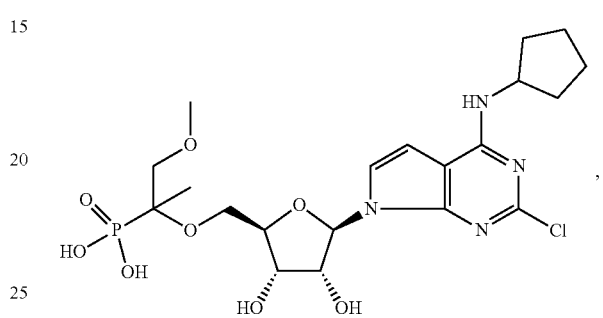
,
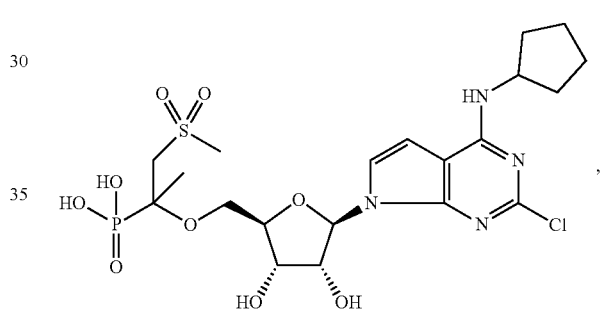
,
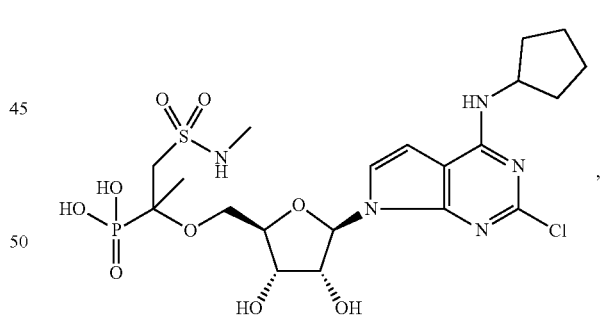
,
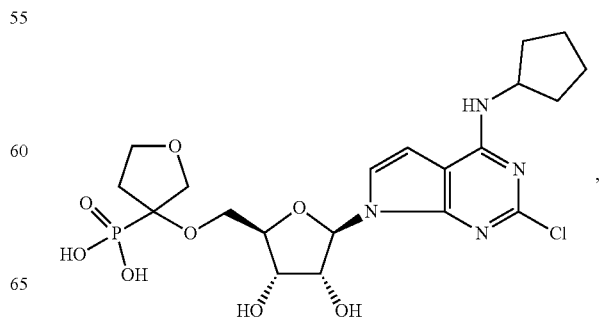
, 249
-continued
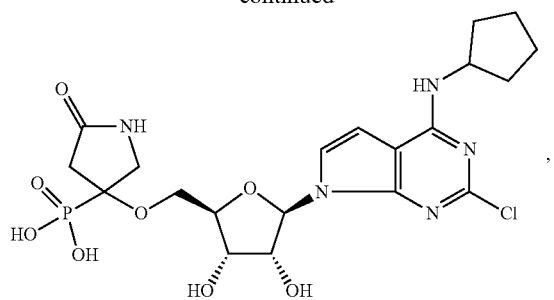
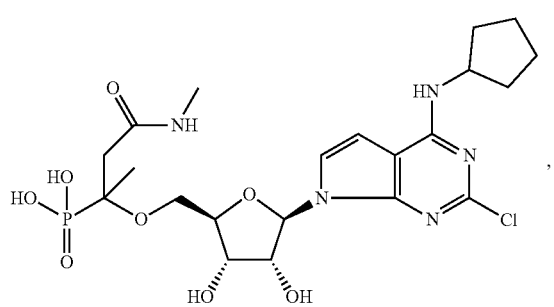
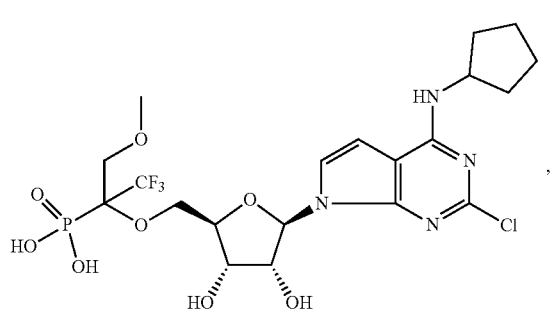
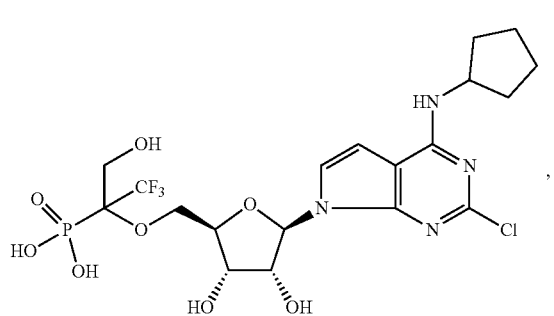
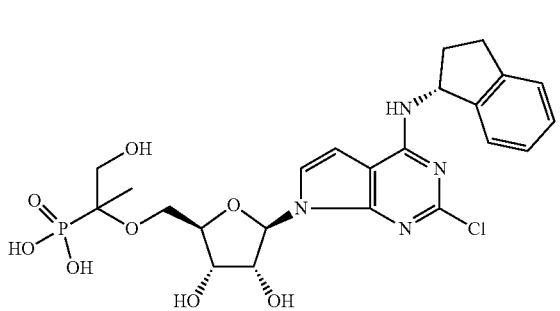
250
-continued
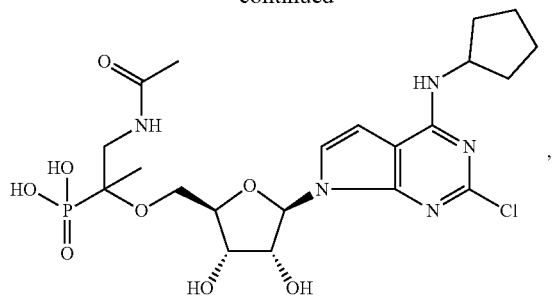
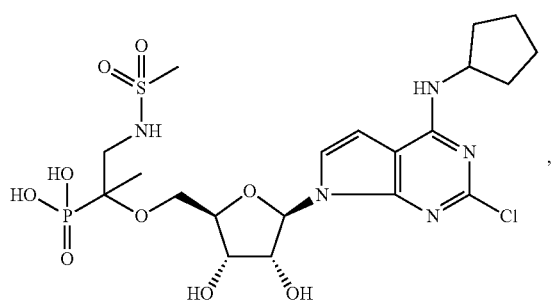
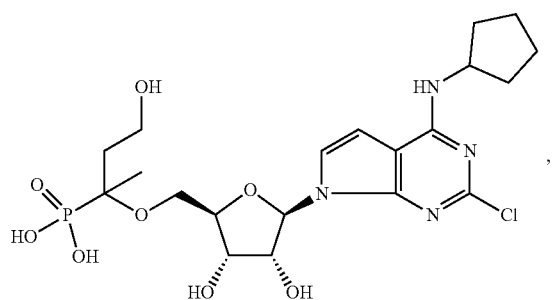
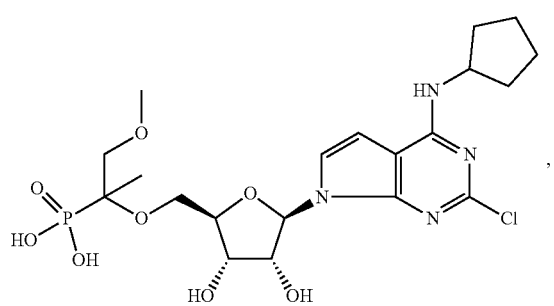
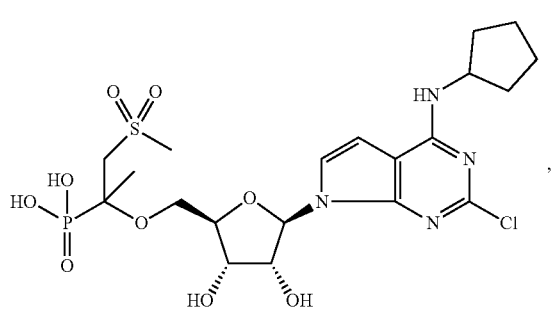

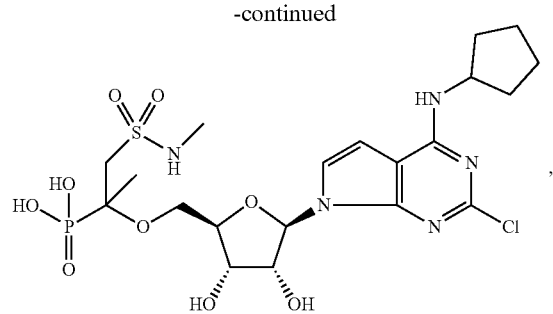
,
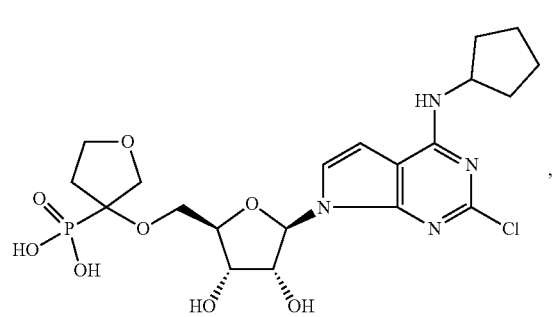
,
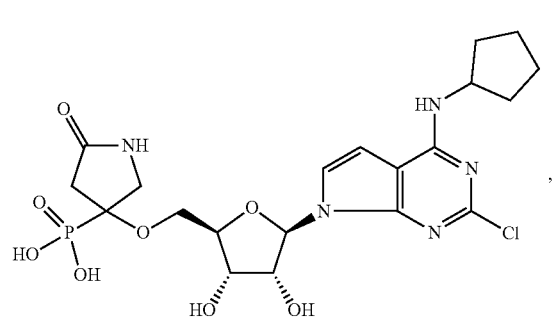
,
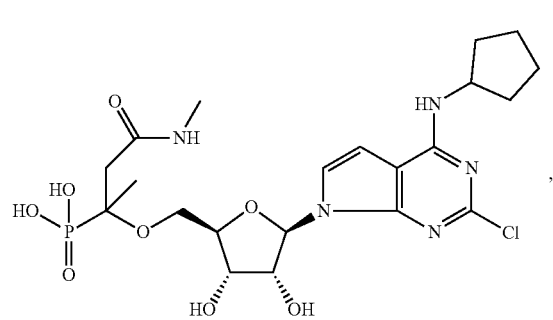
,
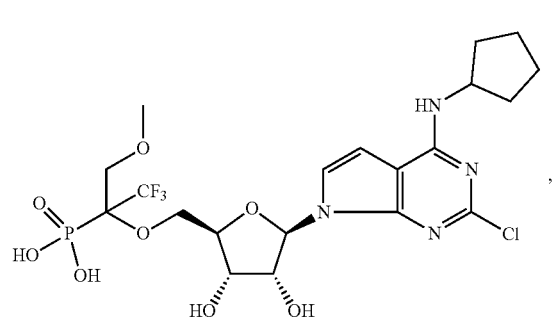
,
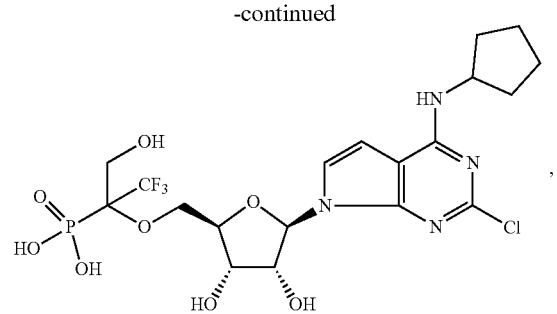
,
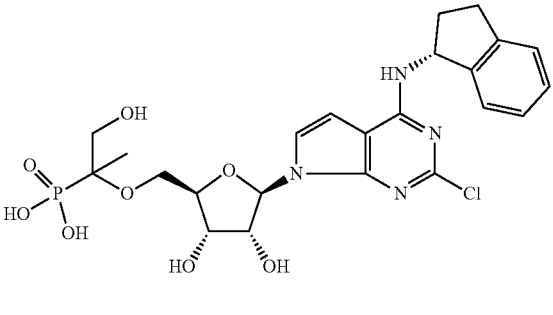
,
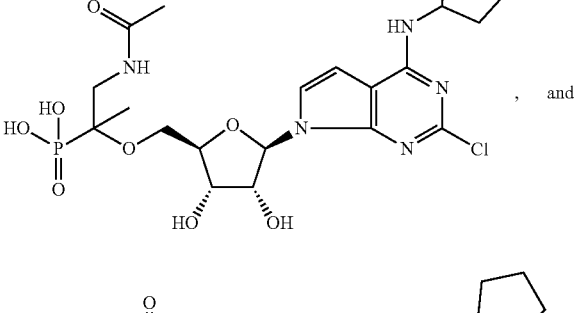
, and
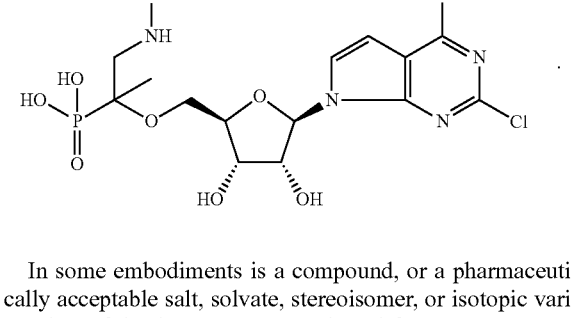
.
In some embodiments is a compound, or a pharmaceutically acceptable salt, solvate, stereoisomer, or isotopic variant thereof, having a structure selected from:
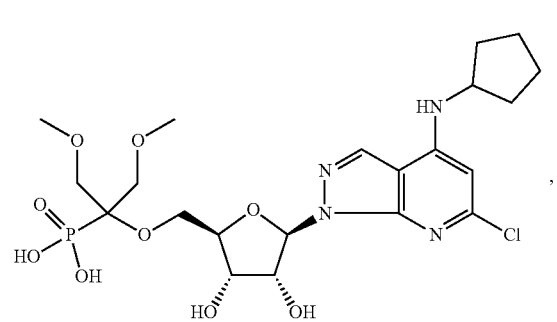
,

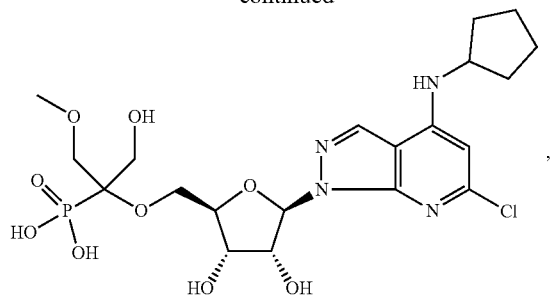
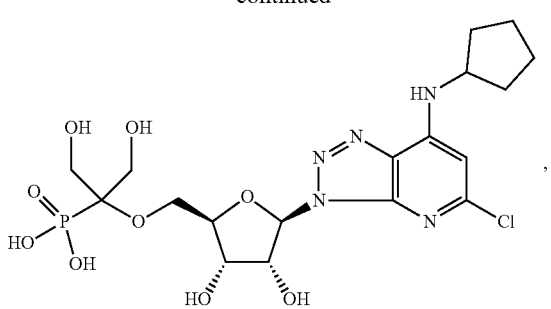
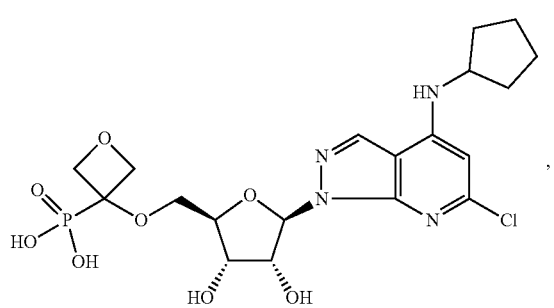
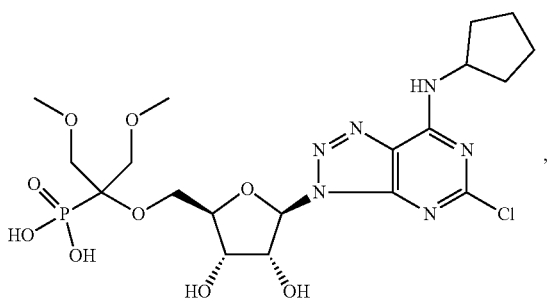
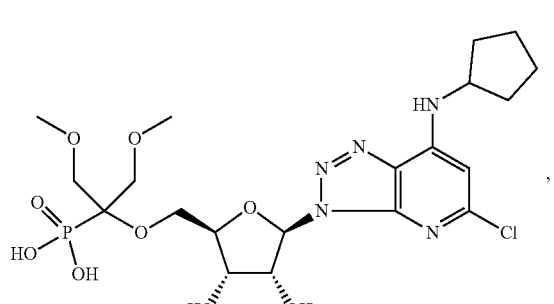
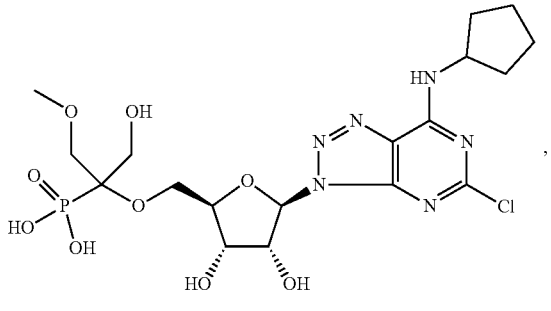
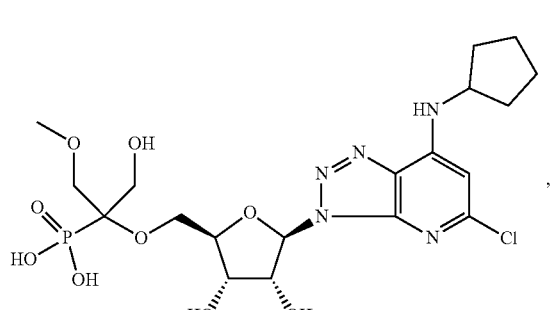
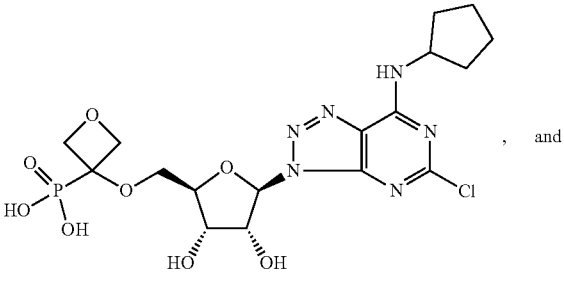, and
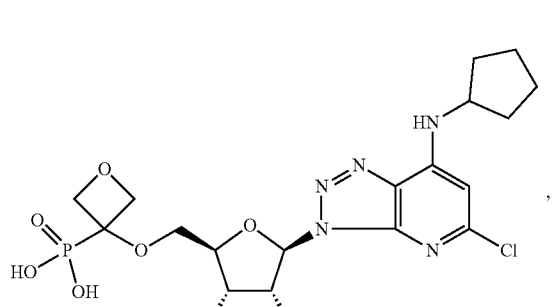
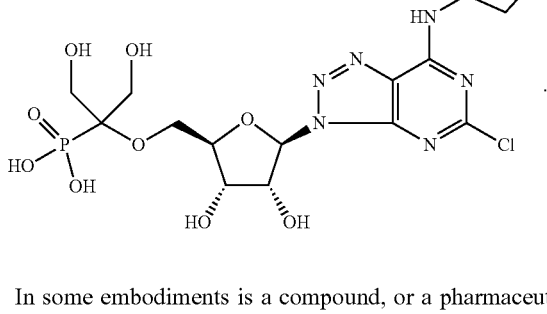
In some embodiments is a compound, or a pharmaceutically acceptable salt, solvate, stereoisomer, or isotopic variant thereof, having a structure selected from:

255
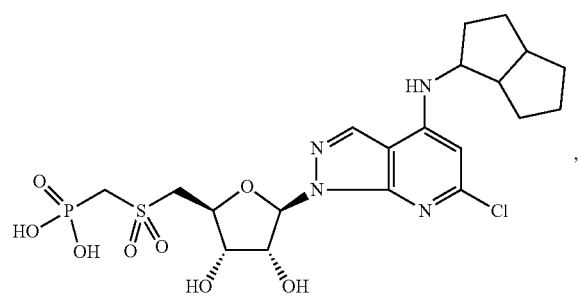
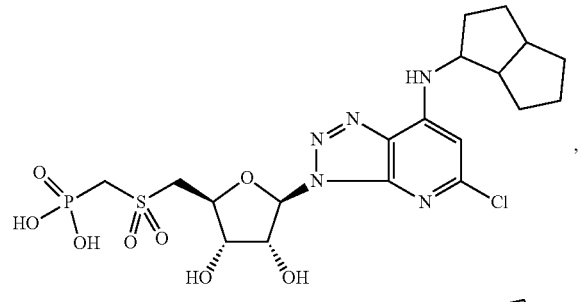
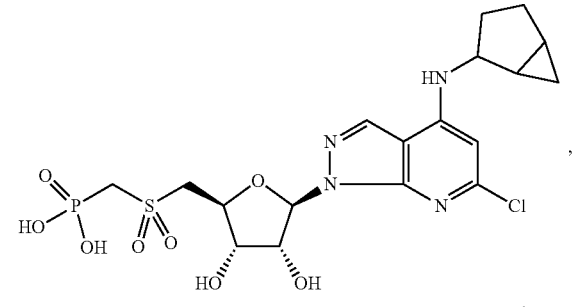
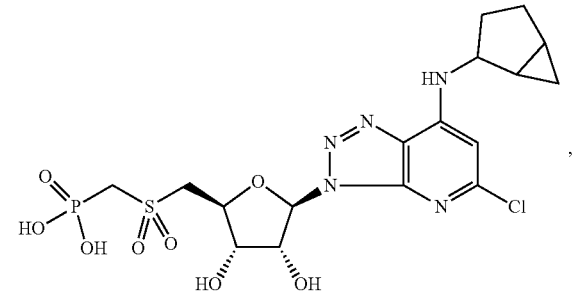
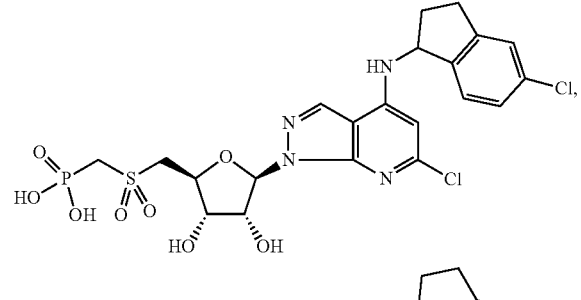
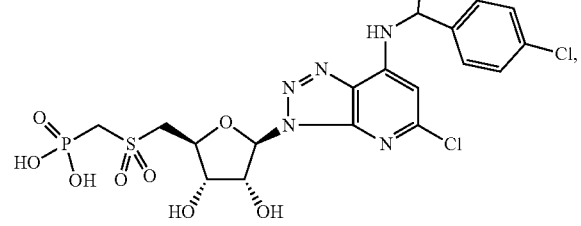
256
-continued
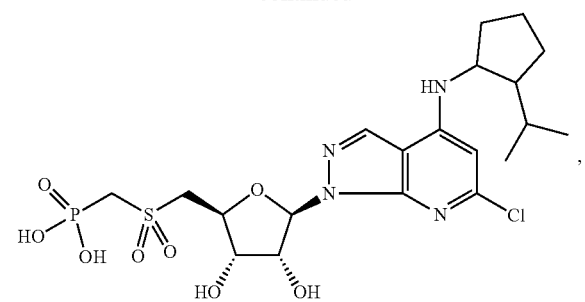
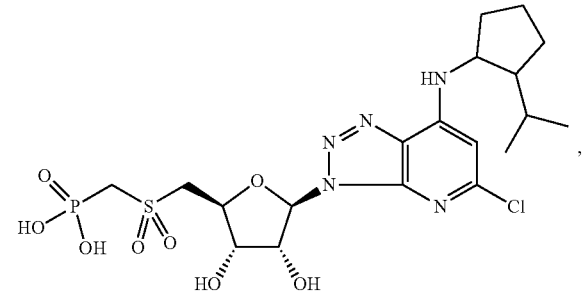
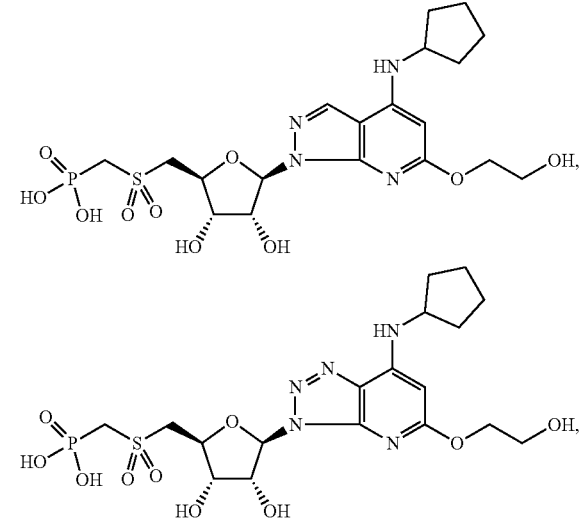
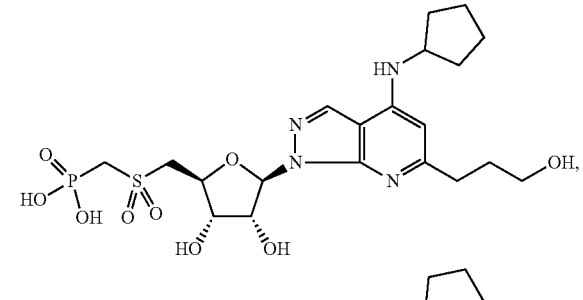
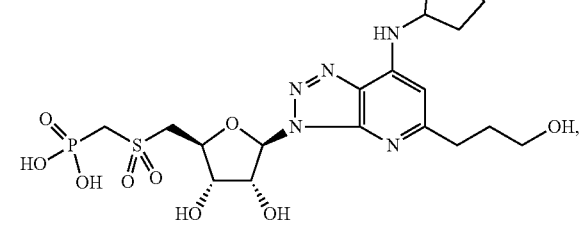

257
-continued
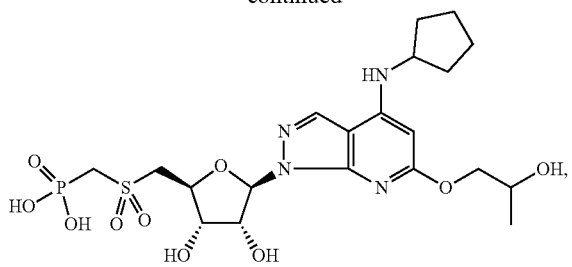
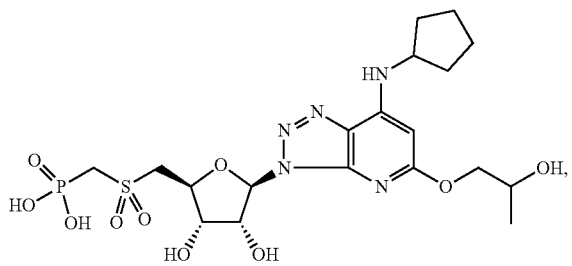
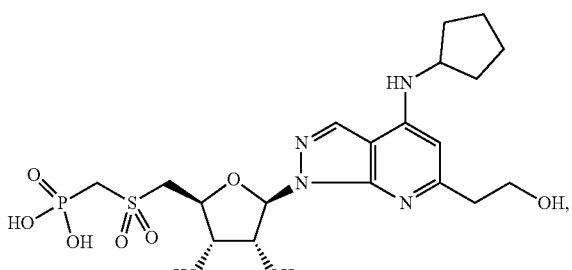
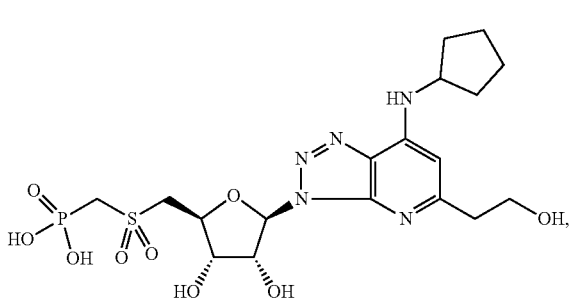
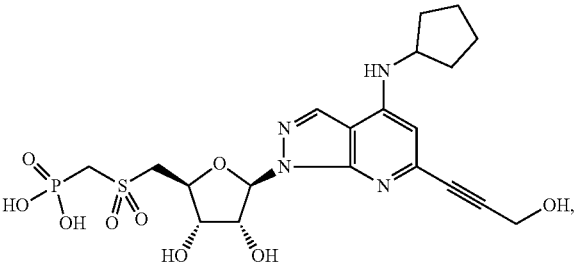
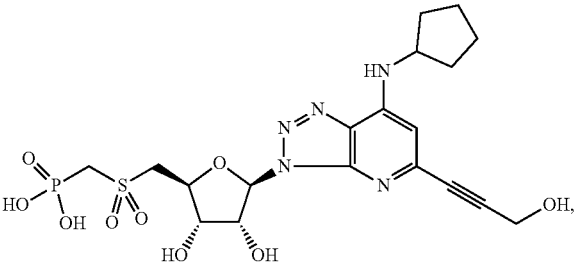
258
-continued
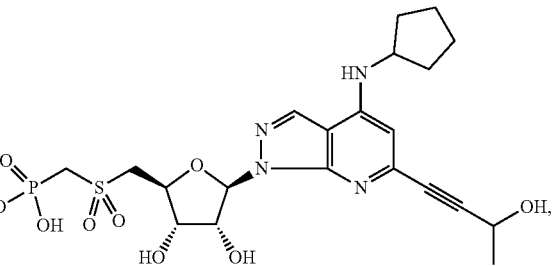
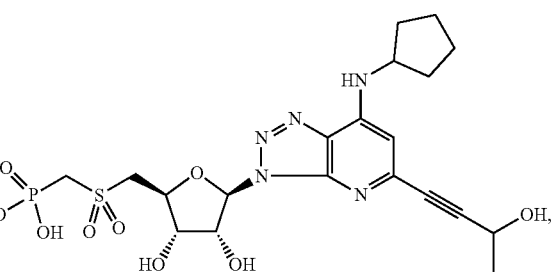
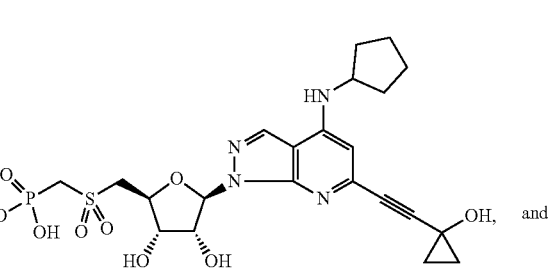
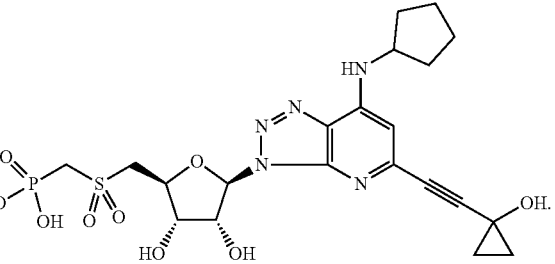 and
In some embodiments is a compound, or a pharmaceutically acceptably salt, solvate, stereoisomer, or isotopic variant thereof, having a structure selected from:
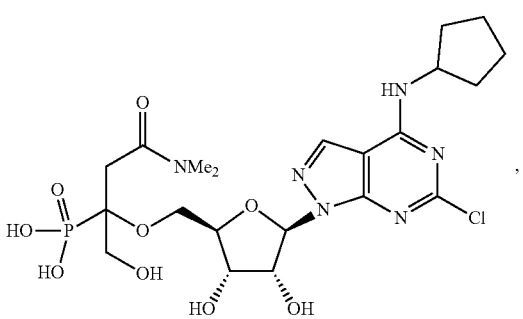

259
-continued
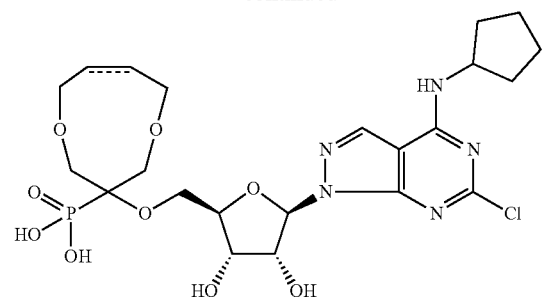
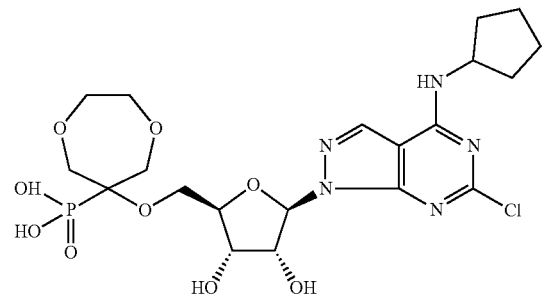
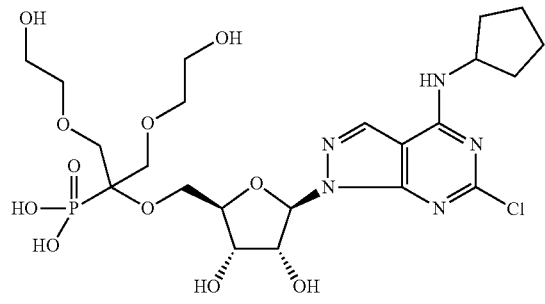
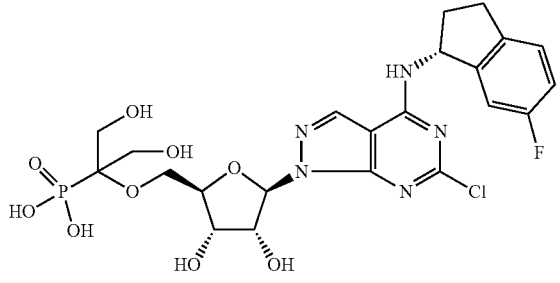
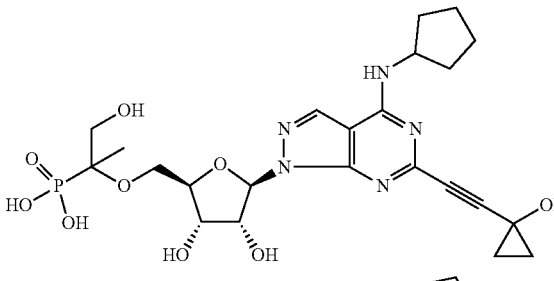
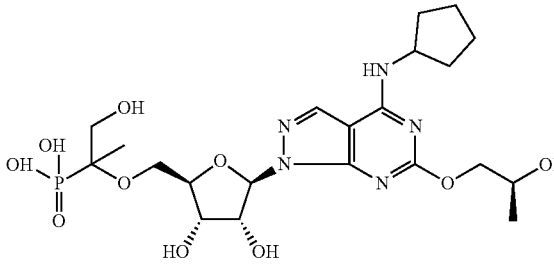
260
-continued
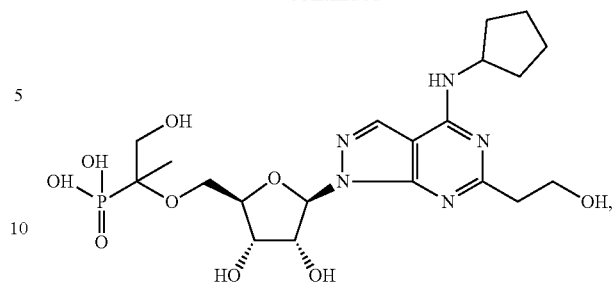
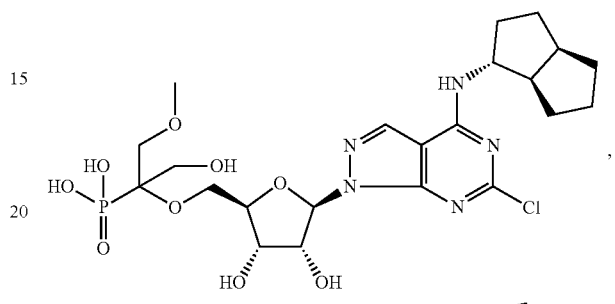
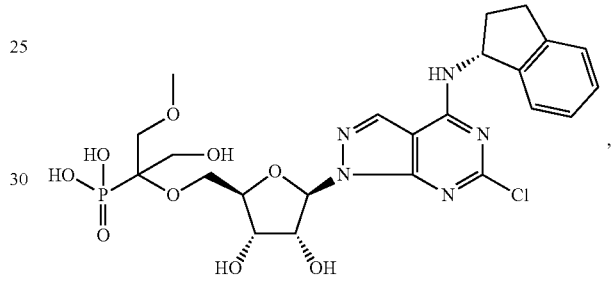
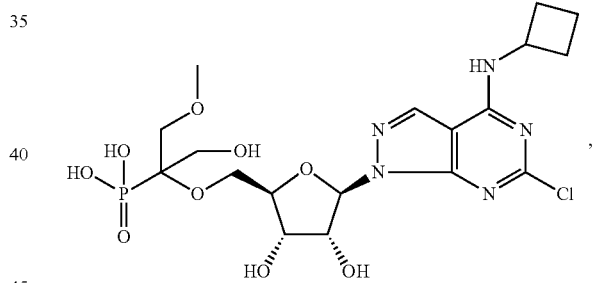
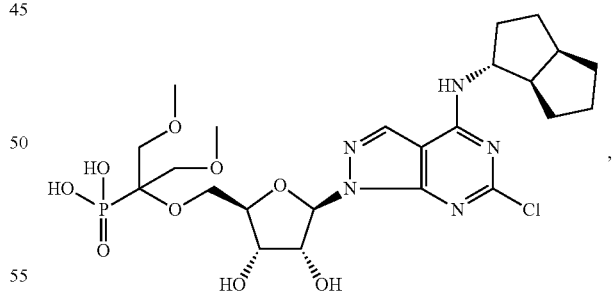
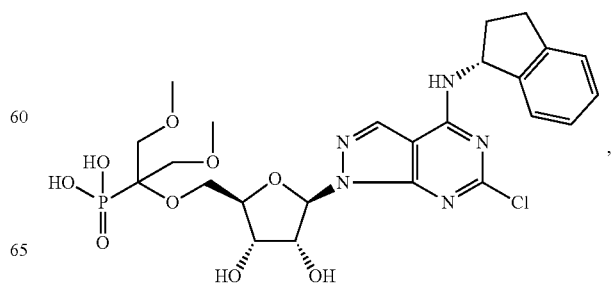

261
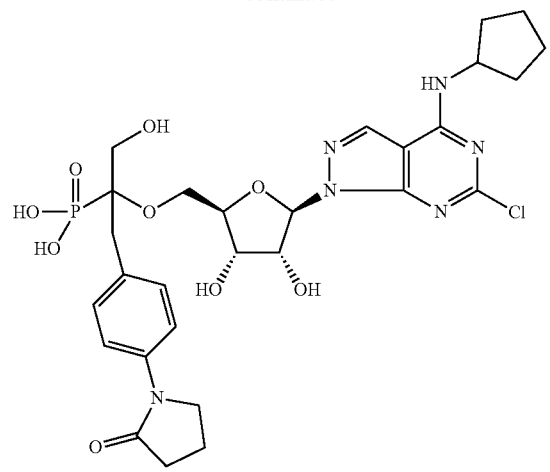
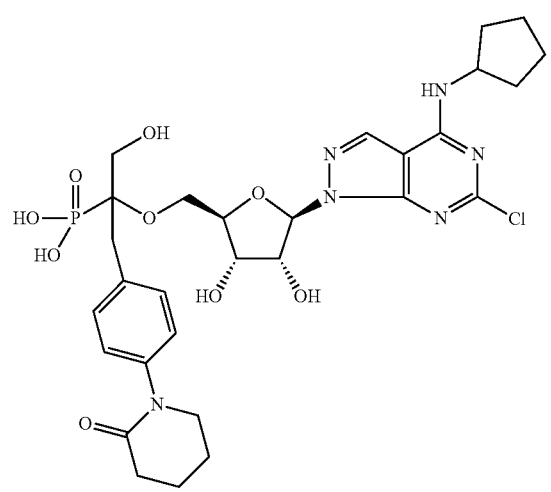
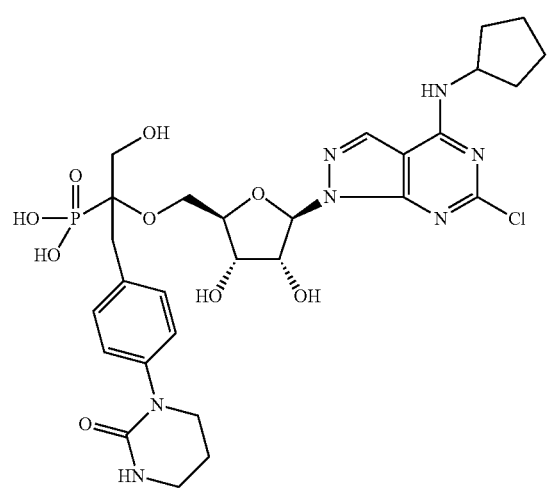
262
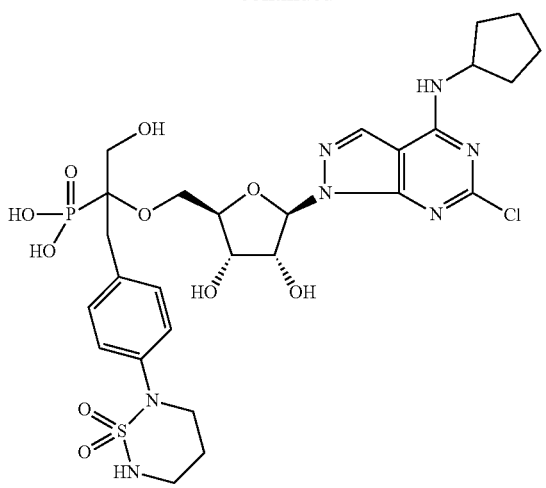
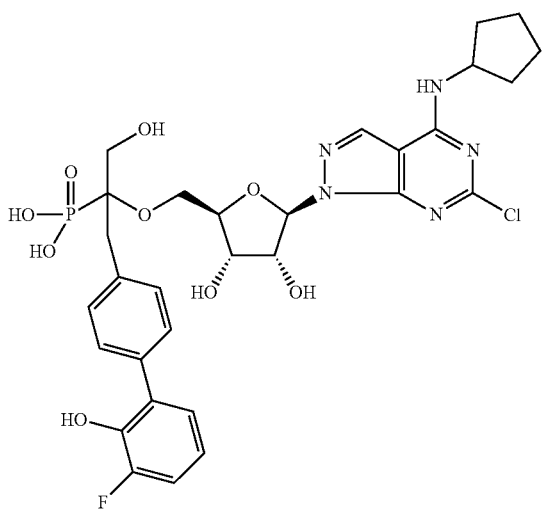
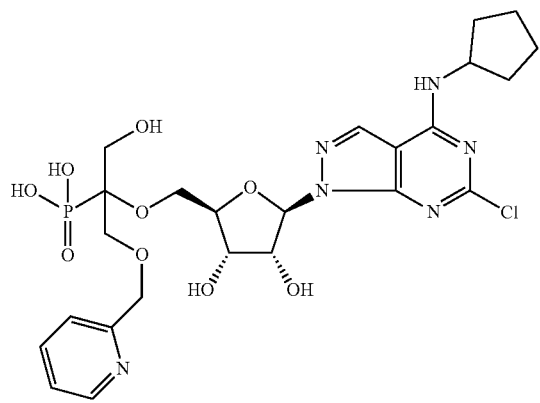

263
-continued
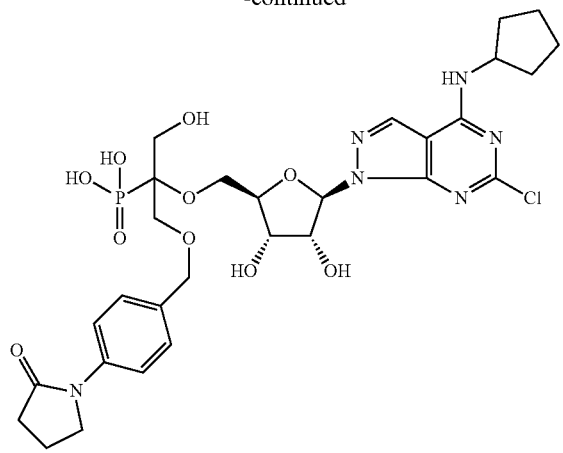
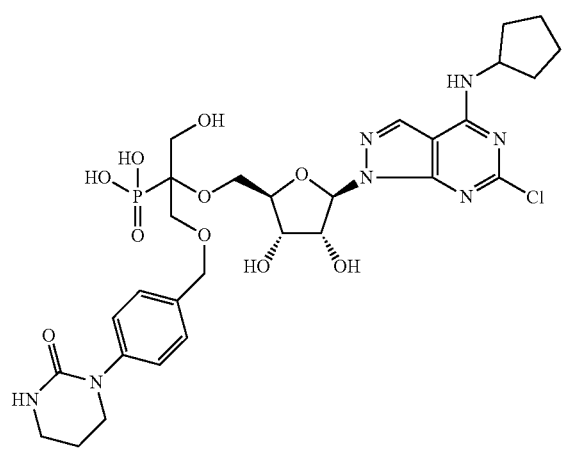
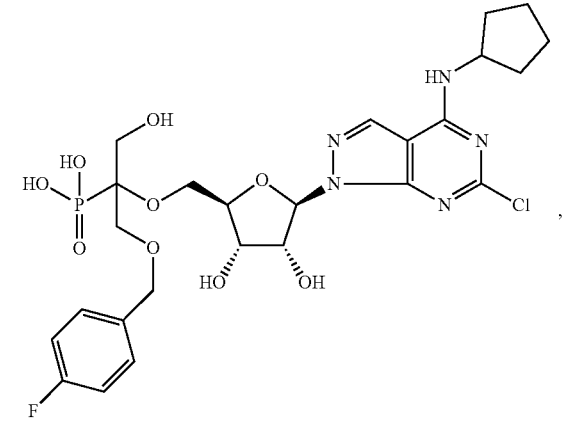
264
-continued
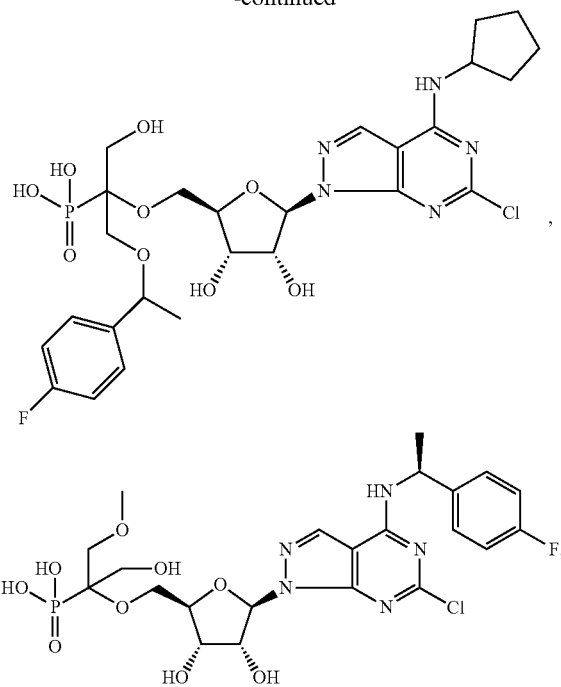
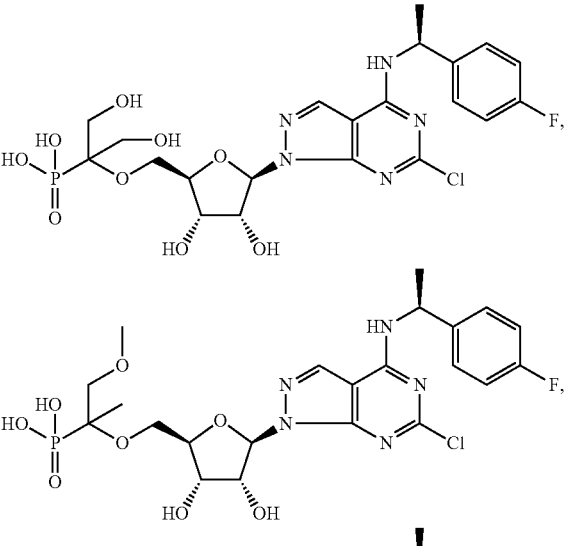
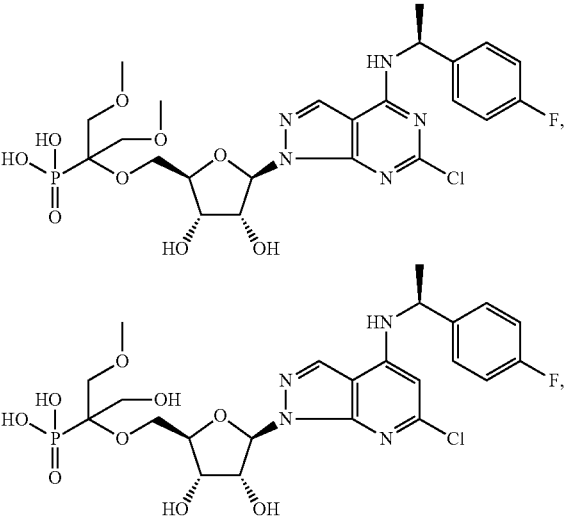

265
-continued
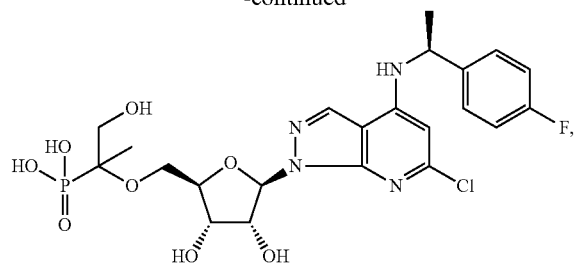
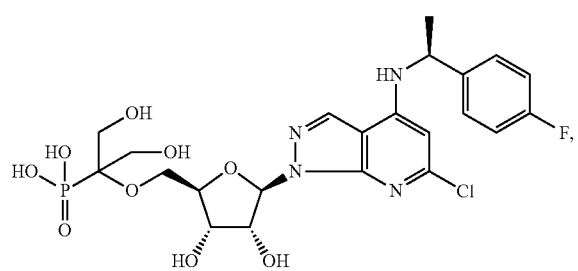
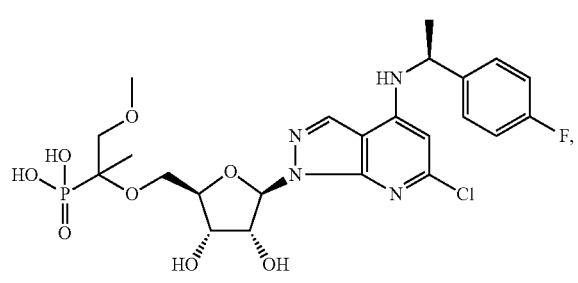
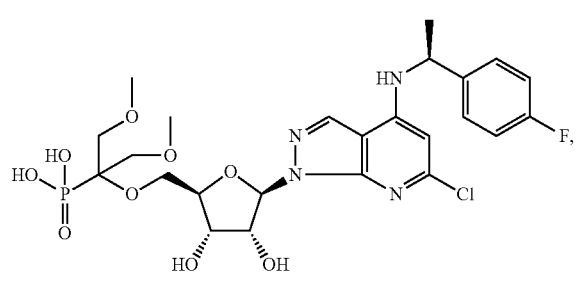
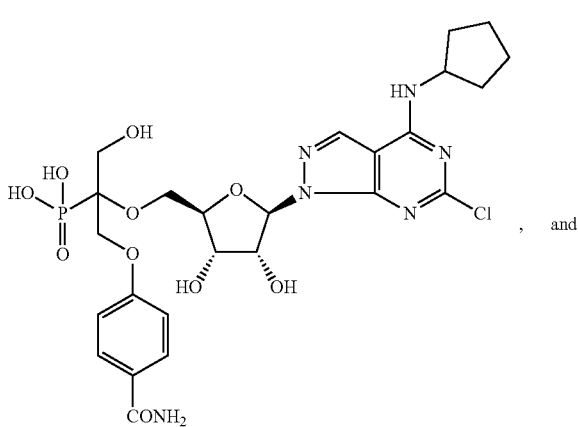
, and
266
-continued
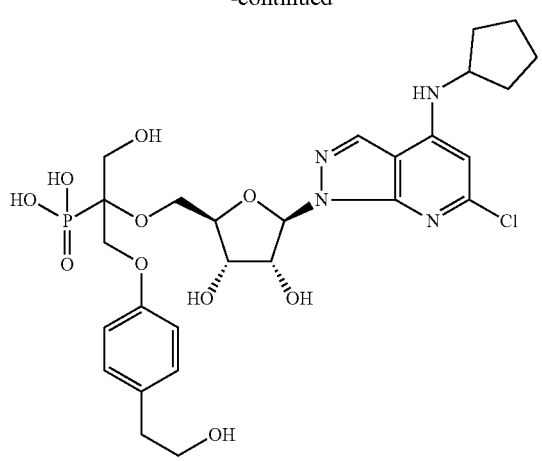
In some embodiments is a compound, or a pharmaceutically acceptable salt, solvate, stereoisomer, or isotopic variant thereof, having a structure selected from:
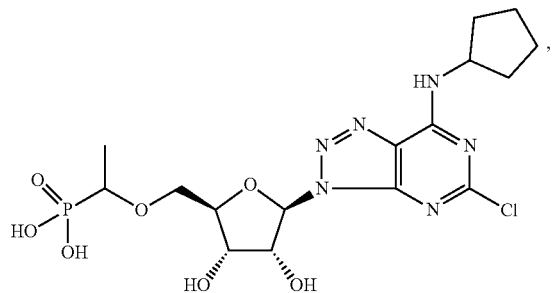
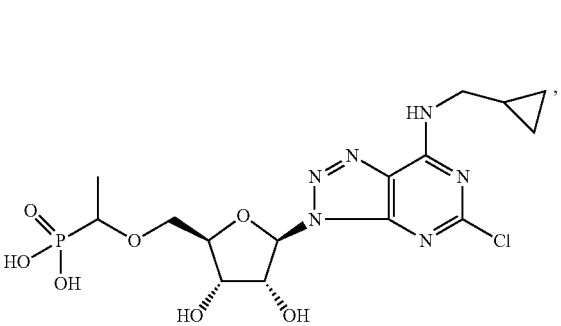
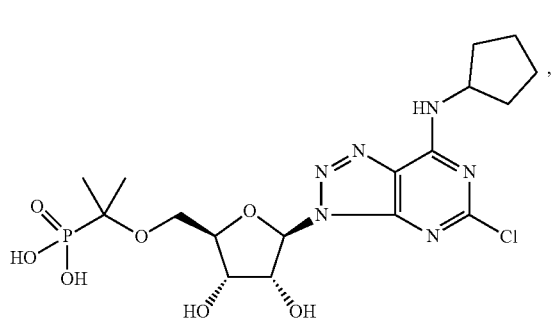

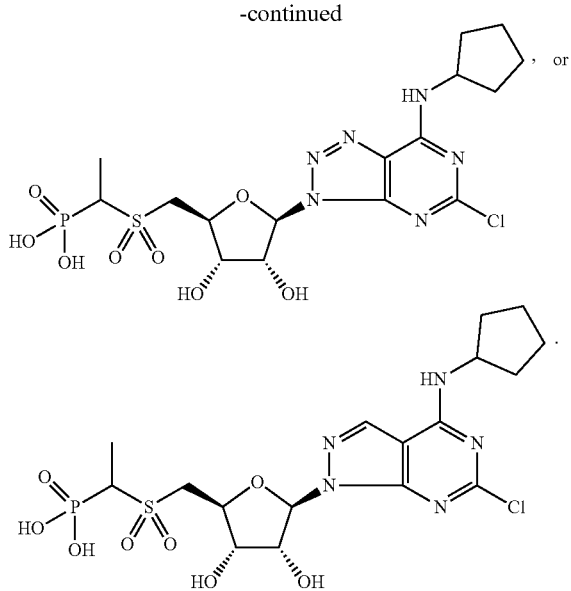

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{15}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, stereoisomer, or isotopic variant thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenyl-butyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid, metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.). Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.). Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA. Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin. Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-

29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available inmost public and university libraries, as well as through on-line databases (contact the American Chemical Society, Washington, D.C for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds described herein are prepared as outlined in Schemes 1-7.

Scheme 1

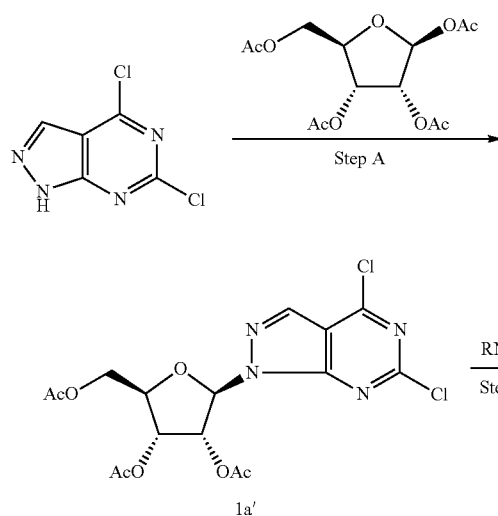
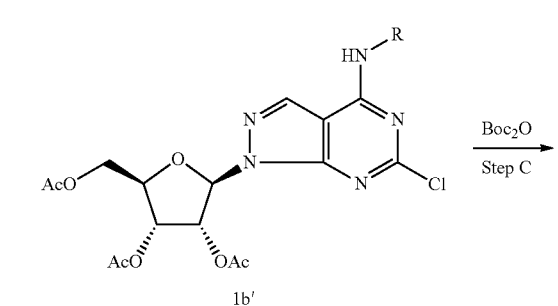
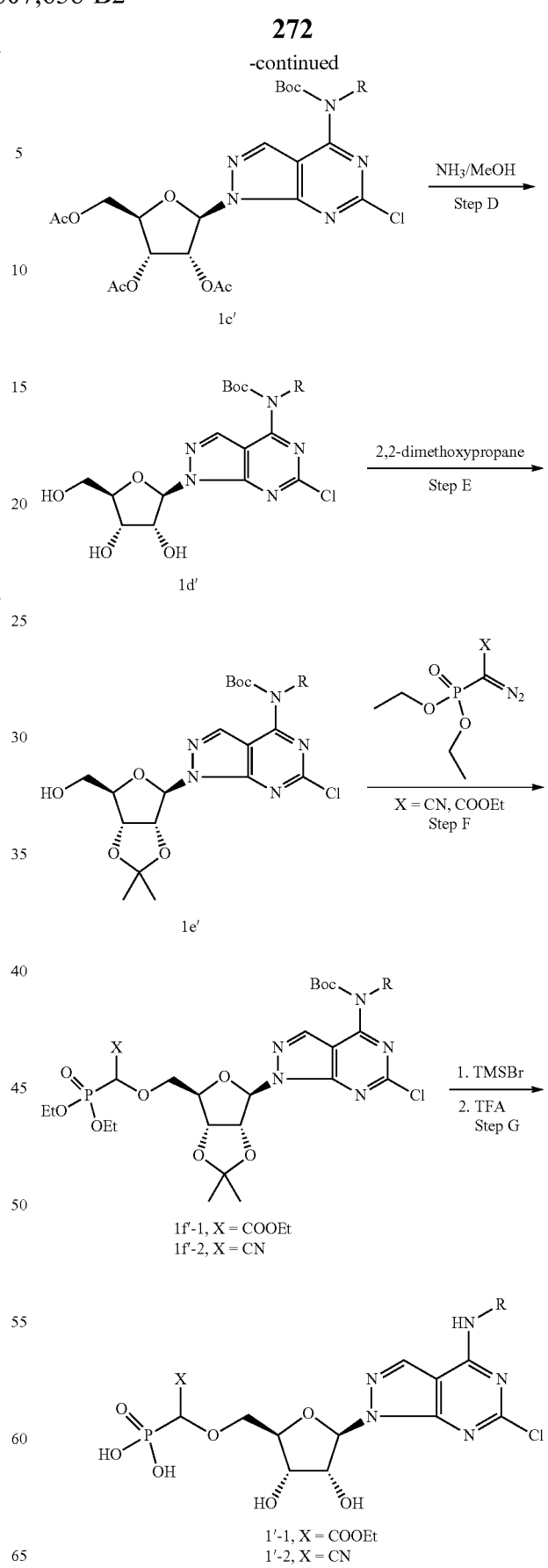

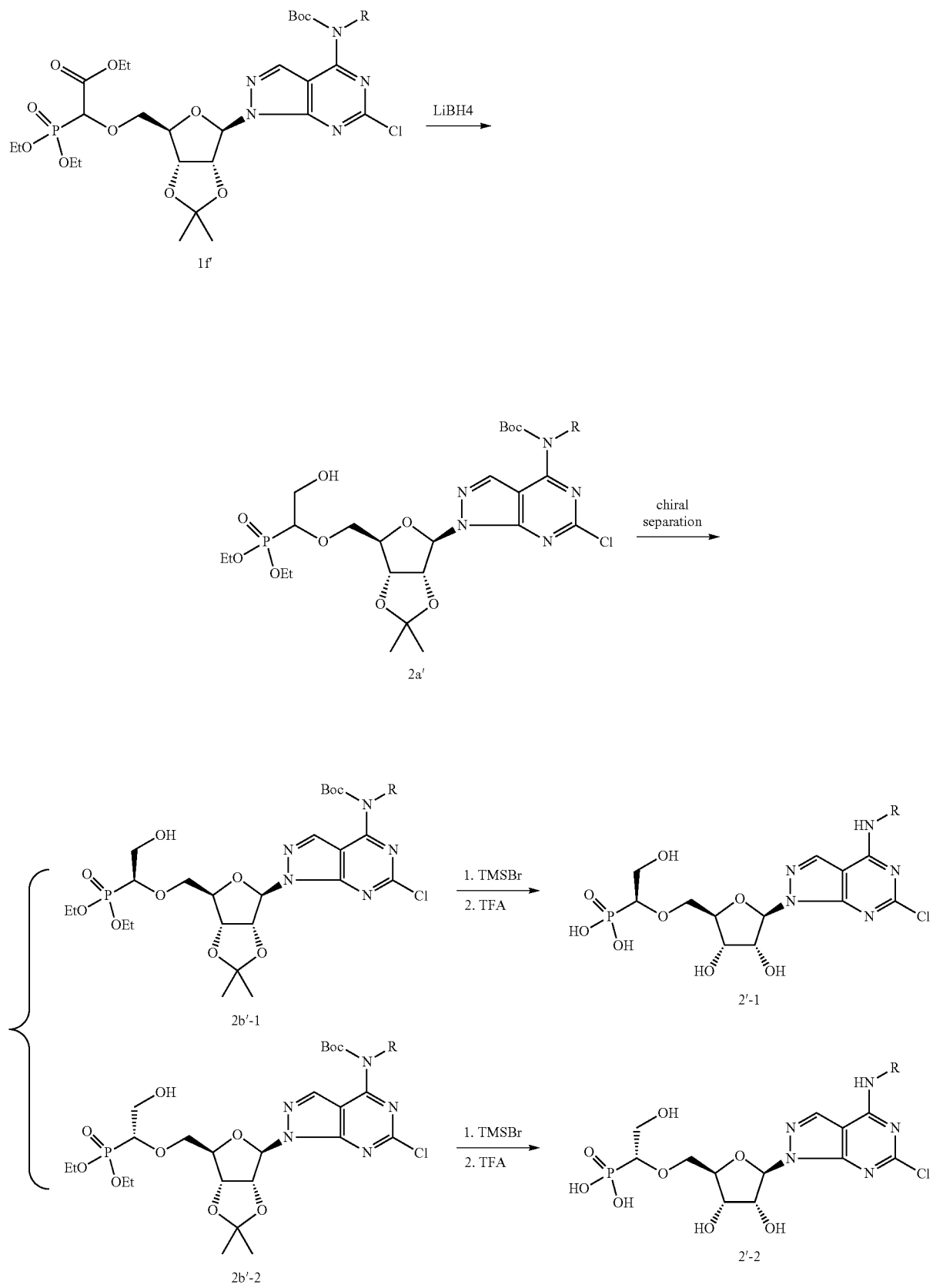
Scheme 2

Scheme 3
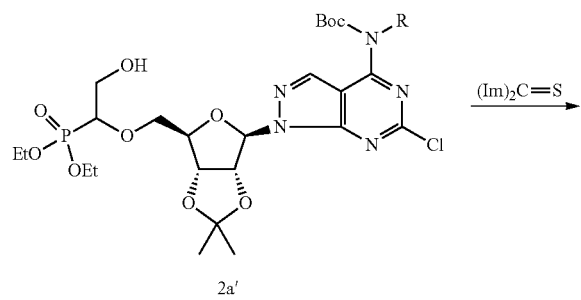
2a'
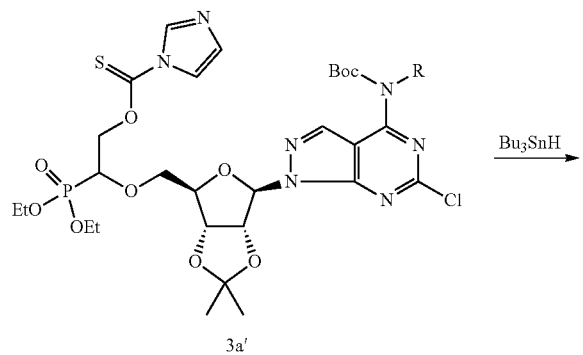
3a'
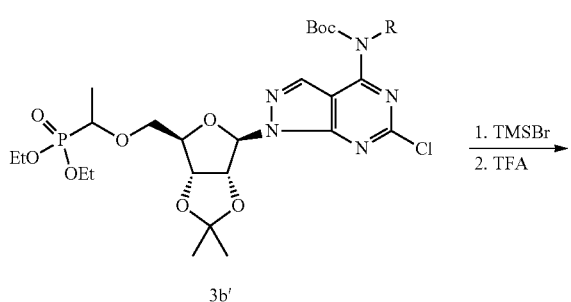
3b'
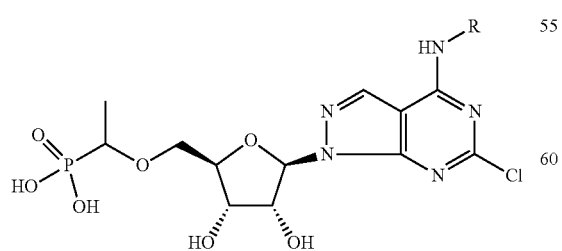
3'
Scheme 4
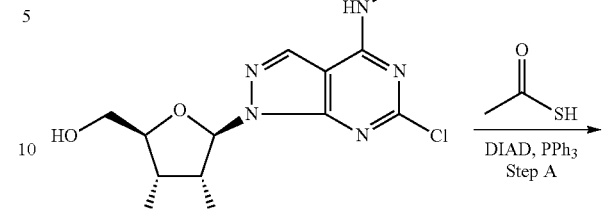

Scheme 5
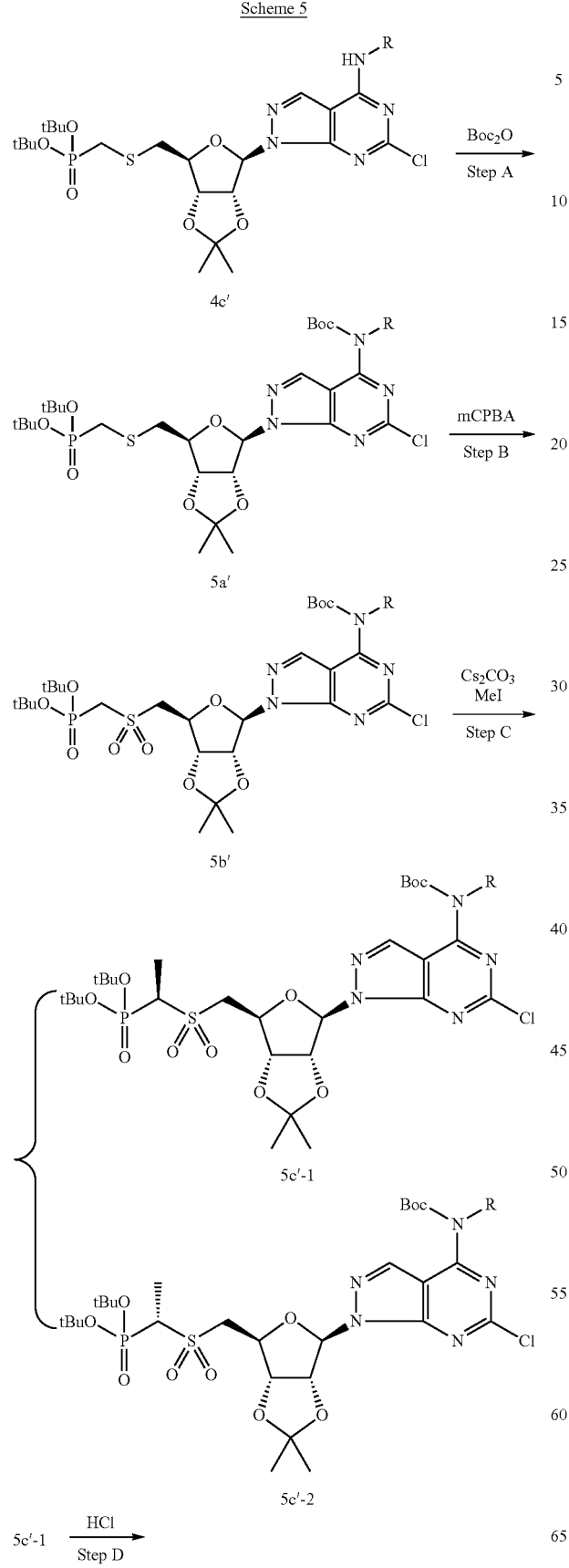
Scheme 6
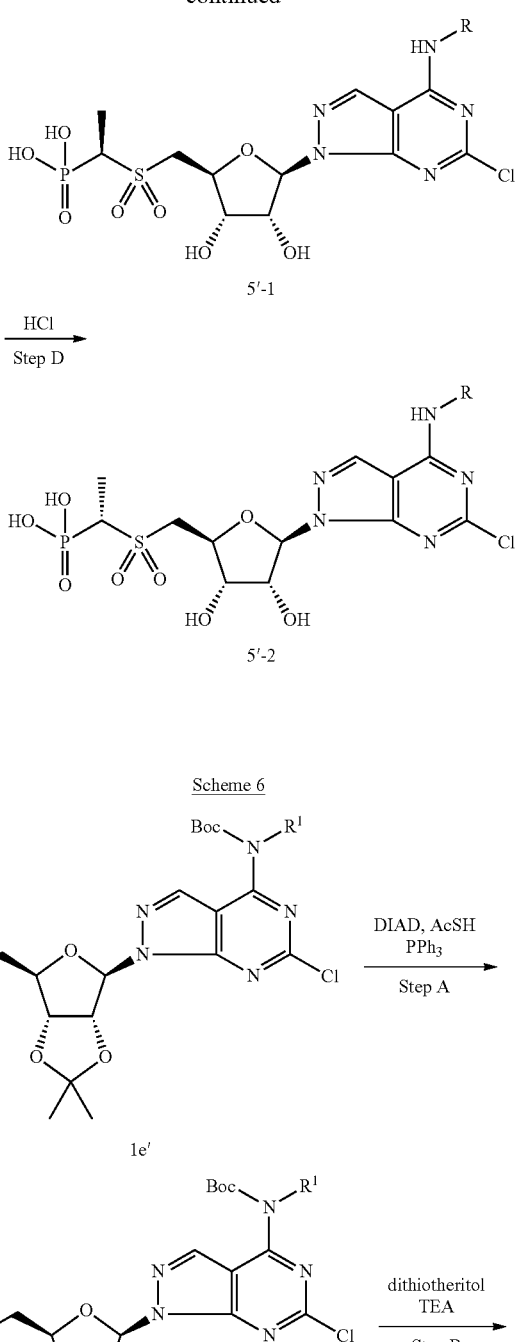
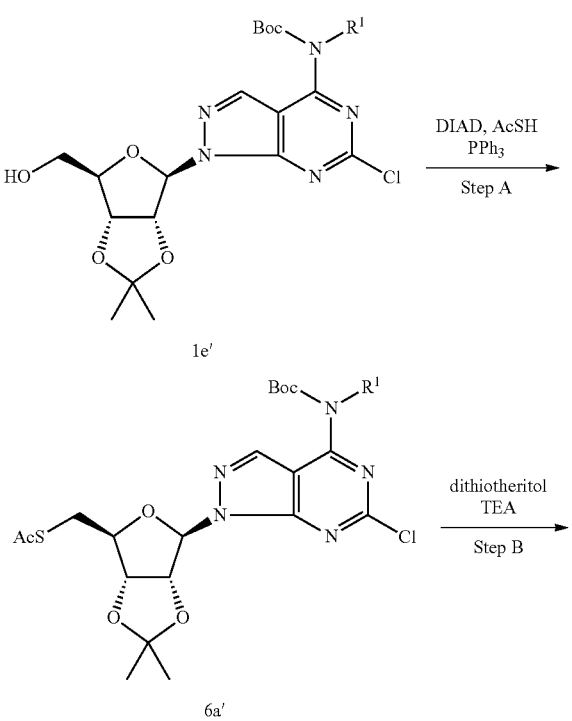

-continued

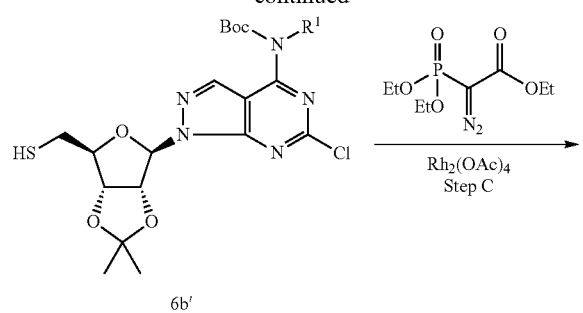

6b'

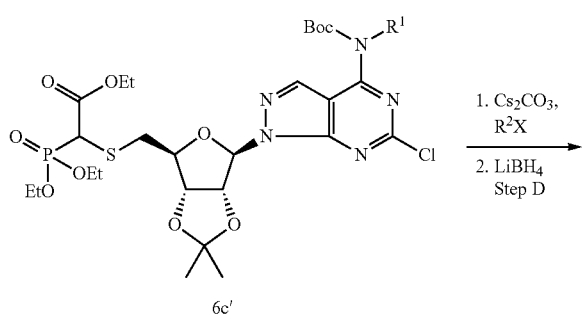

6c'

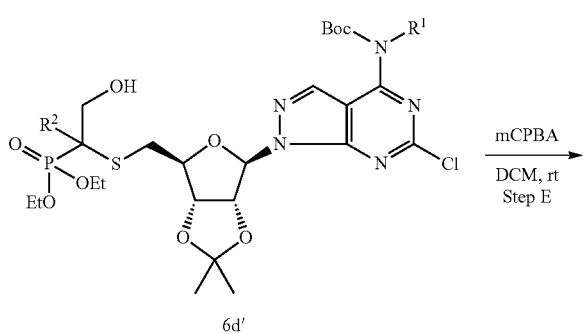

6d'

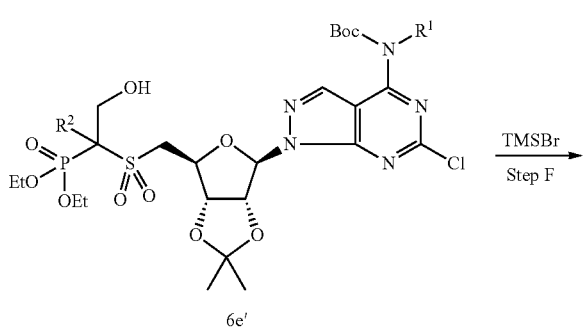

6e'

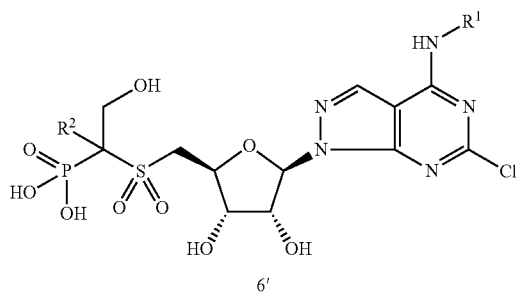

6'

Scheme 7

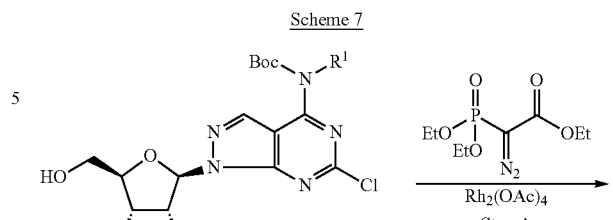

1e'

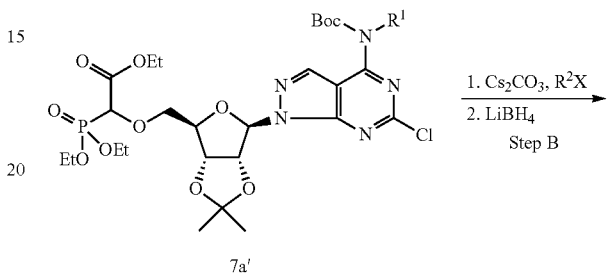

7a'

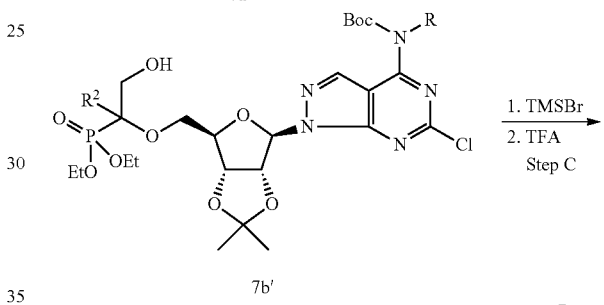

7b'

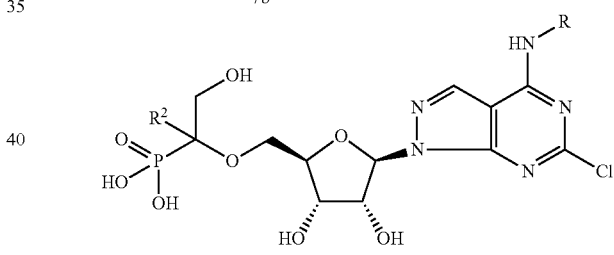

7'

Pharmaceutical Compositions

In certain embodiments, the compound disclosed herein is administered as a pure chemical. In some embodiments, the compound disclosed herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound disclosed herein, or a pharmaceutically acceptable salt, solvate, stereoisomer, or isotopic variant thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound disclosed herein, or a pharmaceutically acceptable salt, solvate, stereoisomer, or isotopic variant thereof.

In certain embodiments, the compound disclosed herein is substantially pure, in that it contains less than about 5%, or less than about 1%, or less than about 0.1%, of other organic small molecules, such as unreacted intermediates or synthesis by -products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Methods of Treatment

The compounds disclosed herein, or a pharmaceutically acceptable salt, solvate, stereoisomer, or isotopic variant thereof, are useful as inhibitors of CD73 and, therefore, useful in the treatment of diseases or disorders in which it is believed CD73 activity plays a role. In some embodiments, the disease or disorder is cancer. In some embodiments, the disease or disorder is an infection. In some embodiments, the disease or disorder is a neurodegenerative disease. In some embodiments, the disease or disorder is a psychiatric disorder.

Disclosed herein are methods of treating a subject with a disorder mediated by CD73 comprising the step of administering to the subject an effective amount of a compound disclosed herein, or a pharmaceutically acceptable salt, solvate, stereoisomer, or isotopic variant thereof.

Cancer

CD73 has been found to be overexpressed in many cancer cell lines and tumor types including breast cancer, colorectal cancer, ovarian cancer, gastric cancer, and gallbladder cancer and associated with poor prognosis. Increasing evidence suggests that CD73 is a key protein molecule in cancer development.

Higher expression levels of CD73 are associated with tumor neovascularization, invasiveness, resistance to chemotherapy and metastasis, and with shorter patient survival time in cancer. In some embodiments, the compounds disclosed herein are useful in reducing tumor neovascularization, invasiveness, resistance to chemotherapy and metastasis, as well as to lengthen patient survival time in cancer patients. In some embodiments, the CD73 inhibitors disclosed herein are used to control tumor neovascularization, progression, resistance to chemotherapy, and metastasis.

One embodiment provides a method of treating cancer in a subject in need thereof, comprising administering to the subject a compound of disclosed herein, or a pharmaceutically acceptable salt, solvate, stereoisomer, or isotopic variant thereof.

In some embodiments, the cancer is chemoresistant cancer, radio resistant cancer, anti-hormonal therapy resistant cancer, or treatment refractory cancer. In some embodiments, the cancer is relapsed cancer, persistent cancer, or recurrent cancer. Another embodiment provided herein describes a method of reducing incidences of cancer recurrence. Also provided here in some embodiments, is a method for treating a therapy-resistant cancer. In some embodiments, the cancer is metastasic cancer.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia, or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML); (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytomal (6) Waldenstrom's macroglobulinernia; (7) monoclonal-gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, aligodendrogliorna, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mutinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prol actin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, non-serninoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcorna; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; (42) reproductive cancers, such as cervical cancer, uterus cancer, ovarian cancer, or testicular cancer; (43) esophagus cancer; (44) laryngeal cancer; (45) head and neck cancers (including mouth, nose, throat, larynx, sinuses, or salivary glands cancers); and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In certain embodiments, the cancer treatable with the methods provided herein is a hematological malignancy. In certain embodiments, the hematological malignancy is a T-cell malignancy. In certain embodiments, T-cell malignancies include peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In certain embodiments, the hematological malignancy is a B-cell malignancy. In certain embodiments, B-cell malignancies include acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitfs lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In certain embodiments, the B-cell malignancy is diffuse large B-cell lymphoma (DLBCL). In certain embodiments, the DLBCL is an activated B-cell DLBCL (ABC-DLBCL), a germinal center B-cell like DLBCL (GBC-DLBCL), a double hit DLBCL (DH-DLBCL), or a triple hit DLBCL (TH-DLBCL).

In certain embodiments, the cancer treatable with the methods provided herein is lung cancer, melanoma, breast cancer, ovarian cancer, colorectal cancer, gastric cancer, gallbladder cancer, or prostate cancer.

Infections

A number of studies have shown changes in the activity of the CD39/CD73 axis during infections induced by a variety of microorganisms. One embodiment provides a method of treating an infection in a subject in need thereof, comprising administering to the subject a compound of disclosed herein, or a pharmaceutically acceptable salt, solvate, stereoisomer, or isotopic variant thereof.

In some embodiments, the infection is a viral infection, a bacterial infection, or a parasitic infection.

Parasitic Infections

In some embodiments, the infection is a parasitic infection. In some embodiments, the parasitic infection is caused by infection of the subject with a protozoan organism. In some embodiments, the protozoan organism selected from the group consisting of the genera *Acanthamoeba, Babesia, Balantidium, Cryptosporidium, Dientamoeba, Eimeria, Entamoeba, Giardia, Isospora, Leishmania, Naegleria, Neospora, Plasmodium, Sarcocystis, Theileria, Toxoplasma, Trichomonas, Trypanosoma*, or any combinations thereof. In some embodiments, the parasitic infection is caused by an infection with *Toxoplasma gondii* (*T. gondii*). In some embodiments, the parasitic infection is toxoplasmosis. In some embodiments, the toxoplasmosis is acute toxoplasmosis, latent toxoplasmosis, or cutaneous toxoplasmosis.

Acute toxoplasmosis: acute toxoplasmosis is often asymptomatic in healthy adults. However, symptoms may manifest and are often influenza-like: swollen lymph nodes, headaches, fever, fatigue, or muscle aches and pains that last for a month or more. Rarely will a human with a fully functioning immune system develop severe symptoms following infection. People with weakened immune systems are likely to experience headache, confusion, poor coordination, seizures, lung problems that may resemble tuberculosis or *Pneumocystis jiroveci* pneumonia (a common opportunistic infection that occurs in people with AIDS), or blurred vision caused by severe inflammation of the retina (ocular toxoplasmosis). Young children and immunocompromised people, such as those with HIV/AIDS, those taking certain types of chemotherapy, or those who have recently received an organ transplant, may develop severe toxoplasmosis. In some instances, toxoplasmosis causes damage to the brain (encephalitis) or the eyes (necrotizing retinochoroiditis). Infants infected via placental transmission may be born with either of these problems, or with nasal malformations, although these complications are rare in newborns. The toxoplasmic trophozoites causing acute toxoplasmosis are referred to as tachyzoites, and are typically found in bodily fluids.

Latent toxoplasmosis: due to its asymptomatic nature, it is easy for a host to become infected with *Toxoplasma gondii* and develop toxoplasmosis without knowing it. Although mild, flu-like symptoms occasionally occur during the first few weeks following exposure, infection with *T. gondii* produces no readily observable symptoms in healthy human adults. In most immunocompetent people, the infection enters a latent phase, during which only bradyzoites (tissue cysts) are present; these tissue cysts and even lesions can occur in the retinas, alveolar lining of the lungs (where an acute infection may mimic a *Pneumocystis jirovecii* infection), heart, skeletal muscle, and the central nervous system (CNS), including the brain. Cysts form in the CNS (brain tissue) upon infection with *T. gondii* and persist for the lifetime of the host. Most infants who are infected while in the womb have no symptoms at birth, but may develop symptoms later in life.

Cutaneous toxoplasmosis: in some embodiments, skin lesions occur in the acquired form of the disease, including roseola and erythema multiforme-like eruptions, prurigo-like nodules, urticaria, and maculopapular lesions. Newborns may have punctate macules or ecchymoses. Diagnosis of cutaneous toxoplasmosis is based on the tachyzoite form of *T. gondii* being found in the epidermis.

Viral Infections

In some embodiments, the infection is a viral infection. In certain embodiments, the viral infection treatable with the methods provided herein includes, but is not limited to, chickenpox, the flu (influenza), herpes, human immunodeficiency virus (HIV/AIDS), human papillomavirus (HPV), Infectious mononucleosis, mumps, measles, rubella, shingles, viral gastroenteritis (stomach flu), viral hepatitis, viral meningitis, and viral pneumonia.

Neurodegenerative Diseases

In the central nervous system, adenosine plays a critical role in controlling a multitude of neural functions. Through the activation of P1 receptors, adenosine is involved in diverse physiological and pathological processes such as regulation of sleep, general arousal state and activity, local neuronal excitability, and coupling of the cerebral blood flow to the energy demand. In some embodiments, the manipulation of adenosine production via CD73 inhibitors has therapeutic potential in neurodegenerative diseases. One embodiment provides a method of treating a neurodegenerative disease in a subject in need thereof, comprising administering to the subject a compound of disclosed herein, or a pharmaceutically acceptable salt, solvate, stereoisomer, or isotopic variant thereof. In certain embodiments, the neurodegenerative disease treatable with the methods provided herein includes, but is not limited to, Alzheimer's disease, Parkinson's disease, and Huntington's disease. One embodiment provides a method of treating a psychiatric disorder in a subject in need thereof, comprising administering to the subject a compound of disclosed herein, or a pharmaceutically acceptable salt, solvate, stereoisomer, or isotopic variant thereof. In some embodiments, the psychiatric disorder is schizophrenia or autism.

Combination Therapy

In certain instances, the compound disclosed herein, or a pharmaceutically acceptable salt, solvate, stereoisomer, or isotopic variant thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound disclosed herein, or a pharmaceutically acceptable salt, solvate, stereoisomer, or isotopic variant thereof, is co-administered with a second therapeutic agent, wherein the compound disclosed herein, or a pharmaceutically acceptable salt, solvate, stereoisomer, or isotopic variant thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound disclosed herein, or a pharmaceutically acceptable salt, solvate, stereoisomer, or isotopic variant thereof, is initiated prior to, during, or after treatment with a second agent described herein, and continues until any time during treatment with the second agent or after termination of treatment with the second agent. It also includes treatments in which a compound disclosed herein, or a pharmaceutically acceptable salt, solvate, stereoisomer, or isotopic variant thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds disclosed herein, or a pharmaceutically acceptable salt, solvate, stereoisomer, or isotopic variant thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In certain embodiments, the second therapeutic agent is an adjuvant. In certain embodiments, the second therapeutic agent is an anti-cancer agent. In certain embodiments, the second therapeutic agent is an antiemetic. In certain embodiments, the second therapeutic agent is an anti-infective agent. In certain embodiments, the second therapeutic agent is an antiviral agent. In certain embodiments, the second therapeutic agent is an antibacterial agent.

In some embodiments, the compound disclosed herein, or a pharmaceutically acceptable salt, solvate, stereoisomer, or isotopic variant thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). In some embodiments, the compound disclosed herein, or a pharmaceutically acceptable salt, solvate, stereoisomer, or isotopic variant thereof, is administered in combination with an anti-cancer agent.

In some embodiments, the anti-cancer agent is a hormone blocking therapy. Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g., tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g., raloxifene, LY353381 (SERM3) and LY357489); steroidal estrogen receptor modulators (e.g., ICI-182,780). Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole and letrozole.

In certain embodiments, compounds disclosed herein are used in combination with one or more passive immunotherapies, including but not limited to, naked monoclonal antibody drugs and conjugated monoclonal antibody drugs. Examples of naked monoclonal antibody drugs that can be used include, but are not limited to, rituximab, an antibody against the CD20 antigen; trastuzumab, an antibody against the HER2 protein; alemtuzumab, an antibody against the CD52 antigen; cetuximab, an antibody against the EGFR protein; and bevacizumab which is an anti-angiogenesis inhibitor of VEGF protein.

Examples of conjugated monoclonal antibodies include, but are not limited to, radiolabeled antibody ibritumomab tiuxetan; radiolabeled antibody tositumomab; and immunotoxin gemtuzumab ozogamicin which contains calicheamicin; BL22, an anti-CD22 monoclonal antibody-immunotoxin conjugate; radiolabeled antibodies such as OncoScint (Registered trademark) and ProstaScint (Registered trademark); brentuximab vedotin; and ado-trastuzumab emtansine.

Further examples of therapeutic antibodies that can be used include, but are not limited to, abciximab, an antibody against the glycoprotein IIb/IIIa receptor on platelets; daclizumab, an immunosuppressive, humanized anti-CD25 monoclonal antibody; edrecolomab, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN (Registered Trademark) a humanized anti-aVbeta 3 integrin antibody; Campath 1H/LDP-03, a humanized anti CD52 IgG1 antibody; Smart M195, a humanized anti-CD33 IgG antibody; epratuzumab, a humanized anti-CD22 IgG antibody; Lymphoscan; visilizumab; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized anti-CD3 IgG; 5G1.1, a humanized anti-complement factor 5 (C5) antibody; D2E7, a humanized anti-TNF-alpha antibody; CDP870, a humanized anti-TNF-alpha Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-alpha IgG4 antibody; LDP-02, a humanized anti-alpha 4beta 7 antibody; OrthoClone OKT4A, a humanized anti-CD4 IgG antibody; ANTOVA (Registered Trademark), a humanized anti-CD40L IgG antibody; ANTEGREN (Registered Trademark), a humanized anti-VLA-4 IgG antibody; and CAT-152, a human anti-TGF-beta 2 antibody.

In some embodiments, the second therapeutic agent for use in combination with a compound disclosed herein, or a pharmaceutically acceptable salt, solvate, stereoisomer, or isotopic variant thereof, include one or more of the following; abiraterone; abarelix; adriamycin; actinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; elformithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; fluorocitabine; fosquidone; fostriecin sodium; fulvestrant; gefitinib; gemcitabine; gemcitabine hydrochloride; gemcitabine cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; iniquimod; interleukin I1 (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazafurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

In some embodiments, the second therapeutic agent is an alkylating agent. Examples of alkylating agents for use in combination with a compound disclosed herein, or a pharmaceutically acceptable salt, solvate, stereoisomer, or isotopic variant thereof, include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In some embodiments, the second therapeutic agent is an immunotherapy agent. Examples of immunotherapy agents for use in combination with a compound disclosed herein, or a pharmaceutically acceptable salt, solvate, stereoisomer, or isotopic variant thereof, include, but are not limited to, checkpoint inhibitors (e.g., anti-PD1 and anti-PD-L1 inhibitors), cancer vaccines (e.g., sipuleucel-T), oncolytic viruses (e.g., talimogene laherparepvec), cytokines (e.g., IL-2 and INF-alpha), CAR-T cells.

In some embodiments, a compound disclosed herein, or a pharmaceutically acceptable salt, solvate, stereoisomer, or isotopic variant thereof, is used in combination with anti-emetic agents to treat nausea or emesis, which results from the use of a compound disclosed herein, or a pharmaceutically acceptable salt, solvate, stereoisomer, or isotopic variant thereof, anti-cancer agent(s) and/or radiation therapy. Anti-emetic agents include, but are not limited to: neurokinin-1 receptor antagonists, 5HT3 receptor antagonists (such as ondansetron, granisetron, tropisetron, palonosetron, and zatisetron), GABAB receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound disclosed herein, or a pharmaceutically acceptable salt, solvate, stereoisomer, or isotopic variant thereof, is used in combination with an agent useful in the treatment of anemia. Such an anemia treatment agent is, for example, a continuous eythropoiesis receptor activator (such as epoetin-α).

In some embodiments, a compound disclosed herein, or a pharmaceutically acceptable salt, solvate, stereoisomer, or isotopic variant thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In one embodiment, a compound disclosed herein, or a pharmaceutically acceptable salt, solvate, stereoisomer, or isotopic variant thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745 337, and NS398).

In some embodiments, a compound disclosed herein, or a pharmaceutically acceptable salt, solvate, stereoisomer, or isotopic variant thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, uterus, and/or cervix. It is also optionally used to treat leukemia and lymphoma (cancers of the blood-forming cells and lymphatic system, respectively).

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1. (1-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-2-ethoxy-2-oxoethyl)phosphonic add (1)

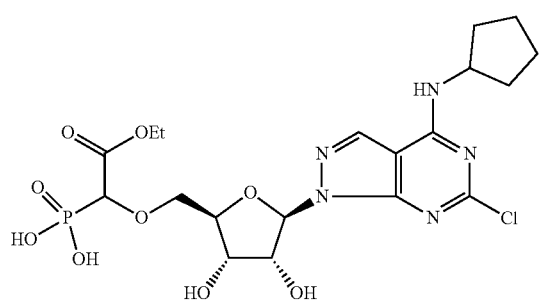 [SMILES: CCOC(=O)C(OC[C@H]1O[C@@H](n2ncc3c(NC4CCCC4)nc(Cl)nc32)[C@H](O)[C@@H]1O)P(=O)(O)O]

Step A: (2R,3R,4R,5R)-2-(Acetoxymethyl)-5-(4,6-dichloro-1H-pyrazolo[3,4-d]pyrimidin-1-yl)tetrahydrofuran-3,4-diyl diacetate (1a)

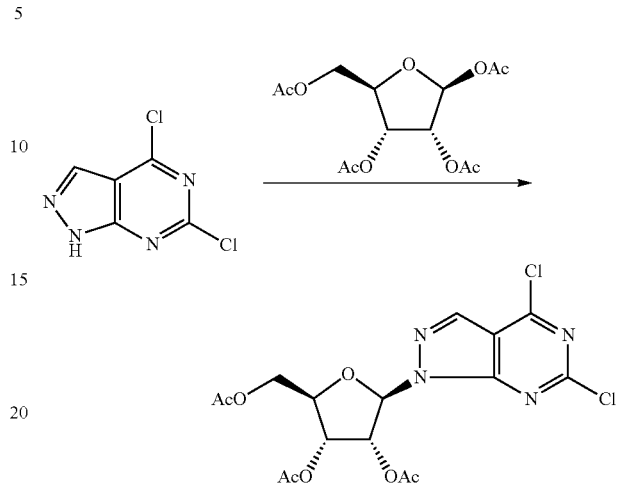

β-D-Ribofuranose 1,2,3,5-tetraacetate (5.73 g, 17.99 mmol) was heated at 90° C. for 10 min, 4,6-dichloro-1H-pyrazolo[3,4-d]pyrimidine (1.5 g, 17.99 mmol) and SnCl₄ (60 mg) was added successively. After the mixture was heated at 130° C. under reduced pressure for 15 min, it was cooled to rt, diluted with water, and extracted with DCM. The combined organics were washed with water, brine, dried and concentrated. The residue was purified by column chromatography (petroleum ether/ethyl acetate from 10:1 to 5:1) to give the title compound (1a) (2.4 g, 68%) as a yellow solid.

Step B: (2R,3R,4R,5R)-2-(Acetoxymethyl)-5-(6-chloro-4-(cyclopentylamino)-1H-pyrazolo[3,4-d]pyrimidin-1-yl)tetrahydrofuran-3,4-diyl diacetate (1b)

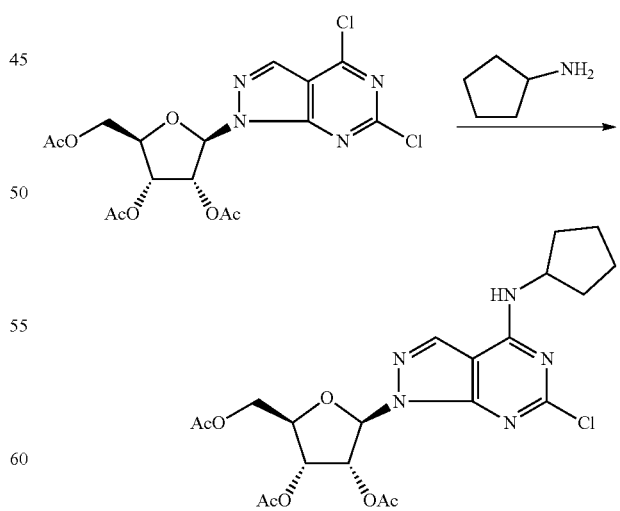

To an oven dried flask was added 1a (5.2 g, 11.63 mmol) followed by ethanol (53.24 mL). To this solution was added triethylamine (2.43 mL, 17.44 mmol) followed by cyclopentylamine (1.38 mL, 13.95 mmol). After the mixture was stirred and heated at 50° C. for 15 min, it was cooled to rt, concentrated, and purified by column chromatography (20 to 45% EtOAc in hexanes, a gradient elution) to provide the title compound (1b) (5.02 g, 87%) as a white solid. m/z (ESI, +ve ion)=496.1 [M+H]⁺.

Step C: (2R,3R,4R,5R)-2-(Acetoxymethyl)-5(4-((tert-butoxycarbonyl)cyclopentyl)amino)-6-chloro-1H-pyrazolo[3,4-d]pyrimidin-1-yl)tetrahydrofuran-3,4-diyl diacetate (1c)

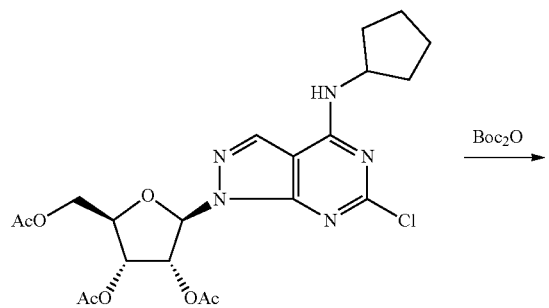

To a solution of 1b (12.6 g, 25.4 mmol) in MeCN (120 mL) was added triethylamine (5.14 g, 50.9 mmol) followed by di-tert-butyl dicarbonate (44.35 g, 203.6 mmol) and 4-dimethylaminopyridine (0.31 g, 2.54 mmol). After the mixture was allowed to stir overnight, it was concentrated and partitioned between EtOAc (50 mL) and sat. NaHCO₃. Organic layer was washed with brine, dried with Na₂SO₄, filtered, concentrated. The residue was purified by column chromatography (petroleum ether/ethyl acetate: 8:1) to provide the title compound (1c) (10.56 g, 70% yield) as a yellow solid. m/z (ESI, +ve ion)=596.72 [M+H]⁺.

Step D: tert-Butyl (6-chloro-1-((2R,3R,4S,5R)-3,4-dihydroxy-5-(hydroxymethyl)tetrahydrofuran-2-yl)-1H-pyrazolo[3,4-d]pyrimidin-4-yl)(cyclopentyl)carbamate (1d)

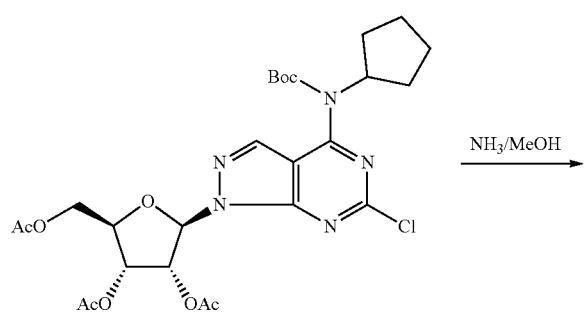

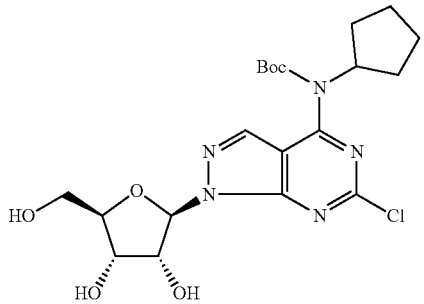

To an oven dried flask was added 1c (10.56 g, 17.78 mmol), followed by ammonia (5.0 M in MeOH, 140 mL) in methanol. The mixture was stirred overnight and then concentrated. The crude oil was purified by column chromatography to afford the title compound (1d) (7.39 g, 89% yield) as a yellow solid. m/z (ESI, +ve ion)=470.3 [M+H]⁺.

Step E. tert-Butyl (6-chloro-1-((3aR,4R,6R,6aR)-6-(hydroxymethyl)-2,2-dimethyltetrahydrofuro[3,4-d][1,3]dioxol-4-yl)-1H-pyrazolo[3,4-d]pyrimidin-4-yl)(cyclopentyl)carbamate (1e)

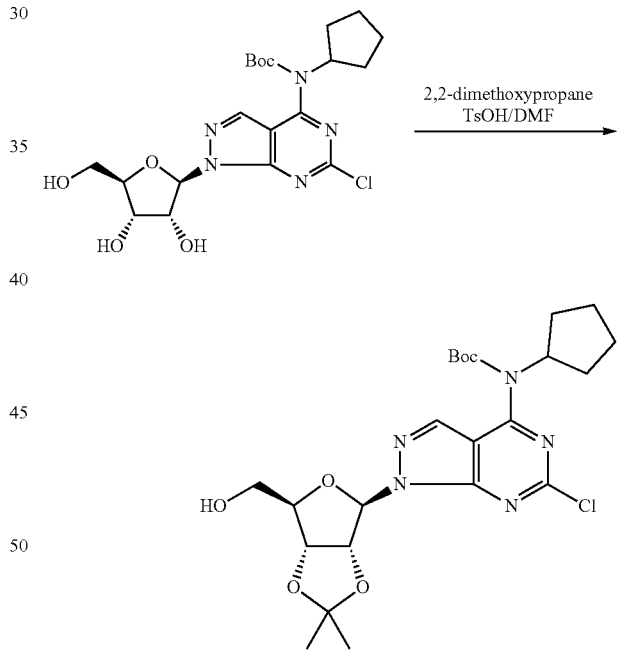

To a solution of 1d (7.39 g, 15.75 mmol) and 2,2-dimethoxypropane (4.92 g, 47.27 mmol) in DMF (75 mL) was added TsOH·H₂O (0.6 g, 3.15 mmol). After the mixture was stirred at 70° C. for 1 h, it was cooled down and quenched with sat. NaHCO₃ (100 mL). The mixture was extracted with EtOAc (50 mL) and the combined organic layers were washed with brine, dried with Na₂SO₄, filtered, concentrated. The crude oil was purified by column chromatography (petroleum ether/ethyl acetate: 8:1) to afford the title compound (1e) (5.5 g 68% yield) as a yellow solid. m/z (ESI, +ve ion)=510.4 [M+H]⁺.

Step F. Ethyl 2-(((3aR,4R,6R,6aR)-6-(4-((tert-butoxycarbonyl)cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)acetate (1f)

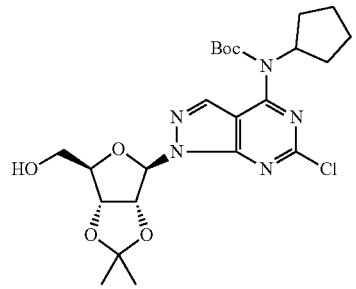
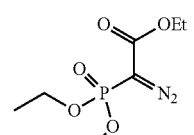

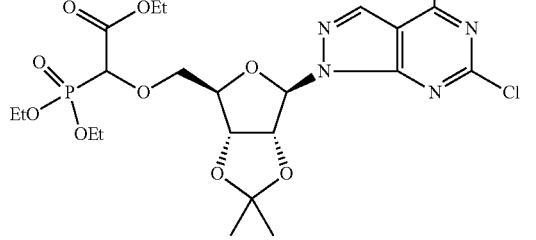

To a solution of ethyl 2-diazo-2-(diethoxyphosphoryl)acetate (13.5 g, 54.13 mmol) and 1e (5.5 g, 10.83 mmol) in toluene (80 mL) was added Rh$_2$(OAc)$_4$ (0.9 g, 2.17 mmol) under N$_2$. After the mixture was stirred at 95° C. overnight, it was concentrated and purified by column chromatography (petroleum ether/ethyl acetate: 5:1) to afford the title compound (1f) (6 g, 76% yield) as a yellow oil. m/z (ESI, +ve ion)=732.2 [M+H]$^+$.

Step G. (1-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-2-ethoxy-2-oxoethyl)phosphonic acid (1)

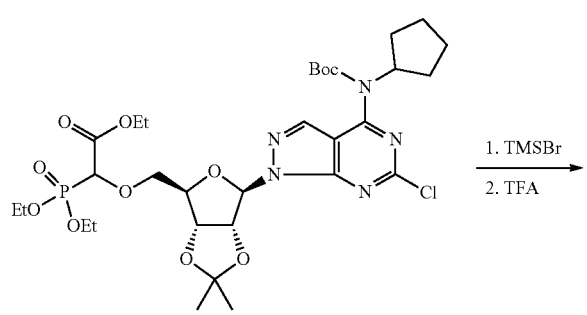

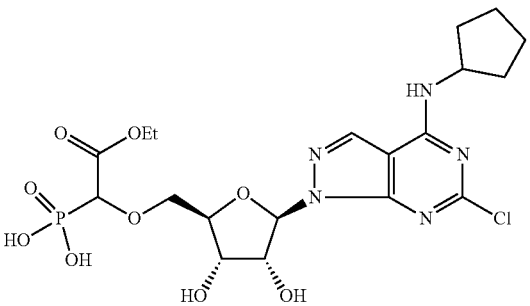

The title compound was prepared from 1f by procedure similar to that described in Example 3, Step C. m/z (ESI, +ve ion)=536.54 [M+H]$^+$.

Example 2. ((((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)(cyano)methyl)phosphonic acid (2)

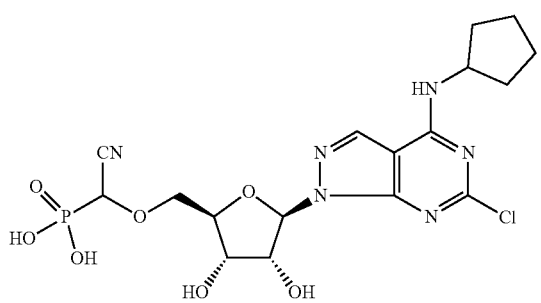 [SMILES: N#CC(OC[C@H]1O[C@@H](n2ncc3c(NC4CCCC4)nc(Cl)nc32)[C@H](O)[C@@H]1O)P(=O)(O)O]

The title compound was prepared from 1e by procedures similar to these described in Example 1, Steps F and G, substituting diethyl (cyano(diazo)methyl)phosphonate for ethyl 2-diazo-2-(diethoxyphosphoryl)acetate in Step F. m/z (ESI, +ve ion)=489.15 [M+H]$^+$.

Example 3. ((S)-1-(((2R,3S,4R,5R)-5-(6-Chloro-4-(cyclopentylamino)-1H-pyrazolo[3,4d]pyrimidin-1-yl)-3,4-dihydroxytetrahydrofuran-2-yl)methoxy)-2-hydroxyethyl)phosphonic acid (3)

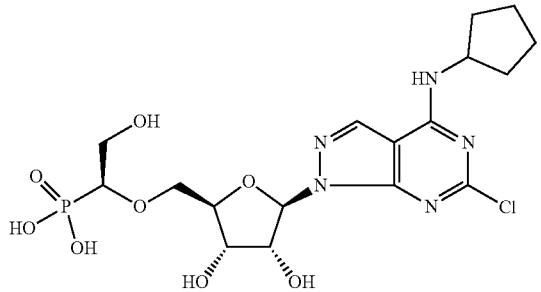 [SMILES: O=P(O)(O)[C@@H](CO)OC[C@H]1O[C@@H](n2ncc3c(NC4CCCC4)nc(Cl)nc32)[C@H](O)[C@@H]1O]

Step A. tert-Butyl (6-chloro-1-((3aR,4R,6R,6aR)-6-((1-(diethoxyphosphoryl)-2-hydroxyethoxy)methyl)-2,2-dimethyltetrahydrofuro[3,4-d][1,3]dioxol-4-yl)-1H-pyrazolo[3,4-d]pyrimidin-4-yl)(cyclopentyl)carbamate (3a)

Step B. tert-Butyl (6-chloro-1-((3aR,4R,6R,6aR)-6-(((S)-1-(diethoxyphosphoryl)-2-hydroxyethoxy)methyl)-2,2-dimethyltetrahydrofuro[3,4-d][1,3]dioxol-4-yl)-1H-pyrazolo[3,4-d]pyrimidin-4-yl)(cyclopentyl)carbamate (3b-1) and tert-butyl (6-chloro-1-((3aR,4R,6R,6aR)-6-(((R)-1-(diethoxyphosphoryl)-2-hydroxyethoxy)methyl)-2,2-dimethyltetrahydrofuro[3,4-d][1,3]dioxol-4-yl)-1H-pyrazolo[3,4-d]pyrimidin-4-yl)(cyclopentyl)carbamate (3b-2)

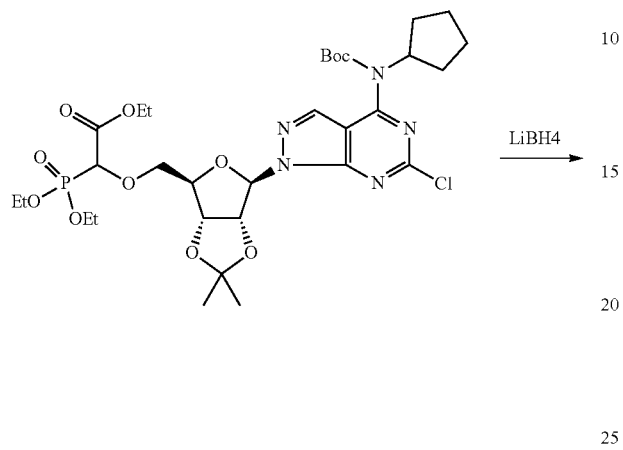

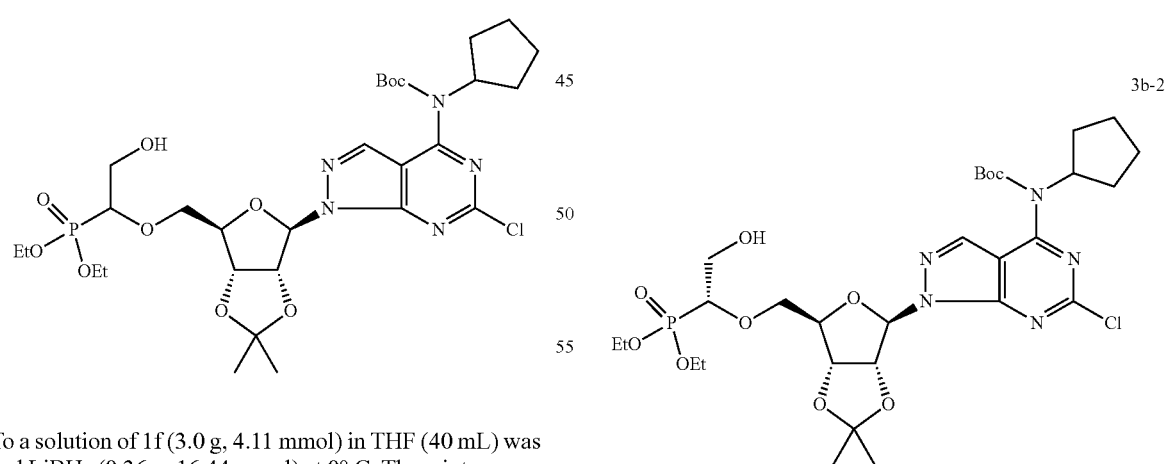

To a solution of 1f (3.0 g, 4.11 mmol) in THF (40 mL) was added LiBH$_4$ (0.36 g, 16.44 mmol) at 0° C. The mixture was stirred at rt for 30 min and then quenched with sat.NH$_4$Cl (10 mL). The solution was extracted with EtOAc and the combined organic layer was washed with brine, dried with Na$_2$SO$_4$, filtered, concentrated. The crude oil was purified by column chromatography (petroleum ether/ethyl acetate: 2:1) to afford the title compound (3a) (1.75 g, 62% yield) as a yellow oil. m/z (ESI, +ve ion)=690.4 [M+H]$^+$.

3a (1.3 g, 1.89 mmol) was separated by chiral preparative HPLC (Chiralpak AD, 15% EtOH in hexanes with 0.1% DEA) to provide the title compound (3b-1)(390 mg, faster eluting isomer) and (3b-2) (525 mg, slower eluting isomer). The stereochemistry of the carbon alpha to the phosphorus center is assigned arbitrarily.

Step C. ((S)-1-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-2-hydroxyethyl)phosphonic acid (3)

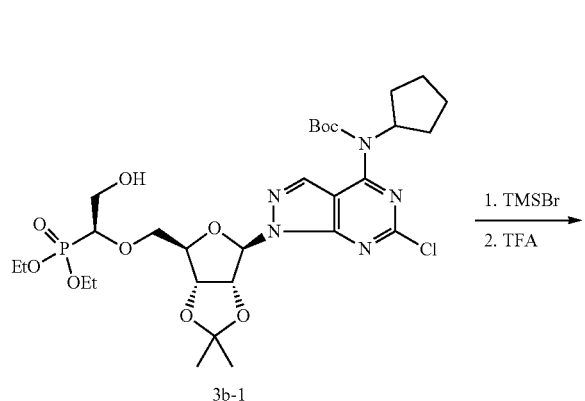

3b-1

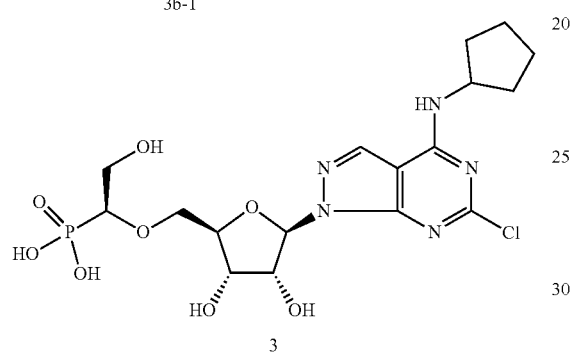

3

To a solution of 3b-1 (390 mg, 0.57 mmol) and TEA (2.29 g, 22.67 mmol) in MeCN (10 mL) was added TMSBr (2.6 g, 17.1 mmol). The mixture was stirred at rt for 2 h and then was concentrated under reduced pressure to afford a crude product, which was used directly without further purification.

To a solution of the crude product was added 50% TFA (15 mL). After the mixture was stirred at rt for 1 h, it was diluted with water (6 mL) and MeCN (5 mL). The solution was purified by reverse preparative HPLC to give the title compound (3) (115 mg, 41% yield). m/z (ESI, +ve ion) =494.3 [M+H]$^+$.

Example 4. ((R)-1-(((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)-2-hydroxyethyl)phosphonic acid (4)

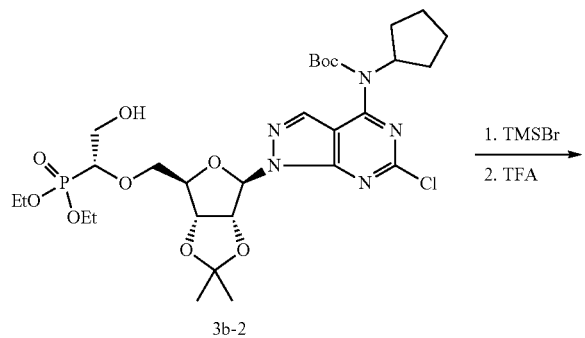

3b-2

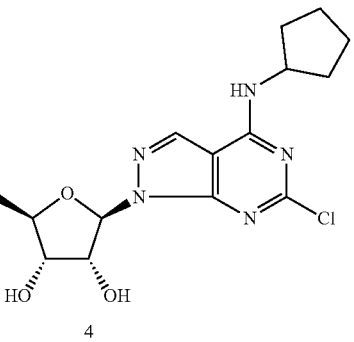

4

The title compound was prepared from 3b-2 by procedure similar to that described in Example 3, Step C. m/z (ESI, +ve ion)=693.9 [M+H]$^+$.

Example 5. (1-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)ethyl)phosphonic acid (5)

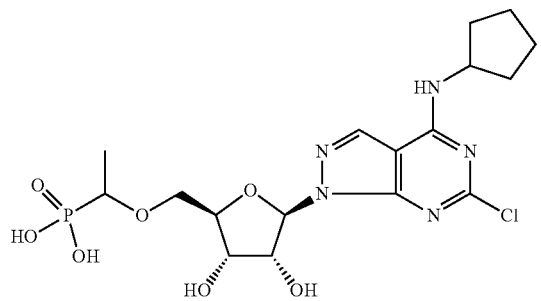 [SMILES: CC(OC[C@H]1O[C@@H](n2ncc3c(NC4CCCC4)nc(Cl)nc32)[C@H](O)[C@@H]1O)P(=O)(O)O]

Step A. O-(2-(((3aR,4R,6R,6aR)-6-(4-((tert-Butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)ethyl) 1H-imidazole-1-carbothioate (5a)

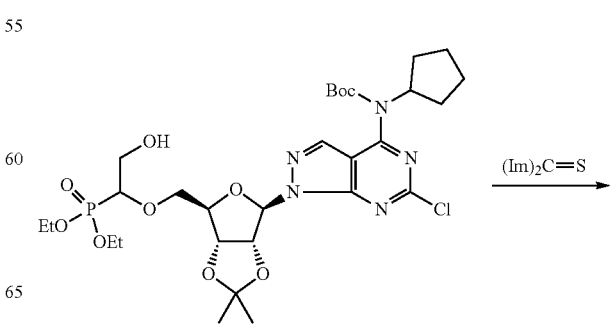

301

-continued

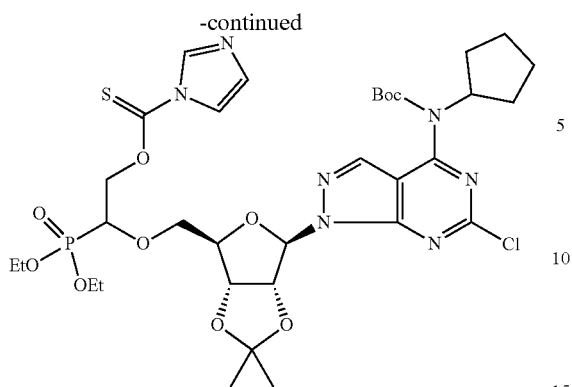

To a solution of 3a (450 mg, 0.65 mmol) and TEA (66 mg, 0.65 mmol) in DCM (10 mL) was added (Im)₂CS (1.17 g, 6.5 mmol). The mixture was stirred at rt overnight, and then quenched with sat.NH₄Cl (10 mL). The mixture was extracted with DCM and combined organic layer was washed with brine, dried with Na₂SO₄, filtered, concentrated. The crude oil was purified by column chromatography to afford the title compound (5a) (260 mg, 56% yield) as a yellow oil. m/z (ESI, +ve ion)=800.7 [M+H]⁺.

Step B. tert-Butyl (6-chloro-1-((3aR,4R,6R,6aR)-6-((1-(diethoxyphosphoryl)ethoxy)methyl)-2,2-dimethyltetrahydrofuro[3,4-d][1,3]dioxo-4-yl)-H-pyrazolo[3,4-d]pyrimidin-4-yl)(cyclopentyl)carbamate (5b)

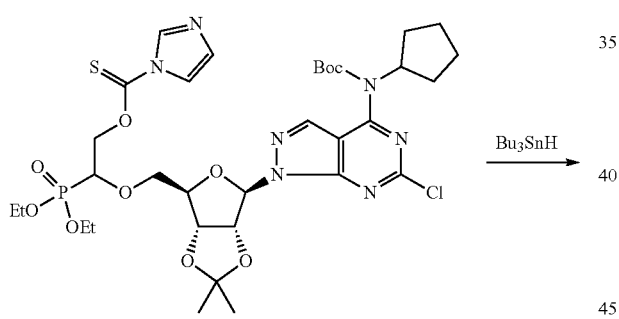

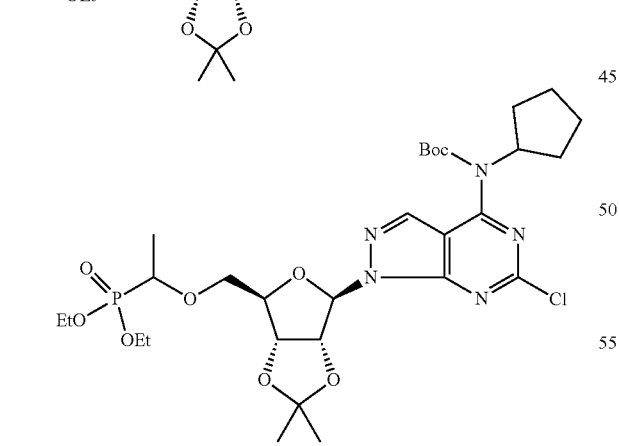

To a solution of Bu₃SnH (110 mg, 0.39 mmol) in toluene (8 mL) was added a solution of 5a (260 mg, 0.33) in toluene (2 mL). The reaction mixture was heated to reflux. After the mixture was stirred at reflux for 2 h, it was concentrated and purified by column chromatography to afford the title compound (5b) (68 mg, 31% yield) as a yellow oil. m/z (ESI, +ve ion)=674.6 [M+H]⁺.

302

Step C. (1-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)ethyl)phosphonic acid (5)

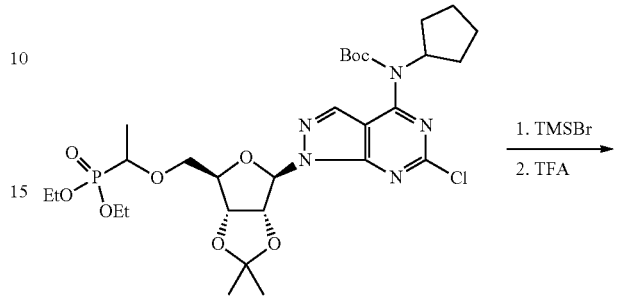

The title compound was prepared from 5b by procedure similar to that described in Example 3, Step C. m/z (ESI, +ve ion)=478.0 [M+H]⁺.

Example 6. ((S)-1-((((2S,3S,4R,5R)-5-(6-Chloro-4-(cyclopentylamino)-1H-pyrazolo[3,4-d]pyrimidin-1-yl)-3,4-dihydroxytetrahydrofuran-2-yl)methyl)sulfonyl)ethyl)phosphonic acid (6)

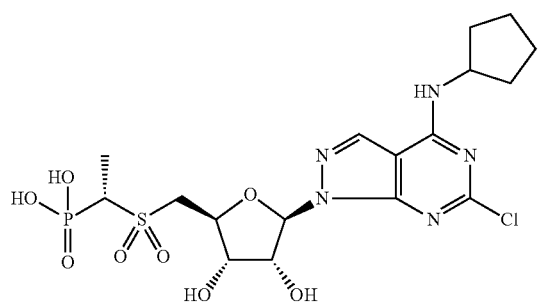 [SMILES: C[C@@H](P(=O)(O)O)S(=O)(=O)C[C@H]1O[C@@H](n2ncc3c(NC4CCCC4)nc(Cl)nc32)[C@H](O)[C@@H]1O]

303

Step A. S-(((3aS,4S,6R,6aR)-6-(6-Chloro-4-(cyclopentyl(methyl)amino)-1H-pyrazolo[3,4-d]pyrimidin-1-yl)-2,2-dimethyltetrahydrofuro[3,4-d][1,3]dioxol-4-yl)methyl)ethanethioate (6a)

Step B. ((3aS,4S,6R,6aR)-6(6-Chloro-4-(cyclopentylamino)-1H-pyrazolo[3,4-d]pyrimidin-1-yl)-2,2-dimethyltetrahydrofuro[3,4-d][1,3]dioxol-4-yl)methanethiol (6b)

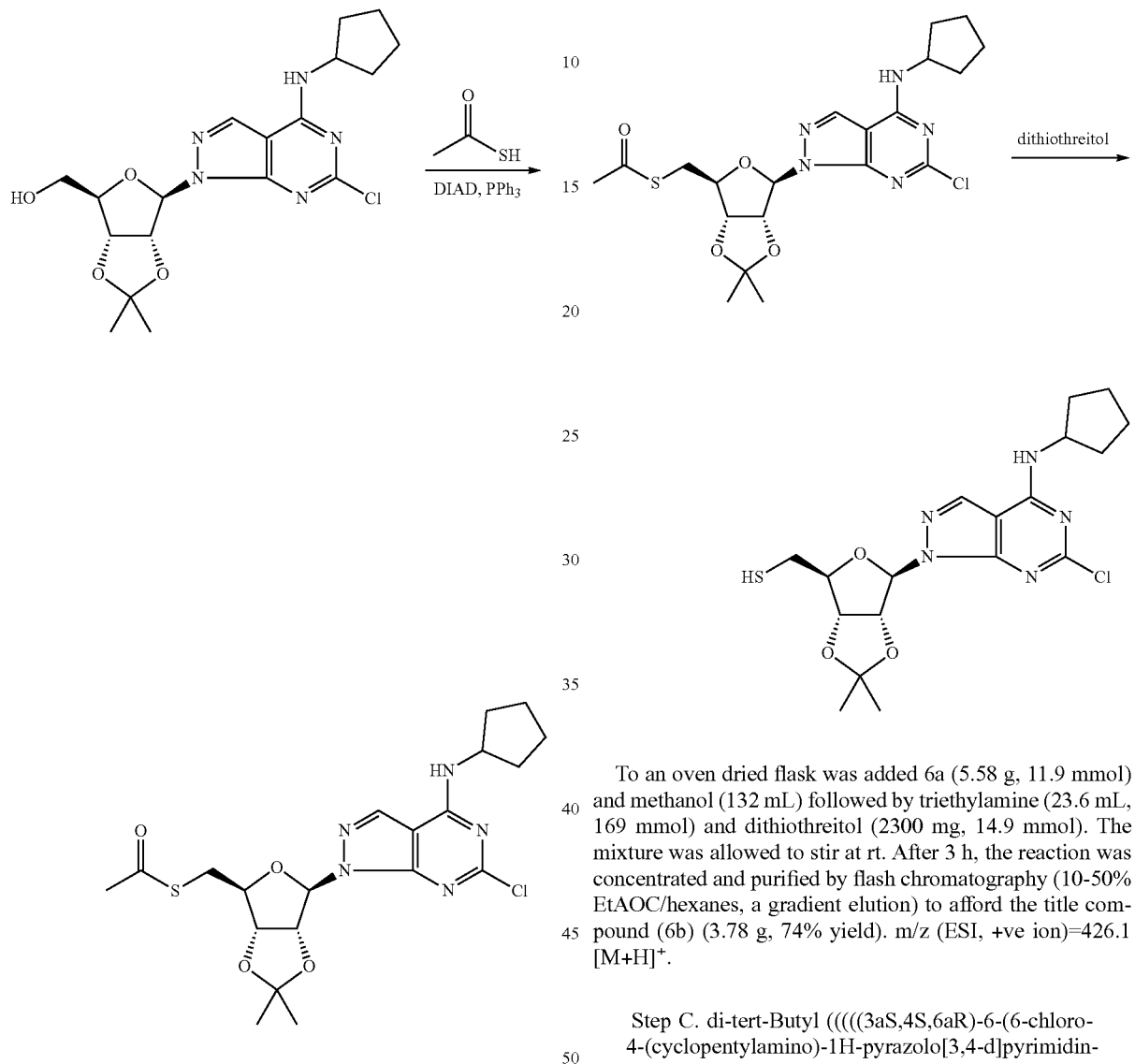

To an oven dried flask was added diisopropyl azodicarboxylate (1.96 mL, 9.93 mmol) and THF (50 mL) followed by triphenylphosphine (2600 mg, 9.93 mmol) at 0° C. The mixture was stirred for 5 min and a white precipitate formed. To the mixture was added ((3aR,4R,6R,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methanol (N-Boc-deprotected analog of 1e) (1.85 g, 4.51 mmol) and thioacetic acid (0.71 mL, 9.9 mmol). The mixture was then stirred overnight and slowly allowed to warm to rt. The clear mixture was quenched with triethylamine (0.3 mL) and concentrated. The residue was purified by flash chromatography (10-50% EtOAc/hexanes, a gradient elution) to give the crude product (6a) (2.9 g, 99% yield), which was used for the next step without further purification. m/z (ESI, +ve ion)=468.1 [M+H]$^+$.

To an oven dried flask was added 6a (5.58 g, 11.9 mmol) and methanol (132 mL) followed by triethylamine (23.6 mL, 169 mmol) and dithiothreitol (2300 mg, 14.9 mmol). The mixture was allowed to stir at rt. After 3 h, the reaction was concentrated and purified by flash chromatography (10-50% EtAOC/hexanes, a gradient elution) to afford the title compound (6b) (3.78 g, 74% yield). m/z (ESI, +ve ion)=426.1 [M+H]$^+$.

Step C. di-tert-Butyl (((((3aS,4S,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methyl)thio)methyl)phosphonate (6c)

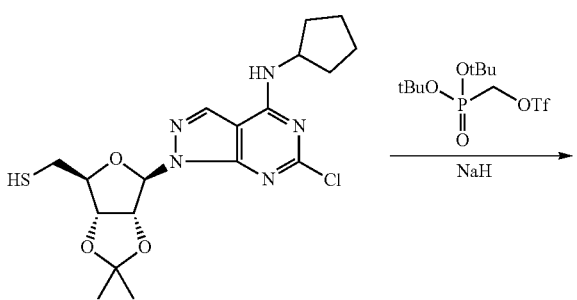

-continued

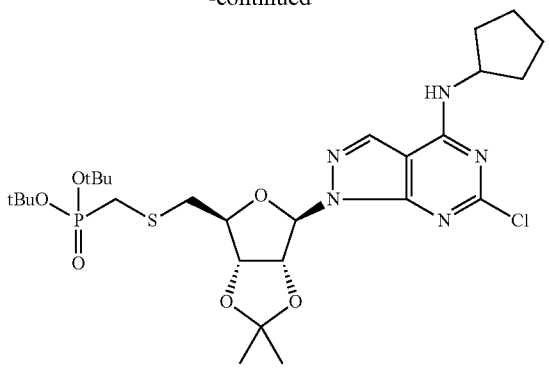

To an oven dried flask was added sodium hydride (380 mg, 9.5 mmol) and DMF (50 mL) and the flask was cooled to 0° C. To this flask was added 6b (3.68 mg, 8.63 mmol) dissolved in DMF (15 mL). After 30 min, ditert-butoxyphosphorylmethyl trifluoromethanesulfonate (4.65 g, 11.2 mmol) dissolved in DMF (4 mL) was added and the mixture was allowed to warm to rt and stirred for 1 h. The reaction mixture was quenched (sat. NH₄Cl) and extracted (EtOAc). The combined organic layers were dried with MgSO₄, filtered, and concentrated. The resulting residue was purified by flash chromatography (50-100% EtOAc/hexanes, a gradient elution) to provide the title compound (6c) (5.4 g, 99% yield). m/z (ESI, +ve ion)=630.2 [M+H]⁺.

Step D. tert-butyl (6-Chloro-1-((3aR,4R,6S,6aS)-6-(((((di-tert-butoxyphosphoryl)methyl)thio)methyl)-2,2-dimethyltetrahydrofuro[3,4-d][1,3]dioxol-4-yl)-1H-pyrazolo[3,4-d]pyrimidin-4-yl)(cyclopentyl)carbamate (6d)

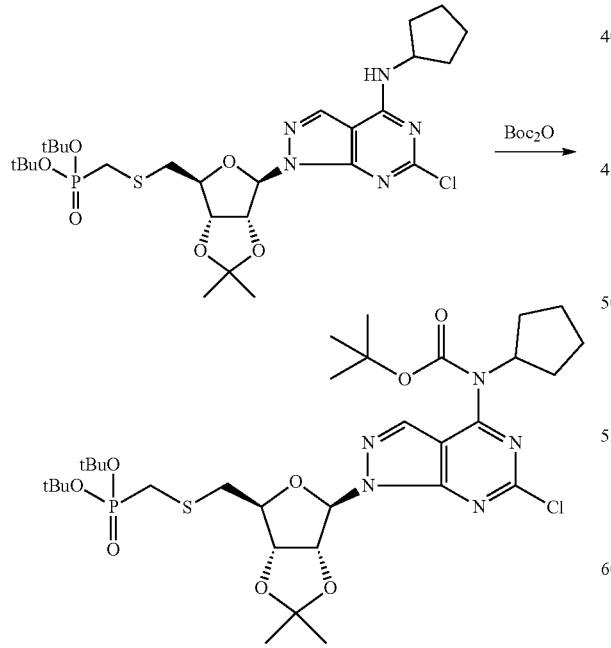

To an oven dried flask with 6c (5.4 g, 8.54 mmol) was added MeCN (77 mL). To this solution was added triethylamine (3.57 mL, 25.6 mmol) followed by di-tert-butyl dicarbonate (5.89 mL, 25.63 mmol) and 4-dimethylaminopyridine (104 mg, 0.850 mmol). The mixture was allowed to stir overnight and then concentrated. The resulting residue was purified by flash chromatography (0-80% EtOAc/hexanes, a gradient elution) to give the title compound (6d) (5.6 g, 90% yield). m/z (ESI, +ve ion)=520.2 [M+H]⁺.

Step E. tert-Butyl (6-Chloro-1-((3aR,4R,6S,6aS)-6-(((((di-tert-butoxyphosphoryl)methyl)sulfonyl)methyl)-2,2-dimethyltetrahydrofuro[3,4-d][1,3]dioxol-4-yl)-1H-pyrazolo[3,4-d]pyrimidin-4-yl)(cyclopentyl)carbamate (6e)

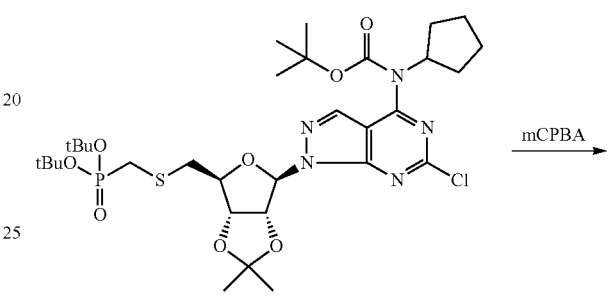

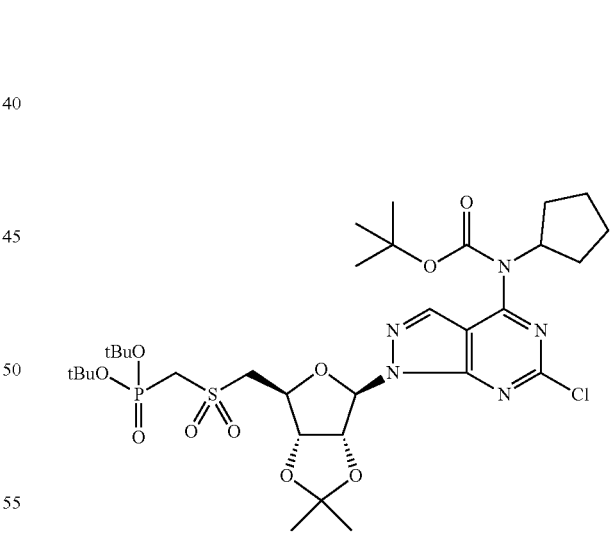

To an oven dried flask was added 6d (5.6 g, 7.7 mmol) followed by DCM (100 mL). To this mixture was added mCPBA (3.52 g, 15.3 mmol). After the mixture was stirred at rt for 3 h, it was quenched with sat. NaHCO₃ and extracted with DCM. The combined organic layers were dried with MgSO₄, filtered, and concentrated. The resulting residue was purified by flash chromatography (0-8% EtOAc/hexanes, a gradient elution) to give the title (6e) (4.8 g, 6.3 mmol, 82% yield). m/z (ESI, +ve ion)=552.1 [M+H]⁺.

307

Step F. tert-Butyl (6-chloro-1-((3aR,4R,6S,6aS)-6-((((R)-1-(di-tert-butoxyphosphoryl)ethyl)sulfanyl)methyl)-2,2-dimethyltetrahydrofuro[3,4-d][1,3]dioxol-4-yl)-1H-pyrazolo[3,4-d]pyrimidin-4-yl)(cyclopentyl)carbamate (6f-1) and tert-butyl (6-chloro-1-((3aR,4R,6S,6aS)-6-((((S)-1-(di-tert-butoxyphosphoryl)ethyl)sulfonyl)methyl)-2,2-dimethyltetrahydrofuro[3,4-d][1,3]dioxol-4-yl)-1H-pyrazolo[3,4-d]pyrimidin-4-yl)(cyclopentyl)carbamate (6f-2)

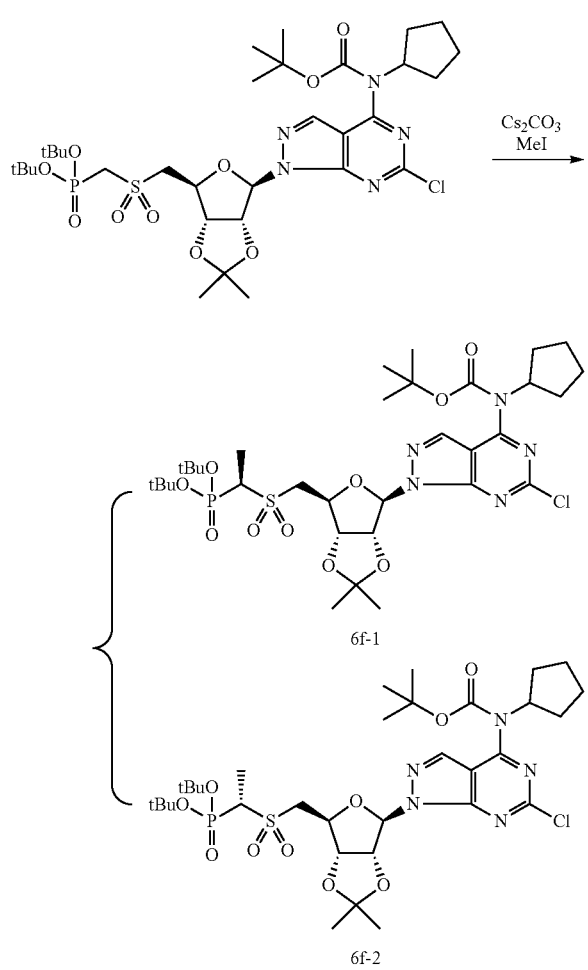

To an oven dried flask was added 6e (187 mg, 0.24 mmol) followed by DMF (7.5 mL). To this solution was added cesium carbonate (168 mg, 0.52 mmol) and the solution was stirred for 20 min. Then methyl iodide (0.03 mL, 0.52 mmol) was added and the mixture was allowed to stir at 45° C. for 4 h. The reaction mixture was cooled to rt and partitioned between water and EtOAc. The aqueous layer was extracted an additional time with EtOAc. The combined organic layers were dried with MgSO$_4$, filtered, and concentrated. The resulting residue was purified by flash column chromatography (0-50% EtOAc/hexanes, a gradient elution) to afford the title compound (6f-2)(56.7 mg, faster eluting isomer) and (6f-1) (58 mg, slower eluting compound). m/z (ESI, +ve ion)=566.0 [M−2tBu−Boc+4H]$^+$. The stereochemistry of the carbon alpha to the phosphorus center is assigned arbitrarily.

308

Step G. ((S)-1-(((2S,3S,4R,5R)-5-(6-Chloro-4-(cyclopentylamino)-1H-pyrazolo[3,4-d]pyrimidin-1-yl)-3,4-dihydroxytetrahydrofuran-2-yl)methyl)sulfonyl)ethyl)phosphonic acid (6)

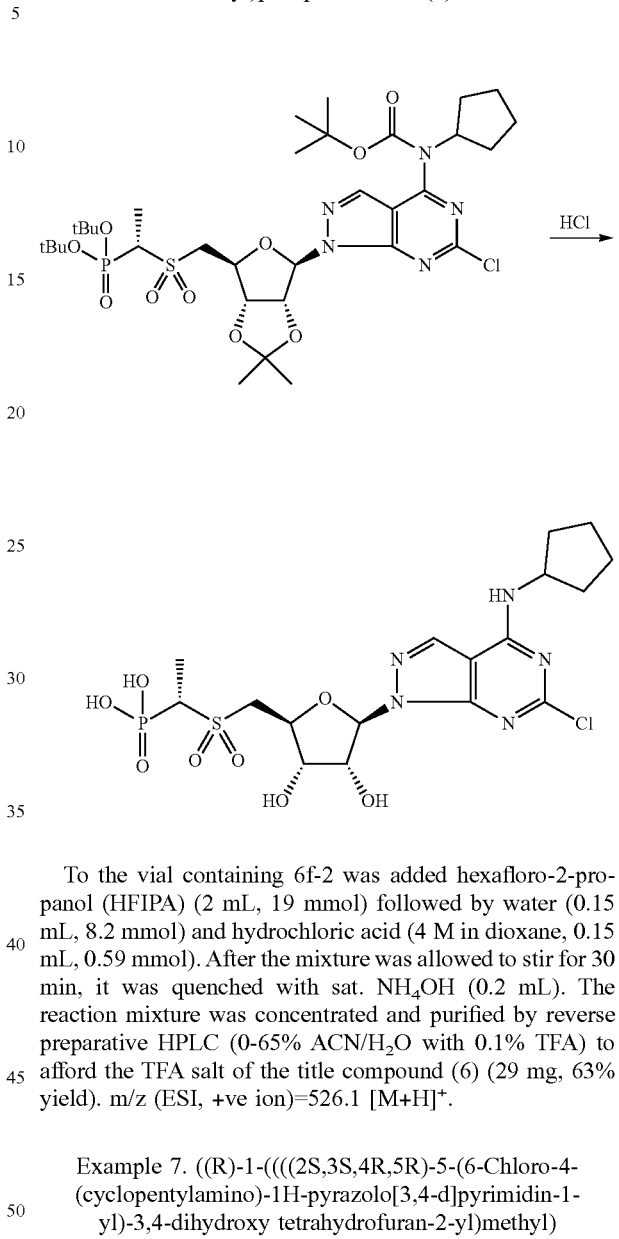

To the vial containing 6f-2 was added hexafloro-2-propanol (HFIPA) (2 mL, 19 mmol) followed by water (0.15 mL, 8.2 mmol) and hydrochloric acid (4 M in dioxane, 0.15 mL, 0.59 mmol). After the mixture was allowed to stir for 30 min, it was quenched with sat. NH$_4$OH (0.2 mL). The reaction mixture was concentrated and purified by reverse preparative HPLC (0-65% ACN/H$_2$O with 0.1% TFA) to afford the TFA salt of the title compound (6) (29 mg, 63% yield). m/z (ESI, +ve ion)=526.1 [M+H]$^+$.

Example 7. ((R)-1-((((2S,3S,4R,5R)-5-(6-Chloro-4-(cyclopentylamino)-1H-pyrazolo[3,4-d]pyrimidin-1-yl)-3,4-dihydroxy tetrahydrofuran-2-yl)methyl)sulfonyl)ethyl)phosphonic acid (7)

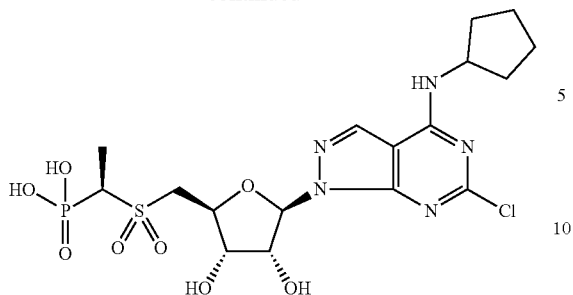

The title compound was prepared from 6f-1 by procedure similar to that described in Example 6, Step G. m/z (ESI, +ve ion)=526.1 [M+H]⁺.

Example 8. (2-((((2S,3S,4R,5R)-5-(6-Chloro-4-(cyclopentylamino)-1H-pyrazolo[3,4-d]pyrimidin-1-yl)-3,4-dihydroxytetrahydrofuran-2-yl)methyl)sulfonyl)-1-hydroxypropan-2-yl)phosphonic acid (8)

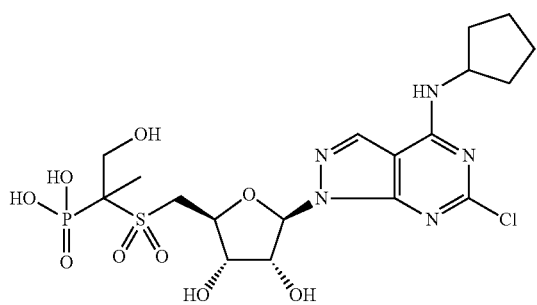 [SMILES: CC(CO)(P(=O)(O)O)S(=O)(=O)C[C@H]1O[C@@H](n2ncc3c(NC4CCCC4)nc(Cl)nc32)[C@H](O)[C@@H]1O]

Step A. S-(((3aS,4S,6R,6aR)-6-(4-((tert-Butoxycarbonyl)cyclopentyl)amino)-6-chloro-1H-pyrazolo[3,4-d]pyrimidin-1-yl)-2,2-dimethyltetrahydrofuro[3,4-d][1,3]dioxol-4-yl)methyl)ethanethioate (8a)

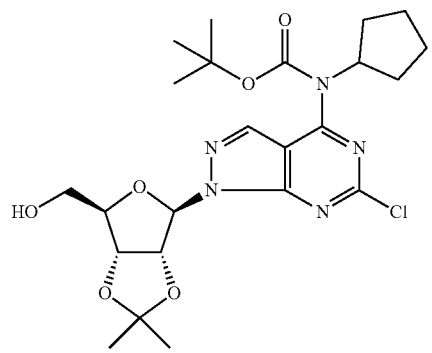

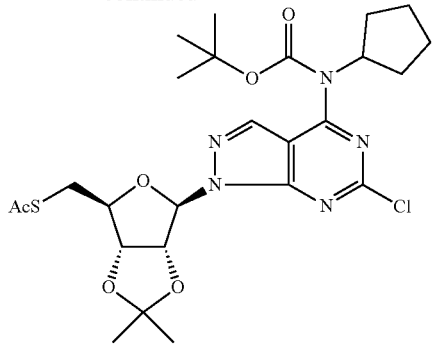

To an oven dried flask was added (E)-diisopropyl azodicarboxylate (1.75 mL, 8.89 mmol) and THF (45 mL) followed by triphenylphosphine (2.33 g, 8.89 mmol) at 0° C. The mixture was stirred for 5 min and a white precipitate formed. To the mixture was added tert-butyl (6-chloro-1-((3aR,4R,6R,6aR)-6-(hydroxymethyl)-2,2-dimethyltetrahydrofuro[3,4-d][1,3]dioxol-4-yl)-1H-pyrazolo[3,4-d]pyrimidin-4-yl)(cyclopentyl)carbamate (1e) (2.06 g, 4.04 mmol) and thioacetic acid (0.64 mL, 8.9 mmol). The mixture was then stirred overnight and slowly allowed to warm to rt. The clear mixture was quenched with triethylamine (0.3 mL) and concentrated. The residue was purified by flash (10-50%, EtOAc/hexanes, a gradient elution) to provide the title compound (8a) (2.9 g, 79% purity, 100% yield). m/z (ESI, +ve ion)=568.2 [M+H]⁺.

Step B. tert-Butyl (6-chloro-1-((3aR,4R,6S,6aS)-6-(mercaptomethyl)-2,2-dimethyltetrahydrofuro[3,4-d][1,3]dioxol-4-yl)-1H-pyrazolo[3,4-d]pyrimidin-4-yl)(cyclopentyl)carbamate (8b)

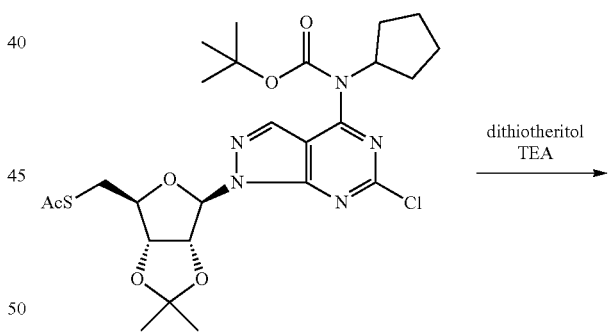

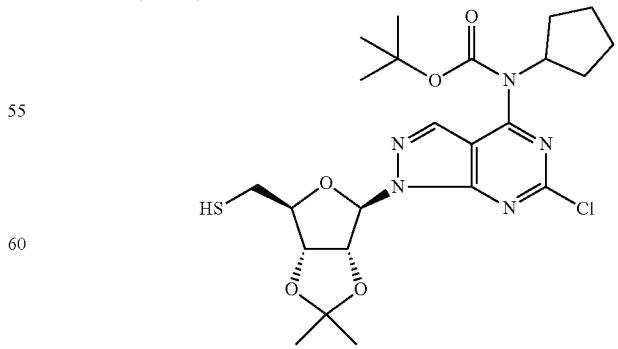

To a flask containing 8a (2.91 g, 4.04 mmol) was added methanol (57 mL) followed by triethylamine (8.0 mL, 57

311 mmol). To this mixture was added DL-dithiothreitol (778 mg, 5.04 mmol). After 2 h, the mixture was concentrated and purified by flash chromatography (0-30% EtOAc/hexanes, a gradient elution) to give the title compound (8b) (1.87 g, 88.0% yield). m/z (ESI, +ve ion)=526.2 [M+H]$^+$.

Step C. Ethyl 2-((((3aS,4S,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methyl)thio)-2-(diethoxyphosphoryl)acetate (8c)

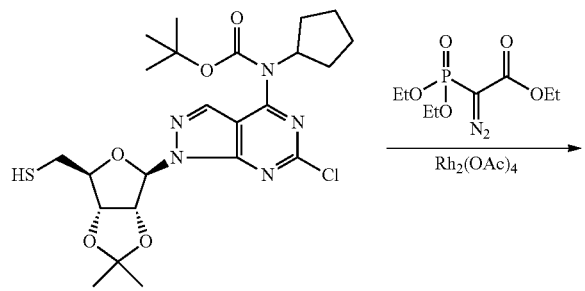

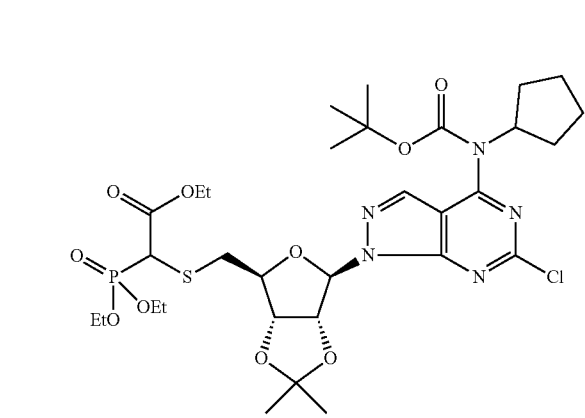

To an oven dried flask was added 8b (515 mg, 0.98 mmol) followed by 1-[diazomethyl(ethoxy)phosphoryl]oxyethane ethyl acetate (274 mg, 1.03 mmol) and dirhodium tetraacetate (8.65 mg, 0.02 mmol). This mixture was dissolved in toluene (16 mL) and heated at 100° C. overnight. More dirhodium tetraacetate (8.65 mg, 0.02 mmol) was added and the mixture was stirred at 100° C. for another 2 h. The mixture was concentrated and purified by flash chromatography (0-80% EtOAc/hexanes, a gradient elution) to afford the title compound (8c) (483 mg, 66.0% yield) as a mixture of two diastereomers. m/z (ESI, +ve ion)=748.3 [M+H]$^+$.

312

Step D. tert-Butyl (6-chloro-1-((3aR,4R,6S,6aS)-6-(((2-(diethoxyphosphoryl-1-hydroxypropan-2-yl)thio)methyl)-2,2-dimethyltetrahydrofuro[3,4-d][1,3]dioxol-4-yl)-1H-pyrazolo[3,4-d]pyrimidin-4-yl)(cyclopentyl)carbamate (8d)

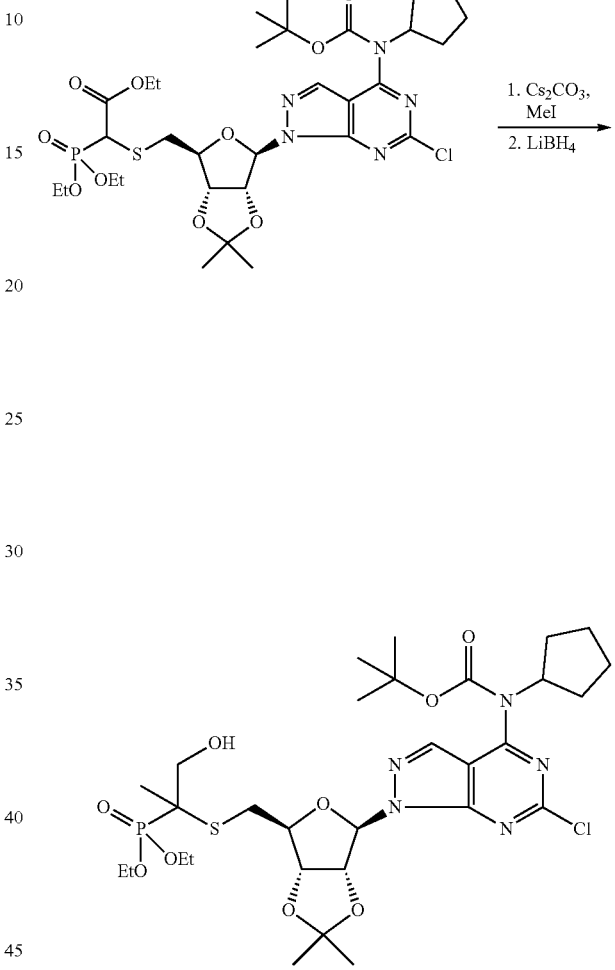

To an oven dried flask was added 8c (600 mg, 0.8 mmol) followed by DMF (8 mL) and cesium carbonate (549 mg, 1.68 mmol). To this mixture was added methyl iodide (0.1 mL, 1.7 mmol). After the solution was stirred overnight, it was cooled to rt and partitioned between water and EtOAc. The aqueous layer was extracted an additional time with EtOAc. The combined organic layers were dried with MgSO$_4$, filtered, and concentrated. The resulting residue was purified by flash column chromatography (0-40% EtOAc/hexanes, a gradient elution) to give the crude product. To the crude product (377 mg, 0.490 mmol) and THF (4.8 mL) was added lithium borohydride (10.8 mg, 0.49 mmol). After 30 min, the reaction was quenched (sat. NH$_4$Cl) and was extracted (EtOAc). The combined organic layers were dried with MgSO$_4$, filtered, and concentrated. The resulting residue was purified by flash chromatography (0-100% EtOAc/hexanes, a gradient elution) to provide the title compound (8d) (139 mg, 39.0% yield) as a mixture of two diastereomers. m/z (ESI, +ve ion)=720.2 [M+H]$^+$.

Step E. tert-Butyl (6-chloro-14(3aR,4R,6S,6aS)-(((2-(diethoxyphosphoryl)-1-hydroxypropan-2-yl)sulfonyl)methyl)-2,2-dimethyltetrahydrofuro[3,4-d][1,3]dioxol-4-yl)-1H-pyrazolo[3,4-d]pyrimidin-4-yl)(cyclopentyl)carbamate (8e)

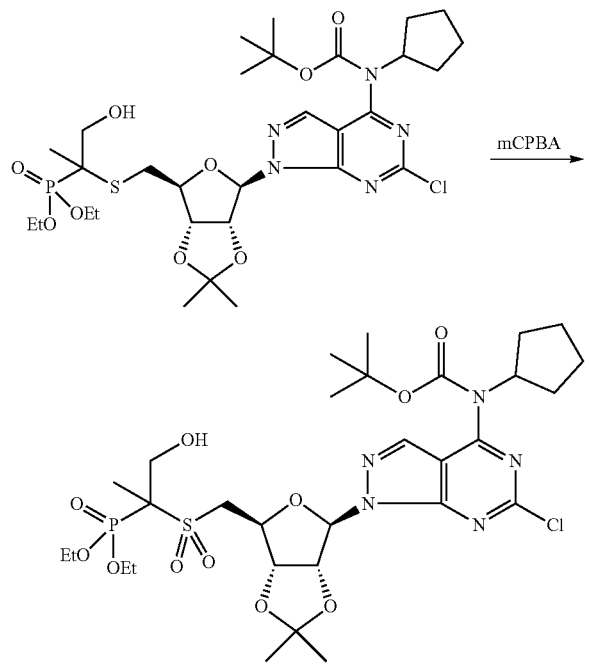

To a vial was added 8d (139 mg, 0.190 mmol) and DCM (7 mL) followed by mCPBA (88.8 mg, 0.39 mmol). The reaction mixture was stirred for 1 h and then quenched with sat NaHCO$_3$. The aqueous layer was extracted with DCM. The combined organic layers were dried with MgSO$_4$, filtered, and concentrated. The resulting residue was purified by flash chromatography (0-100% EtOAc/hexanes, a gradient elution) to give the title compound (Se) (128 mg, 88.2% yield) as a mixture of two diastereomers. m/z (ESI, +ve ion)=752.2 [M+H]$^+$.

Step F. (2-((((2S,3S,4R,5R)-5-(6-chloro-4-(cyclopentylamino)-1H-pyrazolo[3,4-d]pyrimidin-1-yl)-3,4-dihydroxytetrahydrofuran-2-yl)methyl)sulfonyl)-1-hydroxypropan-2-yl)phosphonic acid (8)

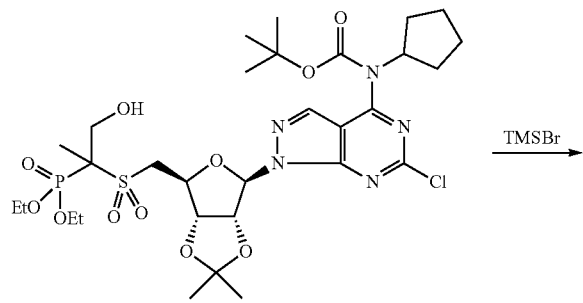

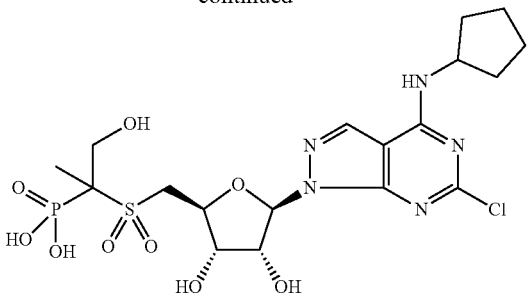

To a vial was added 8e (127 mg, 0.170 mmol) followed by MeCN (2.8 mL). To this solution was added bromo(trimethyl)silane (0.15 mL, 1.2 mmol) and the mixture was allowed to stir. After 4 h. another lot of bromo(trimethyl)silane (0.15 mL, 1.2 mmd) was added. After one additional hour, water (0.40 mL) was added and the mixture was allowed to stir overnight. The following morning, more water (0.40 mL) was added and the reaction was complete after 1 h. The mixture was quenched with aqueous NH$_4$OH (0.5 mL) and concentrated. The resulting residue was purified by reverse preparative HPLC (0-50% ACN/H$_2$O with 0.1% TFA) to give the title compound (8) (73.4 mg, 64.9% yield) as a mixture of two diastereomers. m/z (ESI, +ve ion)=556.1 [M+H]$^+$.

Examples 9-14

Examples 9-14 were synthesized as described in examples 1-8.

| Ex | MS Data |
|----|---------|
| 9  | 602.1 [M + H]$^+$ |
| 10 | 602 [M + H]$^+$ |
| 11 | 508.1 [M + H]$^+$ |
| 12 | 508.1 [M + H]$^+$ |
| 13 | 493.9 [M + H]$^+$ |
| 14 | 492 [M + H]$^+$ |

Example 15. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-hydroxypropan-2-yl)phosphonic acid (15)

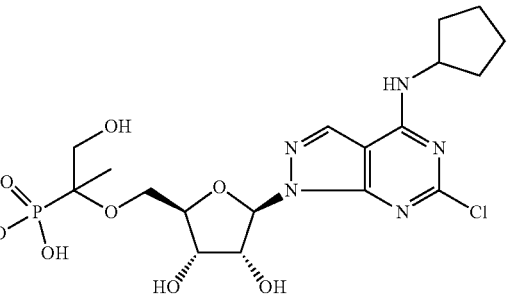

The title compound was prepared from 1e by procedures similar to these described in Example 8, Steps C, D, and F. m/z (ESI, +ve ion)=508.1 [M+H]$^+$.

Example 16. (((((2S,3S,4R,5R)-5-(5-Chloro-7-(cyclopentylamino)-3H-[1,2,3]triazolo[4,5-b]pyridin-3-yl)-3,4-dihydroxytetrahydrofuran-2-yl)methyl)sulfonyl)methylphosphonic acid (16)

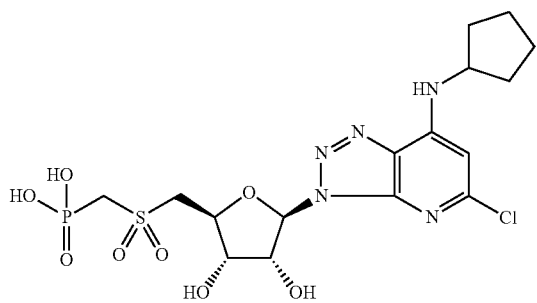 [SMILES: O=P(O)(O)CS(=O)(=O)C[C@H]1O[C@@H](n2nnc3c(NC4CCCC4)cc(Cl)nc32)[C@H](O)[C@@H]1O]

Step 1. ((3aR,4R,6R,6aR)-6-(5-Chloro-7-(cyclopentylamino)-3H-[1,2,3]triazolo[4,5-b]pyridin-3-yl)-2,2-dimethyltetrahydrofuro[3,4-d][1,3]dioxol-4-yl)methanol (16a)

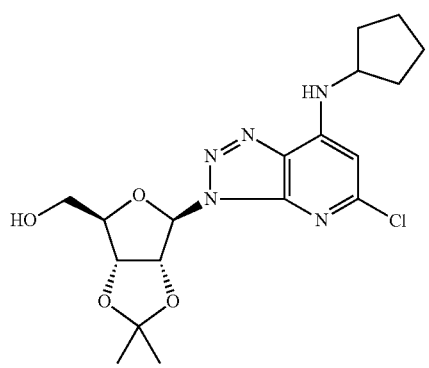 [SMILES: CC1(C)O[C@@H]2[C@H](O1)[C@@H](CO)O[C@H]2n1nnc2c(NC3CCCC3)cc(Cl)nc21]

The title compound was prepared from 5,7-dichloro-3H-[1,2,3]triazolo[4,5-b]pyridine by procedures similar to these described in Example 1, Steps A, B, D, and E, substituting 5,7-dichloro-3H-[1,2,3]triazolo[4,5-b]pyridine for 4,6-dichloro-1H-pyrazol[3,4-d]pyrimidine in Step A.

Step B. (((((2S,3S,4R,5R)-5-(5-Chloro-7-(cyclopentylamino)-3H-[1,2,3]triazolo[4,5-b]pyridin-3-yl)-3,4-dihydroxytetrahydrofuran-2-yl)methyl)sulfonyl)methyl)phosphonic acid (16)

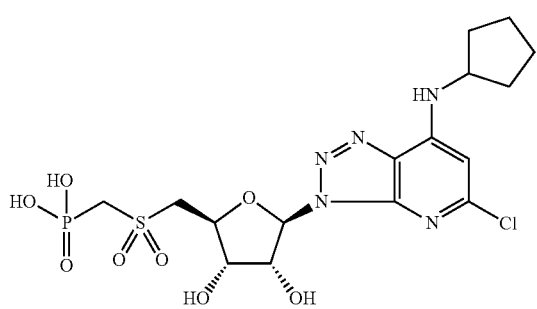 [SMILES: O=P(O)(O)CS(=O)(=O)C[C@H]1O[C@@H](n2nnc3c(NC4CCCC4)cc(Cl)nc32)[C@H](O)[C@@H]1O]

The title compound was prepared from 16a similar to these described in Example 6, Steps A-E, and G, m/z (ESI, +ve ion)=512.3 [M+H]$^+$.

Example 17. ((((2R,3S,4R,5R)-5-(5-Chloro-7-(cyclopentylamino)-3H-[1,2,3]triazolo[4,5-b]pyridin-3-yl)-3,4-dihydroxytetrahydrofuran-2-yl)methoxy)methyl)phosphonic acid (17)

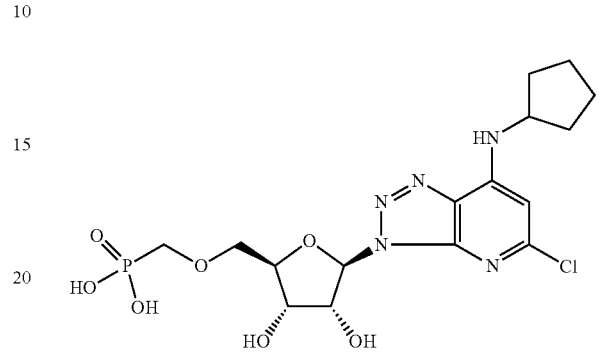

The title compound was prepared from 16a by procedures similar to these described in Example 6, Steps C and G, substituting 16a for 6b in Step C. m/z (ESI, +ve ion)=463.8 [M+H]$^+$.

Examples 18-54

Examples 18-54 were synthesized as described in examples 1-8 and 15-17.

| Ex. | MS Data |
|---|---|
| 18 | 540.3 [M + H]$^+$ |
| 19 | 540.3 [M + H]$^+$ |
| 20 | 463.9 [M + H]$^+$ |
| 21 | 450.1 [M + H]$^+$ |
| 22 | 520.1 [M + H]$^+$ |
| 23 | 447.9 [M − H]$^-$ |
| 24 | 464 [M + H]$^+$ |
| 25 | 498.1 [M + H]$^+$ |
| 26 | 518.1 [M − H]$^-$ |
| 27 | 568.1 [M + H]$^+$ |
| 28 | 508.1 [M + H]$^+$ |
| 29 | 440.4 [M + H]$^+$ |
| 30 | 480.1 [M + H]$^+$ |
| 31 | 508.12 [M + H]$^+$ |
| 32 | 477.9 [M + H]$^+$ |
| 33 | 478.2 [M + H]$^+$ |
| 34 | 556.1 [M + H]$^+$ |
| 35 | 532.1 [M + H]$^+$ |
| 36 | 538.1 [M + H]$^+$ |
| 37 | 582.4 [M + H]$^+$ |
| 38 | 542 [M + H]$^+$ |
| 39 | 541.9 [M + H]$^+$ |
| 40 | 478.3 [M + H]$^+$ |
| 41 | 566 [M − H]$^-$ |
| 42 | 507.98 [M + H]$^+$ |
| 43 | 496.1 [M + H]$^+$ |
| 44 | 522.2 [M + H]$^+$ |
| 45 | 522.1 [M + H]$^+$ |
| 46 | 508.3 [M + H]$^+$ |
| 47 | 563.2 [M + H]$^+$ |
| 48 | 599.2 [M + H]$^+$ |
| 49 | 557 [M + H]$^+$ |
| 50 | 557 [M + H]$^+$ |
| 51 | 520.1 [M + H]$^+$ |
| 52 | 537.2 [M + H]$^+$ |
| 53 | 527.8 [M + H]$^+$ |
| 54 | 542.0 [M + H]$^+$ |

Example 55. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-(methylthio)propan-2-yl)phosphonic acid (55)

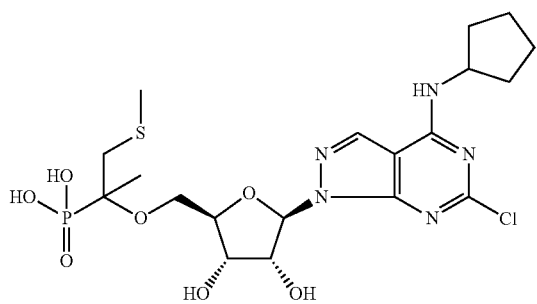 [SMILES: CSCC(C)(OC[C@H]1O[C@@H](n2ncc3c(NC4CCCC4)nc(Cl)nc32)[C@H](O)[C@@H]1O)P(=O)(O)O]

Step A. S-(2-(((3aR,4R,6R,6aR)-6-(4-((tert-Butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)propyl) ethanethioate (55a)

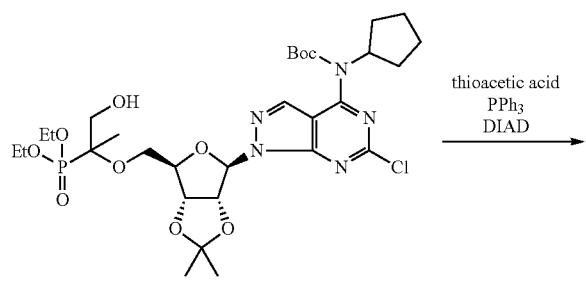

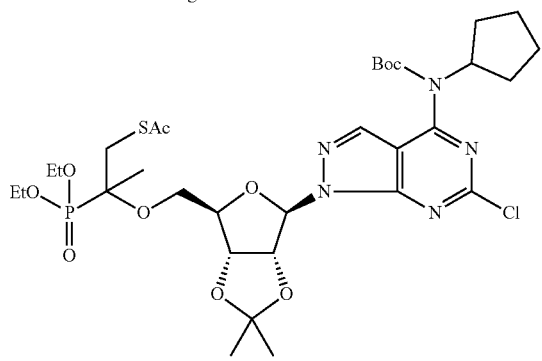

A dried flask was charged with triphenylphosphine (685 mg, 2.61 mmol) and THF (12 mL). After the solution was cooled to 0° C., DIAD (0.51 mL, 2.6 mmol) was added dropwise. The resulting mixture was stirred for 10 min and a white precipitate formed. In a separate flask, tert-butyl N-[1-[(3aR,4R,6R,6aR)-6-[(1-diethoxyphosphoryl-2-hydroxy-1-methyl-ethoxy)methyl]-2,2-dimethyl-3a,4,6,6a-tetrahydrofuro[3,4-d][1,3]dioxol-4-yl]-6-chloro-pyrazolo[3,4-d]pyrimidin-4-yl]-N-cyclopentyl-carbamate (ether analog of 8d) (800 mg, 1.14 mmol) was dissolved in THF (2 mL). This THF solution was added into the first flask, followed by thioacetic acid (0.19 mL, 2.6 mmol). The mixture was stirred and slowly warmed to rt overnight. The reaction was quenched with Et$_3$N (0.3 mL), concentrated and partitioned between water and EtOAc. The organic layer was washed with brine, dried with MgSO$_4$, filtered and concentrated. The crude oil was purified by flash chromatography (0-70% EtOAc/hexanes, a gradient elution) to give the title compound (55a) (400 mg, 0.53 mmol, 46% yield). m/z (ESI, +ve ion)=762.2 [M+H]$^+$.

Step B. tert-Butyl (6-chloro-1-(3aR,4R,6R,6aR)-6-(((2-(diethoxyphosphoryl)-1-mercaptopropan-2-yl)oxy)methyl)-2,2-dimethyltetrahydrofuro[3-d][1,3]dioxol-4-yl)-1H-pyrazolo[3,4-d]pyrimidin-4-yl)(cyclopentyl)carbamate (55b)

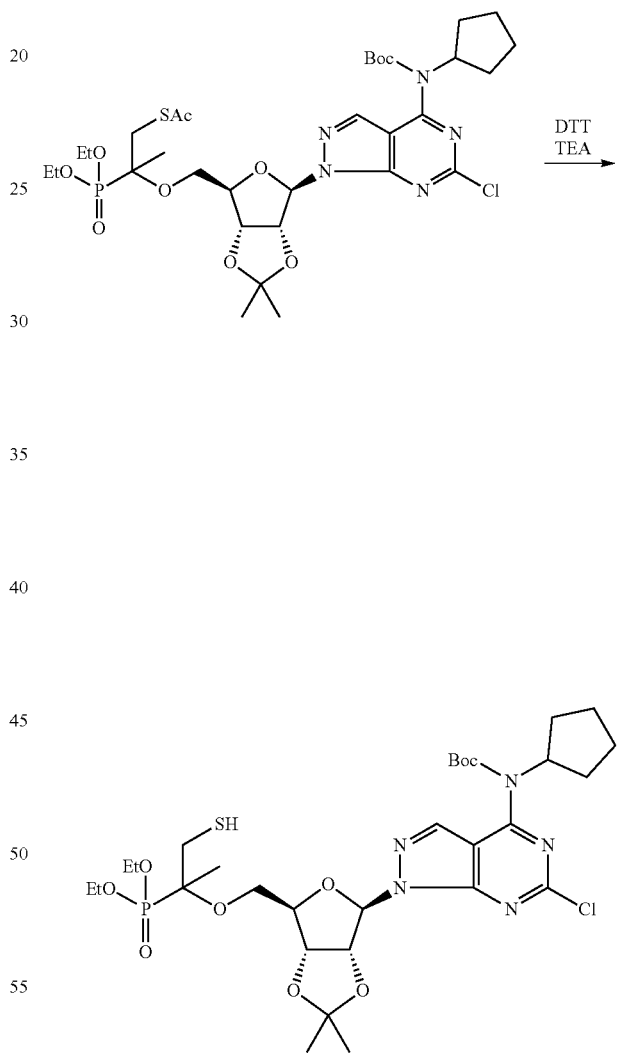

To a flask containing 55a (400 mg, 0.52 mmol) was added methanol (7 mL) followed by triethylamine (1.04 mL, 7.45 mmol). To this mixture was added DL-dithiothreitol (101 mg, 0.660 mmol). After the mixture was stirred at rt for 2 h, it was concentrated and the residue was purified by flash chromatography (0-100% EtOAc/hexanes, a gradient elution) to afford the title compound (55b)(245 mg, 0.340 mmol, 65% yield). m/z (ESI, +ve ion)=720.2 [M+H]$^+$.

Step C. tert-Butyl (6-chloro-1-(((3aR,4R,6R,6aR)-6-(((2-(diethoxyphosphoryl)-1-(methylthio)propan-2-yl)oxy)methyl)-2,2-dimethyltetrahydrofuro[3,4-d][1,3]dioxol-4-yl)-1H-pyrazolo[3,4-d]pyrimidin-4-yl)(cyclopentyl)carbamate (55c)

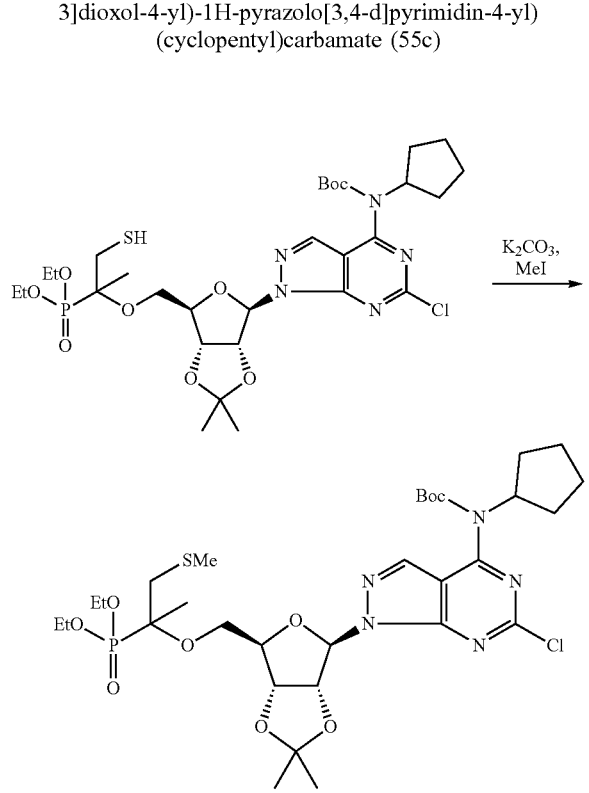

To an oven dried vial was added potassium carbonate (14.4 mg, 0.1 mmol) followed by addition of a solution of 55b (35.mg, 0.046 mmol) in acetone (0.5 mL). To this mixture was added methyl iodide (0.01 mL, 0.1 mmol). After the mixture was stirred at rt for 30 min, it was partitioned between sat. NaHCO$_3$ and EtOAc. The organic layer was washed with brine, dried with MgSO$_4$, filtered and concentrated. The resulting residue was purified by flash chromatography (20-100% EtOAc/hexanes, a gradient elution) to give the title compound (55c) (30 mg, 0.041 mmol, 84% yield). m/z (ESI, +ve ion)=734.2 [M+H]$^+$.

Step D. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-(methylthio)propan-2-yl)phosphonic acid (55)

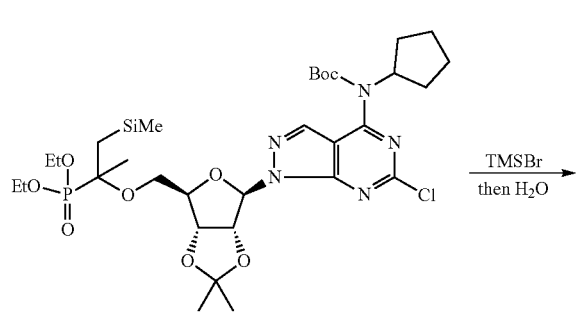

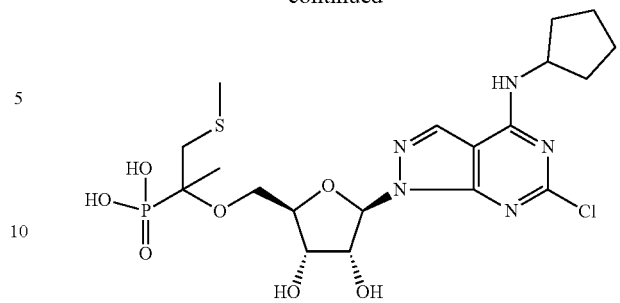

To a vial was added 55c (30 mg, 0.04 mmol) followed by MeCN (0.75 mL). To this solution was added bromo(trimethyl)silane (0.04 mL, 0.28 mmol) and the mixture was allowed to stir at rt. After 4 h, water (0.15 mL) was added and the mixture was allowed to stir for another 2 h. The mixture was quenched with concentrated NH$_4$OH (0.3 mL) and the resulting solution was concentrated. The residue was purified by reverse preparative HPLC (0-65% ACN/H$_2$O containing 0.1% TFA) to give the title compound (55) (7.5 mg, 0.012 mmol, 28% yield) as a TFA salt. m/z (ESI, +ve ion)=538.1 [M+H]$^+$.

Example 56. (2-(((2R,3S,4R,5R)-5-(6-Chloro-4-(cyclopentylamino)-1H-pyrazolo[3,4]pyrimidin-1-yl)-3,4-dihydroxytetrahydrofuran-2-yl)methoxy)-4-hydroxybutan-2-yl)phosphonic acid (56)

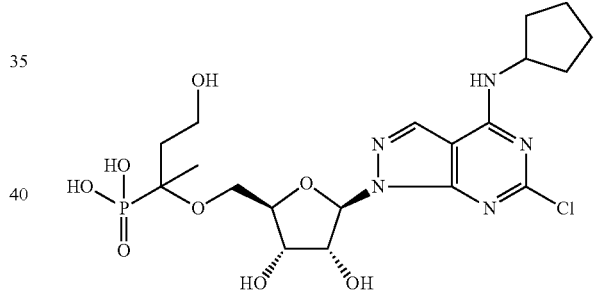

Step A. 2-(((3aR,4R,6R,6aR)-6-(4-((tert-Butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)propanoic acid (56a)

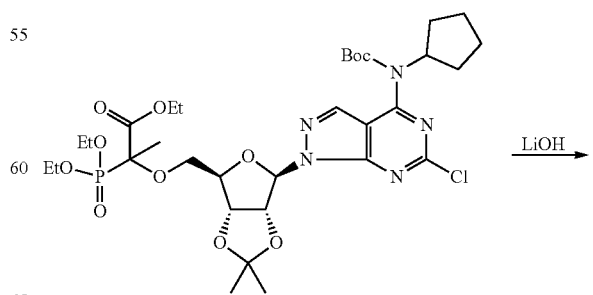

Alpha-methyl substituted 1f

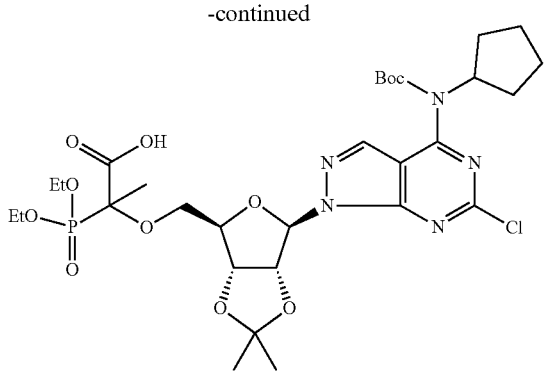

A flask was charged a solution of α-methyl substituted 1f (642 mg, 0.86 mmol) in THF (10 mL). Lithium hydroxide monohydrate (72.2 mg, 1.72 mmol) was weighed in a vial and then added water (0.9 mL). The freshly prepared lithium hydroxide solution was added to the starting material solution. After the mixture was stirred at rt overnight, it was cooled in an ice-bath and the pH was adjusted to 6 with 1M HCl. The nearly neutral solution was extracted with EtOAc. The combined organics were washed with brine, dried with MgSO₄, filtered and concentrated to provide the title compound (56a) (572 mg, 0.8 mmol, 93% yield). m/z (ESI, +ve ion)=718.3 [M+H]⁺.

Step B. Ethyl 3-(((3aR,4R,6R,6aR)-6-(4-((tert-butoxycarbonyl)cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-3-(diethoxyphosphoryl)butanoate (56b)

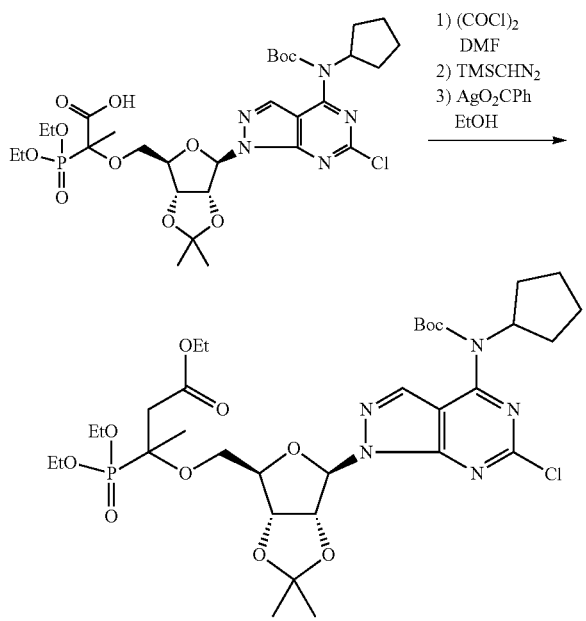

To an oven dried flask was added (56a) (413 mg, 0.58 mmol) followed by DCM (4.1 mL) under N₂. After the solution was cooled to 0° C., two drops of DMF were added followed by oxalyl chloride (0.29 mL, 0.58 mmol). The reaction mixture was warmed to rt and stirred for 1 h. and then concentrated. The residue was dissolved in 1:1 THF: MeCN (8 mL), the resulting solution was cooled to 0° C. and trimethylsilyldiazomethane (2M solution, 0.43 mL, 0.86 mmol) was added dropwise. After the mixture was warmed to rt and stirred for 1 h, it was quenched with sat. NaHCO₃, extracted with EtOAc. The combined organics were washed with brine, dried with MgSO₄, filtered and concentrated. The residue was azeotroped with toluene and dissolved in EtOH (4 mL). The solution was cooled to 0° C. and silver benzoate (131 mg, 0.58 mmol) was added. After the mixture was slowly warmed to rt and stirred overnight, the brown mixture was filtered through celite. The solution was extracted with EtOAc, dried with MgSO₄, filtered, and concentrated. The residue was purified by flash chromatography (35-70% EtOAc/hexanes, a gradient elution) to give the title compound (56b) (42 mg, 0.055 mmol, 9.6% yield). m/z (ESI, +ve ion)=760.3 [M+H]⁺.

Step C. tert-Butyl (6-Chloro-1-((3aR,4R,6R,6aR)-6-(((2-(diethoxyphosphoryl)-4-hydroxybutan-2-yl)oxy)methyl)-2,2-dimethyltetrahydrofuro[3,4d][1,3]dioxol-4-yl)-1H-pyrazolo[3,4-d]pyrimidin-4-yl)(cyclopentyl)carbamate (56c)

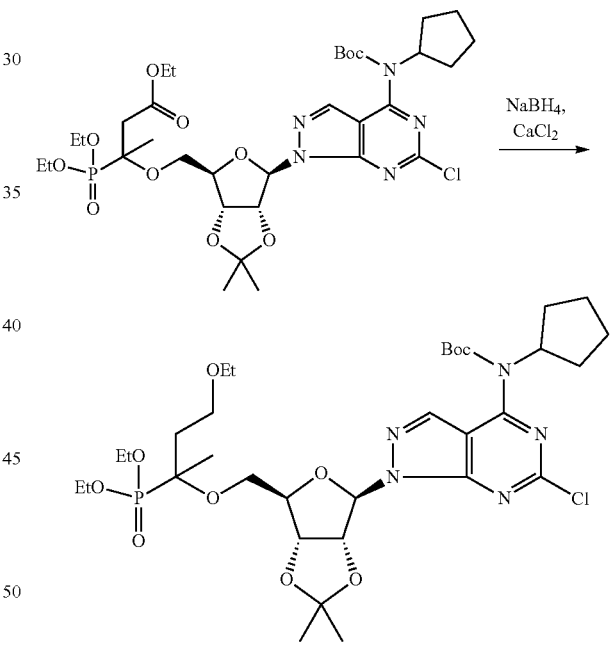

To a flask containing (56b) (62 mg, 0.08 mmol) was added ethanol (1 mL). The solution was then cooled to 0° C. and calcium dichloride (18 mg, 0.16 mmol) was added to the solution, followed by sodium borohydride (6.2 mg, 0.16 mmol) in a single portion. The mixture was removed from the ice bath and allowed to stir at rt overnight. The mixture was quenched with sat. NH₄Cl, extracted with EtOAc. The combined organics were dried, filtered, and concentrated. The residue was purified by flash chromatography (0-100% EtOAc/hexanes followed by 0-10% MeOH/DCM, a gradient elution) to afford the title compound (56c) (11 mg, 0.015 mmol, 19% yield) as an oil. m/z (ESI, +ve ion)=718.3 [M+H]⁺.

323

Step D. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-4-hydroxybutan-2-yl)phosphonic acid (56)

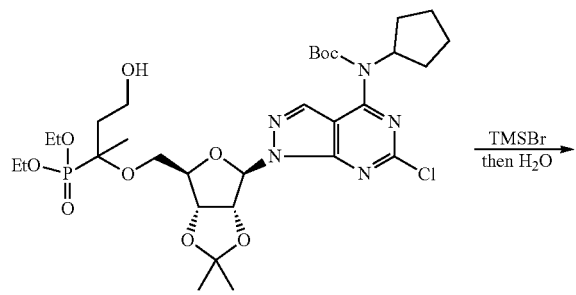

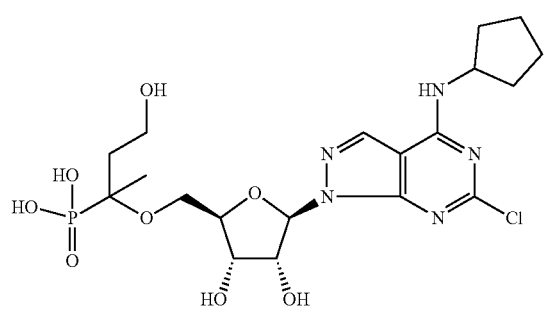

To a vial was added (56c) (11 mg, 0.02 mmol) followed by MeCN (0.25 mL). To this solution was added bromo(trimethyl)silane (0.01 mL, 0.1 mmol) and the mixture was allowed to stir at rt. After 4 h, water (0.05 mL) was added and the mixture was allowed to stir for 2 h. The mixture was quenched with concentrated NH$_4$OH (0.1 mL) and concentrated. The residue was purified by reverse preparative HPLC (0-65% ACN/H$_2$O containing 0.1% TFA, a gradient elution) to afford the title compound (56)(3.3 mg, 0.0052 mmol, 34% yield) as a TFA salt. m/z (ESI, +ve ion)=522.2 [M+H]$^+$.

Example 57. (1-(((2R,3S,4R,5R)-5-(6-Chloro-4-(cyclopentylamino)-1H-pyrazolo[3,4-b]pyridin-1-yl)-3,4-dihydroxytetrahydrofuran-2-yl)methoxy)-2-hydroxyethyl)phosphonic acid (57)

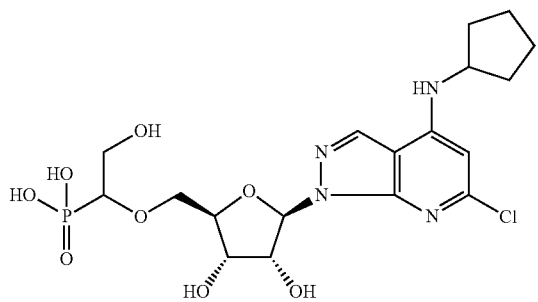 [SMILES: O=P(O)(O)C(CO)OC[C@H]1O[C@@H](n2ncc3c(NC4CCCC4)cc(Cl)nc32)[C@H](O)[C@@H]1O]

324

Step A. (2R,3R,4S,5R)-2-(6-Chloro-4-(cyclopentylamino)-1H-pyrazolo[34-b]pyridin-1-yl)-5-(hydroxymethyl)tetrahydrofuran-3,4-diol (57a)

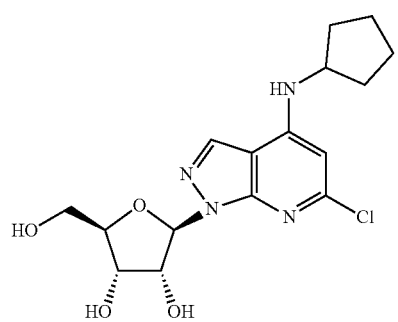

A pressure-sealed tube was charged with [(2R,3R,4R,5R)-3,4-diacetoxy-5-(4,6-dichloropyrazolo[3,4-b]pyridin-1-yl)tetrahydrofuran-2-yl]methyl acetate (0.64 g, 1.44 mmol) followed by ethanol (7 mL). To this solution was added trimethylamine (0.3 mL, 2.16 mmol) and cyclopentylamine (0.17 mL, 1.73 mmol) successively. The mixture was sealed and allowed to stir and heat at 110° C. overnight. The reaction was cooled to rt and was transferred to a round-bottom flask and concentrated under vacuum to afford a brown oil. The crude oil was transferred to a pressure sealed vial. Solvent was removed from the vial and degassed with Ar. Then ammonia solution (7 M NH$_3$ in THF, 5 mL, 34.5 mmol) was added to the vial and the solution was allowed to stir overnight. The reaction solution was concentrated and purified by silica gel chromatography (0-8% MeOH/CH$_2$Cl$_2$, a gradient elution) to give the title compound (57a) (250 mg, 47% yield) as an off-white solid. m/z (ESI, +ve ion)=369.1 [M+H]$^+$.

Step B. tert-Butyl (1-((3aR,4R,6R,6aR)-6-(((tert-butyldimethylsilyl)oxy)ethyl)-2,2-dimethyltetrahydrofuro[3,4-d][1,3]dioxol-4-yl)-6-chloro-1H-pyrazolo[3,4-b]pyridin-4-yl)(cyclopentyl)carbamate (57b)

Step C. tert-Butyl (6-chloro-1-((3aR,4R,6R,6aR)-6-(hydroxymethyl)-2,2-dimethyltetrahydrofuro[3,4-d][1,3]dioxol-4-yl)-1H-pyrazolo[3,4-b]pyridin-4-yl)cyclopentyl)carbamate (57c)

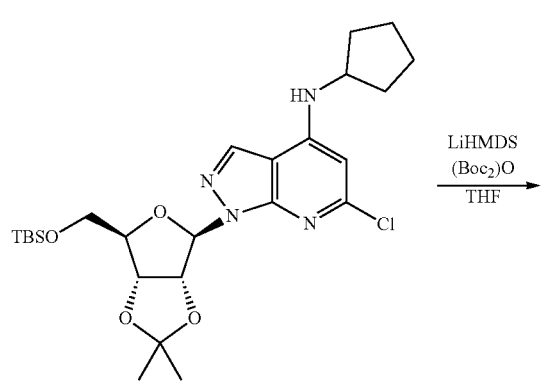

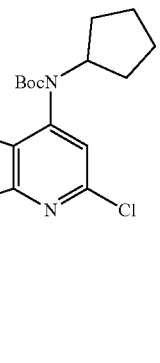

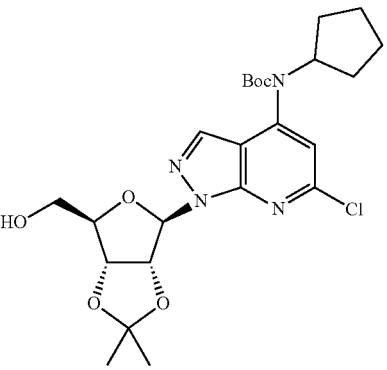

A round bottom flask was charged with 57a (29H) mg, 0.55 mmol) was azeotroped with toluene, flushed with Ar and added 5 mL of THF. LiHMDS solution (1 M in THF, 1.3 mL, 1.3 mmol) was added dropwise at rt and the solution was allowed to stir for 15 min. Then a solution of Boc₂O (375 mg, 1.72 mmol) was added dropwise. After the reaction was allowed to stir under Ar for 2 h, the solvent was removed and the crude residue was partitioned between water (25 mL) and CH₂Cl₂ (25 mL). The organic layers were combined, washed with brine, dried with Na₂SO₄, filtered and concentrated under vacuum to give a crude oil. The oil was purified by silica gel chromatography (0-20% EtOAc/hexane) to afford the title compound (57b) (316 mg, 91% yield) as a white, foamy solid. m/z (ESI, +ve ion)=623.3 [M+H]⁺.

A round bottom flask was charged with 57b (320 mg, 0.51 mmol), degassed with Ar, and added THF (10 mL). The solution was cooled to 0° C., and tetra-n-butylammonium fluoride (1 M in THF, 0.53 mL, 0.53 mmol) was added dropwise. The reaction solution was allowed to warm to rt and was quenched with saturated NaHCO₃ and extracted with EtOAc. The organic layers were combined, washed with brine, dried with Na₂SO₄, filtered and concentrated under vacuum to give a crude oil. The oil was purified by silica gel chromatography (0-50% Acetone/hexane, a gradient elution) to afford the title compound (57c) (245 mg, 94% yield) as a white, foamy solid. m/z (ESI, +ve ion)=509.2 [M+H]⁺.

Step D. (1-(((2R,3S,4R,5R)-5-(6-Chloro-4-(cyclopentylamino)-1H-pyrazolo[3,4-b]pyridin-1-yl)-3,4-dihydroxytetrahydrofuran-2-yl)methoxy)-2-hydroxyethyl)phosphonic acid (57)

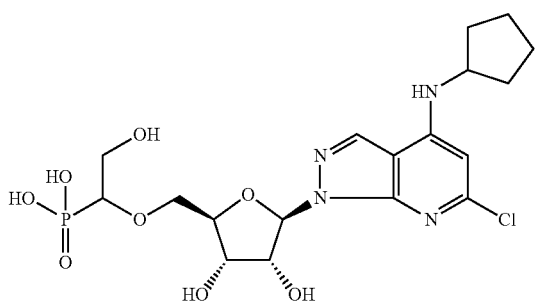 [SMILES: O=P(O)(O)C(CO)OC[C@H]1O[C@@H](n2ncc3c(NC4CCCC4)cc(Cl)nc32)[C@H](O)[C@@H]1O]

The title compound was prepared from 57c by procedures similar to those described in Example 1, Step F, followed by Steps A and C in Example 3. m/z (ESI, +ve ion)=493.1 [M+H]⁺.

Example 58. (1-(((2R,3S,4R,5R)-5-(5-Chloro-7-(cyclopentylamino)-3H-[1,2,3]triazolo[4,5-d]pyrimidin-3-yl)-3,4-dihydroxytetrahydrofuran-2-yl)methoxy)-2-hydroxyethyl)phosphonic acid (58)

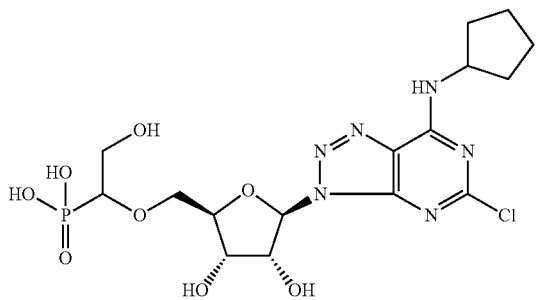 [SMILES: O=P(O)(O)C(CO)OC[C@H]1O[C@@H](n2nnc3c(NC4CCCC4)nc(Cl)nc32)[C@H](O)[C@@H]1O]

Step A. Ethyl 2-diazo-2-(diethoxyphosphoryl)acetate (58a)

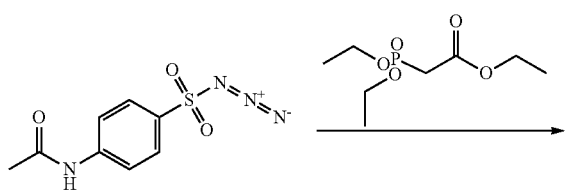

To a mixture of ethyl 2-(diethoxyphosphoryl)acetate (187 g, 0.833 mol) and Cs₂CO₃ (339 g, 1.04 mol) in THF (1.5 L) was added 4-acetamidobenzenesulfonyl azide (100 g, 0.416 mol) in portions at 0° C. The mixture was stirred at rt for 2 h and then diluted with EtOAc/water (1:1, 0.8 L). After the solution was acidified to a pH of 2 with 1 M HCl, the aqueous layer was extracted with EtOAc. The combined organic layers were dried and concentrated in vacuo. The residue was purified by flash chromatography (Petroleum ether/EtOAc=1:1) to give the title compound (58a) (86 g, 83% yield) as a yellow liquid. m/z (ESI, +ve ion)=250.89 [M+H]⁺.

Step B. Ethyl 2-(diethoxyphosphoryl)-2-(((3aR,4R,6R,6aR)-6-methoxy-2,2-dimethyltetrahydrofuro[3,4-d][1,3]dioxol-4-yl)methoxy)acetate (58b)

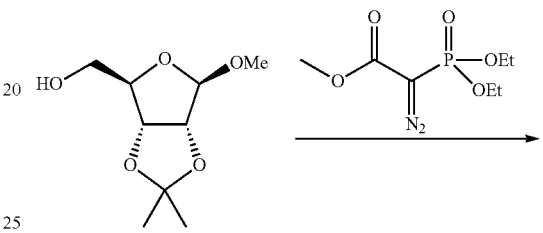

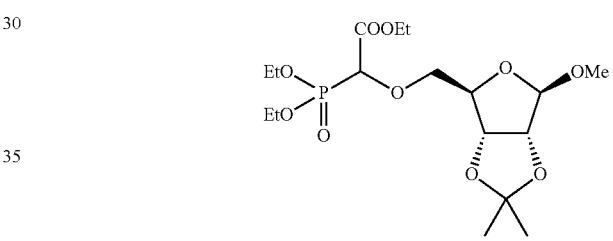

To a solution of ((3aR,4R,6R,6aR)-6-methoxy-2,2-dimethyltetrahydrofuro[3,4-d][1,3]dioxol-4-yl)methanol (100 g, 0.49 mol) and 58a (100 g, 0.4 mol) in toluene (1 L) was added rhodium acetate dimer (10.8 g). The reaction mixture was degassed and heated at 95-100° C. for 1.5 h under N₂. The mixture was cooled to rt and the solvent was evaporated under reduced pressure. The residue was purified by flash chromatography (Petroleum ether/ethyl acetate:=5:1) to afford the title compound (58b) (86.3 g, 41% yield) as an oil. m/z (ESI, +ve ion)=448.9 [M+Na]⁺.

Step C. Diethyl (2-hydroxy-1-(((3aR,4R,6R,6aR)-6-methoxy-2,2-dimethyltetrahydrofuro[3,4-d][1,3]dioxol-4-yl)methoxy)ethyl)phosphonate (58c)

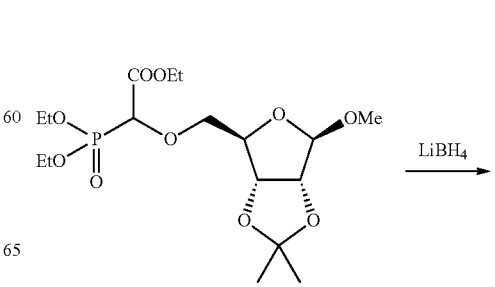

-continued

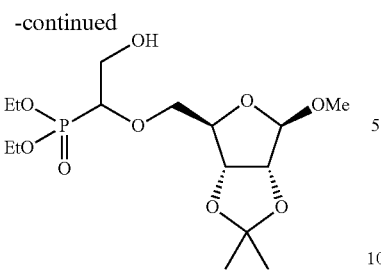

LiBH₄ (2 M in THF, 14 ml, 28 mmol) was added dropwise to a solution of 58b (3.0 g, 7 mmol) in THF (60 mL) at 0° C. and the resulting mixture was stirred at 0° C. for 2 h. The mixture was quenched with water, extracted with EtOAc. The combined organic layers were washed with water, brine, and concentrated. The residue was purified by flash chromatography (Petroleum ether/ethyl acetate=10:1 to 5:1) to give the title compound (58c) (2.7 g, 67% yield). m/z (ESI, +ve ion)=384.7 [M+H]⁺.

Step D. Diethyl (2-hydroxy-1-(((2R,3S,4R,5R)-3,4,5-trihydroxytetrahydrofuran-2-yl)methoxy)ethyl)phosphonate (58d)

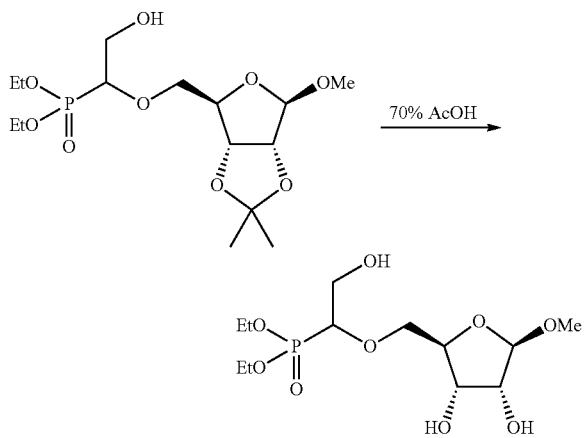

To a solution of 58c (2.5 g, 6.5 mmol) was added 70% acetic acid (25 mL) and the mixture was heated at 90° C. overnight. After the mixture was cooled to rt, it was concentrated and the crude residue (1.6 g) was directly used for next step without further purification.

Step E. (2S,3R,4R,5R)-5-((2-Acetoxy-1-(diethoxyphosphoryl)ethoxy)methyl)tetrahydrofuran-2,3,4-triyl triacetate (58e)

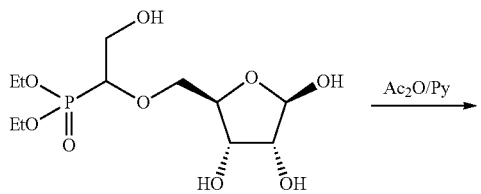

-continued

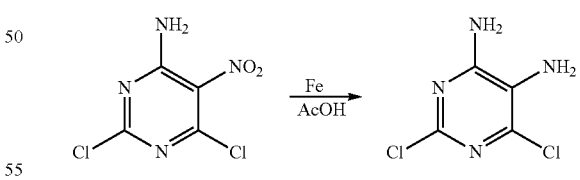

To a solution of 58d (5.2 g, 15.7 mmol) and triethylamine (12.73 g, 126 mmol) in dry DCM (15 mL) was added dropwise acetic anhydride (12.86 g, 126 mmol) at 0° C. After the mixture was stirred at rt overnight, water (30 mL) was added and the solution was extracted with DCM. The combined organic layers were washed with brine, dried, concentrated. The residue was purified by flash chromatography (Petroleum ether/EtOAc=10:1) to afford the tile compound (58e) (4.0 g, 51% yield for the two steps).

Step F. 2,6-Dichloro-5-nitropyrimidin-4-amine (58)

To a solution of 2,4,6-trichloro-5-nitropyrimidine (9.0 g, 39.4 mmol) in THF (540 mL) was added an ammonia solution (10.8 mL, 10 N in EtOH, 78.8 mmol) dropwise at −70° C. After the reaction was stirred at −70° C. for 30 min, it was acidified with AcOH (pH 4-5) and concentrated. the residue was diluted with EtOAc and the resulting mixture was stirred for 30 min and filtered. The solids were washed with EtOAc and the organics were combined and concentrated to afford the title compound (58f) (8.0 g, 97%), which was directly used for the next step without further purification.

Step G. 2,6-Dichloropyrimidine-4,5-diamine (58g)

A mixture of iron powder (10.7 g, 191 mmol), acetic acid (24 ml) and ethanol (30 mL) was heated at 55° C. for 0.5 h. A solution of 58f (8.0 g, 38.3 mmol) in ethanol (50 ml) was added dropwise. After the mixture was stirred at 55° C. for 20 min, it was cooled to rt and filtered. The filtrate was concentrated, the residue was diluted with water and the solution extracted with EtOAc. The combined organics were washed with water and brine, dried and concentrated. The residue was purified by column chromatography (petroleum ether/ethyl acetate: from 5:1 to 3:1) to give the title compound (58g) (4.4 g, 60.4%) as a white solid.

Step H. 5,7-Dichloro-3H-[1,2,3]triazolo[4,5-d]pyrimidine (58h)

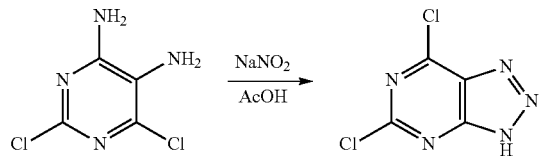

A suspension of 2,6-dichloropyrimidine-4,5-diamine (58g) (4.4 g, 24.58 mmol) in water (47 ml) was heated and the solid was dissolved. The solution was cooled to 0° C. and acetic acid (94 ml) was added, followed by addition of a solution of sodium nitrite (3.05 g, 44.3 mmol) in water (47 mL) during a period of 15 min. The reaction mixture was stirred at 0° C. for another 20 min and then was extracted with EtOAc. The organics were neutralized, dried and concentrated, the crude product was purified by column chromatography (petroleum ether/ethyl acetate: from 3:1 to 2:1) to provide the title compound (58h) (3.4 g, 72.8%) as a yellow solid.

Step I. (2R,3R,4R,5R)-2-((2-Acetoxy-1-(diethoxyphosphoryl)ethoxy)methyl)-5-(5,7-dichloro-3H-[1,2,3]triazolo[4,5-d]pyrimidin-3-yl)tetrahydrofuran-3,4-diyl diacetate (58i)

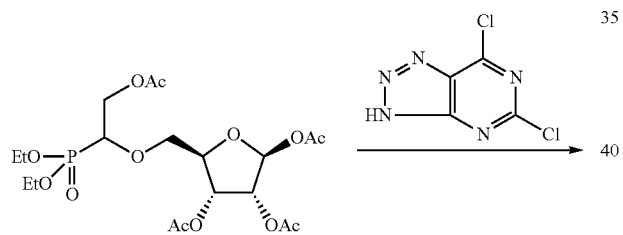

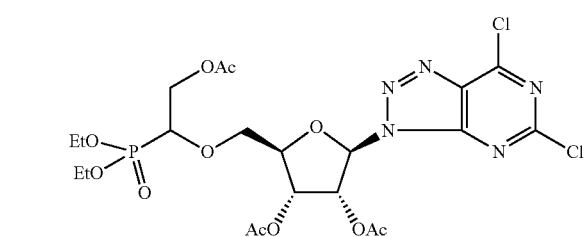

A flask charged with 58e (4.0 g, 0.8 mmol) was heated at 90° C. for 10 min, 56h (1.52 g, 0.8 mmol) and SnCl$_4$ (40 mg, 1%) was added successively. After the mixture was heated at 130° C. for 15 min under reduced pressure distillation, it was cooled to rt, quenched with water, extracted with EtOAc. The combined organic layers were washed with water and brine, dried and concentrated. The residue was purified by flash chromatography (Petroleum ether/EtOAc=10:1 to 5:1) to give the crude product (58i) (3.1 g, 62% yield) as a yellow solid. m/z (ESI, +ve ion)=628.0 [M+H]$^+$.

Step J. (2R,3R,4R,5R)-2-((2-Acetoxy-1-(diethoxyphosphoryl)ethoxy)methyl)-5-(5-chloro-7-(cyclopentylamino)-3H-[1,2,3]triazolo[4,5-d]pyrimidin-3-yl)tetrahydrofuran-3,4-diyl diacetate (58j)

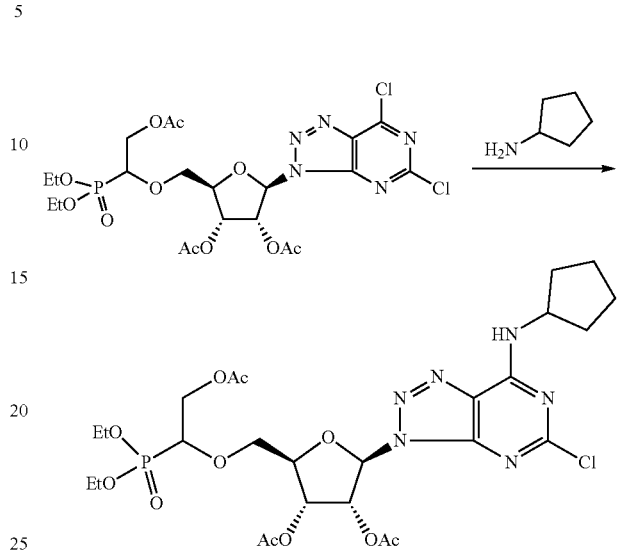

A mixture of 58i (2.2 g, 3.5 mmol), cyclopentanamine (446 mg, 5.25 mmol) and triethylamine (530 mg, 5.25 mmol) in ethanol (40 mL) was stirred at rt for 1 h. The mixture was concentrated in vacuo and the residue was purified by flash chromatography (Petroleum ether/EtOAc=8:1 to 3:1, a gradient elution) to give the title compound (58j) (2.2 g, 93% yield) as a yellow solid. m/z (ESI, +ve ion)=677.1 [M+H]$^+$.

Step K. Diethyl (1-(((2R,3S,4R,5R)-5-(5-chloro-7-(cyclopentylamino)-3H-[1,2,3]triazolo[4,5-d]pyrimidin-3-yl)-3,4-dihydroxytetrahydrofuran-2-yl)methoxy)-2-hydroxyethyl)phosphonate (58k)

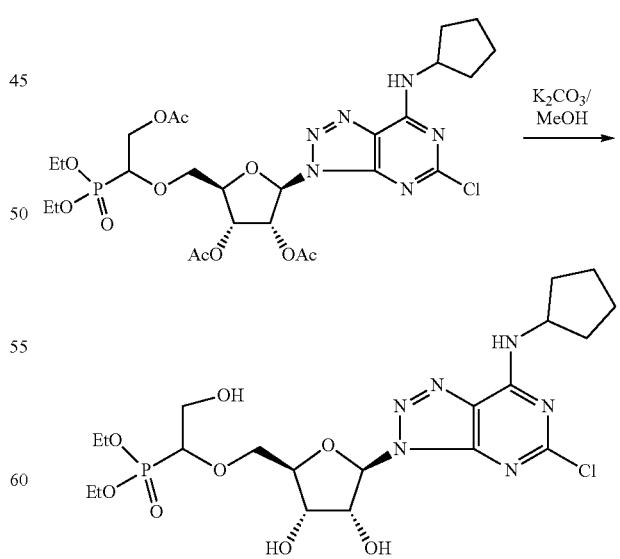

A mixture of 58j (1.1 g, 1.62 mmol), K$_2$CO$_3$ (673 mg, 4.88 mmol) in MeOH (11 mL) was stirred at 0° C. for 15 min, then acetic acid (585 mg) was added. The mixture was concentrated and the residue was extracted with EtOAc. The organics were washed with brine and concentrated to afford the title compound (58k) (450 mg, 47.4% yield for the two steps) as a white solid. m/z (ESI, +ve ion)=551.0 [M+H]$^+$.

Step L. (1-(((2R,3S,4R,5R)-5-(5-Chloro-7-(cyclopentylamino)-3H-[1,2,3]triazolo[4,5-d]pyrimidin-3-yl)-3,4-dihydroxytetrahydrofuran-2-yl)methoxy)-2-hydroxyethyl)phosphonic acid (58)

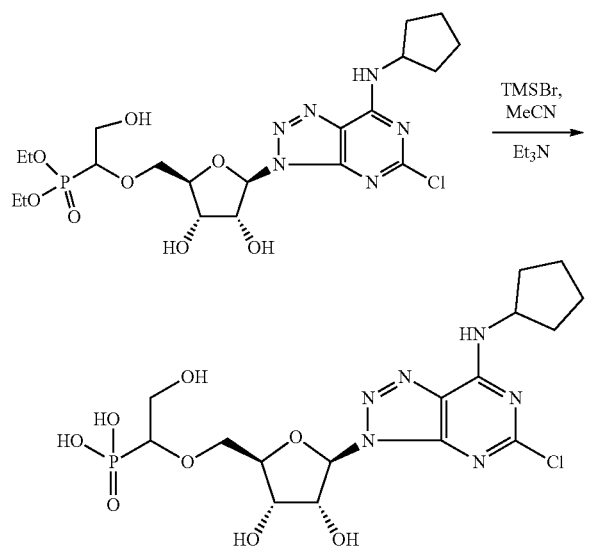

Triethylamine (3.23 g, 31.9 mmol) was added dropwise to a solution of 58k (440 mg, 0.789 mmol) in anhydrous acetonitrile (20 ml). After the mixture was stirred at rt for 5 min, TMSBr (3.66 g, 23.9 mmol) was added dropwise. The mixture was stirred at rt for 2 h and then concentrated. The residue was directly purified by reverse preparative HPLC (30-90% ACN/H$_2$O containing 0.1% TFA) to give the title compound (58) (150 mg, TFA salt, 31% yield) as an off-yellow solid. m/z (ESI, +ve ion)=495.0 [M+H]$^+$.

Examples 59-83

Examples 59-83 were synthesized as described in examples 1-8, 15-17, and 55-58.

| Ex | MS Data |
|---|---|
| 59 | 425.8 [M + H]$^+$ |
| 60 | 493.8 [M + H]$^+$ |
| 61 | 556.4 [M + H]$^+$ |
| 62 | 508.0 [M + H]$^+$ |
| 63 | 508.0 [M + H]$^+$ |
| 64 | 508.0 [M + H]$^+$ |
| 65 | 522.1 [M + H]$^+$ |
| 66 | 508.0 [M + H]$^+$ |
| 67 | 509.1 [M + H]$^+$ |
| 68 | 531.9 [M − H]$^-$ |
| 69 | 522.04 [M + H]$^+$ |
| 70 | 506.09 [M + H]$^+$ |
| 71 | 577.3 [M + H]$^+$ |
| 72 | 538.1 [M + H]$^+$ |
| 73 | 570.1 [M + H]$^+$ |
| 74 | 570.1 [M + H]$^+$ |
| 75 | 494.1 [M + H]$^+$ |
| 76 | 508.1 [M + H]$^+$ |
| 77 | 570.0 [M + H]$^+$ |
| 78 | 556.8 [M + H]$^+$ |
| 79 | 508.0 [M + H]$^+$ |
| 80 | 532.1 [M + H]$^+$ |
| 81 | 535.2 [M + H]$^+$ |
| 82 | 523.1 [M + H]$^+$ |
| 83 | 560.1 [M + H]$^+$ |

Example 84. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid (84)

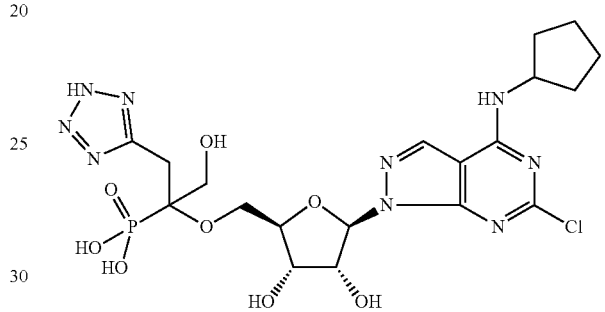

Step A. Ethyl 2-((2-(trimethylsilyl)ethoxy)methyl)-2H-tetrazole-5-carboxylate (84a-1) and ethyl 14(2-(trimethylsilyl)ethoxy)methyl)-1H-tetrazole-5-carboxylate (84a-2)

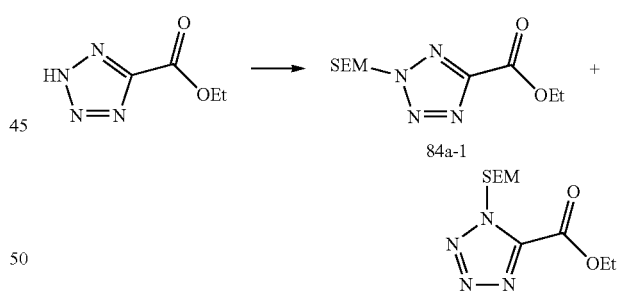

To a stirred solution of ethyl tetrazole-5-carboxylate (2.0 g, 14.1 mmol) in THF (60 mL) was added sodium hydride (60% in mineral oil, 647 mg, 16.2 mmol) in one portion at 0° C. The mixture was allowed to warm to rt and stirred for 15 min. The mixture was then cooled back to 0° C. and 2-(trimethylsilyl)ethoxymethyl chloride (2.84 mL, 16.2 mmol) was added dropwise. The resulting mixture was allowed to warm to rt and stirred for 3 h. Water was added into the reaction mixture and the solution was extracted (3×EtOAc). The combined organic layers were washed (brine), dried (Na$_2$SO$_4$), and concentrated under reduced pressure. Purification of the residue by silica gel column chromatography (87 g SiO$_2$, 5% to 40% EtOAc/hexanes, a gradient elution) provided a mixture of 84a-1 and 84a-2 (60:40 measured by ¹H NMR, 2.88 g, 73%) as a colorless oil.

Step B. (2-((2-(Trimethylsilyl)ethoxy)methyl)-2H-tetrazol-5-yl)methanol (84b)

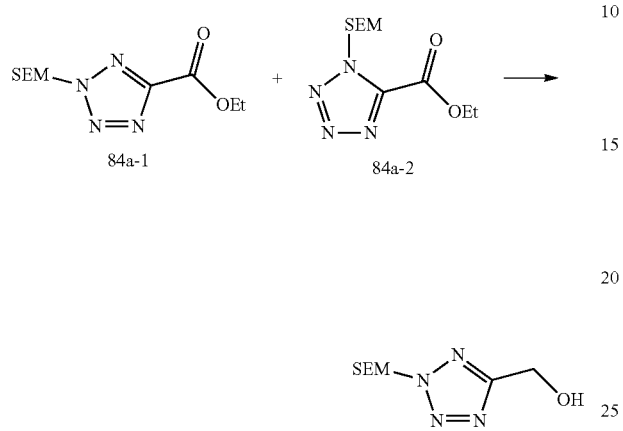

To a stirred solution of ethyl 2-((2-(trimethylsilyl)ethoxy)methyl)-2H-tetrazole-5-carboxylate (84a-1) and ethyl 1-((2-(trimethylsilyl)ethoxy)methyl)-1H-tetrazole-5-carboxylate (84a-2)(1.5 g, 5.51 mmol) in MeOH (15 mL) was added NaBH$_4$ (417 mg, 11.0 mmol) at rt. The reaction mixture was heated at 60° C. for 1 h. After the reaction mixture was cooled to rt, it was quenched with water and extracted (3×EtOAc) and the combined organic layer was washed (brine), dried (Na$_2$SO$_4$), and concentrated under reduced pressure. Purification of the residue by silica gel column chromatography (120 g SiO$_2$, 5% to 60% EtOAc/hexanes, a gradient elution) provided the title compound (84b) (1.06 g, 84%) as a colorless oil. The mixture of 84a-1 and 84a-2 was reduced with NaBH$_4$ to produce only one regioisomer and the structure of 84b was arbitrarily assigned.

Step C. 5-(Bromomethyl)-2-((2-(trimethylsilyl)ethoxy)methyl)-2H-tetrazole (84c)

To a stirred solution of 84b (1.06 g, 4.60 mmol) and triphenylphosphine (2.41 g, 9.20 mmol) in DCM at −40° C. was added N-bromosuccinimide (1.64 g, 9.20 mmol) in one portion. After the mixture was stirred at the same temperature for 2 h, it was quenched with sat. NaHCO$_3$ and the resulting mixture was warmed to rt. The solution was extracted (3×DCM) and the combined organic layer was washed (brine), dried (Na$_2$SO$_4$), and concentrated under reduced pressure. Purification of the residue by silica gel column chromatography (87 g SiO$_2$, 0% to 20% EtOAc/hexanes, a gradient elution) provided the title compound (84c) (1.22 g, 90%) as a colorless oil.

Step D. Ethyl 2-(((3a,4R,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)-3-(2-((2-(trimethylsilyl)ethoxy)methyl)-2H-tetrazol-5-yl)propanoate (84d)

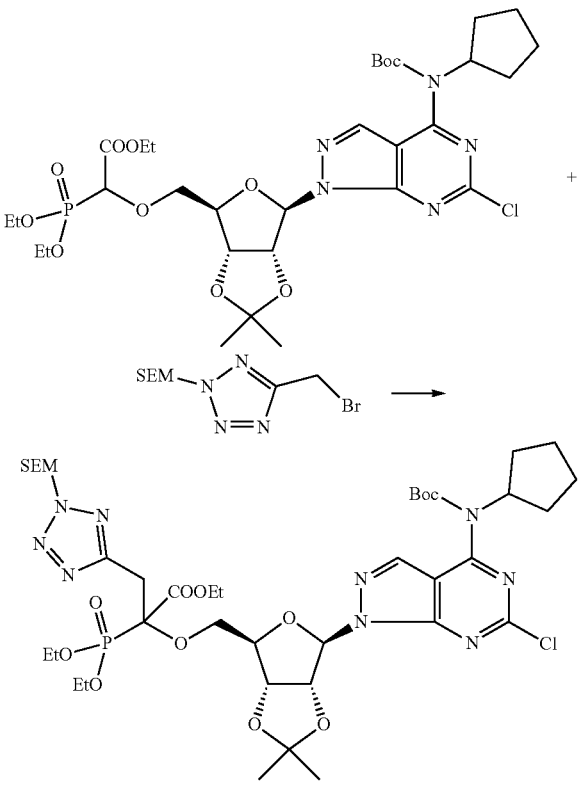

To stirred solution of ethyl 2-(((3aR,4R,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl) acetate (1f) (1.16 g, 1.58 mmol) in THF (27 mL) at −15° C. was added dropwise sodium bis(trimethylsilyl)amide (1.0 M in THF, 2.06 mL, 2.06 mmol). After the reaction mixture was stirred at the same temperature for 25 min, tetrabutylammonium iodide (293 mg, 0.86 mmol) was added, followed by dropwise addition of 5-(bromomethyl)-2-((2-(trimethylsilyl)ethoxy)methyl)-2H-tetrazole (84c) (1.16 g, 3.96 mmol) solution in THF (3 mL) at −15° C. The mixture was stirred at the same temperature for another 3 h and then quenched with sat. NH$_4$Cl. The solution was diluted with EtOAc and water, extracted with EtOAc. The combined organic layer was washed (brine), dried (Na$_2$SO$_4$), and concentrated under reduced pressure. Purification of the residue by silica gel column chromatography (120 g SiO$_2$. 5% to 40% acetone/hexanes, a gradient elution) provided the title compound (84d) (1.07 g, 72%) as a colorless gum. m/z (ESI, +ve ion)=944.2 [M+H]$^+$.

Step E. tert-Butyl (6-chloro-1-((3aR,4R,6R,6aR)-6-(((2-(diethoxyphosphoryl)-1-hydroxy-3-(2-((2-(trimethylsilyl)ethoxy)methyl)-2H-tetrazol-5-yl)propan-2-yl)oxy)methyl)-2,2-dimethyltetrahydrofuro[3,4-d][1,3]dioxol-4-yl)-1H-pyrazolo[3,4-d]pyrimidin-4-yl)(cyclopentyl)carbamate (84e)

Step F. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-hydroxy-3-(2H-tetrazol-5-yl)propan-2-yl)phosphonic acid (84)

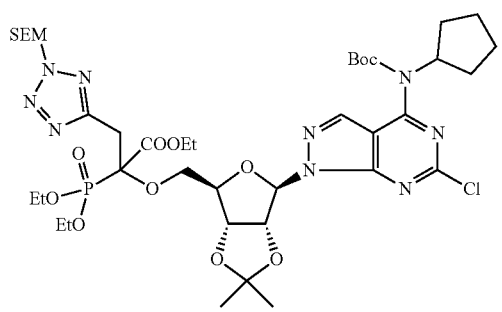

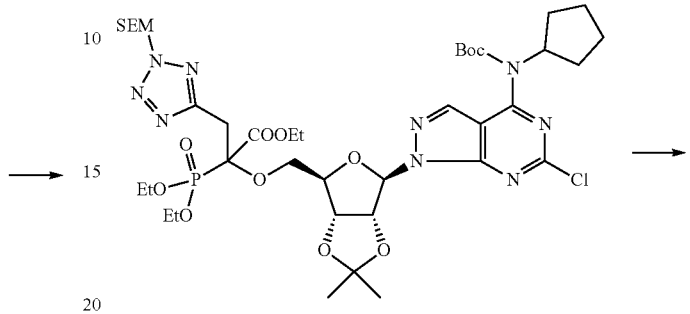

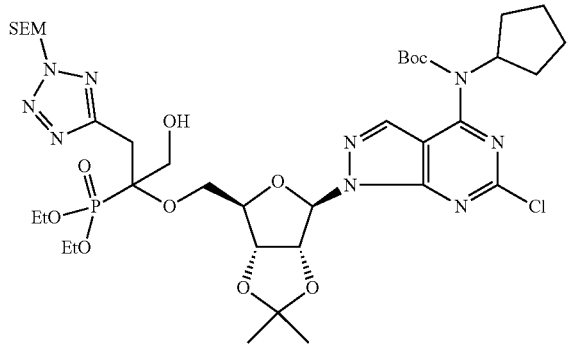

To a stirred solution of 84d (960 mg, 1.02 mmol) in EtOH (15 mL) was added calcium dichloride (395 mg, 3.56 mmol), followed by addition of NaBH$_4$ (135 mg, 3.56 mmol) in a single portion at 0° C. After the reaction was stirred at rt for 3 h, the mixture was quenched with 1H HCl, diluted with EtOAc and water. The solution was extracted (3×EtOAc) and the combined organic layer was washed (brine), dried (Na$_2$SO$_4$), and concentrated under reduced pressure. Purification of the residue by silica gel column chromatography (120 g SiO$_2$, 1% to 5% MeOH/DCM, a gradient elution) provided the title compound (84e) (658 mg, 72%) as a white foamy solid. m/z (ESI, +ve ion)=902.2 [M+H]$^+$.

To a solution of 84e (49 mg, 0.054 mmol) in MeCN (1.0 mL) was added bromotrimethylsilane (0.071 mL, 0.54 mmol). The mixture was stirred at rt for 3 h and then water (0.2 mL) was added. After the mixture was stirred at rt overnight, the solution was purified by reverse preparative HPLC to give the TFA salt of the title compound as a mixture of two diastereomers (84) (60:40 measured by $^1$H NMR, 4.2 mg, 11% yield) as a white solid. $^1$H NMR of the major diastereomer (400 MHz, CD$_3$OD) δ 8.10 (1H, d, J=0.8 Hz), 6.31 (1H, d, J=4.0 Hz), 4.75 (1H, t, J=4.6 ZH), 4.56-4.52 (m, 2H), 4.35-4.31 (1H, m), 4.13-4.03 (3H, m), 3.89 (1H, dd, J=6.2, 12.6 Hz), 3.62-3.53 (1H, dd, J=15.8, 17.6 Hz), 3.42 (1H, dd, J=7.2, 15.6 Hz), 2.13-2.06 (2H, m), 1.89-1.56 (6H, m); $^1$H NMR of the minor diastereomer (400 MHz, CD$_3$OD) δ 8.12 (1H, d, J=0.8 Hz), 6.28 (1H, d, J=4.0 Hz), 4.70 (1H, t, J=6.0 Hz), 4.59 (1H, t, J=5.2 Hz), 4.57-4.45 (1H, m), 4.27 (1H, dd, J=5.2, 9.6 Hz), 4.17 (1H, dd, J=5.2, 9.6 Hz), 4.06 (1H, dd, J=4.2, 9.8 Hz), 3.96 (1H, 7.6, 12.4 Hz), 3.84 (1H, dd, J=6.6, 12.6 Hz), 3.57 (1H, dd, J=12.8, 15.6 Hz), 3.47 (1H, dd, J=8.8, 15.6 Hz), 2.11-2.06 (2H, m), 1.89-1.57 (6, m). m/z (ESI, +ve ion)=576.1 [M+H]$^+$.

Example 85. (2-(((2R,3S,4R,5R)-5-(6-Chloro-4-(cyclopentylamino)-1H-pyrazolo[3,4]pyrimidin-1-yl)-3,4-dihydroxytetrahydrofuran-2-yl)methoxy)-1-(2-hydroxyethoxy)propan-2-yl)phosphonic acid (85)

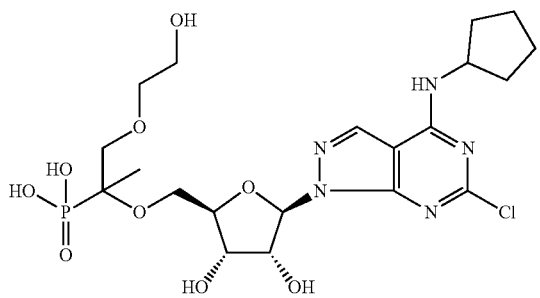 [SMILES: CC(COCCO)(OC[C@H]1O[C@@H](n2ncc3c(NC4CCCC4)nc(Cl)nc32)[C@H](O)[C@@H]1O)P(=O)(O)O]

Step A. Ethyl 2-(2-(((3aR,4R,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)propoxy)acetate (85a)

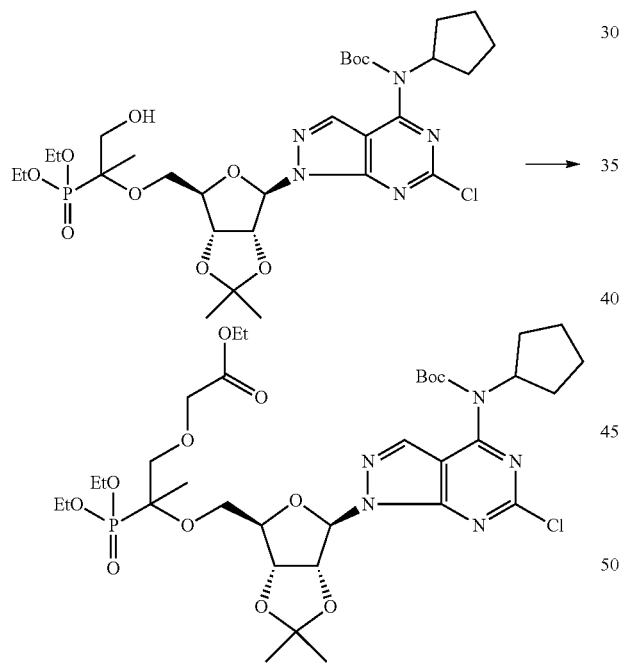

To a solution of tert-butyl (6-chloro-1-((3aR,4R,6R,6aR)-6-(((2-(diethoxyphosphoryl)-1-hydroxypropan-2-yl)oxy)methyl)-2,2-dimethyltetrahydrofuro[3,4-d][1,3]dioxol-4-yl)-1H-pyrazolo[3,4-d]pyrimidin-4-yl)(cyclopentyl)carbamate (ether analog of 8d) (500 mg, 0.71 mmol) in DMF (15 mL) was added ethyl bromoacetate (0.39 mL, 3.6 mmol) at 0° C. To this solution was added NaH (60% mineral oil, 85.2 mg, 2.13 mmol) in one portion. After the mixture was stirred at 0° C. for 4 h, it was quenched with sat. NH₄Cl. The solution was extracted with EtOAc and the combined organics were washed with brine and dried with Na₂SO₄. The slurry was filtered and concentrated. The resulting residue was purified by flash chromatography (0-100% EtOAc/hexanes, a gradient elution) to afford the title compound (85a) (337 mg, 0.43 mmol, 60% yield) as a foaming solid. m/z (ESI, +ve ion)=860.3 [M+H]$^+$.

Step B. tert-Butyl (6-chloro-1-((3aR,4R,6R,6aR)-6-(((2-(diethoxyphosphoryl)-1-(2-hydroxyethoxy)propan-2-yl)oxy)methyl)-2,2-dimethyltetrahydrofuro[3,4-d][1,3]dioxol-4-yl)-1H-pyrazolo[3,4-d]pyrimidin-4-yl)(cyclopentyl)carbamate (85b)

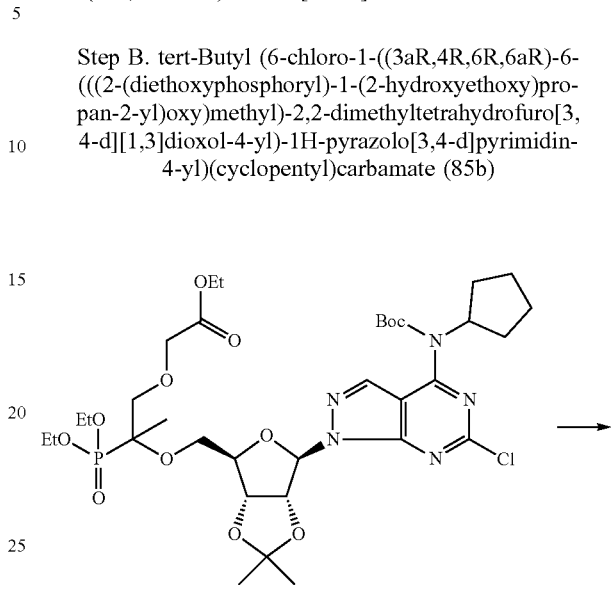

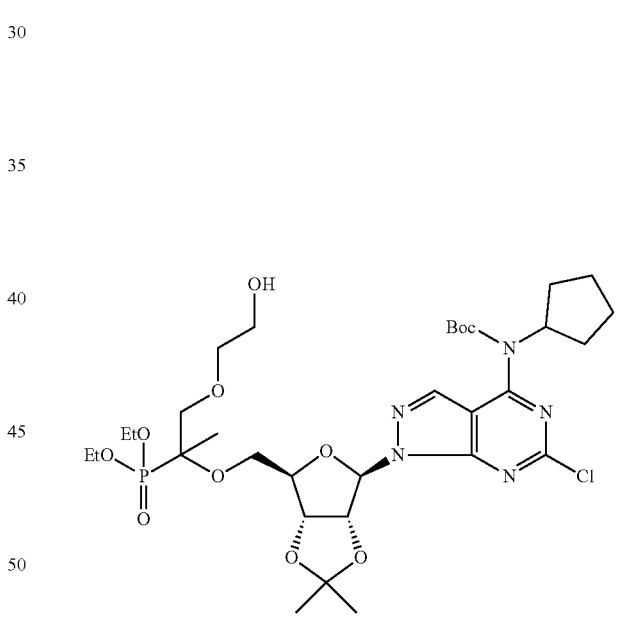

To an oven-dried flask containing 85a (337 mg, 0.43 mmol) was added ethanol (6.5 mL). To the mixture was added calcium dichloride (146 mg, 1.28 mmol), followed by sodium borohydride (48.4 mg, 1.28 mmol) at 0° C. After the mixture was warmed to rt and stirred for 1.5 h, it was cooled to 0° C. and quenched with sat. NH₄Cl. The resulting solution was extracted with EtOAc and the combined organic layers were washed with brine, dried with MgSO₄, filtered and concentrated. The resulting residue was purified by flash chromatography (60-100% EtOAc/hexanes, a gradient elution) to afford the title compound (85b) (230 mg, 0.31 mmol, 72% yield) as a white foamy solid. m/z (ESI, +ve ion)=748.2 [M+H]$^+$.

Step C. (2-(((2R,3S,4R,5R)-5-(6-Chloro-4-(cyclopentylamino)-1H-pyrazolo[3,4-d]pyrimidin-1-yl)-3,4-dihydroxytetrahydrofuran-2-yl)methoxy)-1-(2-hydroxyethoxy)propan-2-yl)phosphonic acid (85)

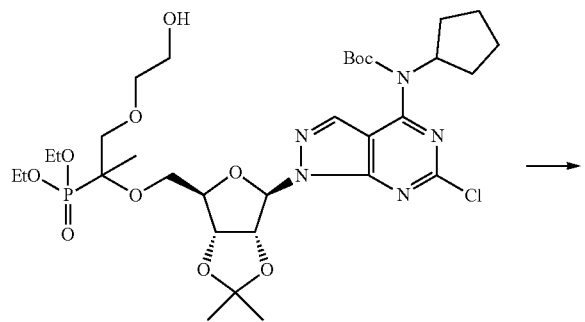

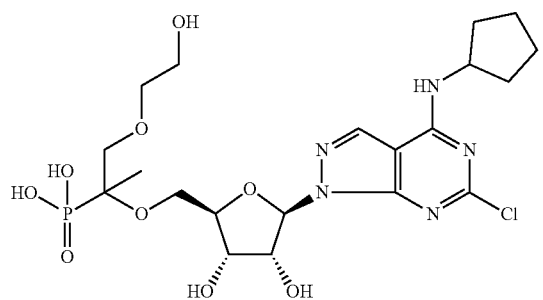

To a vial was added 85b (130 mg, 0.17 mmol) followed by addition of MeCN (2.7 mL). To this solution was added bromo(trimethyl)silane (0.16 mL, 1.2 mmol) and the mixture was allowed to stir for 4 h. Water (0.54 mL) was then added and the mixture was allowed to stir overnight. the mixture was concentrated to remove the MeCN and diluted with MeOH (1.5 mL). The solution was purified by prep HPLC (20-40% ACN/H₂O with 0.1% TFA, a gradient elution) to provide the TFA salt of title compound (85) (24 mg, 0.036 mmol, 21% yield) as a mixture of diastereomers. $^1$H NMR (400 MHz, DMSO-d6) δ ppm 1.19-1.32 (m, 3H) 1.48-1.86 (m, 6H) 1.94-2.09 (m, 2H) 3.38-3.47 (m, 4H) 3.49-3.56 (m, 1H) 3.57-3.71 (m, 2H) 3.73-3.90 (m, 1H) 3.90-3.98 (m, 1H) 4.15-4.22 (m, 1H) 4.38-4.48 (m, 1H) 4.52-4.61 (m, 1H) 5.93-6.19 (m, 1H), 8.19-8.31 (m, 1H) 8.65-8.85 (m, 1H). m/z (ESI, +ve ion)=552.2 [M+H]⁺.

Example 86. [1-[[(2R,3S,4R,5R)-5-[6-Chloro-4-(cyclopentylamino)pyrazolo[3,4-d]pyrimidin-1-yl]-3,4-dihydroxy-tetrahydrofuran-2-yl]methoxy]-2-hydroxy-1-(hydroxymethyl)ethyl]phosphonic acid (86)

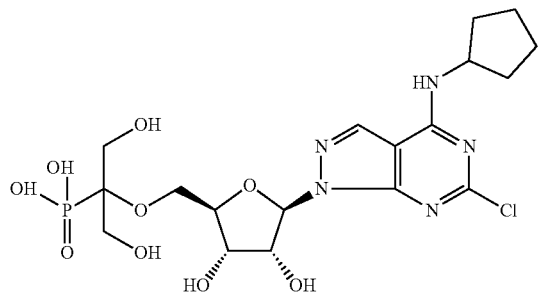 [SMILES: O=P(O)(O)C(CO)(CO)OC[C@H]1O[C@@H](n2ncc3c(NC4CCCC4)nc(Cl)nc32)[C@H](O)[C@@H]1O]

Step A. Ethyl 2-[[(3aR,4R,6R,6aR)-4-[4-[tert-butoxycarbonyl(cyclopentyl)amino]-6-chloro-pyrazolo[3,4-d]pyrimidin-1-yl]-2,2-dimethyl-3a,4,6,6a-tetrahydrofuro[3,4-d][1,3]dioxol-6-yl]methoxy]-2-diethoxyphosphoryl-3-(2-trimethylsilylethoxy)propanoate (86a)

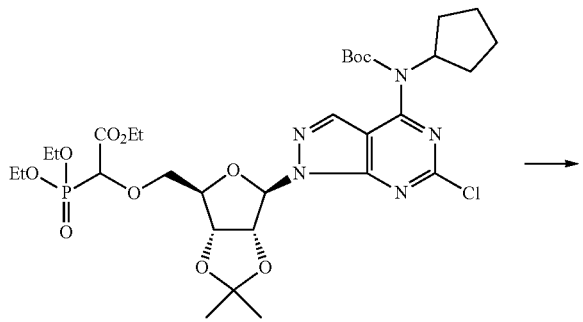

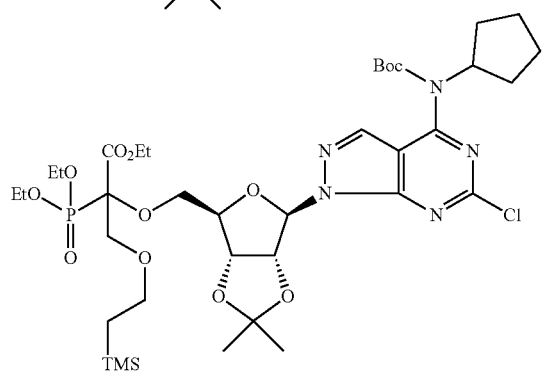

To a solution of ethyl 2-[[(3aR,4R,6R,6aR)-4-[4-[tert-butoxycarbonyl(cyclopentyl)amino]-6-chloro-pyrazolo[3,4-d]pyrimidin-1-yl]-2,2-dimethyl-3a,4,6,6a-tetrahydrofuro[3,4-d][1,3]dioxol-6-yl]methoxy]-2-diethoxyphosphoryl-acetate (1f) (1.6 g, 2.19 mmol) in THF (44 mL) was added dropwise sodium bis(trimethylsilyl)amide (2.84 mL, 2.84 mmol) at −15° C. After stirring at −15° C. for 25 min, tetra-n-butylammonium iodide (403.6 mg, 1.09 mmol) was added, immediately followed by the dropwise addition of 2-(chloromethoxy)ethyl](trimethyl)silane (1.18 mL, 6.56 mmol). After the solution was allowed to stir for 75 min at this temperature, it was quenched with sat. aq. NH₄Cl and subsequently diluted with EtOAc. The mixture was allowed to stir at rt for 5 min. To the mixture was added deionized water to dissolve some salts and the layers were separated. The organic layer was washed with additional sat. aq. NH₄Cl and the combined aqueous layers were then extracted with EtOAc (3×). The combined organic layers were washed with brine, dried over Na₂SO₄, filtered, and concentrated under reduced pressure. The crude residue was purified by flash column chromatography (0-75% EtOAc/Hexanes, a gradient elution) to afford the title compound (86a) (1.454 g, 84%) as a light yellow oil.

Step B. tert-Butyl N-[1-[(3aR,4R,6R,6aR)-6-[[1-diethoxyphosphoryl-1-(hydroxymethyl)-2-(2-trimethylsilylethoxy)ethoxy]methyl]-2,2-dimethyl-3a,4,6,6a-tetrahydrofuro[3,4-d][1,3]dioxol-4-yl]-6-chloro-pyrazolo[3,4-d]pyrimidin-4-yl]-N-cyclopentyl-carbamate (86b)

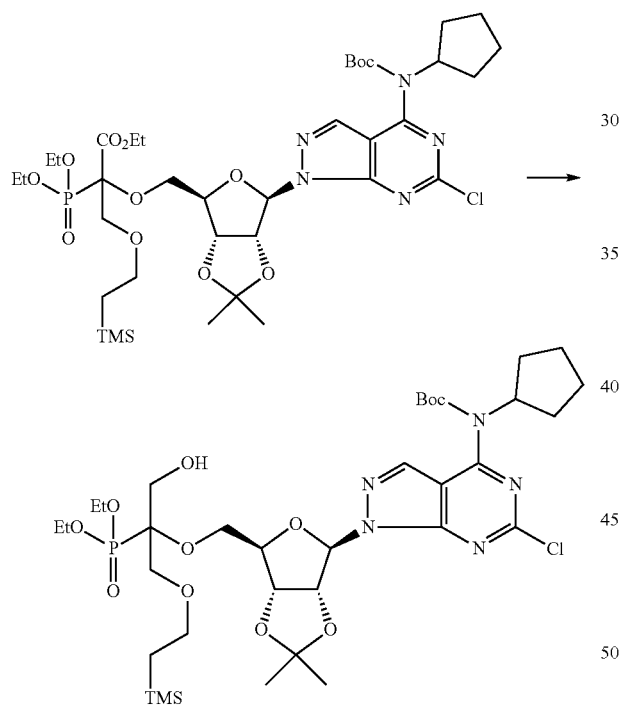

To a solution of 86a (1.45 g, 1.68 mmol) in ethanol (30 mL) was added calcium dichloride (769.45 mg, 6.73 mmol) at 0° C. followed by sodium borohydride (254.42 mg, 6.73 mmol). The mixture was warmed to rt and stirred for 4.5 h before being placed back into an ice bath. Once cooled, the reaction was quenched with 1 N HCl (35 mL), and then diluted with EtOAc (30 mL). The flask was allowed to stir at rt for 5 min and the organic layer was washed with additional 1 N HCl. the combined aqueous layers were extracted with EtOAc (2×) and the combined organic layers were then washed with brine, dried over Na₂SO₄, filtered, and concentrated under reduced pressure. The resulting crude residue was purified by flash column chromatography (0-100% EtOAc/Hexanes, a gradient elution) to afford the title compound (86b) (1.11 g, 88%). m/z (ESI, +ve ion)= 890.3 [M+H]⁺.

Step C. 2-[[(3aR,4R,6R,6aR)-4-[6-Chloro-4-(cyclopentylamino)pyrazolo[3,4-d]pyrimidin-1-1]-2,2-dimethyl-3a,4,6,6a-tetrahydrofuro[3,4-d][1,3]dioxol-6-yl]methoxy]-2-diethoxyphosphoryl-propane-1,3-diol (86c)

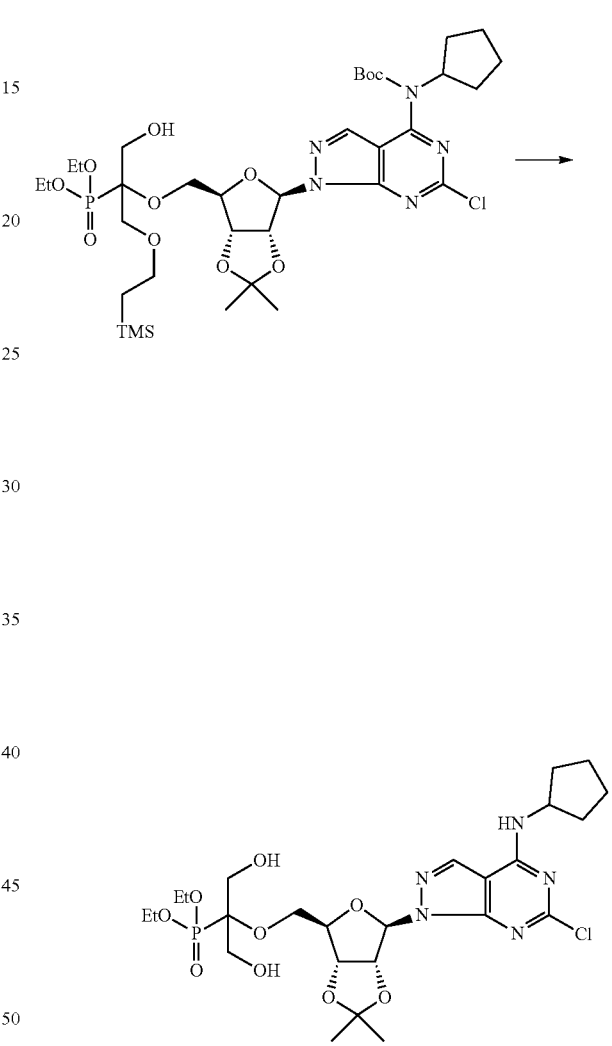

To a solution of 86b (920 mg, 1.12 mmol) in DCM (56 mL) was added dropwise boron trifluoride diethyl etherate (0.74 mL, 2.8 mmol) at 0° C. The reaction was allowed to warm to rt. After stirring for 75 min the reaction was quenched with triethylamine (20 mL). the solution was diluted with EtOAc (100 mL), and sat. aq. NaHCO₃ (100 mL) was added. Following separation of the layers, the aqueous layer was extracted with EtOAc (3×). The combined organic layers were then washed with brine, dried over Na₂SO₄, filtered, and concentrated under reduced pressure. The resulting crude residue was purified by flash column chromatography (0-75% EtOAc/Hexanes, a gradient elution and then 0-10% MeOH/DCM) to afford the title compound (86c) (469 mg, 67%) as an off-white foam. m/z (ESI, +ve ion)=620.2 [M+H]⁺.

Step D. [1-[[(2R,3S,4R,5R)-5-[6-Chloro-4-(cyclopentylamino)pyrazolo[3,4-d]pyrimidin-1-yl]-3,4-dihydroxy-tetrahydrofuran-2-yl]methoxy]-2-hydroxy-1-(hydroxymethyl)ethyl]phosphonic acid (86)

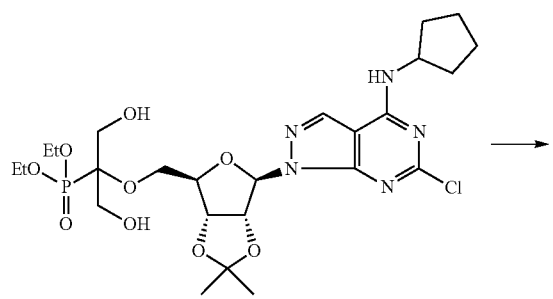

To a solution of 86c (460 mg, 0.74 mmol) in MeCN (37 mL) was added triethylamine (2.07 mL, 14.84 mmol). Bromo(trimethyl)silane (1.51 mL, 11.13 mmol) was then added dropwise to this mixture at rt. After stirring for 5 h, the mixture was concentrated under reduced pressure. The resulting residue was suspended in deionized water (12 mL), to which trifluoroacetic acid (4 mL) was added. After stirring at rt for 75 min, the solution was concentrated under reduced pressure to remove all volatile organics. The remaining aqueous solution was diluted with MeOH, and the resulting solution was then purified by reverse phase HPLC (15-40% ACN/H$_2$O with 0.1% TFA, a gradient elution) to provide the TFA salt of the title compound (86) (229.5 mg, 48%) as an off-white powder. $^1$H NMR (400 MHz, CD$_3$OD) δ 8.14 (s, 1H), 6.23 (d, J=4.8 Hz, 1H), 4.86 (t, J=5.0 Hz, 1H), 4.61-4.45 (m, 2H), 4.22 (q, J=4.0 Hz, 1H), 4.05 (dd, J=10.0, 3.2 Hz, 1H), 3.99 (dd, J=10.0, 4.8 Hz, 1H), 3.96-3.84 (m, 4H), 2.19-2.01 (m, 2H), 1.88-1.74 (m, 2H), 1.74-1.50 (m, 4H). m/z (ESI, +ve ion)=524.1 [M+H]$^+$.

Example 87. 1-[[(2R,3S,4R,5R)-5-[6-Chloro-4-(cyclopentylamino)pyrazolo[3,4-d]pyrimidin-1-yl]-3,4-dihydroxy-tetrahydrofuran-2-yl]methoxy]-2-methoxy-1-(methoxymethyl)ethyl]phosphonic acid (87)

Step A. Ethyl 2-(((3aR,4R,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)-3-methoxypropanoate (87a)

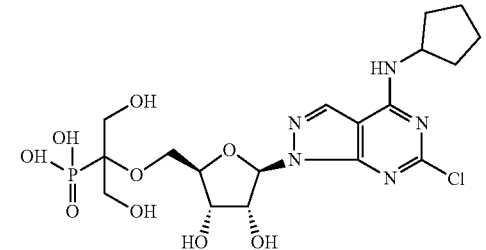

To a solution of ethyl 2-[[(3aR,4R,6R,6aR)-4-[4-[tert-butoxycarbonyl(cyclopentyl)amino]-6-chloro-pyrazolo[3,4-d]pyrimidin-1-yl]-2,2-dimethyl-3a,4,6,6a-tetrahydrofuro[3,4-d][1,3]dioxol-6-yl]methoxy]-2-diethoxyphosphoryl-acetate (1f) (2.9 g, 3.96 mmol) in THF (75 mL) was added dropwise sodium bis(trimethylsilyl)amide (5.15 mL, 5.15 mmol) at −15°. After stirring at −15° C. for 25 min, tetra-n-butylammonium iodide (731.52 mg, 1.98 mmol) was added, immediately followed by the dropwise addition of chloromethyl methyl ether (1.12 mL, 13.86 mmol). The solution was allowed to stir for 65 min at this temperature. The reaction was then quenched with sat. aq. NH$_4$Cl, and subsequently diluted with EtOAc. The mixture was allowed to stir at rt for 5 min. To the mixture was added deionized water to dissolve some salts and the layers were then separated. The organic layer was washed with additional sat. aq. NH$_4$Cl and the combined aqueous layers were extracted with EtOAc (3×). The combined organic layers were then washed with brine, dried over Na$_2$SO$_4$, filtered, and concentrated under reduced pressure. The crude residue was purified by flash column chromatography (0-75% EtOAc/Hexanes, a gradient elution) to afford the title compound (87a) (2.8558 g, 91%) as a yellow syrup. m/z (ESI, +ve ion)=846.3 [M+H]$^+$.

Step B. tert-Butyl N-[1-[(3aR,4R,6R,6aR)-6-[[1-diethoxyphosphoryl-1-(hydroxymethyl)-2-methoxy-ethoxy]methyl]-2,2-dimethyl-3a,4,6,6a-tetrahydro-furo[3,4-d][1,3]dioxol-4-yl]-6-chloro-pyrazolo[3,4-d]pyrimidin-4-yl]-N-cyclopentyl-carbamate (87b)

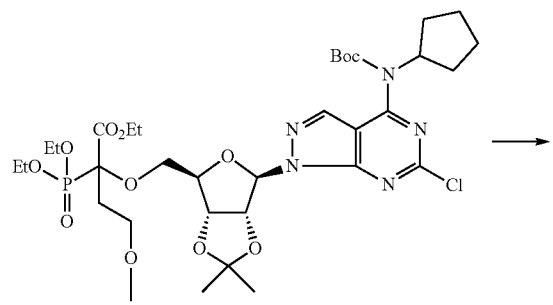

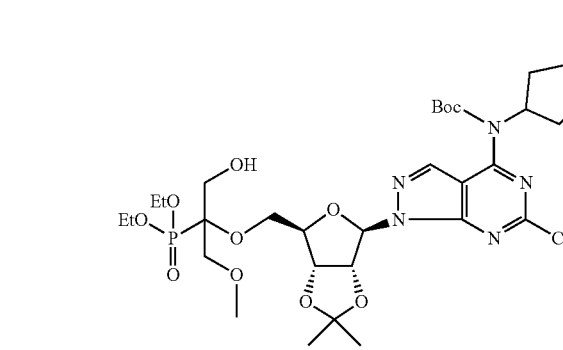

To a solution of 87a (1.61 g, 2.07 mmol) in ethanol (34 mL) that had been cooled to 0° C. using an ice bath, was added calcium dichloride (0.71 g, 6.22 mmol) followed by sodium borohydride (235.4 mg, 6.22 mmol). The mixture was warmed to rt, where it was stirred for 5 h before being placed back into an ice bath. Once cooled, the reaction was quenched with 1 N HCl (30 mL), and then diluted with EtOAc (30 mL). The flask was emoved from the bath and allowed to stir at rt for 20 min. The organic layer was washed with additional 1 N HCl and the combined aqueous layers were extracted with EtOAc (2×). The combined organic layers were then washed with brine, dried over Na$_2$SO$_4$, filtered, and concentrated under reduced pressure. The resulting crude residue was purified by flash column chromatography (0-100% EtOAc/Hex and then 0-10% MeOH/DCM, gradient elution) to yield the title compound (87b) (1.23 g, 87%) as a white foam. m/z (ESI, +ve ion)=734.2 [M+H]$^+$.

Step C. Butyl N-[1-[(3aR,4R,6R,6aR)-6-[[1-diethoxyphosphoryl-2-methoxy-1-(methoxymethyl)ethoxy]methyl]-2,2-dimethyl-3a,4,6,6a-tetrahydro-furo[3,4-d][1,3]dioxol-4-yl]-6-chloro-pyrazolo[3,4-d]pyrimidin-4-yl]-N-cyclopentyl-carbamate (87c)

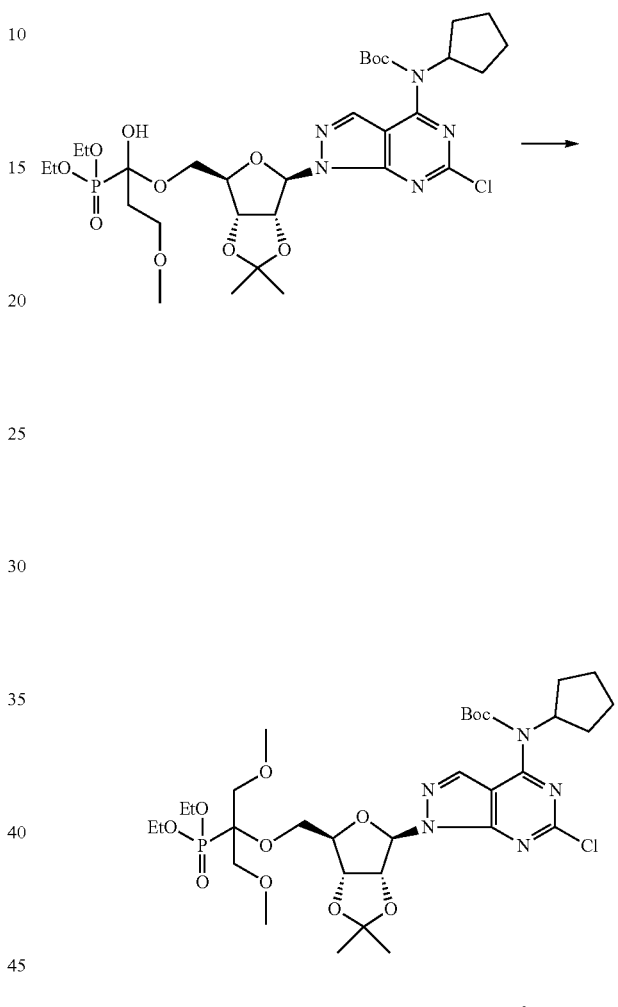

To a round bottom flask containing activated 4 Å MS was added a solution of 87b (1.1 g, 1.5 mmol) in DCM (40 mL). To this stirring solution was added 1,8-bis(dimethylamino)naphthalene (2.01 g, 9.36 mmol), followed by the addition of trimethyloxonium tetrafluoroborate (1.22 g, 7.84 mmol). After stirring at rt for 7 h, the reaction was quenched with sat. aq. NaHCO$_3$ (20 mL). The biphasic solution was filtered to remove the MS, and the MS were washed with deionized water and DCM. After separating the two layers, the organic layer was washed with additional sat. aq. NaHCO$_3$ (20 mL). The combined aqueous layers were extracted with DCM (2×) and the combined organic layers were then washed with 1 N HCl (2×). The aqueous layers were combined and extracted with DCM (2×) again and the combined organic layers were washed with brine, dried over Na$_2$SO$_4$, filtered, and concentrated under reduced pressure. The resulting crude residue was purified via flash column chromatography (silica gel, 0-100% EtOAc/Hexanes, a gradient elution) to give the title compound (87c) (588.4 mg, 52%) as a clear colorless oil. m/z (ESI, +ve ion)=748.3 [M+H]$^+$.

Step D. [1-[[(2R,3S,4R,5R)-5-[6-Chloro-4-(cyclopentylamino)pyrazolo[3,4-d]pyrimidin-1-yl]-3,4-dihydroxy-tetrahydrofuran-2-yl]methoxy]-2-methoxy-1-(methoxymethyl)ethyl]phosphonic acid (87)

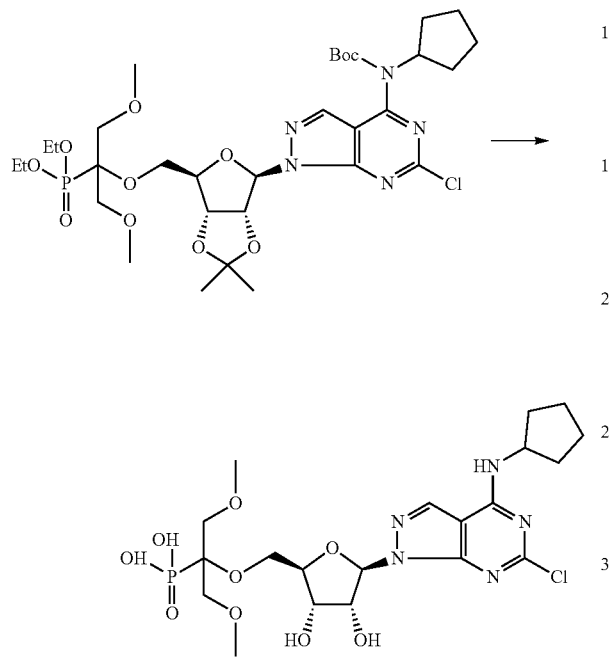

The title compound was prepared from 87c by procedures similar to those described in Example 86, Step D. $^1$H NMR (400 MHz, CD$_3$OD) δ 8.14 (s, 1H), 6.20 (d, J=4.4 Hz, 1H), 4.86 (t, J=4.8 Hz, 1H), 4.54 (p, J=6.9 Hz, 1H), 4.47 (t, J=4.6 Hz, 1H), 4.16 (q, J=4.9 Hz, 1H), 3.99 (dd, J=10.0, 4.8 Hz, 1H), 3.87 (dd, J=10.2, 5.8 Hz, 1H), 3.86-3.64 (m, 4H), 3.33 (s, 3H), 3.31 (s, 3H), 2.19-2.03 (m, 2H), 1.89-1.74 (m, 2H), 1.74-1.53 (m, 4H). m/z (ESI, +ve ion)=552.1 [M+H]$^+$.

Example 88. (2-(((2R,3S,4R,5R)-5-(4-(Cyclopentylamino)-6-(3-hydroxypropyl)-1H-pyrazolo[3,4-d]pyrimidin-1-yl)-3,4-dihydroxytetrahydrofuran-2-yl)methoxy)-1-hydroxypropan-2-yl)phosphonic acid (88)

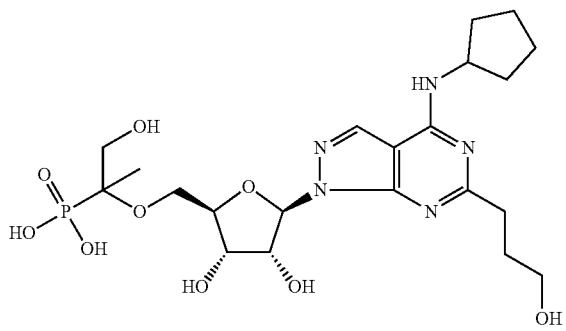 [SMILES: CC(CO)(OC[C@H]1O[C@@H](n2ncc3c(NC4CCCC4)nc(CCCO)nc32)[C@H](O)[C@@H]1O)P(=O)(O)O]

Step A. Ethyl (E)-3-(4-((tert-butoxycarbonyl)cyclopentyl)amino)-1-((3aR,4R,6R,6aR)-6-(((2-(diethoxyphosphoryl)-1-ethoxy-1-oxopropan-2-yl)oxy)methyl)-2,2-dimethyltetrahydrofuro[3,4-d][1,3]dioxol-4-yl)-1H-pyrazolo[3,4-d]pyrimidin-6-yl) acrylate (88a)

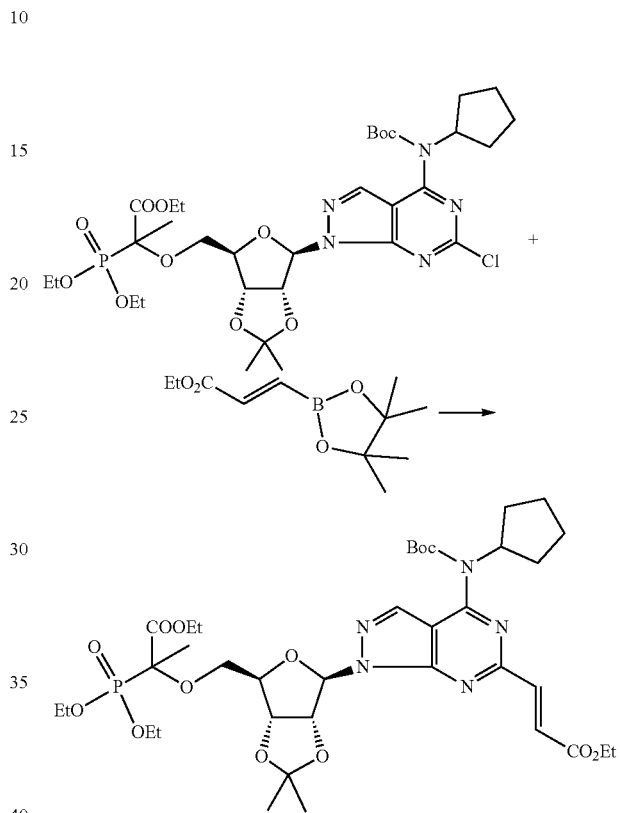

To a solution of ethyl 2-(((3aR,4R,6R,6aR)-6-(4-((tert-butoxycarbonyl)(cyclopentyl)amino)-6-chloro-1H-pyrazolo[3,4-d]pyrimidin-1-yl)-2,2-dimethyltetrahydrofuro[3,4-d][1,3]dioxol-4-yl)methoxy)-2-(diethoxyphosphoryl)propanoate (alpha-methyl substituted 1f) (930 mg, 1.25 mmol) in dioxane (50 mL) was added (E)-ethyl 3-(4,4,5,5-tetramethyl-1,3,2-dioxaborolan-2-yl)acrylate (565 mg, 2.5 mmol), Na$_2$CO$_3$ (400 mg, 3.75 mmol) and water (15 mL). After the mixture was degassed by N$_2$ three times, Pd(PPh$_3$)$_4$ (200 mg) was added and the resulting mixture was degassed for another 5 min. The mixture was stirred at 90° C. for 6 h, cooled to rt. quenched with water, and extracted with EtOAc. The combined organic layers were washed with brine, dried over anhydrous Na$_2$SO$_4$ and concentrated under reduced pressure. The residue was purified by column chromatography to afford the title compound (88a) (600 mg, 59% yield) as a yellow oil. m/z (ESI, +ve ion)=879.36 [M+H]$^+$.

Step B. Ethyl 2-(((3aR,4R,6R,6aR)-6-(4-((tert-butoxycarbonyl)(cyclopentyl)amino)-6-(3-ethoxy-3-oxopropyl)-1H-pyrazolo[3,4-d]pyrimidin-1-yl)-2,2-dimethyltetrahydrofuro[3,4-d][1,3]dioxol-4-yl)methoxy)-2-(diethoxyphosphoryl)propanoate (88b)

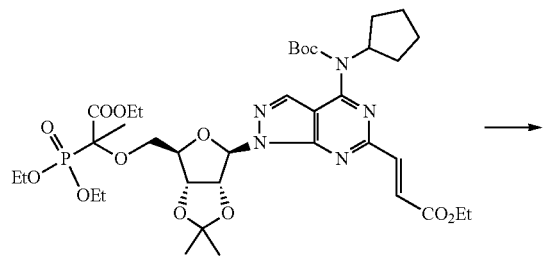

To a solution of 88a (500 mg, 0.62 mmol) in MeOH (70 mL) was added 10% Pd—C (0.1 g). After the mixture was stirred under 1 atm of $H_2$ at rt for 3 h, it was filtered and the filtrate was concentrated under reduced pressure. The residue was purified by column chromatography to afford the title compound (88b) (360 mg, 0.44 mmol, 72% yield) as a yellow oil.

Step C. tert-Butyl cyclopentyl(1-((3aR,4R,6R,6aR)-6-(((2-(diethoxyphosphoryl)-1-hydroxypropan-2-yl)oxy)methyl)-2,2-dimethyltetrahydrofuro[3,4-d][1,3]dioxol-4-yl)-6-(3-hydroxypropy)-1H-pyrazolo[3,4-d]pyrimidin-4-yl)carbamate (88c)

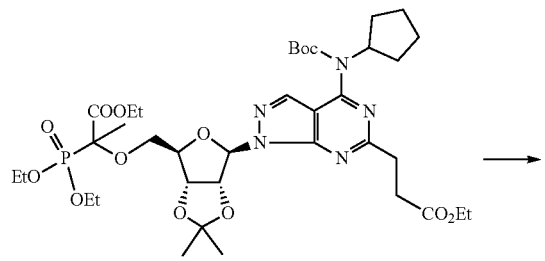

To a solution of 88b (360 mg, 0.44 mmol) in THF (10 mL) was added $LiBH_4$ (1.8 mL, 2.0M in THF) at 0° C. The mixture was stirred at rt for 2 h and then quenched with sat.$NH_4Cl$ (5 mL). The solution was extracted with EtOAc and the combined organic layer was washed with brine, dried with $Na_2SO_4$, filtered, concentrated. The crude oil was purified by column chromatography to provide the title compound (88c) (110 mg, 34% yield) as a yellow oil. m/z (ESI, +ve ion)=727.36 $[M+H]^+$.

Step D. 2-(((2R,3S,4R,5R)-5-(4-(Cyclopentylamino)-6-(3-hydroxypropyl)-1H-pyrazolo[3,4d]pyrimidin-1-yl)-3,4-dihydroxytetrahydrofuran-2-yl)methoxy)-1-hydroxypropan-2-ylphosphonic acid (88)

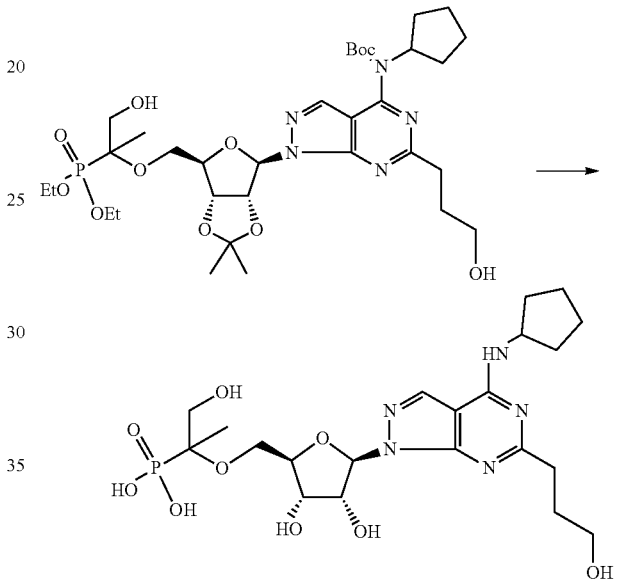

The title compound was prepared from 88c by procedures similar to those described in Example 86, Step D. $^1$H NMR (400 MHz, $D_2O$) δ 8.34-8.26 (m, 1H), 6.22 (m, 1H), 4.88 (m, 1H), 4.44 (m, 1H), 4.30 (m, 1H), 4.18 (m, 1H), 3.74-3.70 (m, 3H), 3.63-3.51 (m, 3H), 2.95 (t, J=7.6 Hz, 1H), 2.84 (t, J=7.6 Hz, 1H), 2.04-1.92 (m, 4H), 1.65-1.56 (m, 6H), 1.20 (d, J=13.2 Hz, 3H). m/z (ESI, +ve ion)=531.27 $[M+H]^+$.

Example 89. (2-(((2R,3S,4R,5R)-5-(4-(Cyclopentylamino)-6-(3-hydroxyprop-1-yn-1-yl)-1H-pyrazolo[3,4-d]pyrimidin-1-yl)-3,4-dihydroxytetrahydrofuran-2-yl)methoxy)-1-hydroxypropan-2-yl)phosphonic acid (89)

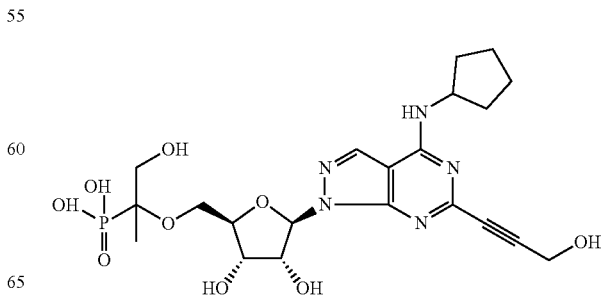

353

Step A. tert-Butyl (1-((3aR,4R,6R,6aR)-6-(((tert-butyldiphenylsilyl)oxy)methyl)-2,2-dimethyltetrahydrofuro[3,4-d][1,3]dioxol-4-yl)-6-chloro-1H-pyrazolo[3,4-d]pyrimidin-4-yl)(cyclopentyl)carbamate (89a)

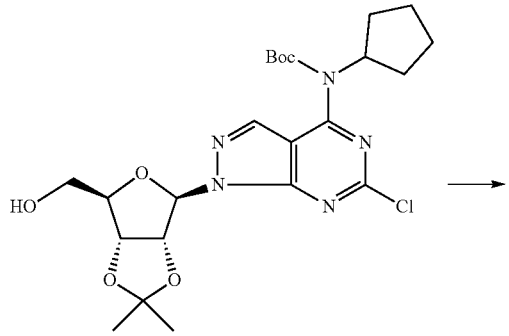

To a solution of 1e (2.25 g, 4.42 mmol) in DCM (25 mL) was added TBDPSCl (2.06 g, 7.5 mmol), Et₃N (1.01 g, 10 mmol) and DMAP (53.7 mg, 0.44 mmol). After the mixture was stirred at rt overnight, it was washed with water (15 mL), saturated aqueous NaHCO₃ (15 mL) and brine (15 mL). The organic phase was dried over anhydrous Na₂SO₄ and concentrated under reduced pressure. The residue was purified by column chromatography to provide the title compound (89a) (3.0 g, 89% yield) as a white solid. m/z (ESI, +ve ion)=748.24 [M+H]⁺.

Step B. tert-Butyl (6-amino-1-((3aR,4R,6R,6aR)-6-(((tert-butyldiphenylsilyl)oxy)methyl)-2,2-dimethyltetrahydrofuro[3,4-d][1,3]dioxol-4-yl)-1H-pyrazolo[3,4-d]pyrimidin-4-yl)(cyclopentyl)carbamate (89b)

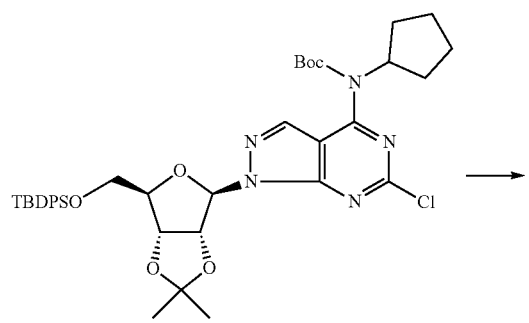

354

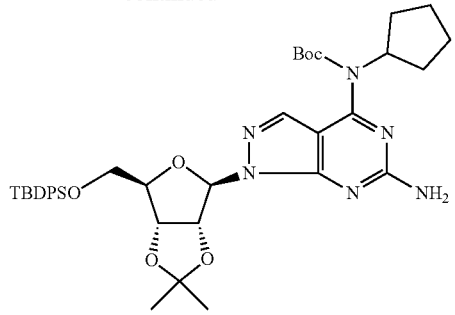

To a high pressure reactor was added 89a (3.0 g, 40.1 mmol), dioxane (90 mL) and NH₃ (300 mL, 5.0 N in methanol). The reaction mixture was stirred at 87° C. overnight and concentrated. The residue was purified by column chromatography to afford the title compound (89b) (1.6 g, 55% yield) as a white solid. m/z (ESI, +ve ion)= 729.17 [M+H]⁺.

Step C. tert-Butyl (1-((3aR,4R,6R,6aR)-6-(((tert-butyldiphenylsilyl)oxy)methyl)-2,2-dimethyltetrahydrofuro[3,4-d][1,3]dioxo-4-yl)-6-iodo-1H-pyrazolo[3,4-d]pyrimidin-4-yl)(cyclopentyl)carbamate (89c)

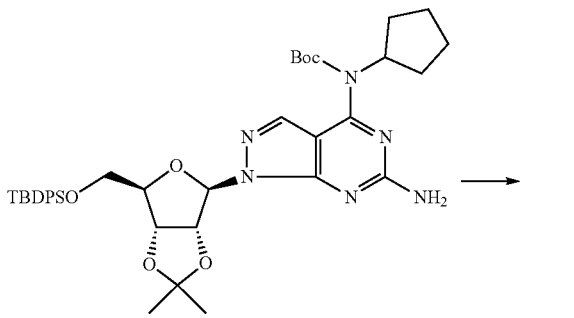

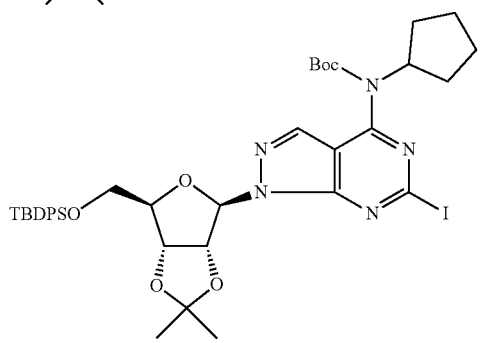

To a solution of 89b (5.9 g, 8.1 mmol) in THF (70 mL) was added CuI (2.0 g, 10.5 mmol), I₂ (2.67 g, 10.5 mmol) and CH₂I₂ (2.89 g, 10.5 mmol). Me mixture was degassed by N₂ three times, subsequently, tert-butyl nitrite (3.34 g, 32.4 mmol) was added and the resulting mixture was degassed for another 5 min. The mixture was stirred at reflux for 2 h and then cooled to rt. The mixture was filtered and the filtrate was extracted with EtOAc. The organic layers was washed with brine, dried over anhydrous Na₂SO₄ and concentrated under reduced pressure. The residue was purified by column chromatography to afford the title compound (89c) (2.3 g, 34% yield) as a yellow solid. m/z (ESI, +ve ion)=909.26 [M+H]+.

Step D. tert-Butyl (1-((3aR,4R,6R,6aR)-6-(((tert-butyldiphenylsilyl)oxy)methyl)-2,2-dimethyltetrahydrofuro[3,4-d][1,3]dioxol-4-yl)-6-(3-((tetrahydro-2H-pyran-2-yl)oxy)prop-1-yn-1-yl)-1H-pyrazolo[3,4-d]pyrimidin-4-yl)(cyclopentyl)carbamate (89d)

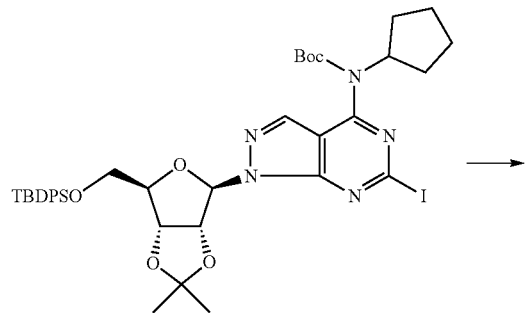

To a solution of 89c (1.5 g, 1.8 mmol) in dioxane (20 mL) was added CuI (20 mg), 2-(prop-2-ynyloxy)tetrahydro-2H-pyran (0.326 g, 2.5 mmd) and TEA (10 mL). After the mixture was degassed by N₂ three times, Pd(PPh₃)₂Cl₂ (38 mg, 0.03 eq) was added and the resulting mixture was degassed for 5 min. The mixture was stirred at 40° C. for 1 h and then cooled to rt. The mixture was added water and extracted with EtOAc. The organic layers was washed with brine, dried over anhydrous Na₂SO₄ and concentrated under reduced pressure. The residue was purified by column chromatography to afford the title compound (89d) (1.3 g, 85% yield) as a yellow solid. m/z (ESI, +ve ion)=851.43 [M+H]+.

Step E. tert-Butyl cyclopentyl(1-((3aR,4R,6R,6aR)-6-(hydroxymethyl)-2,2-dimethyltetrahydrofuro[3,4-d][1,3]dioxol-4-yl)-6-(3-((tetrahydro-2H-pyran-2-yl)oxy)prop-1-yn-1-yl)-1H-pyrazolo[3,4-d]pyrimidin-4-yl)carbamate (89e)

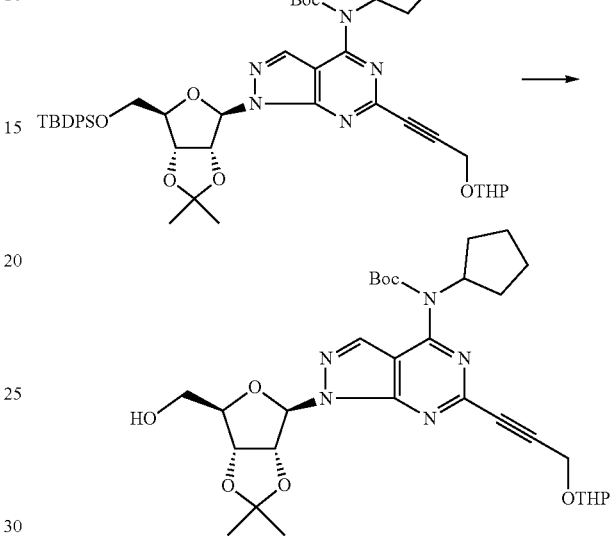

To a solution of 89d (1.3 g, 1.5 mmol) in THF (20 mL) at 0° C. was added TBAF (0.75 g, 2.4 mmol). After the mixture was stirred at 25° C. for 1 h, it was quenched with saturated NaHCO₃ and extracted with EtOAc. The organic layers were washed with brine, dried over anhydrous Na₂SO₄ and concentrated under reduced pressure. The residue was purified by column chromatography to afford the title compound (89e) (0.69 g, 73% yield) as a purple solid. m/z (ESI, +ve ion)=613.31 [M+H]+.

Step F. (2-(((2R,3S,4R,5R)-5-(4-(Cyclopentylamino)-6-(3-hydroxyprop-1-yn-1-yl)-1H-pyrazolo[3,4-d]pyrimidin-1-yl)-3,4-dihydroxytetrahydrofuran-2-yl)methoxy)-1-hydroxypropan-2-yl)phosphonic acid (89)

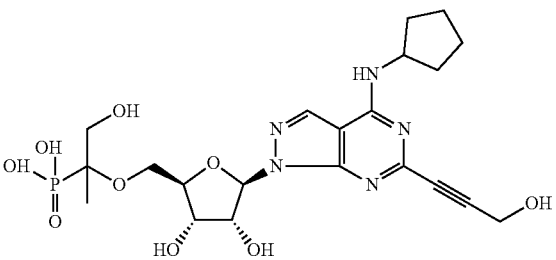 [SMILES: CC(CO)(OC[C@H]1O[C@@H](n2ncc3c(NC4CCCC4)nc(C#CCO)nc32)[C@H](O)[C@@H]1O)P(=O)(O)O]

The title compound was prepared from 89e by procedures similar to these described in Example 8, Steps C, D, and F. ¹H NMR (400 MHz, D₂O) δ ¹H NMR (400 MHz, D₂O) δ 8.31-8.19 (m, 1H), 6.13 (m, 1H), 4.85 (m, 1H), 4.43-4.40 (m, 3H), 4.34-4.17 (m, 2H), 3.80-3.60 (m, 3H), 3.52-3.47 (m, 1H), 1.96 (m, 2H), 1.65-1.55 (m, 6H), 1.18 (d, J=14 Hz, 3H). m/z (ESI, +ve ion)=527.18 [M+H]+.

Example 90. (2-(((2R,3S,4R,5R)-5-(4-(Cyclopentylamino)-6-(hydroxymethyl)-1H-pyrazolo[3,4-d]pyrimidin-1-yl)-3,4-dihydroxytetrahydrofuran-2-yl)methoxy)-1-methoxypropan-2-yl)phosphonic acid (90)

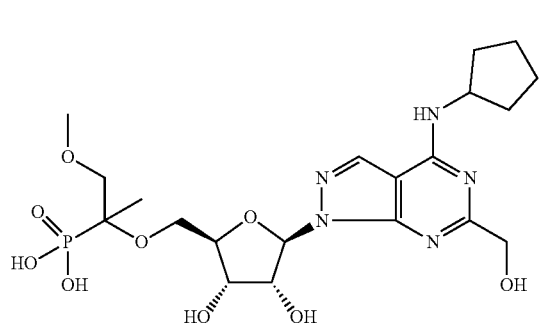 [SMILES: COCC(C)(OC[C@H]1O[C@@H](n2ncc3c(NC4CCCC4)nc(CO)nc32)[C@H](O)[C@@H]1O)P(=O)(O)O]

Step A. ((3aR,4R,6R,6aR)-6-(4-(tert-Butoxycarbonyl)(cyclopentyl)amino)-6-choro-1H-pyrazolo[3,4-d]pyrimidin-1-yl)-2,2-dimethyltetrahydrofuro[3,4-d][1,3]dioxol-4-yl)methyl benzoate (90a)

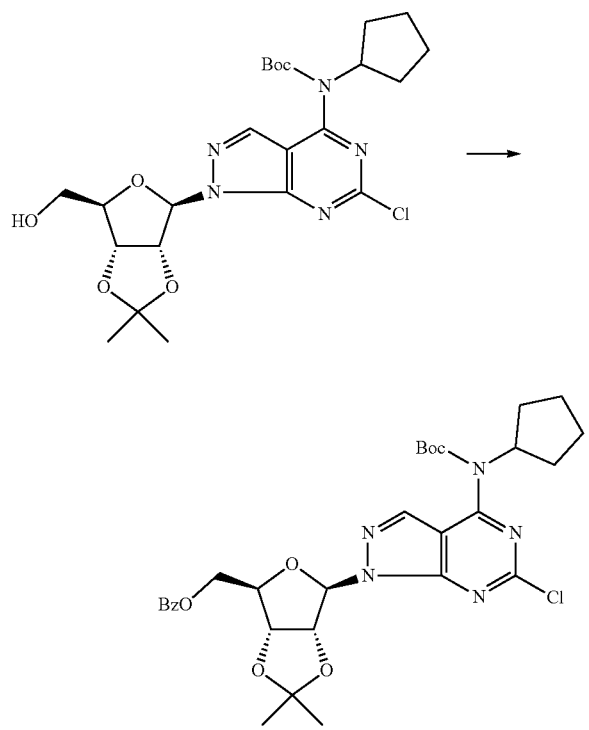

To a solution of 1e (5.0 g, 9.8 mmol), triethylamine (2.98 g, 29.5 mmol) and DMAP (300 mg, 2.5 mmol) in DCM (100 mL) was added dropwise BzCl (2.07 g, 14.7 mmol) at 0° C. over 10 min. The mixture was allowed to warm to rt and stirred overnight. The mixture was washed with aq. NaHCO₃. The organic layer was dried and concentrated in vacuo. The residue was purified by column chromatography to afford the title compound (90a) (5.2 g, 87% yield).

Step B. ((3aR,4R,6R,6aR)-6-(4-((tert-Butoxycarbonyl)(cyclopentyl)amino)-6-((E)-styryl)-1H-pyrazolo[3,4-d]pyrimidin-1-yl)-2,2-dimethyltetrahydrofuro[3,4-d][1,3]dioxol-4-yl)methylbenzoate (90b)

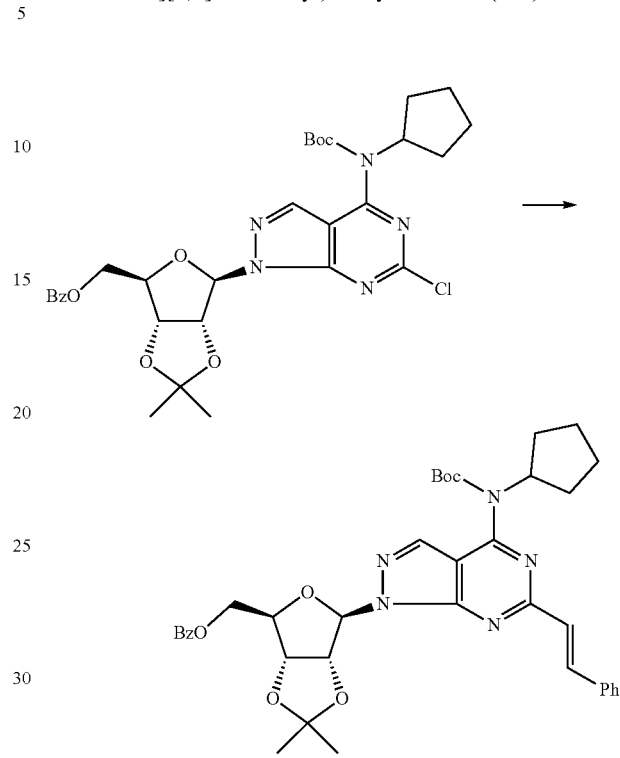

Pd(PPh₃)₄ (987 mg, 0.85 mmol) was added to a mixture of 90a (5.2 g, 8.48 mmol), (E)-styrylboronic acid (1.88 g, 12.7 mmol), and Na₂CO₃ (2.7 g, 25.4 mmol) in THF (120 mL) and water (40 mL). The reaction mixture was refluxed under nitrogen overnight. After the mixture was cooled to rt, it was diluted with water and extracted with ethyl acetate. The organic layer was washed with brine, dried and concentrated in vacuo. The residue was purified by column chromatography to give the title compound (90b) (5 g, 86% yield). m/z (ESI, +ve ion)=688.8 [M+H]⁺.

Step C. ((3aR,4R,6R,6aR 6(4-((tert-Butoxycarbonyl)(cyclopentyl)amino)-6-formyl-1H-pyrazolo[3,4-d]pyrimidin-1-yl)-2,2-dimethyltetrahydrofuro[3,4-d][1,3]dioxol-4-yl)methyl benzoate (90c)

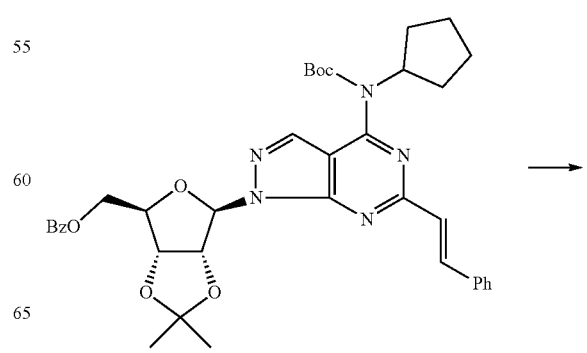

-continued

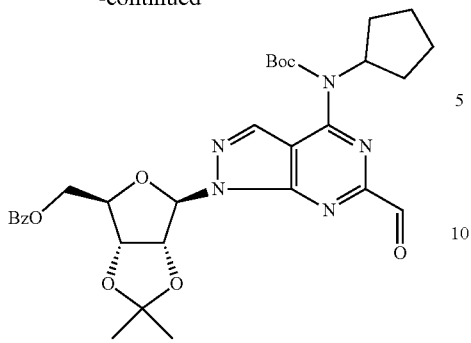

To a solution of 90b (5 g, 7.34 mmol) and 2,6-lutidine (1.57 g, 14.7 mmol) in THF (200 mL) and water (100 mL) was added NaIO$_4$ (9.43 g, 44.1 mmol) followed by addition of K$_2$OsO$_4$.2H$_2$O (67 mg, 0.2 mmol). The mixture was stirred at rt overnight and then diluted with water and extracted with EtOAc. The organic layer was washed with sat. Na$_2$S$_2$O$_3$, brine, dried and concentrated in vacuo. The residue was purified by column chromatography to afford the title compound (90c) (4 g, 90% yield). m/z (ESI, +ve ion)=629.9 [M+Na]$^+$.

Step D. ((3aR,4R,6R,6aR)-6-(4-((tert-Butoxycarbonyl)(cyclopentyl)amino)-6-(hydroxymethyl)-1H-pyrazolo[3,4-d]pyrimidin-1-yl)-2,2-dimethyltetrahydrofuro[3,4-d][1,3]dioxol-4-yl)methyl benzoate (90d)

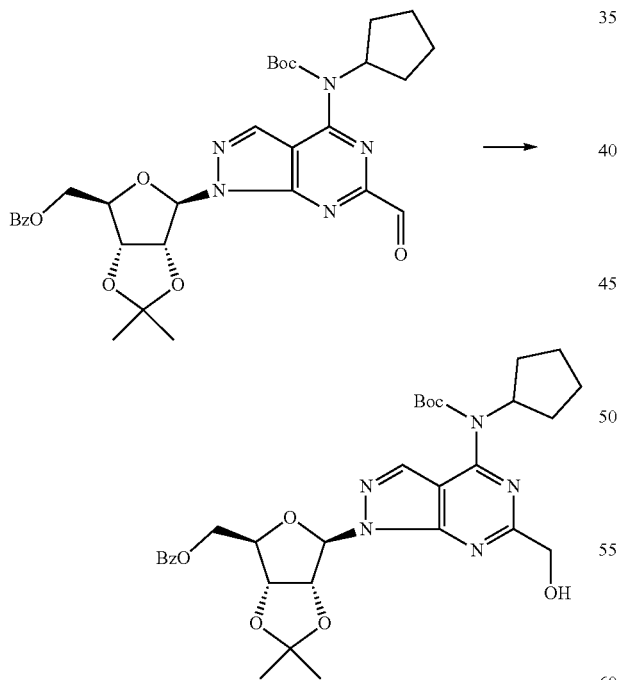

NaBH$_4$ (375 mg, 9.88 mmol) was added to a solution of 90c (4 g, 6.59 mmol) in methanol (100 mL). After the mixture was stirred at rt for 1 h, it was concentrated in vacuo and purified by column chromatography to provide the title compound (90d)(3.8 g, 95% yield). m/z (ESI, +ve ion)= 10.0 [M+H]$^+$.

Step E. ((3aR,4R,6R,6aR)-6-(4-((tert-Butoxycarbonyl)(cyclopentyl)amino)-6-(((tetrahydro-2H-pyran-2-yl)oxy)methyl)-1H-pyrazol[3,4-d]pyrimidin-1-yl)-2,2-dimethyltetrahydrofuro[3,4-d][1,3]dioxol-4-yl) methyl benzoate (90e)

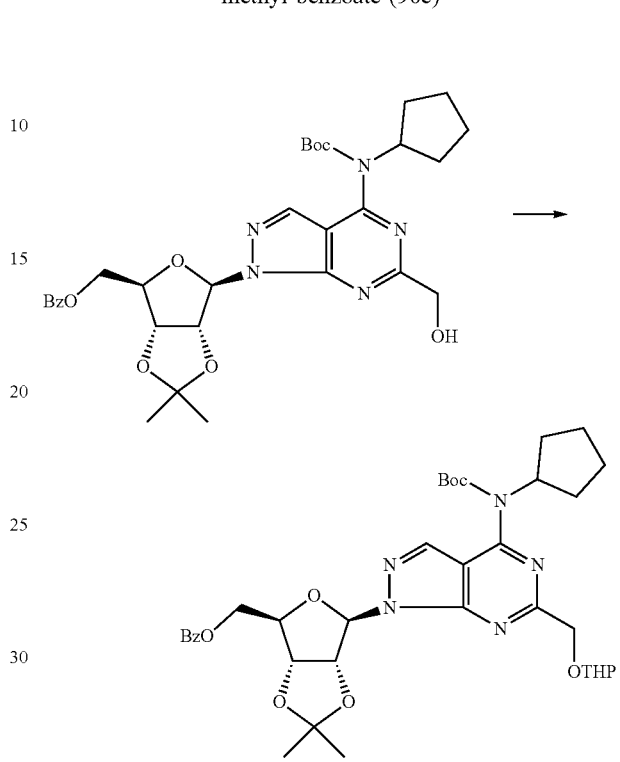

PPTS (470 mg, 1.87 mmol) was added to a solution of 90d (3.8 g, 6.2 mmol) and 3,4-dihydro-2H-pyran (5.2 g, 62 mmol) in DCM (120 mL). After the mixture was stirred at rt overnight, it was washed with sat. NaHCO$_3$. The organic layer was washed with brine, dried and concentrated. The residue was purified by column chromatography to afford the title compound (90e) (4 g, 92% yield). m/z (ESI, +e ion)=694.6 [M+H]$^+$.

Step F. tert-butyl Cyclopentyl(1-((3aR,4R,6R,6aR)-4-(hydroxymethyl)-2,2-dimethyltetrahydrofuro[3,4-d][1,3]dioxol-4-yl)-6-(((tetrahydro-2H-pyran-2-yl)oxy)methyl)-1H-pyrazolo[3,4-d]pyrimidin-4-yl) carbamate (90f)

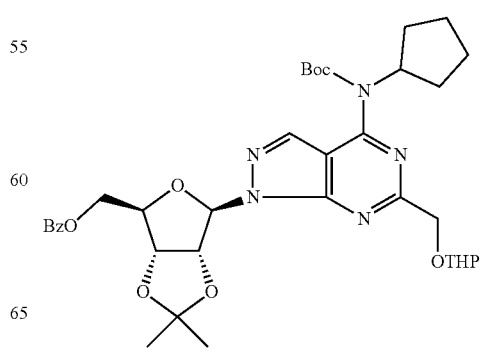

-continued

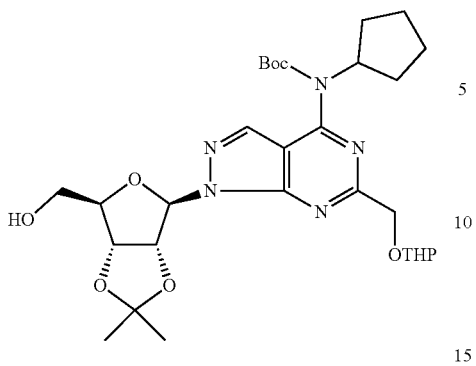

K$_2$CO$_3$ (1.19 g, 8.66 mmol) was added to a solution of 90e (4 g, 5.84 mmol) in methanol (150 mL). After the mixture was stirred at rt for 1 h, it was poured into brine and extracted with EtOAc. The organic layer was dried, concentrated and purified by column chromatography to give the title compound 90f (3 g, 88% yield). m/z (ESI, +ve ion)= 590.2 [M+H]$^+$.

Step G. (2-(((2R,3S,4R,5R)-5-(4-(Cyclopentylamino)-6-(hydroxymethyl)-1H-pyrazolo[3,4d1]pyrimidin-1-yl)-3,4-dihydroxytetrahydrofuran-2-yl)methoxy)-1-methoxypropan-2-yl)phosphonic acid (90)

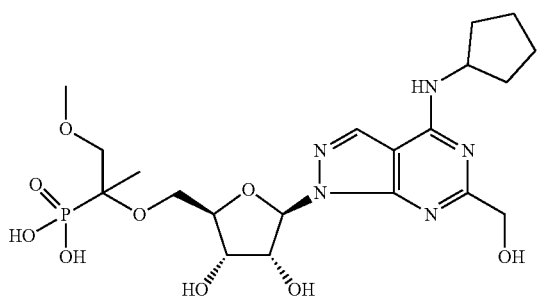 [SMILES: COCC(C)(OC[C@H]1O[C@@H](n2ncc3c(NC4CCCC4)nc(CO)nc32)[C@H](O)[C@@H]1O)P(=O)(O)O]

The title compound was prepared from 90f by procedures similar to those described in Example 8, Steps C and D, followed by Steps C and D in Example 87. 1H NMR (D$_2$O, 400 MHz) δ 8.24-8.48 (m, 1H), 6.23 (m, 1H), 4.79-4.74 (m, 3H), 4.43 (m, 2H), 4.16 (m, 1H), 3.78 (m, 2H), 3.52-3.46 (m, 2H), 3.18 (s, 3H), 2.04 (m, 2H), 1.65 (m, 6H), 1.22-1.16 (dd, J=14.8 Hz, 6.4 Hz, 3H). m/z (ESI, +ve ion)=517.8.0 [M+H]$^+$.

Example 91. (2-(((2R,3S,4R,5R)-5-(2-Chloro-4-(cyclopentylamino)-7H-pyrrolo[2,3-d]pyrimidin-7-yl)-3,4-dihydroxytetrahydrofuran-2-yl)methoxy)-1-hydroxypropan-2-yl)phosphonic acid (91)

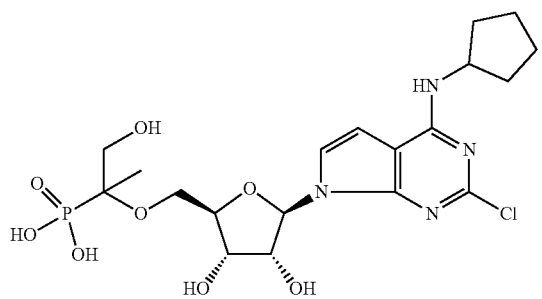 [SMILES: CC(CO)(OC[C@H]1O[C@@H](n2ccc3c(NC4CCCC4)nc(Cl)nc32)[C@H](O)[C@@H]1O)P(=O)(O)O]

Step A. 2-Chloro-N-cyclopentyl-7H-pyrrolo[2,3-d]pyrimidin-4-amine (91a)

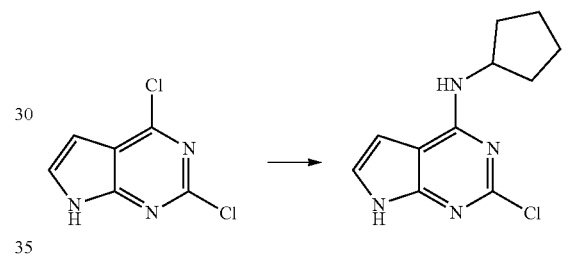

A mixture of 2,4-dichloro-7H-pyrrolo[2,3-d]pyrimidine (5 g, 26.74 mmol), cyclopentanamine (3.41 g, 40.11 mmol) and triethylamine (5.4 g, 53.48 mmol) in ethanol (50 mL) was refluxed overnight. The mixture was concentrated to dryness, the residue was treated with water (50 mL) and the mixture was stirred for 1 h. The solid was filtered and dried under vacuum to afford the title compound (91a) (6 g, 95% yield). m/z (ESI, +ve ion)=237.0 [M+H]$^+$.

Step B. (3aR,6R,6aR)-6-(Hydroxymethyl)-2,2-dimethyltetrahydrofuro[3,4-d][1,3]dioxol-4-ol (91b)

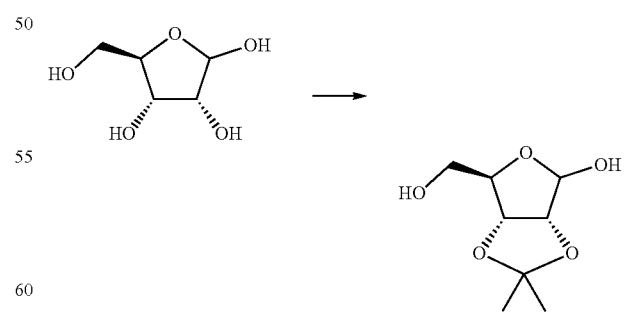

Concentrated sulfuric acid (0.3 mL) was added to a suspension of D-ribose (12.5 g, 90 mmol) in acetone (125 mL). The reaction mixture was stirred at rt for 90 min to obtain a clear solution which was then neutralized with saturated aqueous sodium carbonate. The mixture was filtered over celite and the filtrate was concentrated in vacuo to afford the title compound (91b) (16 g), which was used in next step without purification.

Step C. ((3aR,4R,6aR)-6-Hydroxy-2,2-dimethyltetrahydrofuro[3,4-d][1,3]dioxol-4-yl)methyl benzoate (84c)

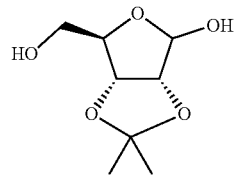

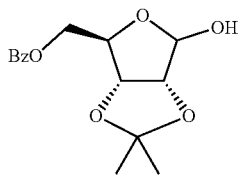

To a solution of 91b (16 g, 90 mmol) in pyridine (60 mL) was added dropwise BzCl (12.9 g, 91 mmol) at 0° C. After the mixture was stirred at rt overnight, it was concentrated in vacuo. The residue was treated with EtOAc and the solution was washed with 5% aq. citric acid. The organic layer was dried and concentrated in vacuo and the residue was purified by column chromatography (20% EtOAc/Petroleum) to afford the title compound (91c) (12 g, 49% yield over two steps). m/z (ESI, +ve ion)=316.4 [M+Na]$^+$ Step D. ((3aR,4R,6aR)-6-Bromo-2,2-dimethyltetrahydrofuro[3,4-d][1,3]dioxol-4-yl)methyl benzoate (91d)

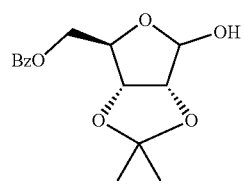

To a solution of 91c (3.3 g, 11.22 mmol) in dry DCM (60 mL) was added dropwise TMSBr (5.15 g, 33.66 mmol) at 0° C. After the mixture was allowed to warm to rt and stirred for 2 h, it was concentrated in vacuo at rt. The residue was used in next step immediately.

Step E. ((3aR,4R,6R,6aR)-6-(2-Chloro-4-(cyclopentylamino)-7H-pyrrolo[2,3-d]pyrimidin-7-yl)-2,2-dimethyltetrahydrofuro[3,4-d][1,3]dioxol-4-yl)methyl benzoate (91e)

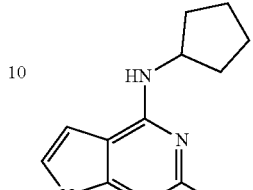

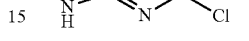

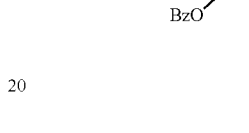

To a suspension of 91a (608 mg, 2.58 mmol) in dry MeCN (20 mL) was added NaH (60% in mineral oil, 155 mg, 3.86 mmol). After the mixture was stirred at rt for 0.5 h, a solution of 91d (1.1 g, 3.09 mmol) in dry MeCN (10 mL) was added to the solution above. The reaction mixture was stirred at rt overnight and then poured into sat. NH$_4$Cl. The solution was extracted with EtOAc and the organic layer was washed with brine, dried and concentrated in vacuo. The residue was purified by column chromatography to give the title compound (91e) (1 g, 76% yield). m/z (ESI, +ve ion)=535.1 [M+Na]$^+$.

Step F. ((3aR,4R,6R,6aR)-6-(2-Chloro-4-(cyclopentylamino)-7H-pyrrolo[2,3-d]pyrimidin-7-yl)-2,2-dimethyltetrahydrofuro[3,4-d][1,3]dioxol-4-yl)methanol (91f)

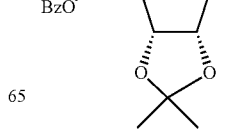

365
-continued

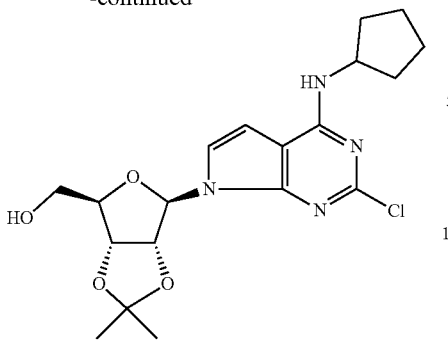

K₂CO₃ (248 mg, 1.85 mmol) was added to a solution of 91e (460 mg, 0.90 mmol) in MeOH (10 mL). After the mixture was stirred at rt for 0.5 h, it was quenched with acetic acid and concentrated to dryness. The residues was purified by column chromatography to provide the tile compound (91f) (350 mg, 95% yield). m/z (ESI, +ve ion)= 430.7 [M+Na]⁺.

Step G. 7-((3aR,4R,6R,6aR)-6-(((tert-Butyldiphenylsilyl)oxy)methyl)-2,2-dimethyltetrahydrofuro[3,4-d][1,3]dioxol-4-yl)-2-chloro-N-cyclopentyl-7H-pyrrolo[2,3-d]pyrimidin-4-amine (91g)

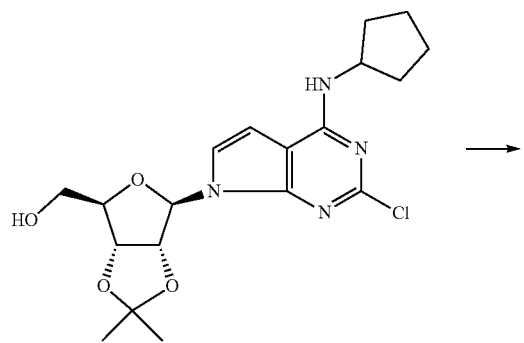

TBDPSCl (405 mg, 1.47 mmol) was added dropwise to a solution of 91f (400 mg, 0.98 mmol) and imidazole (200 mg, 2.94 mmol) in DMF (10 mL) at 0° C. The mixture was allowed to warm to rt and stirred overnight. The reaction mixture was poured into water and the solution was extracted with EtOAc. The organic layer was washed with brine, dried and concentrated. The residue was purified by column chromatography to afford the title compound (91g) (500 mg, 86% yield). m/z (ESI, +ve ion)=646.54 [M+H]⁺.

366

Step H. tert-Butyl (7-((3aR,4R,6R,6aR)-6-(((tert-butyldiphenylsilyl)oxy)methyl)-2,2-dimethyltetrahydrofuro[3,4-d][1,3]dioxol-4-yl)-2-chloro-7H-pyrrolo[2,3-d]pyrimidin-4-yl)(cyclopentyl)carbamate (91h)

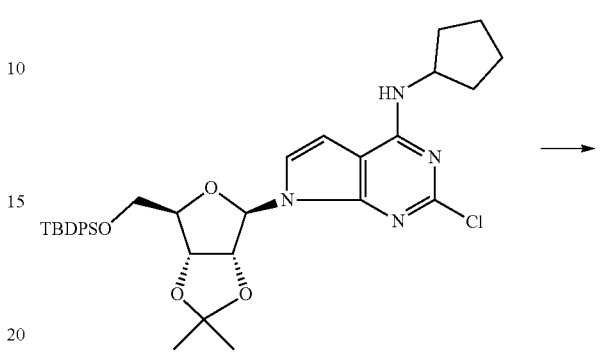

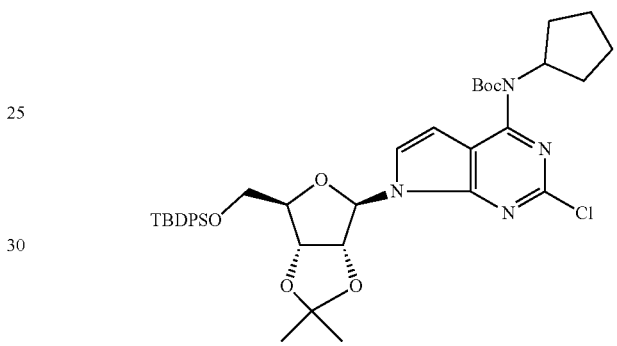

Boc₂O (506.2 mg, 2.32 mmol) was added to a solution of 91g (500 mg, 0.84 mmol), triethylamine (258 mg, 2.55 mmol) and DMAP (19 mg, 0.15 mmol) in DMF (10 mL). After the mixture was stirred at rt for 2 days, it was poured into water and the solution was extracted with EtOAc. The organic layer was washed with brine, dried and concentrated. The residue was purified by column chromatography to afford the title compound (91h) (140 mg, 24% yield).

Step I. tert-Butyl (2-chloro-7-((3aR,4R,6R,6aR)-6-(hydroxymethyl)-2,2-dimethyltetrahydrofuro[3,4-d][1,3]dioxol-4-yl)-7H-pyrrolo[2,3-d]pyrimidin-4-yl)(cyclopentyl)carbamate (91i)

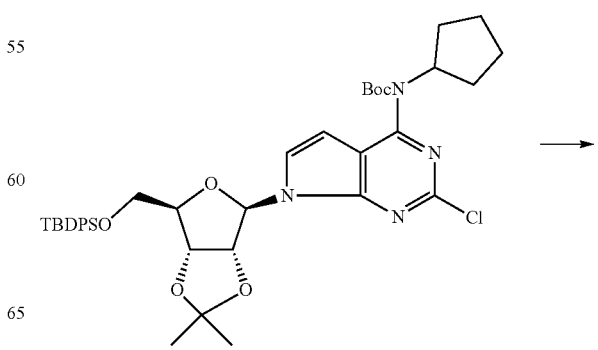

-continued

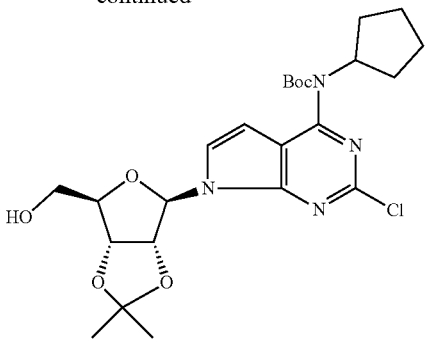

TBAF (98 mg, 0.38 mmol) was added to a solution of 91h (140 mg, 0.19 mmol) in THF (10 mL). After the mixture was stirred at rt overnight. it was poured into water and the solution was extracted with EtOAc. The organic layer was washed with brine, dried and concentrated. The residue was purified by column chromatography to afford the title compound (91i) (90 mg, 95% yield). m/z (ESI, +ve ion)=508.7 [M+H]$^+$.

Step J. (2-(((2R,3S,4R,5R)-5-(2-Chloro-4-(cyclopentylamino)-7H-pyrrolo[2,3-d]pyrimidin-7-yl)-3,4-dihydroxytetrahydrofuran-2-yl)methoxy)-1-hydroxypropan-2-yl)phosphonic add (91)

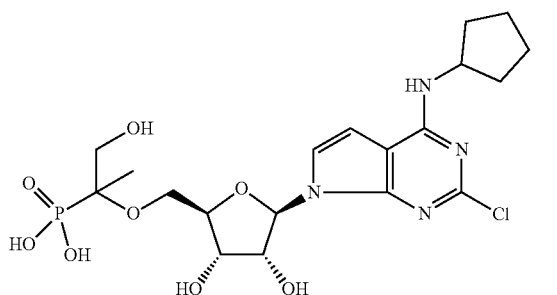 [SMILES: CC(CO)(OC[C@H]1O[C@@H](n2ccc3c(NC4CCCC4)nc(Cl)nc32)[C@H](O)[C@@H]1O)P(=O)(O)O]

The title compound was prepared from 91i by procedures similar to those described in Example 8, Steps C, D, and F. $^1$H NMR (D$_2$O, 400 MHz) δ 7.31-7.30 (d, J=3.2 Hz, 1H), 6.55 (d, J=2.8 Hz, 1H), 6.27 (d, J=4.8 Hz, 1H), 4.56 (m, 1H), 4.30 (m, 2H), 4.18 (m, 1H), 3.88-3.58 (m, 4H), 1.92 (m, 2H), 1.61-1.51 (m, 6H), 1.30-1.26 (d, J=14.4 Hz, 3H). m/z (ESI, +ve ion)=506.91 [M+H]$^+$.

Examples 92-248

Examples 92-248 were synthesized as described in examples 1-8, 15-17, 55-58, and 84-91.

| Ex | MS Data |
|---|---|
| 92 | 575.0 [M + H]$^+$ |
| 93 | 585.3 [M + H]$^+$ |
| 94 | 588.1 [M + H]$^+$ |
| 95 | 606.1 [M + H]$^+$ |
| 96 | 590.2 [M + H]$^+$ |
| 97 | 546.2 [M + H]$^+$ |
| 98 | 546.1 [M + H]$^+$ |
| 99 | 574.0 [M + H]$^+$ |
| 100 | 598.2 [M + H]$^+$ |
| 101 | 494.3 [M + H]$^+$ |
| 102 | 494.3 [M + H]$^+$ |
| 103 | 576.1 [M + H]$^+$ |
| 104 | 576.2 [M + H]$^+$ |
| 105 | 522.1 [M + H]$^+$ |
| 106 | 522.1 [M + H]$^+$ |
| 107 | 586.1 [M + H]$^+$ |
| 108 | 574.2 [M + H]$^+$ |
| 109 | 523.0 [M + H]$^+$ |
| 110 | 523.2 [M + H]$^+$ |
| 111 | 521.1 [M + H]$^+$ |
| 112 | 552.1 [M + H]$^+$ |
| 113 | 572.0 [M + H]$^+$ |
| 114 | 566.2 [M + H]$^+$ |
| 115 | 566.2 [M + H]$^+$ |
| 116 | 510.1 [M + H]$^+$ |
| 117 | 493.0 [M + H]$^+$ |
| 118 | 566.2 [M + H]$^+$ |
| 119 | 560.0 [M + H]$^+$ |
| 120 | 560.0 [M + H]$^+$ |
| 123 | 574.2 [M + H]$^+$ |
| 122 | 574.2 [M + H]$^+$ |
| 123 | 534.1 [M + H]$^+$ |
| 124 | 552.1 [M + H]$^+$ |
| 125 | 538.3 [M + H]$^+$ |
| 126 | 534.1 [M + H]$^+$ |
| 127 | 503.9 [M + H]$^+$ |
| 128 | 503.9 [M + H]$^+$ |
| 129 | 505.9 [M − H]$^−$ |
| 130 | 494.3 [M + H]$^+$ |
| 131 | 507.9 [M + H]$^+$ |
| 132 | 509.8 [M + H]$^+$ |
| 133 | 548.1 [M + H]$^+$ |
| 134 | 534.1 [M + H]$^+$ |
| 135 | 534.1 [M + H]$^+$ |
| 136 | 534.1 [M + H]$^+$ |
| 137 | 584.1 [M + H]$^+$ |
| 138 | 584.1 [M + H]$^+$ |
| 139 | 507.9 [M + H]$^+$ |
| 140 | 507.8 [M + H]$^+$ |
| 141 | 548.1 [M + H]$^+$ |
| 142 | 509.1 [M + H]$^+$ |
| 143 | 521.92 [M + H]$^+$ |
| 144 | 493.94 [M + H]$^+$ |
| 145 | 547.9 [M + H]$^+$ |
| 146 | 562.2 [M + H]$^+$ |
| 147 | 534.3 [M + H]$^+$ |
| 148 | 521.97 [M + H]$^+$ |
| 149 | 494.2 [M + H]$^+$ |
| 150 | 538.1 [M + H]$^+$ |
| 151 | 538.1 [M + H]$^+$ |
| 152 | 507.2 [M + H]$^+$ |
| 153 | 561.9 [M + H]$^+$ |
| 154 | 571.1 [M + H]$^+$ |
| 155 | 571.1 [M + H]$^+$ |
| 156 | 535.9 [M + H]$^+$ |
| 157 | 507.9 [M + H]$^+$ |
| 158 | 522.1 [M + H]$^+$ |
| 159 | 507.9 [M + H]$^+$ |
| 160 | 508.1 [M + H]$^+$ |
| 161 | 507.9 [M + H]$^+$ |
| 162 | 511.0 [M + H]$^+$ |
| 163 | 578.2 [M + H]$^+$ |
| 164 | 564.0 [M + H]$^+$ |
| 165 | 547.8 [M + H]$^+$ |
| 166 | 538.1 [M + H]$^+$ |
| 167 | 564.1 [M + H]$^+$ |
| 168 | 586.1 [M + H]$^+$ |
| 169 | 552.1 [M + H]$^+$ |
| 170 | 578.2 [M + H]$^+$ |
| 171 | 578.2 [M + H]$^+$ |
| 172 | 568.2 [M + H]$^+$ |
| 173 | 547.9 [M + H]$^+$ |
| 174 | 537.8 [M + H]$^+$ |
| 175 | 578.2 [M + H]$^+$ |
| 176 | 590.0 [M + H]$^+$ |

-continued

| Ex | MS Data |
|---|---|
| 177 | 626.1 [M + H]+ |
| 178 | 567.1 [M + H]+ |
| 179 | 614.2 [M + H]+ |
| 180 | 614.1 [M + H]+ |
| 181 | 564.0 [M + H]+ |
| 182 | 547.9 [M + H]+ |
| 183 | 561.7 [M + H]+ |
| 184 | 562.0 [M + H]+ |
| 185 | 580.2 [M + H]+ |
| 186 | 534.1 [M + H]+ |
| 187 | 628.0 [M + H]+ |
| 188 | 628.2 [M + H]+ |
| 189 | 586.2 [M + H]+ |
| 190 | 628.2 [M + H]+ |
| 191 | 564.0 [M + H]+ |
| 192 | 556.1 [M + H]+ |
| 193 | 506.9 [M + H]+ |
| 194 | 506.8 [M + H]+ |
| 195 | 591.1 [M + H]+ |
| 196 | 562.2 [M + H]+ |
| 197 | 562.2 [M + H]+ |
| 198 | 582.1 [M + H]+ |
| 199 | 528.0 [M + H]+ |
| 200 | 523.2 [M + H]+ |
| 201 | 580.0 [M + H]+ |
| 202 | 506.2 [M + H]+ |
| 203 | 580.0 [M + H]+ |
| 204 | 550.2 [M + H]+ |
| 205 | 528.0 [M + H]+ |
| 206 | 592.2 [M + H]+ |
| 207 | 606.1 [M + H]+ |
| 208 | 606.1 [M + H]+ |
| 209 | 590.2 [M + H]+ |
| 210 | 566.2 [M + H]+ |
| 211 | 537.9 [M + H]+ |
| 212 | 590.2 [M + H]+ |
| 213 | 562.2 [M + H]+ |
| 214 | 562.2 [M + H]+ |
| 215 | 567.1 [M + H]+ |
| 216 | 567.1 [M + H]+ |
| 217 | 572.2 [M + H]+ |
| 218 | 572.2 [M + H]+ |
| 219 | 575.2 [M + H]+ |
| 220 | 552.1 [M + H]+ |
| 221 | 552.1 [M + H]+ |
| 222 | 578.1 [M + H]+ |
| 223 | 576.3 [M + H]+ |
| 224 | 572.0 [M + H]+ |
| 225 | 576.2 [M + H]+ |
| 226 | 606.1 [M + H]+ |
| 227 | 657.9 [M + H]+ |
| 228 | 537.8 [M + H]+ |
| 229 | 629.2 [M + H]+ |
| 230 | 615.3 [M + H]+ |
| 231 | 643.2 [M + H]+ |
| 232 | 566.2 [M + H]+ |
| 233 | 566.2 [M + H]+ |
| 234 | 590.2 [M + H]+ |
| 235 | 586.2 [M + H]+ |
| 236 | 580.2 [M + H]+ |
| 237 | 524.1 [M + H]+ |
| 238 | 524.2 [M + H]+ |
| 239 | 550.1 [M + H]+ |
| 240 | 562.2 [M + H]+ |
| 241 | 562.2 [M + H]+ |
| 242 | 538.1 [M + H]+ |
| 243 | 610.2 [M + H]+ |
| 244 | 610.2 [M + H]+ |
| 245 | 582.3 [M + H]+ |
| 246 | 582.1 [M + H]+ |
| 247 | 538.2 [M + H]+ |
| 248 | 566.2 [M + H]+ |

II. Biological Evaluation

Example A1: Biochemical Assay

Assay Reaction Conditions
  Assay Volume: 70 μl
  Reaction Volume: 50 μl
  CD73: 0.3208 nM
  AMP: 15 μM
  Assay Buffer: 2 5 mM Tris-HCL, pH 7.4, 0.01% Brij-35, 0.01% BSA, 5 mM MgCl$_2$
Assay Procedure:
  Used 384 clear plate.
  Made dose titration of testing compounds in assay buffer, 10 points ½ log titrations in duplicates starting at 100 μM.
  Added 25 μl of CD73 to each well for a final concentration of 320 pM.
  Incubated at RT for 15 min.
  Added 25 μl of AMP to each well for a final concentration of 15 μM.
  Incubated at RT for 10 min.
  Added 10 μl of Malachite Green Reagent A, incubate at RT for 10 min.
  Added 10 μl of Malachite Green Reagent B. incubate at RT for 45 min.
  Read the Absorbance on Envision plate reader using excitation filter: Cy5 620 nM.

The ability of the compounds disclosed herein to inhibit CD73 activity was quantified and the respective IC$_{50}$ values were determined. Table 2 provides the biochemical IC$_{50}$ values of compounds disclosed herein.

| Ex | Biochemical IC$_{50}$ |
|---|---|
| 1 | A |
| 2 | B |
| 3 | A |
| 4 | A |
| 5 | A |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 17 | B |
| 20 | B |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | B |
| 35 | A |
| 36 | A |
| 37 | A |
| 38 | B |
| 39 | A |
| 40 | A |
| 41 | B |
| 42 | A |
| 53 | A |

| Ex | Biochemical IC$_{50}$ |
|---|---|
| 54 | A |
| 55 | A |
| 56 | A |
| 57 | A |
| 58 | A |
| 59 | B |
| 60 | A |
| 61 | A |
| 62 | A |
| 63 | A |
| 64 | A |
| 65 | A |
| 66 | A |
| 67 | A |
| 68 | A |
| 69 | A |
| 70 | B |
| 71 | C |
| 72 | A |
| 73 | A |
| 74 | A |
| 75 | A |
| 76 | A |
| 77 | A |
| 78 | A |
| 79 | A |
| 80 | B |
| 81 | C |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | B |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | B |
| 113 | A |
| 114 | A |
| 115 | A |
| 116 | A |
| 117 | A |
| 118 | A |
| 119 | A |
| 120 | A |
| 121 | A |
| 112 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | B |
| 188 | B |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |

-continued

| Ex | Biochemical IC$_{50}$ |
|---|---|
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | B |
| 221 | A |
| 222 | A |
| 224 | A |
| 227 | A |
| 228 | A |

A: IC$_{50}$ ≤ 100 nM;
B: 100 nM < 1050 ≤ 1 nM
C: 1 μM < 1050
NT: Not Tested

The examples and embodiments described herein are for illustrative purposes only and in some embodiments, various modifications or changes are to be included within the purview of disclosure and scope of the appended claims.

What is claimed is:

1. A method of treating cancer in a subject, comprising administering to the subject a compound of Formula (IV), or a pharmaceutically acceptable salt thereof:

wherein:

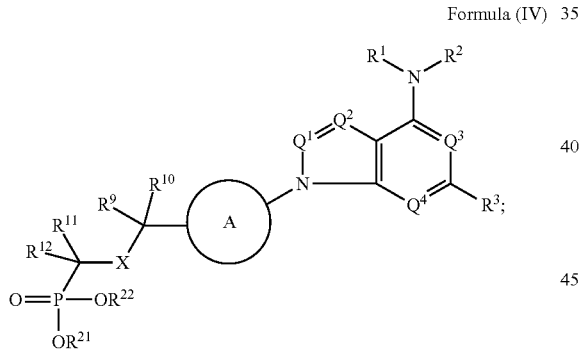

Formula (IV)

Ring A is

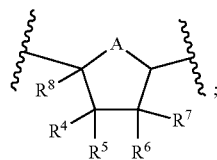

$Q^2$ is N or CW;
$Q^3$ is N and $Q^4$ is CW;
or $Q^3$ is CW and $Q^4$ is N;
each W is independently hydrogen, halogen, —CN, —OR$^b$, NR$^c$R$^d$, C$_1$-C$_6$ alkyl, or C$_1$-C$_6$ haloalkyl;
A is —O— or —CH$_2$—;
X is —O—, —S—, —S(=O)$_2$—, —NR$^{17}$—, or —C(R$^{18}$)$_2$—;

$R^1$ and $R^2$ are independently hydrogen, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl, Amyl, alkynyl, cycloalkyl, heterocycloalkyl, aryl, and heteroaryl is independently, optionally substituted with one, two, or three R$^{1a}$;

or $R^1$ and $R^2$ are taken together with the nitrogen atom to which they are attached to form a heterocycloalkyl optionally substituted with one, two, or three R$^{1b}$;

each R$^{1a}$ and R$^{1b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NR$^b$S(=O)$_2$R$^a$, —S(=O)$_2$ NR$^c$R$^d$, —C(=O)OR$^b$, —OC(=O)OR$^b$; —C(=O)NR$^c$R$^d$, —OC(=O)NR$^c$R$^d$, —NR$^b$C(=O) NR$^c$R$^d$, —NR$^b$C(=O)R$^a$, —NR$^b$C(=O)OR$^b$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl);

R$^3$ is hydrogen, halogen, —CN, —OR$^b$, —SR$^b$, —NR$^c$R$^d$, C$_1$-C$_6$ alkyl, C$_2$-C$_6$ alkenyl, C$_2$-C$_6$ alkynyl, C$_1$-C$_6$ haloalkyl, C$_1$-C$_6$ hydroxyalkyl, C$_1$-C$_6$ heteroalkyl, cycloalkyl, heterocycloalkyl, aryl, heteroaryl, C$_1$-C$_6$ alkyl(aryl), C$_1$-C$_6$ alkyl(heteroaryl), C$_1$-C$_6$ alkyl(cycloalkyl), or C$_1$-C$_6$ alkyl(heterocycloalkyl); wherein each alkyl; alkenyl, alkynyl, cycloalkyl, heterocycloalkyl, aryl, and heteroaryl is independently optionally substituted with one, two; or three R$^{3a}$;

each R$^{3a}$ is independently oxo (when feasible), halogen, —CN, —OR$^b$, —NR$^c$R$^d$, —C(=O)R$^a$, —C(=O)OR$^b$, —C(=O)NR$^c$R$^d$, C$_1$-C$_6$ alkyl, C$_1$-C$_6$ fluoroalkyl, C$_2$-C$_6$ alkenyl, C$_2$-C$_6$ alkynyl, cycloalkyl, heterocycloalkyl, aryl, or heteroaryl, R$^4$ and R$^7$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl; or heteroaryl;

R$^5$ and R$^6$ are independently hydrogen, halogen, —OR$^b$, C$_1$-C$_6$ alkyl, C$_1$-C$_6$ haloalkyl, C$_2$-C$_6$ alkenyl, C$_2$-C$_6$ alkynyl, cycloalkyl, heterocycloalkyl, aryl, or heteroaryl;

R$^8$ is hydrogen, halogen, —OR$^b$, —NR$^c$R$^d$, C$_1$-C$_6$ alkyl, or C$_1$-C$_6$ haloalkyl;

R$^9$ and R$^{10}$ are independently hydrogen, halogen, C$_1$-C$_6$ alkyl, or C$_1$-C$_6$ haloalkyl;

R$^{11}$ is hydrogen, halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O) R$^{14}$, —OC(=O)R$^{14}$, —C(=O)OR$^{13}$, —OC(=O) OR$^{13}$, NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl, wherein each alkyl, alkenyl, alkynyl, cycloalkyl, heterocycloalkyl, aryl, and heteroaryl is independently optionally substituted with one, two, or three R$^{11a}$;

R$^{12}$ is halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$ R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_1$-C$_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{12a}$;

or $R^{11}$ and $R^{12}$ are taken together to form a cycloalkyl or heterocycloalkyl each optionally substituted with one, two, or three $R^{11b}$;

each $R^{11a}$, $R^{11b}$, and $R^{12a}$ is independently oxo (when feasible), halogen, —CN, —OR$^{13}$, —SR$^{13}$, —S(=O)R$^{14}$, —NO$_2$, —NR$^{15}$R$^{16}$, —S(=O)$_2$R$^{14}$, —NR$^{13}$S(=O)$_2$R$^{14}$, —S(=O)$_2$NR$^{15}$R$^{16}$, —C(=O)R$^{14}$, —OC(=O)R$^{14}$, —C(=O)OR$^{13}$, —OC(=O)OR$^{13}$, —C(=O)NR$^{15}$R$^{16}$, —OC(=O)NR$^{15}$R$^{16}$, —NR$^{13}$C(=O)NR$^{15}$R$^{16}$, —NR$^{13}$C(=O)R$^{14}$, —NR$^{13}$C(=O)OR$^{13}$, $C_1$-$C_6$ alkyl, $C_1$-$C_6$ haloalkyl, $C_2$-$C_6$ alkenyl, $C_2$-$C_6$ alkynyl, $C_1$-$C_6$ hydroxyalkyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{11c}$;

each $R^{11c}$ is independently oxo (when feasible), halogen, —CN, —OR$^b$, —SR$^b$, —S(=O)R$^a$, —NO$_2$, —NR$^c$R$^d$, —S(=)$_2$R$^a$, —NR$^b$S(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{13}$ is independently hydrogen, $C_1$-$C_6$ alkyl, $C_1$-$C_6$ haloalkyl, $C_2$-$C_6$ alkenyl, alkynyl, $C_1$-$C_6$ heteroalkyl, cycloalkyl, heterocycloalkyl, aryl, or heteroaryl; wherein each alkyl alkenyl, alkynyl, cycloalkyl, heterocycloalkyl, aryl, and heteroaryl is independently optionally substituted with one, two, or three $R^{13a}$;

each $R^{14}$ is independently $C_1$-$C_6$ alkyl, $C_1$-$C_6$ haloalkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{14a}$;

each $R^{15}$ and $R^{16}$ is independently hydrogen, $C_1$-$C_6$ alkyl; $C_1$-$C_6$ haloalkyl, alkenyl, $C_2$-$C_6$ alkynyl, $C_1$-$C_6$ heteroalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{15a}$;

or $R^{15}$ and $R^{16}$ are taken together with the nitrogen atom to which they are attached to form a heterocycloalkyl optionally substituted with one, two, or three $R^{15b}$;

each $R^{13a}$, $R^{14a}$, $R^{15a}$, and $R^{15b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(50 O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl; $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three oxo (when feasible), halogen, —CN, —OR$^b$, —S(=O)R$^a$, —NO$_2$, —NR$^c$R$^d$; —S(=O)$_2$R$^a$, —S(=O)$_2$NR$^c$R$^d$, —C(=O)R$^a$, —C(=O)OR$^b$, —C(=O)NR$^c$R$^d$, $C_1$-$C_6$ alkyl, $C_1$-$C_6$ haloalkyl, $C_2$-$C_6$ alkenyl, or $C_2$-$C_6$ alkynyl;

$R^{17}$ is hydrogen, —CN, —OR$^b$, —S(=O)$_2$R$^a$, —C(=O)R$^a$, —C(=O)OR$^b$; —C(=O)NR$^a$, $C_1$-$C_6$ alkyl, $C_1$-$C_6$ fluoroalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^{18}$ is independently hydrogen, halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl);

$R^{21}$ and $R^{22}$ are independently hydrogen, $C_1$-$C_{20}$ alkyl, cycloalkyl, heterocycloalkyl, aryl, heteroaryl, $C_1$-$C_6$ alkyl(aryl), $C_1$-$C_6$ alkyl(heteroaryl), $C_1$-$C_6$ alkyl(cycloalkyl), $C_1$-$C_6$ alkyl(heterocycloalkyl); wherein each alkyl, cycloalkyl, heterocycloalkyl, aryl, and heteroaryl is independently optionally substituted with one, two, or three $R^{21a}$;

or $R^{21}$ and $R^{22}$ are taken together with the atoms to which they are attached to form a heterocycloalkyl optionally substituted with one, two, or three $R^{21b}$;

each $R^{21a}$ and $R^{21b}$ is independently oxo (when feasible), halogen, —CN, —OR$^b$, —SR$^b$, —S(=O)R$^a$, —NO$_2$, —NR$^c$R$^d$, —S(=O)$_2$R$^a$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$ alkyl, $C_2$-$C_6$ alkenyl, $C_2$-$C_6$ alkynyl, cycloalkyl, heterocycloalkyl, aryl, heteroaryl, alkyl(aryl), $C_1$-$C_6$ alkyl(heteroaryl), $C_1$-$C_6$ alkyl(cycloalkyl), or $C_1$-$C_6$ alkyl(heterocycloalkyl);

each $R^a$ is independently $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

each $R^b$ is independently hydrogen, $C_1$-$C_6$ alkyl, $C_2$-$C_6$ alkenyl, $C_2$-$C_6$ alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl; and each $R^c$ and $R^d$ is independently hydrogen, $C_1$-$C_6$ alkyl, $C_2$-$C_6$ alkenyl, alkynyl, $C_1$-$C_6$ heteroalkyl, cycloalkyl, heterocycloalkyl, aryl, or heteroaryl; wherein the alkyl, alkenyl, alkynyl, heteroalkyl, cycloalkyl, heterocycloalkyl, aryl, and heteroaryl is independently optionally substituted with one, two, or three oxo (when feasible), halogen, —OH, $C_1$-$C_6$ alkyl, or $C_1$-$C_6$ haloalkyl;

or $R^c$ and $R^d$ are taken together with the nitrogen atom to which they are attached to form a heterocycloalkyl optionally substituted with one, two, or three oxo, halogen, $C_1$-$C_6$ or $C_1$-$C_6$ haloalkyl; and wherein the cancer is selected from lung cancer, melanoma, breast cancer, ovarian cancer, colorectal cancer, gastric cancer, gallbladder cancer, prostate cancer, renal cancer, multiple myeloma, and lymphoma.

2. The method of claim 1, wherein in the compound of Formula (IV), or a pharmaceutically acceptable salt thereof, $Q^2$ is CW.

3. The method of claim 1, wherein in the compound of Formula (IV), or a pharmaceutically acceptable salt thereof, $Q^2$ is N.

4. The method of claim 1, wherein in the compound of Formula (IV), or a pharmaceutically acceptable salt thereof, $Q^3$ is N and $Q^4$ is CW.

5. The method of claim 1, wherein in the compound of Formula (IV), or a pharmaceutically acceptable salt thereof, $Q^4$ is N and $Q^3$ is CW.

6. The method of claim 1, wherein in the compound of Formula (IV), or a pharmaceutically acceptable salt thereof, each W is independently hydrogen, halogen, or $C_1$-$C_6$ alkyl.

7. The method of claim 1, wherein in the compound of Formula (IV), or a pharmaceutically acceptable salt thereof, $R^3$ is halogen, —$OR^b$, $C_1$-$C_6$ alkyl, $C_2$-$C_6$ alkynl, $C_1$-$C_6$ haloalkyl, $C_1$-$C_6$ hydroxyalkyl, or $C_1$-$C_6$ heteroalkyl; wherein each alkyl and alkynyl is independently optionally substituted with one, two, or three $R^{3a}$.

8. The method of claim 1, wherein in the compound of Formula (IV), or a pharmaceutically acceptable salt thereof, $R^3$ is halogen, —$OR^b$, $C_2$-$C_6$ alkynyl, or $C_1$-$C_6$ hydroxyalkyl; wherein each alkyl and alkynyl is independently optionally substituted with one, two, or three $R^{3a}$.

9. The method of claim 1, wherein in the compound of Formula (IV), or a pharmaceutically acceptable salt thereof, $R^1$ is $C_1$-$C_6$ alkyl, $C_1$-$C_6$ haloalkyl, cycloalkyl, heterocycloalkyl, $C_1$-$C_6$ alkyl(aryl), $C_1$-$C_6$ alkyl(heteroaryl), $C_1$-$C_6$ alkyl(cycloalkyl), or $C_1$-$C_6$ alkyl(heterocycloalkyl); wherein each alkyl, cycloalkyl, heterocycloalkyl, aryl, and heteroaryl is independently optionally substituted with one, two, or three $R^{1a}$.

10. The method of claim 9, wherein in the compound of Formula (IV), or a pharmaceutically acceptable salt thereof, $R^1$ is $C_1$-$C_6$ alkyl, cycloalkyl, $C_1$-$C_6$ alkyl(aryl), or $C_1$-$C_6$ alkyl(cycloalkyl); wherein each alkyl, cycloalkyl, and aryl is independently optionally substituted with one, two, or three $R^{1a}$.

11. The method of claim 1, wherein in the compound of Formula (IV), or a pharmaceutically acceptable salt thereof, each $R^{1a}$ is independently halogen or $C_1$-$C_6$ alkyl.

12. The method of claim 1, wherein in the compound of Formula (IV), or a pharmaceutically acceptable salt thereof, $R^2$ is hydrogen or $C_1$-$C_6$ alkyl.

13. The method of claim 10, wherein in the compound of Formula (IV), or a pharmaceutically acceptable salt thereof, $R^2$ is hydrogen.

14. The method of claim 1, wherein in the compound of Formula (IV), or a pharmaceutically acceptable salt thereof, $R^8$ is hydrogen or $C_1$-$C_6$ alkyl.

15. The method of claim 14, wherein in the compound of Formula (IV), or a pharmaceutically acceptable salt thereof, $R^8$ is hydrogen.

16. The method of claim 1, wherein in the compound of Formula (IV), or a pharmaceutically acceptable salt thereof, $R^9$ and $R^{10}$ are independently, hydrogen or $C_1$-$C_6$ alkyl.

17. The method of claim 16, wherein in the compound of Formula (IV), or a pharmaceutically acceptable salt thereof, $R^9$ and $R^{10}$ are hydrogen.

18. The method of claim 1, wherein in the compound of Formula (IV), or a pharmaceutically acceptable salt thereof, A is —O—.

19. The method of claim 1, wherein the cancer is multiple myeloma.

\* \* \* \* \*